US006218431B1

(12) United States Patent
Schoen et al.

(10) Patent No.: US 6,218,431 B1
(45) Date of Patent: *Apr. 17, 2001

(54) SUBSTITUTED BIPHENYLS

(75) Inventors: William R. Schoen, Madison; Gaetan H. Ladouceur, Branford; James H. Cook, II, East Hampton; Timothy G. Lease, Guilford; Donald J. Wolanin, Orange; Richard H. Kramss, Guilford; Donald L. Hertzog, Madison, all of CT (US); Martin H. Osterhout, Raleigh, NC (US)

(73) Assignees: Bayer Corporation, Pittsburgh, PA (US); Bayer Aktiengesellschaft, Leverkusen (DE)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/904,119

(22) Filed: Jul. 31, 1997

(51) Int. Cl.[7] ...................... A61K 31/275; C07C 255/54; C07C 39/28; C07C 39/10

(52) U.S. Cl. .......................... 514/520; 514/712; 514/736; 558/412; 568/47; 568/746; 568/764

(58) Field of Search .................................... 568/746, 764, 568/47; 514/712, 736, 520; 558/412

(56) References Cited

U.S. PATENT DOCUMENTS

| | | | |
|---|---|---|---|
| 4,655,816 | 4/1987 | Lee et al. | 504/195 |
| 4,886,546 | 12/1989 | Yagihara et al. | 504/292 |
| 4,906,624 | 3/1990 | Chucholowski et al. | 514/210 |
| 4,937,255 | 6/1990 | Hubsch et al. | 514/427 |
| 4,973,598 | 11/1990 | Fey et al. | 514/392 |
| 4,988,711 | 1/1991 | Angerbauer et al. | 514/326 |
| 4,992,462 | 2/1991 | Hubsch et al. | 514/428 |
| 4,997,837 | 3/1991 | Chucholowski et al. | 514/256 |
| 5,006,530 | 4/1991 | Angerbauer et al. | 514/277 |
| 5,032,602 | 7/1991 | Fey et al. | 514/345 |
| 5,034,399 | 7/1991 | Hubsch et al. | 514/300 |
| 5,072,023 | 12/1991 | Robl | 560/67 |
| 5,075,311 | 12/1991 | Hubsch et al. | 514/258 |
| 5,120,782 | 6/1992 | Hubsch et al. | 514/300 |
| 5,137,881 | 8/1992 | Hubsch et al. | 514/81 |
| 5,138,090 | 8/1992 | Fey et al. | 560/59 |
| 5,145,959 | 9/1992 | Hubsch et al. | 544/279 |
| 5,164,506 | 11/1992 | Fey et al. | 546/296 |
| 5,169,857 | 12/1992 | Angerbauer et al. | 514/344 |
| 5,183,897 | 2/1993 | Angerbauer et al. | 546/330 |
| 5,401,746 | 3/1995 | Angerbauer et al. | 514/277 |

FOREIGN PATENT DOCUMENTS

| | | | |
|---|---|---|---|
| 03805884 | 9/1989 | (DE) . | |
| 3905908 | 9/1990 | (DE) . | |
| 0300278 | 1/1989 | (EP) . | |
| 0306929 | 3/1989 | (EP) | C07D/405/06 |
| 0325129 | 7/1989 | (EP) | C07D/213/55 |
| 0325130 | 7/1989 | (EP) | C07D/213/65 |
| 0330057 | 8/1989 | (EP) . | |
| 0352575 | 1/1990 | (EP) . | |
| 0182769 | 8/1990 | (EP) . | |
| 0133612 | 2/1991 | (EP) . | |
| 0444533 | 9/1991 | (EP) | C07F/9/58 |
| 0603699 | 6/1994 | (EP) | C07D/405/06 |
| 0742208 | 11/1996 | (EP) | C07D/211/26 |
| 0796846 | 9/1997 | (EP) | C07D/213/30 |

OTHER PUBLICATIONS

Robl, et al., Phosphorus–Containing Inhibitors of HMG–CoA Reductase. 2.[1] Synthesis and Biological Activities of a Series of Substituted Pyridines Containing a Hydroxyphosphinyl Moiety[2], J. Med. Chem., 34, 2804–2815 (1991).

*Primary Examiner*—Alan L. Rotman

(57) ABSTRACT

Substituted biphenyls having glucagon receptor antagonistic activity. Claimed compounds have the formula

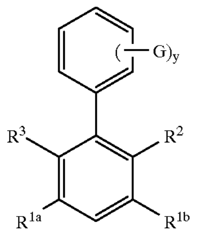

wherein $R^{1a}$ and $R^{1b}$ independently represent ($C_1$–$C_6$) alkyl; $R^2$ represents ($C_1$–$C_{10}$) alkyl or substituted ($C_1$–$C_{10}$) alkyl wherein the substituents are independently from 1 to 3 of —$SR^7$; $R^7$ represents phenyl, or substituted phenyl wherein the substituents are independently 1–5 of halogen, trifluoromethyl, ($C_1$–$C_6$) alkyl, ($C_1$–$C_6$) alkoxy, nitro, cyano, or hydroxyl; $R^3$ represents substituted ($C_1$–$C_6$) alkyl wherein the substituents are 1–2 hydroxyl groups; G represents a substituent selected from the group consisting of halogen, ($C_1$–$C_6$) alkyl, and $OR^4$ wherein $R^4$ is H or ($C_1$–$C_6$) alkyl; and y is 0 or an integer of 1–3. Pharmaceutical compositions containing such compounds and methods of treatment of glucagon-mediated conditions by administering such compounds are also claimed.

6 Claims, No Drawings

SUBSTITUTED BIPHENYLS

FIELD

This application claims the benefit of U.S. Provisional application No. 60/228,822.

BACKGROUND

The present invention concerns certain substituted pyridines, processes for the production thereof, and the use thereof in pharmaceutical products. It also concerns certain substituted biphenyls, processes for their production, pharmaceutical compositions containing them, and methods for their use.

7-(polysubstituted pyridyl) hept-6-enoates for the treatment of arteriosclerosis, lipoproteinemia, and hyperlipoproteinemia are known from U.S. Pat. No. 5,169,857. In addition, the production of 7-(4-aryl-3-pyridyl)-3,5-dihydroxy-hept-6-enoate is described in EP 325 130.

Glucagon is a peptide hormone whose main function is to increase hepatic glucose production. Insulin, on the other hand, functions to decrease glucose production. Together, these two hormones are necessary for maintaining a correct level of glucose in the blood.

Diabetes is a complex disease characterized by hyperglycemia resulting from defects in insulin secretion, insulin action, or both. Diabetes is also associated with elevated glucagon levels. The heterogeneous nature of the disease requires different strategies to address the different abnormalities in metabolism found in affected individuals.

In the diabetic state (all forms of Type I and Type II), hyperglycemia often is associated with elevated glucagon levels. Accordingly, a means of treating all forms of diabetes is to block the glucagon receptor with a suitable antagonist, thereby inhibiting glucose production by the liver and reducing glucose levels in the patient.

Glucagon receptor antagonists, materials which block the action of endogenous glucagon, are known to have many and varied applications. Among these applications are the following:

1. Treatment of hyperglycemia associated with diabetes of any cause and associated with any other diseases or conditions. A glucagon receptor antagonist can be used either alone or in combination with any other therapies to treat hyperglycemia.
2. Treatment of impaired glucose tolerance (IGT).
3. Treatment of insulin resistance syndromes including those due to obesity, polycystic ovarian syndrome, “Syndrome X”, drugs and hormones, endocrinopathies and genetic syndromes.
4. To decrease free fatty acid levels and treat conditions associated with elevated free fatty acids levels such as insulin resistance, obesity, all or part of Syndrome X, Type I and II diabetes, hyperlipidemias and elevated hepatic glucose output associated with insulin resistance, Type I and Type II diabetes, obesity, and Syndrome X.
5. To treat conditions associated with genetic defects in insulin action due to alterations in insulin receptor structure and function or alterations in post receptor signal transduction. To treat diabetes associated with anti-insulin antibodies, drug induced diabetes, diabetes associated with endocrinopathies and diabetes associated with genetic syndromes.
6. To treat gestational diabetes mellitus.

7. To treat autoimmune and non autoimmune causes of Type I diabetes including those due to known genetic defects of the beta cell, pancreatic diseases, drug or toxin induced beta cell dysfunction, endocrinopathies, infectious causes, malnutrition associated and idiopathic Type I diabetes.
8. To prevent and treat diabetic ketoacidosis and decrease hepatic ketone body production
9. To treat hyperglycemia of exercise in diabetes.
10. To reduce fasting and postprandial glucose.
11. Treatment of insulin resistance in liver, muscle, and fat.
12. Treatment of conditions of hyperlipidemia.
13. To treat glucagonomas and all other conditions associated with elevated glucagon levels.
14. To treat conditions of increased futile cycling of glucose in the liver.
15. To increase insulin secretion.
16. To decrease glucose toxicity.
17. To decrease the renal prostaglandin response to protein and amino acids.
18. To decrease elevated GFR and albumin clearance due to diabetes or proteins or amino acids.
19. To decrease renal albumin clearance and excretion.
20. To treat acute pancreatitis.
21. To treat cardiovascular disease including causes of increased cardiac contractility.
22. To treat cardiac hypertrophy and its consequences.
23. As a diagnostic agent and as a diagnostic agent to identify patients having a defect in the glucagon receptor.
24. Treatment of gastrointestinal disorders, treatment of decreased gut motility.
25. As a therapy to increase gastric acid secretions.
26. To reverse intestinal hypomobility due to glucagon administration.
27. To reverse catabolism and nitrogen loss in states of negative nitrogen balance and protein wasting including all causes of Type I and Type II diabetes, fasting, AIDS, cancer, anorexia, aging and other conditions.
28. To treat any of the above conditions or diseases in post-operative or operative period.
29. To decrease satiety and increase energy intake.

Glucagon receptor antagonists of the prior art, such as those described in WO9518153-A and references cited therein, are predominantly peptide analogues of glucagon. They are susceptible to the actions of endogenous proteases, may precipitate antibody production and immune reactions and can be difficult and expensive to manufacture. Such peptides are usually unsuitable for oral delivery.

One non-peptide glucagon receptor antagonist has been reported (Collins, et al; *BioMed. Chem Lett.* 1992, 2, 915–918). This quinoxaline derivative, CP-99,711, was shown to inhibit glucagon binding and glucagon action in rat liver membrane at micromolar concentrations.

It would be desirable to have inhibitors of CETP which possess valuable pharmacological properties that are superior to those of the state of the art. Certain of the substituted pyridine compounds of the invention are highly effective inhibitors of cholesterol ester transfer proteins (CETP) and stimulate reverse cholesterol transport. They cause a reduction in LDL cholesterol levels in the blood, while at the same time increasing HDL cholesterol levels. They can therefore be used for the treatment of hyperlipoproteinemia or arteriosclerosis.

It would also be desirable to have readily prepared non-peptidic glucagon receptor antagonists which are metabolically more stable than peptidic antagonists of the prior art, and which afford good activity and bioavailability. Certain of the substituted pyridine compounds as well as the substituted biphenyls of the invention are highly effective inhibitors of the glucagon receptor. Accordingly, these compounds may be used to treat glucagon-mediated conditions such as those listed above.

SUMMARY

The present invention concerns substituted biaryl compounds which fall within the three general formulae (IA), (IB), and (IC) shown below. The definitions of these general formulae are given broadly in the following text. In the subsequent detailed description sections, each of these broad general formulae is discussed in more detail in terms of its preferred and most preferred molecular constituents, procedures for making, examples of particular materials made, testing procedures, and results obtained.

It should be noted that in the text below, and in the subsequent detailed description sections, the definitions of the various constituent and substituent groups apply only to the particular subset of the compounds of the invention then under consideration. The same symbols may have different definitions in connection with the other subsets of compounds.

The present invention concerns substituted pyridines of the general formula (IA)

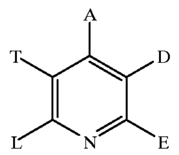

in which

A stands for aryl with 6 to 10 carbon atoms, which is optionally substituted up to 3 times in an identical manner or differently by halogen, hydroxy, trifluoromethyl, trifluoromethoxy, or by straight-chain or branched alkyl, acyl, or alkoxy with up to 7 carbon atoms each, or by a group of the formula $-NR^1R^2$, wherein $R^1$ and $R^2$ are identical or different and denote hydrogen, phenyl, or straight-chain or branched alkyl with up to 6 carbon atoms, D stands for straight-chain or branched alkyl with up to 8 carbon atoms, which is substituted by hydroxy, E and L are either identical or different and stand for straight-chain or branched alkyl with up to 8 carbon atoms, which is optionally substituted by cycloalkyl with 3 to 8 carbon atoms, or stand for cycloalkyl with 3 to 8 carbon atoms, or E has the above-mentioned meaning and L in this case stands for aryl with 6 to 10 carbon atoms, which is optionally substituted up to 3 times in an identical manner or differently by halogen, hydroxy, trifluoromethyl, trifluoromethoxy, or by straight-chain or branched alkyl, acyl, or alkoxy with up to 7 carbon atoms each, or by a group of the formula $-NR^3R^4$, wherein $R^3$ and $R^4$ are identical or different and have the meaning given above for $R^1$ and $R^2$, or E stands for straight-chain or branched alkyl with up to 8 carbon atoms, or stands for aryl with 6 to 10 carbon atoms, which is optionally substituted up to 3 times in an identical manner or differently by halogen, hydroxy, trifluoromethyl, trifluoromethoxy, or by straight-chain or branched alkyl, acyl, or alkoxy with up to 7 carbon atoms each, or by a group of the formula $-NR^5R^6$, wherein $R^5$ and $R^6$ are identical or different and have the meaning given above for $R^1$ and $R^2$, and L in this case stands for straight-chain or branched alkoxy with up to 8 carbon atoms or for cycloalkyloxy with 3 to 8 carbon atoms, T stands for a radical of the formula

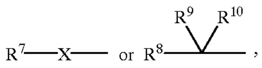

wherein $R^7$ and $R^8$ are identical or different and denote cycloalkyl with 3 to 8 carbon atoms, or aryl with 6 to 10 carbon atoms, or denote a 5- to 7-member aromatic, optionally benzo-condensed, heterocyclic compound with up to 3 heterocyclic atoms from the series S, N and/or O, which are optionally substituted up to 3 times in an identical manner or differently by trifluoromethyl, trifluoromethoxy, halogen, hydroxy, carboxyl, by straight-chain or branched alkyl, acyl, alkoxy, or alkoxycarbonyl with up to 6 carbon atoms each, or by phenyl, phenoxy, or thiophenyl, which can in turn be substituted by halogen, trifluoromethyl, or trifluoromethoxy, and/or the rings are substituted by a group of the formula $-NR^{11}R^{12}$, wherein $R^{11}$ and $R^{12}$ are identical or different and have the meaning given above for $R^1$ and $R^2$, X denotes a straight or branched alkyl chain or alkenyl chain with 2 to 10 carbon atoms each, which are optionally substituted up to 2 times by hydroxy, $R^9$ denotes hydrogen, and $R^{10}$ denotes hydrogen, halogen, azido, trifluoromethyl, hydroxy, mercapto, trifluoromethoxy, straight-chain or branched alkoxy with up to 5 carbon atoms, or a radical of the formula $-NR^{13}R^{14}$, wherein $R^{13}$ and $R^{14}$ are identical or different and have the meaning given above for $R^1$ and $R^2$, or $R^9$ and $R^{10}$ form a carbonyl group together with the carbon atom, and the salts thereof.

The present invention also concerns substituted pyridines of general formula (IB)

(IB)

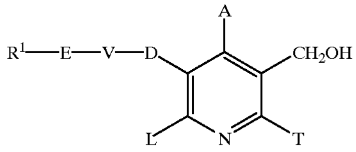

in which

A stands for aryl with 6 to 10 carbon atoms, which is optionally substituted up to 3 times in an identical manner or differently by halogen, hydroxy, trifluoromethyl, trifluoromethoxy, or by straight-chain or branched alkyl, acyl, or alkoxy with up to 7 carbon atoms each, or by a group of the formula $—NR^2R^3$ and/or $—WR^4$, wherein $R^2$ and $R^3$ are the same or different and denote hydrogen, phenyl, or straight-chain or branched alkyl with up to 6 carbon atoms, W denotes an oxygen or sulfur atom, $R^4$ denotes aryl with 6 to 10 carbon atoms, which is optionally substituted up to 3 times in an identical manner or differently by halogen, trifluoromethyl, trifluoromethoxy, hydroxy, or by straight-chain or branched alkyl or alkoxy with up to 6 carbon atoms each, D and E are identical or different and stand for a straight-chain or branched alkyl chain with up to 8 carbon atoms, or E stands for a bond, V stands for an oxygen or sulfur atom or for a group of the formula $—NR^5—$, wherein $R^5$ denotes hydrogen or straight-chain or branched alkyl with up to 6 carbon atoms or phenyl, $R^1$ stands for cycloalkyl with 3 to 6 carbon atoms, or stands for aryl with 6 to 10 carbon atoms or for a 5- to 7-member, optionally benzocondensed, saturated or unsaturated, mono-, bi-, or tricyclic heterocyclic compound with up to 4 carbon atoms from the series S, N, and/or O, in which the heterocycles, also via the N function in the case of nitrogen-containing rings, are optionally substituted up to 3 times in an identical manner or differently by halogen, trifluoromethyl, hydroxy, cyano, carboxyl, trifluoromethoxy, straight-chain or branched acyl, alkyl, alkylthio, alkylalkoxy, alkoxy, or alkoxycarbonyl with up to 6 carbon atoms each, by aryl with 6 to 10 carbon atoms, or by an optionally benzocondensed, aromatic 5- to 7-member heterocyclic compound with up to 3 heterocyclic atoms from the series S, N, and/or O, and/or are substituted by a group of the formula $—OR^6$, $—SR^7$, $—SO_2R^8$, or $—NR^9R^{10}$, wherein $R^6$, $R^7$, and $R^8$ are identical or different and denote aryl with 6 to 10 carbon atoms, which in turn is substituted up to 2 times in an identical manner or differently by phenyl or halogen or by straight-chain or branched alkyl with up to 4 carbon atoms, $R^9$ and $R^{10}$ are identical or different and have the above-indicated meaning of $R^2$ and $R^3$, L and T are identical or different and stand for trifluoromethyl or straight-chain or branched alkyl with up to 8 carbon atoms, which are optionally substituted by cycloalkyl with 3 to 7 carbon atoms, or by aryl with 6 to 10 carbon atoms, which in turn can be substituted up to 2 times in an identical manner or differently by halogen, trifluoromethyl, trifluoromethoxy, or by straight-chain or branched alkyl, acyl, or alkoxy with up to 7 carbon atoms each, or L and/or T stand for cycloalkyl with 3 to 7 carbon atoms or stand for aryl with 6 to 10 carbon atoms or for a 5- to 7-member, saturated, partially unsaturated, or unsaturated heterocyclic compound with up to 3 heterocyclic atoms from the series S, N and/or O, with binding in the case of a nitrogen atom also being possible via this atom, with the heterocycles optionally being substituted up to 3 times in an identical manner or differently by halogen, nitro, trifluoromethyl, trifluoromethoxy, or by straight-chain or branched alkyl, acyl, or alkoxy with up to 7 carbon atoms each, and the salts thereof.

This invention also relates to compounds having glucagon receptor antgonistic activity and the general formula (IC) shown below.

(IC)

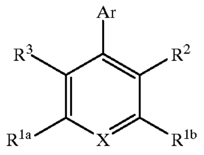

In general formula IC, the groups X, $R^{1a}$, $R^{1b}$, $R^2$, $R^3$, and Ar have the following meanings:

X represents N or $CR^8$.

$R^8$ represents hydrogen, halogen, trifluoromethyl, phenyl, substituted phenyl, $(C_1–C_{10})$-alkyl, substituted $(C_1–C_{10})$-alkyl, $(C_1–C_6)$-alkoxy, $(C_3–C_7)$-cycloalkyl, phenyl-$(C_1–C_3)$-alkoxy, $(C_1–C_6)$-alkanoyloxy, $(C_1–C_6)$-alkoxycarbonyl, carboxy, formyl, or $—NR^4R^5$. The substituents on the substituted phenyl or substituted alkyl $R^8$ groups are from 1 to 3 of, for example, hydroxy, fluoro, $(C_1–C_6)$-alkoxy, $(C_3–C_7)$-cycloalkyl, phenyl, phenyl-$(C_1–C_3)$-alkoxy, $(C_1–C_6)$-alkanoyloxy, $(C_1–C_6)$-alkoxycarbonyl, carboxy, formyl, or $—NR^4R^5$.

The groups $R^4$ and $R^5$ are independently hydrogen, $(C_1–C_6)$-alkyl, $(C_3–C_6)$-alkenyl, $(C_3–C_7)$-cycloalkyl, $(C_3–C_7)$-cycloalkyl-$(C_1–C_6)$-alkyl, phenyl, substituted phenyl, phenyl-$(C_1–C_6)$-alkyl, substituted phenyl-$(C_1–C_6)$-alkyl, naphthyl, substituted naphthyl, naphthyl-$(C_1–C_6)$-alkyl, or substituted naphthyl-$(C_1–C_6)$-alkyl. The substitutents on the substituted phenyl or substituted naphthyl $R^4$ and $R^5$ groups are 1 to 3 of, for example, halogen, cyano, trifluoromethyl, $(C_1–C_4)$-alkyl, or $(C_1–C_4)$-alkoxy groups.

$R^4$ and $R^5$ may be joined together to form $—(CH_2)_rA(CH_2)_s—$ wherein the subscripts r and s are independently 1 to 3 and A is $CHR^6$, $NR^6$, O, or $S(O)_n$ in which n is 0, 1, or 2; and $R^6$ is hydrogen, $(C_1–C_6)$-alkyl, piperidin-1-yl, phenyl, or phenyl-$(C_1–C_6)$-alkyl.

$R^{1a}$ and $R^{1b}$ are independently trifluoromethyl, $(C_1–C_{10})$-alkyl, substituted $(C_1–C_{10})$-alkyl, $(C_2–C_{10})$-alkenyl, substituted $(C_2–C_{10})$-alkenyl, $(C_2–C_{10})$-alkynyl, substituted $(C_2–C_{10})$-alkynyl, $(C_3–C_7)$-cycloalkyl, $(C_3–C_7)$-cycloalkenyl, or $(C_1–C_6)$-alkanoyl. The substituents on the substituted alkyl, substituted alkenyl, and substituted alkynyl $R^{1a}$ and $R^{1b}$ groups are independently from 1 to 3 of, for example, $—OR^4$, $—C(O)R^4$, $—CO_2R^4$, $—C(O)NR^4R^5$, —$NR^4R^5$, or phenyl which is optionally substituted with from 1 to 3 of, for example, halogen, ($C_1$–$C^4$)-alkyl, or ($C_1$–$C_4$)-alkoxy groups.

$R^2$ is ($C_1$–$C_{10}$)-alkyl, substituted ($C_1$–$C_{10}$)-alkyl, ($C_2$–$C_{10}$)-alkenyl, substituted ($C_2$–$C_{10}$)-alkenyl, ($C_2$–$C_{10}$)-alkynyl, substituted ($C_2$–$C_{10}$)-alkynyl, ($C_3$–$C_6$)-cycloalkyl-($C_1$–$C_6$)-alkyl, or substituted ($C_3$–$C_6$)-cycloalkyl-($C_1$–$C_6$)-alkyl. The substitutents on the substituted alkyl, substituted alkenyl, substituted alkynyl, and substituted cycloalkyl $R^2$ groups are independently from 1 to 3 of halogen, phenyl, substituted phenyl, 1,3-dioxolan-2-yl, —C(O)$NR^4R^5$, or —$S(O)_mR^7$ wherein m is 0, 1, or 2. The substituents on the substituted phenyl $R^2$ substituent group are from 1 to 3 of, for example, halogen, ($C_1$–$C_4$)-alkyl, or ($C_1$–$C_4$)-alkoxy.

$R^7$ is ($C_1$–$C_6$)-alkyl, phenyl, substituted phenyl, phenyl-($C_1$–$C_6$)-alkyl, substituted phenyl-($C_1$–$C_6$)-alkyl, pyridyl, substituted pyridyl, pyridyl-($C_1$–$C_6$)-alkyl, substituted pyridyl-($C_1$–$C_6$)-alkyl, naphthyl, substituted naphthyl, naphthyl-($C_1$–$C_6$)-alkyl, or substituted naphthyl-($C_1$–$C_6$)-alkyl. The substitutents on the substituted phenyl, substituted pyridyl or substituted naphthyl $R^7$ groups are from 1 to 5 of, for example, halogen, trifluoromethyl, ($C_1$–$C_6$)-alkyl, ($C_1$–$C_6$)-alkoxy, nitro, cyano, or hydroxy.

$R^2$ and $R^{1b}$ may be joined to form an alkylene bridge containing from 3 to 5 carbon atoms, between the ring carbon atoms to which $R^2$ and $R^{1b}$ are attached.

$R^3$ is hydroxy, trifluoroacetyl, ($C_1$–$C_6$)-alkanoyl, substituted ($C_1$–$C_6$)-alkyl, or substituted ($C_3$–$C_6$)-alkenyl. The substitutents on the substituted alkyl and substituted alkenyl $R^3$ groups are from 1 to 3 hydroxy or trifluoromethyl groups.

Ar is an optionally substituted aromatic or heteroaromatic ring. Examples of possible Ar groups are: phenyls, naphthyls, pyridyls, furanyls, thiophenyls, pyrrolyls, imidazolyls, pyrazolyls, triazolyls, tetrazolyls, oxazolyls, isoxazolyls, thiazolyls and isothiazolyls. The optional substitutents on the group Ar are independently 1 to 3 of, for example, halogen, ($C_1$–$C_6$)-alkyl, substituted ($C_1$–$C_6$)-alkyl, ($C_2$–$C_6$)-alkenyl, substituted ($C_2$–$C_6$)-alkenyl, ($C_2$–$C_6$)-alkynyl, substituted ($C_2$–$C_6$)-alkynyl, ($C_3$–$C_7$)-cycloalkyl, cyano, nitro, trifluoromethyl, —$OR^4$, —C(O)$R^4$, —OC(O)$R^4$, —$CO_2R^4$, —$NR^4R^5$, —C(O)$NR^4R^5$, or —$S(O)_mR^7$. The substitutents on the substituted alkyl, substituted alkenyl, and substituted alkynyl substituent groups on Ar are from 1 to 3 of, for example, halogen, hydroxy, —$NR^4R^5$, phenyl, or substituted phenyl in which the phenyl group may bear, for example, one or more halogen, ($C_1$–$C_4$) alkyl, or ($C_1$–$C_4$) alkoxy groups.

Pharmaceutically acceptable salts of these materials are within the scope of the invention.

The invention also relates to a pharmaceutical product containing the substituted pyridines according to general formula (IA) and, if appropriate, a pharmacologically tolerable formulation adjuvant. It further relates to such pharmaceutical product for the inhibition of cholesterol ester transfer proteins, and to the use of the claimed substituted pyridines for the production of pharmaceutical products, and to use of the claimed substituted pyridines for the production of cholesterol ester transfer protein inhibitors.

The invention further relates to a pharmaceutical product containing the substituted pyridines 3-heteroalkyl-aryl-substituted pyridines according to general formula (IB) and, if appropriate, a pharmacologically tolerable formulation adjuvant. It further relates to such pharmaceutical product for the treatment of hyperlipoproteinemia, and to the use of the claimed substituted pyridines for the production of pharmaceutical products, and to use of the claimed substituted pyridines for the production of pharmaceutical products for the treatment of hyperlipoproteinemia.

The invention also relates to a pharmaceutical composition for use in treating a glucagon-mediated condition, which comprises: a compound having glucagon receptor antagonistic activity and a structure within general structural formula IC, plus a pharmaceutically acceptable carrier.

The invention further relates to a method for treating a glucagon-mediated condition which comprises administering to a subject an effective amount of a compound having glucagon receptor antagonistic activity and a structure within general structural formula IC.

DETAILED DESCRIPTION WITH REFERENCE TO COMPOUNDS OF GENERAL FORMULA (IA)

The substituted pyridines according to the invention can also occur in the form of the salts thereof. In general, salts with organic or inorganic bases or acids are mentioned here.

Within the context of the present invention, physiologically safe salts are preferred. Physiologically safe salts of the compounds according to the invention can be salts of substances according to the invention with mineral acids, carboxylic acids, or sulfonic acids. Salts with, for example, hydrochloric acid, hydrobromic acid, sulfuric acid, phosphoric acid, methanesulfonic acid, ethanesulfonic acid, toluenesulfonic acid, benzenesulfonic acid, naphthalene disulfonic acid, acetic acid, propionic acid, lactic acid, tartaric acid, citric acid, fumaric acid, maleic acid, or benzoic acid are particularly preferred.

Physiologically safe salts can also be metallic or ammonium salts of the compounds according to the invention that possess a free carboxyl group. For example, sodium salts, potassium salts, magnesium salts, or calcium salts, as well as ammonium salts, that are derived from ammonia, or organic amines such as ethylamine, di- or triethylamine, di- or triethanolamine, dicyclohexylamine, dimethylaminoethanol, arginine, lysine, ethylenediamine, or 2-phenyl-ethylamine are particularly preferred.

The compounds according to the invention can exist in stereoisomeric forms, which either behave like an image and mirror image (enantiomers) or do not behave like an image and mirror image (diastereomers). The invention concerns both enantiomers or diastereomers or the mixtures thereof. These mixtures of enantiomers and diastereomers can be separated in the known manner into stereoisomerically homogeneous components.

Within the context of the invention, the heterocyclic compound, which is optionally benzo-condensed, stands in general for a saturated or unsaturated, 5-to 7-member, preferably 5- to 6-member, heterocyclic compound that can contain up to 3 heteroatoms from the series S, N, and/or O. Indolyl, isoquinolyl, quinolyl, benzothiazolyl, benzo[b]thiophene, benzo[b]furanyl, benzoxazolyl, pyridyl, thienyl, furyl, pyrrolyl, thiazolyl, oxazolyl, imidazolyl, morpholinyl, or piperidyl are cited as examples. Quinolyl, pyridyl, indolyl, benzothiazolyl, or benzoxazolyl are preferred.

Compounds of the general formula (IA) are preferred, in which

A stands for naphthyl or phenyl, which are optionally substituted up to 3 times in an identical manner or differently by fluorine, chlorine, bromine, hydroxy, trifluoromethyl, trifluoromethoxy, or by straight-chain or branched alkyl, acyl, or alkoxy with up to 6 carbon atoms each, or by a group of the formula —$NR^1R^2$, wherein $R^1$ and $R^2$ are identical or different and denote hydrogen, phenyl, or straight-chain or branched alkyl with up to 4 carbon atoms, D stands for straight-chain or branched alkyl with up to 6 carbon atoms, which is substituted by hydroxy, E and L are either identical or different and stand for straight-chain or branched alkyl with up to 6 carbon atoms, which is optionally substituted by cyclopropyl, cyclobutyl, cyclopentyl, cyclohexyl, or cycloheptyl, or stand for cyclopropyl, cyclobutyl, cyclopentyl, cyclohexyl, or cycloheptyl, or E has the above-mentioned meaning and L in this case stands for naphthyl or phenyl, which are optionally substituted up to 3 times in an identical manner or differently by fluorine, chlorine, bromine, hydroxy, trifluoromethyl, trifluoromethoxy, or by straight-chain or branched alkyl or alkoxy with up to 6 carbon atoms each, or by a group of the formula $—NR^3R^4$, wherein $R^3$ and $R^4$ are identical or different and have the meaning given above for $R^1$ and $R^2$, for E stands for straight-chain or branched alkyl with up to 5 carbon atoms, or stands for naphthyl or phenyl, which are optionally substituted up to 3 times in an identical manner or differently by fluorine, chlorine, bromine, hydroxy, trifluoromethyl, trifluoromethoxy, or by straight-chain or branched alkyl, acyl, or alkoxy with up to 6 carbon atoms each, or by a group of the formula $—NR^5R^6$, wherein $R^5$ and $R^6$ are identical or different and have the meaning given above for $R^1$ and $R^2$, and L in this case stands for straight-chain or branched alkoxy with up to 6 carbon atoms, or for cyclopropyloxy, cyclobutyloxy, cyclopentyloxy, cyclohexyloxy, or cycloheptyloxy, T stands for a radical of the formula

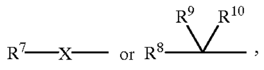

wherein $R^7$ and $R^8$ are identical or different and denote cyclopropyl, cyclobutyl, cyclopentyl, cyclohexyl, cycloheptyl, or adamantyl, or denote naphthyl, phenyl, pyridyl, quinolyl, indolyl, benzothiazolyl, or benzoxazolyl, which are optionally substituted up to 3 times in an identical manner or differently by trifluoromethyl, trifluoro-methoxy, fluorine, chlorine, bromine, hydroxy, carboxyl, by straight-chain or branched alkyl, alkoxy, or alkoxycarbonyl with up to 5 carbon atoms each, or by phenyl, phenoxy, or thiophenyl, which can in turn by substituted by fluorine, chlorine, bromine, trifluoromethyl, or trifluoromethoxy, and/or the rings are optionally substituted by a group of the formula $—NR^{11}R^{12}$, wherein $R^{11}$ and $R^{12}$ are identical or different and have the meaning given above for $R^1$ and $R^2$, X denotes a straight or branched alkyl chain or alkenyl chain with 2 to 8 carbon atoms each, which are optionally substituted up to 2 times by hydroxy, $R^9$ denotes hydrogen, and $R^{10}$ denotes hydrogen, fluorine, chlorine, bromine, azido, trifluoromethyl, hydroxy, mercapto, trifluoromethoxy, straight-chain or branched alkoxy with up to 4 carbon atoms, or a radical of the formula $—NR^{13}R^{14}$, wherein $R^{13}$ and $R^{14}$ are identical or different and have the meaning given above for $R^1$ and $R^2$, or $R^9$ and $R^{10}$ form a carbonyl group together with the carbon atom, and the salts thereof.

Compounds of the general formula (IA) are particularly preferred, in which

A stands for phenyl, which is optionally substituted up to 2 times in an identical manner or differently by fluorine, chlorine, bromine, hydroxy, trifluoromethyl, trifluoromethoxy, or by straight-chain or branched alkyl or alkoxy with up to 5 carbon atoms each, D stands for straight-chain or branched alkyl with up to 5 carbon atoms, which is substituted by hydroxy, E and L are either identical or different and stand for straight-chain or branched alkyl with up to 5 carbon atoms, which is optionally substituted by cyclopropyl, cyclobutyl, cyclopentyl, cyclohexyl, or cycloheptyl, or stand for cyclopropyl, cyclobutyl, cyclopentyl, cyclohexyl, or cycloheptyl, or E has the above-mentioned meaning and L in this case stands for phenyl, which is optionally substituted up to 2 times in an identical manner or differently by fluorine, chlorine, bromine, hydroxy, trifluoromethyl, trifluoromethoxy, or by straight-chain or branched alkyl or alkoxy with up to 5 carbon atoms each, or E stands for straight-chain or branched alkyl with up to 4 carbon atoms, or stands for phenyl, which is optionally substituted up to 2 times in an identical manner or differently by fluorine, chlorine, bromine, hydroxy, trifluoromethyl, trifluoromethoxy, or by straight-chain or branched alkyl or alkoxy with up to 5 carbon atoms each, and L in this case stands for straight-chain or branched alkoxy with up to 5 carbon atoms, or for cyclopropyloxy, cyclobutyloxy, cyclopentyloxy, cyclohexyloxy, or cycloheptyloxy, T stands for a radical of the formula

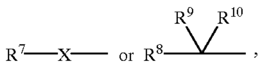

wherein $R^7$ and $R^8$ are identical or different and denote cyclopropyl, cyclobutyl, cyclopentyl, cyclohexyl, cycloheptyl, or adamantyl, or denote phenyl, pyridyl, quinolyl, indolyl, naphthyl, benzothiazolyl, or benzoxazolyl, which are optionally substituted up to 2 times in an identical manner or differently by trifluoromethyl, trifluoromethoxy, fluorine, chlorine, bromine, hydroxy, carboxyl, by straight-chain or branched alkyl, alkoxy, or alkoxycarbonyl with up to 4 carbon atoms each, or by phenyl, phenoxy, or thiophenyl, which can in turn be substituted by fluorine, chlorine, bromine, trifluoromethyl, or trifluoromethoxy, X denotes a straight or branched alkyl chain with 2 to 6 carbon atoms each, which are optionally substituted up to 2 times by hydroxy, $R^9$ denotes hydrogen, and $R^{10}$ denotes hydrogen, fluorine, chlorine, bromine, azido, amino, trifluoromethyl, hydroxy, mercapto, trifluoromethoxy, straight-chain or branched alkoxy with up to 3 carbon atoms, or $R^9$ and $R^{10}$ form a carbonyl group together with the carbon atom, and the salts thereof.

Compounds according to the invention of the general formula (IA) are most preferred, in which A stands for phenyl, which is optionally substituted by fluorine, chlorine, or methyl.

Furthermore, a process for the production of compounds according to the invention of the general formula (IA) has been discovered, characterized by the fact that compounds of the general formula (II) or (III)

(II)

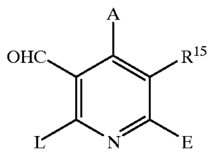

(III)

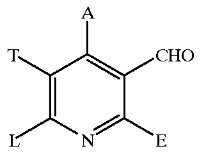

in which

A, E, L, and T have the above-mentioned meanings, and $R^{15}$ stands for straight-chain or branched alkoxycarbonyl with up to 4 carbon atoms, are either first reacted, using the Grignard or Wittig reaction, in an inert solvent, with further derivatization optionally being carried out according to the customary methods, and then are reduced in inert solvents, or, in the case of compounds of the general formula (III), direct reductions are carried out, optionally via several steps.

The compounds according to the invention can be explained, for example, by means of the following reaction diagram:

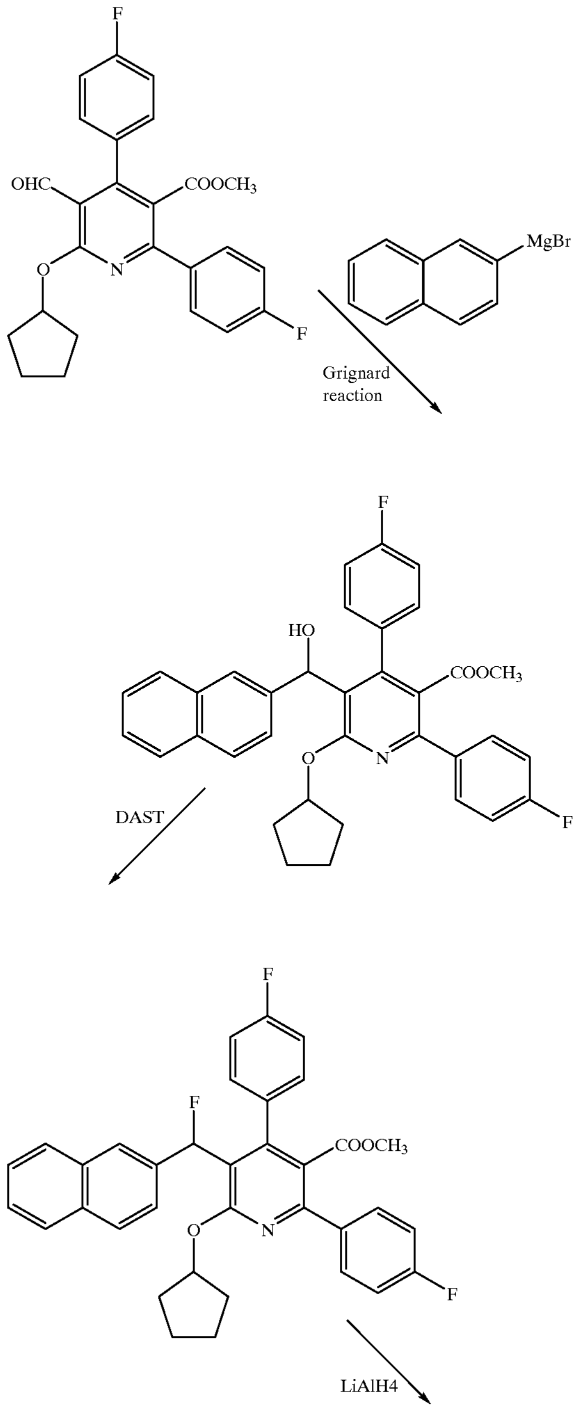

-continued

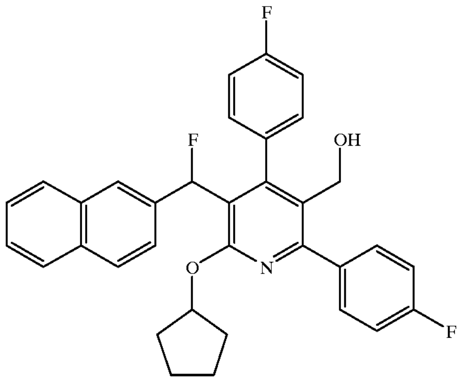

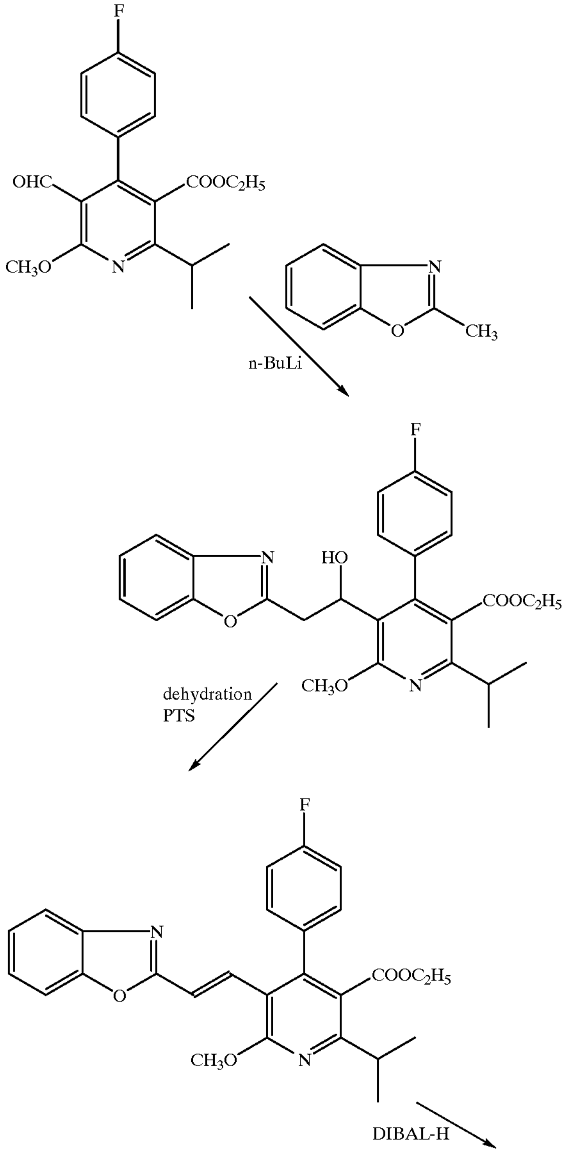

-continued

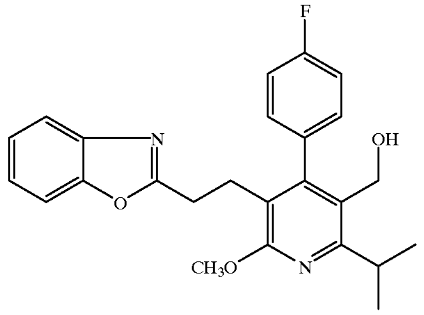

Suitable solvents are ethers, such as diethyl ether, dioxane, tetrahydrofuran, or glycol dimethyl ether, or hydrocarbons, such as benzene, toluene, xylene, hexane, or cyclohexane, or petroleum fractions, or halocarbons, such as dichloromethane, trichloromethane, tetrachloromethane, dichloroethylene, or trichloroethylene, or chlorobenzene, or ethyl acetate, or triethylamine, pyridine, dimethyl sulfoxide, dimethyl formamide, hexamethylphosphoric triamide, acetonitrile, acetone, or nitromethane. It is likewise possible to use mixtures of said solvents. Dichloromethane is preferred.

Suitable organometallic reagents are systems such as Mg/bromobenzene trifluoride and p-trifluoromethylphenyllithium. The Mg/bromobenzene trifluoride system is preferred.

The reductions and derivatizations are carried out according to the above-mentioned methods.

In general, the reductions are carried out in ethers, such as dioxane, tetrahydrofuran, or diethyl ether, or in hydrocarbons, such as benzene, hexane, or toluene. Toluene and tetrahydrofuran are preferred.

Suitable reductants are complex metal hydrides, such as lithium aluminum hydride, sodium cyanoborohydride, sodium aluminum hydride, diisobutylaluminum hydride, dimethoxymethylaluminate sodium salt, or sodium-bis-(2-methoxyethoxy)-dihydroaluminate (Red-Al). Diisobutylaluminum hydride and dimethoxymethylaluminate sodium salt are preferred.

The reductant is generally added in a quantity ranging from 4 moles to 10 moles, preferably from 4 moles to 5 moles, relative to 1 mole of the compound to be reduced.

The reduction generally takes place within a temperature range of −78° C. to +50° C., preferably from −78° C. to 0° C., and most preferably at −78° C., depending on the choice of both the reductant and the solvent.

The reduction generally takes place at normal pressure, but it is also possible to work at increased or reduced pressure.

However, the reductions can also be carried out with reductants that are suitable for the reduction of ketones to hydroxy compounds. Particularly suitable in this regard is reduction using metal hydrides or complex metal hydrides in inert solvents, if appropriate in the presence of a trialkyl borane. Preferably, the reduction is carried out using complex metal hydrides, such as lithium borohydride, sodium borohydride, potassium borohydride, zinc borohydride, lithium trialkyl borohydride, or lithium aluminum hydride.

More particularly preferably, the reduction is carried out using sodium borohydride in the presence of triethylborane.

The reaction can also take place via hydrogenation. The hydrogenation takes place according to the customary methods using hydrogen in the presence of noble metal catalysts, such as Pd/C, Pt/C, or Raney nickel in one of the above-mentioned solvents, preferably in alcohols such as methanol, ethanol, or propanol, within a temperature range of −20° C. to +100° C., preferably from 0° C. to +50° C., at normal pressure or elevated pressure.

As derivatizations, the following types of reactions are cited by way of examples: oxidations, reductions, hydrogenations, halogenation, Wittig reactions/Grignard reactions, and amidation/sulfoamidation.

The customary strong basic compounds can be used as auxiliary agents. Among these are, preferably, organolithium compounds, such as n-butyllithium, sec-butyllithium, tert-butyllithium, or phenyllithium, or amides, such as lithium diisopropylamide, sodium amide, or potassium amide, or lithium hexamethylsilylamide, or alkali hydrides, such as sodium hydride or potassium hydride. Particularly preferably, n-butyllithium, or sodium hydride are used.

Furthermore, the customary inorganic bases are suitable bases. Among these are, preferably, alkali hydroxides or alkaline earth hydroxides, such as sodium hydroxide, potassium hydroxide, or barium hydroxide, or alkali carbonates, such as sodium carbonate, potassium carbonate, or sodium hydrogen carbonate. Particularly preferably, sodium hydroxide or potassium hydroxide are used.

Alcohols, such as methanol, ethanol, propanol, butanol, or tert-butanol, are also suitable solvents for the individual reaction steps. Tert-butanol is preferred.

It may possibly be necessary to carry out several reaction steps under a protective gas atmosphere.

The halogenation generally takes place in one of the above-mentioned chlorinated hydrocarbons, whereby methylene chloride is preferred.

Diethylamino sulfur trifluoride (DAST) or $SOCl_2$, for example, are suitable halogenation agents.

The halogenation generally takes place within a temperature range of −78° C. to +50° C., preferably from −78° C. to 0° C., and most preferably at −78° C., depending on the choice of both the halogenation agent and the solvent.

The halogenation generally takes place at normal pressure, but it is also possible to work at increased or reduced pressure.

The customary reagents are suitable as Wittig reagents. 3-Trifluoro-methylbenzyl triphenylphosphonium bromide is preferred.

One of the above-mentioned bases are generally suitable as bases, preferably Li-bis-(triethylbutyl)amide.

The base is introduced in a quantity ranging from 0.1 mole to 5 moles, preferably from 0.5 mole to 2 moles, relative to 1 mole of the starting compound.

The reaction using Wittig reagents is generally carried out within a temperature range of 0° C. to 150° C., preferably at 25° C. to 40° C.

In general, the Wittig reactions are carried out at normal pressure. However, it is also possible to carry out the process at reduced pressure or high pressure (e.g., within a range from 0.5 to 5 bar).

Compounds of the general formula (II) in the case wherein L is other than alkoxy/cyclooxy (L) are known or can be produced by processing compounds of the general formula (IV)

(IV)

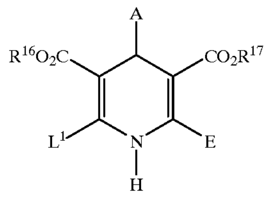

in which

A, E, and L' have the above-mentioned meanings, $R^{16}$ and $R^{17}$ are identical or different and stand for straight-chain or branched alkyl with up to 4 carbon atoms, in inert solvents with oxidants, and selectively reducing the alkoxycarbonyl function ($CO_2R^{17}$) to the hydroxy function in a second step.

Suitable solvents for the oxidation are ethers, such as diethyl ether, dioxane, tetrahydrofuran, or glycol dimethyl ether, or hydrocarbons, such as benzene, toluene, xylol, hexane, or cyclohexane, or petroleum fractions, or halocarbons, such as dichloromethane, trichloromethane, tetrachloromethane, dichloroethylene, or trichloroethylene, or chlorobenzene, or ethyl acetate, or triethylamine, pyridine, dimethyl sulfoxide, dimethyl formamide, hexamethylphosphoric triamide, acetonitrile, acetone, or nitromethane. It is likewise possible to use a mixture of said solvents. Dichloromethane is preferred.

Suitable oxidants are, for example, 2,3-dichloro-5,6-dicyanobenzoquinone, pyridinium chlorochromate (PCC), osmium tetroxide, and manganese dioxide. For the above-mentioned step, 2,3-dichloro-5,6-dicyanobenzoquinone (DDQ) is preferred.

The oxidant is introduced in a quantity ranging from 1 mole to 10 moles, preferably from 2 moles to 5 moles, relative to 1 mole of the compound of the general formula (IV).

The oxidation generally takes place within a temperature range of −50° C. to +100° C., preferably from 0° C. to room temperature.

The oxidation generally takes place at normal pressure. However, it is also possible to carry out the oxidation at increased or reduced pressure.

1,4-Dihydropyridine-3,5-dicarboxylic acid esters of the general formula (IV) are known and can be produced according to known methods.

The reaction is generally carried out at normal pressure. However, it is also possible to carry out the process at reduced pressure or high pressure (e.g., within a range of 0.5 to 5 bar).

Compounds of the general formula (II) in the case wherein L is alkoxy/cyclooxy (L') are known and can be produced by first oxidizing compounds of the general formula (V)

(V)

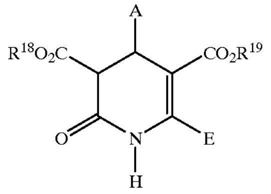

in which

A and E have the above-mentioned meanings and $R^{18}$ and $R^{19}$ have the meaning given above for $R^{16}$ and $R^{17}$ and are identical to or different from these, with ceric(IV) ammonium nitrate into compounds of the general formula (VI)

(VI)

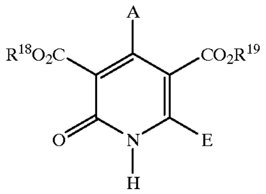

in which

A, E, $R^{18}$, and $R^{19}$ have the above-mentioned meanings, then, by reaction with alkylation agents of the general formula (VII)

$R^{20}$—Y (VII)

in which $R^{20}$ stands for cycloalkyl with 3 to 8 carbon atoms, or stands for straight-chain or branched alkyl with up to 8 carbon atoms, and Y stands for halogen, preferably for bromine or iodine, in inert solvents and in the presence of a base, converting them into compounds of the general formula (VIII)

(VIII)

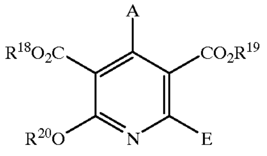

in which

A, E, $R^{18}$, $R^{19}$, and $R^{20}$ have the above-mentioned meanings, and finally, as described above, carrying out a selective reduction with diisobutylaluminum hydride of the alkoxycarbonyl group —$CO_2R^{18}$ to the hydroxymethylene function, followed by an oxidation to the corresponding aldehyde, likewise as described above, preferably with PCC.

The individual reaction steps each take place in one of the above-mentioned solvents and/or bases; preferably, the oxidation is carried out with ceric(IV) ammonium nitrate in acetonitrile, the alkylation is carried out with dimethyl formamide and sodium hydride, and the reduction is carried out in toluene within a temperature range of −30° C. to 100° C., at normal pressure, and, if applicable, under a protective gas atmosphere.

Compounds of the general formulas (V) and (VII) are known in and of themselves or can be produced according to the customary methods.

Compounds of the general formulas (VI) and (VIII) are known in part or are novel and can therefore be produced according to the above-mentioned process.

Compounds of the general formula (III) are novel and are produced by converting compounds of the general formula (IX)

(IX)

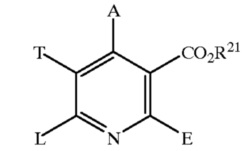

in which

A, E, L, and T have the above-mentioned meanings and $R^{21}$ denotes a straight-chain or branched alkoxycarbonyl with up to 3 carbon atoms, first by reduction of the alkoxycarbonyl function, into compounds of the general formula (Ia)

(Ia)

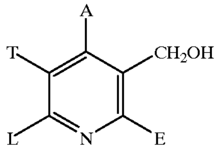

in which

A, E, L, and T have the above-mentioned meanings, and in a second step, oxidizing the hydroxymethyl function into the aldehyde according to the above-mentioned conditions, preferably with pyridinium chlorochromate (PCC).

The individual reaction steps are generally carried out within a temperature range of −10° C. to +160° C., preferably 0° C. to +100° C., and at normal pressure.

Compounds of the general formula (IX) are produced analogously to the methods described above for the production of compounds of the general formula (II).

Compounds of the general formula (Ia) are also novel and can be produced as described above.

Compounds of the general formulas (IA) and (Ia) according to the invention have an unforeseeable pharmacological spectrum of action.

Compounds of the general formulas (IA) and (Ia) according to the invention possess valuable pharmacological properties that are superior to those of the state of the art; in particular, they are highly effective inhibitors of cholesterol ester transfer proteins (CETP) and stimulate reverse cholesterol transport. The active compounds according to the invention cause a reduction in LDL cholesterol levels in the blood, while at the same time increasing HDL cholesterol levels. They can therefore be used for the treatment of hyperlipoproteinemia or arteriosclerosis.

The invention additionally concerns the combination of compounds according to the invention with a glucosidase and/or amylase inhibitor for the treatment of familial hyperlipidemia, obesity (adiposis), and diabetes mellitus. Within the context of the invention, glucosidase and/or amylase inhibitors are, for example, acarbose, adiposine, voglibose, miglitol, emiglitate, MDL-25637, camiglibose (MDL-73945), tendamistat, AI-3688, testatin, pradimicin-Q and salbostatin.

The combination of acarbose, miglitol, emiglitate, or voglibose and one of the above-mentioned compounds of the general formula (IA) according to the invention is preferred.

The pharmacological action of the substances according to the invention was determined in the following test:

CETP Inhibition Test

1. Obtaining CETP

CETP is obtained in partially purified form from human plasma by differential centrifugation and column chromatography and is used for testing. In so doing, human plasma is adjusted with NaBr to a density of 1.21 g per ml and is centrifuged for 18 h at 50,000 rpm at 4° C. The bottom fraction (d>1.21 g/ml) is applied to a Sephadex® Phenyl-Sepharose 4B (Pharmacia) column, washed with 0.15 m NaCl/0.001 m TrisHCl, pH 7.4, and then eluted with dist. water. The CETP-active fractions were pooled, dialyzed against 50 mM Na acetate, pH 4.5, and applied to a CM-Sepharose® (Pharmacia) column. They were then eluted with a linear gradient (0–1 M NaCl). The pooled CETP fractions were dialyzed against 10 mM TrisHCl, pH 7.4, and were then further purified by chromatography over a Mono Q® column (Pharmacia).

2. Obtaining Radioactively Tagged HDL 50 ml of fresh human EDTA plasma was adjusted with NaBr to a density of 1.12 and centrifuged at 4° C. for 18 h at 50,000 rpm in the Ty 65 rotor. The upper phase was used to obtain cold LDL. The lower phase was dialyzed against 3×4 l of PDB buffer (10 mM Tris/HCl, pH 7.4, 0.15 mM NaCl, 1 mM EDTA, 0.02% $NaN_3$). 20 $\mu$l 3H cholesterol (Du Pont NET-725; 1 -$\mu$C/$\mu$l dissolved in ethanol) was subsequently added per 10 ml of dialysis residue volume and incubated for 72 h at 37° C. under $N_2$.

The sediment was then adjusted with NaBr to a density of 1.21 and centrifuged in the Ty 65 rotor for 18 h at 50,000 rpm at 20° C. The upper phase was obtained and the lipoprotein fractions were purified by gradient centrifugation. In so doing, the isolated, tagged lipoprotein fraction was adjusted with NaBr to a density of 1.26. Every 4 ml of this solution was covered in centrifuge tubes (SW 40 rotor) with 4 ml of a solution with a density of 1.21 and 4.5 ml of a solution with a density of 1.063 (density solutions from PDB buffer and NaBr) and then centrifuged for 24 h at 38,000 rpm and 20° C. in the SW 40 rotor. The intermediate layer between the densities 1.063 and 1.21 that contained the tagged HDL was dialyzed against 3×100 volumes of PDB buffer at 4° C.

The dialysis residue contained radioactively tagged $^3$H-CE-HDL, which was adjusted to approx. $5\times10^6$ cpm per ml and used for the test.

3. Conducting the Test

In order to test the CETP activity, the transfer of $^3$H cholesterol ester from human HD lipoproteins to biotinylated LD lipoproteins was measured.

The reaction was ended by adding Streptavidin-SPA® beads (Amersham), and the transferred radioactivity was determined directly in the liquid scintillation counter.

In the test batch, 10 $\mu$l HDL-$^3$H cholesterol ester (≈50,000 cpm) was incubated for 18 h at 37° C. with 10 $\mu$l biotin-LDL (Amersham) in 50 mM HEPES/0.15 m NaCl/0.1% bovine serum albumin/0.05% $NaN_3$, pH 7.4, with 10 $\mu$l CETP (1 mg/ml) and 3 $\mu$l solution of the substance to be tested (dissolved in 10% DMSO/ 1% BSA). Then 200 $\mu$l of the SPA-Streptavidin bead solution (Amersham TRKQ 7005) was added, and the mixture was further incubated for 1 h under agitation and subsequently measured in the scintillation counter. Corresponding incubations with 10 $\mu$l buffer, 10 $\mu$l CETP at 4° C., and 10 $\mu$l CETP at 37° C. served as controls.

The transferred activity in the control batches with CETP at 37° C. was assessed as 100% transfer. The substance concentration in which this transfer was reduced by half was indicated as an $IC_{50}$ value.

CETP Inhibitory Activity of the Following Compounds:

| Example No. | $IC_{50}$ ($\mu$M) |
|---|---|
| 7 | 0.6 |
| 24 | 1.0 |

Syrian golden hamsters from the company's own breeding were anesthetized after fasting for 24 h (0.80 mg/kg atropine, 0.80 mg/kg Ketavet® s.c., 30' later 50 mg/kg Nembutal i.p.). The jugular vein was then exposed and cannulated. The test substance was dissolved in a suitable solvent (as a rule, Adalat placebo solution: 60 g glycerin, 100 ml $H_2O$, ad 100 ml PEG-400) and administered to the animals via a PE catheter inserted into the jugular vein. The control animals received the same volume of solvent without any test substance. The vein was then ligated and the wound closed up. At different intervals—up to 24 hours after administration of the test substance—blood was drawn from the animals by puncture of the retroorbital venous plexus (approx. 250 $\mu$l). Coagulation was completed by incubating at 4° C. overnight, then the blood was centrifuged for 10 minutes at 6000 g. The cholesterol and triglyceride content in the serum obtained in this manner was determined using modified commercially available enzyme tests (cholesterol enzymatic 14366 Merck, triglyceride 14364 Merck). The serum was diluted in a suitable manner with physiological saline solution.

100 $\mu$l serum dilution was mixed with 100 $\mu$l test substance in 96-hole perforated plates and incubated 10 minutes at room temperature. The optical density was then determined with an automatic plate reader at a wavelength of 492 nM (SLT-Spectra). The triglyceride/cholesterol concentration contained in the samples was determined using a parallel-measured standard curve.

The determination of the HDL cholesterol content was carried out after precipitation of the lipoproteins containing Apo B by means of a reagent mixture (Sigma 352-4 HDL cholesterol reagent) according to the manufacturer's instructions.

In attempting to determine oral efficacy, the test substance, which was dissolved in DMSO and suspended in 0.5% methylcellulose, was administered orally to Syrian golden hamsters from the company's own breeding via a pharyngeal tube. The control animals received identical volumes of solvent without any test substance. Feed was then withheld from the animals and blood was drawn at different intervals—up to 24 hours after administration of the substance—via puncture of the retroorbital venous plexus. It was further processed as described above.

The new active compounds can be converted in a known manner into the customary formulations, such as tablets, coated tablets, pills, granules, aerosols, syrups, emulsions, suspensions, and solutions, using inert, non-toxic, pharmaceutically suitable excipients or solvents. In this connection, the therapeutically active compound should be present in each case in a concentration of about 0.5% to 90% by weight, i.e., in amounts that are sufficient to achieve the dosage range indicated.

The formulations are prepared, for example, by extending the active compounds using solvents and/or excipients, if appropriate using emulsifiers and/or dispersants, where, for example, in the case of the use of water as a diluent, organic solvents can be used, if appropriate, as auxiliary solvents.

The administration takes place in a customary manner, preferably orally or parenterally, in particular, perlingually or intravenously.

In the case of parenteral use, solutions of the active compound can be employed using suitable liquid excipients.

In general, it has proved advantageous in intravenous administration to administer amounts of about 0.001 to 1 mg/kg, preferably about 0.01 to 0.5 mg/kg of body weight, to attain effective results, and in oral administration, the dosage is about 0.01 to 20 mg/kg, preferably 0.1 to 10 mg/kg of body weight.

In spite of this, it may be necessary to deviate from the amounts mentioned, depending on the body weight or the type of administration route, individual behavior toward the medication, the type of formulation thereof, and the time or interval at which administration takes place. Thus, in some cases it may be sufficient to manage with less than the minimum amount previously mentioned, whereas in other cases the upper limit mentioned must be exceeded. If larger amounts are administered, it may be advisable to divide these into several individual doses over the day.

STARTING COMPOUNDS

Example I

Diethyl 4-(4-Fluorophenyl)-6-isopropyl-(1H)-pyrid-2-one-3,5-dicarboxylate

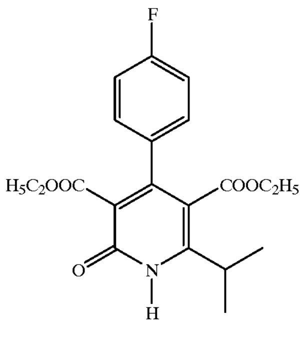

149 g (0.395 mmol) of diethyl 3,4-dihydro-4-(4-fluorophenyl)-6-isopropyl-(1H)-pyrid-2-one-3,5-dicarboxylate is dissolved in 800 ml of acetonitrile, mixed with 475 g (0.867 mol) of ceric(IV) ammonium nitrate dissolved in 500 ml of $H_2O$, and subsequently stirred for 3 h. The aqueous phase is extracted two times with ethyl acetate. The combined ethyl acetate phases are washed with salt water, dried, and concentrated. The residue is mixed with isopropanol immediately thereafter, whereby crystallization is started by cooling with ice. The product is drawn off by suction and dried in a high vacuum.

Yield: 58.8 g (39.6% of theory)

$R_f$=0.5 (toluene/ethyl acetate 1:1)

Example II

Diethyl 4-(4-Fluorophenyl)-6-isopropyl-2-methoxy-3,5-dicarboxylate

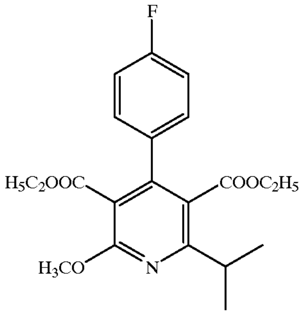

1.72 mg (42.9 mmol; 1.61 eq.) of sodium hydride (60% dispersion in mineral oil) is added to 10 g (26.6 mmol) of the compound from Example I dissolved in 40 g of DMF, and the mixture is suspended in 30 ml at −20° C. Afterwards, the suspension is heated to +30° C., 3.3 ml (53.2 mmol; 2 eq.) of methyl iodide is added, and it is heated for 2.5 hours to 80° C.–100° C. The reaction solution is mixed with 500 ml ethyl acetate and 300 ml $H_2O$, and the aqueous layer is separated off and extracted one time with ethyl acetate. The combined ethyl acetate phases are washed with water and saline solution, dried, and concentrated. The crude product is dissolved in 20 ml of toluene and chromatographed over 200 ml of silica gel 60 using toluene as the eluant.

Yield: 10 g (96.4% of theory)

$R_f$=0.28 (toluene)

Example III

Ethyl 4-(4-Fluorophenyl)-6-isopropyl-2-methoxy-3-hydroxymethyl-pyridine-5-carboxylate

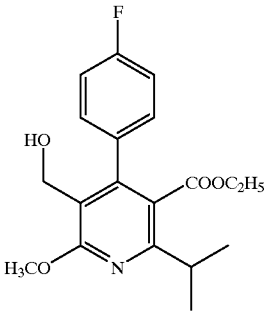

500 mg (1.284 mmol) of the compound from Example II in 40 g of toluene p.a. is mixed under argon at −78° C. with 3.21 ml (3.852 mmol) of diisobutylaluminum hydride (DIBAL-H, 1.2 molar in toluene). The mixture is stirred 30 min at −78° C., and the batch is allowed to stand overnight at −30° C. in the refrigerator. It is further cooled to −70° C., 20% potassium sodium tartrate solution is added, and the mixture is extracted with ethyl acetate. The organic layer is dried with $Na_2SO_4$ and concentrated.

Yield: 287 mg (64.5% of theory)

$R_f$=0.41 (toluene/ethyl acetate 9:1)

Example IV

Ethyl 4-(4-Fluorophenyl)-6-isopropyl-2-methoxy-3-formyl-pyridine-5-carboxylate

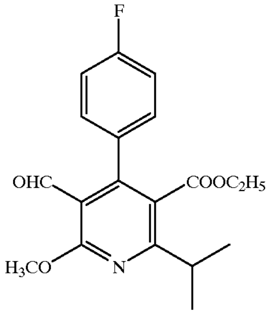

21.3 g (0.0988 mol, 3.8 eq.) of pyridinium chlorochromate (PCC) is added to a solution of 9.07 g (0.026 mol) of the compound from Example III in 400 ml $CH_2Cl_2$ in the presence of neutral $Al_2O_3$ (10.07 g=0.0988 mol), and the mixture is stirred for 1 h at room temperature. It is drawn off by suction over silica gel and subsequently washed with $CH_2Cl_2$, then the filtrate is concentrated in a vacuum and chromatographed on silica gel 60 (500 ml) using toluene/ethyl acetate (8:2).

Yield: 8.88 g (98.4% of theory)

$R_f$=0.62 (toluene/ethyl acetate 9:1)

Example V

Ethyl 4-(4-Fluorophenyl)-6-isopropyl-2-methoxy-3-[2-(benzoxazol-2-yl)-1-hydroxy-ethyl]-pyridine-5-carboxylate

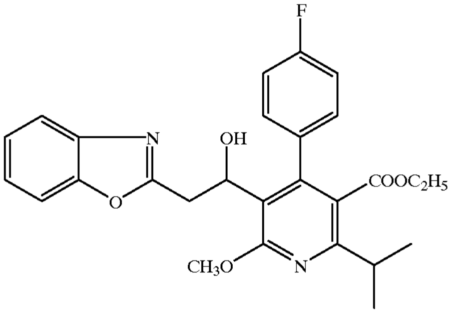

400 mg (3 mmol) of 2-methylbenzoxazole dissolved in 5 g THF p.a. is cooled under argon to −78° C. 1.83 ml (3 mmol) of n-butyllithium (1.6 molar in hexane) is added to this, and the mixture is stirred for 120 min at −78° C. 1.036 g (3 mmol) of the compound from Example IV is then added by drops at −78° C.; the mixture is stirred for 10 min at −78° C. and overnight until it reaches room temperature. After adding 50 ml of water, it is extracted by shaking with 100 ml of ethyl acetate. The aqueous phase is separated off, washed two times with saline solution, dried over $Na_2SO_4$, and concentrated. The residue is chromatographed on 60 ml of silica gel using toluene and toluene/ethyl acetate (8:2). The concentrated fractions are dried in a high vacuum.

Yield: 450 mg (31.4% of theory)

$R_f$=0.22 (toluene/ethyl acetate 9:1)

Example VI

Ethyl 4-(4-Fluorophenyl)-6-isopropyl-2-methoxy-3-[2-(benzoxazol-2-yl)-ethenyl]-pyridine-5-carboxylate

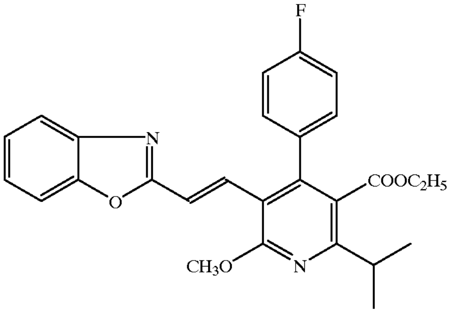

100 mg (0.209 mmol) of the compound from Example V is boiled in 10 g toluene p.a. under argon in the presence of 25 mg (0.131 mmol) of p-toluenesulfonic acid hydrate for 6 h under reflux, and afterwards the mixture is stirred at room temperature overnight. The reaction solution is then applied to a column filled with 40 ml of silica gel and consecutively eluted with toluene and toluene/ethyl acetate (9.5:0.5). The desired fractions are concentrated and dried in a high vacuum.

Yield: 91 mg (94.6% of theory)

$R_f$=0.59 (toluene/ethyl acetate 9:1)

Example VII

Diethyl 1,4-Dihydro-2,6-diisopropyl-4-(4-fluorophenyl)pyridine-3,5-dicarboxylate

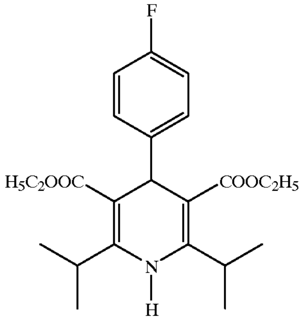

528 g (2 mol) of (E/Z)-4-carboxymethyl-5-(4-fluorophenyl)-2-methyl-pent-4-en-3-one and 350 g (2 mol) of 90% ethyl 3-amino-4-methyl-pent-2-enoate are stirred in 1800 ml ethanediol overnight at a bath temperature of 200° C. The mixture is cooled slowly and poured into a large glass beaker at approx. 80° C. After further cooling to 0° C., the solution is drawn off by suction from the precipitated sediment, then the sediment is washed well with ice cold ethanol and dried in a desiccator. The ethanol solution is concentrated, and the residue together with the ethanediol mother liquor is extracted four times with 1.5 l ether each time. The combined ether phases are washed three times each with 500 ml of 10% hydrochloric acid and once each with 500 ml of saturated sodium hydrogen carbonate solution and water, dried over magnesium sulfate, filtered, and allowed to stand overnight at room temperature. The solution is drawn off by suction from the precipitated sediment, subsequently washed with ice cold ethanol, and dried in a desiccator. The ethanol solution and the ether mother liquor are concentrated together in a vacuum to a volume of approx. 2 l, allowed to stand overnight again, and drawn off by suction from the precipitated sediment.

Total yield: 556.9 g (69.1% of theory)

$^1$H-NMR ($CDCl_3$): δ=1.1–1.3 (m, 18H); 4.05–4.25 (m, 6H); 5.0 (s, 1H); 6.13 (s, 1H); 6.88 (m, 2OH); 7.2 (m, 2H) ppm.

Example VIII

Diethyl 2,6-diisopropyl-4-(4-fluorophenyl)-pyridine-3,5-dicarboxylate

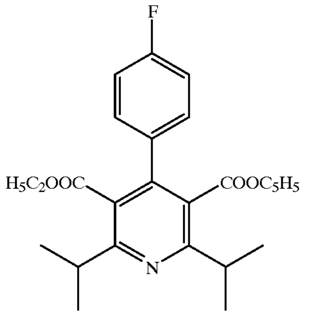

171.7 g (0.757 mol) of 2,3-dichloro-5,6-dicyano-p-benzoquinone is added to a solution of 304.8 g (0.757 mol) of the compound from Example VII in 2 l of dichloromethane, and the mixture is stirred overnight at room temperature. The mixture is drawn off by suction over diatomaceous earth and subsequently washed well with dichloromethane. After concentration of the dichloromethane phase to a volume of approx. 800 ml, it is chromatographed on a column (2 kg of silica gel 70–230 mesh) with dichloromethane.

Yield: 222 g (73.4% of theory)

$^1$H-NMR ($CDCl_3$): δ=0.98 (t, 6H); 1.41 (d, 12H); 3.1 (m, 2H); 4.11 (q, 4H); 7.04 (m, 2H); 7.25 (m, 2H) ppm.

Example IX

Ethyl 2,6-Diisopropyl-4-(4-fluorophenyl)-3-hydroxymethylpyridine-5-carboxylate

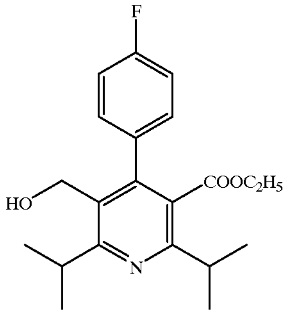

257 ml (0.9 mol) of a 3.5 molar solution of sodium-bis-(2-methoxy-ethoxy)dihydroaluminate is steadily added by drops under nitrogen to a solution of 120 g (0.3 mol) of the compound from Example VIII in 800 ml of dried tetrahydrofuran at room temperature, and the mixture is subsequently stirred for 5 h. After cooling to 0° C., 500 ml of water is carefully added by drops, the phases are separated, and the aqueous phase is extracted three times with 250 ml ethyl acetate each time. The combined organic phases are washed with saturated sodium chloride solution, dried over magnesium sulfate, and evaporated in a vacuum. The residue is mixed with petroleum ether, drawn off by suction, and dried in a desiccator.

Yield: 69.1 g (64.2% of theory)

$^1$H-NMR ($CDCl_3$): δ=0.95 (t, 3H); 1.31 (m, 12H); 3.05 (m, 1H); 3.48 (m, 1H); 3.95 (q, 2H); 4.93 (d, 2H); 7.05–7.31 (m, 4H) ppm.

Example X

Ethyl 2,6-Diisopropyl-4-(4-fluorophenyl)-3-formyl-pyridine-5-carboxylate

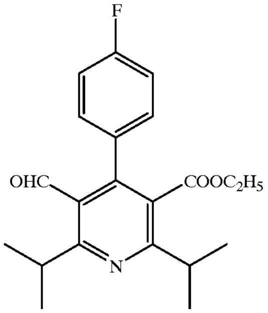

14.18 g (0.139 mol) of neutral $Al_2O_3$ and 29.96 g (0.13 mol) of pyridinium chlorochromate (PCC) are added to a solution of 25.0 g (0.0695 mol) of the compound from Example IX in 500 ml $CH_2Cl_2$ and the mixture is stirred for 1 h at room temperature. It is drawn off by suction over silica gel and subsequently washed with $CH_2Cl_2$, and the filtrate is concentrated in a vacuum, whereby the product precipitates out.

Yield: 20 g (80.48% of theory)

$^1$H-NMR (DMSO-$d_6$): δ=0.92 (t, 3H); 1.39 (dd, 6H); 3.02–3.13 (m, 1H); 3.75–3.86 (m, 1H); 3.95–4.05 (q, 2H); 7.32 (m, 4H); 9.8 (s, 1H) ppm.

Example XI

Ethyl 2,6-Diisopropyl-4-(4-fluorophenyl)-3-[(4-fluorophenyl)hydroxymethyl]-pyridine-5-carboxylate

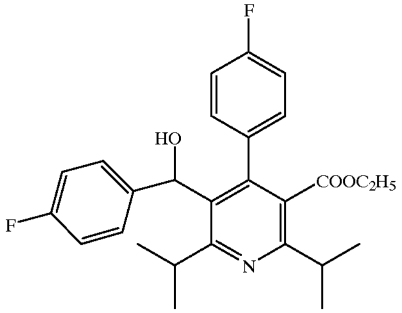

10.0 g (27.98 mmol) of aldehyde from Example X is cooled to −70° C. in 100 g THF p.a. under argon, 33.6 ml (33.58 mmol, 1.2 eq.) of p-fluorophenyl magnesium bromide solution is added by drops at −70° C., and the mixture is then stirred for another 2 h at −70° C. The reaction solution is mixed with 200 ml of conc. $NH_4Cl$ solution, the cooling bath is removed, and the solution is adjusted with 1 molar HCl, pH=6. After extraction with 400 ml of $CH_2Cl_2$ and drying over $Na_2SO_4$, the organic phase is concentrated in a vacuum and the rigid foam is crystallized using n-heptane.

Yield: 8.97 g (70.7% of theory)

$R_f$=0.18 (toluene)

Example XII

Ethyl 2,6-Diisopropyl-4-(4-fluorophenyl)-3-[(4-fluorophenyl)-chloromethyl]-pyridine-5-carboxylate

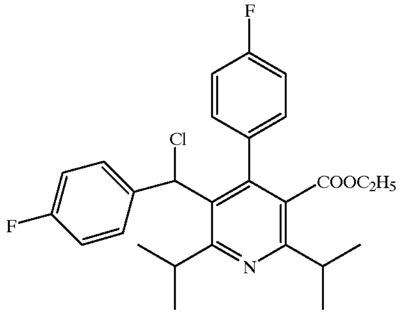

907 mg (2 mmol) of the compound from Example XI is dissolved in 20 g of $CH_2Cl_2$ p.a. and cooled under argon at −40° C., and 0.44 ml (6 mmol) $SOCl_2$ are added. The solution is stirred for 1.5 h from −40° C. to −5° C. and afterwards agitated in 50 ml of ethyl acetate/40 ml of $NaHCO_3$ solution. The organic phase is separated off, dried over $Na_2SO_4$, concentrated in a vacuum, and chromatographed on diatomaceous earth using toluene.

Yield: 899 mg (95% of theory)

$R_f$=0.79 (toluene)

Example XIII

3-Ethyl 5-Methyl 3,4-Dihydro-4-(4-fluorophenyl)-6-p-fluorophenyl-(1H)-pyrid-2-one-3,5-dicarboxylate

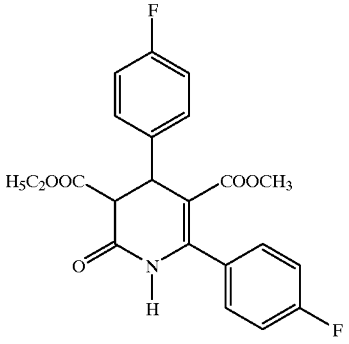

30.69 g (115.3 mmol) of ethyl 1-carboethoxy-2-(4-fluorophenyl)-propenate, 22.5 g (115.3 mmol) of methyl 3-amino-3-(4-fluorophenyl)-acrylate, 115 mg of sodium methylate, and 0.6 ml of ethanol are stirred for 48 h at a bath temperature of 140° C. The reaction mixture is absorbed in ethyl acetate, washed three times with water, dried over $Na_2SO_4$, and concentrated in a vacuum.

Yield: 43.2 g (90.2% of theory)

$R_f$=0.26 (toluene/ethyl acetate 9:1)

Example XIV

3-Ethyl 5-Methyl 4-(4-Fluorophenyl)-6-p-fluorophenyl-(1H)-pyrid-2-one-3,5-dicarboxylate

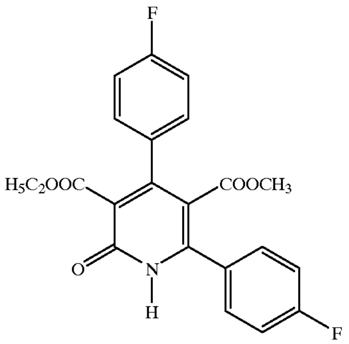

Analogously to Example I, 1.00 g (0.2407 mol) of the compound from Example XIII is stirred with 277 g (0.506 mol) of ceric(IV) ammonium nitrate in 600 ml of acetonitrile and 600 ml of water for 3 h at room temperature. After extraction with ethyl acetate, the residue is crystallized from isopropanol.

Yield: 28.59 g (28.7% of theory)

$R_f$=0.16 (toluene/ethyl acetate 8:2)

Example XV

3-Ethyl 5-Methyl 4-(4-Fluorophenyl)-6-(4-fluorophenyl)-2-cyclopentoxy-3,5-dicarboxylate

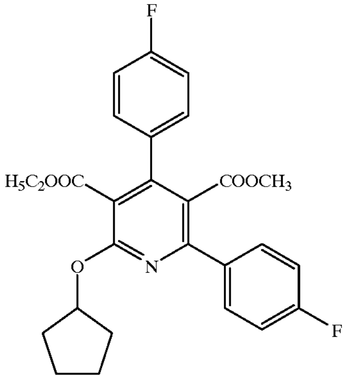

Following the instructions in Example II, 5.0 g (0.0121 mol) of the mixture from Example XIV in 20 ml of DMF is reacted in the presence of 0.783 g (0.0196 mol) of 60% NaH with 3.61 g (0.0242 mol) of cyclopentyl bromide. After chromatography on silica gel using toluene, 5.14 g (88.3% of theory) is obtained.

$R_f$=0.34 (toluene)

Example XVI

Methyl 4-(4-Fluorophenyl)-6-(4-fluorophenyl)-2-cyclopentoxy-3-hydroxymethyl-pyridine-5-carboxylate

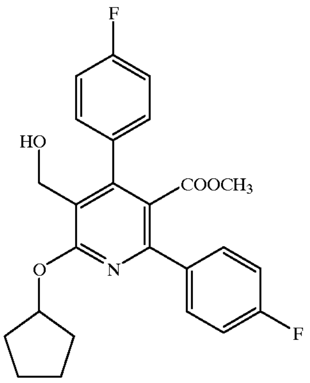

Analogously to Example III, 3.719 g (7.72 mmol) of the compound from Example XV in 150 g of toluene is stirred with 11.58 ml (11.58 mmol) of DIBAL-H (1.0 molar) for 2.5 h at −78° C. The compound is chromatographed on silica gel first with toluene and then with toluene/ethyl acetate (9:1).

Yield: 1.648 g (48.5% of theory)

$R_f$=0.45 (toluene/ethyl acetate 9:1)

Example XVII

Methyl 4-(4-Fluorophenyl)-6-(4-fluorophenyl)-2-cyclopentoxy-3-formyl-pyridine-5-carboxylate

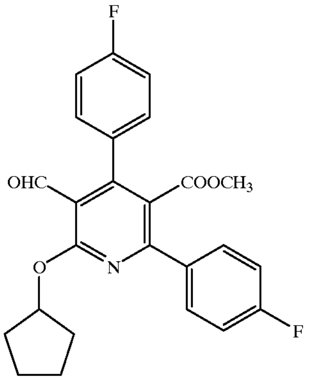

Following the instructions in Example IV, 1.636 g (3.72 mmol) of the compound from Example XVI in 150 ml of $CH_2Cl_2$ is stirred with 0.759 g (7.44 mmol) of $Al_2O_3$ (neutral) and 1.604 g (7.44 mmol) of PCC for 1.5 h. The crude product is purified by chromatography on silica gel using toluene.

Yield: 1.484 g (91.2% of theory)

$R_f$=0.59 (toluene/ethyl acetate 9:1)

Example XVIII

Methyl 4-(4-Fluorophenyl)-6-(4-fluorophenyl)-2-cyclopentoxy-3-[(naphthyl-2)-hydroxy-methyl]-pyridine-5-carboxylate

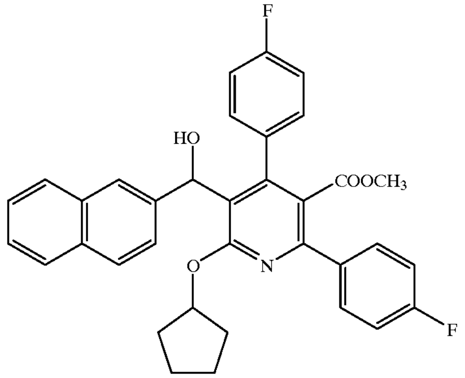

53.4 mg (2.2 mmol) of magnesium shavings is heated to reflux in 10 ml of THF p.a. under argon. 313 mg (1.51 mmol) of 2-bromonaphthalene dissolved in 15 ml of THF is added to this and the solution is boiled 75 min to reflux in the presence of iodine crystals (=Grignard reagent). 220 mg (0.503 mmol) of the compound from Example XVII is dissolved in 5 ml of THF p.a. and cooled under argon to −70° C., and the Grignard reagent is sprayed in. The batch is subsequently stirred for one hour without cooling. The reaction solution is distributed in ethyl acetate/ammonium chloride solution, and the organic phase is separated off, washed with NaCl solution, dried, and concentrated. Chromatography is then carried out on silica gel using toluene.

Yield: 261 mg (91.9% of theory)

$R_f$=0.57 (toluene/ethyl acetate 9:1)

Example XIX

Methyl 4-(4-Fluorophenyl)-6-(4-fluorophenyl)-2-cyclopentoxy-3-[(naphthyl-2)-fluoromethyl]-pyridine-5-carboxylate

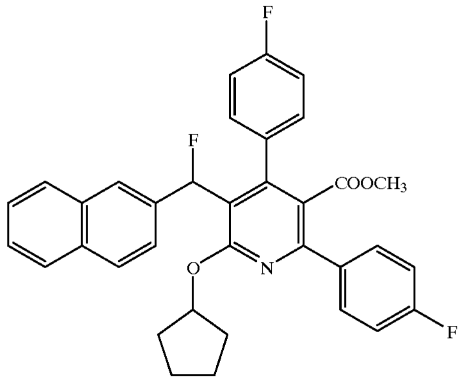

0.08 mmol (0.602 mmol) of diethylamino sulfur trifluoride (DAST) is added to a solution of 227 mg (0.401 mmol) of the compound from Example XVIII in 10 g of $CH_2Cl_2$ at −40° C. under argon, the cooling bath is removed, and the solution is stirred for 20 min. The reaction solution is subsequently distributed in ethyl acetate/$NaHCO_3$ solution, and the organic layer is dried with $Na_2SO_4$ and concentrated in a vacuum. The crude product is chromatographed on silica gel using toluene.

Yield: 224 mg (98.6% of theory)

$R_f$=0.67 (toluene)

PRODUCTION EXAMPLES

Example 1

2,6-Diisopropyl-3-p-fluorobenzyl-4-p-fluorophenyl-5-hydroxymethyl-pyridine

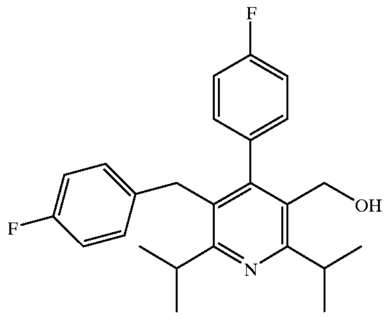

5.7 g (150 mmol) of $LiAlH_4$ are suspended in 200 ml of THF, heated to 80° C., and mixed by drops with a solution of 23.7 g of the compound from Example XII in 150 ml of THF. After being stirred for 5 h, the mixture is cooled, carefully neutralized with 20% Na—K-tartrate solution, and extracted three times with ethyl acetate, and the organic phase is dried, concentrated, and chromatographed over silica gel 60 (toluene).

Yield: 13.6 g (69% of theory)

$R_f$=0.59 (toluene/ethyl acetate=9/1)

The compounds listed in Table 1(A) are produced in analogy to the instructions in Example I:

TABLE 1

(A):

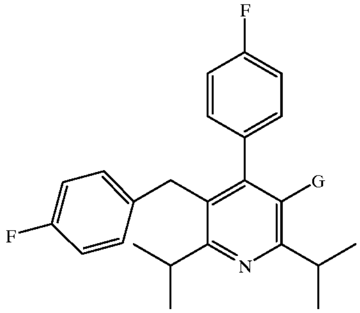

| Ex. No. | G | $R_f$ | Solvent |
|---|---|---|---|
| 2 | 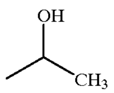 | 0.60 | toluene/ ethyl acetate 9:1 |
| 3 | 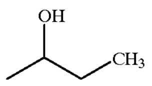 | 0.74 | toluene/ ethyl acetate 9:1 |

TABLE 1-continued (A):

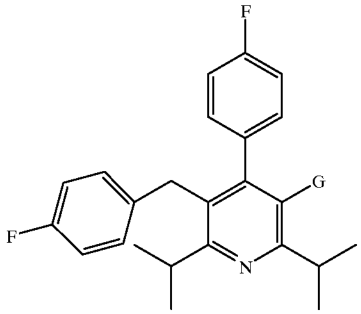

| Ex. No. | G | $R_f$ | Solvent |
|---|---|---|---|
| 4 | 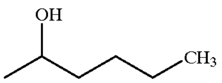 | 0.75 | toluene/ ethyl acetate 9:1 |

Example 5

4-(4-Fluorophenyl)-6-(4-fluorophenyl)-2-cyclopentoxy3-[(naphthyl-2)-fluoromethyl]-5-hydroxymethyl-pyridine

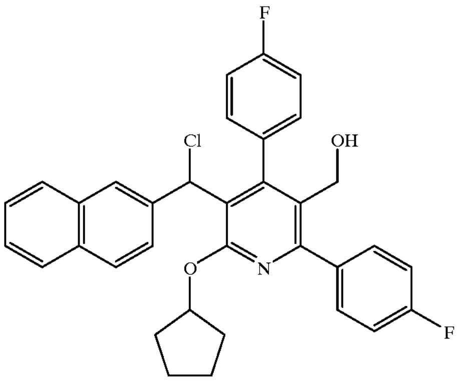

Analogously to the instructions of Example 1, 182 mg (0.321 mmol) of the compound from Example XIX in 10 ml of THF p.a. is boiled with 18.3 mg (0.481 mmol) of $LiAlH_4$ for 1 h under reflux. The compound is purified by chromatography on silica gel first with toluene and then with toluene/ethyl acetate (9:1).

Yield: 86 mg (49.7% of theory)

$R_f$=0.47

The compounds listed in Table 2(B) are produced in analogy to the instructions of Example 5:

TABLE 2

(B):

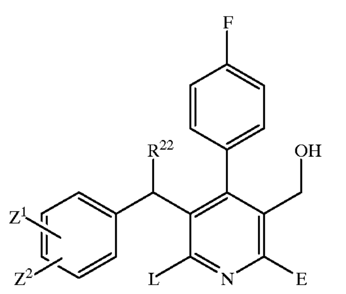

| Ex. No. | E | $R^{22}$ | $Z^1/Z^2$ | L | $R_f$ (solvent) |
|---|---|---|---|---|---|
| 6 | cyclo-$C_6H_{11}$ | H | p-F/H | $CH(CH_3)_2$ | 0.59 toluene/ethyl acetate 9:1 |
| 7 | $CH(CH_3)_2$ | $NH_2$ | p-F/H | $CH(CH_3)_2$ | 0.60 toluene/ethyl acetate 1:1 |
| 8 | $CH(CH_3)_2$ | SH | p-F/H | $CH(CH_3)_2$ | 0.31 toluene/ethyl acetate 9:1 |
| 9 | $CH(CH_3)_2$ | Cl | p-$CF_3$/H | $CH(CH_3)_2$ | 0.54 toluene/ethyl acetate 9:1 |
| 10 | $CH(CH_3)_2$ | H | 3,4-$F_2$ | $CH(CH_3)_2$ | 0.26 toluene |
| 11 | 4-F-$C_6H_4$ | F | p-$CF_3$/H | $—OCH_3$ | 0.48 toluene/ethyl acetate 9:1 |
| 12 | $CH(CH_3)_2$ | F | p-F/H | $CH(CH_3)_2$ | 0.21 toluene |
| 13 | 4-F-$C_6H_4$ | F | p-$CF_3$/H | (cyclo-$C_7H_{13}$)O | 0.28 petroleum ether/ethyl acetate 5:1 |

Example 14

2-Isopropyl-6-methoxy-4-(4-fluorophenyl)-5-[2-(benzoxazol-2-yl)ethyl]-3-hydroxymethylpyridine

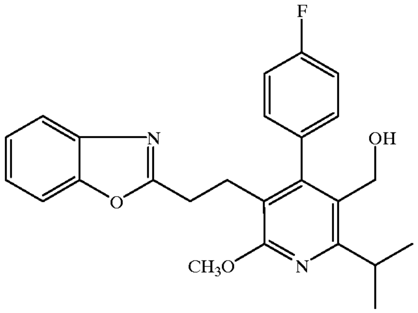

69 mg (0.15 mmol) of the compound from Example VI is dissolved in 5 g of toluene and mixed with 0.6 ml DIBAL-H (1.0 molar in toluene). The mixture is then stirred without a cooling bath for 4 h to +15° C. 30 ml of ethyl acetate and 15 ml of a 20% potassium sodium tartrate solution is added, and the solution is stirred for 10 min. The aqueous layer is separated off, and the organic phase is dried, concentrated, and chromatographed. After chromatography on 20 ml of silica gel using toluene/ethyl acetate (9:1), 19 mg (30.2% of theory) is obtained.

$R_f$=0.28 (toluene/ethyl acetate 9:1)

DETAILED DESCRIPTION WITH REFERENCE TO COMPOUNDS OF GENERAL FORMULA (IB)

The compounds according to the invention can also occur in the form of the salts thereof. In general, salts with organic or inorganic bases or acids are mentioned here.

Within the context of the present invention, physiologically safe salts are preferred. Physiologically safe salts from the compounds according to the invention can be salts of substances according to the invention with mineral acids, carboxylic acids, or sulfonic acids. Salts with, for example, hydrochloric acid, hydrobromic acid, sulfuric acid, phosphoric acid, methanesulfonic acid, ethanesulfonic acid, toluenesulfonic acid, benzenesulfonic acid, naphthalene disulfonic acid, acetic acid, propionic acid, lactic acid, tartaric acid, citric acid, fumaric acid, maleic acid, or benzoic acid are particularly preferred.

Physiologically safe salts can also be metallic or ammonium salts of the compounds according to the invention that possess a free carboxyl group. For example, sodium salts, potassium salts, magnesium salts, or calcium salts, as well as ammonium salts, that are derived from ammonia, or organic amines such as ethylamine, di- or triethylamine, di- or triethanolamine, dicyclohexylamine, dimethylaminoethanol, arginine, lysine, ethylenediamine, or 2-phenylethylamine are particularly preferred.

The compounds according to the invention can exist in stereoisomeric forms, which either behave like an image and mirror image (enantiomers) or do not behave like an image and mirror image (diastereomers). The invention concerns both enantiomers or diastereomers or the mixtures thereof. These mixtures of enantiomers and diastereomers can be separated in the known manner into stereoisomerically homogeneous components.

Within the context of the invention, the heterocyclic compound, which is optionally benzo-condensed, stands in general for a saturated or unsaturated, 5- to 7-member, and preferably 5- to 6-member, heterocyclic compound that can contain up to 3 heteroatoms from the series S, N, and/or O. Tetrazolyl, isoquinolyl, quinolyl, benzo[b]thiophene, benzo[b]furanyl, pyridyl, pyrimidinyl, pyrazinyl, thienyl, furyl, pyrinyl, benzothiazolyl, phenoxathinzyl, benzoxazolyl, tetrahydropyrimidyl, pyrazolopyrimidyl, pyrrolyl, thiazolyl, oxazolyl, and imidazolyl are cited as examples. Quinolyl, furyl, pyridyl, tetrahydropyrimidyl, indolyl, benzothiazolyl, benzoxazolyl, pyrinyl, and pyrazolopyrimidyl are preferred.

This also includes 5- to 7-member saturated heterocyclic compounds bound via N, which can also contain up to 2 oxygen, sulfur, and/or nitrogen atoms as heteroatoms, such as piperidyl, morpholinyl, or piperazine or pyrrolidinyl. Piperidyl and pyrrolidinyl are particularly preferred.

Compounds of general formula (IB) are preferred, in which

A stands for naphthyl or phenyl, which are optionally substituted up to 3 times in an identical manner or differently by fluorine, chlorine, hydroxy, trifluoromethyl, trifluoromethoxy, or by straight-chain or branched alkyl, acyl, or alkoxy with up to 6 carbon atoms each, or by a group of the formula $—NR^2R^3$ and/or by a group of the formula $—W—R^4$, wherein $R^2$ and $R^3$ are identical or different and denote hydrogen, phenyl, or straight-chain or branched alkyl with up to 4 carbon atoms, W denotes an oxygen or sulfur atom, $R^4$ denotes phenyl or benzyl, which are optionally substituted up to 3 times in an identical manner or differently by fluorine, chlorine, trifluoromethyl, trifluoromethoxy, hydroxy, or by straight-chain or branched alkyl or alkoxy with up to 5 carbon atoms each, D and E are identical or different and stand for a straight-chain or branched alkyl chain with up to 6 carbon atoms, or E stands for a bond, V stands for an oxygen or sulfur atom or for a group of the formula —$NR^5$, wherein $R^5$ denotes hydrogen or straight-chain or branched alkyl with up to 4 carbon atoms or phenyl, $R^1$ stands for cyclopropyl, cyclopentyl, or cyclohexyl, or tetrahydropyrimidyl stands for phenyl, naphthyl, pyridyl, tetrazolyl, pyrimidinyl, pyrazinyl, pyrrolidinyl, tetrahydropyrimidinyl, indolyl, morpholinyl, imidazolyl, benzothiazolyl, phenoxathiin-2-yl, benzoxazolyl, furyl, quinolyl, pyrazolopyrimidyl, or purine-yl, with the rings, also via the N function in the case of nitrogen-containing rings, being optionally substituted up to 3 times in an identical manner or differently by fluorine, chlorine, bromine, trifluoromethyl, hydroxy, cyano, carboxyl, trifluoromethoxy, straight-chain or branched acyl, alkyl, alkylthio, alkylalkoxy, alkoxy, or alkoxycarbonyl with up to 4 carbon atoms each, triazolyl, tetrazolyl, benzoxathiazolyl, or phenyl, and/or by a group of the formula —$OR^6$, —$SR^7$, or —$SO_2R^8$, wherein $R^6$, $R^7$, and $R^8$ are identical or different and denote phenyl, which in turn is substituted up to 2 times in an identical manner or differently by phenyl, fluorine, chlorine, or by straight-chain or branched alkyl with up to 4 carbon atoms, L and T are identical or different and stand for trifluoromethyl, pyrrolidinyl, or for straight-chain or branched alkyl with up to 7 carbon atoms, which is optionally substituted by cyclopropyl, cyclobutyl, cyclopentyl, cyclohexyl, cycloheptyl, naphthyl, or phenyl, which in turn can be substituted up to 2 times in an identical manner or differently by fluorine, chlorine, bromine, trifluoromethyl, trifluoromethoxy, or by straight-chain or branched alkyl, acyl, or alkoxy with up to 6 carbon atoms each, or L and/or T stand for cyclopropyl, cyclobutyl, cyclopentyl, cyclohexyl, or cycloheptyl, or for naphthyl, phenyl, pyridyl, or furyl, which optionally can be substituted up to 3 times in an identical manner or differently by fluorine, chlorine, bromine, nitro, trifluoromethyl, trifluoromethoxy, or by straight-chain or branched alkyl, acyl, or alkoxy with up to 6 carbon atoms each, and the salts thereof.

Compounds of general formula (IB) are particularly preferred, in which

A stands for phenyl, which is optionally substituted up to 2 times in an identical manner or differently by fluorine, chlorine, hydroxy, trifluoromethyl, trifluoromethoxy, or by straight-chain or branched alkyl, acyl, or alkoxy with up to 4 carbon atoms each or by benzyloxy, which in turn can be substituted by fluorine or chlorine.

D and E are identical or different and stand for a straight-chain or branched alkyl chain with up to 3 carbon atoms, or E stands for a bond, V stands for an oxygen or sulfur atom or for a group of the formula —$NR^5$, wherein $R^5$ denotes hydrogen or straight-chain or branched alkyl with up to 3 carbon atoms, $R^1$ stands for cyclopropyl, cyclopentyl, or cyclohexyl, or tetrahydropyrinidyl stands for phenyl, naphthyl, pyridyl, tetrazolyl, pyrimidyl, pyrazinyl, tetrahydropyrimidyl, phenoxathiin-2-yl, indolyl, imidazolyl, pyrrolidinyl, morpholinyl, benzothiazolyl, benzoxazolyl, furyl, quinolyl, pyrazolopyrimidyl, or purine-yl, with the rings, also via the N-function in the case of nitrogen-containing rings, optionally being substituted up to 3 times in an identical manner or differently by fluorine, chlorine, trifluoromethyl, hydroxy, cyano, carboxyl, trifluoromethoxy, straight-chain or branched alkyl, alkylthio, alkylalkoxy, alkoxy, or alkoxycarbonyl with up to 3 carbon atoms each, triazolyl, tetrazolyl, benzoxathiazolyl, or phenyl, and/or substituted by a group of the formula —$OR^6$, —$SR^7$, or —$SO_2R^8$, wherein $R^6$, $R^7$, and $R^8$ are identical or different and denote phenyl, which in turn is substituted up to 2 times in an identical manner or differently by phenyl, fluorine, chlorine, or is substituted by straight-chain or branched alkyl with up to 3 carbon atoms, L and T are identical or different and stand for trifluoromethyl, pyrrolidinyl, or for straight-chain or branched alkyl with up to 6 carbon atoms, which are optionally substituted by cyclopropyl, cyclobutyl, cyclopentyl, cyclohexyl, cycloheptyl, or phenyl, which in turn may be substituted up to 2 times in an identical manner or differently by fluorine, chlorine, trifluoromethyl, trifluoromethoxy, or by straight-chain or branched alkyl or alkoxy with up to 4 carbon atoms each, or L and/or T stand for cyclopropyl, cyclobutyl, cyclopentyl, cyclohexyl, or cycloheptyl, or stand for naphthyl, phenyl, or furyl, which are optionally substituted up to 2 times in an identical manner or differently by fluorine, chlorine, trifluoromethyl, trifluoromethoxy, or by straight-chain or branched alkyl or alkoxy with up to 3 carbon atoms each, and the salts thereof.

The compounds according to the invention of general formula (IB) are particularly preferred, in which A stands for phenyl, which is optionally substituted up to 2 times in an identical manner or differently by fluorine, chlorine, trifluoromethyl, methoxy, methyl, or by fluorine- or chlorine-substituted benzyloxy.

Moreover, a process for the production of compounds according to the invention of general formula (IB) has been discovered, characterized in that

[A] in the case of V=O compounds of general formula (II)

(II)

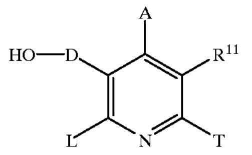

in which

A, D, L, and T have the indicated meaning, and $R^{11}$ stands for straight-chain or branched alkoxycarbonyl with up to 4 carbon atoms or for the group of the formula $—CH_2—O—Si(CH_3)_2C(CH_3)_3$, are reacted with compounds of general formula (III)

$R^1$-E-Z (III)

in which $R^1$ and E have the indicated meaning and

Z stands for halogen, preferably chlorine or bromine, in inert solvents, optionally in the presence of bases and/or auxiliary agents, and reductive separation is then carried out, depending on the meaning of the group $R^{11}$, or

[B] compounds of general formula (II) are first converted by reactions with compounds of general formula (IV)

(IV)

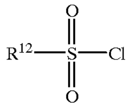

in which $R^{12}$ stands for straight-chain alkyl with up to 4 carbon atoms, into compounds of general formula (V)

(V)

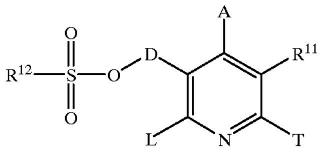

in which

A, D, L, T, $R^{11}$, and $R^{12}$ have the indicated meaning, and these are then reacted with compounds of general formula (VI)

$R^1$-E-V—H (VI)

in which $R^1$, E, and V have the indicated meaning, and reductive separation is carried out, and optionally, the groups listed under substituents A, L, T, and $R^1$ are introduced or varied according to customary methods.

The processes according to the invention can be explained, for example, by means of the following reaction diagrams:

[A]

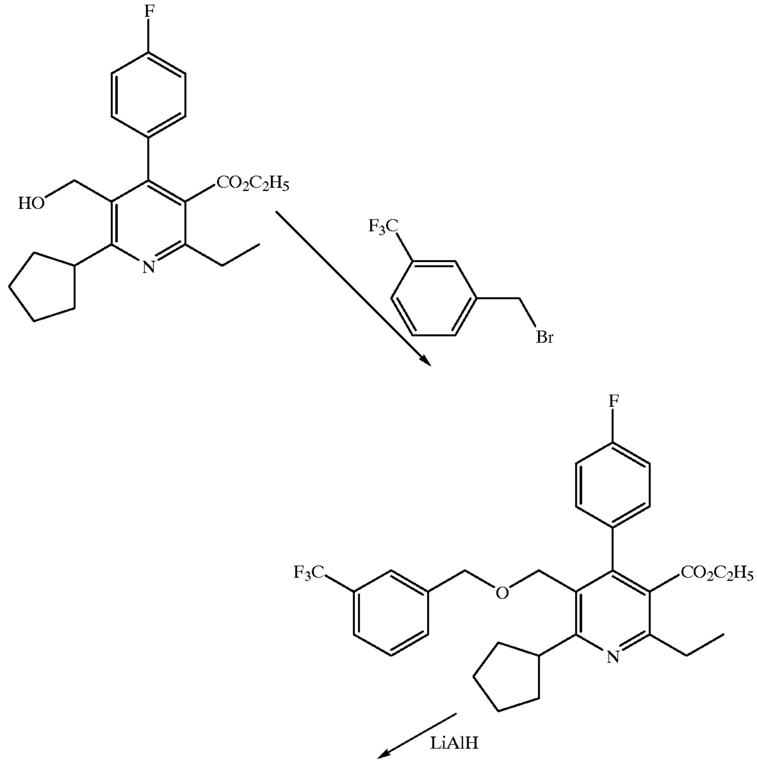

-continued
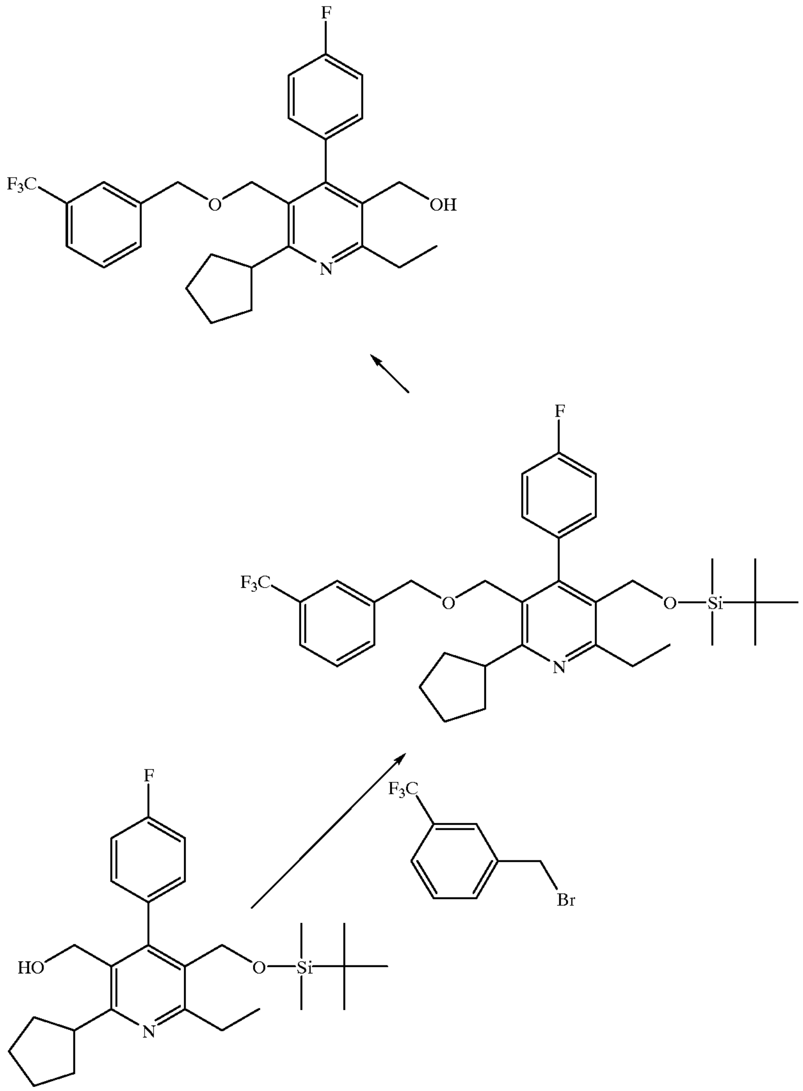
[B]
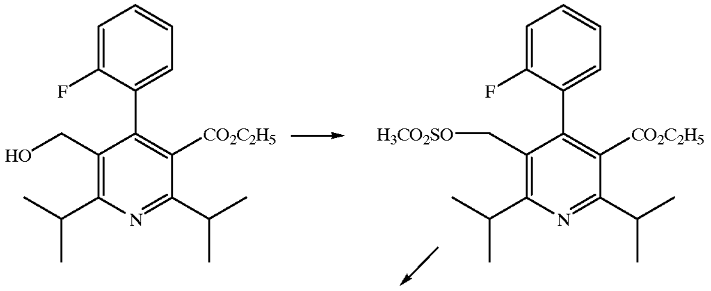

-continued
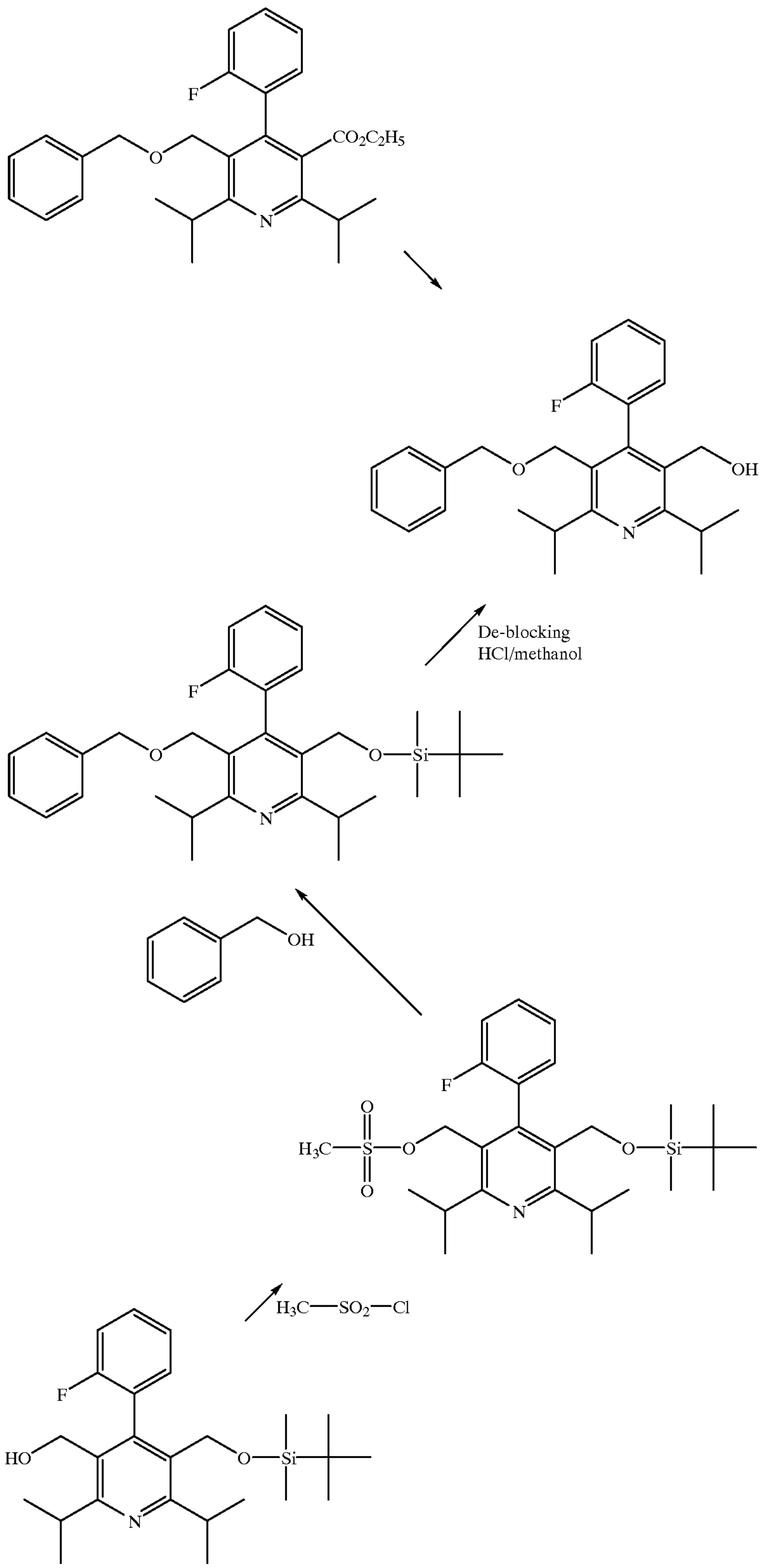

-continued

[C]

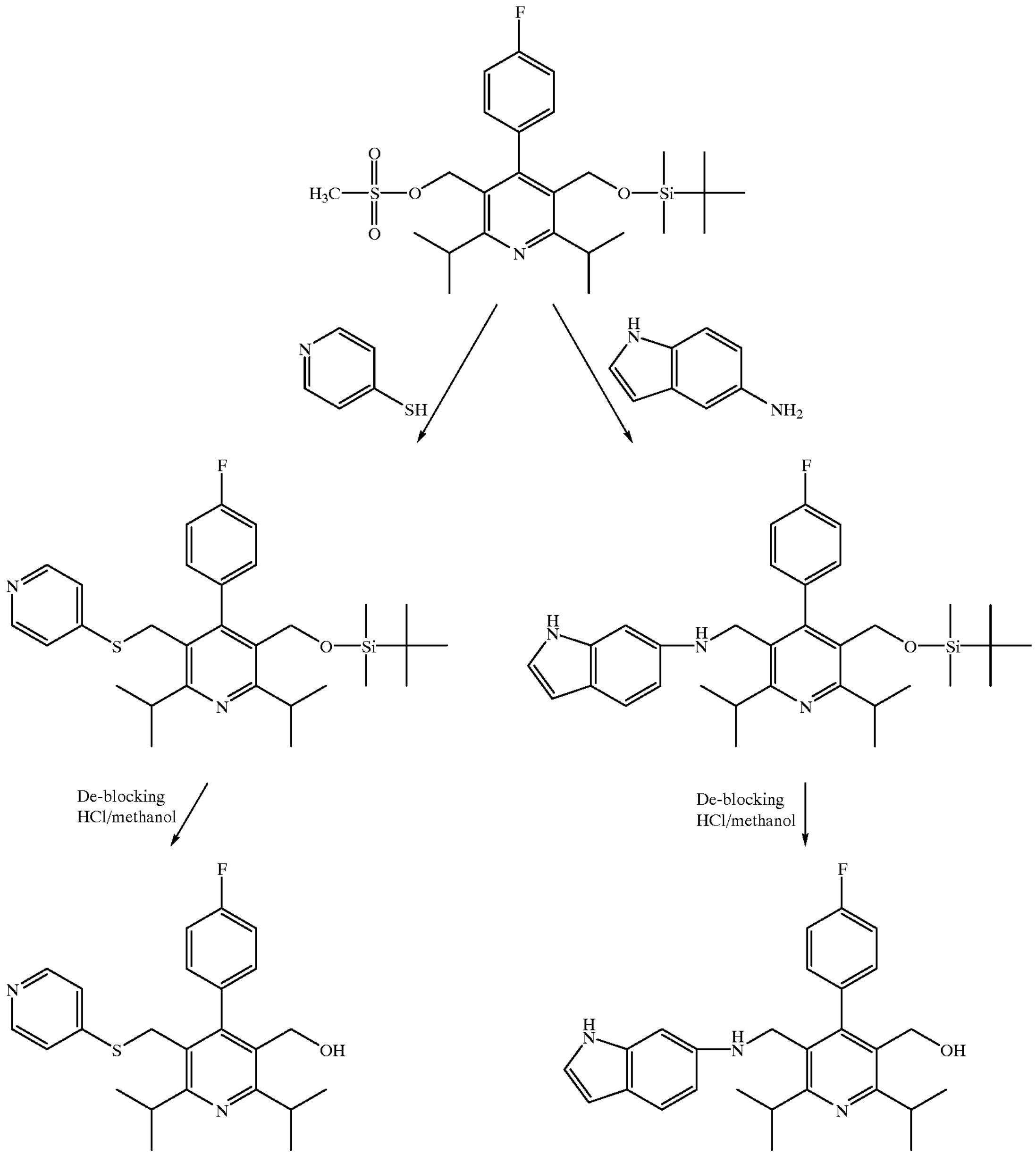

Suitable solvents for this process are inert organic solvents which do not change under the reaction conditions. These include ethers such as diethyl ether or tetrahydrofuran, halocarbons such as dichloromethane, trichloromethane, tetrachloromethane, 1,2-dichloroethane, trichloroethane, tetrachloroethane, 1,2-dichloroethane, or trichloroethylene, hydrocarbons such as benzene, xylene, toluene, hexane, cyclohexane, or petroleum fractions, nitromethane, dimethylformamide, acetone, acetonitrile, or hexamethylphosphoric triamide. It is also possible to use mixtures of the solvents. Dichloromethane, tetrahydrofuran, toluene, or dimethylformamide are particularly preferred.

In general, as auxiliary agents for the process according to the invention, inorganic or organic bases may be used. These preferably include alkali hydroxides such as sodium hydroxide or potassium hydroxide, alkaline earth hydroxides such as barium hydroxide, alkali carbonates such as sodium carbonate or potassium carbonate, alkaline earth carbonates such as calcium carbonate, or alkali or alkaline earth alcoholates such as sodium or potassium ethanolate, sodium or potassium methanolate, or potassium tert-butylate, or organic amines (trialkyl($C_1$–$C_6$)amines) such as triethylamine, or heterocyclic compounds such as 1,4-diazabicyclo[2.2.2]octane (DABCO), 1,8-diazabicyclo[5.4.0]undec-7-ene (DBU), pyridine, diaminopyridine, methylpiperidine, or morpholine. It is also possible to use alkali metals such as sodium and hydrides thereof such as sodium hydride as bases. Sodium and potassium carbonate and triethylamine are preferred.

As bases, the usual strongly basic compounds can be used for the individual steps. These preferably include lithium organic compounds such as n-butyl lithium, sec-butyl lithium, tert-butyl lithium, or phenyl lithium, or amides such as lithium diisopropylamide, sodium amide or potassium amide, or lithiumhexamethylsilyl amide, or alkali hydrides such as sodium hydride or potassium hydride. N-butyl lithium or sodium hydride should preferably be used.

The bases are used in a mixture of 1 mole to 5 moles, and preferably 1 mole to 3 moles, relative to 1 mole of the compound of general formula (II).

In general, the reaction is carried out in a temperature range of 0° C. to 150° C., and preferably from +20° C. to +110° C.

The reaction can be carried out at normal, increased, or reduced pressure (for example, 0.5 to 5 bar). In general, the reaction is carried out at normal pressure.

As derivatizations, the following types of reactions are cited as examples: oxidations, reductive separation, reductions, hydrogenations, halogenation, Wittig/Grignard reactions, and amidation/sulfoamidation.

Suitable solvents are ethers such as diethyl ether, dioxane, tetrahydrofuran, or glycol dimethyl ether, or hydrocarbons such as benzene, toluene, xylene, hexane, or cyclohexane, or petroleum fractions, or halocarbons such as dichloromethane, trichloromethane, tetrachloromethane, dichloroethylene, or trichloroethylene, or chlorobenzene, or ethyl acetate, or triethylamine, pyridine, dimethyl sulfoxide, dimethyl formamide, hexamethylphosphoric triamide, acetonitrile, acetone, or nitromethane. It is also possible to use mixtures of said solvents. Dichloromethane is preferred.

Suitable organometallic reagents are Grignard systems such as Mg/bromobenzotrifluoride and p-trifluoromethylphenyl lithium. The Mg/bromobenzotrifluoride system is preferred.

The reductions and derivatizations are carried out according to the above-mentioned methods.

In general, the reductions are carried out in ethers such as dioxane, tetrahydrofuran, or diethyl ether, or in hydrocarbons such as benzene, hexane, or toluene. Toluene and tetrahydrofuran are preferred.

Suitable reductants are complex metal hydrides such as lithium aluminum hydride, sodium cyanoborohydride, sodium aluminum hydride, diisobutyl aluminum hydride, dimethoxymethyl aluminate sodium salt, or sodium-bis(2-methoxyethoxy) dihydroaluminate (Red-Al). Diisobutyl aluminum hydride and dimethoxymethylaluminate sodium salt are preferred.

The reductant is generally added in the amount of 4 moles to 10 moles, and preferably from 4 moles to 5 moles, relative to 1 mole of the compound to be reduced.

The reduction generally takes place within a temperature range of −78° C. to +50° C., preferably from −78° C. to 0° C., and particularly preferably at −78° C., depending on the choice of both the reductant and the solvent.

The reduction generally takes place at normal pressure, but it is also possible to work at increased or reduced pressure.

However, the reductions can also be carried out with reductants that are suitable for the reduction of ketones to hydroxy compounds. Particularly suitable in this regard is reduction using metal hydrides or complex metal hydrides in inert solvents, if appropriate, in the presence of a trialkyl borane. Preferably, the reduction is carried out using complex metal hydrides such as lithium borohydride, sodium borohydride, potassium borohydride, zinc borohydride, lithium trialkylborohydride, or lithium aluminum hydride. More preferably, the reaction is carried out using sodium borohydride in the presence of triethyl borane.

The hydrogenation takes place according to the customary methods using hydrogen in the presence of noble metal catalysts such as Pd/C, Pt/C, or Raney nickel in one of the above-mentioned solvents, preferably in alcohols such as methanol, ethanol, or propanol, within a temperature range of −20° C. to +100° C., preferably from 0° C. to 50° C., at normal pressure or elevated pressure.

As derivatizations, the following types of reactions are cited by way of examples: oxidations, reductions, hydrogenations, halogenation, Wittig/Grignard reactions, and amidation/sulfoamidation.

The customary strongly basic compounds can be used as bases for the individual steps. These preferably include organolithium compounds such as n-butyl lithium, sec-butyl lithium, tert-butyl lithium, or phenyl lithium, or amides such as lithium diisopropylamide, sodium amide, or potassium amide, or lithium hexamethylsilyl amide, or alkali hydrides such as sodium hydride or potassium hydride. n-butyl lithium or sodium hydride are particularly preferred.

Furthermore, the customary inorganic bases are suitable bases. These preferably include alkali hydroxides or alkaline earth hydroxides such as sodium hydroxide, potassium hydroxide, or barium hydroxide, or alkali carbonates such as sodium carbonate, potassium carbonate, or sodium hydrogencarbonate. Sodium hydroxide or potassium hydroxide are particularly preferred.

Alcohols such as methanol, ethanol, propanol, or tert-butanol are also suitable solvents for the individual reaction steps. Tert butanol is preferred.

It may possibly be necessary to carry out several reaction steps under a protective gas atmosphere.

The halogenations generally take place in one of the above-mentioned chlorinated hydrocarbons, with methylene chloride being preferred.

Diethylamino sulfur trifluoride (DAST) or $SOCl_2$, for example, are suitable halogenation agents.

The halogenation generally takes place within a temperature range of −78° C. to +50° C., preferably from −78° C. to 0° C., and particularly preferably at −78° C., depending on the choice of both the halogenation agent and the solvent.

The halogenation generally takes place at normal pressure, but it is also possible to work at increased or reduced pressure.

The customary reagents are suitable as Wittig reagents. 3-Trifluoro-methylbenzyltriphenylphosphonium bromide is preferred.

In general, one of the above-mentioned bases is suitable as a base, preferably Li-bis-(triethylbutyl)amide.

The base is used in an amount of 0.1 moles to 5 moles, preferably 0.5 moles to 2 moles, in relation to 1 mole of the parent compound.

The reaction with Wittig reagents is generally carried out in a temperature range of 0° C. to 150° C., preferably at 25° C. to 40° C.

The Wittig reactions are generally carried out at normal pressure. However, it is also possible to carry out the process at reduced or high pressure (e.g., within a range of 0.5 to 5 bar).

The compounds of general formula (II) are known in part or new and can then be produced from the corresponding dihydropyridines of general formula (VII)

(VII)

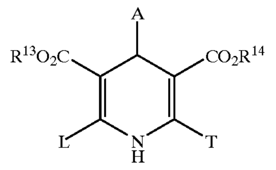

in which

A, L, and T have the above-indicated meaning, and $R^{13}$ and $R^{14}$ are identical or different and denote straight-chain or branched alkyl with up to 4 carbon atoms, through oxidation into the corresponding pyridines and finally depending on the substituents a reduction according to conventional methods can be carried out.

Suitable solvents for the oxidation are ethers such as diethyl ether, dioxane, tetrahydrofuran, or glycol dimethyl ether; or hydrocarbons such as benzene, toluene, xylene, hexane, or cyclohexane, or petroleum fractions, or halocarbons such as dichloromethane, trichloromethane, tetrachloromethane, dichloroethylene, or trichloroethylene, or chlorobenzene, or ethyl acetate, or triethylamine, pyridine, dimethylsulfoxide, dimethylformamide, hexamethylphosphoric triamide, acetonitrile, acetone, or nitromethane. It is also possible to use a mixture of said solvents. Dichloromethane is preferred.

Suitable oxidants are, for example, 2,3-dichloro-5,6-dicyanobenzoquinone, pyridinium chlorochromate (PCC), osmium tetroxide, and manganese dioxide. For the above-mentioned step, 2,3-dichloro-5,6-dicyanobenzoquinone (DDQ) is preferred.

The oxidant is introduced in an amount of 1 mole to 10 moles, preferably 2 moles to 5 moles, relative to 1 mole of the compound of general formula (VII).

The oxidation generally takes place within a temperature range of −50° C. to +100° C., preferably from 0° C. to room temperature.

The oxidation generally takes place at normal pressure. However, it is also possible to carry out the oxidation at increased or reduced pressure.

The dihydropyridines of general formula (VII) are known per se or can be produced by customary methods.

The compounds of general formulas (III), (IV), and (VI) are known per se or can be produced by customary methods.

The compounds of general formula (V) are new or can be manufactured as described above.

The 3-heteroalkyl-aryl-substituted pyridines according to the invention possess valuable pharmacological properties that are superior to those of the state of the art; in particular, they are highly effective inhibitors of cholesterol ester transfer proteins (CETP) and stimulate reverse cholesterol transport. The active compounds according to the invention cause a reduction in LDL cholesterol levels in the blood, while at the same time increasing HDL cholesterol levels. They can therefore be used for the treatment of hyperlipoproteinemia or arteriosclerosis.

The invention additionally concerns the combination of compounds according to the invention with a glucosidase and/or amylase inhibitor for the treatment of familial hyperlipidemia, obesity (adiposis), and diabetes meritus. Within the context of the invention, glucosidase and/or amylase inhibitors are, for example, acarbose, adiposine, voglibose, miglitol, emiglitate, MDL-25637, camiglibose (MDL-73945), tendamistate, AI-3688, testratin, pradimicin-Q, and salbostatin.

The combination of acarbose, miglitol, emiglitate, or voglibose and one of the above-mentioned compounds of general formula (IB) according to the invention is preferred.

CETP Inhibition Test

1. Obtaining CETP

CETP was obtained in partially purified form from human plasma by differential centrifugation and column chromatography and was used for testing. In so doing, human plasma was adjusted with NaBr to a density of 1.21 g/ml and was centrifuged for 18 h at 50,000 rpm at 4° C. The bottom fraction (d>1.21 g/ml) was applied to a Sephadex® Phenyl-Sepharose 4B (Pharmacia) column, washed with 0.15 m NaCl/0.001 m Tris HCl, pH 7.4, and then eluted with dist. water. The CETP-active fractions were pooled, dialyzed against 50 mM Na acetate, pH 4.5, and applied to a CM-Sepharose® (Pharmacia) column. They were then eluted with a linear gradient (0–1 M NaCl). The pooled CETP fractions were dialyzed against 10 mM Tris HCl, pH 7.4, and were then further purified by chromatography over a Mono Q® column (Pharmacia).

2. Obtaining Radioactively-Labeled HDL 50 ml of fresh human EDTA plasma was adjusted with NaBr to a density of 1.12 and centrifuged at 4° C. for 18 h at 50,000 rpm in the Ty 65 rotor. The upper phase was used to obtain cold LDL. The lower phase was dialyzed against 3–4 l PDB buffer (10 mM Tris/HCl, pH 7.4, 0.15 mM NaCl, 1 mM EDTA, 0.02% $NaN_3$). 20 $\mu$l of 3H cholesterol (Du Pont NET-725; 1 -$\mu$C/$\mu$l dissolved in ethanol) was subsequently added per 10 ml of dialysis residue volume and incubated for 72 h at 37° C. under $N_2$.

The sediment was then adjusted with NaBr to a density of 1.21 and centrifuged in the Ty 65 rotor for 18 h at 50,000 rpm at 20° C. The upper phase was obtained, and the lipoprotein fractions were purified by gradient centrifugation. In so doing, the isolated, tagged lipoprotein fraction was adjusted with NaBr to a density of 1.26. Every 4 ml of this solution was covered in centrifuge tubes (SW 40 rotor) with 4 ml of a solution with a density of 1.21 and 4.5 ml of a solution with a density of 1.063 (density solutions from PDB buffer and NaBr) and then centrifuged for 24 h at 38,000 rpm and 20° C. in the SW 40 rotor. The intermediate layer between the density of 1.063 and 1.21 that contained the labeled HDL was dialyzed against 3×100 volumes of PDB buffer at 4° C.

The dialysis residue contained radioactively-labeled $^3$H-CE-HDL, which was adjusted to approx. $5\times10^6$ cmp per ml and used for the test.

3. Conducting the Test

In order to test the CETP activity, the transfer of $^3$H cholesterol ester from human HD lipoproteins to biotinylated LD lipoproteins was measured.

The reaction was ended by adding Streptavidin-SPA® beads (Amersham), and the transferred radioactivity was determined directly in the liquid scintillation counter.

In the test batch, 10 $\mu$l of HDL-$^3$H cholesterol ester (~50,000 cpm) was incubated for 18 h at 37° C. with 10 $\mu$l of biotin-LDL (Amersham) in 50 mM HEPES/0.15 m NaCl/0.1% bovine serum albumin/0.05% $NaN_3$, pH 7.4, with 10 $\mu$l of CETP (1 mg/ml) and 3 $\mu$l solution of the substance to be tested (dissolved in 10% DMSO/1% BSA). Then, 200 $\mu$l of the SPA-Streptavidin bead solution (Amersham TRKQ 7005) was added, and the mixture was further incubated for 1 h under agitation and subsequently measured in the scintillation counter. Corresponding incubations with 10 μl buffer, 10 μl CETP at 4° C., and 10 μl CETP at 37° C. served as controls.

The transferred activity in the control batches with CETP at 37° C. was assessed as 100% transfer. The substance concentration in which this transfer was reduced by half was indicated as the $IC_{50}$ value.

Syrian golden hamsters from the company's own breeding were anesthetized after fasting for 24 h (0.88 mg/kg atropine, 0.80 mg/kg Ketavet® s.c., 30' later 50 mg/kg Nembutal i.p.). The jugular vein was then exposed and cannulated. The test substance was dissolved in a suitable solvent (as a rule, Adalat placebo solution: 60 g glycerin, 100 ml $H_2O$, ad 100 ml PEG-400) and administered to the animals via a PE catheter inserted into the jugular vein. The control animals received the same volume of solvent without any test substance. The vein was then ligated and the wound closed up. At different intervals—up to 24 h after administration of the test substance blood was drawn from the animals by puncture of the retroorbital venous plexus (approx. 250 μl). Coagulation was completed by incubating at 4° C. overnight, and the blood was then centrifuged for 10 minutes at 6,000 g. The cholesterol and triglyceride content in the serum obtained in this manner was determined using modified commercially-available enzyme tests (cholesterol enzymatic 14366 Merck, triglyceride 14364 Merck). The serum was diluted in a suitable manner with physiological saline solution. 100 μl serum dilution was mixed with 100 μl of test substance in 96well plates and incubated for 10 minutes at room temperature. The optical density was then determined with an automatic plate reader at a wavelength of 492 nm (SLT-Spectra). The triglyceride/cholesterol concentration contained in the samples was determined using a parallel-measured standard curve.

The determination of the HDL cholesterol content was carried out after precipitation of the lipoproteins containing Apo B by means of a reagent mixture (Sigma 352-4 HDL cholesterol reagent) according to the manufacturer's instructions.

In attempting to determine oral efficacy, the test substance, which was dissolved in DMSO and suspended in 0.5% methylcellulose, was administered orally to Syrian golden hamsters from the company's own breeding via a pharyngeal tube. The control animals received identical volumes of solvent without any test substance. Feed was then withheld from the animals, and blood was drawn at different intervals—up to 24 h after administration of the substance—via puncture of the retroorbital venous plexus. Further processing was carried out as described above.

The new active compounds can be converted in a known manner into the customary formulations, such as tablets, coated tablets, pills, granules, aerosols, syrups, emulsions, suspensions, and solutions, using inert, nontoxic, pharmaceutically-suitable excipients or solvents. In this connection, the therapeutically-active compound should be present in each case in a concentration of about 0.5% to 90% by weight, i.e., in amounts that are sufficient to achieve the dosage range indicated.

The formulations are prepared, for example, by extending the active compounds using solvents and/or excipients, if appropriate using emulsifiers and/or dispersants, with it being possible, for example, in the case of the use of water as a diluent, to use organic solvents, if appropriate, as auxiliary solvents.

Administration takes place in a customary manner, preferably orally or parenterally, in particular, perlingually or intravenously.

In the case of parenteral use, solutions of the active compound can be employed using suitable liquid excipients.

In general, it has proved to be advantageous in intravenous administration to administer amounts of about 0.001 to 1 mg/kg, preferably about 0.01 to 0.5 mg/kg of body weight, to obtain effective results, and in oral administration, the dosage is about 0.01 to 20 mg/kg, preferably 0.1 to 10 mg/kg of body weight.

In spite of this, it may be necessary to deviate from the amounts mentioned, depending on the body weight or the type of administration route, individual response to the medication, the type of formulation thereof, and the time or interval at which administration takes place. Thus in some cases, it may be sufficient to manage with less than the minimum amount previously mentioned, whereas in other cases, the upper limit mentioned must be exceeded. If larger amounts are administered, it may be advisable to divide these into several individual doses over the day.

I. Mobile Solvents for Thin-Layer Chromatography $A_1$=PE 98:EE 2

$A_2$=PE 95:EE 5

$A_3$=PE 9:EE 1

$A_4$=PE 85:EE 15

$A_5$=PE 8:EE 2

$A_6$=PE 75:EE 25

$A_7$=PE 7:EE 3

$A_8$=PE 65:EE 35

$A_9$=PE 6:EE 4

$A_{10}$=PE 55:EE 45

$A_{11}$=PE 1:EE 1

$A_{12}$=Toluene/ethyl acetate 1/1

$A_{13}$=Toluene/ethyl acetate 8/2

$A_{14}$=Acetonitrile/water 9/1

PE=petroleum ether; EE=ethyl acetate

Example I 1,4-Dihydro-2-cyclopentyl-6-ethyl-4-(4-fluorophenyl)pyridine-3,5-dicarboxylic acid-3-methylester-5-ethylester

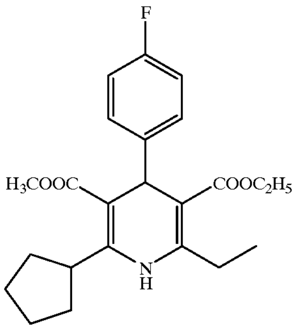

6.2 g (50 mmol) of 4-fluorobenzaldehyde, 8.5 g (50 mmol) of 3-amino-cyclopentylprop-2-ene-carboxylic methylester, and 7.2 g (50 mmol) of 4-methylacetoacetic ethylester are heated for 18 hours to 130° C. while stirring. After cooling to room temperature, chromatography is carried out over silica gel (200 g of silica gel, 230–400 mesh; d 3.5 cm, mobile solvent ethyl acetate/petroleum ether 1:9).

Yield: 2.8 g (14% of theory)

$R_f$ (ethyl acetate/petroleum ether 2:8)=0.31

Example II

2-Cyclopentyl-6-ethyl-4-(4-fluorophenyl)pyridine-3,5-dicarboxylic acid-3-methylester-5-ethylester

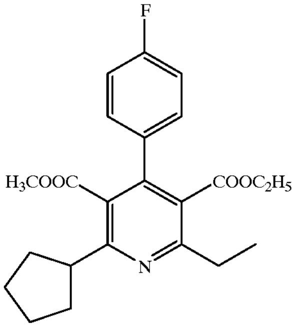

2.8 g (6.98 mmol) of 1,4-dihydro-2-cyclopentyl-6-ethyl-4-(4-fluorophenyl)pyridine-3,5-dicarboxylic acid-3-methylester-5-ethylester is dissolved in 100 ml of absol. methylene chloride, and after addition of 1.6 g (6.98 mmol) of 2,3-dichloro-5,6-dicyano-p-benzoquinone (DDQ), the mixture is stirred for 1 hour at room temperature. After this, it is drawn off by suction over diatomaceous earth and concentrated in a vacuum. The residue is chromatographed over silica gel (100 g of silica gel, 230–400 mesh, d 3.5 cm, mobile solvent ethyl acetate/petroleum ether 5:95).

Yield: 2.1 g (75.4% of theory)

$R_f$ (ethyl acetate/petroleum ether 1:9)=0.56

$^1$H-NMR ($CDCl_3$): δ=0.95 (t, 3H); 1.32 (t, 3H); 1.6–2.1 (m, 8H); 2.83 (q, 2H); 3.14 (m, 1H); 3.53 (s, 3H); 4.02 (q, 2H); 7.0–7.3 (m, 4H) ppm.

Example III and Example IV

2-Cyclopentyl-6-ethyl-4-(4-fluorophenyl)-3-hydroxymethylpyridine-5-carboxylic Acid Ethylester (Example III) and 2-Cyclopentyl-6-ethyl-4-(4-fluorophenyl)-5-hydroxymethylpyridine-3-carboxylic Acid Methylester (Example IV)

(III)

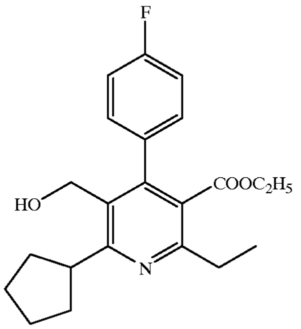

-continued (IV)

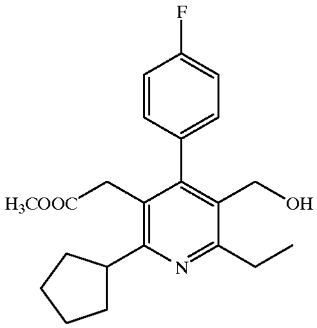

Under argon, 2.1 g (5.26 mmol) of 2-cyclopentyl-6-ethyl-4-(4-fluorophenyl)pyridine-3,5-dicarboxylic acid-3-methylester5-ethylester is dissolved in 50 ml of absol. toluene. 26.6 ml of diisobutyl aluminum hydride (1 M solution in toluene) is added dropwise to this solution at −60° C. After this, the mixture is stirred for 15 minutes at −60° C., and the reaction solution is then cooled at −30° C. for 18 h. After heating to 0° C., 50 ml of water is added, and the resulting sediment is drawn off by suction and washed 4 times with 50 ml of ethyl acetate. The aqueous phase is washed with 100 ml of ethyl acetate, and the combined organic phases are shaken out with 150 ml of saturated sodium chloride solution, dried with sodium sulfate, and concentrated in a vacuum. The residue is chromatographed over silica gel (100 g of silica gel, 230–400 mesh, d 3.5 cm, mobile solvent ethyl acetate/petroleum ether 15:85).

Yield (Example III): 0.263 g (13.5% of theory)

$R_f$ (ethyl acetate/petroleum ether 2:8)=0.42

$^1$H-NMR ($CDCl_3$): δ=0.95 (t, 3H); 1.28 (t, 3H); 1.6–2.1 (m, 8H); 2.76 (q, 4H); 3.55 (m, 1H); 3.97 (q, 4H); 4.48 (d, 2H); 7.0–7.3 (m, 4H) ppm.

Yield (Example IV): 0.907 g (48.3% of theory)

$R_f$ (ethyl acetate/petroleum ether 2:8)=0.32

$^1$H-NMR ($CDCl_3$): δ=1.32 (t, 3H); 1.6–2.1 (m, 8H); 2.97 (t, 3H); 3.06 (m, 1H); 3.45 (s, 3H); 4.45 (d, 2H) ppm.

The compounds shown in Table I(B) are produced analogously to the instructions for Examples I–IV:

TABLE I (B)

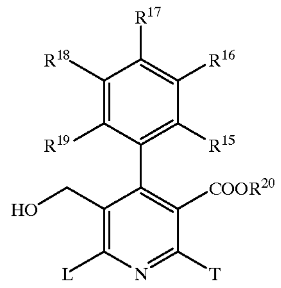

| Ex. | $R^{15}$ | $R^{16}$ | $R^{17}$ | $R^{18}$ | $R^{19}$ | $R^{20}$ | T | L | $R_f$ (solvent) |
|---|---|---|---|---|---|---|---|---|---|
| V | H | H | F | H | H | $C_2H_5$ | $CH(CH_3)_2$ | $CH(CH_3)_2$ | 0.51 (A5) |
| VI | H | H | F | H | H | $C_2H_5$ | $CH(CH_3)_2$ | $CH_3$ | 0.28 (A5) |
| VII | H | H | F | H | H | $C_2H_5$ | $CH_3$ | $CH_3$ | 0.33 (A7) |
| VIII | H | H | F | H | H | $C_2H_5$ | $CH(CH_3)_2$ | cyclo-$C_3H_5$ | 0.41 (A5) |
| IX | H | H | F | H | H | $C_2H_5$ | cyclo-$C_3H_5$ | cyclo-$C_3H_5$ | 0.44 (A5) |
| X | H | H | H | H | H | $C_2H_5$ | $CH(CH_3)_2$ | $CH(CH_3)_2$ | 0.41 (A5) |
| XI | H | H | F | H | H | $C_2H_5$ | $CH(CH_3)_2$ | cyclo-$C_4H_7$ | 0.45 (A5) |
| XII | H | H | F | H | H | $C_2H_5$ | $CH(CH_3)_2$ | cyclo-$C_5H_9$ | 0.46 (A5) |
| XIII | H | H | F | H | H | $CH_3$ | cyclo-$C_5H_9$ | $CH(CH_3)_2$ | 0.41 (A5) |
| XIV | H | $CH_3$ | F | H | H | $C_2H_5$ | $CH(CH_3)_2$ | $CH(CH_3)_2$ | 0.26 (A3) |
| XV | $CH_3$ | H | F | H | H | $C_2H_5$ | $CH(CH_3)_2$ | $CH(CH_3)_2$ | 0.48 (A5) |
| XVI | H | H | F | H | H | $C_2H_5$ | $CH(CH_3)_2$ | sec-$C_4H_9$ | 0.58 (A5) |
| XVII | H | H | F | H | H | $CH_3$ | sec-$C_4H_9$ | $CH(CH_3)_2$ | 0.53 (A5) |
| XVIII | H | H | F | H | H | $C_2H_5$ | $CH(CH_3)_2$ | $CH(OCH_3)_2$ | 0.45 (A5) |
| XIX | H | H | F | H | H | $C_2H_5$ | $CH_2CH_3$ | $CH(CH_3)_2$ | 0.49 (A5) |
| XX | H | H | F | H | H | $C_2H_5$ | $CH(CH_3)_2$ | $CH_2CH_3$ | 0.44 (A5) |
| XXI | H | H | OH | H | H | $C_2H_5$ | $CH(CH_3)_2$ | $CH(CH_3)_2$ | 0.21 (A7) |
| XXII | H | H | $CH_3$ | H | H | $C_2H_5$ | $CH(CH_3)_2$ | $CH(CH_3)_2$ | 0.25 (A3) |
| XXIII | H | H | F | H | H | $CH_3$ | $CH_3$ | cyclo-$C_3H_5$ | 0.43 (A7) |
| XXIV | H | H | F | H | H | $CH_3$ | cyclo-$C_3H_5$ | $CH_3$ | 0.36 (A7) |
| XXV | H | H | F | H | H | $C_2H_5$ | thiophen-2-yl | $CH(CH_3)_2$ | 0.5 (A5) |
| XXVI | H | H | F | H | H | $C_2H_5$ | $C_6H_5$ | $CH(CH_3)_2$ | 0.42 (A5) |
| XXVII | H | H | F | H | H | $C_2H_5$ | $CH(CH_3)_2$ | 4-F-$C_6H_4$ | 0.49 (A5) |
| XXVIII | H | H | F | H | H | $CH_3$ | 4-F-$C_6H_4$ | $CH(CH_3)_2$ | 0.34 (A5) |
| XXIX | H | H | F | H | H | $C_2H_5$ | furan-2-yl | $CH(CH_3)_2$ | 0.36 (A5) |
| XXX | H | H | F | H | H | $C_2H_5$ | $CH(CH_3)_2$ | $C_6H_5CH_2CHCH_3$ | 0.42 (A5) |
| XXXI | H | H | F | H | H | $C_2H_5$ | $CH(CH_3)_2$ | $CH(C_2H_5)_2$ | 0.47 (A5) |
| XXXII | H | H | F | H | H | $C_2H_5$ | $CH(CH_3)_2$ | $C_6H_5CHCH_3$ | 0.45 (A5) |
| XXXIII | H | H | H | H | H | $C_2H_5$ | $CH(CH_3)_2$ | cyclo-$C_3H_5$ | 0.37 (A5) |
| XXXIV | H | H | F | H | H | $C_2H_5$ | $CH(CH_3)_2$ | n-$C_3H_7$ | 0.24 (A3) |
| XXXV | H | H | F | H | H | $C_2H_5$ | $CH(CH_3)_2$ | n-$C_4H_9$ | 0.27 (A3) |
| XXXVI | H | H | F | H | H | $C_2H_5$ | $CH(CH_3)_2$ | $C_6H_5(CH_2)_2$ | 0.4 (A5) |
| XXXVII | H | H | F | H | H | $C_2H_5$ | 4-$CH_3O$—$C_6H_4$ | $CH(CH_3)_2$ | 0.52 (A7) |
| XXXVIII | H | H | F | H | H | $C_2H_5$ | 2-F-$C_6H_4$ | $CH(CH_3)_2$ | 0.34 (A5) |
| XXXIX | H | H | F | H | H | $C_2H_5$ | pyrrolidin-1-yl | $CH(CH_3)_2$ | 0.35 (A5) |
| XL | H | H | F | H | H | $C_2H_5$ | piperidin-1-yl | $CH(CH_3)_2$ | 0.47 (A5) |
| XLI | H | H | F | H | H | $C_2H_5$ | cyclo-$C_6H_{11}$ | $CH(CH_3)_2$ | 0.53 (A5) |
| XLII | H | H | F | H | H | $C_2H_5$ | piperidin-4-yl | $CH(CH_3)_2$ | 0.38 (A11) |
| XLIII | H | H | F | H | H | $C_2H_5$ | piperidin-3-yl | $CH(CH_3)_2$ | 0.44 (A11) |
| XLIV | H | H | F | H | H | $C_2H_5$ | 3-$CH_3O$—$C_6H_4$ | $CH(CH_3)_2$ | 0.30 (A5) |
| XLV | H | H | F | H | H | $C_2H_5$ | 4-$NO_2$—$C_6H_4$ | $CH(CH_3)_2$ | 0.38 (A5) |
| XLVI | H | H | F | H | H | $C_2H_5$ | $CH(CH_3)_2$ | $C_6F_5$ | 0.22 (A3) |
| XLVII | H | H | F | H | H | $C_2H_5$ | 2-$CH_3$—$C_6H_4$ | $CH(CH_3)_2$ | 0.44 (A5) |
| XLVIII | H | H | F | H | H | $C_2H_5$ | 4-Cl-$C_6H_4$ | $CH(CH_3)_2$ | 0.21 (A3) |
| XLIX | H | H | H | H | H | $C_2H_5$ | $CH(CH_3)_2$ | 4-F-$C_6H_4$ | 0.37 (A3) |
| L | H | H | H | H | H | $CH_3$ | 4-F-$C_6H_4$ | $CH(CH_3)_2$ | 0.2 (A3) |
| LI | $C_6H_5CH_2O$ | H | H | H | H | $C_2H_5$ | $CH(CH_3)_2$ | 4-F-$C_6H_4$ | 0.27 (A4) |
| LII | $C_6H_5CH_2O$ | H | H | H | H | $CH_3$ | 4-F-$C_6H_4$ | $CH(CH_3)_2$ | 0.18 (A4) |
| LIII | 2-F-$C_6H_4CH_2O$ | H | H | H | H | $C_2H_5$ | $CH(CH_3)_2$ | $CH(CH_3)_2$ | 0.23 (A3) |
| LIV | 4-F-$C_6H_4CH_2O$ | H | H | H | H | $C_2H_5$ | $CH(CH_3)_2$ | $CH(CH_3)_2$ | 0.21 (A4) |
| LV | 4-Cl-$C_6H_4CH_2O$ | H | H | H | H | $C_2H_5$ | $CH(CH_3)_2$ | $CH(CH_3)_2$ | 0.12 (A4) |
| LVI | H | 2-F-$C_6H_4CH_2O$ | H | H | H | $C_2H_5$ | $CH(CH_3)_2$ | $CH(CH_3)_2$ | 0.17 (A3) |
| LVII | H | H | H | H | H | $CH_3$ | 4-F-$C_6H_4$ | $CH_3$ | 0.21 (A7) |
| LVIII | H | H | F | H | H | $C_2H_5$ | 3-Cl-$C_6H_4$ | $CH(CH_3)_2$ | 0.4 (A5) |
| LIX | H | H | F | H | H | $CH_3$ | $CH(CH_3)_2$ | 4-F-$C_6H_4CH_2$ | 0.19 (A3) |
| LX | H | H | F | H | H | $CH_3$ | 4-F-$C_6H_4CH_2$ | $CH(CH_3)_2$ | 0.28 (A4) |
| LXI | H | H | F | H | H | $CH_3$ | $CH(CH_3)_2$ | 4-F-$C_6H_4CH_2$ | 0.23 (A4) |
| LXII | H | H | $OCH_3$ | H | H | $CH_3$ | 4-F-$C_6H_4$ | $CH(CH_3)_2$ | 0.18 (A5) |
| LXIII | H | H | Cl | H | H | $CH_3$ | 4-F-$C_6H_4$ | $CH(CH_3)_2$ | 0.16 (A3) |
| LXIV | H | Cl | H | H | H | $CH_3$ | 4-F-$C_6H_4$ | $CH(CH_3)_2$ | 0.28 (A3) |

TABLE I-continued (B)

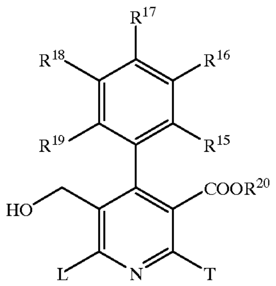

| Ex. | $R^{15}$ | $R^{16}$ | $R^{17}$ | $R^{18}$ | $R^{19}$ | $R^{20}$ | T | L | $R_f$ (solvent) |
|---|---|---|---|---|---|---|---|---|---|
| LXV | H | H | F | H | H | $CH_3$ | 4-F-$C_6H_4$ | $CH(CH_3)_2$ | 0.32 (A4) |
| LXVI | H | Cl | Cl | H | H | $CH_3$ | 4-F-$C_6H_4$ | $CH(CH_3)_2$ | 0.29 (A4) |
| LXVII | H | $CF_3$ | H | H | H | $CH_3$ | 4-F-$C_6H_4$ | $CH(CH_3)_2$ | 0.44 (A5) |
| LXVIII | H | $CH_3$ | H | H | H | $CH_3$ | 4-F-$C_6H_4$ | $CH(CH_3)_2$ | 0.34 (A5) |
| LXIX | H | H | $CH_3$ | H | H | $CH_3$ | 4-F-$C_6H_4$ | $CH(CH_3)_2$ | 0.31 (A5) |
| LXX | H | Cl | H | Cl | H | $CH_3$ | 4-F-$C_6H_4$ | $CH(CH_3)_2$ | 0.22 (A5) |
| LXXI | F | H | H | H | H | $CH_3$ | 4-F-$C_6H_4$ | $CH(CH_3)_2$ | 0.22 (A5) |
| LXXII | H | $OCH_3$ | H | H | H | $CH_3$ | 4-F-$C_6H_4$ | $CH(CH_3)_2$ | 0.25 (A5) |
| LXXIII | $OCH_3$ | H | H | H | H | $CH_3$ | 4-F-$C_6H_4$ | $CH(CH_3)_2$ | 0.2 (A5) |
| LXXIV | Cl | Cl | H | H | H | $CH_3$ | 4-F-$C_6H_4$ | $CH(CH_3)_2$ | 0.14 (A4) |
| LXXV | H | $CF_3$ | Cl | H | H | $CH_3$ | 4-F-$C_6H_4$ | $CH(CH_3)_2$ | 0.21 (A4) |
| LXXVI | H | $CF_3$ | F | H | H | $CH_3$ | 4-F-$C_6H_4$ | $CH(CH_3)_2$ | 0.24 (A4) |
| LXXVII | H | Cl | $CF_3$ | H | H | $CH_3$ | 4-F-$C_6H_4$ | $CH(CH_3)_2$ | 0.23 (A3) |
| LXXVIII | H | H | F | H | H | $CH_3$ | 4-F-$C_6H_4$ | cyclo-$C_5H_9$ | 0.39 (A5) |
| LXXIX | H | H | F | H | H | $CH_3$ | 4-F-$C_6H_4$ | cyclo-$C_3H_5$ | 0.28 (A5) |
| LXXX | H | F | H | H | H | $CH_3$ | 4-F-$C_6H_4$ | $CH(CH_3)_2$ | 0.28 (A5) |
| LXXXI | H | H | $CF_3$ | H | H | $CH_3$ | 4-F-$C_6H_4$ | $CH(CH_3)_2$ | 0.39 (A5) |
| LXXXII | H | H | F | H | H | $CH_3$ | 4-F-$C_6H_4$ | 4-F-$C_6H_4CH_2$ | 0.3 (A5) |
| LXXXIII | H | H | F | H | H | $CH_3$ | cyclo-$C_3H_5$ | cyclo-$C_3H_5$ | 0.3 (A5) |
| LXXXIV | Cl | Cl | H | H | H | $CH_3$ | 4-F-$C_6H_4$ | 4-F-$C_6H_4$ | 0.36 (A7) |
| LXXXV | H | $CF_3$ | F | H | H | $CH_3$ | $CH(CH_3)_2$ | $CH(CH_3)_2$ | 0.41 (A5) |
| LXXXVI | H | $CF_3$ | F | H | H | $CH_3$ | 4-F-$C_6H_4$ | 4-F-$C_6H_4$ | 0.25 (A5) |
| LXXXVII | $CH_3$ | H | H | H | H | $CH_3$ | 4-F-$C_6H_4$ | $CH(CH_3)_2$ | 0.32 (A5) |
| LXXXVIII | Cl | H | H | H | H | $CH_3$ | $CH(CH_3)_2$ | $CH(CH_3)_2$ | 0.21 (A5) |
| LXXXIX | Cl | H | H | H | H | $CH_3$ | 4-F-$C_6H_4$ | $CH(CH_3)_2$ | 0.13 (A5) |
| XC | Cl | H | H | H | H | $CH_3$ | 4-F-$C_6H_4$ | 4-F-$C_6H_4$ | 0.35 (A5) |
| XCI | Cl | H | Cl | H | H | $CH_3$ | 4-F-$C_6H_4$ | $CH(CH_3)_2$ | 0.23 (A5) |
| XCII | Cl | H | Cl | H | H | $CH_3$ | 4-F-$C_6H_4$ | 4-F-$C_6H_4$ | 0.31 (A5) |
| XCIII | H | H | F | H | H | $CH_3$ | 3-$CF_3$-$C_6H_4$ | $CH(CH_3)_2$ | 0.31 (A5) |
| XCIV | H | H | F | H | H | $CH_3$ | 3-$CH_3$-$C_6H_4$ | $CH(CH_3)_2$ | 0.31 (A5) |
| XCV | H | H | F | H | H | $CH_3$ | 4-$CH_3$-$C_6H_4$ | $CH(CH_3)_2$ | 0.27 (A5) |
| XCVI | H | H | F | H | H | $CH_3$ | 2-Cl-$C_6H_4$ | $CH(CH_3)_2$ | 0.27 (A5) |
| XCVII | H | H | F | H | H | $CH_3$ | 4-$CH_3O$-$C_6H_4$ | $CH(CH_3)_2$ | 0.22 (A5) |
| XCVIII | H | H | F | H | H | $CH_3$ | 2-$CH_3O$-$C_6H_4$ | $CH(CH_3)_2$ | 0.43 (A7) |
| XCIX | H | H | F | H | H | $CH_3$ | 3-$CH_3O$-$C_6H_4$ | $CH(CH_3)_2$ | 0.25 (A5) |
| C | H | H | F | H | H | $C_2H_5$ | cyclo-$C_6H_{11}$ | 4-F-$C_6H_4$ | 0.45 (A5) |
| CI | H | H | F | H | H | $CH_3$ | 4-F-$C_6H_4$ | cyclo-$C_6H_{11}$ | 0.33 (A5) |
| CII | H | H | F | H | H | $C_2H_5$ | 4-Cl-$C_6H_4$ | cyclo-$C_5H_9$ | 0.22 (A4) |
| CIII | H | H | F | H | H | $CH_3$ | 3-$CF_3$-$C_6H_4$ | cyclo-$C_5H_9$ | 0.29 (A5) |
| CIV | H | H | F | H | H | $CH_3$ | 4-F-$C_6H_4CH_2$ | cyclo-$C_4H_7$ | 0.2 (A5) |
| CV | H | H | F | H | H | $C_2H_5$ | cyclo-$C_7H_{13}$ | 4-F-$C_6H_4$ | 0.4 (A5) |
| CVI | H | H | F | H | H | $CH_3$ | 4-F-$C_6H_4$ | cyclo-$C_7H_{13}$ | 0.3 (A5) |
| CVII | H | H | F | H | H | $C_2H_5$ | furan-2-yl | 4-F-$C_6H_4$ | 0.32 (A6) |
| CVIII | H | H | F | H | H | $CH_3$ | 4-F-$C_6H_4$ | furan-2-yl | 0.21 (A6) |
| CIX | H | H | F | H | H | $CH_3$ | 4-F-$C_6H_4$ | (cyclo-$C_5H_9$)$CH_2$ | 0.11 (A4) |
| CX | H | H | F | H | H | $C_2H_5$ | (cyclo-$C_6H_{11}$)$CH_2$ | 4-F-$C_6H_4$ | 0.31 (A5) |
| CXI | H | H | F | H | H | $CH_3$ | 4-F-$C_6H_4$ | (cyclo-$C_6H_{11}$)$CH_2$ | 0.21 (A5) |
| CXII | H | H | F | H | H | $C_2H_5$ | $CF_3$ | 4-F-$C_6H_4$ | 0.26 (A5) |
| CXIII | H | H | F | H | H | $CH_3$ | cyclo-$C_5H_9$ | 4-$CF_3$-$C_6H_4$ | 0.30 (A4) |
| CXIV | H | H | F | H | H | $C_2H_5$ | 4-$CF_3$-$C_6H_4$ | cyclo-$C_5H_9$ | 0.19 (A4) |
| CXV | H | H | F | H | H | $C_2H_5$ | 1-naphthyl | cyclo-$C_5H_9$ | 0.21 (A4) |
| CXVI | H | H | F | H | H | $CH_3$ | cyclo-$C_5H_9$ | 3,5-$(CF_3)_2$-$C_6H_3$ | 0.25 (A3) |
| CXVII | H | H | F | H | H | $C_2H_5$ | 2-naphthyl | cyclo-$C_5H_9$ | 0.23 (A3) |
| CXVIII | H | H | F | H | H | $CH_3$ | 3-$CH_3$-$C_6H_4$ | cyclo-$C_5H_9$ | 0.32 (A5) |
| CXIX | H | H | F | H | H | $CH_3$ | 2-$CF_3$-$C_6H_4$ | cyclo-$C_5H_9$ | 0.2 (A5) |
| CXX | H | H | F | H | H | $CH_3$ | cyclo-$C_5H_9$ | 2-$CF_3$-$C_6H_4$ | 0.17 (A5) |
| CXXI | H | H | F | H | H | $C_2H_5$ | 4-F-$C_6H_4CH_2$ | cyclo-$C_5H_9$ | 0.4 (A5) |
| CXXII | H | H | F | H | H | $CH_3$ | cyclo-$C_5H_9$ | 4-F-$C_6H_4CH_2$ | 0.32 (A5) |
| CXXIII | H | H | F | H | H | $C_2H_5$ | 4-F-$C_6H_4CH_2$ | 4-F-$C_6H_4$ | 0.28 (A5) |
| CXXIV | H | H | F | H | H | $CH_3$ | cyclo-$C_5H_9$ | 2,4-$F_2$-$C_6H_3$ | 0.32 (A5) |

TABLE I-continued (B)

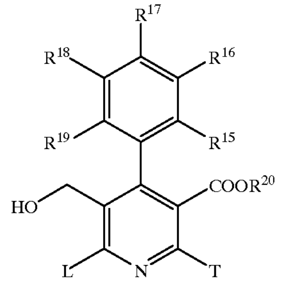

| Ex. | $R^{15}$ | $R^{16}$ | $R^{17}$ | $R^{18}$ | $R^{19}$ | $R^{20}$ | T | L | $R_f$ (solvent) |
|---|---|---|---|---|---|---|---|---|---|
| CXXV | H | H | F | H | H | $C_2H_5$ | 3,4-$F_2$-$C_6H_4CH_2$ | cyclo-$C_5H_9$ | 0.23 (A4) |
| CXXVI | H | H | F | H | H | $CH_3$ | cyclo-$C_5H_9$ | cyclo-$C_5H_9$ | 0.34 (A4) |
| CXXVII | H | H | F | H | H | $C_2H_5$ | 4-F-$C_6H_4CH_2$ | 4-F-$C_6H_4CH_2$ | 0.4 (A7) |
| CXXVIII | H | H | F | H | H | $C_2H_5$ | 3-$CF_3$-$C_6H_4(CH_2)_2$ | cyclo-$C_5H_9$ | 0.36 (A5) |
| CXXIX | H | H | F | H | H | $CH_3$ | cyclo-$C_5H_9$ | 3-$CF_3$-$C_6H_4(CH_2)_2$ | 0.34 (A5) |
| CXXX | H | H | F | H | H | $C_2H_5$ | 3-$CF_3$-$C_6H_4CH_2$ | 3-$CF_3$-$C_6H_4(CH_2)_2$ | 0.35 (A5) |
| CXXXI | H | H | F | H | H | $C_2H_5$ | $C_2H_5$ | cyclo-$C_5H_9$ | 0.41 (A5) |
| CXXXII | H | H | F | H | H | $CH_3$ | cyclo-$C_5H_9$ | $C_2H_5$ | 0.32 (A5) |
| CXXXIII | H | H | F | H | H | $C_2H_5$ | $C_2H_5$ | $C_2H_5$ | 0.22 (A7) |
| CXXXIV | H | H | F | H | H | $C_2H_5$ | 3-$CF_3$-$C_6H_4CH_2$ | cyclo-$C_5H_9$ | |
| CXXXV | H | H | F | H | H | $CH_3$ | cyclo-$C_5H_9$ | 4-F-$C_6H_4CH_2$ | |
| CXXXVI | H | H | F | H | H | $C_2H_5$ | (cyclo-$C_5H_9$)$(CH_2)_2$ | (cyclo-$C_5H_9$)$(CH_2)_2$ | |
| CXXXVII | H | H | F | H | H | $C_2H_5$ | (cyclo-$C_5H_9$)$(CH_2)_2$ | 4-F-$C_6H_4$ | |
| CXXXVIII | H | H | F | H | H | $CH_3$ | 4-F-$C_6H_4$ | (cyclo-$C_5H_9$)$(CH_2)_2$ | |

Example CXXXIX

2-Cyclopentyl-6-ethyl-4-(4-fluorophenyl)-3-(3-trifluoromethylbenzyloxy-methyl)-pyridine-5-carboxylic Acid Ethylester

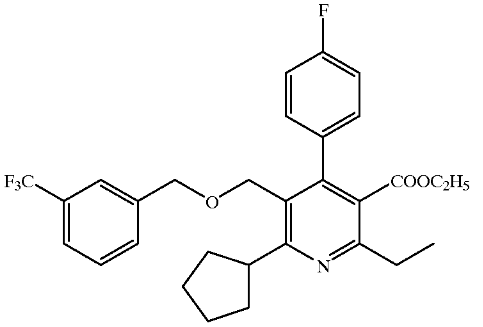

186 mg (0.5 mmol) of 2-cyclopentyl-6-ethyl-4-(4-fluorophenyl)-3-hydroxy-methylpyridine-5-carboxylic acid ethylester dissolved in 5 ml of absol. dimethyl formamide is added dropwise at 0° C. while stirring to a suspension of 18 mg (0.5 mmol) of sodium hydride (80%) in 5 ml of dimethyl formamide and subsequently stirred for 30 minutes. After this, 143 mg (0.6 mmol) of trifluoromethylbenzylbromide dissolved in 3 ml of dimethyl formamide is added, and the mixture is stirred for 18 h at room temperature. After addition of 25 ml of water, the mixture is extracted twice with 50 ml of ethyl acetate each time, and the combined ethyl acetate phases are shaken out with 10 ml of saturated sodium chloride solution, dried with sodium sulfate, and concentrated in a vacuum. The residue is chromatographed over silica gel (100 g of silica gel, 230–400 mesh, diameter 3.5 cm, mobile solvent ethyl acetate/petroleum ether 1:9).

Yield: 0.246 g (93.1% of theory)

$R_f$ value (ethyl acetate/petroleum ether 1:9)=0.35

$^1$H-NMR ($CDCl_3$): δ=0.95 (t, 3H); 1.32 (t, 3H); 1.6–2.1 (m, 8H); 2.78 (q, 4H); 3.44 (m, 1H); 3.95 (q, 4H); 4.28 (s, 2H); 4.42 (s, 2H); 7.0–7.6 (m, 8H) ppm.

Example CXL 2,6-Diisopropyl-4-(4-fluorophenyl)pyridine-3,5-dicarboxylic Acid Diethylester

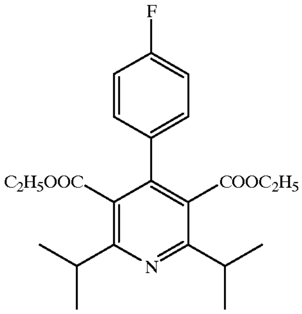

3.8 g (16.4 mmol) of 2,3-dichloro-5,6-dicyano-p-benzoquinone is added to a solution of 6.6 g (16.4 mmol) of 1,4-dihydro-2,6-diisopropyl-4-(4-fluorophenyl)pyridine-3,5-dicarboxylic acid diethylester in 200 ml of analysis grade methylene chloride, and the mixture is then stirred for 1 h at room temperature. After this, it is drawn off by suction over diatomaceous earth, and the methylene chloride phase is extracted 3 times with 100 ml of water each time and dried on magnesium sulfate. After concentrating in a vacuum, the residue is chromatographed on a column (100 g of silica gel, 70–230 mesh, diameter 3.5 cm, with ethyl acetate/petroleum ether 1:9).

Yield: 5.8 g (87.9% of theory)

$^1$H-NMR ($CDCl_3$): δ=0.98 (t, 6H); 1.41 (d, 12H); 3.1 (m, 2H); 4.11 (q, 4H); 7.04 (m, 2H); 7.25 (m, 2H) ppm.

Example CXLI 2,6-Diisopropyl-4-(4-fluorophenyl)-5-hydroxymethyl-pyridine-3,5-carboxylic Acid Ethylester

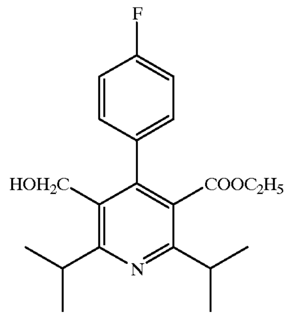

Under nitrogen, 21 ml (80.5 mmol) of a 3.5 molar solution of sodium bis(2-methoxyethoxy)dihydroaluminate in toluene is added to a solution of 9.2 g (23 mmol) of the compound from Example CXL in 100 ml of dried tetrahydrofuran at −10° C. to −5° C., and the mixture is stirred for 5 h at room temperature. After cooling to 0° C., 100 ml of water is carefully added dropwise, and extraction is carried out 3 times with 100 ml of ethyl acetate each time. The combined organic phases are washed with saturated sodium chloride solution, dried over magnesium sulfate, and evaporated in a vacuum. The residue is chromatographed on a column (200 g of silica gel, 70–230 mesh, diameter 4.5 cm, with ethyl acetate/petroleum ether 3:7).

Yield: 7.2 g (87.2% of theory)

$^1$H-NMR ($CDCl_3$): δ=0.95 (t, 3H); 1.31 (m, 12H); 3.05 (m, 1H); 3.48 (m, 1H); 3.95 (q, 2H); 4.93 (d, 2H); 7.05–7.31 (m, 4H) ppm.

Example CXLII 5-(tert-Butyldimethylsilyloxymethyl)-2,6-diisopropyl-4-(4-fluorophenyl)-pyridine-3-carboxylic Acid Ethylester

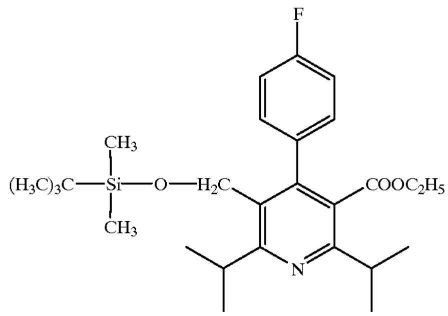

2.1 g (13.8 mmol) of tert-Butyldimethylsilyl chloride, 1.8 g (27.5 mmol) of imidazole, and 0.05 g of 4-dimethylaminopyridine are added to a solution of 4.5 g (12.5 mmol) of the compound from Example CXLI in 50 ml of dimethyl formamide at room temperature. The mixture is stirred overnight at room temperature, 200 ml of water is added, and the mixture is adjusted to a pH of 3 with 1 N hydrochloric acid. The mixture is extracted 3 times with 100 ml of ether each time, and the combined organic phases are washed once with saturated sodium chloride solution, dried over magnesium sulfate, and concentrated in a vacuum. The residue is chromatographed on a column (150 g of silica gel, 70–230 mesh, diameter 4 cm, with ethyl acetate/petroleum ether 1:9).

Yield: 4.2 g (73.7% of theory)

$R_f$=0.75 (A3)

Example CXLIII 3-(tert-Butyldimethylsilyloxymethyl)-2,6-diisopropyl-4-(4-fluorophenyl)-5-hydroxymethylpyridine

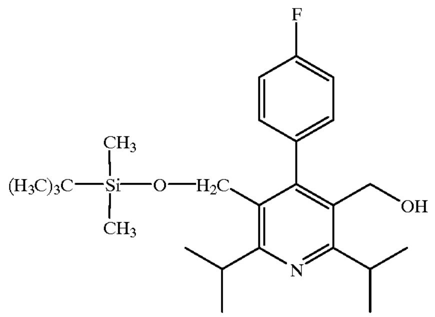

Under argon, 76.0 ml (0.266 mmol; 3.6 eq.) of a 3.5 molar solution of sodium bis(2methoxyethoxy)dihydroaluminate (Red-Al) in toluene is slowly added to a solution of 35.0 g (0.0738 mmol) of the compound from Example CXLII in 500 ml of analysis-grade THF at room temperature, and stirring is then carried out for 3 h. The reaction solution is mixed under ice cooling with 50 ml of a 20% potassium sodium tartrate solution and extracted with 200 ml of ethyl acetate. The organic phase is washed once with a saturated NaCl solution, dried over $Na_2SO_4$, and concentrated in a vacuum. The residue is chromatographed over silica gel 60 with toluene/ethyl acetate (8:2).

Yield: 30.2 g (94.7% of theory)

$R_f$=0.71 (toluene/ethyl acetate 8:2)

Example CXLIV 3-(tert-Butyldimethylsilyloxymethyl)-2,6-diisopropyl-4-(4-fluorophenyl)-5-methylsulfonyloxymethylpyridine

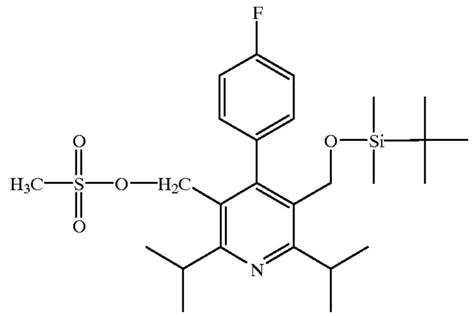

16.94 g (39.24 mmol) of 3-(tert-butyldimethylsilyloxymethyl)-2,6-diisopropyl-4-(4-fluorophenyl)-5-hydroxymethylpyridine is dissolved in 220 g of analysis grade $CH_2Cl_2$, cooled to −60° C., and mixed dropwise with 11.0 ml (78.48 mmol; 2 eq.) of triethylamine and 6.1 ml (78.48 mmol; 2 eq.) of methanesulfonyl chloride under nitrogen while stirring. Stirring is carried out for 1 h at −60° C. to −20° C. and for 30 minutes at 0° C. After this, the reaction solution is washed with cold $NaHCO_3$ solution, dried over $Na_2SO_4$, concentrated, dried for 60 min. in a high vacuum, and then stored at −20° C.

Yield: 19.8 g (99% of theory)

$R_f$=0.77 (toluene/ethyl acetate 8:2)

Example CXLV 3-(tert-Butyldimethylsilyloxymethyl)-2,6-diisopropyl-4-(4-fluorophenyl)-5-(1-methylimidazole-2-thiomethyl)pyridine

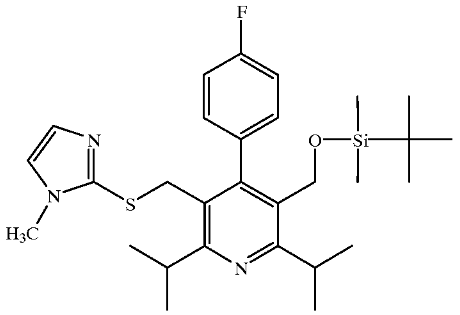

1.0 g (1.96 mmol) of 3-(tert-butyldimethylslyloxymethyl)-2,6-diisopropyl-4-(4fluorophenyl)-5-methylsulfonyloxymethylpyridine is placed in 15 ml of analysis-grade DMF. 0.256 g (2.25 mmol; 1.15 eq.) of 2-mercapto-1-methylimidazole and 0.41 ml (2.35 mmol; 1.2 eq.) of N,N-diisopropylamine are added, and the mixture is stirred overnight at 60° C. After this, 80 ml of ethyl acetate is added, and the mixture is then successively washed with saturated $NaHCO_3$__ solution, 1 N $H_2SO_4$, and saturated NaCl solution. The organic phase is dried over $Na_2SO_4$, filtered, and concentrated.

Yield: 0.93 g (89.8% of theory)

$R_f$=0.35 (toluene/ethyl acetate 8:2)

Example CXLVI 3-(tert-Butyldimethylsilyloxymethyl)-2,6-diisopropyl-4-(4-fluorophenyl)-5-(indolyl-5-aminomethyl)pyridine

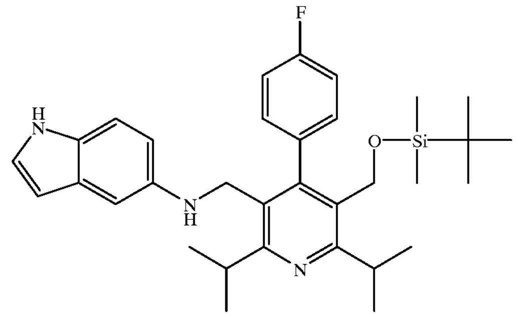

2.0 g (3.92 mmol) of 3-(tert-butyldimethylsilyloxymethyl)-2,6-diisopropyl-4-(4-fluorophenyl)-5-methylsulfonyloxymethylpyridine is reacted in 20 ml of analysis grade DMF under nitrogen with 0.674 g (5.1 mmol; 1.3 eq.) of 5-aminoindole and 0.82 ml (4.71 mmol) of N,N-diisopropylethylamine analogously to the instructions of Example CXLII.

Yield: 2.05 g (95.8% of theory)

$R_f$=0.75 (toluene/ethyl acetate 8:2)

PRODUCTION EXAMPLES

Example 1

2-Cyclopentyl-6-ethyl-4-(4-fluorophenyl)-5-hydroxymethyl-3-(3-trifluoromethylbenzyloxymethyl)pyridine

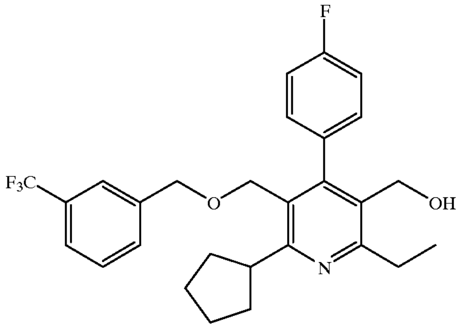

A suspension of 30 mg (0.8 mmol) of lithium aluminum hydride in 10 ml of absol. tetrahydrofuran is heated under argon. After this, 212 mg (0.4 mmol) of 2-cyclopentyl-6-ethyl-4-(4-fluorophenyl)-3-(3trifluoromethylbenzyloxymethyl)-pyridine-5-carboxylic acid ethylester dissolved in 10 ml of absolute tetrahydrofuran is added. Next, the mixture is refluxed for 1 h. After cooling to room temperature, 10 ml of a 10% potassium hydroxide solution is added. The resulting sediment is drawn off by suction and boiled off several times with 10 ml of diethyl ether. The combined mother liquors are dried with sodium sulfate, concentrated in a vacuum, and chromatographed over silica gel (mobile solvent ethyl acetate/petroleum ether 2:8).

Yield: 149 mg (76.5% of theory)

$R_f$ value (ethyl acetate/petroleum ether 2:8)=0.08

$^1$H-NMR ($CDCl_3$): δ=1.32 (t, 3H); 1.6–2.1 (m, 8H); 2.95 (q, 4H); 3.41 (m, 1H); 4.16 (s, 2H); 4.38 (s, 2H); 7.0–7.6 (m, 8H) ppm.

Example 2

2,6-Diisopropyl-4-(4-fluorophenyl)-5-(1-methylimidazole-2-thiomethyl)-3-hydroxymethylpyridine

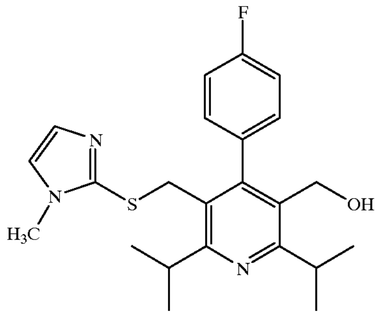

10 ml of 3 N hydrochloric acid is added to 0.5 g (0.947 mmol) of the compound from Example CXLII dissolved in 10 ml of methanol, and the mixture is stirred for 3 h at room temperature. The mixture is concentrated in a vacuum, covered with a layer of ethyl acetate, and adjusted to a pH of 8.0 with a saturated $NaHCO_3$ solution, and the organic phase is separated off. The aqueous phase is again extracted with ethyl acetate, and the combined organic phases are washed with salt water, dried over $Na_2SO_4$, and concentrated.

Yield: 230 mg (58.7% of theory)

$R_f$=0.76 (toluene/ethyl acetate 1:1)

The compounds listed in Tables 1(B) through 5(B) are produced analogously to the procedures of Examples 1 and 2:

TABLE 1(B)

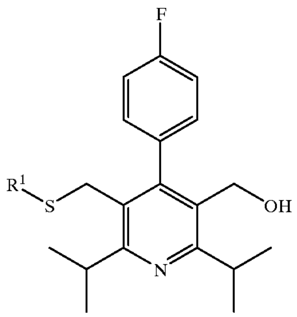

| Example No. | $R^1$ | Rf (solvents) |
|---|---|---|
| 3 | 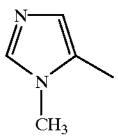 | 0.56 (A12) |

TABLE 1(B)-continued

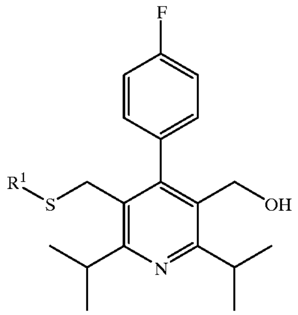

| Example No. | $R^1$ | Rf (solvents) |
|---|---|---|
| 4 | 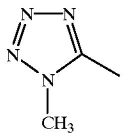 | 0.42 (A13) |
| 5 | 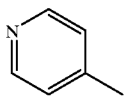 | 0.12 (A13) |
| 6 | 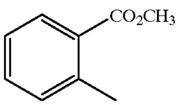 | 0.62 (A13) |
| 7 | 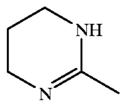 | 0.42 (A14) |
| 8 | 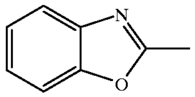 | 0.54 (A13) |
| 9 | 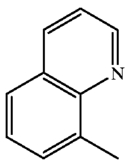 | 0.59 (A13) |
| 10 | 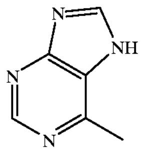 | 0.23 (A12) |
| 11 | 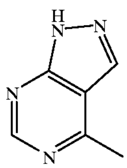 | 0.54 (A12) |

TABLE 1(B)-continued

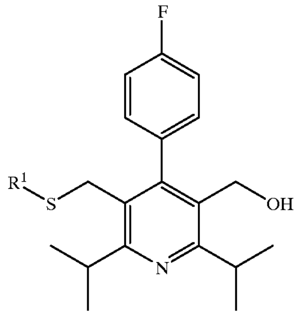

| Example No. | $R^1$ | Rf (solvents) |
|---|---|---|
| 12 | 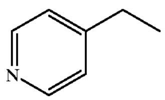 | 0.5 (A12) |
| 13 | 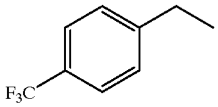 | 0.68 (A13) |
| 14 | 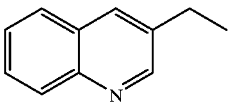 | 0.71 (A13) |

Example 15

2,6-Diisopropyl-4-(4-fluorophenyl)-5-(indolyl-5-aminomethyl)-3-hydroxymethylpyridine

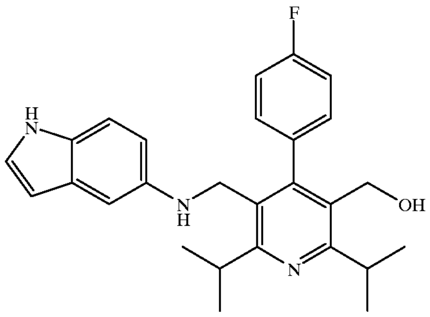

Analogously to Example 2, 2.3 g (4.21 mmol) of the compound from Example CXLIII is desilylated in methanol in the presence of 3 N hydrochloric acid.

Yield: 720 mg (39.6% of theory)

$R_f$=0.48 (A13)

The compounds listed in Table 2(B) are synthesized according to these instructions:

TABLE 2(B)

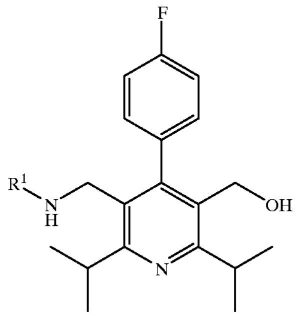

| Example No. | $R^1$ | $R_f$ (solvents) |
|---|---|---|
| 16 | 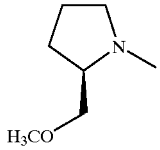 | 0.46 (A13) |
| 17 | 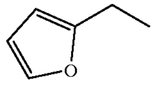 | 0.33 (A13) |
| 18 | 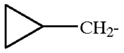 | 0.86 (A13) |
| 19 | 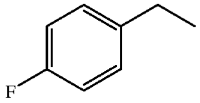 | 0.48 (A13) |
| 20 | 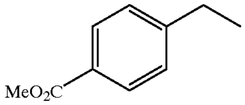 | 0.35 (A13) |
| 21 | 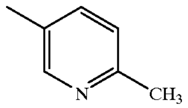 | 0.39 (A13) |

TABLE 3(B)

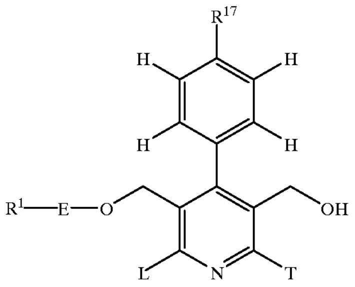

| Ex. | $R^{17}$ | $R^1$-E | T | L | $R_f$ (solvent) |
|---|---|---|---|---|---|
| 22 | F | 4-F—$C_6H_4$ | $CH(CH_3)_2$ | $CH(CH_3)_2$ | 0.43 (A5) |
| 23 | F | 4-$CF_3$—$C_6H_4$ | $CH(CH_3)_2$ | $CH(CH_3)_2$ | 0.40 (A5) |
| 24 | F | 3-$CF_3$—$C_6H_4$ | $CH(CH_3)_2$ | $CH(CH_3)_2$ | 0.47 (A5) |
| 25 | F | 2-F—$C_6H_4$ | $CH(CH_3)_2$ | $CH(CH_3)_2$ | 0.41 (A5) |
| 26 | F | 4-F—$C_6H_4(CH_2)_2$ | $CH(CH_3)_2$ | $CH(CH_3)_2$ | 0.17 (A3) |
| 27 | H | 2-$CF_3$—$C_6H_4(CH_2)_2$ | $CH(CH_3)_2$ | $CH(CH_3)_2$ | 0.38 (A5) |
| 28 | F | 2-F—$C_6H_4(CH_2)_2$ | $CH(CH_3)_2$ | $CH(CH_3)_2$ | 0.16 (A3) |
| 29 | F | 4-$CF_3$—$C_6H_4CHCH_3$ | $CH(CH_3)_2$ | $CH(CH_3)_2$ | 0.17 (A3) |
| 30 | F | 3-$CF_3$—$C_6H_4(CH_2)_2$ | $CH(CH_3)_2$ | $CH(CH_3)_2$ | 0.49 (A5) |
| 31 | F | 3-$CF_3C_6H_4CHCH_3$ | $CH(CH_3)_2$ | $CH(CH_3)_2$ | 0.47 (A5) |
| 32 | F | 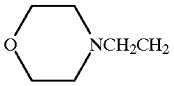 | $CH(CH_3)_2$ | $CH(CH_3)_2$ | 0.20 (A11) |
| 33 | F | (4-pyridyl)$CH_2$ | $CH(CH_3)_2$ | $CH(CH_3)_2$ | 0.16 (A9) |
| 34 | F | (3-pyridyl)$CH_2$ | $CH(CH_3)_2$ | $CH(CH_3)_2$ | 0.20 (A9) |
| 35 | F | (2-pyridyl)$CH_2$ | $CH(CH_3)_2$ | $CH(CH_3)_2$ | 0.38 (A9) |
| 36 | F | 4-Ph—$C_6H_4$ | $CH(CH_3)_2$ | $CH(CH_3)_2$ | 0.24 (A4) |
| 37 | F | 3-Ph—$C_6H_4$ | $CH(CH_3)_2$ | $CH(CH_3)_2$ | 0.27 (A4) |
| 38 | F | 2-Ph—$C_6H_4$ | $CH(CH_3)_2$ | $CH(CH_3)_2$ | 0.26 (A4) |
| 39 | F | 4-F—$C_6H_4(CH_2)_3$ | $CH(CH_3)_2$ | $CH(CH_3)_2$ | 0.13 (A3) |
| 40 | F | 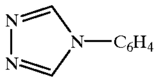 | $CH(CH_3)_2$ | $CH(CH_3)_2$ | 0.13 (A9) |
| 41 | F | (1-naphthyl)$CH_2$ | $CH(CH_3)_2$ | $CH(CH_3)_2$ | 0.14 (A3) |
| 42 | F | 2-naphthyl$(CH_2)_2$ | $CH(CH_3)_2$ | $CH(CH_3)_2$ | 0.15 (A3) |
| 43 | F | 1-naphthyl$(CH_2)_2$ | $CH(CH_3)_2$ | $CH(CH_3)_2$ | 0.15 (A3) |
| 44 | F | $C_6H_5$ | 4-F—$C_6H_4$ | $CH(CH_3)_2$ | 0.54 (A5) |
| 45 | F | 4-F—$C_6H_4$ | 4-F—$C_6H_4$ | $CH(CH_3)_2$ | 0.42 (A5) |
| 46 | F | 4-$CF_3$—$C_6H_4$ | 4-F—$C_6H_4$ | $CH(CH_3)_2$ | 0.40 (A5) |
| 47 | F | 3-$CF_3$—$C_6H_4$ | 4-F—$C_6H_4$ | $CH(CH_3)_2$ | 0.45 (A5) |

TABLE 3(B)-continued

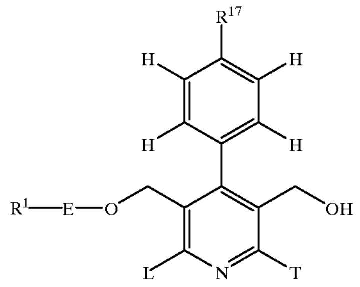

| Ex. | $R^{17}$ | $R^1$-E | T | L | $R_f$ (solvent) |
|---|---|---|---|---|---|
| 48 | F | $2\text{-}CF_3—C_6H_4$ | $4\text{-}F—C_6H_4$ | $CH(CH_3)_2$ | 0.33 (A5) |
| 49 | F | $4\text{-}F—C_6H_4(CH_2)_2$ | $4\text{-}F—C_6H_4$ | $CH(CH_3)_2$ | 0.15 (A3) |
| 50 | H | $2\text{-}CF_3—C_6H_4(CH_2)_2$ | $4\text{-}F—C_6H_4$ | $CH(CH_3)_2$ | 0.41 (A5) |
| 51 | F | $2\text{-}F—C_6H_4(CH_2)_2$ | $4\text{-}F—C_6H_4$ | $CH(CH_3)_2$ | 0.14 (A3) |
| 52 | F | $4\text{-}CF_3—C_6H_4CHCH_3$ | $4\text{-}F—C_6H_4$ | $CH(CH_3)_2$ | 0.11 (A3) |
| 53 | F | $3\text{-}CF_3—C_6H_4(CH_2)_2$ | $4\text{-}F—C_6H_4$ | $CH(CH_3)_2$ | 0.43 (A5) |
| 54 | F | $3\text{-}CF_3—C_6H_4CHCH_3$ | $4\text{-}F—C_6H_4$ | $CH(CH_3)_2$ | 0.42 (A5) |
| 55 | F | 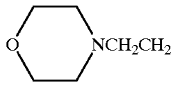 | $4\text{-}F—C_6H_4$ | $CH(CH_3)_2$ | 0.48 (A9) |
| 56 | F | (2-pyridyl)$CH_2$ | $4\text{-}F—C_6H_4$ | $CH(CH_3)_2$ | 0.20 (A9) |
| 57 | F | (3-pyridyl)$CH_2$ | $4\text{-}F—C_6H_4$ | $CH(CH_3)_2$ | 0.19 (A9) |
| 58 | F | $4\text{-}F—C_6H_4(CH_2)_3$ | $4\text{-}F—C_6H_4$ | $CH(CH_3)_2$ | 0.33 (A5) |
| 59 | F | (4-pyridyl)$CH_2$ | $4\text{-}F—C_6H_4$ | $CH(CH_3)_2$ | 0.25 (A11) |
| 60 | F | 2-Ph-$C_6H_4$ | $4\text{-}F—C_6H_4$ | $CH(CH_3)_2$ | 0.38 (A5) |
| 61 | F | 3-Ph-$C_6H_4$ | $4\text{-}F—C_6H_4$ | $CH(CH_3)_2$ | 0.32 (A5) |
| 62 | F | 4-Ph-$C_6H_4$ | $4\text{-}F—C_6H_4$ | $CH(CH_3)_2$ | 0.33 (A5) |
| 63 | F | 2-naphthyl($CH_2$) | $4\text{-}F—C_6H_4$ | $CH(CH_3)_2$ | 0.33 (A5) |
| 64 | F | 1-naphthyl($CH_2$) | $4\text{-}F—C_6H_4$ | $CH(CH_3)_2$ | 0.32 (A5) |
| 65 | F | 2-naphthyl$(CH_2)_2$ | $4\text{-}F—C_6H_4$ | $CH(CH_3)_2$ | 0.34 (A5) |
| 66 | F | 1-naphthyl$(CH_2)_2$ | $4\text{-}F—C_6H_4$ | $CH(CH_3)_2$ | 0.34 (A3) |
| 67 | F | $4\text{-}CF_3O—C_6H_4CH_2$ | $4\text{-}F—C_6H_4$ | $CH(CH_3)_2$ | 0.31 (A5) |
| 68 | F | $3\text{-}CF_3O—C_6H_4CH_2$ | $4\text{-}F—C_6H_4$ | $CH(CH_3)_2$ | 0.34 (A5) |
| 69 | F | $3\text{-}CF_3—C_6H_4(CH_2)_3$ | $4\text{-}F—C_6H_4$ | $CH(CH_3)_2$ | 0.16 (A4) |
| 70 | F | $4\text{-}CF_3O—C_6H_4CH_2$ | $4\text{-}F—C_6H_4$ | cyclo-$C_5H_9$ | 0.35 (A5) |
| 71 | F | $3\text{-}CF_3O—C_6H_4CH_2$ | $4\text{-}F—C_6H_4$ | cyclo-$C_5H_9$ | 0.33 (A5) |
| 72 | F | $3\text{-}CF_3—C_6H_4(CH_2)_3$ | $4\text{-}F—C_6H_4$ | cyclo-$C_5H_9$ | 0.28 (A4) |
| 73 | F | $4\text{-}F—C_6H_4O(CH_2)_2$ | $4\text{-}F—C_6H_4$ | cyclo-$C_5H_9$ | 0.67 (A7) |
| 74 | F | $3\text{-}CF_3—C_6H_4$ | $4\text{-}F—C_6H_4$ | cyclo-$C_5H_9$ | 0.46 (A5) |
| 75 | F | $4\text{-}CF_3—C_6H_4$ | $4\text{-}F—C_6H_4$ | cyclo-$C_5H_9$ | 0.42 (A5) |

TABLE 3(B)-continued

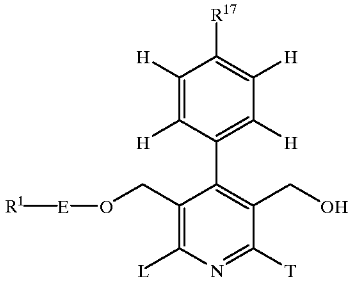

| Ex. | $R^{17}$ | $R^1$-E | T | L | $R_f$ (solvent) |
|---|---|---|---|---|---|
| 76 | F | $3-CF_3—C_6H_4(CH_2)_2$ | $4-F—C_6H_4$ | cyclo-$C_5H_9$ | 0.42 (A5) |
| 77 | F | $3-CF_3O—C_6H_4CH_2$ | $3-CF_3—C_6H_4$ | cyclo-$C_5H_9$ | 0.33 (A5) |
| 78 | F | $3-CF_3—C_6H_4CH_2$ | $4-F—C_6H_4$ | $4-F—C_6H_4$ | 0.20 (A7) |

TABLE 4(B)

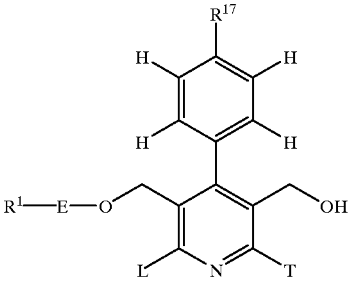

| Ex. | $R^1$-E | T | L | Rf (solvent) |
|---|---|---|---|---|
| 79 | $2-CN—C_6H_4CH_2$ | $CH(CH_3)_2$ | $CH(CH_3)_2$ | 0.16 (A3) |
| 80 | $3-CN—C_6H_4CH_2$ | $CH(CH_3)_2$ | $CH(CH_3)_2$ | 0.10 (A3) |
| 81 | $4-CN—C_6H_4CH_2$ | $CH(CH_3)_2$ | $CH(CH_3)_2$ | 0.10 (A3) |
| 82 | $4-F—C_6H_4CH_2$ | cyclo-$C_3H_5$ | $CH(CH_3)_2$ | 0.46 (A5) |
| 83 | $4-F—C_6H_4CH_2$ | $C_2H_5$ | $CH(CH_3)_2$ | 0.36 (A5) |
| 84 | $C_6H_5CH_2$ | $C_2H_5$ | $CH(CH_3)_2$ | 0.36 (A5) |
| 85 | $4-F—C_6H_4CH_2$ | $CH(CH_3)_2$ | pyrrolidin-1-yl | 0.10 (A3) |
| 86 | $3-CF_3—C_6H_4CH_2$ | $CH(CH_3)_2$ | cyclo-$C_6H_{11}$ | 0.15 (A3) |
| 87 | $4-F—C_6H_4CH_2$ | $CH(CH_3)_2$ | cyclo-$C_6H_{11}$ | 0.15 (A3) |
| 88 | $4-F—C_6H_4CH_2$ | $CH(CH_3)_2$ | $2-CH_3—C_6H_4$ | 0.12 |

TABLE 4(B)-continued

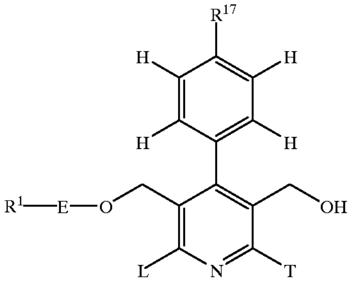

| Ex. | $R^1$-E | T | L | Rf (solvent) |
|---|---|---|---|---|
| | | | | (A3) |
| 89 | $4-F—C_6H_4CH_2$ | $CH(CH_3)_2$ | $4-Cl—C_6H_4$ | 0.19 (A3) |
| 90 | $4-F—C_6H_4CH_2$ | $4-F—C_6H_4(CH_2)_2$ | $CH(CH_3)_2$ | 0.11 (A3) |
| 91 | $3-CF_3—C_6H_4CH_2$ | $4-F—C_6H_4$ | $CF_3$ | 0.24 (A5) |
| 92 | $4-F—C_6H_4CH_2$ | $4-F—C_6H_4$ | $CF_3$ | 0.25 (A5) |
| 93 | $3-CF_3—C_6H_4CH_2$ | $2,4-F_2—C_6H_3$ | cyclo-$C_5H_9$ | 0.18 (A4) |
| 94 | $4-CF_3—C_6H_4CH_2$ | $2,4-F_2—C_6H_3$ | cyclo-$C_5H_9$ | 0.22 (A4) |

TABLE 5(B)

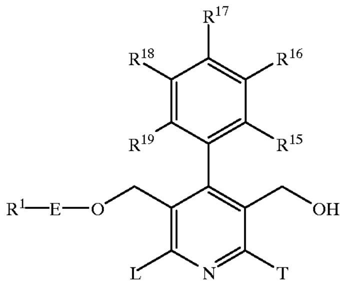

| Ex. | $R^{15}$ | $R^{16}$ | $R^{17}$ | $R^{18}$ | $R^{19}$ | $R^1$-E |
|---|---|---|---|---|---|---|
| 95 | H | H | F | H | H | $C_6H_5CH_2$ |
| 96 | H | H | F | H | H | 4-F—$C_6H_4CH_2$ |
| 97 | H | H | F | H | H | 3-F—$C_6H_4CH_2$ |
| 98 | H | H | F | H | H | 2-F—$C_6H_4CH_2$ |
| 99 | H | H | F | H | H | 4-(benzothiazol-2-yl)-$C_6H_4CH_2$ |
| 100 | H | H | F | H | H | 4-$CF_3O$—$C_6H_4CH_2$ |
| 101 | H | H | F | H | H | 2-naphthyl-$CH_2$ |
| 102 | H | H | F | H | H | 4-[(4-tolyl)$SO_2$]—$C_6H_4CH_2$ |
| 103 | H | H | F | H | H | 4-Cl—$C_6H_4CH_2$ |
| 104 | H | H | F | H | H | 4-$CH_3O$—$C_6H_4CH_2$ |
| 105 | H | H | F | H | H | 3-$CH_3O$—$C_6H_4CH_2$ |
| 106 | H | H | F | H | H | 3,4-$F_2$—$C_6H_3CH_2$ |
| 107 | H | H | F | H | H | 2,4-$F_2$—$C_6H_3CH_2$ |
| 108 | H | H | F | H | H | 2-$CH_3$—$C_6H_4CH_2$ |
| 109 | H | H | F | H | H | 3-$CH_3$—$C_6H_4CH_2$ |
| 110 | H | H | F | H | H | 4-$CH_3$—$C_6H_4CH_2$ |
| 111 | H | H | F | H | H | 4-F—$C_6H_4CHCH_3$ |
| 112 | H | H | F | H | H | 2,6-$(CH_3)_2$-4-($t$-$C_4H_9$)—$C_6H_2CH_2$ |
| 113 | H | H | F | H | H | 4-($i$-$C_3H_7$)—$C_6H_4CH_2$ |
| 114 | H | H | F | H | H | 2,4,6-($i$-$C_3H_7$)$_3$—$C_6H_2CH_2$ |
| 115 | H | H | F | H | H | 3-($C_6H_5O$)-5-$CH_3$—$C_6H_3CH_2$ |
| 116 | H | H | F | H | H | 2,4-$Cl_2$—$C_6H_3CH_2$ |
| 117 | H | H | F | H | H | 3-$CF_3$-4-Cl—$C_6H_3CH_2$ |
| 118 | H | H | F | H | H | 3-$CF_3$—$C_6H_4CH_2$ |
| 119 | H | H | F | H | H | $C_6H_5CH_2$ |
| 120 | H | H | F | H | H | 4-F—$C_6H_4CH_2$ |
| 121 | H | H | F | H | H | 4-F—$C_6H_4CH_2$ |
| 122 | H | H | F | H | H | $C_6H_5CH_2$ |
| 123 | H | H | F | H | H | $C_6H_5CH_2$ |
| 124 | H | H | F | H | H | 4-F—$C_6H_4CH_2$ |
| 125 | H | H | F | H | H | $C_6H_5CH_2$ |
| 126 | H | H | F | H | H | $C_6H_5CH_2$ |
| 127 | H | H | F | H | H | 4-F—$C_6H_4CH_2$ |
| 128 | H | H | F | H | H | 3-F—$C_6H_4CH_2$ |
| 129 | H | H | F | H | H | 2-F—$C_6H_4CH_2$ |
| 130 | H | H | F | H | H | 4-(benzothiazol-2-yl)-$C_6H_4CH_2$ |
| 131 | H | H | F | H | H | 2-naphthyl-$CH_2$ |
| 132 | H | H | F | H | H | 4-$CF_3O$—$C_6H_4CH_2$ |
| 133 | H | H | F | H | H | 4-[4-tolyl)$SO_2$]—$C_6H_4CH_2$ |
| 134 | H | H | F | H | H | 4-F—$C_6H_4CH_2$ |
| 135 | H | H | F | H | H | 4-F—$C_6H_4CH_2$ |
| 136 | H | H | F | H | H | 4-Cl—$C_6H_4CH_2$ |
| 137 | H | H | F | H | H | 4-($i$-$C_3H_7$)—$C_6H_4CH_2$ |
| 138 | H | H | F | H | H | 3-(2-F—$C_6H_4O$)—$C_6H_3CH_2$ |
| 139 | H | H | F | H | H | 3-(4-F—$C_6H_4O$)—$C_6H_3CH_2$ |
| 140 | H | H | F | H | H | 3,4-$F_2$—$C_6H_3CH_2$ |
| 141 | H | H | F | H | H | 2,4-$F_2$—$C_6H_3CH_2$ |
| 142 | H | H | F | H | H | 2-$CH_3$—$C_6H_4CH_2$ |
| 143 | H | H | F | H | H | 3-$CH_3$—$C_6H_4CH_2$ |
| 144 | H | H | F | H | H | 4-$CH_3$—$C_6H_4CH_2$ |
| 145 | H | H | F | H | H | 2-$CF_3$—$C_6H_4CH_2$ |
| 146 | H | H | F | H | H | 4-F—$C_6H_4CHCH_3$ |
| 147 | H | H | F | H | H | 2,4-$Cl_2$—$C_6H_3CH_2$ |
| 148 | H | H | F | H | H | 3-$CF_3$-4-Cl—$C_6H_3CH_2$ |
| 149 | H | H | F | H | H | 3-$CF_3$—$C_6H_4CH_2$ |
| 150 | H | H | F | H | H | 2-Cl-4-$CF_3$—$C_6H_3CH_2$ |
| 151 | H | H | F | H | H | 3-[4-($C_6H_5$)—$C_6H_4O$]$C_6H_4CH_2$ |
| 152 | H | H | F | H | H | 2-F—$C_6H_4CH_2$ |
| 153 | H | H | F | H | H | 3-F—$C_6H_4CH_2$ |
| 154 | H | H | F | H | H | 3-($C_6H_5O$)-5-$CH_3$—$C_6H_3CH_2$ |

TABLE 5(B)-continued

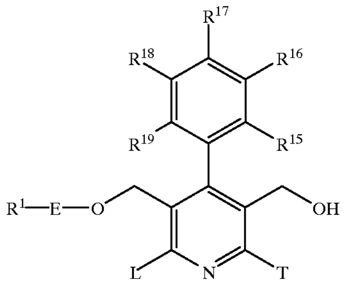

| | | | | | | |
|---|---|---|---|---|---|---|
| 155 | H | H | F | H | H | 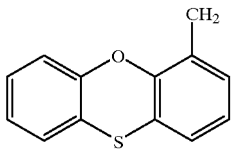 |
| 156 | H | H | F | H | H | 3,5-$(CF_3)_2$—$C_6H_3CH_2$ |
| 157 | H | H | F | H | H | 4-F—$C_6H_4CH_2$ |
| 158 | H | H | F | H | H | 4-F—$C_6H_4CH_2$ |
| 159 | H | H | F | H | H | 3-$CF_3$—$C_6H_4CH_2$ |
| 160 | H | H | F | H | H | 4-F—$C_6H_4CH_2$ |
| 161 | H | H | F | H | H | 4-F—$C_6H_4CH_2$ |
| 162 | H | H | F | H | H | 3-$CH_3$—$C_6H_4CH_2$ |
| 163 | H | H | F | H | H | 4-F—$C_6H_4CH_2$ |
| 164 | H | H | F | H | H | 3,4-$F_2$—$C_6H_3CH_2$ |
| 165 | H | H | F | H | H | 4-F—$C_6H_4CH_2$ |
| 166 | H | H | F | H | H | 4-Cl—$C_6H_4CH_2$ |
| 167 | H | H | F | H | H | 2-$CH_3$—$C_6H_4CH_2$ |
| 168 | H | H | F | H | H | 4-$CH_3$—$C_6H_4CH_2$ |
| 169 | H | H | F | H | H | 3-$CF_3$—$C_6H_4CH_2$ |
| 170 | H | H | F | H | H | 2,4-$Cl_2$—$C_6H_3CH_2$ |
| 171 | H | H | F | H | H | 4-F—$C_6H_4CH_2$ |
| 172 | H | H | F | H | H | 4-F—$C_6H_4CH_2$ |
| 173 | H | H | F | H | H | 3-$CF_3$—$C_6H_4CH_2$ |
| 174 | H | H | F | H | H | 3,4-$F_2$—$C_6H_3CH_2$ |
| 175 | H | H | F | H | H | 2,4-$F_2$—$C_6H_3CH_2$ |
| 176 | H | H | F | H | H | 3,4-$Cl_2$—$C_6H_3CH_2$ |
| 177 | $C_6H_5CH_2O$ | H | F | H | H | 4-F—$C_6H_4CH_2$ |
| 178 | $C_6H_5CH_2O$ | H | F | H | H | 4-F—$C_6H_4CH_2$ |
| 179 | 2-F—$C_6H_4CH_2O$ | H | F | H | H | 4-F—$C_6H_4CH_2$ |
| 180 | 4-F—$C_6H_4CH_2O$ | H | F | H | H | 4-F—$C_6H_4CH_2$ |
| 181 | 4-Cl—$C_6H_4CH_2O$ | H | F | H | H | 4-F—$C_6H_4CH_2$ |
| 182 | H | 2-F—$C_6H_4CH_2O$ | F | H | H | 4-F—$C_6H_4CH_2$ |
| 183 | H | H | F | H | H | 4-F—$C_6H_4CH_2$ |
| 184 | H | H | F | H | H | 3,4-$F_2$—$C_6H_3CH_2$ |
| 185 | H | H | F | H | H | 3-$CF_3$—$C_6H_4CH_2$ |
| 186 | H | H | F | H | H | 3,4-$F_2$—$C_6H_4CH_2$ |
| 187 | H | H | F | H | H | 4-F—$C_6H_4CH_2$ |
| 188 | H | H | F | H | H | 4-F—$C_6H_4CH_2$ |
| 189 | H | H | F | H | H | 3,4-$F_2$—$C_6H_3CH_2$ |
| 190 | H | H | F | H | H | 4-F—$C_6H_4CH_2$ |
| 191 | H | H | F | H | H | 4-F—$C_6H_4CH_2$ |
| 192 | H | H | $OCH_3$ | H | H | 4-F—$C_6H_4CH_2$ |
| 193 | H | H | Cl | H | H | 4-F—$C_6H_4CH_2$ |
| 194 | H | H | Cl | H | H | 3-$CF_3$—$C_6H_4CH_2$ |
| 195 | H | Cl | H | H | H | 4-F—$C_6H_4CH_2$ |
| 196 | H | Cl | H | H | H | 3-$CF_3$—$C_6H_4CH_2$ |
| 197 | H | H | F | H | H | 4-F—$C_6H_4CH_2$ |
| 198 | H | H | F | H | H | 3-$CF_3$—$C_6H_4CH_2$ |
| 199 | H | Cl | Cl | H | H | 4-F—$C_6H_4CH_2$ |
| 200 | H | $CF_3$ | H | H | H | 4-F—$C_6H_4CH_2$ |
| 201 | H | $CH_3$ | H | H | H | 4-F—$C_6H_4CH_2$ |
| 202 | H | $CH_3$ | H | H | H | 3-$CF_3$—$C_6H_4CH_2$ |
| 203 | H | H | $CH_3$ | H | H | 4-F—$C_6H_4CH_2$ |
| 204 | H | Cl | H | Cl | H | 4-F—$C_6H_4CH_2$ |
| 205 | H | $OCH_3$ | H | H | H | 4-F—$C_6H_4CH_2$ |
| 206 | $OCH_3$ | H | H | H | H | 4-F—$C_6H_4CH_2$ |
| 207 | Cl | Cl | H | H | H | 4-F—$C_6H_4CH_2$ |
| 208 | H | $CF_3$ | Cl | H | H | 4-F—$C_6H_4CH_2$ |
| 209 | H | $CF_3$ | F | H | H | 4-F—$C_6H_4CH_2$ |
| 210 | H | Cl | $CF_3$ | H | H | 4-F—$C_6H_4CH_2$ |

TABLE 5(B)-continued

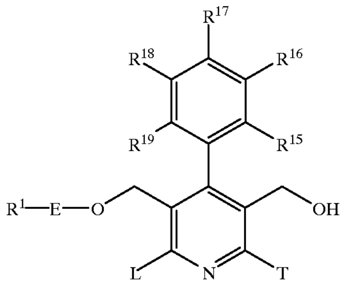

| | | | | | | |
|---|---|---|---|---|---|---|
| 211 | H | H | F | H | H | 4-F—$C_6H_4CH_2$ |
| 212 | H | H | F | H | H | 3,5-$(CF_3)_2$—$C_6H_3CH_2$ |
| 213 | H | H | F | H | H | 3-$CF_3$—$C_6H_4CH_2$ |
| 214 | H | H | F | H | H | 2,4-$Cl_2$—$C_6H_3CH_2$ |
| 215 | H | H | F | H | H | 3-$CF_3$-4-Cl—$C_6H_3CH_2$ |
| 216 | H | H | F | H | H | 4-F—$C_6H_4CH_2$ |
| 217 | H | H | F | H | H | 3-$CF_3$—$C_6H_4CH_2$ |
| 218 | H | H | F | H | H | 2,4-$Cl_2$—$C_6H_3CH_2$ |
| 219 | H | H | F | H | H | 4-F—$C_6H_4CH_2$ |
| 220 | H | H | $CF_3$ | H | H | 4-F—$C_6H_4CH_2$ |
| 221 | H | H | F | H | H | 4-F—$C_6H_4CH_2$ |
| 222 | H | H | F | H | H | 4-F—$C_6H_4CH_2$ |
| 223 | Cl | Cl | H | H | H | 4-F—$C_6H_4CH_2$ |
| 224 | Cl | H | H | H | H | 4-F—$C_6H_4CH_2$ |
| 225 | Cl | H | H | H | H | 4-F—$C_6H_4CH_2$ |
| 226 | Cl | H | Cl | H | H | 4-F—$C_6H_4CH_2$ |
| 227 | Cl | H | Cl | H | H | 4-F—$C_6H_4CH_2$ |
| 228 | H | H | F | H | H | 3-$CF_3$—$C_6H_4CH_2$ |
| 229 | H | H | F | H | H | 4-F—$C_6H_4CH_2$ |
| 230 | H | H | F | H | H | 4-F—$C_6H_4CH_2$ |
| 231 | H | H | F | H | H | 3-$CF_3$—$C_6H_4CH_2$ |
| 232 | H | H | F | H | H | 4-F—$C_6H_4CH_2$ |
| 233 | H | H | F | H | H | 3-$CF_3$—$C_6H_4CH_2$ |
| 234 | H | H | F | H | H | 3-$CF_3$—$C_6H_4CH_2$ |
| 235 | H | H | F | H | H | 4-F—$C_6H_4CH_2$ |
| 236 | H | H | F | H | H | 3-$CF_3$—$C_6H_4CH_2$ |
| 237 | H | H | F | H | H | 4-F—$C_6H_4CH_2$ |
| 238 | H | H | F | H | H | 3-$CF_3$—$C_6H_4CH_2$ |
| 239 | H | H | F | H | H | 4-F—$C_6H_4CH_2$ |
| 240 | H | H | F | H | H | 3-$CF_3$—$C_6H_4CH_2$ |
| 241 | H | H | F | H | H | 4-F—$C_6H_4CH_2$ |
| 242 | H | H | F | H | H | 3-$CF_3$—$C_6H_4CH_2$ |
| 243 | H | H | F | H | H | 4-F—$C_6H_4CH_2$ |
| 244 | H | H | F | H | H | 3-$CF_3$—$C_6H_4CH_2$ |
| 245 | H | H | F | H | H | 4-F—$C_6H_4CH_2$ |
| 246 | H | H | F | H | H | 3-$CF_3$-4-Cl—$C_6H_3CH_2$ |
| 247 | H | H | F | H | H | 2,4-$Cl_2$—$C_6H_3CH_2$ |
| 248 | H | H | F | H | H | 3-$CF_3$—$C_6H_4CH_2$ |
| 249 | H | H | F | H | H | 3-$CF_3$—$C_6H_4CH_2$ |
| 250 | H | H | F | H | H | 4-F—$C_6H_4CH_2$ |
| 251 | H | H | F | H | H | 3-$CF_3$—$C_6H_4CH_2$ |
| 252 | H | H | F | H | H | 4-F—$C_6H_4CH_2$ |
| 253 | H | H | F | H | H | 3-$CF_3$—$C_6H_4CH_2$ |
| 254 | H | H | F | H | H | 4-F—$C_6H_4CH_2$ |
| 255 | H | H | F | H | H | 3-$CF_3$—$C_6H_4CH_2$ |
| 256 | H | H | F | H | H | 4-F—$C_6H_4CH_2$ |
| 257 | H | H | F | H | H | 3-$CF_3$—$C_6H_4CH_2$ |
| 258 | H | H | F | H | H | 3-$CF_3$—$C_6H_4CH_2$ |
| 259 | H | H | F | H | H | 4-F—$C_6H_4CH_2$ |
| 260 | H | H | F | H | H | 3-$CF_3$—$C_6H_4CH_2$ |
| 261 | H | H | F | H | H | 3,5-$(CF_3)_2$—$C_6H_3CH_2$ |
| 262 | H | H | F | H | H | 3-$CF_3$—$C_6H_4CH_2$ |
| 263 | H | H | F | H | H | 4-F—$C_6H_4CH_2$ |
| 264 | H | H | F | H | H | 3-$CF_3$—$C_6H_4CH_2$ |
| 265 | H | H | F | H | H | 4-$CF_3$—$C_6H_4CH_2$ |
| 266 | H | H | F | H | H | 3-$CF_3$—$C_6H_4CH_2$ |
| 267 | H | H | F | H | H | 4-$CF_3$—$C_6H_4CH_2$ |
| 268 | H | H | F | H | H | 3-$CF_3$—$C_6H_4CH_2$ |
| 269 | H | H | F | H | H | 4-$CF_3$—$C_6H_4CH_2$ |
| 270 | H | H | F | H | H | 3-$CF_3$—$C_6H_4CH_2$ |
| 271 | H | H | F | H | H | 4-$CF_3$—$C_6H_4CH_2$ |
| 272 | H | H | F | H | H | 4-$CF_3$—$C_6H_4CH_2$ |
| 273 | H | H | F | H | H | 3-$CF_3$—$C_6H_4CH_2$ |

TABLE 5(B)-continued

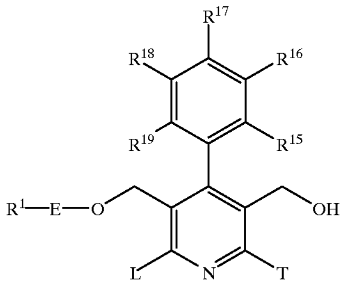

| | | | | | | |
|---|---|---|---|---|---|---|
| 274 | H | H | F | H | H | 3-$CF_3$—$C_6H_4CH_2$ |
| 275 | H | H | F | H | H | 4-$CF_3$—$C_6H_4CH_2$ |
| 276 | H | H | F | H | H | 3-$CF_3$—$C_6H_4CH_2$ |
| 277 | H | H | F | H | H | 4-$CF_3$—$C_6H_4CH_2$ |
| 278 | H | H | F | H | H | 3-$CF_3$—$C_6H_4CH_2$ |
| 279 | H | H | F | H | H | 4-$CF_3$—$C_6H_4CH_2$ |
| 280 | H | H | F | H | H | 3-$CF_3$—$C_6H_4CH_2$ |
| 281 | H | H | F | H | H | 4-$CF_3$—$C_6H_4CH_2$ |
| 282 | H | H | F | H | H | 3-$CF_3$—$C_6H_4CH_2$ |
| 283 | H | H | F | H | H | 4-$CF_3$—$C_6H_4CH_2$ |
| 284 | H | H | F | H | H | 3-$CF_3$—$C_6H_4CH_2$ |

| Ex. | T | L | $R_f$ (solvent) |
|---|---|---|---|
| 95 | $CH(CH_3)_2$ | $CH(CH_3)_2$ | 0.41 (A3) |
| 96 | $CH(CH_3)_2$ | $CH(CH_3)_2$ | 0.20 (A3) |
| 97 | $CH(CH_3)_2$ | $CH(CH_3)_2$ | 0.17 (A3) |
| 98 | $CH(CH_3)_2$ | $CH(CH_3)_2$ | 0.21 (A3) |
| 99 | $CH(CH_3)_2$ | $CH(CH_3)_2$ | 0.09 (A3) |
| 100 | $CH(CH_3)_2$ | $CH(CH_3)_2$ | 0.25 (A3) |
| 101 | $CH(CH_3)_2$ | $CH(CH_3)_2$ | 0.20 (A3) |
| 102 | $CH(CH_3)_2$ | $CH(CH_3)_2$ | 0.13 (A4) |
| 103 | $CH(CH_3)_2$ | $CH(CH_3)_2$ | 0.23 (A4) |
| 104 | $CH(CH_3)_2$ | $CH(CH_3)_2$ | 0.17 (A3) |
| 105 | $CH(CH_3)_2$ | $CH(CH_3)_2$ | 0.27 (A3) |
| 106 | $CH(CH_3)_2$ | $CH(CH_3)_2$ | 0.15 (A3) |
| 107 | $CH(CH_3)_2$ | $CH(CH_3)_2$ | 0.25 (A3) |
| 108 | $CH(CH_3)_2$ | $CH(CH_3)_2$ | 0.30 (A3) |
| 109 | $CH(CH_3)_2$ | $CH(CH_3)_2$ | 0.68 (A5) |
| 110 | $CH(CH_3)_2$ | $CH(CH_3)_2$ | 0.61 (A5) |
| 111 | $CH(CH_3)_2$ | $CH(CH_3)_2$ | 0.21 (A3) |
| 112 | $CH(CH_3)_2$ | $CH(CH_3)_2$ | 0.25 (A3) |
| 113 | $CH(CH_3)_2$ | $CH(CH_3)_2$ | 0.22 (A3) |
| 114 | $CH(CH_3)_2$ | $CH(CH_3)_2$ | 0.36 (A3) |
| 115 | $CH(CH_3)_2$ | $CH(CH_3)_2$ | 0.25 (A3) |
| 116 | $CH(CH_3)_2$ | $CH(CH_3)_2$ | 0.24 (A3) |
| 117 | $CH(CH_3)_2$ | $CH(CH_3)_2$ | 0.19 (A3) |
| 118 | $CH(CH_3)_2$ | $CH(CH_3)_2$ | 0.13 (A3) |
| 119 | $CH(CH_3)_2$ | $CH_3$ | 0.11 (A3) |
| 120 | $CH(CH_3)_2$ | $CH_3$ | 0.29 (A5) |
| 121 | $CH(CH_3)_2$ | $CH_3$ | 0.13 (A11) |
| 122 | $CH_3$ | cyclo-$C_3H_5$ | 0.14 (A3) |
| 123 | $CH(CH_3)_2$ | $CH(CH_3)_2$ | 0.53 (A5) |
| 124 | $CH(CH_3)_2$ | $CH(CH_3)_2$ | 0.47 (A5) |
| 125 | $CH(CH_3)_2$ | cyclo-$C_5H_9$ | 0.57 (A5) |
| 126 | $CH(CH_3)_2$ | $CH(CH_3)_2$ | 0.23 (A3) |
| 127 | $C_6H_5$ | $CH(CH_3)_2$ | 0.43 (A5) |
| 128 | $C_6H_5$ | $CH(CH_3)_2$ | 0.13 (A3) |
| 129 | $C_6H_5$ | $CH(CH_3)_2$ | 0.16 (A3) |
| 130 | $C_6H_5$ | $CH(CH_3)_2$ | 0.33 (A5) |
| 131 | $C_6H_5$ | $CH(CH_3)_2$ | 0.31 (A4) |
| 132 | $C_6H_5$ | $CH(CH_3)_2$ | 0.31 (A4) |
| 133 | $C_6H_5$ | $CH(CH_3)_2$ | 0.15 (A5) |
| 134 | $CH(CH_3)_2$ | 4-F—$C_6H_4$ | 0.46 (A5) |
| 135 | 4-F—$C_6H_4$ | $CH(CH_3)_2$ | 0.57 (A5) |
| 136 | 4-F—$C_6H_4$ | $CH(CH_3)_2$ | 0.21 (A3) |
| 137 | 4-F—$C_6H_4$ | $CH(CH_3)_2$ | 0.20 (A3) |
| 138 | 4-F—$C_6H_4$ | $CH(CH_3)_2$ | 0.44 (A5) |
| 139 | 4-F—$C_6H_4$ | $CH(CH_3)_2$ | 0.41 (A5) |
| 140 | 4-F—$C_6H_4$ | $CH(CH_3)_2$ | 0.17 (A3) |
| 141 | 4-F—$C_6H_4$ | $CH(CH_3)_2$ | 0.18 (A3) |
| 142 | 4-F—$C_6H_4$ | $CH(CH_3)_2$ | 0.09 (A2) |
| 143 | 4-F—$C_6H_4$ | $CH(CH_3)_2$ | 0.22 (A3) |

TABLE 5(B)-continued

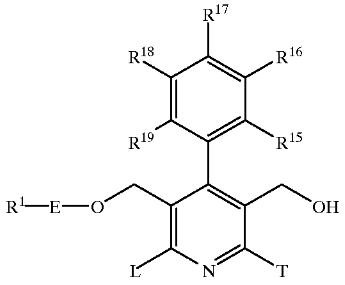

| | | | |
|---|---|---|---|
| 144 | 4-F—$C_6H_4$ | $CH(CH_3)_2$ | 0.23 (A3) |
| 145 | 4-F—$C_6H_4$ | $CH(CH_3)_2$ | 0.12 (A3) |
| 146 | 4-F—$C_6H_4$ | $CH(CH_3)_2$ | 0.28 (A3) |
| 147 | 4-F—$C_6H_4$ | $CH(CH_3)_2$ | 0.23 (A3) |
| 148 | 4-F—$C_6H_4$ | $CH(CH_3)_2$ | 0.16 (A3) |
| 149 | 4-F—$C_6H_4$ | $CH(CH_3)_2$ | 0.48 (A5) |
| 150 | 4-F—$C_6H_4$ | $CH(CH_3)_2$ | 0.35 (A4) |
| 151 | 4-F—$C_6H_4$ | $CH(CH_3)_2$ | 0.19 (A5) |
| 152 | 4-F—$C_6H_4$ | $CH(CH_3)_2$ | 0.42 (A5) |
| 153 | 4-F—$C_6H_4$ | $CH(CH_3)_2$ | 0.46 (A5) |
| 154 | 4-F—$C_6H_4$ | $CH(CH_3)_2$ | 0.46 (A5) |
| 155 | 4-F—$C_6H_4$ | $CH(CH_3)_2$ | 0.42 (A5) |
| 156 | 4-F—$C_6H_4$ | $CH(CH_3)_2$ | 0.28 (A5) |
| 157 | 2-F—$C_6H_4$ | $CH(CH_3)_2$ | 0.36 (A5) |
| 158 | pyrrolidin-1-yl | $CH(CH_3)_2$ | 0.14 (A3) |
| 159 | cyclo-$C_6H_{11}$ | $CH(CH_3)_2$ | 0.58 (A5) |
| 160 | cyclo-$C_6H_{11}$ | $CH(CH_3)_2$ | 0.53 (A5) |
| 161 | 2-$CH_3$—$C_6H_4$ | $CH(CH_3)_2$ | 0.15 (A3) |
| 162 | 4-Cl—$C_6H_4$ | $CH(CH_3)_2$ | 0.19 (A3) |
| 163 | 4-Cl—$C_6H_4$ | $CH(CH_3)_2$ | 0.28 (A3) |
| 164 | 4-Cl—$C_6H_4$ | $CH(CH_3)_2$ | 0.18 (A3) |
| 165 | 4-Cl—$C_6H_4$ | $CH(CH_3)_2$ | 0.20 (A3) |
| 166 | 4-Cl—$C_6H_4$ | $CH(CH_3)_2$ | 0.25 (A3) |
| 167 | 4-Cl—$C_6H_4$ | $CH(CH_3)_2$ | 0.49 (A5) |
| 168 | 4-Cl—$C_6H_4$ | $CH(CH_3)_2$ | 0.51 (A5) |
| 169 | 4-Cl—$C_6H_4$ | $CH(CH_3)_2$ | 0.29 (A4) |
| 170 | 4-Cl—$C_6H_4$ | $CH(CH_3)_2$ | 0.19 (A3) |
| 171 | $CH(CH_3)_2$ | 4-F—$C_6H_4$ | 0.36 (A5) |
| 172 | 4-F—$C_6H_4$ | $CH(CH_3)_2$ | 0.42 (A5) |
| 173 | 4-F—$C_6H_4$ | $CH(CH_3)_2$ | 0.30 (A4) |
| 174 | 4-F—$C_6H_4$ | $CH(CH_3)_2$ | 0.09 (A3) |
| 175 | 4-F—$C_6H_4$ | $CH(CH_3)_2$ | 0.13 (A3) |
| 176 | 4-F—$C_6H_4$ | $CH(CH_3)_2$ | 0.13 (A3) |
| 177 | $CH(CH_3)_2$ | 4-F—$C_6H_4$ | 0.08 (A3) |
| 178 | 4-F—$C_6H_4$ | $CH(CH_3)_2$ | 0.11 (A3) |
| 179 | $CH(CH_3)_2$ | $CH(CH_3)_2$ | 0.11 (A3) |
| 180 | $CH(CH_3)_2$ | $CH(CH_3)_2$ | 0.17 (A3) |
| 181 | $CH(CH_3)_2$ | $CH(CH_3)_2$ | 0.11 (A3) |
| 182 | $CH(CH_3)_2$ | $CH(CH_3)_2$ | 0.17 (A3) |
| 183 | 4-F—$C_6H_4$ | $CH_3$ | 0.10 (A5) |
| 184 | 4-F—$C_6H_4$ | $CH_3$ | 0.31 (A7) |
| 185 | 4-F—$C_6H_4$ | $CH_3$ | 0.28 (A7) |
| 186 | 3-Cl—$C_6H_4$ | $CH(CH_3)_2$ | 0.73 (A7) |
| 187 | 3-Cl—$C_6H_4$ | $CH(CH_3)_2$ | 0.62 (A5) |
| 188 | $CH(CH_3)_2$ | 4-F—$C_6H_4(CH_2)_2$ | 0.31 (A5) |
| 189 | $CH(CH_3)_2$ | 4-F—$C_6H_4(CH_2)_2$ | 0.37 (A5) |
| 190 | 4-F—$C_6H_4CH_2$ | $CH(CH_3)_2$ | 0.22 (A3) |
| 191 | $CH(CH_3)_2$ | 4-F—$C_6H_4CH_2$ | 0.19 (A3) |
| 192 | 4-F—$C_6H_4$ | $CH(CH_3)_2$ | 0.45 (A5) |
| 193 | 4-F—$C_6H_4$ | $CH(CH_3)_2$ | 0.65 (A5) |
| 194 | 4-F—$C_6H_4$ | $CH(CH_3)_2$ | 0.09 (A3) |
| 195 | 4-F—$C_6H_4$ | $CH(CH_3)_2$ | 0.15 (A3) |
| 196 | 4-F—$C_6H_4$ | $CH(CH_3)_2$ | 0.29 (A5) |
| 197 | 4-F—$C_6H_4$ | $CH(C_2H_5)_2$ | 0.29 (A3) |
| 198 | 4-F—$C_6H_4$ | $CH(C_2H_5)_2$ | 0.56 (A5) |
| 199 | 4-F—$C_6H_4$ | $CH(CH_3)_2$ | 0.19 (A3) |
| 200 | 4-F—$C_6H_4$ | $CH(CH_3)_2$ | 0.44 (A5) |
| 201 | 4-F—$C_6H_4$ | $CH(CH_3)_2$ | 0.51 (A5) |
| 202 | 4-F—$C_6H_4$ | $CH(CH_3)_2$ | 0.08 (A3) |
| 203 | 4-F—$C_6H_4$ | $CH(CH_3)_2$ | 0.55 (A5) |
| 204 | 4-F—$C_6H_4$ | $CH(CH_3)_2$ | 0.37 (A3) |
| 205 | 4-F—$C_6H_4$ | $CH(CH_3)_2$ | 0.37 (A5) |
| 206 | 4-F—$C_6H_4$ | $CH(CH_3)_2$ | 0.32 (A5) |

TABLE 5(B)-continued

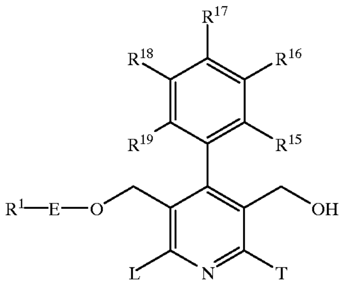

| | | | |
|---|---|---|---|
| 207 | 4-F—$C_6H_4$ | $CH(CH_3)_2$ | 0.19 (A5) |
| 208 | 4-F—$C_6H_4$ | $CH(CH_3)_2$ | 0.43 (A5) |
| 209 | 4-F—$C_6H_4$ | $CH(CH_3)_2$ | 0.44 (A5) |
| 210 | 4-F—$C_6H_4$ | $CH(CH_3)_2$ | 0.54 (A5) |
| 211 | 4-F—$C_6H_4$ | cyclo-$C_5H_9$ | 0.31 (A5) |
| 212 | 4-F—$C_6H_4$ | cyclo-$C_5H_9$ | 0.37 (A5) |
| 213 | 4-F—$C_6H_4$ | cyclo-$C_5H_9$ | 0.23 (A4) |
| 214 | 4-F—$C_6H_4$ | cyclo-$C_5H_9$ | 0.49 (A5) |
| 215 | 4-F—$C_6H_4$ | cyclo-$C_5H_9$ | 0.47 (A5) |
| 216 | 4-F—$C_6H_4$ | cyclo-$C_3H_5$ | 0.34 (A5) |
| 217 | 4-F—$C_6H_4$ | cyclo-$C_3H_5$ | 0.14 (A4) |
| 218 | 4-F—$C_6H_4$ | cyclo-$C_3H_5$ | 0.49 (A5) |
| 219 | 4-F—$C_6H_4$ | $CH(CH_3)_2$ | 0.38 (A5) |
| 220 | 4-F—$C_6H_4$ | $CH(CH_3)_2$ | 0.42 (A5) |
| 221 | 4-F—$C_6H_4$ | 4-F—$C_6H_4$ | 0.33 (A5) |
| 222 | 4-F—$C_6H_4$ | 4-F—$C_6H_4$ | 0.24 (A5) |
| 223 | 4-F—$C_6H_4$ | $CH(CH_3)_2$ | 0.42 (A5) |
| 224 | $CH(CH_3)_2$ | $CH(CH_3)_2$ | 0.33 (A5) |
| 225 | 4-F—$C_6H_4$ | 4-F—$C_6H_4$ | 0.18 (A5) |
| 226 | 4-F—$C_6H_4$ | $CH(CH_3)_2$ | 0.50 (A5) |
| 227 | 4-F—$C_6H_4$ | 4-F—$C_6H_4$ | 0.34 (A5) |
| 228 | 3-$CF_3$—$C_6H_4$ | $CH(CH_3)_2$ | 0.46 (A5) |
| 229 | 3-$CF_3$—$C_6H_4$ | $CH(CH_3)_2$ | 0.47 (A5) |
| 230 | 3-$CH_3$—$C_6H_4$ | $CH(CH_3)_2$ | 0.25 (A4) |
| 231 | 3-$CH_3$—$C_6H_4$ | $CH(CH_3)_2$ | 0.22 (A4) |
| 232 | 4-$CH_3$—$C_6H_4$ | $CH(CH_3)_2$ | 0.32 (A4) |
| 233 | 4-$CH_3$—$C_6H_4$ | $CH(CH_3)_2$ | 0.25 (A4) |
| 234 | 2-Cl—$C_6H_4$ | $CH(CH_3)_2$ | 0.20 (A5) |
| 235 | 2-Cl—$C_6H_4$ | $CH(CH_3)_2$ | 0.21 (A5) |
| 236 | 4-$CH_3O$—$C_6H_4$ | $CH(CH_3)_2$ | 0.26 (A5) |
| 237 | 4-$CH_3O$—$C_6H_4$ | $CH(CH_3)_2$ | 0.27 (A5) |
| 238 | 2-$CH_3O$—$C_6H_4$ | $CH(CH_3)_2$ | 0.18 (A5) |
| 239 | 2-$CH_3O$—$C_6H_4$ | $CH(CH_3)_2$ | 0.21 (A5) |
| 240 | 3-$CH_3O$—$C_6H_4$ | $CH(CH_3)_2$ | 0.14 (A4) |
| 241 | 3-$CH_3O$—$C_6H_4$ | $CH(CH_3)_2$ | 0.15 (A4) |
| 242 | cyclo-$C_6H_{11}$ | 4-F—$C_6H_4$ | 0.40 (A5) |
| 243 | cyclo-$C_6H_{11}$ | 4-F—$C_6H_4$ | 0.45 (A5) |
| 244 | 4-F—$C_6H_4$ | cyclo-$C_6H_{11}$ | 0.37 (A5) |
| 245 | 4-F—$C_6H_4$ | cyclo-$C_6H_{11}$ | 0.43 (A5) |
| 246 | 4-F—$C_6H_4$ | cyclo-$C_6H_{11}$ | 0.29 (A5) |
| 247 | 4-F—$C_6H_4$ | cyclo-$C_6H_{11}$ | 0.35 (A5) |
| 248 | 4-Cl—$C_6H_4$ | cyclo-$C_5H_9$ | 0.56 (A5) |
| 249 | 3-$CF_3$—$C_6H_4$ | cyclo-$C_5H_9$ | 0.44 (A5) |
| 250 | 3-$CF_3$—$C_6H_4$ | cyclo-$C_5H_9$ | 0.41 (A5) |
| 251 | 4-F—$C_6H_4$ | cyclo-$C_4H_7$ | 0.36 (A5) |
| 252 | 4-F—$C_6H_4$ | cyclo-$C_4H_7$ | 0.38 (A5) |
| 253 | cyclo-$C_7H_{13}$ | 4-F—$C_6H_4$ | 0.35 (A5) |
| 254 | cyclo-$C_7H_{13}$ | 4-F—$C_6H_4$ | 0.33 (A5) |
| 255 | 4-F—$C_6H_4$ | cyclo-$C_7H_{13}$ | 0.39 (A5) |
| 256 | 4-F—$C_6H_4$ | cyclo-$C_7H_{13}$ | 0.44 (A5) |
| 257 | furan-2-yl | 4-F—$C_6H_4$ | 0.13 (A5) |
| 258 | 4-F—$C_6H_4$ | furan-2-yl | 0.18 (A5) |
| 259 | 4-F—$C_6H_4$ | (cyclo-$C_5H_9$)$CH_2$ | 0.25 (A5) |
| 260 | 4-F—$C_6H_4$ | (cyclo-$C_5H_9$)$CH_2$ | 0.23 (A5) |
| 261 | 4-F—$C_6H_4$ | (cyclo-$C_5H_9$)$CH_2$ | 0.27 (A5) |
| 262 | 4-F—$C_6H_4$ | (cyclo-$C_6H_{11}$)$CH_2$ | 0.24 (A5) |
| 263 | 4-F—$C_6H_4$ | (cyclo-$C_6H_{11}$)$CH_2$ | 0.25 (A5) |
| 264 | 4-$CF_3$—$C_6H_4$ | cyclo-$C_5H_9$ | 0.40 (A5) |
| 265 | 4-$CF_3$—$C_6H_4$ | cyclo-$C_5H_9$ | 0.30 (A4) |
| 266 | 1-naphthyl | cyclo-$C_5H_9$ | 0.24 (A5) |
| 267 | 1-naphthyl | cyclo-$C_5H_9$ | 0.14 (A4) |
| 268 | 2-naphthyl | cyclo-$C_5H_9$ | 0.32 (A5) |
| 269 | 2-naphthyl | cyclo-$C_5H_9$ | 0.23 (A4) |

TABLE 5(B)-continued

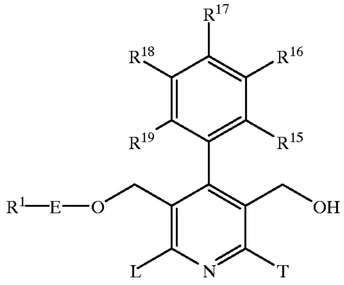

| | | | |
|---|---|---|---|
| 270 | 3-$CH_3$—$C_6H_4$ | cyclo-$C_5H_9$ | 0.22 (A4) |
| 271 | 3-$CH_3$—$C_6H_4$ | cyclo-$C_5H_9$ | 0.21 (A4) |
| 272 | 2-$CF_3$—$C_6H_4$ | cyclo-$C_5H_9$ | 0.13 (A5) |
| 273 | 2-$CF_3$—$C_6H_4$ | cyclo-$C_5H_9$ | 0.18 (A5) |
| 274 | 4-F—$C_6H_4CH_2$ | cyclo-$C_5H_9$ | 0.24 (A5) |
| 275 | 4-F—$C_6H_4CH_2$ | cyclo-$C_5H_9$ | 0.26 (A5) |
| 276 | 3,4-$F_2$—$C_6H_3$ | cyclo-$C_5H_9$ | 0.29 (A4) |
| 277 | 3,4-$F_2$—$C_6H_3$ | cyclo-$C_5H_9$ | 0.30 (A4) |
| 278 | cyclo-$C_5H_9$ | cyclo-$C_5H_9$ | 0.23 (A3) |
| 279 | cyclo-$C_5H_9$ | cyclo-$C_5H_9$ | 0.27 (A3) |
| 280 | 3-$CF_3$—$C_6H_4(CH_2)_2$ | cyclo-$C_5H_9$ | 0.35 (A5) |
| 281 | 3-$CF_3$—$C_6H_4(CH_2)_2$ | cyclo-$C_5H_9$ | 0.33 (A5) |
| 282 | 3-$CF_3$—$C_6H_4(CH_2)_2$ | 3-$CF_3$—$C_6H_4(CH_2)_2$ | 0.20 (A7) |
| 283 | 3-$CF_3$—$C_6H_4(CH_2)_2$ | 3-$CF_3$—$C_6H_4(CH_2)_2$ | 0.20 (A7) |
| 284 | $C_2H_5$ | cyclo-$C_5H_9$ | 0.36 (A6) |

DETAILED DESCRIPTION WITH REFERENCE TO COMPOUNDS OF GENERAL FORMULA (IC)

In the above structural formula (IC) the following terms have the indicated meanings:

The term alkyl means alkyl groups which are straight chain or branched and have the designated number of carbon atoms. Examples of such alkyl groups are methyl, ethyl, propyl, isopropyl, n-butyl, sec-butyl, tertiary butyl, pentyl, isopentyl, hexyl, and isohexyl.

The term cycloalkyl means an alkyl group which is in the form of a ring and contains the designated number of carbon atoms. Examples include the cyclopropyl, cyclobutyl, cyclopentyl, cyclohexyl and cycloheptyl groups.

The term alkoxy means a group in which the alkyl portion is straight or branched and has the designated number of carbon atoms. Examples of such alkoxy groups are methoxy, ethoxy, propoxy, isopropoxy, butoxy, isobutoxy, tertiary butoxy, pentoxy, isopentoxy, hexoxy, and isohexoxy.

The term alkanoyl means groups of formula —C(O)—alkyl in which the alkyl group has the designated number of carbon atoms. Examples include: acetyl, propionyl and butanoyl.

The term alkanoyloxy means groups of formula —OC(O)—alkyl in which the alkyl group has the designated number of carbon atoms. Examples include —OC(O)$CH_3$,—OC(O)$C_2H_5$, and —OC(O)$C_3H_7$.

The term alkoxycarbonyl means groups of formula —C(O)O—alkyl in which the alkyl group has the designated number of carbon atoms. Examples include —C(O)O$CH_3$, —C(O)O$C_2H_5$, and —C(O)O$C_3H_7$.

The term cycloaLkyl-alkyl means groups in which an alkyl group bears a cycloalkyl substituent, and the cycloalkyl and alkyl portions each contain the designated number of carbon atoms. Examples include —$C_2H_4$—$C_5H_9$.

The term phenyl-alkyl means groups in which an alkyl group bears a phenyl substituent, and the alkyl portion contains the designated number of carbon atoms. Examples include —$C_2H_4$—$C_6H_5$.

The term naphthyl-alkyl means groups in which an alkyl group bears a naphthyl substituent, and the alkyl portion contains the designated number of carbon atoms. Examples include —$C_2H_4$—$C_{10}H_7$.

The term pyridyl-alkyl means groups in which an alkyl group bears a pyridyl substituent, and the alkyl portion contains the designated number of carbon atoms. Examples include —$C_2H_4$—pyridyl.

The term alkenyl means straight chain or branched groups having the designated number of carbon atoms and containing a carbon-carbon double bond. Examples include: ethenyl, propen-1-yl, propen-2-yl and penten-1-yl.

The term alkynyl means straight chain or branched groups having the designated number of carbon atoms and containing a carbon-carbon triple bond. Examples include ethynyl, propyn-1-yl and butyn-1-yl.

The term halogen means the halogen atoms fluorine, chlorine, bromine and iodine.

The term "substituted" is defined implicitly by the exemplary substituents disclosed for the various substituted groups in the above discussion of general formula (IC). These lists of exemplary substituents are not intended to be considered as limiting; those skilled in the art will recognize that other similar substituents can also be employed.

Certain of the above defined terms may occur more than once in the formulae employed herein, and upon such occurrence each term shall be defined independently of the other.

Preferred and most preferred groups constituting the compounds of general formula (IC) are as follows:

X preferably represents $CR^8$.

When X is $CR^8$, $R^8$ is preferably hydrogen, halogen, trifluoromethyl or ($C_1$–$C_{10}$) alkyl. $R^8$ is most preferably hydrogen.

$R^{1a}$ and $R^{1b}$ preferably are independently trifluoromethyl, ($C_1$–$C_{10}$)-alkyl, substituted ($C_1$–$C_{10}$)-alkyl, ($C_2$–$C_{10}$)-alkenyl, substituted ($C_2$–$C_{10}$)-alkenyl, ($C_3$–$C_7$)-cycloalkyl, or ($C_3$–$C_7$)-cycloalkenyl. $R^{1a}$ and $R^{1b}$ most preferably are independently ($C_1$–$C_6$)-alkyl or ($C_2$–$C_6$)-alkenyl.

$R^2$ is preferably ($C_1$–$C_{10}$)-alkyl, substituted ($C_1$–$C_{10}$)-alkyl, ($C_2$-$C_{10}$l)-alkenyl or substituted ($C_2$–$C_{10}$)-alkenyl. The substituents on the substituted alkyl and substituted alkenyl $R^2$ groups preferably are independently from 1 to 3 of halogen, phenyl, substituted phenyl, —C(O)$NR^4R^5_1$ or —$S(O)_mR^7$ wherein m is 0, 1, or 2. Most preferably, the substituents are halogen or —$S(O)_mR^7$ wherein m=0.

The groups $R^4$ and $R^5$ are preferably independently hydrogen, ($C_1$–$C_6$) alkyl, ($C_3$–$C_6$)-alkenyl, ($C_3$–$C_7$)-cycloalkyl, phenyl, substituted phenyl, phenyl-($C_1$–$C_6$)-alkyl, substituted phenyl-($C_1$–$C_6$)-alkyl, naphthyl, substituted naphthyl, naphthyl-($C_1$–$C_6$)-alkyl, or substituted naphthyl-($C_1$–$C_6$)-alkyl. $R^4$ and $R^5$ are most preferably independently hydrogen, ($C_1$–$C_6$)-alkyl, ($C_3$–$C_7$)-cycloalkyl, phenyl, substituted phenyl, phenyl ($C_1$–$C_6$)-alkyl or substituted phenyl ($C_1$–$C_6$)-alkyl.

When $R^4$ and $R^5$ are joined together to form —$(CH_2)_rA(CH_2)_s$—, in this linkage it is preferable that the subscripts r and s are independently 1 to 3, and A is $CHR^6$, $NR^6$, O, or $S(O)_n$ wherein n is 0, 1, or 2, and $R^6$ is hydrogen, ($C_1$–$C_6$) alkyl, phenyl, or phenyl ($C_1$–$C_6$) alkyl.

$R^7$ is preferably ($C_1$–$C_6$)-alkyl, phenyl, substituted phenyl, phenyl-($C_1$–$C_6$)-alkyl, substituted phenyl-($C_1$–$C_6$)-alkyl, pyridyl, substituted pyridyl, pyridyl-($C_1$–$C_6$)-alkyl, or substituted pyridyl-($C_1$–$C_6$)-alkyl. $R^7$ is most preferably ($C_1$–$C_6$)-alkyl, phenyl, substituted phenyl, phenyl ($C_1$–$C_6$)-alkyl or substituted phenyl ($C_1$–$C_6$)-alkyl. The substituents on the substituted $R^7$ groups are preferably 1–3 of halogen, trifluoromethyl, or (C1–C6) alkyl.

When $R^2$ and $R^{1b}$ are joined to form an alkylene bridge, this bridge preferably contains 3 or 4 carbon atoms.

$R^3$ is preferably ($C_1$–$C_6$) alkanoyl, substituted ($C_1$–$C_6$)-alkyl, or substituted ($C_3$–$C_6$)-alkenyl, wherein the substitutents are preferably from 1 to 3 hydroxyl groups. Most preferably, $R^3$ is substituted ($C_1$–$C_6$)-alkyl or substituted ($C_3$–$C_6$)-alkenyl where the substitutents are from 1 to 2 hydroxyl groups.

Preferences for the aromatic and heteroaromatic groups Ar of structural formula (IC) are presented below. Compounds of general formula (IC) are further classified into four subsets represented by structural formulae 1A, 1B, 1C, and 1D, which relate respectively to 4-heteroaryl-substituted pyridines, 4aryl-substituted pyridines, heteroaryl-substituted benzenes, and aryl-substituted benzenes.

The 4-heteroaryl pyridine compounds included within formula (IC) have the formula 1A

1A

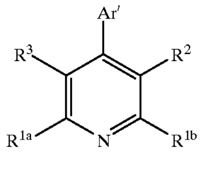

wherein $R^{1a}$ and $R^{1b}$ are independently trifluoromethyl, ($C_1$–$C_{10}$)-alkyl, substituted ($C_1$–$C_{10}$)-alkyl, ($C_2$–$C_{10}$)-alkenyl, substituted ($C_2$–$C_{10}$)-alkenyl, ($C_2$–$C_{10}$)-alkynyl, substituted ($C_2$–$C_{10}$)-alkynyl, ($C_3$–$C_7$)-cycloalkyl, ($C_3$–$C_7$)-cycloalkenyl, or ($C_1$–$C_6$)-alkanoyl. The substituents on the substituted alkyl, substituted alkenyl, and substituted alkynyl $R^{1a}$ and $R^{1b}$ groups are independenfly from 1 to 3 of, for example, —$OR^4$, —C(O)$R^4$, —$CO_2R^4$, —C(O)$NR^4R^5$, —$NR^4R^5$, or phenyl which is optionally substituted with from 1 to 3 of, for example, halogen, ($C_1$–$C_4$)-alkyl, or ($C_1$–$C_4$)-alkoxy groups.

The groups $R^4$ and $R^5$ are independently hydrogen, ($C_1$–$C_6$)-alkyl, ($C_3$–$C_6$)-alkenyl, ($C_3$–$C_7$)-cycloalkyl, ($C_3$–$C_7$)-cydoalkyl-($C_1$–$C_6$)-alkyl, phenyl, substituted phenyl, phenyl-($C_1$–$C_6$)-alkyl, substituted phenyl-($C_1$–$C_6$)-alkyl, naphthyl, substituted naphthyl, naphthyl-($C_1$–$C_6$)-alkyl, or substituted naphthyl-($C_1$–$C_6$)-alkyl. The substitutents on the substituted phenyl or substituted naphthyl $R^4$ and $R^5$ groups are 1 to 3 of, for example, halogen, cyano, trifluoromethyl, ($C_1$–$C_4$)-alkyl, or ($C_1$–$C_4$)-alkoxy groups.

$R^4$ and $R^5$ may be joined together to form —$(CH_2)_rA(CH_2)_s$— wherein the subscripts r and s are independently 1 to 3 and A is $CHR^6$, $NR^6$, O, or $S(O)_n$ in which n is 0, 1, or 2; and R6 is hydrogen, ($C_1$–$C_6$)-alkyl, piperidin-1-yl, phenyl, or phenyl-($C_1$–$C_6$)alkyl.

$R^2$ is ($C_1$–$C_{10}$)-alkyl, substituted ($C_1$–$C_{10}$)-alkyl, ($C_2$–$C_{10}$)-alkenyl, substituted ($C_2$–$C_{10}$)-alkenyl, ($C_2$–$C_{10}$)-alkynyl, substituted ($C_2$–$C_{10}$)-alkynyl, ($C_3$–$C_6$)-cycloalkyl-($C_1$–$C_6$)-alkyl, or substituted ($C_3$–$C_6$cyloalkyl-($C_1$–$C_6$)-alkyl. The substitutents on the substituted alkiyl, substituted alkenyl, substituted alkynyl, and substituted cycloalkyl $R^2$ groups are independently from 1 to 3 of halogen, phenyl, substituted phenyl, 1,3dioxolan-2-yl, —C(O)$NR^4R^5$, or —$S(O)_mR^7$ wherein m is 0, 1, or 2. The substituents on the substituted phenyl $R^2$ substituent group are from 1 to 3 of, for example, halogen, ($C_1$–$C_4$)-alkyl, or ($C_1$–$C_4$)-alkoxy.

$R^7$ is ($C_1$–$C_6$)-alkyl, phenyl, substituted phenyl, phenyl-($C_1$–$C_6$)-alkyl, substituted phenyl-($C_1$–$C_6$)-alkyl, pyridyl, substituted pyridyl, pyridyl-($C_1$–$C_6$)-alkyl, substituted pyridyl-($C_1$–$C_6$)-alkyl, naphthyl, substituted naphthyl, naphthyl-($C_1$–$C_6$)-alkyl, or substituted naphthyl-($C_1$–$C_6$)-alkyl. The substitutents on the substituted phenyl, substituted pyridyl or substituted naphthyl $R^7$ groups are from 1 to 5 of, for example, halogen, trifluoromethyl, ($C_1$–$C_6$)-alkyl, ($C_1$–$C_6$)-alkoxy, nitro, cyano, or hydroxy.

$R^2$ and $R^{1b}$ may be joined to form an alkylene bridge containing from 3 to 5 carbon atoms, between the ring carbon atoms to which $R^2$ and $R^{1b}$ are attached.

$R^3$ is hydroxy, trifluoroacetyl, ($C_1$–$C_6$)-alkanoyl, substituted ($C_1$–$C_6$)-alkyl, or substituted ($C_3$–$C_6$)-alkenyl. The substitutents on the substituted alkyl and substituted alkenyl $R^3$ groups from 1 to 3 hydroxy or trifluoromethyl groups.

Ar' is an optionally substituted heteroaromatic ring. Examples of possible Ar' groups are pyridyls, furanyls, thiophenyls, pyrrolyls, imidazolyls, pyrazolyls, triazolyls, tetrazolyls, oxazolyls, isoxazolyls, thiazolyls and isothiazolyls. The optional substitutents on the group Ar' are independently 1 to 3 of, for example, halogen, ($C_1$–$C_6$)-alkyl, substituted ($C_1$–$C_6$)-alkyl, ($C_2$–$C_6$)-alkenyl, substituted ($C_2$–$C_6$)-alkenyl, ($C_2$–$C_6$)-alkynyl, substituted ($C_2$–$C_6$)-alkynyl, ($C_3$–$C_7$)-cycloalkyl, cyano, nitro, trifluoromethyl, —$OR^4$ C(O)$R^4$, —OC(O)$R^4$, —$CO_2R^4$, —$NR^4R^5$, —C(O)$NR^4R^5$, or —$S(O)_mR^7$. The substituents on the substituted alkyl, substituted alkenyl, and substituted alkynyl substituent groups on Ar' are from 1 to 3 of, for example, halogen, hydroxy, —$NR^4R^5$, phenyl, or substituted phenyl in which the phenyl group may bear, for example, one or more halogen, ($C_1$–$C_4$) alkyl, or ($C_1$–$C_4$) alkoxy groups.

Pharmaceutically acceptable salts of these materials are within the scope of the invention.

In formula 1A, the preferred and most preferred groups $R^{1a}$, $R^{1b}$, $R^2$, $R^3$, as well as the additional groups $R^4$, $R^5$, $R^6$, and $R^7$ embedded therein, and the various substituent groups thereon, are as defined in connection with general formula (IC) above.

In formula 1A, heteroaromatic ring Ar' is preferably selected from the group consisting of pyridyls, furanyls, thiophenyls, pyrazolyls, triazolyls, oxazolyls and thiazolyls, and the optional substitutents on Ar' are preferably independently from 1 to 3 of, for example, halogen, ($C_1$–$C_6$)-alkyl, ($C_2$–$C_6$)-alkenyl, ($C_2$–$C_6$)-alkynyl, ($C_3$–$C_7$)-cycloalkyl, cyano, —$OR^4$, or —$OC(O)R^4$ where $R^4$ is hydrogen, ($C_1$–$C_6$) alkyl, phenyl ($C_1$–$C_6$) alkyl or substituted phenyl ($C_1$–$C_6$) alkyl where the phenyl substitutents are from 1 to 3 of halogen or ($C_1$–$C_4$) alkyl. Heteroaromatic ring Ar' is most preferably selected from the group consisting of pyridyls, furanyls and thiophenyls, and the optional substitutents thereon are most preferably independently from 1 to 3 of, for example, halogen, ($C_1$–$C_6$)-alkyl, ($C_2$-$C_6$)-alkenyl, —$OR^4$, or —$OC(O)R^4$ where $R^4$ is hydrogen or ($C_1$–$C_6$) alkyl.

The 4-aryl-substituted pyridines included within formula (IC) have the formula 1B

1B

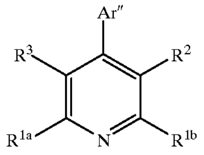

wherein $R^{1a}$ and $R^{1b}$ are independently trifluoromethyl, ($C_1$–$C_{10}$)-alkyl, substituted ($C_1$–$C_{10}$)-alkyl, ($C_2$–$C_{10}$)-alkenyl, substituted ($C_2$–$C_{10}$)-alkenyl, ($C_2$–$C_{10}$)-alkynyl, substituted ($C_2$–$C_{10}$)-alkynyl, ($C_3$–$C_7$)-cycloalkyl, ($C_3$–$C_7$)-cycloalkenyl, or ($C_1$–$C_6$)-alkanoyl. The substituents on the substituted alkyl, substituted alkenyl, and substituted alkynyl $R^{1a}$ and $R^{1b}$ groups are independently from 1 to 3 of, for example, —$OR^4$, —C(O) $R^4$, —$CO_2R^4$, —$C(O)NR^4R^5$, -$NR^4R^5$, or phenyl which is optionally substituted with from 1 to 3 halogen, ($C_1$–$C_4$)-alkyl, or ($C_1$–$C_4$)-alkoxy groups.

The groups $R^4$ and $R^5$ are independently hydrogen, ($C_1$–$C_6$)alkyl, ($C_3$–$C_6$)-alkenyl, ($C_3$–$C_7$)-cycloalkyl, ($C_3$–$C_7$)-cycloalkyl-($C_1$–$C_6$)-alkyl, phenyl, substituted phenyl, phenyl-($C_1$–$C_6$)-alkyl, substituted phenyl-($C_1$–$C_6$)-alkyl, naphthyl, substituted naphthyl, naphthyl-($C_1$–$C_6$)-alkyl, or substituted naphthyl-($C_1$–$C_6$)-alkyl. The substitutents on the substituted phenyl or substituted naphthyl $R^4$ and $R^5$ groups are 1 to 3 of, for example, halogen, cyano, trifluoromethyl, ($C_1$–$C_4$)-alkyl, or ($C_1$–$C_4$)-alkoxy groups.

$R^4$ and $R^5$ may be joined together to form —$(CH_2)_rA(CH_2)_s$— wherein the subscripts r and s are independently 1 to 3 and A is $CHR^6$, $NR^6$, O, or $S(O)_n$ in which n is 0, 1, or 2; and $R^6$ is hydrogen, ($C_1$–$C_6$)-alkyl, piperidin-1-yl, phenyl, or phenyl-($C_1$–$C_6$)-alkyl.

$R^2$ is ($C_1$–$C_{10}$-alkyl, substituted ($C_1$–$C_{10}$)-alkyl, ($C_2$–$C_{10}$)-alkenyl, substituted ($C_2$–$C_{10}$)-alkenyl, ($C_2$–$C_{10}$)-alkynyl, substituted ($C_2$-$C_{10}$)-alkynyl, ($C_3$–$C_6$)-cycloalkyl-($C_1$–$C_6$)-alkyl, or substituted ($C_3$–$C_6$)-cycloalkyl-($C_1$–$C_6$)-alkyl. The substitutents on the substituted alkyl, substituted alkenyl, substituted alkynyl, and substituted cycloalkyl $R^2$ groups are independently from 1 to 3 of halogen, phenyl, substituted phenyl, 1,dioxolan-2-yl, —$C(O)NR^4R^5$, or —$S(O)_mR^7$ wherein m is 0, 1, or 2. The substituents on the substituted phenyl $R^2$ substituent group are from 1 to 3 of, for example, halogen, ($C_1$–$C_4$)alkyl, or ($C_1$–$C_4$)-alkoxy.

$R^7$ is ($C_1$–$C_6$)-alkyl, phenyl, substituted phenyl, phenyl-($C_1$–$C_6$)-alkyl, substituted phenyl-($C_1$–$C_6$)-alkyl, pyridyl, substituted pyridyl, pyridyl-($C_1$–$C_6$)-alkyl, substituted pyridyl-($C_1$–$C_6$)-alkyl, naphthyl, substituted naphthyl, naphthyl-($C_1$–$C_6$)-alkyl, or substituted naphthyl-($C_1$–$C_6$)-alkyl. The substitutents on the substituted phenyl, substituted pyridyl or substituted naphthyl $R^7$ groups are from 1 to 5 of, for example, halogen, trifluoromethyl, ($C_1$–$C_6$)-alkyl, ($C_1$–$C_6$)-alkoxy, nitro, cyano, or hydroxy.

$R^2$ and $R^{1b}$ may be joined to form an alkylene bridge containing from 3 to 5 carbon atoms, between the ring carbon atoms to which $R^2$ and $R^{1b}$ are attached.

$R^3$ is hydroxy, trifluoroacetyl, ($C_1$–$C_6$)-alkanoyl, substituted ($C_1$–$C_6$)-alkyl, or substituted ($C_3$–$C_6$)-alkenyl. The substitutents on the substituted alkyl and substituted alkenyl $R^3$ groups are from 1 to 3 hydroxy or trifluoromethyl groups.

Ar" is an optionally substituted aromatic ring. Examples of possible Ar" groups are phenyls and naphthyls. The optional substitutents on the group Ar" are independently 1 to 3 of, for example, halogen, ($C_1$–$C_6$)-alkyl, substituted ($C_1$–$C_6$)-alkyl, ($C_2$–$C_6$)-alkenyl, substituted ($C_2$–$C_6$)-alkenyl, ($C_2$–$C_6$)-alkynyl, substituted ($C_2$–$C_6$)-alkynyl, ($C_3$–$C_7$)-cycloalkyl, cyano, nitro, trifluoromethyl, —$OR^4$, —$C(O)R^4$, —$OC(O)R^4$, —$CO_2R^4$, —$NR^4R^5$, —$C(O)NR^4R^5$, or —$S(O)_mR^7$. The substitutents on the subsfituted alkyl, substituted alkenyl, and substituted alkynyl substituent groups on Ar" are from 1 to 3 of, for example, halogen, hydroxy, —$NR^4R^5$, phenyl, or substituted phenyl in which the phenyl group may bear, for example, one or more halogen, ($C_1$–$C_4$) alkyl, or ($C_1$–$C_4$) alkoxy groups.

Pharmaceutically acceptable salts of these materials are within the scope of the invention.

In formula 1B, the preferred and most preferred groups $R^{1a}$, $R^{1b}$, $R^2$, $R^3$, as well as the additional groups $R^4$, $R^5$, $R^6$, and $R^7$ embedded therein, and the various substituent groups thereon, are as defined in connection with general formula (IC) above.

In formula 1B, aromatic ring Ar" preferably is a phenyl ring wherein the optional substitutents are preferably independently from 1 to 3 of, for example, rhalogen, ($C_1$–$C_6$)-alkyl, ($C_2$–$C_6$)-alkenyl, ($C_2$–$C_6$)-alkynyl, ($C_3$–$C_7$)-cycloalkyl, cyano, —$OR^4$ or —$OC(O)R^4$, where $R^4$ is hydrogen, ($C_1$–$C_6$) alkyl, phenyl ($C_1$–$C_6$) alkyl or substituted phenyl ($C_1$–$C_6$) alkyl where the phenyl substitutents are from 1 to 3 of halogen or ($C_1$–$C_4$) alkyl. Most preferably, the optional substitutents are from 1 to 3 of, for example, halogen, ($C_1$–$C_6$)-alkyl, ($C_2$–$C_6$)-alkenyl, —$OR^4$ or —OC (O)$R^4$, where $R^4$ is hydrogen or ($C_1$–$C_6$) alkyl.

The heteroaryl-substituted benzenes included within formula (IC) have the formula 1C

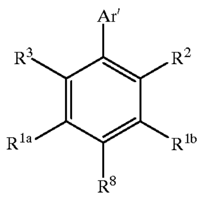

1C wherein $R^8$ represents hydrogen, halogen, trifluoromethyl, phenyl, substituted phenyl, ($C_1$–$C_{10}$)-alkyl, substituted ($C_1$–$C_{10}$)-alkyl, ($C_1$–$C_6$)-alkoxy, ($C_3$–$C_7$)-cycloalkyl, phenyl-($C_1$–$C_3$)-alkoxy, ($C_1$–$C_6$)-alkanoyloxy, ($C_1$–$C_6$)-alkoxycarbonyl, carboxy, formyl, or —$NR^4R^5$. The substituents on the substituted phenyl or substituted alkyl $R^8$ groups are from 1 to 3 of, for example, hydroxy, fluoro, ($C_1$–$C_6$)-alkoxy, ($C_3$–$C_7$)-cycloalkyl, phenyl, phenyl-($C_1$–$C_3$)-alkoxy, ($C_1$–$C_6$)-alkanoyloxy, ($C_1$–$C_6$)-alkoxycarbonyl, carboxy, formyl, or —$NR^4R^5$.

The groups $R^4$ and $R^5$ are independently hydrogen, ($C_1$–$C_6$)-alkyl, ($C_3$–$C_6$)-alkenyl, ($C_3$–$C_7$)-cycloalkyl, ($C_3$–$C_7$)-cycloalkyl-($C_1$–$C_6$)-alkyl, phenyl, substituted phenyl, phenyl-($C_1$–$C_6$)-alkyl, substituted phenyl-($C_1$–$C_6$)-alkyl, naphthyl, substituted naphthyl, naphthyl-($C_1$–$C_6$)-alkyl, or substituted naphthyl-($C_1$–$C_6$)-alkyl. The substitutents on the substituted phenyl or substituted naphthyl $R^4$ and $R^5$ groups are 1 to 3 of, for example, halogen, cyano, trifluoromethyl, ($C_1$–$C_4$)-alkyl, or ($C_1$–$C_4$)-alkoxy groups.

$R^4$ and $R^5$ may be joined together to form —$(CH_2)_rA(CH_2)_s$— wherein the subscripts r and s are independently 1 to 3 and A is $CHR^6$, $NR^6$, O, or $S(O)_n$ in which n is 0, 1, or 2; and $R^6$ is hydrogen, ($C_1$–$C_6$)-alkyl, piperidin-1-yl, phenyl, or phenyl-($C_1$–$C_6$)-alkyl.

$R^{1a}$ and $R^{1b}$ are independently trifluoromethyl, ($C_1$–$C_{10}$)-alkyl, substituted ($C_1$–$C_{10}$)-alkyl, ($C_2$–$C_{10}$)-alkenyl, substituted ($C_2$–$C_{10}$)-alkenyl, ($C_2$–$C_{10}$)-alkynyl, substituted ($C_2$–$C_{10}$)-alkynyl, ($C_3$–$C_7$)-cycloalkyl, ($C_3$–$C_7$)-cycloalkenyl, or ($C_1$–$C_6$)-alkanoyl. The substituents on the substituted alkyl, substituted alkenyl, and substituted alkynyl $R^{1a}$ and $R^{1b}$ groups are independently from 1 to 3 of, for example, —$OR^4$, —$C(O)R^4$, —$CO_2R^4$, —$C(O)NR^4R^5$, —$NR^4R_5$ or phenyl which is optionally substituted with from 1 to 3 of, for example, halogen, ($C_1$–$C_4$)-alkyl, or ($C_1$–$C_4$)-alkoxy groups.

$R^2$ is ($C_1$–$C_{10}$)-alkyl, substituted ($C_1$–$C_{10}$)-alkyl, ($C_2$–$C_{10}$)-alkenyl, substituted ($C_2$–$C_{10}$)-alkenyl, ($C_2$–$C_{10}$)-alkynyl, substituted ($C_2$–$C_{10}$)-alkynyl, ($C_3$–$C_6$)-cycloalkyl-($C_1$–$C_6$)-alkyl, or substituted ($C_3$–$C_6$)-cycloalkyl-($C_1$–$C_6$)-alkyl. The substitutents on the substituted alkyl, substituted alkenyl, substituted alkynyl, and substituted cycloalkyl $R^2$ groups are independently from 1 to 3 of halogen, phenyl, substituted phenyl, 1,3dioxolan-2-yl, —$C(O)NR^4R^5$, or —$S(O)_mR^7$ wherein m is 0, 1, or 2. The substituents on the substituted phenyl $R^2$ substituent group are from 1 to 3 of, for example, halogen, ($C_1$–$C_4$)-alkyl, or ($C_1$–$C_4$)-alkoxy.

$R^7$ is ($C_1$–$C_6$)-alkyl, phenyl, substituted phenyl, phenyl-($C_1$–$C_6$)-alkyl, substituted phenyl-($C_1$–$C_6$)-alkyl, pyridyl, substituted pyridyl, pyridyl-($C_1$–$C_6$)-alkyl, substituted pyridyl-($C_1$–$C_6$)-alkyl, naphthyl, substituted naphthyl, naphthyl-($C_1$–$C_6$)-alkyl, or substituted naphthyl-($C_1$–$C_6$)-alkyl. The substitutents on the substituted phenyl, substituted pyridyl or substituted naphthyl $R^7$ groups are from 1 to 5 of, for example, halogen, trifluoromethyl, ($C_1$–$C_6$)-alkyl, ($C_1$–$C_6$)-alkoxy, nitro, cyano, or hydroxy.

$R^2$ and $R^{1b}$ may be joined to form an alkylene bridge containing from 3 to 5 carbon atoms, between the ring carbon atoms to which $R^2$ and $R^{1b}$ are attached.

$R^3$ is hydroxy, trifluoroacetyl, ($C_1$–$C_6$)-alkanoyl, substituted ($C_1$–$C_6$)-alkyl, or substituted ($C_3$–$C_6$)-alkenyl. The substitutents on the substituted alkyl and substituted alkenyl $R^3$ groups are from 1 to 3 hydroxy or trifluoromethyl groups.

Ar' is an optionally substituted heteroaromatic ring. Examples of possible Ar' groups are: pyridyls, furanyls, thiophenyls, pyrrolyls, imidazolyls, pyrazolyls, triazolyls, tetrazolyls, oxazolyls, isoxazolyls, thiazolyls and isothiazolyls. The optional substitutents on the group Ar' are independently 1 to 3 of, for example, halogen, ($C_1$–$C_6$)-alkyl, substituted ($C_1$–$C_6$)-alkyl, ($C_2$-$C_6$)-alkenyl, substituted ($C_2$–$C_6$)-alkenyl, ($C_2$–$C_6$)-alkynyl, substituted ($C_2$–$C_6$)-alkynyl, ($C_3$-$C_7$)-cycloalkyl, cyano, nitro, trifluoromethyl, —$OR^4$, —$C(O)R^4$, —$OC(O)R^4$, —$CO_2R^4$, —$NR^4R^5$, —$C(O)NR^4R^5$, or —$S(O)_mR^7$. The substitutents on the substituted alkyl, substituted alkenyl, and substituted alkynyl substituent groups on Ar' are from 1 to 3 of, for example, halogen, hydroxy, —$NR^4R^5$, phenyl, or substituted phenyl in which the phenyl group may bear, for example, one or more halogen, ($C_1$–$C_4$)-alkyl, or ($C_1$–$C_4$)-alkoxy groups.

Pharmaceutically acceptable salts of these materials are within the scope of the invention.

In formula 1C, the preferred and most preferred groups $R^{1a}$, $R^{1b}$, $R^2$, $R^3$, and $R^8$, as well as the additional groups $R^4$, $R^5$, $R^6$, and $R^7$ embedded therein, and the various substituent groups thereon, are as defined in connection with general formula (IC) above.

In formula 1C, heteroaromatic ring Ar' is preferably selected from the group consisting of pyridyls, furanyls, thiophenyls, pyrazolyls, triazolyls, oxazolyls and thiazolyls, and the optional substitutents on the group Ar' are preferably independently from 1 to 3 of, for example, halogen, ($C_1$–$C_6$)-alkyl, ($C_2$–$C_6$)-alkenyl, ($C_2$–$C_6$)-alkynyl, ($C_3$–$C_7$)-cycloalkyl, cyano, —$OR^4$, or —$OC(O)R^4$, where $R^4$ is hydrogen, ($C_1$–$C_6$) alkyl, phenyl ($C_1$–$C_6$) alkyl or substituted phenyl ($C_1$–$C_6$) alkyl where the phenyl substitutents are from 1 to 3 of halogen or ($C_1$–$C_4$) alkyl. Heteroaromatic ring Ar' is most preferably selected from the group consisting of pyridyls, furanyls and thiophenyls, and the optional substitutents thereon are most preferably independently from 1 to 3 of, for example, halogen, ($C_1$–$C_6$) alkyl, ($C_2$–$C_6$) alkenyl, —$OR^4$, or $OC(O)R^4$, where $R^4$ is hydrogen or ($C_1$–$C_6$) alkyl.

The aryl-substituted benzenes included within formula (IC) have the formula 1D

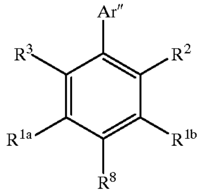

1D wherein $R^8$ represents hydrogen, halogen, trifluoromethyl, phenyl, substituted phenyl, $(C_1-C_{10})$-alkyl, substituted $(C_1-C_{10})$-alkyl, $(C_1-C_6)$-alkoxy, $(C_3-C_7)$-cycloalkyl, phenyl-$(C_1-C_3)$-alkoxy, $(C_1-C_6)$-alkanoyloxy, $(C_1-C_6)$-alkoxycarbonyl, carboxy, formyl, or —$NR^4R^5$. The substituents on the substituted phenyl or substituted alkyl $R^8$ groups are from 1 to 3 of, for example, hydroxy, fluoro, $(C_1-C_6)$-alkoxy, $(C_3-C_7)$-cycloalkyl, phenyl, phenyl-$(C_1-C_3)$-alkoxy, $(C_1-C_6)$-alkanoyloxy, $(C_1-C_6)$-alkoxycarbonyl, carboxy, formyl, or —$NR^4R^5$.

The groups $R^4$ and $R^5$ are independently hydrogen, $(C_1-C_6)$-alkyl, $(C_3-C_6)$-alkenyl, $(C_3-C_7)$-cycloalkyl, $(C_3-C_7)$-cycloalkyl-$(C_1-C_6)$alkyl, phenyl, substituted phenyl, phenyl-$(C_1-C_6)$-alkyl, substituted phenyl-$(C_1-C_6)$-alkyl, naphthyl, substituted naphthyl, naphthyl-$(C_1-C_6)$-alkyl, or substituted naphthyl-$(C_1-C_6)$-alkyl. The substitutents on the substituted phenyl or substituted naphthyl $R^4$ and $R^5$ groups are 1 to 3 of, for example, halogen, cyano, trifluoromethyl, $(C_1-C_4)$-alkyl, or $(C_1-C_4)$-alkoxy groups.

$R^4$ and $R^5$ may be joined together to form —$(CH_2)_rA(CH_2)_s$— wherein the subscripts r and s are independently 1 to 3 and A is $CHR^6$, $NR^6$, O, or $S(O)_n$ in which n is 0, 1, or 2; and $R^6$ is hydrogen, $(C_1-C_6)$-alkyl, piperidin-1-yl, phenyl, or phenyl-$(C_1-C_6)$-alkyl.

$R^{1a}$ and $R^{1b}$ are independently trifluoromethyl, $(C_1-C_{10})$-alkyl, substituted $(C_1-C_{10})$-alkyl, $(C_2-C_{10})$-alkenyl, substituted $(C_2-C_{10})$-alkenyl, $(C_2-C_{10})$-alkynyl, substituted $(C_2-C_{10})$-alkynyl, $(C_3-C_7)$-cycloakyl, $(C_3-C_7)$ cycloalkenyl, or $(C_1-C_6)$-alkanoyl. The substituents on the substituted alkyl, substituted alkenyl, and substituted alkynyl $R^{1a}$ and $R^{1b}$ groups are independently from 1 to 3 of, for example, —$OR^4$, —$C(O)R^4$, —$CO_2R^4$, —$C(O)NR^4R^5$, —$NR^4R^5$, or phenyl which is optionally substituted with from 1 to 3 of, for example, halogen, $(C_1-C_4)$-alkyl, or $(C_1-C_4)$-alkoxy groups.

$R^2$ is $(C_1-C_{10})$-alkyl, substituted $(C_1-C_{10})$-alkyl, $(C_2-C_{10})$-alkenyl, substituted $(C_2-C_{10})$-alkenyl, $(C_2-C_{10})$-alkynyl, substituted $(C_2-C_{10})$-alkynyl, $(C_3-C_6)$-cycloalkyl-$(C_1-C_6)$-alkyl, or substituted $(C_3-C_6)$-cycloalkyl-$(C_1-C_6)$-aklyl. The substitutents on the substituted alkyl, substituted alkenyl, substituted alkynyl, and substituted cycloalkyl $R^2$ groups are independently from 1 to 3 of halogen, phenyl, substituted phenyl, 1,3-dioxolan-2-yl, —$C(O)NR^4R^5$, or —$S(O)_mR^7$ wherein m is 0, 1, or 2. The substituents on the substituted phenyl $R^2$ substituent group are from 1 to 3 of, for example, halogen, $(C_1-C_4)$-alkyl, or $(C_1-C_4)$ alkoxy.

$R^7$ is $(C_1-C_6)$-alkyl, phenyl, substituted phenyl, phenyl-$(C_1-C_6)$-alkyl, substituted phenyl-$(C_1-C_6)$-alkyl, pyridyl, substituted pyridyl, pyridyl-(Cl-C6)-alkyl, substituted pyridyl-$(C_1-C_6)$-alkyl, naphthyl, substituted naphthyl, naphthyl-$(C_1-C_6)$-alkyl, or substituted naphthyl-$(C_1-C_6)$-alkyl. The substitutents on the substituted phenyl, substituted pyridyl or substituted naphthyl $R^7$ groups are from 1 to 5 of, for example, halogen, trifluoromethyl, $(C_1-C_6)$-alkyl, $(C_1-C_6)$-alkoxy, nitro, cyano, or hydroxy.

$R^2$ and $R^{1b}$ may be joined to form an alkylene bridge containing from 3 to 5 carbon atoms, between the ring carbon atoms between the ring carbon atoms to which $R^2$ and $R^{1b}$ are attached.

$R^3$ is hydroxy, trifluoroacetyl, $(C_1-C_6)$-alkanoyl, substituted $(C_1-C_6)$-alkyl, or substituted $(C_3-C_6)$-alkenyl. The substitutents on the substituted alkyl and substituted alkenyl $R^3$ groups are from 1 to 3 hydroxy or trifluoromethyl groups.

Ar" is an optionally substituted aromatic ring. Examples of possible Ar" groups are phenyls and naphthyls. The optional substitutents on the group Ar are independently 1 to 3 of, for example, halogen, $(C_1-C_6)$-alkyl, substituted $(C_1-C_6)$-alkyl, $(C_2-C_6)$-alkenyl, substituted $(C_2-C_6)$alkenyl, $(C_2-C_6)$-alkynyl, substituted $(C_2-C_6)$-alkynyl, $(C_3-C_7)$cycloalkyl, cyano, nitro, trifluoromethyl, —$OR^4$, —$C(O)R^4$, —$OC(O)R^4$, —$CO_2{}^4$, —$NR^4R^5$, —$C(O)NR^4R^5{}_1$ or —$S(O)_mR^7$. The substitutents on the substituted alkyl, substituted alkenyl, and substituted alkynyl substituent groups on Ar are from 1 to 3 of, for example, halogen, hydroxy, —$NR^4R^5$, phenyl, or substituted phenyl in which the phenyl group may bear, for example, one or more halogen, $(C_1-C_4)$-alkyl, or $(C_1-C_4)$-alkoxy groups.

Pharmaceutically acceptable salts of these materials are within the scope of the invention.

In formula ID, the preferred and most preferred groups $R^{1a}$, $R^{1b}$, $R^2$, $R^3$, and $R^8$, as well as the additional groups $R^4$, $R^5$, $R^6$, and $R^7$ embedded therein, and the various substituent groups thereon, are as defined in connection with general formula (IC) above.

In formula iD, aromatic ring Ar" preferably is a phenyl ring wherein the optional substitutents are preferably from 1 to 3 of, for example, halogen, $(C_1-C_6)$-alkyl, $(C_2-C_6)$-alkenyl, $(C_2-C_6)$-alkynyl, $(C_3-C_7)$-cycloalkyl, cyano, —$OR^4$ or —$OC(O)R^4$, where $R^4$ is hydrogen, $(C_1-C_6)$ alkyl, phenyl $(C_1-C_6)$ alkyl or substituted phenyl $(C_1-C_6)$ alkyl where the phenyl substitutents are from 1 to 3 of halogen or $(C_1-C_4)$ alkyl. Most preferably, the substitutents are from 1 to 3 of, for example, halogen, $(C_1-C_6)$-alkyl, $(C_2-C_6)$-alkenyl, —$OR^4$ or —$OC(O)R^4$, where $R^4$ is hydrogen or $(C_1-C_6)$ alkyl.

Basic compounds of the invention are generally isolated in the form of their pharmaceutically acceptable add addition salts derived using inorganic or organic acids. Examples of such materials are hydrochloric, nitric, sulfuric, phosphoric, formic, acetic, trifluoroacetic, propionic, maleic, succinic, and malonic acids. Compounds of the invention which contain an acidic functionality such as a carboxyl group can be isolated in the form of pharmaceutically acceptable addition salts derived using inorganic or organic bases. The salt forming ion derived from such bases can be a metal ion such as sodium, potassium, lithium, calcium, magnesium, etc., or an ion of an organic base, such as an ammonium or substituted ammonium ion derived from an amine. Examples of suitable amines for this purpose include ammonia, arylalkylamines such as dibenzylamine and N,N-dibenzylethylenediamine, lower alkylamines such as methylamine, t-butylamine, procaine, lower alkylpiperidines such as N-ethylpiperidine, cycloalkylamines such as cyclohexylamine or dicyclohexylamine, 1-adamantylamine, benzathine, or salts derived from amino acids such as arginine or lysine.

The present invention also encompasses pharmaceutically acceptable "prodrugs" of the compounds of formula (IC) which form such derivatives. These are typically acylated derivatives of alcohol-containing compounds of the invention, though other types of prodrugs are known. Preparation of such derivatives is within the skill of the art.

The inhibitors of the present invention are contemplated for use in veterinary and human applications. For such applications, the active agent(s) are employed in pharmaceutical compositions which comprise the active ingredient (s) plus a pharmaceutically acceptable carrier which contains one or more diluents, fillers, binders, or other excipients, depending on the administration mode and dosage form contemplated. Examples of such agents include carriers such as sucrose, lactose, or starch; lubricating agents such as magnesium stearate; adjuvants, such as wetting agents; excipients such as cocoa butter or suppository wax; emulsifying and suspending agents, and sweetening, flavoring and perfuming agents and buffering agents.

The pharmaceutical compositions of the invention may also include one or more known antidiabetic agents in addition to a compound of structural formula (IC). Examples of such antidiabetic agents are: α-glucosidase inhibitors such as acarbose or voglibose, insulin sensitizers such as bromocriptine, thiazolidinediones such as troglitazone, insulin secretagogues such as glimepride, sulfonylureas such as glyburide, GLP-1 and its derivatives such as insulinotropin, amylin and its derivatives such as AC-137, calcitonin, insulin and its derivatives such as HOE-901, biguanides such as metformin, aldose reductase inhibitors such as tolrestat, $\beta_3$ agonists such as BTA-243, and hypocholesterolemics such as lovastatin.

The method of treating glucagon-mediated conditions by administering a glucagon receptor antagonist of the present invention may be practiced in mammals, including humans, which exhibit such conditions. A typical application is treatment of diabetes.

The compounds of this invention can be administered by oral, parenteral (e.g., intramuscular, intraperitoneal, intravenous or subcutaneous injection or implant), nasal, vaginal, rectal, sublingual, or topical routes of administration and can be formulated in dosage forms appropriate for each route of administration.

Solid dosage forms for oral administration include capsules, tablets, pills, powders and granules. In such solid dosage forms, the active compound is admixed with at least one inert pharmaceutically acceptable carrier such as sucrose, lactose, or starch. Such dosage forms can also comprise, as is normal practice, additional substances other than inert diluents, e.g., lubricating agents such as magnesium stearate. In the case of capsules, tablets and pills, the dosage forms may also comprise buffering agents. Tablets and pills can additionally be prepared with enteric coatings such as the OROS-CT/Osmet™ and PULSINCAP™ systems from ALZA and Scherer Drug Delivery Systems.

Liquid dosage forms for oral administration include pharmaceutically acceptable emulsions, solutions, suspensions, syrups, the elixirs containing inert diluents commonly used in the art, such as water. Besides such inert diluents, compositions can also include adjuvants, such as wetting agents, emulsifying and suspending agents, and sweetening, flavoring and perfuming agents.

Preparations according to this invention for parenteral administration include sterile aqueous or non-aqueous solutions, suspensions, or emulsions. Examples of non-aqueous solvents or vehicles are propylene glycol, polyethylene glycol, vegetable oils, such as olive oil and corn oil, gelatin, and injectable organic esters such as ethyl oleate. Such dosage forms may also contain adjuvants such as preserving, wetting, emulsifying, and dispersing agents. Alternatively intramuscular, intraarticular or subcutaneous depot injection with or without encapsulation of the drug into degradable microspheres e.g., comprising poly(DL-lactide-co-glycolide) may be used to obtain prolonged sustained drug release. For improved convenience of the dosage form it may be possible to use an i.p. implanted reservoir and septum such as the Percuseal system available from Pharmacia. Improved convenience and patient compliance may also be achieved by the use of either injector pens (e.g. the NovoPen or Spen) or needle-free jet injectors (e.g. from Bioject, Mediject or Becton Dickinson). Prolonged zero-order or other precisely controlled release such as pulsatile release can also be achieved as needed using implantable pumps with delivery of the drug through a cannula into the synovial spaces. Examples include the subcutaneously implanted osmotic pumps available from ALZA, such as the ALZET osmotic pump.

Compositions for nasal or sublingual administration are also prepared with standard excipients well known in the art.

Compositions for rectal or vaginal administration are preferably suppositories which may contain, in addition to the active substance, excipients such as cocoa butter or a suppository wax.

The compounds of this invention can be manufactured into the above listed formulations by the addition of various therapeutically inert, inorganic or organic carriers well known to those skilled in the art. Examples of these include, but are not limited to, lactose, corn starch or derivatives thereof, talc, vegetable oils, waxes, fats, polyols such as polyethylene glycol, water, saccharose, alcohols, glycerin and the like. The formulations may be sterilized by, for example, filtration through a bacteria-retaining filter, by incorporating sterilizing agents into the compositions, by irradiating the compositions, or by heating the compositions. They can also be manufactured in the form of sterile solid compositions which can be dissolved in sterile water, or some other sterile injectable medium immediately before use. Various preservatives, emulsifiers, dispersants, flavorants, wetting agents, antioxidants, sweeteners, colorants, stabilizers, salts, buffers and the like are also added, as required to assist in the stabilization of the formulation or to assist in increasing bioavailability of the active ingredient(s) or to yield a formulation of acceptable flavor or odor in the case of oral dosing.

The amount of the pharmaceutical composition to be employed will depend on the recipient and the condition being treated. The requisite amount may be determined without undue experimentation by protocols known to those skilled in the art. Alternatively, the requisite amount may be calculated, based on a determination of the amount of target receptor which must be inhibited to treat the condition. An effective amount of active ingredient is generally in the range 0.0001 mg/kg to 100 mg/kg of body weight.

The treatment method of the invention is not limited to administration of the above-described pharmaceutical composition. Rather, this treatment regimen may be employed in combination with conventional treatments of diabetes (both Type I and Type II) or of other conditions which are sometimes found in diabetic subjects. Thus, for example, treatment may be administered in conjunction with (a) diet restrictions and exercise; (b) insulin, or other drugs used to treat ketoaddosis; (c) any drug used for the treatment of hyperlipidemia, such as lovastatin, or cardiovascular disease, such as enalapril; (d) drugs used to treat diabetic complications, such as epalrestat and (e) drugs that lower body weight, such as dexfenfluramine.

The glucagon receptor antagonists of the invention are useful not only for treatment of the pathophysiological conditions discussed above, but are also useful in other applications such as a diagnostic agent. For example, these compounds can be administered to humans in vivo in the fasting state as a diagnostic tool to directly determine whether the glucagon receptor is functional. Serum samples taken before and after such administration can be assayed for glucose levels; comparison of the amounts of blood glucose in each of these samples would be a means for directly determining the ability of the patient's glucagon receptor to modulate hepatic glucose output. Altematively, compounds of the present invention may be useful for finding new glucagon antagonists. For example, a binding assay employing a radiolabeled derivative (such as $^3H$) of a compound of formula (IC) would be useful in identifyig new compounds that competitively bind to the glucagon receptor. Such an assay is useful in identifying structurally novel antagonists that may offer advantages in ease of chemical modification, selectivity and oral bioavailability.

The compounds of the present invention may contain asymmetric centers on the molecule, depending upon the nature of the various substituents. Each such asymmetric center will produce two optical isomers. In certain instances, asymmetry may also be present due to restricted rotation about the central bond adjoining the two aromatic rings of the specified compounds. For example, for certain compounds of Formula (IC) wherein Ar is taken as substituted phenyl, there exist additional isomers due to restricted rotation about the central aryl-aryl bond, depending on the substitution pattern.

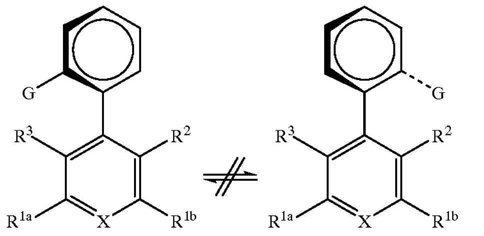

It is intended that all isomers, either by nature of asymmetric centers or by restricted rotation as described above, as separated, pure or partially purified isomers or racemic mixtures thereof, be included within the ambit of the instant invention. In the case of compounds of Formula (IC) wherein $R^3$ is taken as 1-hydroxyethyl, it has been found that the isomer in which the hydroxy substituent is above the plane of the structure, as seen in Formula Ic, is more active and thus more preferred over the compound in which the hydroxy substituent is below the plane of the structure.

IC

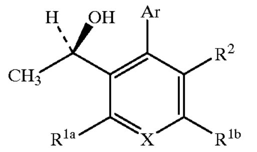

Representative examples of the nomenclature employed herein are given below:

2,6-Dimethyl-3-hydroxymethyl-4-(3-bromophenyl)-5-isobutylpyridine

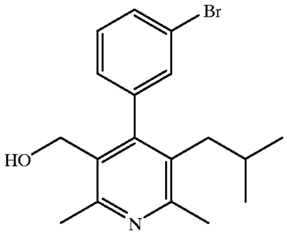

3,5Di-t-butyl-2-(phenylthio)methyl-6-hydroxymethyl-3',5'-dichloro-1,1'-biphenyl

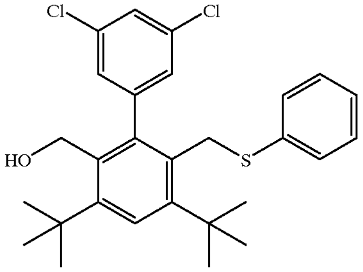

The compounds of general formula (IC) of the present invention are prepared as indicated in the following reaction Schemes.

The phenylpyridine compounds of formula (IC) (X=N) are prepared from a common intermediate 6 using the well-known Hantzsch pyridine synthesis, as shown in Scheme 1 (Stout, D. M.; Myers, A. I. *Chem. Rev.* 1982,223).

SCHEME 1

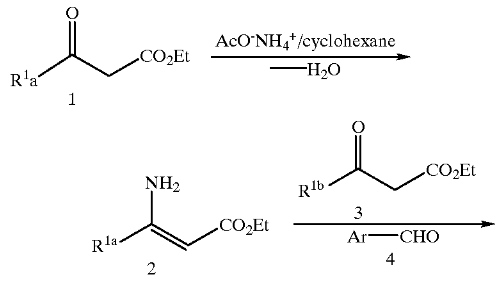

-continued

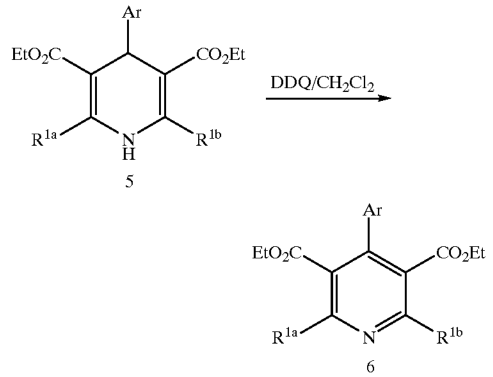

5

6

The ketoester 1, (commercially available or prepared according to the procedure of Deslongchamps, *Synth. Comm.,* 1976, 6, 169) is treated with an ammonium salt such as ammonium acetate, in an inert solvent such as cyclohexane capable of forming an azeotrope with water, to give the enamine 2. Compound 2 is then treated with the ketoester 3. which may or may not be identical to the ketoester 1, and an aromatic aldehyde, in a polar solvent such as ethanol, to produce the dihydropyridine 5. Certain substituents on aldehyde 4 may need to be protected during the Hantzsch pyridine synthesis. A description of suitable protecting groups may be found in: *Protective Groups in Organic Synthesis*, Second Edition, T. W. Greene, John Wiley and Sons, New York, 1991. Oxidation of 5 is achieved by any of several known methods. For example, treatment of 5 with 2,3-dichloro-5,6dicyanobenzoquinone (DDQ) in a solvent such as methylene chloride ($CH_2Cl_2$), or with ceric ammonium nitrate (CAN) in a mixture of solvents such as aqueous acetone, affords the intermediate 6. Separation of unwanted side products and purification of intermediates is achieved by chromatography on silica gel, employing flash chromatography (Still, W. C.; Khan, M.; Mitra, A. *J. Org. Chem.,* 1978, 43, 2923)

An alternative Hantzsch pyridine synthesis of the intermediate 6 where $R^{1a}$ and $R^{1b}$ of formula (IC) are identical, can be accomplished following the procedure of Chucholowski (U.S. Pat. No. 4,950,675), Scheme 2. By heating two equivalents of ketoester 1 with ammonium hydroxide and the aldehyde 4 in a polar solvent such as methanol, the dihydropyridine 5 is obtained directly. Compound 5 is oxidized to pyridine 6, according to the procedure described in Scheme 1.

SCHEME 2

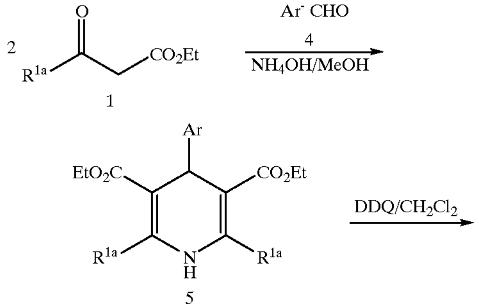

1

5

-continued

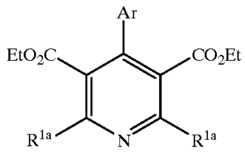

6

In Scheme 3, another alternative Hantzsch pyridine synthesis of intermediate 6 is described. Ketoester 1 is condensed with aldehyde 4 by treatment with catalysts such as acetic acid and piperidine without solvent to afford intermediate 7. Treatment of 7 with ketoester 3 in the presence of a base such as sodium methoxyde, in a polar solvent such as methanol produces the diketone 8. Cyclization of 8 is achieved by treatment with an ammonium salt such as ammonium acetate in a polar solvent such as acetic add to afford the previously described dihydropyridine 5 (Scheme 1), which is oxidized to the pyridine 6 according to the procedure as indicated in Scheme 1.

SCHEME 3

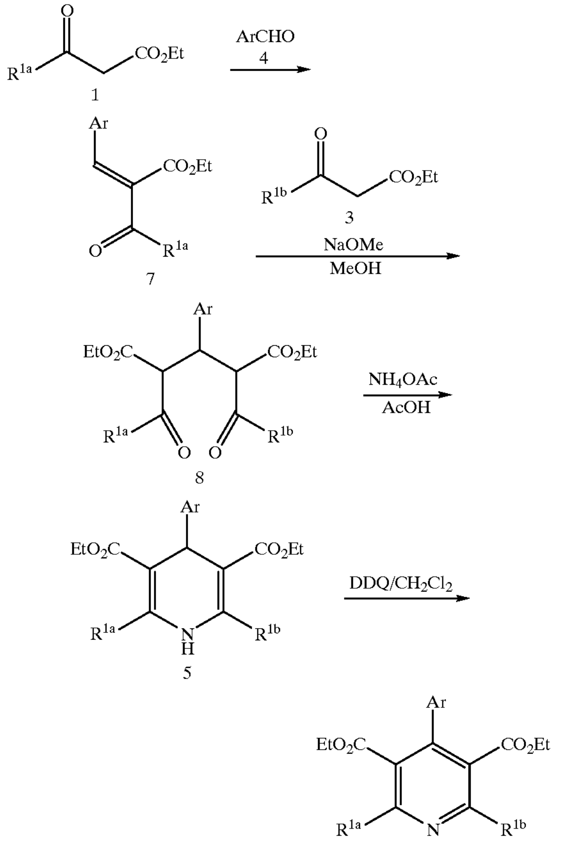

1

3

7

8

5

6

The synthesis of aryl pyridine derivatives of formula (IC) wherein $R^2$ is alkyl and $R^3$ is hydroxymethyl (IIa) is described in Scheme 4.

SCHEME 4

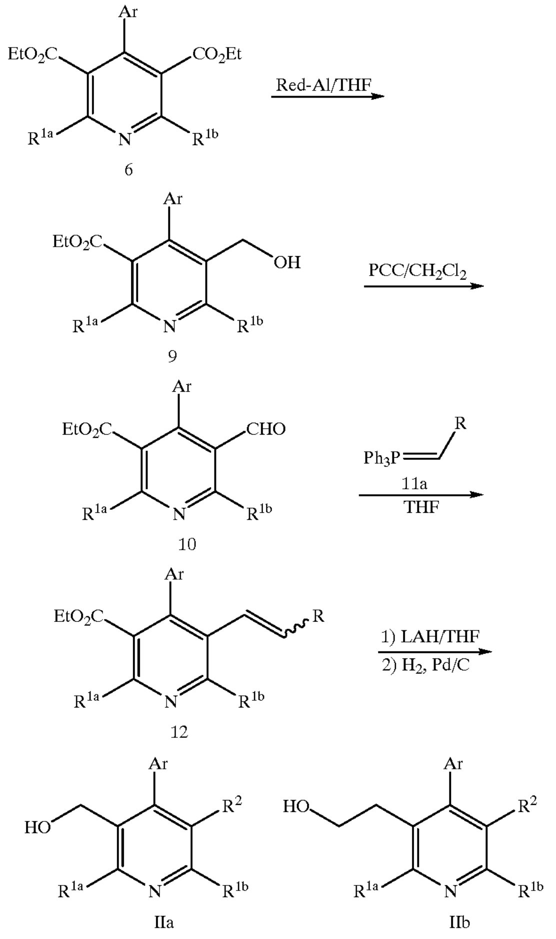

6

9

10

12

IIa

IIb

Chemical reducing agents such as sodium bis(2-methoxyethoxy)aluminum hydride (Red-Al) in an inert solvent, such as tetrahydrofuran (THF) or diethyl ether ($Et_2O$), can result in a monoreduction of the pyridinediester 6 to give the alcohol 9. Oxidants such as pyridinium chlorochromate (PCC), in a solvent such as $CH_2Cl_2$, convert compound 9 to the aldehyde 10. Wittig reaction with compound 10 and an ylide 11a in an inert solvent such as THF or $Et_2O$, affords olefin 12 obtained usually, but not always, as a mixture of E and Z isomers . The reagent 11a is prepared from an alkyl triphenyl phosphonium salt, wherein the alkyl group may contain a heteroatom, and a suitable base such as butyllithium or sodium amide, according to known methods (Maercker, A. in *Organic Reactions*, Vol. 14, Ed.; Wiley, New York, 1965, Chapter 3). Olefin 12 is successively treated with a reducing agent such as lithium aluminum hydride (LAH), in an inert solvent such as THF or $Et_2O$, and hydrogen in the presence of a metal catalyst, such as palladium on carbon, in a polar solvent such as ethanol, to afford compounds of formula IIa. In some of these compounds, $R^2$ may contain substituents such as alcohol, acetate, ester, carboxylic add, and amide. These products can be obtained directly by the procedures of Scheme 4, with or without the use of appropriate protecting groups, or by additional steps familiar to those skilled in the art. For example, a primary alcohol can be converted to a carboxylic acid by standard methods of oxidation, such as those described by Eisenbraun (Eisenbraun, E. J. *Org. Syn. Coll.,* 1973, 5, 310).

If the Wittig reaction is performed with methoxymethyl triphenyl-phosphonium as ylide (11b), followed by treatment with an add such as hydrochloric add, the homologous aldehyde 13 is obtained. This can undergo another Wittig reaction to afford olefin 14, (Scheme 5). This known procedure (Wittg, G.; Walter, B.; Kruck, K.-H. Chem. Ber. 1962, 2514) allows one to synthesize extended alkyl chain ($R^2$) analogs of formula IIa, which may not be directly prepared by usual Wittig reaction due to limited availability of the requisite alkyl triphenylphosphonium salt.

Oxidation of the compounds of formula IIa by the method described in Scheme 4 affords intermediates that can be converted to homologues of compounds of formula IIa, containing the $—CH_2—CH_2—$ linkage between the pyridine nucleus and the hydroxy group (IIb).

SCHEME 5

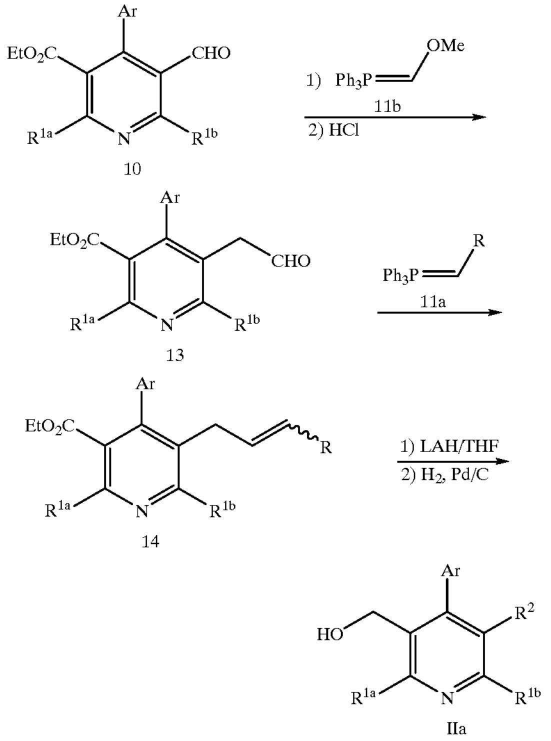

10

13

14

IIa

Synthesis of aryl pyridine derivatives of formula (IC) wherein $R^2$ is alkyl containing a heteroatom such as sulfur and $R^3$ is hydroxymethyl (IIa and IIIb), is outlined in Scheme 6. Alcohol 9 is converted to an alkyl halide 15 by treatment with a suitable reagent such as dibromotriphenylphosphorane in an inert solvent. Treatment of 15 with a thiol and a base such as N-methyl morpholine in an inert solvent produces intermediate 16. The sulfur atom of compounds 16 can be oxidized (n=1 or 2) by any of several known methods. For example, it can be accomplished by treatment of 16 wherein n=0, with an oxidant such as m-chloroperbenzoic acid in a solvent such as $CH_2Cl_2$. Chemical reducing agents such as lithium aluminum hydride (LAH) in an inert solvent such as tetrahydrofuran or diethyl ether, can reduce the ester 16 to a compound of formula IIIa. Intermediate 15 can also react with alcohols following the methods outlined in Scheme 6, to afford compounds of formula IIIc.

SCHEME 6

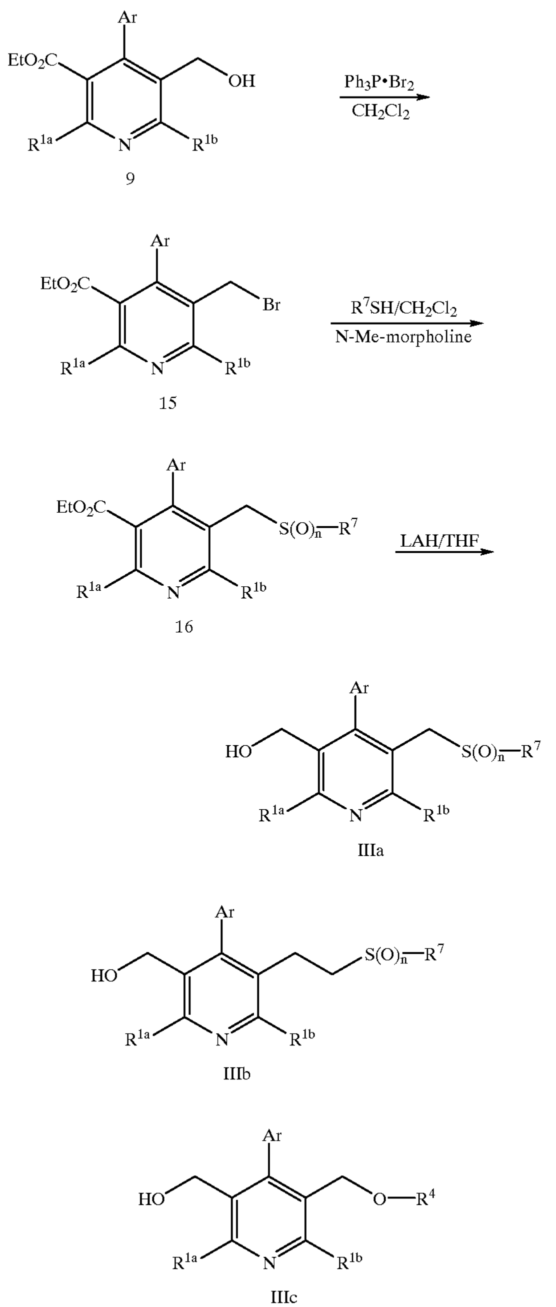

9, 15, 16, IIIa, IIIb, IIIc

The synthesis of aryl pyridine derivatives of formula (IC) wherein $R^2$ is alkyl containing a heteroatom such as nitrogen and $R^3$ is hydroxymethyl (IVa), is outlined in Scheme 7. Treatment of 15 with a primary or secondary amine in an inert solvent results in the intermediate 17. Chemical reducing agents such as lithium aluminum hydride in an inert solvent, such as tetrahydrofuran or diethyl ether, can reduce ester 17 to a compound of formula IVa. Reduction of aldehyde 13 by the method outlined in Scheme 4 affords an intermediate that can be converted to homologues of compounds of formula ma and IVa, containing the $—CH_2—CH_2—$linkage between the pyridine nucleus and the sulfur or nitrogen substituent (IIIb and IVb).

SCHEME 7

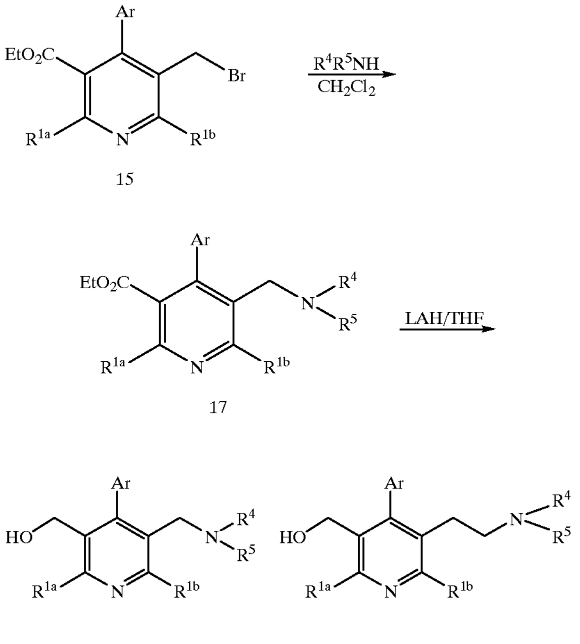

15, 17, IVa, IVb

Synthesis of aryl pyridine derivatives of formula (IC) wherein $R^2$ is alkyl and $R^3$ is 1-hydroxyethyl (Va), is outlined in Scheme 8. Oxidants such as pyridinium chlorochromate (PCC), are used to convert compounds of formula II to the aldehyde 18. Treatment of 18 with an organometallic reagent such as methyl magnesium bromide or methyl lithium in an inert solvent such as THF or $Et_2O$ affords racemic compounds of formula Va. Chiral 1-hydroxyethyl aryl pyridine derivatives of formula Vb are obtained by resolution of the racemates Va by classical methods. For example, resolution can be achieved by formation of diastereomeric adducts of the racemic compounds with optically active reagents such as α-methoxy-α-(trifluoromethyl) phenylacetic acid (Dale, J. A.; Dull, D. L.; Mosher, H. S. *J. Org. Chem.* 1969, 34, 2543). Alternatively, separation of enantiomers is achieved by HPLC on chiral solid phase. Determination of absolute stereochemistry can be achieved in a number of ways familiar to those skilled in the art, including X-ray analysis of a suitable crystalline derivative, such as a Mosher ester.

SCHEME 8

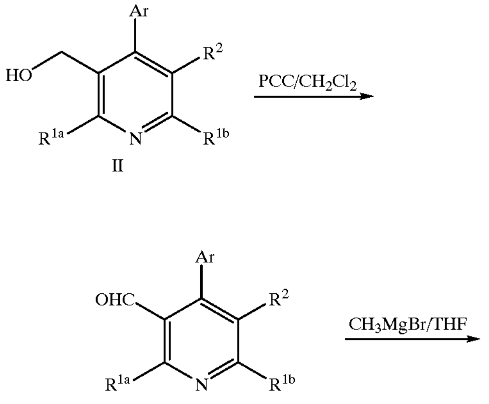

II

18

-continued

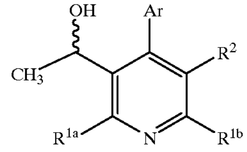

Va

An alternative synthesis of aryl pyridine derivatives of formula Vb is achieved by treating aldehyde 18 with the anion of methyl toluylsulfoxide 19 to give a diastereomeric mixture of alcohols 20 as shown in Scheme 9 (B3lase, F. R.; Le H. *Tet. Lett.* 1995, 36, 4559). The diastereomers are separated by flash chromatography and treated separately with Raney nickel and hydrogen in ethanol to provide pure enantiomers (>99% enantiomeric excess, e.e.) of the compounds of formula Vb. Alternatively, the chromatographic step is avoided by a two step sequence consisting of (1) oxidation of the mixture 20 with manganese dioxide in an inert solvent, followed by (2) reduction of the ketone with a chemical reductant such as LAH, to provide the enantiomerically pure alcohol 21. Treatment of 21 with Raney nickel and hydrogen in a polar solvent provides pure enantiomer (>99% e.e.) of the compounds of formula Vb.

SCHEME 9

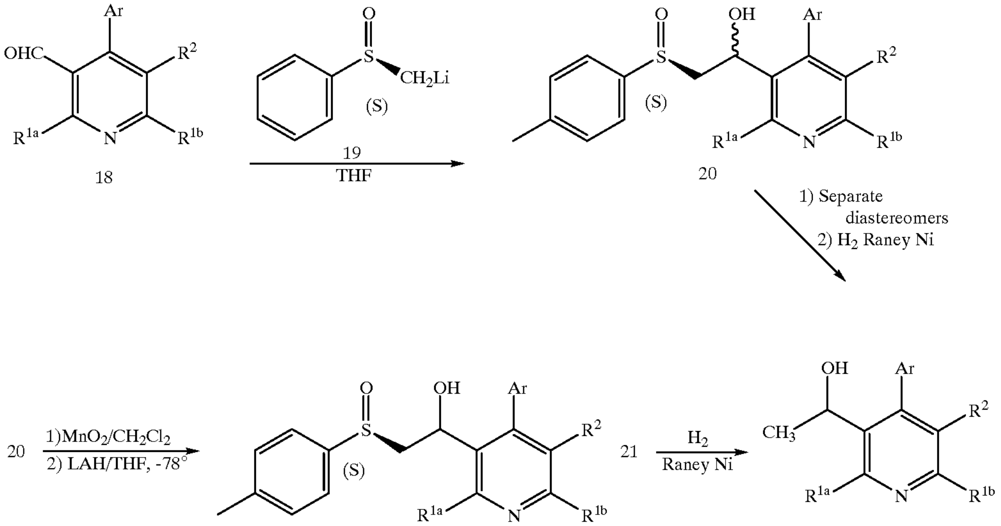

18

20

20

21

Vb

A preferred alternative enantioselective synthesis of aryl pyridine derivatives of formula Vb is shown in Scheme 10. Treatment of the racemic mixture of compounds of formula Va with an oxidant such as pyridinium chlorochromate (PCC), gives the ketone 22. Reduction of 22 with a complex of LAH and N-mefflylephedrine (Kawasaki, M.; Susuki, Y.; Terashima, S. *Chem. Lett.* 1984, 239) in an inert solvent, provides the alcohol of formula Vb with an enantiomeric excess of 95%.

SCHEME 10

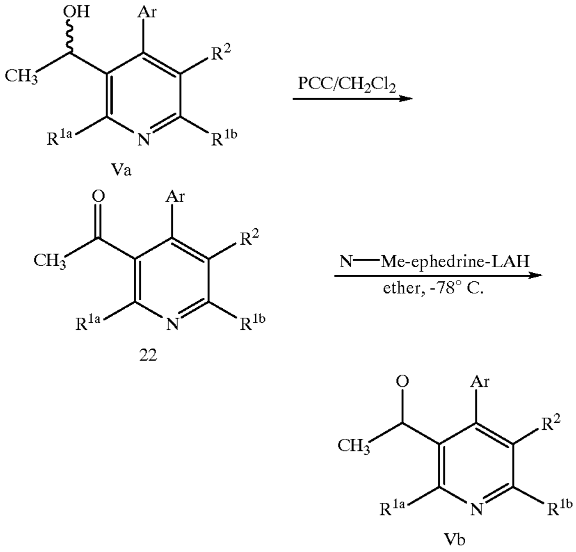

The synthesis of aryl pyridine derivatives of formula (IC) wherein $R^2$ is alkyl and $R^3$ is 1,2-dihydroxyalkyl (VI), is described in Scheme 11. A methyl triphenylphosphonium salt is treated with a suitable base such as butyllithium in an inert solvent and reacted with intermediate 18 to afford olefin 23. Treatment of compound 23 with a suitable oxidant such as osmium tetroxide in a polar solvent such as pyridine gives the compounds of formula VI.

SCHEME 11

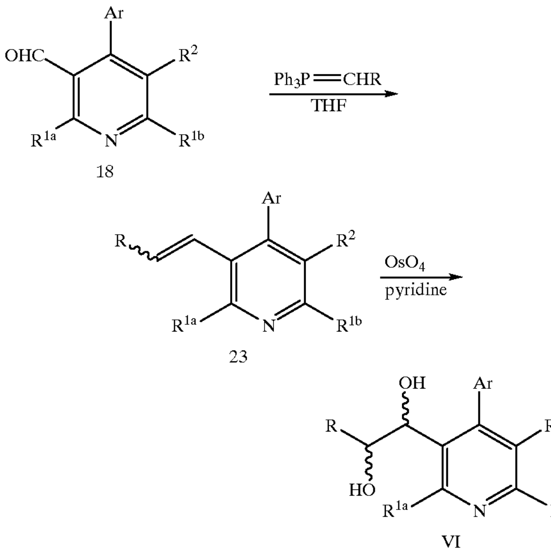

The synthesis of aryl pyridine derivatives of formula (IC) wherein $R^2$ and $R^{1b}$ are taken together to form an alkylene bridge and $R^3$ is hydroxymethyl (VIIa), 15 is described in Scheme 12. The ketoester 1 is treated with an aromatic aldehyde and catalysts such acetic acid and piperidine, in ethanol, to afford the α,β-unsaturated ketoester 24. Treatment of 24 with the cyclic ketone 25 and a base such as lithium bis(trimethylsilyl)amide in an inert solvent such as THF affords an intermediate which is treated with ammonium acetate and copper acetate in acetic acid to give the pyridine 26. Chemical reducing agents reduce the ester 26 to analogs of formula VIIa. It may be appreciated that these analogs can be used as intermediates to generate new derivatives of formula (IC) wherein $R^2$ and $R^{1b}$ are taken together and $R^3$ is 1-hydroxyethyl (VIIb) according to the procedures described in Scheme 8.

SCHEME 12

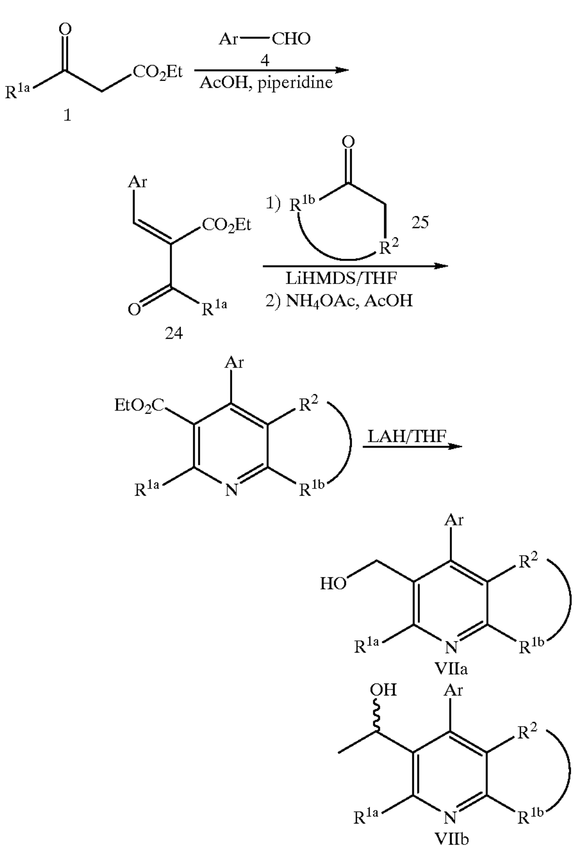

The synthesis of the aryl pyridine derivative IIa wherein $R^{1b}$ is $CH_2OH$ is described in Scheme 13. Alcohol 27 (aryl pyridine IIa in which $R^{1b}$ is $CH_3$) is treated with a trialkylsilyl chloride, such as tert-butyldiphenylsilyl chloride, and a base to yield silyl ether 28. Treatment of 28 with meta-chloroperbenzoic acid in an inert solvent, such as chloroform, provides the N-oxide 29. The N-oxide is treated with acetic anhydride to afford pyridine acetate 30. Treatment of 30 with aqueous methanol in the presence of potassium carbonate, yields alcohol 31. The silyl ether is cleaved with tetrabutylammonium fluoride in nHF to provide aryl pyridine derivative 32.

SCHEME 13

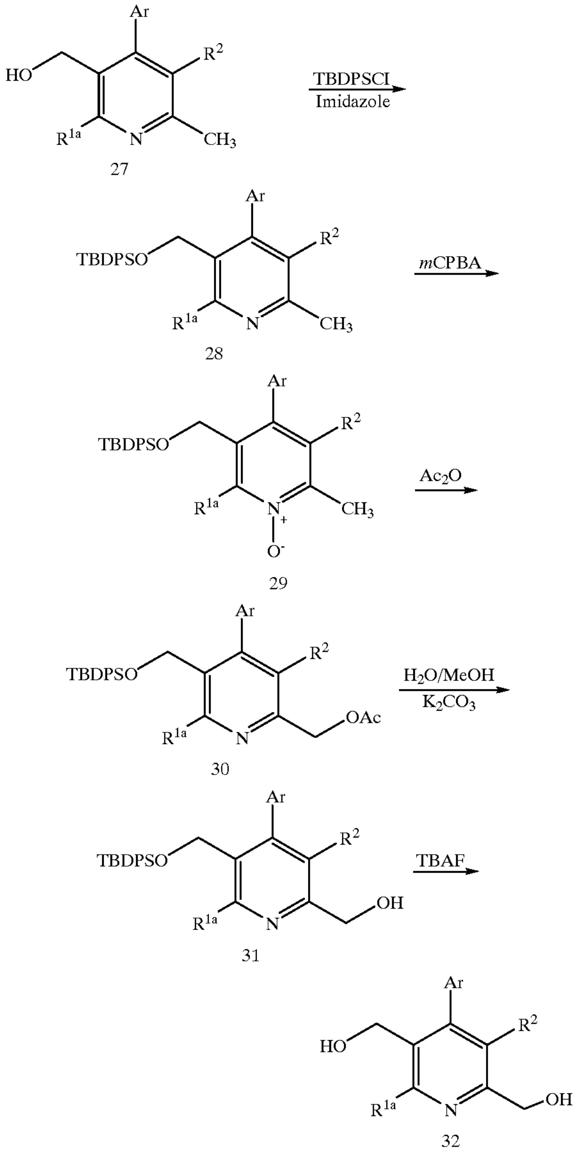

27
28
29
30
31
32

The synthesis of aryl pyridine derivatives Xa wherein $R^{1b}$ is —$CH_2NR^4R^5$ is described in Scheme 14. Oxddation of alcohol 31 as described in Scheme 4 yields aldehyde 33. Treatment of the aldehyde with an amine in the presence of a Lewis acid, such as zinc chloride, and a reducing agent, such as sodium cyanoborohydride, provides the amine 34. Deprotection of the alcohol as described in Scheme 13 affords aryl pyridine derivative Xa.

SCHEME 14

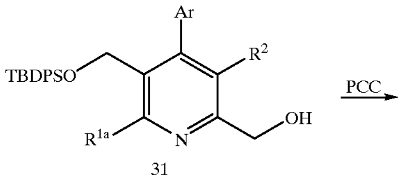

31

-continued

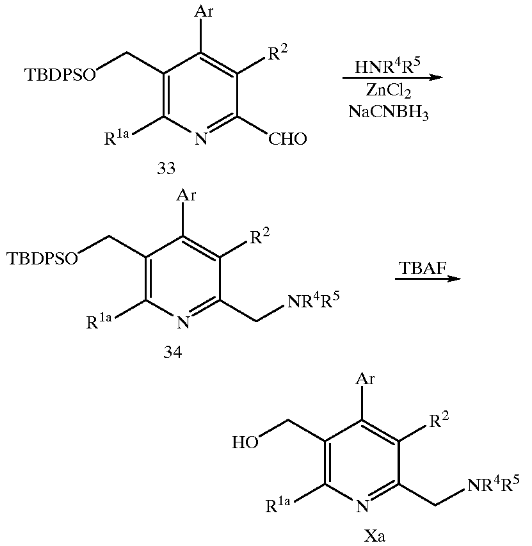

33
34
Xa

An alternative synthesis of amine 34 is shown in Scheme 15. Treatment of pyridine N-oxide 29 with phosphorus oxychloride and a base, such as triethylamine, in $CH_2Cl_2$, yields chloromethylpyridine 35. The chloride is treated with an amine providing amine 34.

SCHEME 15

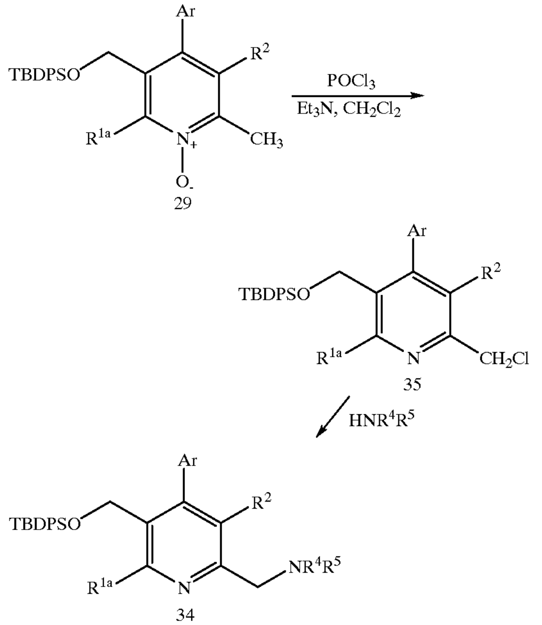

29
35
34

The synthesis of aryl pyridine derivatives Xb wherein $R^{1b}$ is —CH═CHR is described in Scheme 16. Alcohol 31 is converted to the corresponding bromide as described in Scheme 6. Treatment of 36 with sodium phosphite in benzene yields phosphonate 37. The phosphonate is treated with a base, such as sodium hydride, and subsequently with an aldehyde affording olefin 38. Deprotection of the alcohol as described affords aryl pyridine Xb.

SCHEME 16

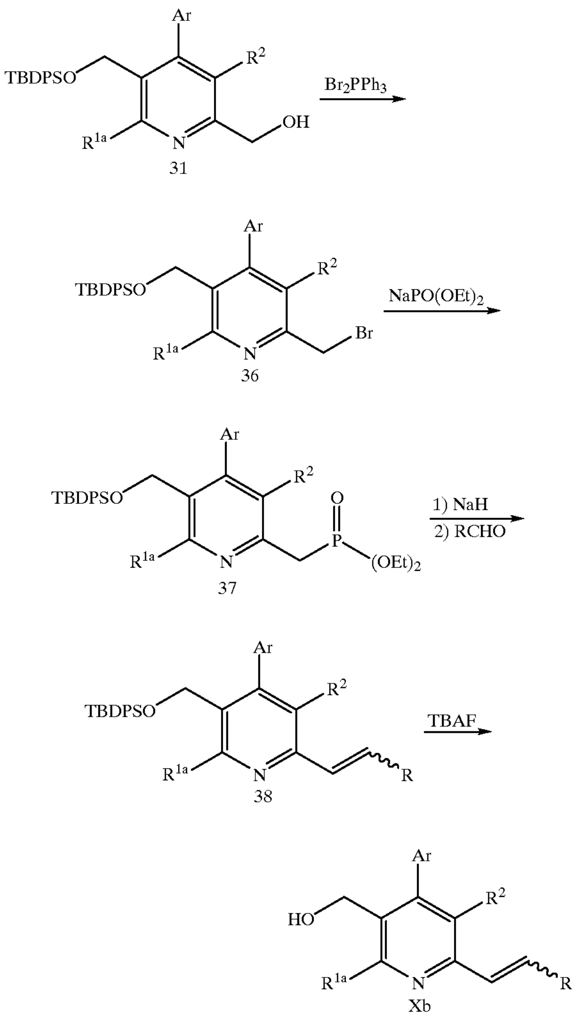

31, 36, 37, 38, Xb

An alternative synthesis of olefin 38 is shown in Scheme 17. Aldehyde 33 is treated with an ylide as described in Scheme 4 to yield olefin 38.

SCHEME 17

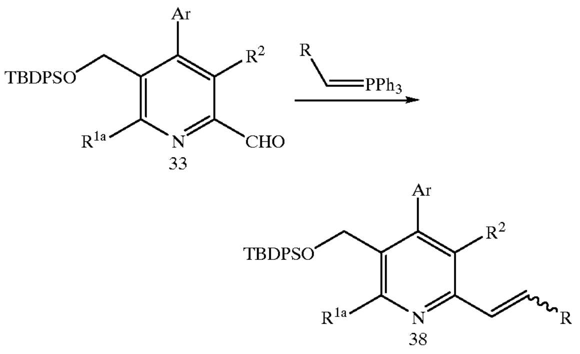

33, 38

The synthesis of aryl pyridine derivative Xc wherein $R^{1b}$ is —$CH_2CH_2R$ is described in Scheme 18. Hydrogenation of olefin Xb as described in Scheme 4 yields the alkane Xc.

SCHEME 18

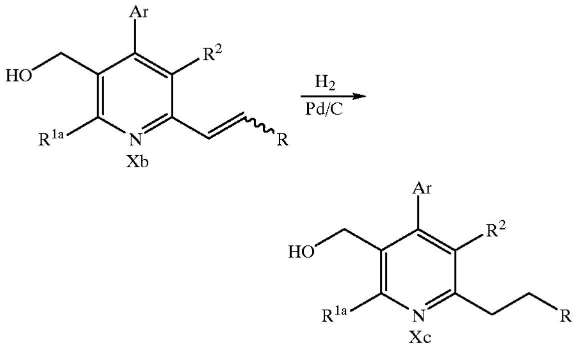

Xb, Xc

The synthesis of aryl pyridine derivative Xd wherein $R^{1b}$ is —CH(OH)R is described in Scheme 19. Treatment of aldehyde 33 with a Grignard reagent in an inert solvent, such as THF, yields alcohol 39. Deprotection of the alcohol as described affords aryl pyridine derivative Xd.

SCHEME 19

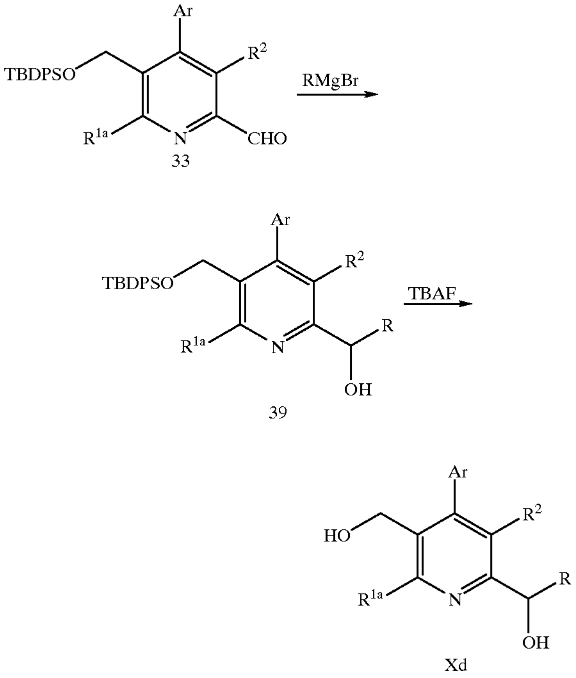

33, 39, Xd

The synthesis of aryl pyridine derivatives Xe wherein $R^{1b}$ is —COR is described in Scheme 20. Oxddation of alcohol 39 as described in Scheme 4 yields ketone 40. Deprotection of the alcohol as described affords the aryl pyridine derivative Xe.

SCHEME 20

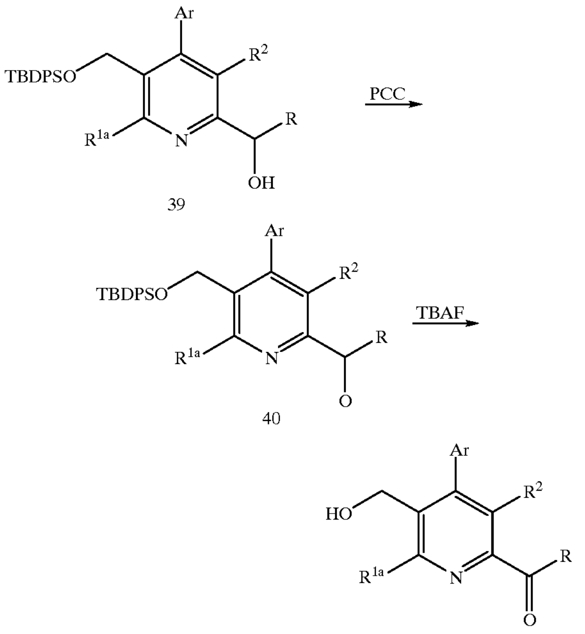

39 40 Xe

The synthesis of aryl pyridine derivatives Xf wherein $R^{1b}$ is —C(OH)RR' is described in Scheme 21. Grignard addition to ketone 40 as described in Scheme 19 yields alcohol 41. Deprotection of the alcohol as described affords the aryl pyridine derivative Xf.

SCHEME 21

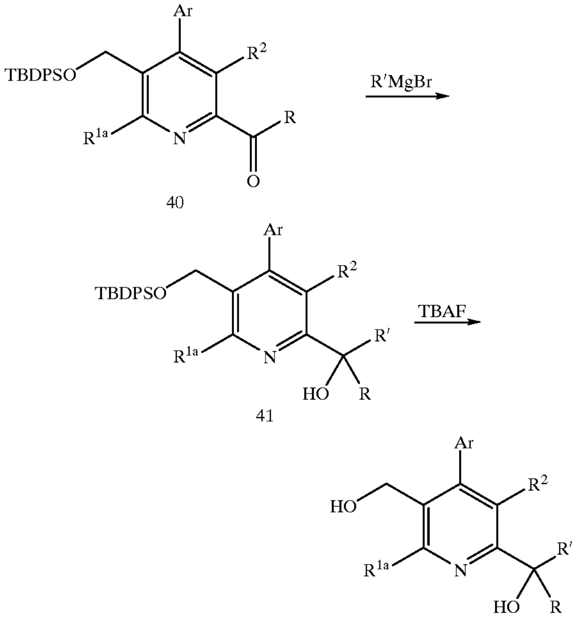

40 41 Xf

The synthesis of aryl pyridine derivatives Xg wherein $R^{1b}$ is —C($OR^4$)RR' is described in Scheme 22. Treatment of alcohol 41 with a base, such as sodium hydride, and an alkylating agent in THF, yields ether 42. Deprotection of the alcohol as described affords the aryl pyridine derivative Xg.

SCHEME 22

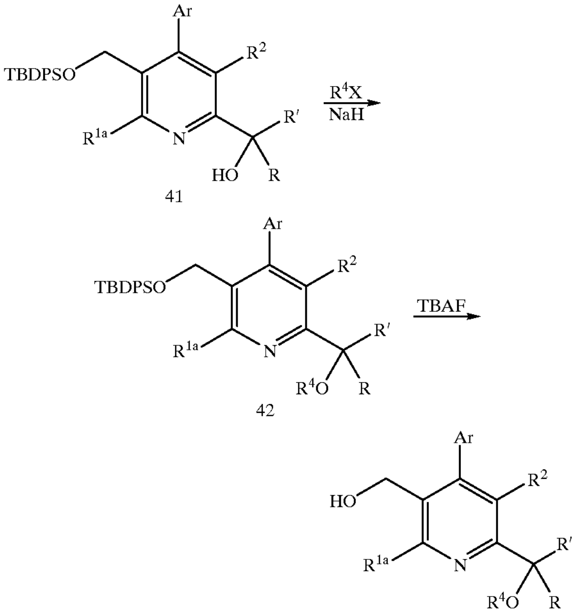

41 42 Xg

The biphenyl analogs described in formula (IC) (X=C—$R^8$, wherein $R^8$ is H), are prepared by the methods described by Fey, et al. US Patent 5,138,090. The key step of the synthesis is the coupling of an arylpalladium dimer with an aryl Grignard reagent (Scheme 23).

SCHEME 23

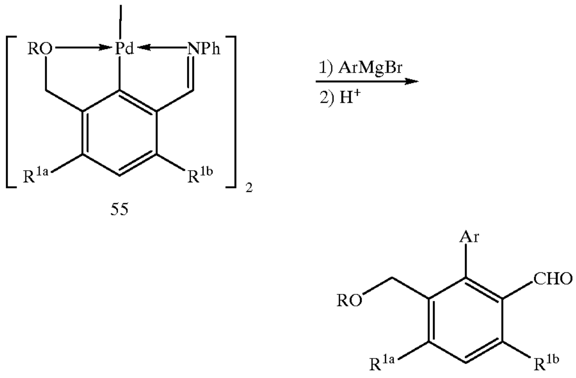

55 56

A specific example of this method is shown in Scheme 24. Treatment of diol 43 (prepared according to the procedure of Fey, et al. U.S. Pat. No. 5,138,090) with (2-methoxy)ethoxymethyl chloride and diisopropylethylamine in $CH_2Cl_2$ solvent gives MEM ether 44. Oxidation of the remaining alcohol of 44 as described in Scheme 4 provides aldehyde 45. Treatment of the aldehyde with aniline in the presence of a catalytic amount of p-toluenesulfonic acid (pTSA) and molecular sieves in toluene solvent gives imine 46. The imine is converted to the palladium dimer 47 upon treatment with palladium acetate in acetic acid solvent. Treatment of 47 with triphenylphosphine, then with 4-fluorophenylmagnesium bromide (prepared from 1-bromo4-fluorobenzene and magnesium metal), and finally with aqueous hydrochloric acid in benzene solvent yields biphenyl 48. The aldehyde moiety of biphenyl 48 is converted to a pentyl group by the methods described in Scheme 4. MEM ether 50 is treated with trimethylsilyl chloride and sodium iodide in acetonitrile solvent, and subsequently with sodium acetate in DMF solvent to provide acetate 51. Saponification of the acetate using potassium hydroxide in methanol solvent provides alcohol 52. Hydroxymethyl biphenyl 52 is transformed to racemic hydroxyethyl biphenyl 54 as described in Scheme 8.

SCHEME 24

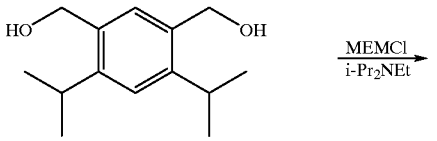

43

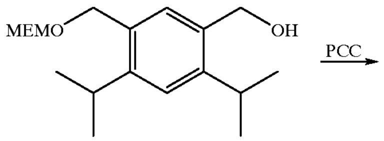

44

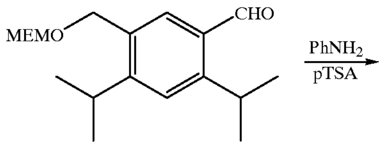

45

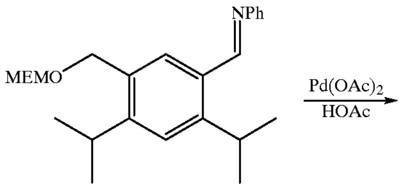

46

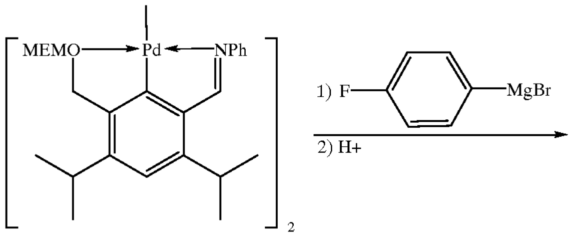

47

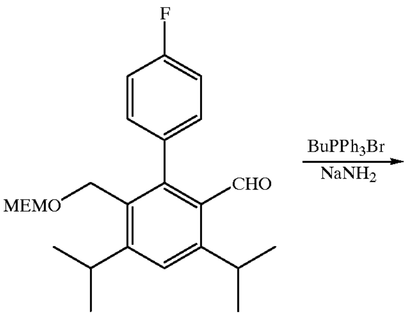

48

-continued

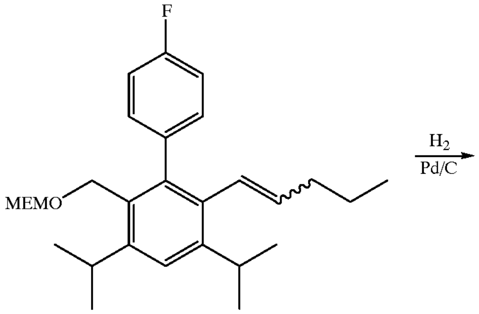

49

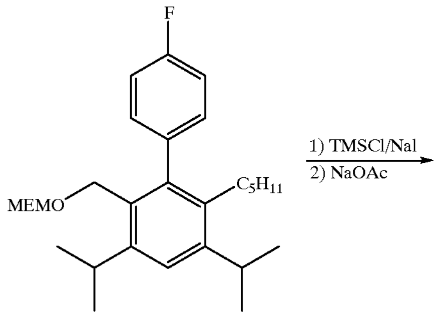

50

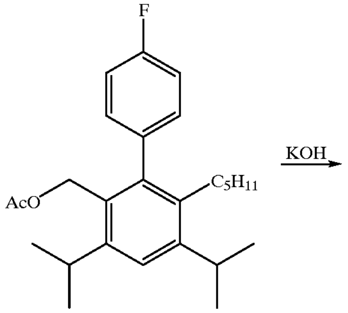

49

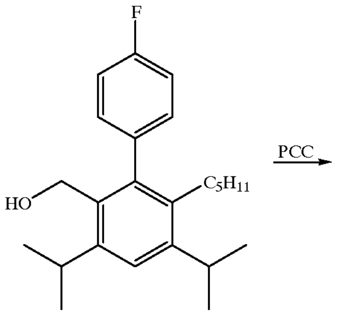

50

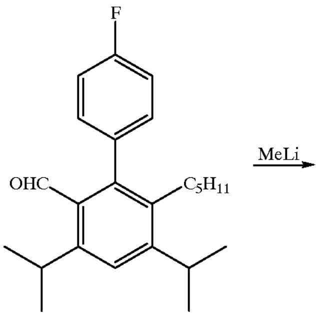

51

-continued

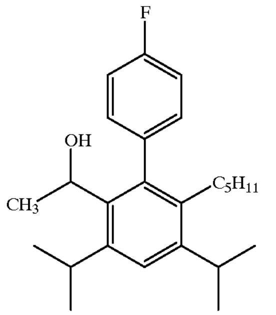

52

An alternative synthesis of biphenyls of formula (IC) is the coupling of a suitably functionalized benzene derivative 57 (where X can be trifluoromethanesulfonate, methoxy, bromide, or iodide) with an arylmetal reagent $ArMY_n$ (where M may be B, Sn, or Mg, and Y is a ligand).

SCHEME 25

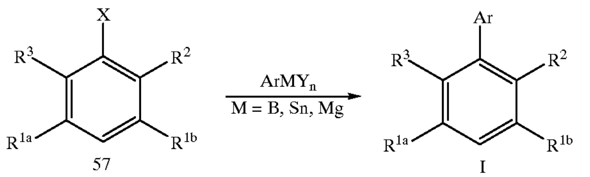

57
X = OTf, OMe, Br, I
I

An example of such a biaryl coupling is the Suzuki reaction (Myaura, N., Yanagi, T., Suzuki, A. *Synth. Comm.* 1981, 11, 513–519; Oh-e, T., Miyaura, N., Suzuki, A. *J. Org. Chem.* 1993, 58, 2201–2208) in which a benzene derivative 58 (in which X can be trifluoromethanesulfonate, bromide, or iodide) is coupled with an arylboronic acid (Scheme 26).

SCHEME 26

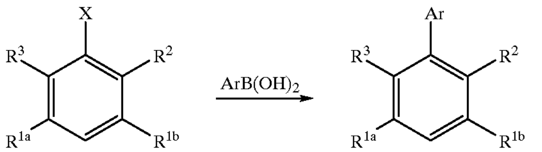

58
X = OTf, Br, I
I

The requisite arylboronic acid 60 may be prepared by sequential reaction of an aryl halide 59 (X=Br or I) with magnesium metal, a boronic ester, and hydrochloric acid.

SCHEME 27

ArX
X = Br, I
59

1) Mg
2) $B(OR)_3$
3) HCl $ArB(OH)_2$
60

A specific example of the use of the Suzuki reaction to synthesize a biphenyl analog is depicted in Scheme 28. Phenol 61 is treated sequentially with sodium hydride and allyl bromide in dimethylformamide solvent to afford allyl ether 62. Claisen rearrangement of the ether provides phenol 63. The phenol is treated with trifluoromethanesulfonic anhydride (triflic anhydride) and pyridine in $CH_2Cl_2$ solvent to give triflate 64. Treatment with 4fluorophenylboronic acid, tetrakistriphenylphosphine palladium (0), potassium phosphate (tribasic), and potassium bromide in 1,4dioxane solvent affords biphenyl 65. Catalytic hydrogenation as described in Scheme 4, and reduction of the ketone with lithium aluminum hydride in THF solvent provides the desired biphenyl analog 67.

SCHEME 28

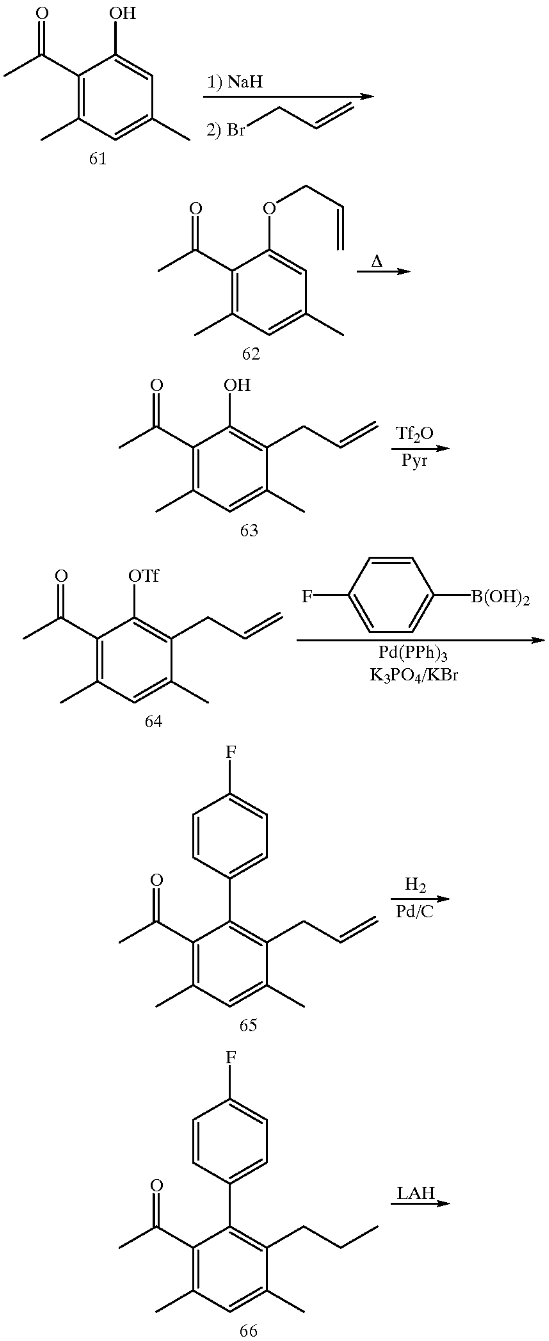

61
62
63
64
65
66

-continued

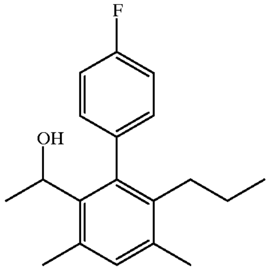

67

An alternative synthesis of biphenyls of type I uses a cycloaromatization of a ketodiester 68 with a diketone in the presence of a catalytic amount of sodium methoxide in methanol solvent to give a phenol 69. The phenol is then coupled with an arylboronic acid as described in Scheme 28 to afford biphenyl diester 70. The diester is then transformed as described in Schemes 4, 8, and 10 to give the analog with the desired $R^2$ and $R^3$ groups.

SCHEME 29

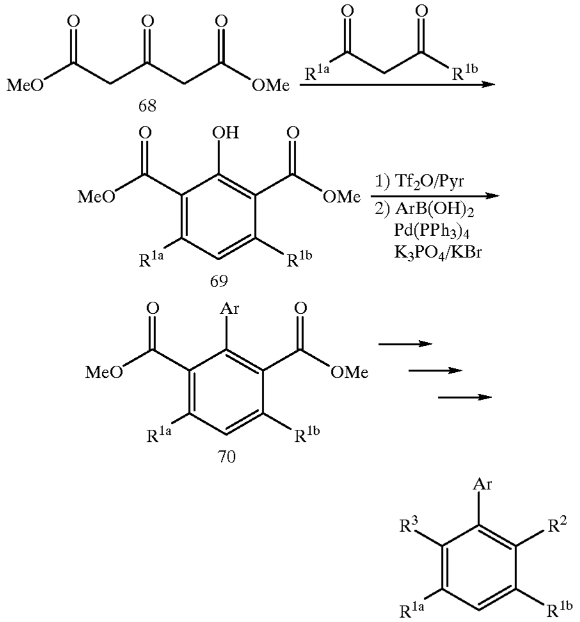

68

69

70

I

An alternative method of transforming phenol 69 to biphenyl 70 is shown in Scheme 30. Treatment of the phenol with dimethylsulfate and a base such as potassium carbonate yields the methyl ether 71. The ether is treated with an aryl Grignard reagent to afford biphenyl 70.

SCHEME 30

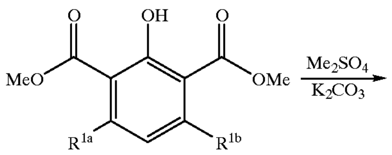

69

-continued

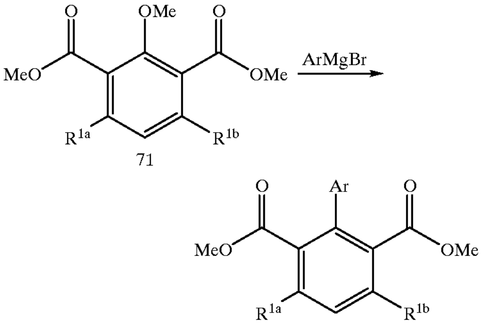

71

70

The diester 70 can be further transformed by an alternative method shown in Scheme 31, to give the analogs with the desired $R^2$ and $R^3$ groups. Chemical reducing agents such as sodium bis-(2-methoxyethoxy)-aluminum hydride (Red-Al), can result in a mono reduction of the diester 70 to give the alcohol 72. Alcohol 72 can be attached to a polymeric support such as Wang resin, by treatment with a base such as sodium hydride in DMF, to give the intermediate 73. The ester group of intermediate 73 can be transformed to an alkyl halide in a two step process; 73 is treated with a reducing agent such as LAH, then Phosphorous tribromide to afford compound 74. The allyl halide 74 is treated with an alkyl thiol and a base such as N-methyl morpholine, then by TFA to cleave the ether linkage with the polymeric resin, to afford the alcohol 75.

SCHEME 31

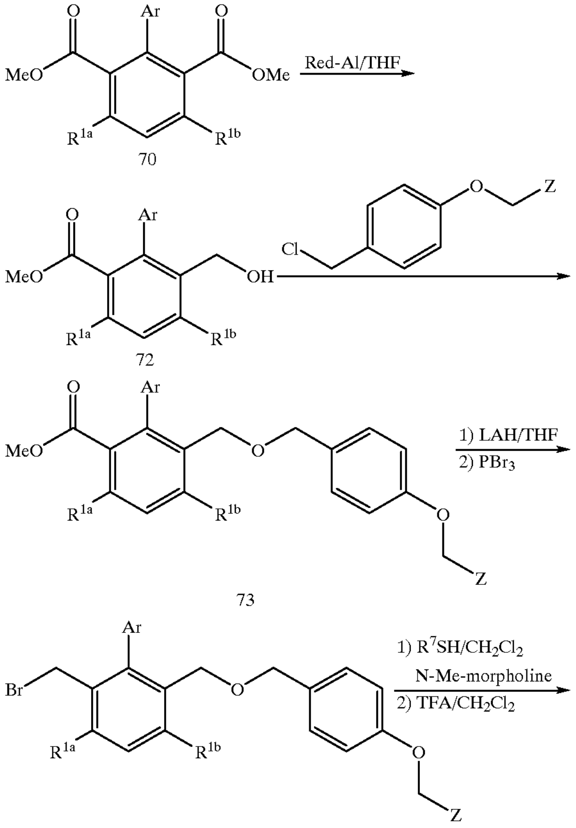

70

72

73

74

-continued

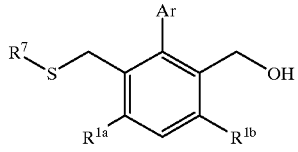

75

Z = Polystyrene

It will be appreciated that synthesis of some compounds of formula (IC) may require use of protecting groups at various stages of the procedures. These are removed in subsequent steps. For example, the removal of O-benzyl ether protecting groups is carried out by treatment with hydrogen in the presence of a metal catalyst, such as palladium on carbon, in a polar solvent such as ethanol. The removal of silyl ether protecting groups is carried out by treatment with fluoride salts, such as tetrabutylamonium fluoride in a solvent such as THF. Conditions required to remove other protecting groups which may be present can be found in: *Protective Groups in Orsanic Synthesis*, Second Edition, T. W. Greene, John Wiley and Sons, New York, 1991.

The order of carrying out the steps of the foregoing reaction schemes is not always significant, and it is within the skill of the art to vary the order of reactions to facilitate the reaction or to avoid unwanted reaction products.

The following examples are provided for the purpose of further illustration only and are not intended to limit the disclosed invention.

EXAMPLE 1

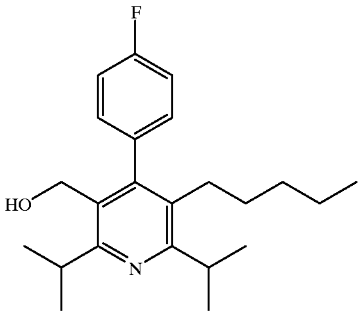

2,6-Diisopropyl-3-hydroxymethyl-4-(4-fluorophenyl)-5-pentylpyridine

Step A: 3-Amino-4-methyl-2-pentenoic acid, ethyl ester

To 100 g (0.63 mol) of ethyl isobutyryl acetate was added ammonium acetate (68.2 g, 0.89 mol), cyclohexane (230 mL) and isopropanol (74 mL). The mixture was heated at reflux under argon atmosphere with a Dean-Stark trap. After 2 hours, a second portion of ammonium acetate (14.6 g, 0.19 mol) was added to the reaction. The reaction was heated at reflux for 12 hours and then allowed to cool to room temperature. A total of ~30 mL of water was collected in the Dean-Stark trap. An ice bath was used to cool the reaction to 10° C. and then ammonium hydroxide (63 mL) was added dropwise. The organic layer was separated, dried with sodium sulfate, filtered, and concentrated to yield a yellow oil. The crude product (90.9 g, 0.58 mol, 92%) was taken directly to the next step without any further purification.

Step B: Diethyl 1,4-dihydro-2,6-diisopropyl-4-(4-fluorophenyl)-3,5-pyridinedicarboxylate To ethyl 3-amino-4methylpent-2-enoate (Step A) (90 g, 57 mmol) was added ethyl isobutyryl acetate (90 g, 57 mmol) and 4-fluorobenzaldehyde (61.4 mL, 0.57 mmol). The mixture was heated under argon at 130° C. for 26 hours (Precaution: Check the reflux condenser after a few hours as excess ammonium acetate will clog the condenser). The reaction was allowed to cool to room temperature and left to crystallize for 4 days. The solid was collected by filtration with vacuum (46.9 g, 116 mmol, 20%) and taken directly to the next step without further purification.

Step C: Diethyl 2,6-diisopropyl-4-(4-fluorophenyl)-3,5-pyridinedicarboxylate

To the intermediate obtained in Step B (33 g, 82 mmol) in dichloromethane (400 ml) was added 2,3-dichloro-5,6-dicyanobenzoquinone (DDQ, 20.5 g, 90 mmol) under argon and the mixture was stirred for 2 hours. The stirring was stopped to allow the precipitate to settle. The precipitate was filtered, washed with dichloromethane (3x30 mL), and discarded. The filtrate was concentrated to afford a brown solid, which was subjected to flash chromatography (6/4 mixture of dichloromethane/hexanes) resulting in a pure white solid (25.8 g, 64.3 mmol, 78%). $^1H$ NMR (300 MHz, $CDCl_3$): δ7.28 (m, 2 H), 7.06 (m, 2 H), 4.03 (q, J=7.0 Hz, 4 H), 3.11 (septet, J=6.6 Hz, 2 H), 1.32 (d, J=6.5 Hz, 12 H), 0.979 (t, J=3.3 Hz, 6 H). FAB-MS: calculated for ($C_{23}H_{28}NO_4F$) 401, found 402 (M+H). Anal. calc for $C_{23}H_{28}NO_4F$: C, 68.64; H, 7.24; N, 3.48; F, 4.72. Found: C, 69.12; H, 6.98; N, 3.42; F, 4.96. mp 72–74° C. $R_f$=0.4 (10% ethyl acetate/hexane).

Step D: Ethyl 2,6-diisopropyl-4-(4-fluorophenyl)-5-hydroxymethyl-3-pyridineacarboxylate To a solution of the intermediate obtained in Step C (23.4 g, 58.3 mmol) in anhydrous tetrahydrofuran (300 mL) stirred under argon at 0° C. was added a solution of 3.4M of sodium bis(2-methoxyethoxy)aluminum hydride in toluene (Red-Al) (61 mL, 204 mmol, 65 wt % in toluene) via syringe over 20 min. The reaction mixture was allowed to stir at room temperature for 7 hr, then cooled again to 0° C. and carefully quenched by the dropwise addition of water. The solution was decanted from the solid which forms and the solvent removed in vacuo. The residue was purified by flash chromatography (300 g silica) via step gradient. Elution with 5% diethyl ether/hexane afforded 6.6 g (16.4 mmol, 28%) of recovered starting material and elution with 40% diethyl ether($Et_2O$)/hexane yielded the desired product as a yellow waxy solid (14 g, 39 mmol, 67%). $^1H$ NMR (300 MHz, $CDCl_3$): δ7.27 (m, 2 H), 7.10 (m, 2 H), 4.46 (d, J=5.2 Hz, 2 H), 3.98 (q, J=7 Hz, 2 H), 3.48 (sept, J=6.6 Hz, 1 H), 3.05 (sept, J =6.6 Hz, 1 H), 1.32 (t, J=6.6 Hz, 12 H), 0.97 (t, J=7 Hz, 3 H). FAB-MS: calculated for ($C_{21}H_{26}FNO_3$) 359, found 360 (M+H). $R_f$=0.2 (20% ethyl acetate/hexane).

Step E: 5-Carboethoxy-2,6-diisopropyl-4-(4-fluorophenyl)-3-pyridinecarboxaldehyde To a solution of the intermediate obtained in Step D (13 g, 36 mmol) in dichloromethane (1 L) was added Brockman I neutral alumina (7.4 g, 72 mmol). The suspension was stirred at room temperature and treated with pyridinium chlorochromate (PCC) (16 g, 72 mmol) in three portions.

The suspension was stirred at room temperature for 1 hr, then poured into 1:1 diethyl ether/hex (1 L), filtered through a pad of silica, the pad washed with diethyl ether (500 mL) and the combined eluent concentrated to afford a viscous oil which slowly solidified (12.8 g, 35.9 miol, 99%): $R_f$=0.31 (10% ethyl acetate/hexane). $^1$H NMR (300 MHz, $CDCl_3$): δ9.85 (s, 1 H), 7.27 (m, 2 H), 7.13 (m, 2 H), 4.04 (q, J=7 Hz, 2 H), 3.88 (sept, J=6.6 Hz, 1 H), 3.12 (sept, J=6.6 Hz, 1 H), 1.33 (t, J=6.6 Hz, 12 H), 1.00 (t, J=7 Hz, 3 H). EI-MS calcd for ($C_{21}H_{24}FNO_3$) 357, found 358 (M+H). Anal. Calcd for $C_{21}H_{24}FNO_3$: C, 70.57; H, 6.77; N, 3.92. Found: C, 70.62; H, 6.78; N, 3.84.

Step F: Ethyl 2,6-diisopropyl4-(4-fluorophenyl)-5-(-pentenyl)-3-pyridinecarboxylate Butyltriphenylphosphonium bromide (2.7 g, 6.76 mmol) was suspended in anhydrous THF (75 mL) under argon and stirred at −78° C. A 1.6 M solution of n-butyllithium in hexanes (4.2 mL, 6.76 mmol) was added dropwise. The reaction mixture was allowed to come to 0° C. and was stirred at that temperature for 1.5 hr. The resulting brightly colored solution was cooled again to −78° C. and treated dropwise with a solution of the intermediate obtained in Step E (2 g, 5.60 mmol) in THF (20 mL). The reaction mixture was allowed to stir at 0° C. for 1 hr, then quenched by the addition of water (5 mL). The nTF was removed in vacua, the residue partitioned between ethyl ether (200 mL) and water (50 mL). The organic layer was washed with brine (50 mL), dried over $MgSO_4$ and concentrated. Flash chromatography through silica (5% diethyl ether/hexane) affords a viscous oil (2 g, 5 mmol, 90%) (E,Z mixture). $^1$H NMR (300 MHz, $CDCl_3$): δ7.14 (m, 2 H), 7.02 (m, 2 h), 6.10 (dt, J=1.8, 11.4 Hz, 0.4 H), 6.04 (dt, J=1.5, 16.2 Hz, 0.6 H), 5.48 (dt, J=7, 11.4 Hz, 0.4 H), 5.33 (dt, J=7, 16.2 Hz, 0.6 H), 4.00 (q, J=7 Hz, 0.8 H), 3.98 (q, J=7 Hz, 1.2 H), 3.39 (sept, J=6.6 Hz, 0.6 H), 3.27 (sept, J=6.6 Hz, 0.4 H), 3.06 (m, 1 H), 1.95 (dq, J=1.5, 7 Hz, 1 H), 1.26 (m, 13 H), 1.19 (m, 2 H), 0.97 (t, J=7 HZ, 3 H), 0.77 (t, J=7 Hz, 1.2 H), 0.76 (t, J=7 Hz, 1.8 H). EI-MS calculated for ($C_{25}H_{32}FNO_2$) 397 found 397 ($M^+$). $R_f$=0.5 (10% ethyl acetate/hexane).

Step G: 2,6-Diisopropyl-3-hydroxymethyl-4-(4-fluorophenyl)-5-(1-pentenyl)pyridine The intermediate obtained in Step F (2 g, 5.03 mmol) was dissolved in anhydrous THF (100 mL) under argon and treated dropwise at room temperature with lithium aluminum hydride (1.0 M in THF, 10 mL, 10 mmol). The reaction mixture was stirred at reflux for 1 hr, cooled to room temperature and quenched by the addition of 0.38 mL $H_2O$, 0.38 mL 20% aqueous NaOH and 1.1 mL $H_2O$. The resulting suspension was filtered through a cake of Celite and the filtrate concentrated and purified by chromatography through silica (5% ethyl acetate/hexane) to afford the product as a white foam (1.42 g, 4.0 mmol, 80%). $R_f$=0.2 (10% ethyl acetate/hexane).

Step H: 2,6Diisopropyl-3-hydroxymethyl-4-(4-fluorophenyl)-5-pentylpyridine

The intermediate obtained in Step G was dissolved in absolute ethanol (50 mL) under argon, treated with 10% palladium on carbon (140 mg, 0.1 eq), then stirred under a hydrogen atmosphere for 2 hr. After purging the system with argon, the catalyst was removed by filtration through a pad of Celite. The solvent was removed and the product dried in vacuo to afford the title compound as a white solid (1.4 g, 3.9 mmol, 98%). $^1$H NMR (300 MHz, $CDCl_3$): δ7.15 (m, 4 H), 4.33 (d, J=4.4 Hz, 2 H), 3.41 (sept, J=6.6 Hz, 1 H), 3.23 (sept, J =6.6 Hz, 1 H), 2.26 (m, 2 H), 1.33 (d, J=6.6 Hz, 6 H), 1.30 (d, J=6.6 Hz, 6 H), 1.27 (m, 2 H), 1.13 (m, 5 H), 0.79 (t, J=6.6 Hz, 3 H). FAB-MS: calculated for ($C_{23}H_{32}FNO$) 357, found 358 (M+H). Anal. calcd for $C_{23}H_{32}FNO$: C, 77.27; H, 9.02; N, 3.92. Found: C, 77.46; H, 8.95; N, 3.78. $R_f$=0.3 (20% ethyl acetate/hexane). mp 100–101° C.

EXAMPLE 2

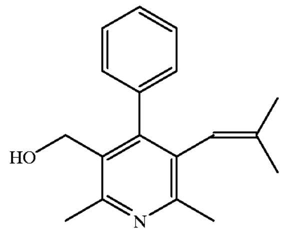

2,6Dimethyl-3hydroxymethyl4-phenyl-5-(2-methyl-1-propenyl)-pyridine

The title compound was prepared from ethyl acetoacetate, benzaldehyde and isopropyl triphenylphosphonium iodide according to the procedures described in Example 1, Steps A–G. $^1$H NMR (300 MHz, $CDCl_3$): δ7.34 (m, 3 H), 7.10 (m, 2 H), 5.70 (s, 1 H), 4.42 (s, 2 H), 2.69 (s, 3 H), 2.43 (s, 3 H), 1.60 (s, 3 H), 1.35 (s, 3 H). EI-MS calculated for ($C_{18}H_{21}NO$) 267, found 267 ($M^+$). mp 48–50° C. $R_f$=0.3 (90% ethyl acetate/hexane).

EXAMPLE 3

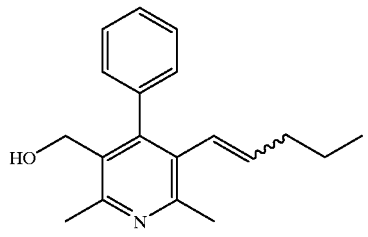

2,6Dimethyl-3-hydroxymethyl4-phenyl-5-(1-pentenyl)pyridine

The title compound was prepared from ethyl acetoacetate, benzaldehyde and butyl triphenylphosphonium bromide according to the procedures described in Example 1, Steps A–G. The product was obtained as a mixture 3:1 trans:cis isomers; gummy oil. $^1$H NMR (300 MHz, $CDCl_3$): δ7.37 (m, 3 H), 7.12 (m, 2 H), 5.94 (m, 1 H), 5.40 (m, 1 H), 4.41 (bs, 2 H), 2.71 & 2.68 (2s, 3 H), 2.57 & 2.46 (2s, 3 H), 1.91 & 1.69 (2q, J=7 Hz, 2 H), 1.52 (bs, 1 H), 1.19 (m, 2 H), 0.77 (m, 3 H). EI-MS: calculated for ($C_{19}H_{23}NO$) 281, found 281. $R_f$=0.4 (90% ethyl acetate/hexane).

EXAMPLE 4

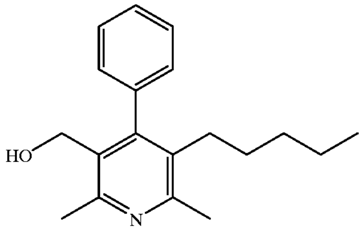

2,6-Dimethyl-3-hydroxymethyl-4phenyl-5pentylpyridine

The title compound was prepared from 2,6dimethyl-3-hydroxymethyl-4-phenyl-5-(1-pentenyl)pyridine (Example 3) according to the procedure described in Example 1, Step H. $^1$H NMR (300 MHz, $CDCl_3$): δ7.42 (m, 3 H), 7.15 (m, 2 H), 4.33 (s, 2 H), 2.65 (s, 3 H), 2.56 (s, 3 H), 2.27 (m, 2 H), 1.29 (m, 2 H), 1.11 (m, 4 H), 0.76 (t, J =7 Hz, 3 H). EI-MS: calculated for ($C_{19}H_{25}NO$) 283, found 283 ($M^+$). Anal. calculated for $C_{19}H_{25}NO$: C, 80.52; H, 8.89; N, 4.94. Found: C, 80.39; H, 8.85; N, 4.85. mp 99–100° C. $R_f$=0.3 (90% ethyl acetate/hexane).

EXAMPLE 5

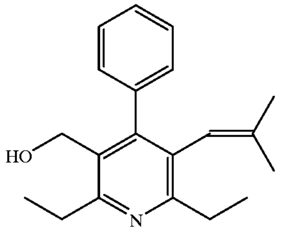

2,6Diethyl-3-hydroxymethyl-4-phenyl-5-(2-methyl-1-propenyl)pyridine

The title compound was prepared from etyl propionylacetate, benzaldehyde an isopropyl triphenylphosphonium iodide according to the procedures described in Example 1, Steps A–G. $^1$H NMR (300 MHz, $CDCl_3$): δ7.34 (m, 3 H), 7.11 (m, 2 H), 5.76 (s, 1 H), 4.44 (d, J=5.5 Hz, 2 H), 3.01 (q, J=7.4 Hz, 2 H), 2.75 (q, J=7.4 Hz, 2 H), 1.58 (s, 3 H), 1.35 (m, 7 H), 1.21 (t, J=7.4 Hz, 3 H). FAB-MS: calculated for ($C_{20}H_{25}NO$) 295, found 296 (M+H). Anal. Calcd for $C_{20}H_{25}NO$: C, 81.31; H, 8.53; N, 4.74. Found: C, 81.03; H, 8.55; N, 4.65. mp 103–104° C. $R_f$=0.4 (50% ethyl acetate/hexane).

EXAMPLE 6

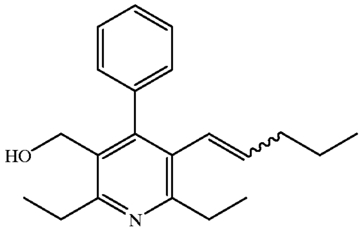

2,6-Diethyl-3-hydroxymethyl-4-phenyl-5-(1-pentenyl)pyridine

The title compound was prepared from ethyl propionylacetate, benzaldehyde and butyl triphenylphosphonium bromide according to the procedures described in Example 1, Steps A–G. The product was obtained as a mixture 6:4 trans:cis isomers. $^1$H NMR (300 MHz, $CDCl_3$): δ7.36 (m, 3 H), 7.14 (m, 2 H), 6.00 (m, 1 H), 5.37 (m, 1 H), 4.42 (m, 2 H), 2.90 (m, 4 H), 1.89 & 1.67 (2q, J=7 Hz, 2 H), 1.25 (m, 9 H), 0.76 (m, 3 H). FAB-MS: calculated for ($C_{21}H_{27}NO$) 309, found 310 (M+H); Anal. Calcd for $C_{21}H_{27}NO$: C, 81.51; H, 8.79; N, 4.53. Found: C, 81.95; H, 8.90; N, 4.45. mp 74–76° C. $R_f$=0.5 (50% ethyl acetate/hexane)

EXAMPLE 7

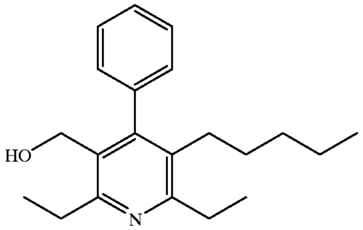

2,6-Diethyl-3-hydroxymethyl-4-phenyl-5-pentylpyridine

The title compound was prepared from 2,6-diethyl-3-hydroxymethyl-4-phenyl-5-(1-pentenyl)pyridine (Example 6) according to the procedure described in Example 1, Step H. $^1$H NMR (300 MHz, $CDCl_3$): δ7.42 (m, 3 H), 7.18 (m, 2 H), 4.34 (d, J=6 Hz, 2 H), 2.96 (q, J=7.7 Hz, 2 H), 2.84 (q, J=7.7 Hz, 2 H), 2.28 (m, 2 H), 1.34 (m, 9 H), 1.09 (m, 4 H), 0.76 (t, J=7 Hz, 3 H). FAB-MS: calculated for ($C_{21}H_{29}NO$) 311, found 312 (M+H). mp 76–77C. $R_f$=0.5 (50% ethyl acetate/hexane).

EXAMLE 8

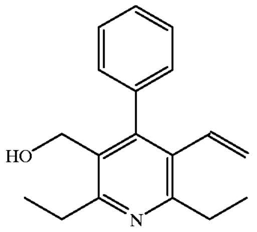

2,6-Diethyl-3-hydroxymethyl4-phenyl-5-(1-ethenyl) pyridine

The title compound was prepared from ethyl propionylacetate, benzaldehyde and methyl triphenylphosphonium bromide/sodium amide according to the procedures descnbed in Example 1, Steps A–G. $^1$H NMR (300 MHz, $CDCl_3$): δ7.40 (m, 3 H), 7.20 (m, 2 H), 6.36 (dd, J=11, 18 Hz, 1 H), 5.22 (dd, J=11, 2Hz, 1 H), 5.00 (dd, J=18, 2 Hz, 1 H), 4.41 (d, J=6 Hz, 2 H), 2.96 (m, 4 H), 1.35 (m, 7 H). FAB-MS: calculated for ($C_{18}H_{21}NO$) 267, found 268 (M+H). Anal. Calcd for $C_{18}H_{21}NO$: C, 80.86; H, 7.92; N, 5.24. Found: C, 80.65; H, 8.06; N, 5.09. mp 84–85° C. $R_f$=0.4 (50% ethyl acetate/hexane).

EXAMPLE 9

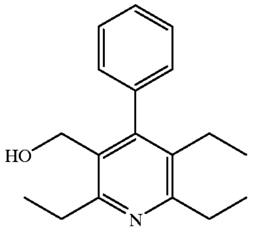

2,5,6-Triethyl-3-hydroxymethyl-4-phenylpyridine

The title compound was prepared from 2,6-diethyl-3-hydroxymethyl-4-phenyl-5-(1-ethenyl)pyridine (Example 8) according to the procedure described in Example 1, Step H. $^1$H NMR (300 MHz, $CDCl_3$): δ7.44 (m, 3 H), 7.18 (m, 2 H), 4.33 (d, J=6 Hz, 2 H), 2.97 (q, J=8 Hz, 2 H), 2.86 (q, J=8 Hz, 2 H), 2.36 (q, J=328 Hz, 2 H), 1.34 (m, 7 H), 0.93 (t, J=8 Hz, 3 H). FAB-MS: calculated for ($C_{18}H_{23}NO$) 269, found 270 (M+H). Anal. Calcd for $C_{18}H_{23}NO$: C, 80.26; H, 8.61; N, 5.20. Found: C, 79.70; H, 8.54; N, 5.08. mp 100° C. $R_f$=0.4 (50% ethyl acetate/hexane).

EXAMPLE 10

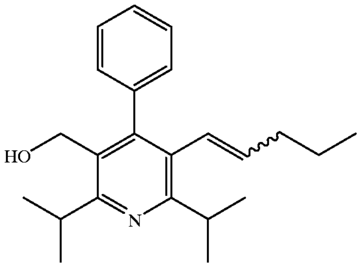

2,6-Diisopropyl-3-hydroxymethyl-4-phenyl-5-(1-pententyl)pyridine

The title compound was prepared from ethyl isobutyrylacetate, benzaldehyde and butyl triphenylphosphonium bromide according to the procedures described in Example 1, Steps A–G. $^1$H NMR (300 MHz, $CDCl_3$): δ7.35 (m, 3 H), 7.14 (m, 2 H), 5.99 (m, 1 H), 5.35 (m, 1 H), 4.41 (m, 2 H), 3.36 (m, 2 H), 1.89 & 1.70 (2q, J =7 Hz, 2 H), 1.24 (m, 15 H), 0.80 & 0.72 (2t, J=7 Hz, 3 H). FAB-MS: calculated for ($C_{23}H_{31}NO$) 337, found 338 (M+H). Anal. Calcd for $C_{23}H_{31}NO$: C, 81.85; H, 9.26; N, 4.15. Found: C, 81.88; H, 9.22; N, 3.93. mp 67–73° C. $R_f$=0.1 (10% ethyl acetate/hexane).

EXAMPLE 11

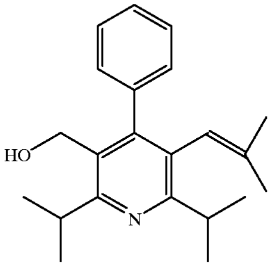

2,6-Diisopropyl-3-hydroxymethyl-phenyl-5-(2-methyl-1-propenyl)-pyridine

The title compound was prepared from ethyl isobutyrylacetate, benzaldehyde and isopropyl triphenylphosphonium iodide according to the procedures described in Example 1, Steps A–G. $^1$H NMR (300 MHz, $CDCl_3$): δ7.32 (m, 3 H), 7.11 (m, 2 H), 5.75 (s, 1 H), 4.43 (bs, 2 H), 3.46 (sept, J=6.6 Hz, 1 H), 3.18 (sept, J=6.6 Hz, 1 H), 1.57 (s, 3 H), 1.31 (m, 15 H). FAB-MS: calculated for ($C_{22}H_{29}NO$) 323, found 324 (M+H). Anal. Calcd for $C_{22}H_{29}NO$: C, 81.69; H, 9.04; N, 4.33. Found: C, 81.59; H, 8.94; N, 4.29. mp 93–95° C. $R_f$=0.1 (10% ethyl acetate/hexane).

EXAMPLE12

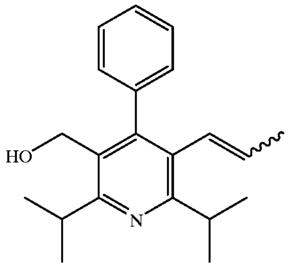

2,6Diisopropyl-3-hydroxymethyl-4-phenyl-5-(1-propenyl)pyridine

The title compound was prepared from ethyl isobutyrylacetate, benzaldehyde and ethyl triphenylphosphonium bromide according to the procedures described in Example 1, Steps A–G. The product was obtained as a mixture 1:1 trans:cis isomers; gummy oil. $^1$H NMR (300 MHz, $CDCl_3$): δ7.4 (m, 3 H), 7.2 (m, 2 H), 6.0 (m, 1 H), 5.5 & 5.4 (2m, 1 H), 4A (m, 2 H), 3.4 & 3.2 (2m, 2 H), 1.6 (m, 2 H), 1.4 (m, 7 H), 1.3 (m, 7 H). FAB-MS: calculated for (C21H27NO) 309, found 310 (M+H). Anal. Calcd for $C_{21}H_{27}NO$: C, 81.53; H, 9.98; N, 3.96. Found: C, 79.06; H, 9.65; N, 3.61. $R_f$=0.4 (20% ethyl acetate/hexane).

EXAMPLE 13

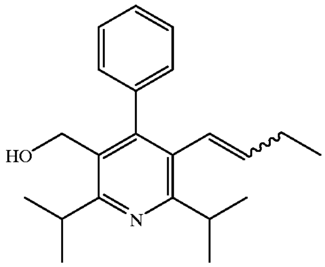

2,6Diisopropyl-3-hydroxymethyl4-phenyl-5-(1-butenyl)pyridine

The title compound was prepared from ethyl isobutyrylacetate, benzaldehyde and propyl triphenylphosphonium bromide according to the procedures described in Example 1, Steps A–G. The product was obtained as a mixture 1:1 trans:cis isomers; gummy oil. $^1$H NMR (300 MHz, $CDCl_3$): δ7.4 (m, 3 H), 7.2 (m, 2 H), 6.0 (m, 1 H), 5.4 (m, 1 H), 4.4 (m, 2 H), 3.3 (m, 3 H), 1.9 & 1.7 (2m , 2 H), 1.3 (m, 12 H), 0.7 (m, 3 H). FAB-MS: calculated for ($C_{22}H_{29}NO$) 323, found 324 (M+H). $R_f$=0.4 (20% ethyl acetate/hexane).

EXAMPLE 14

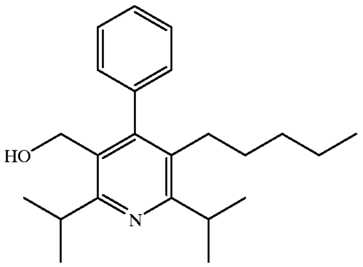

2,6-Diisopropyl-3-hydroxymethyl-phenyl-5-pentylpyridine

The title compound was prepared from 2,6-diisoproyl-3-hydroxymethyl1-phenyl-5-(1-pentenyl)pyridine (Example 10) according to the procedure described in Example 1, Step H. $^1$H NMR (300 MWz, $CDCl_3$) δ7.41 (m, 3 H), 7.18 (m, 2 H), 4.33 (s, 2 H), 3.42 (sept, J=6.6 Hz, 1 H), 3.23 (sept, J=6.6 Hz, 1 H), 2.26 (m, 2 H), 1.32 (m, 13 H), 1.11 (m, 5 H), 0.76 (t, J=7 Hz, 3 H). FAB(HR)-MS calcd for $C_{23}H_{33}NO$ 339.2640; found 340.2640 (M+H). mp 81–82° C. $R_f$=0.1 (10% ethyl acetate/hexane).

EXAMPLE 15

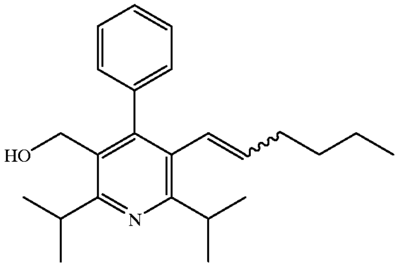

2,6Diisopropyl-3-hydroxymethyl-4-phenyl-5-(1-hexenyl)pyridine

The title compound was prepared from ethyl isobutyrylacetate, benzaldehyde and pentyl triphenylphosphonium bromide according to the procedures described in Example 1, Steps A–G. The product was obtained as a mixture 1:1 trans:cis isomers; gummy oil. $^1$H NMR (300 MHz, $CDCl_3$): δ7.35 (m, 3 H), 7.14 (m, 2 H), 5.99 (m, 1 H), 5.35 (m, 1 H), 4.40 (m, 2 H), 3.36 (m, 2 H), 1.92 & 1.70 (2m, 2 H), 1.20 (m, 17 H), 0.80 (m, 3 H). FAB-MS: calculated for ($C_{24}H_{33}NO$) 351, found 352 (M+H). Anal. Calcd for $C_{24}H_{33}NO$: C, 82.00; H, 9.46; N, 3.98. Found: C, 81.58; H, 9.50; N, 4.62. $R_f$=0.1 (10% ethyl acetate/hexane);

EXAMPLE 16

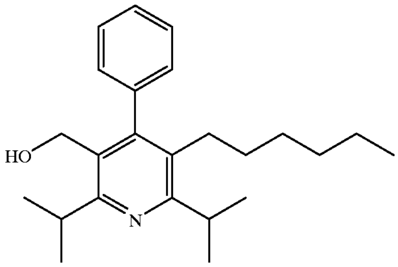

2,6Diisopropyl-3-hydroxymethyl-4-phenyl-5-hexylpyridine

The title compound was prepared from 2,6-diisopropyl-3-hydroxymethyl-phenyl-5-(1-hexenyl)pyridine (Example 15) according to the procedure described in Example 1, Step H. $^1$H NMR (300 MHz, $CDCl_3$): δ7.40 (m, 3 H), 7.18 (m, 2 H), 4.33 (d, J=5 Hz, 2 H), 3.42 (septet, J=7 Hz, 1 H), 3.23 (septet, J=7 Hz, 1 H), 2.26 H), 1.31 (m, 13 H), 1.12 (m, 8 H), 0.80 (t, J=7 Hz, 3 H). FAB-MS: calculated for ($C_{24}H_{35}NO$) 353, found 354 (M+H). Anal. Calcd for $C_{24}H_{35}NO$: C, 81.53; H, 9.98; N, 3.96. Found: C, 79.06; H, 9.65; N, 3.61. mp 71–72° C. $R_f$=0.1 (10% ethyl acetate/hexane).

EXAMPLE 17

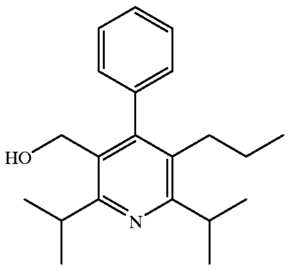

2,6-Diisoropyl-3-hydroxyethyl-4-phenyl-5-propylpyridine

The title compound was prepared from 2,6-diisopropyl-3-hydroxymethyl-4-phenyl-5-(1-propenyl)pyridine (Example 12) according to the procedure described in Example 1, Step H. $^1$H NMR (300 MHz, $CDCl_3$): δ7.41 (m, 3 H), 7.17 (m, 2 H), 4.33 (s, 2 H), 3.42 (sept, J=6.6 Hz, 1 H), 3.23 (sept, J=6.6 Hz, 1 H), 2.25 (m, 2 H), 1.33 (d, J=6.6 Hz, 6 H), 1.30 (d, J=6.6 Hz, 6 H), 1.27 (m, 2 H), 1.20 (m, 1H), 0.74 (t, J=7 Hz, 3 H). FAB-MS: calculated for ($C_{21}H_{29}NO$) 311, found 312 (M+H). Anal. Calcd for $C_{21}H_{29}NO$: C, 80.98; H, 9.38; N, 4.50. Found: C, 80.72; H, 9.47; N, 4.38. mp 89–90° C. $R_f$=0.4 (20% ethyl acetate/hexane).

EXAMPLE 18

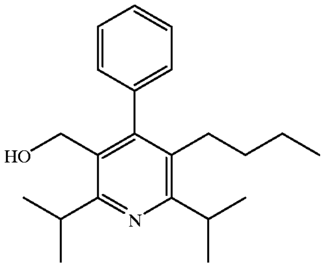

2,6-Diisopropyl-3-hydroxymethyl-4-phenyl-5-butylpyridine

The title compound was prepared from 2,6-diisopropyl-3-hydroxymethyl-4-phenyl-5-(1-butenyl)pyridine (Example 13) according to the procedure described in Example 1, Step H. $^1$H NMR (300 MHz, $CDCl_3$): δ7.41 (m, 3 H), 7.17 (m, 2 H), 4.33 (s, 2 H), (sept, J=6.6 Hz, 1 H), 3.24 (sept, J=6.6 Hz, 1 H), 2.28 (m, 2 H), 1.33 (d, J=6.6 Hz, 6 H), 1.31 (d, J=6.6 Hz, 6 H), 1.28 (m, 2 H), 1.14 (m, 3 H), 0.71 (t, J=7 Hz, 3 H). FAB-MS: calculated for ($C_{22}H_{31}NO$) 325, found 326 (M+H). Anal. Calcd for $C_{22}H_{31}NO$: C, 81.18; H, 9.60; N, 4.30. Found: C, 81.28; H, 9.87; N, 4.07. mp 83–84° C. $R_f$=0.4 (20% ethyl acetate/hexane).

EXAMPLE 19

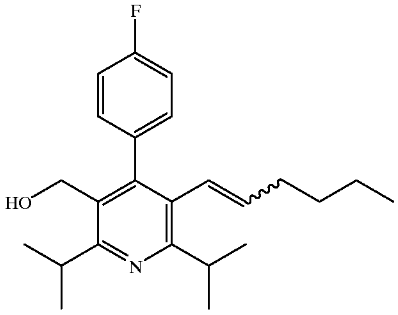

2,6-Diisproyl-3-hyroxymethyl-4-(4-fluorophenyl)-5-(1-hexenyl)-pyridine

The title compound was prepared from ethyl isobutyrylacetate, 4-fluorobenzaldehyde and pentyl triphenylphosphonium bromide according to the procedures described in Example 1, Steps A–G. The product was obtained as a mixture 6:4 trans:cis isomers; gummy oil. $^1$H NMR (300 MHz, $CDCl_3$): δ7.10 (m, 4 H), 5.98 (m, 1 H), 5.42 (dt, J=7, 11.4 Hz, 0.4 H), 5.29 (dt, J=7, 16.2 Hz, 0.6 H), 4.40 (d, J=5.5 Hz, 2 H), 3.44 (m, 1 H), 3.36 (sept, J=6.6 Hz, 0.6 H), 3.24 (sept, J=6.6 Hz, 0.4 H), 1.94 (m, 1 H), 1.36 (m, 6 H), 1.23 (m, 8 H), 1.12 (m, 4 H), 0.82 (m, 3 H). FAB-MS: calculated for ($C_{24}H_{32}FNO$) 369, found 370 (M+H). $R_f$=0.4 (20% ethyl acetate/hexane).

EXAMPLE 20

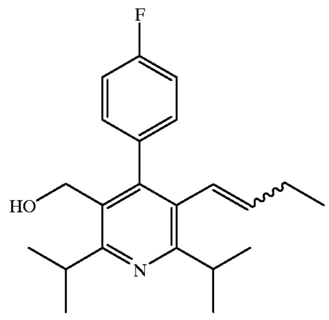

2,6-Diisopropyl-3-hydroxymethyl-4-(4-fluorophenyl)-5-(l-butenyl)-pyridine

The title compound was prepared from ethyl isobutyrylacetate, 4-fluorobenzaldehyde and propyl triphenylphosphonium bromide according to the procedures described in Example 1, Steps A–G. The product was obtained as a mixture 1:1 trans:cis isomers; gummy oil. $^1$H NMR (300 MHz, $CDCl_3$): δ7.10 (m, 4 H), 5.97 (m, 1 H), 5.39 (dt, J=7, 11.4 Hz, 0.5 H), 5.32 (dt, J=7, 16.2 Hz, 0.5 H), 4.41 (d, J=5.5 Hz, 2 H), 3.45 (m, 1 H), 3.36 (sept, J=6.6 Hz, 0.5 H), 3.24 (sept, J=6.6 Hz, 0.5 H), 1.95 (m, 1 H), 1.70 (m, 1 H), 1.35 (d, J=6.6 Hz, 3 H), 1.34 (d, J=6.6 Hz, 3 H), 1.25 (m, 7 H), 0.79 (t, J=7.5 Hz, 1.5 H), 0.78 (t, J=7.5 Hz, 1.5 H). FAB-MS: calculated for ($C_{22}H_{28}FNO$) 341, found 342 (M+H). $R_f$=0.4 (20% ethyl acetate/hexane).

EXAMPLE 21

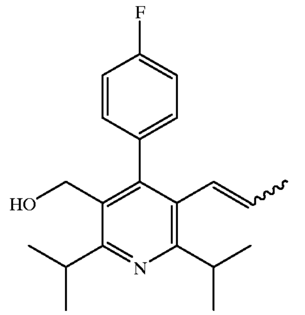

2,6-Diisopropyl-3-hydroxymethyl-4-(4-fluorophenyl)-5-(1-propenyl)-pyridine

The title compound was prepared from ethyl isobutyrylacetate, 4-fluorobenzaldehyde and ethyl triphenylphosphonium bromide according to the procedures described in Example 1, Steps A–G. The product was obtained as a mixture 1:1 trans:cis isomers. $^1$H NMR (300 MHz, $CDCl_3$): δ7.11 (m, 4 H), 6.04 (d, J=11.7 Hz, 0.5 H), 5.96 (d, J=16.1 Hz, 0.5 H), 5.53 (m, 0.5 H), 5.33 (m, 0.5 H) 5.33 (m, 0.5 H), 4.41 (m, 3 H), 3.42 (m, 1.5 H), 3.20 (sept, J=6.6 Hz, 0.5 H), 1.61 (d, J=6 Hz, 2 H), 1.3 (m, 13 H). FABMS: calculated for ($C_{21}H_{26}FNO$) 327, found 328 (M+H). Anal. Calcd for $C_{21}H_{26}FNO$: C, 77.03; H, 8.00; N, 4.28. Found: C, 77.15; H, 8.07; N, 4.11. mp 46–47° C. $R_f$=0.4 (20% ethyl acetate/hexane).

EXAMPLE 22

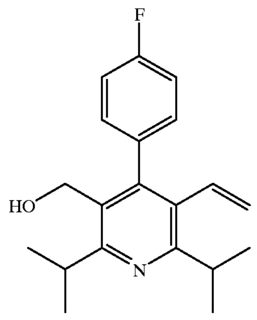

2,6Diisopropyl-3-hydroxymethyl-4-(4-fluorophenyl)-5-ethenylpyridine

The title compound was prepared from ethyl isobutyrylacetate, 4-fluorobenzaldehyde and methyl triphenylphosphonium bromide/sodium amide according to the procedures described in Example 1, Steps A–G. $^1$H NMR (300 MHz, $CDCl_3$): δ7.12 (m, 4 H), 6.35 (dd, J=11.5,18 Hz, 1 H), 5.24 (dd, J=1.5, 11.4 Hz, 1 H), 4.97 (dd, J=1.5, 18 Hz, 1 H), 4.41 (d, J=5.5 Hz, 2 H), 3.44 (sept, J=6.6 Hz, 2 H), 1.35 (d, J=6.6 Hz, 6 H), 1.28 (d, J=6.6 Hz, 6 H), 1.25 (m, 1 H). FAB-MS: calculated for ($C_{20}OH_{24}FNO$) 313, found 314 (M+H). Anal. Calcd for $C_2OH_{24}FNO$: C, 76.65; H, 7.72; N, 4.47. Found: C, 76.87; H, 7.79; N, 4.33. mp 119–120° C. $R_f$=0.4 (20% ethyl acetate/hexane).

EXAMPLE 23

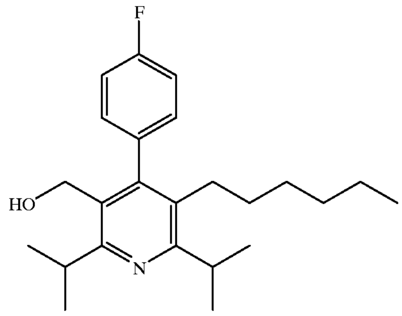

2,6-Diisopropyl-3-hydroxymethyl-4-(4-fluorophenyl)-5-hexylpyridine

The title compound was prepared from 2,6-diisopropyl-3-hydroxymethyl-4-(4-fluorophenyl)-5-(1-hexenyl)pyridine (Example 19) according to the procedure described in Example 1, Step H. $^1$H NMR (300 MHz, $CDCl_3$): δ7.14 (m, 4 H), 4.33 (s, 2 H), 3.41 (sept, J=6.6 Hz, 1 H), 3.23 (sept, J=6.6 Hz, 1 H), 2.26 (m, 2 H) 1.33 (d, J=6.6 Hz, 6 H), 1.30 (d, J=6.6 Hz, 6 H), 1.26 (m, 1 H), 1.14 (m, 7 H), 0.82 (t, J=7 Hz, 3 H). FAB-MS: calculated for ($C_{24}H_{34}FNO$) 371, found 372 (M+H). mp 93–95° C. $R_f$=0.4 (20% ethyl acetate/hexane).

EXAMPLE 24

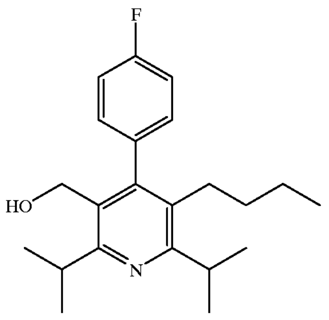

2,6-Diisopropyl-3-hydroxymethal-4-(4fluorophenyl)-5-butylpyridine

The title compound was prepared from 2,-diisopropyl-3-hydroxymethyl-4-(4-fluorophenyl)-5-(1-butenyl)pyridine (Example 20) according to the procedure described in Example 1, Step H. $^1$H NMR (300 MHz, $CDCl_3$): δ7.15 (m, 4 H), 4.33 (d, J=5.2 Hz, 2 H), 3.41 (sept, J=6.6 Hz, 1 H), 3.23 (sept, J=6.6 Hz, 1 H), 2.27 (m, 2 H), 1.34 (d, J=6.6 Hz, 6 H), 1.30 (d, J=6.6 Hz, 6 H), 1.27 (m, 1 H), 1.16 (m, 3 H), 0.73 (t, J=7 Hz, 3 H). FAB-MS: calculated for ($C_{22}H_{30}FNO$) 343, found 344 (M+H). Anal. Calcd for $C_{22}H_{30}FNO$: C, 76.93; H, 8.80; N, 4.08. Found: C, 76.93; H, 8.70; N, 3.96. mp 45–50° C. $R_f$=0.4 (20% ethyl acetate/hexane).

EXAMPLE 25

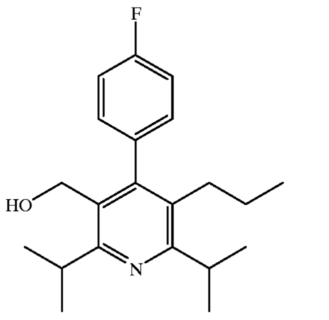

2,6-Diisopropyl-3-hydroxymethyl-4-(4-fluorophenyl)-5-propylpyridine

The title compound was prepared from 2,6-diisopropyl-3-hydroxymethyl-4-(4-fluorophenyl)-5-(1-propenyl) pyridine (Example 21) according to the procedure described in Example 1, Step H. $^1$H NMR (300 MHz, $CDCl_3$): δ7.15 (m, 4 H), 4.33 (s, 2 H), 3.41 (sept, J=6.6 Hz, 1 H), 3.23 (sept, J=6.6 Hz, 1 H), 2.25 (m, 2 H), 1.33 (d, J=6.6 Hz, 6 H), 1.30 (d, J=6.6 Hz, 6 H), 1.27 (m, 1 H), 1.19 (m, 1 H), 0.76 (t, J=7 Hz, 3 H). FAB-MS: calculated for ($C_{21}H_{20}FNO$) 329, found 330 (M+H). Anal. Calcd for $C_{21}H_{28}FNO$: C, 76.56; H, 8.57; N, 4.25. Found: C, 76.55; H, 8.48; N, 4.11. mp 49–54°C. $R_f$=0.4 (20% ethyl acetate/hexane).

EXAMPLE 26

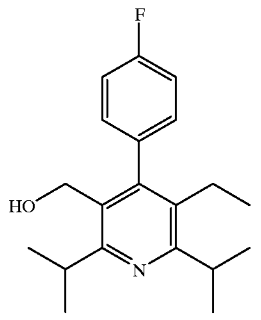

2,6Diisopropyl-3-hydroxymethyl-4-(4-fluorophenyl)-5-ethylpyridine

The title compound was prepared from 2,6dusopropyl-3-hydroxymethyl-4-(4-fluorophenyl)-5ethenylpyridine (Example 22) according to the procedure described in Example 1, Step H. $^1$H NMR (300 MHz, $CDCl_3$): δ7.15 (m, 4 H), 4.33 (d, J=3.6 Hz, 2 H), 3.41 (sept, J=6.6 Hz, 1 H), 3.26 (sept, J=6.6 Hz, 1 H), 2.34 (q, J=7.35 Hz, 2 H), 1.33 (d, J=6.6 Hz, 6 H), 1.31 (d, J=6.6 Hz, 6 H), 1.19 (m, 1 H), 0.93 (t, J=7.35 Hz, 3 H). FAB-MS: calculated for ($C_{20}H_{26}FNO$) 315, found 316 (M+H). Anal. Caled for $C_{20}H_{26}FNO$: C, 76.16; H, 8.31; N, 4.44. Found: C, 75.74; H, 8.50; N, 4.27. mp 126–129° C. $R_f$=0.4 (20% ethyl acetate/hexane).

EXAMPLE 27

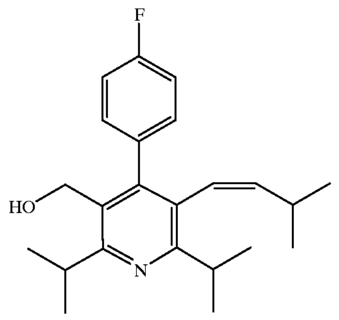

2,6-Diisopropyl-3-hydroxymethyl-4-(4-fluorophenyl)-5-(3-methyl-1-butenyl)pyridine The title compound was prepared from ethyl isobutyrylacetate, 4-fluorobenzaldehyde and isobutyl triphenylphosphonium bromide according to the procedures described in Example 1, Steps A–G. $^1$H NMR (300 MHz, $CDCl_3$): δ7.07 (m, 4 H), 5.92 (d, J=10.7 Hz, 1 H), 5.20 (dd, J=10.7, 11.4 Hz, 1 H), 4.42 (bs, 2 H), 3.45 (sept, J=6.6 Hz, 1 H), 3.30 (sept, J=6.6 Hz, 1 H), 2.06 (m, 1 H), 1.35 (d, J=6.6 Hz, 6 H), 1.31 (m, 1 H), 1.24 (m, 5 H), 0.69 (bs, 6 H). FAB-MS: calculated for ($C_{23}H_{30}FNO$) 355, found 356 (M+H). Anal. Calcd for $C_{23}H_{30}FNO$: C, 77.71; H, 8.51; N, 3.94. Found: C, 77.94; H, 8.59; N, 3.79. mp 112° C. $R_f$=0.3 (20% ethyl acetate/hexane).

EXAMPLE 28

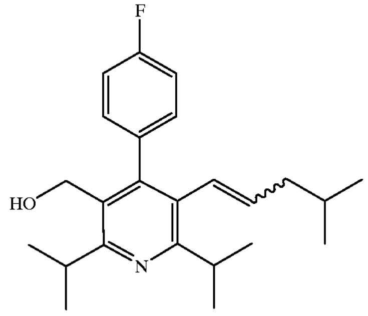

2,6Diisopropyl-3-hydroxymethyl-4-(4-fluorophenyl)-5-(4-methyl-1-pentenyl)pyridine The title compound was prepared from ethyl isobutyrylacetate, 4-fluorobenzaldehyde and isoamyl triphenylphosphonium bromide according to the procedures described in Example 1, Steps A–G. The product is obtained as a 6:4 mixture of trans:cis isomers. $^1$H NMR (300 MHz, $CDCl_3$): δ7.11 (m, 4 H), 6.04 (dt, J=1.5, 11 Hz, 0.4 H), 5.96 (dt, J=1.5, 16 Hz, 0.6 H), 5.47 (dt, J=7, 11 Hz, 0.4 H), 5.32 (dt, J=7, 16 Hz, 0.6 H), 4.41 (m, 2 H), 3.44 (m, 0.8 H), 3.38 (sept, J=6.6 Hz, 0.6 H), 3.24 (sept, J=6.6 Hz, 0.6 H), 1.84 (m, 1 H), 1.45 (m, 1 H), 1.35 (m, 6 H), 1.24 (m, 7 H), 0.79 (d, J=6.6 Hz, 2.4 H), 0.73 (d, J=6.6 Hz, 3.6 H). FAB-MS: calculated for ($C_{24}H_{32}FNO$) 369, found 370 (M+H). Anal. Calcd for $C_{24}H_{32}FNO$: C, 78.01; H, 8.73; N, 3.79. Found: C, 78.14; H, 8.62; N, 3.50. mp 48–50° C. $R_f$=0.3 (20% ethyl acetate/hexane).

EXAMPLE 29

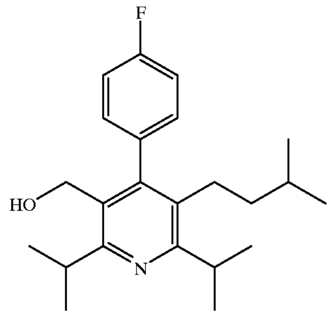

2,6-Diisopropyl-3-hydroxymethyl-4-(4-fluorophenyl)-5-(3-methylbutyl)pyridine

The title compound was prepared from 2,6-diisopropyl-3-hydroxymethyl-4-(4fluorophenyl)-5-(3-methyl-1-butenyl)pyridine (Example 27) according to the procedure described in Example 1, Step H. $^1$H NMR (300 MHz, $CDCl_3$): δ7.14 (m, 4 H) 4.33 (d, J=5.5 Hz, 2 H), 3.41 (sept, J=6.6 Hz, 1 H), 3.22 (sept, J=6.6 Hz, 1 H), 2.27 (m, 2 H), 1.35 (m, 1 H), 1.33 (d, J=7 Hz, 6 H), 1.30 (d, J=7 Hz, 6 H), 1.17 (m, 3 H), 0.70 (d, J=6.6 Hz, 6 H). FAB-MS: calculated for ($C_{23}H_{32}FNO$) 357, found 358 (M+H). Anal. Calcd for $C_{23}H_{32}FNO$: C, 77.27; H, 9.02; N, 3.92. Found: C, 77.34; H, 9.15; N, 3.69. mp 43–45° C. $R_f$=0.2 (20% ethyl acetate/hexane).

EXAMPLE 30

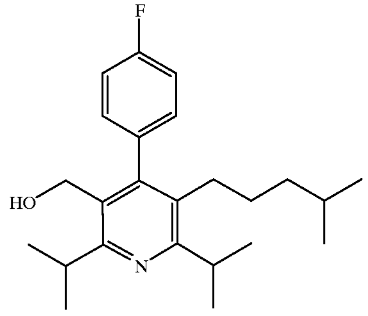

2,6-Diisopropyl-3-hydroxymethyl-4-(4-fluorophenyl)-5-(4-methylpentyl)pyridine

The title compound was prepared from 2,6-diisopropyl-3-hydroxymethyl-4-(4-fluorophenyl)-5-(4-methyl-1-pentenyl)pyridine (Example 28) according to the procedure described in Example 1, Step H. $^1$H NMR (300 MHz, $CDCl_3$): δ7.14 (m, 4 H), 4.33 (d, J=5 Hz, 2 H), 3.41 (sept, J=6.6 Hz, 1 H), 3.22 (sept, J=6.6 Hz, 1 H), 2.23 (m, 2 H), 1.38 (m, 1 H), 1.33 (d, J=6.6 Hz, 6 H), 1.30 (d, J=6.6 Hz, 6 H), 1.27 (m, 1 H), 1.17 (m, 1 H), 1.00 (m, 3 H), 0.76 (d, J=6.6 Hz, 6 H). FAB-MS: calculated for ($C_{24}H_{34}FNO$) 371, found 372 (M+H). Anal. Calcd for C24H34FNO: C, 77.59; H, 9.22; N, 3.77. Found: C, 77.63; H, 9.39; N, 3.58. mp 101–103° C. $R_f$=0.3 (20% ethyl acetate/hexane).

EXAMPLE 31

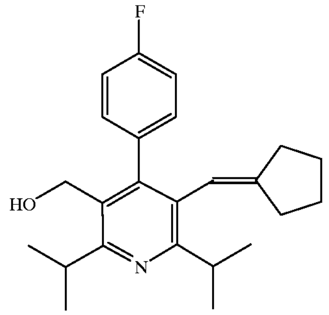

2,6-Diisopropyl-3-hydroxymethyl-4-(4-flurorphenyl)-5-(cyclopentyl-idenemethylene) pyridine The title compound was prepared from ethyl isobutyrylacetate, 4-fluorobenzaldehyde and cyclopentyl triphenylphosphonium bromide according to the procedures described in Example 1, Steps A–G. $^1$H NMR (300 MHz, $CDCl_3$): δ7.13 (m, 2 H), 7.07 (m, 2 H), 5.88 (s, 1 H), 4.43 (d, J=5.5 Hz, 2 H), 3.44 (sept, J=6.6 Hz, 1 H), 3.21 (sept, J=6.6 Hz, 1 H), 2.11 (m, 2 H), 1.75 (m, 2 H), 1.47 (m, 4 H), 1.34 (d, J=6.6 Hz, 6 H), 1.29 (m, 1 H), 1.21 (d, J=6.6 Hz, 6 H). FAB-MS: calculated for ($C_{24}H_{30}FNO$) 367, found 368 (M+H). Anal. Calcd for $C_{24}H_{30}FNO$: C, 78.44; H, 8.23; N, 3.81. Found: C, 78.46; H, 8.18; N, 3.63. mp 97–98° C. $R_f$=0.3 (20% ethyl acetate/hexane).

EXAMPLE 32

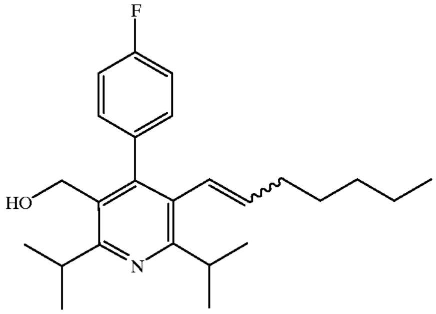

2,6-Diisopropyl-3-hydroxymethyl-4-(4-fluorophenyl)-5-(1-heptenyl)-pyridine

The title compound was prepared from ethyl isobutyrylacetate, 4-fluorobenzaldehyde and n-hexyl triphenylphosphonium bromide according to the procedures described in Example 1, Steps A–G. The product was obtained as a mixture 1:1 trans:cis isomers; gummy oil. $^1$H NMR (300 MHz, $CDCl_3$): δ7.11 (m, 4 H), 5.99 (m, 1 H), 5.42 (dt, J=7, 11 Hz, 0.5 H), 5.30 (dt, J=7, 16 Hz, 0.5 H), 4.4 (d, J=5.5 Hz, 2 H), 3.45 (m, 1 H), 3.37 (sept, J=6.6 Hz, 0.5 H), 3.24 (sept, J=6.6 Hz, 0.5 H), 1.94 (m, 1 H), 1.35 (m, 6 H), 1.29 (m, 1 H), 1.26 (d, J=6.6 Hz, 3 H), 1.22 (m, 6 H), 1.15 (m, 4 H), 0.86 (m, 3 H). FAB-MS: calculated for ($C_{25}H_{34}FNO$) 383, found 384 (M+H). Anal. Calcd for $C_{25}H_{34}FNO$: C, 78.29; H, 8.93; N, 3.65. Found: C, 78.37; H, 8.88; N, 3.57. $R_f$=0.4 (20% ethyl acetate/hexane).

EXAMPLE 33

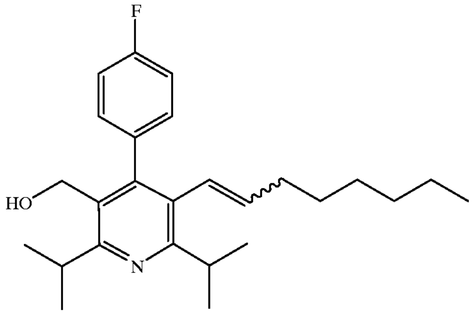

2,6-Diisopropyl-3-hydroxymethyl-4-(4-fluorophenyl)-5-(1-octenyl)-pyridine

The title compound was prepared from ethyl isobutyrylacetate, 4-fluorobenzaldehyde and n-heptyl triphenylphosphonium bromide according to the procedures described in Example 1, Steps A–G. The product was obtained as a mixture 1:1 trans:cis isomers; gummy oil. $^1$H NMR (300 MHz, $CDCl_3$): δ7.11 (m, 4 H), 5.98 (m, 1 H), 5.42 (dt, J=7, 11 Hz, 0.5 H), 5.30 (dt, J=7, 16 Hz, 0.5 H), 4.4 (d, J=5.5 Hz, 2 H), 3.44 (m, 1 H), 3.37 (sept, J=6.6 Hz, 0.5 H), 3.24 (sept, J=6.6 Hz, 0.5 H), 1.94 (m, 1 H), 1.35 (m, 6 H), 1.30 (m, 1 H), 1.26 (d, J=6.6 Hz, 6 H), 1.22 (m, 4 H), 1.16 (m, 5 H), 0.87 (m, 3 H). FAR-MS: calculated for ($C_{26}H_{36}FNO$) 397, found 398 (M+H). Anal. Calcd for $C_{26}H_{36}FNO$: C, 78.55; H, 9.13; N, 3.52. Found: C, 78.63; H, 9.16; N, 3.48. $R_f$=0.4 (20% ethyl acetate/hexane)

EXAMPLE 34

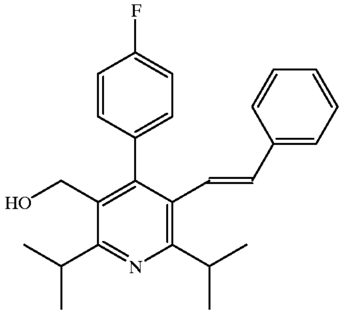

2,6-Diisopropyl-3hydroxymethyl-4-(4-fluorophenyl)-5-[2(E)-phenyl-ethenyl]pyridine The title compound was prepared from ethyl isobutyrylacetate, 4-fluorobenzaldehyde and benzyl triphenylphosphonium bromide/sodium amide according to the procedures described in Example 1, Steps A–G. $^1$H NMR (300 MHz, $CDCl_3$): δ7.21 (m, 9 H), 6.70 (d, J=16.5 Hz, 1 H), 6.26 (d, J=16.5 Hz, 1 H), 4.45 (d, J=5.5 Hz, 2 H), 3.48 (sept, J=6.6 Hz, 2 H), 1.37 (d, J=6.6 Hz, 6 H), 1.31 (d, J =6.6 Hz, 6 H), 1.29 (m, 1 H). FAB-MS: calculated for ($C_{26}H_{28}FNO$) 389, found 390 (M+H). Anal. Calcd for $C_{26}H_{28}FNO$: C, 80.17; H, 7.25; N, 3.60. Found: C, 79.89; H, 7.28; N, 3.49. mp 107–110° C. $R_f$=0.3 (20% ethyl acetate/hexane).

EXAMPLE 35

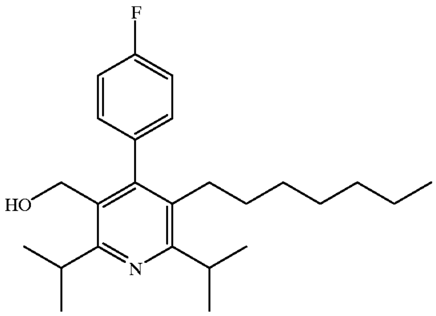

2,6-Diisopropyl-3-hydroxymethyl-4-(4-fluorophenyl)-5-heptylpyridine

The title compound was prepared from 2,6-diisopropyl-3-hydroxymethyl-(4-fluorophenyl)-5-(1-heptenyl)pyridine (Example 32) according to the procedure described in Example 1, Step H. $^1$H NMR (300 MHz, $CDCl_3$): δ7.13 (m, 4 H), 4.33 (s, 2 H), 3.41 (sept, J=6.6 Hz, 1 H), 3.22 (sept, J=6.6 Hz, 1 H), 2.26 (m, 2 H), 1.33 (d, J=6.6 Hz, 6 H), 1.30 (d, J=6.6 Hz, 6 H), 1.22 (m, 3 H), 1.11 (m, 8 H), 0.85 (t, J=7 Hz, 3 H). FAB-MS: calculated for ($C_{25}H_{36}FNO$) 385, found 386 (M+H). Anal. Calcd for $C_{25}H_{36}FNO$: C, 77.88; H, 9.41; N, 3.63. Found: C, 77.86; H, 9.66; N, 3.59. mp 73–75° C. $R_f$=0.3 (20% ethyl acetate/hexane).

EXAMPLE 36

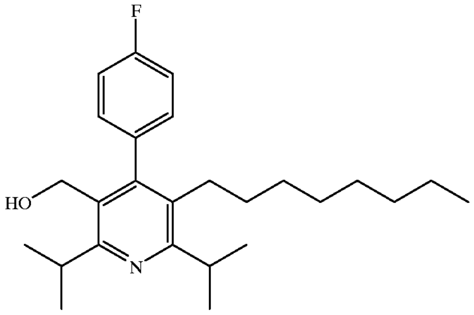

2,6-Diisopropyl-3-hydroxymethyl-4-(4-fluorophenyl)-5-octylpyridine

The title compound was prepared from 2,6diisopropyl-3-hydroxymethyl-4-(4-fluorophenyl)-5-(1-octenyl)pyridine (Example 33) according to the procedure described in Example 1, Step H. $^{1}$H NMR (300 MHz, $CDCl_3$): δ7.14 (m, 4 H), 4.33 (d, J=5.5 Hz, 2 H), 3.41 (sept, J=6.6 Hz, 1 H), 3.23 (sept, J=6.6 Hz, 1 H), 2.26 (m, 2 H), 1.33 (d, J=6.6 Hz, 6 H), 1.30 (d, J=6.6 Hz, 6 H), 1.25 (m, 3 H), 1.15 (m, 10 H), 0.87 (t, J=7 Hz, 3 H). FAB-MS: calculated for ($C_{26}H_{38}FNO$) 399, found 400 (M+H). Anal. Calcd for $C_{26}H_{38}FNO$: C, 78.15; H, 9.59; N, 3.51. Found: C, 78.27; H, 9.81; N, 3.43. Gummy oil; $R_f$=0.3 (20% ethyl acetate/hexane).

EXAMPLE 37

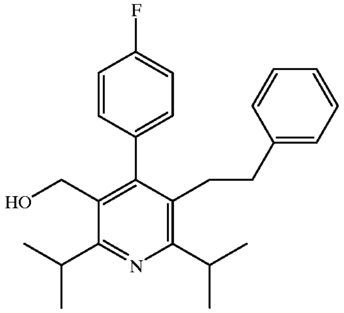

2,6-Diisopropyl-3-hydroxymethyl-4-(4-fluorophenyl)-5-(2-phenylethyl)pyridine

The title compound was prepared from 2,6-diisopropyl-3-hydroxymethyl-4-(4-fluorophenyl)-[2(E)-phenylethenyl] pyridine (Example 34) according to the procedure described in Example 1, Step H. $^{1}$H NMR (300 MHz, $CDCl_3$): δ7.19 (m, 7 H), 6.86 (m, 2 H), 4.36 (d, J=5.5 Hz, 2 H), 3.44 (sept, J=6.6 Hz, 1 H), 3.35 (sept, J=6.6 Hz, 1 H), 2.58 (m, 4 H), 1.35 (d, J=6.6 Hz, 6 H), 1.34 (d, J=6.6 Hz, 6 H), 1.19 (t, J =5.5 Hz, 1 H). FAB-MS: calculated for ($C_{26}H_{30}FNO$) 391, found 392 (M+H). Anal. Calcd for $C_{26}H_{30}FNO$: C, 79.76; H, 7.72; N, 3.58. Found: C, 79.57; H, 7.61; N, 3.44. mp 158–159° C. $R_f$=0.3 (20% ethyl acetate/hexane).

EXAMPLE 38

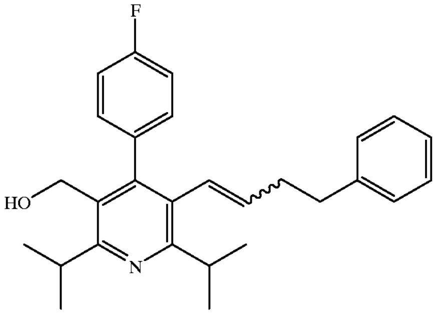

2,6-Diisopropyl-3-hydroxymethyl-4-(4-fluorophenyl)-5-(4phenyl-1-butenyl)pyridine The title compound was prepared from ethyl isobutyrylacetate, 4-fluorobenzaldehyde and 3phenylpropyl triphenylphosphonium bromide according to the procedures described in Example 1, Steps A–G. The product was obtained as a mixture 5:1 trans:cis isomers; gummy oil. $^{1}$H NMR (300 MHz, $CDCl_3$): δ7.26 (m, 2 H), 7.19 (m, 1 H), 7.09 (m, 6 H), 6.05 (d, J=11 Hz, 0.2 H), 5.98 (d, J=16 Hz, 0.8 H), 5.47 (dt, J=7, 11 Hz, 0.2 H), 5.33 (dt, J=7, 16 Hz, 0.8 H), 4.40 (d, J=5 Hz, 2 H), 3.43 (m, 1 H), 3.26 (sept, J=6.6 Hz, 1 H), 2.51 (m, 2 H), 2.29 (m, 1.6 H), 2.05 (m, 0.4 H), 1.34 (m, 6 H), 1.25 (m, 1 H), 1.22 (d, J=6.6 Hz, 6 H). FAB-MS: calculated for ($C_{28}H_{32}FNO$) 417, found 418 (M+H). Anal. Calcd for $C_{28}H_{32}FNO$: C, 80.54; H, 7.72; N, 3.35. Found: C, 80.56; H, 7.56; N, 3.32. $R_f$=0.3 (20% ethyl acetate/hexane).

EXAMPLE 39

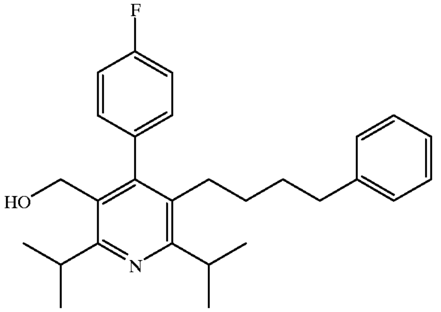

2,6-Diisopropyl-3-hydroxymethyvl-4-fluorophenyl)-5-(4-phenylbutyl)pyridine

The title compound was prepared from 2,6-diisopropyl-3-hydroxymethyl-4-(4-fluorophenyl)-5-(4-phenyl-1-butenyl)pyridine (Example 38) according to the procedure described in Example 1, Step H. Gummy oil; $^{1}$H NMR (300 MHz, $CDCl_3$): δ7.24 (m, 3 H), 7.08 (m, 6 H), 4.31 (d, J=5.5 Hz, 2 H), 3.40 (sept, J=6.6 Hz, 1 H), 3.17 (sept, J=6.6 Hz, 1 H), 2.46 (t, J=7.5 Hz, 2 H), 2.29 (m, 2 H), 1.47 (m, 2 H), 1.32 (d, J=6.6 Hz, 6 H), 1.30 (m, 2 H), 1.27 (d, J=6.6 Hz, 6 H), 1.15 (t, J=5.5 Hz, 1 H). FAB-MS: calculated for ($C_{28}H_{34}FNO$) 419, found 420 (M+H). Anal. Calcd for $C_{28}H_{34}FNO$: C, 80.15; H, 8.17; N, 3.34. Found: C, 80.06; H, 7.94; N, 3.28. $R_f$=0.3 (20% ethyl acetate/hexane).

EXAMPLE 40

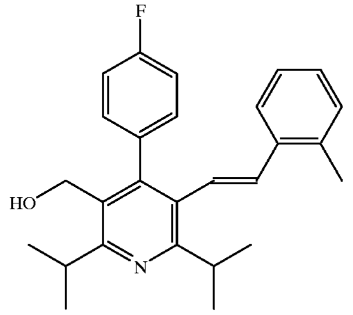

2,6-Diisopropyl-3-hydroxymethyl-4-(4-fluorophenyl)-5-[2(E)-(2-methyl-phenyl)ethenyl] pyridine The title compound was prepared from ethyl isobutyrylacetate, 4-fluorobenzaldehyde and 2-methylbenzyl triphenylphosphonium bromide according to the procedures described in Example 1, Steps A–G. $^1H$ NMR (300 MHz, $CDCl_3$): δ7.22 (m, 3 H), 7.10 (m, 5 H), 6.62 (d, J=17 Hz, 1 H), 6.45 (d, J=17 Hz, 1 H), 4.45 (d, J=5.5 Hz, 2 H), 3.48 (m, 2 H), 2.12 (s, 3 H), 1.37 (d, J=6.6 Hz, 6 H), 1.33 (d, J=6.6 Hz, 6 H), 1.31 (m, 1 H). FAB-MS: calculated for ($C_{27}H_{30}FNO$) 403, found 404 (M+H). Anal. Calcd for $C_{27}H_{30}FNO$: C, 80.36; H, 7.49; N, 3.47. Found: C, 80.23; H, 7.23; N, 3.44. mp 108–111° C. $R_f$=0.3 (20% ethyl acetate/hexane).

EXAMPLE 41

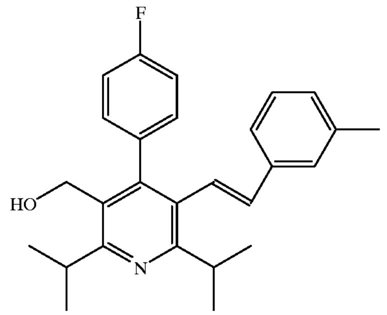

2,6-Diisopropyl-3-hydroxvmethyl-4-(4fluorophenyl)-5-[2(E)-(3-methyl-phenyl)ethenyl] pyridine The title compound was prepared from ethyl isobutyrylacetate, 4-fluorobenzaldehyde and 3-methylbenzyl triphenylphosphonium chloride according to the procedures described in Example 1, Steps A–G. $^1H$ NMR (300 MHz, $CDCl_3$): δ7.18 (m, 3 H), 7.11 (m, 2 H), 7.00 (m, 3 H), 6.68 (d, J=17 Hz, 1 H), 6.23 (d, J=17 Hz, 1 H), 4.44 (d, J=5.5 Hz, 2 H), 3.47 (m, 2 H), 2.32 (s, 3 H), 1.37 (d, J=6.6 Hz, 6 H), 1.31 (d, J=6.6 Hz, 6 H), 1.28 (m, 1 H). FAB-MS: calculated for ($C_{27}H_{30}FNO$) 403, found 404 (M+H). Anal. Calcd for $C_{27}H_{30}FNO$: C, 80.36; H, 7.49; N, 3.47. Found: C, 80.38; H, 7.45; N, 3.45. mp 97–99° C. $R_f$=0.3 (20% ethyl acetate/hexane).

EXAMPLE 42

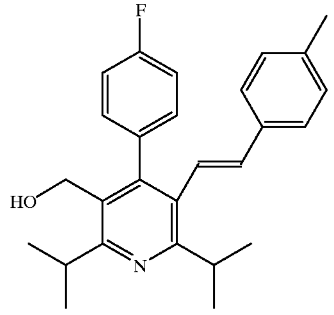

2,6-Diisopropyl-3-hydroxymethyl-4-(4-fluorophenyl)-5-[2(E)-(4-methyl-phenyl)ethenyl] pyridine The title compound was prepared from ethyl isobutyrylacetate, 4-fluorobenzaldehyde and 4-methylbenzyl triphenylphosphonium bromide according to the procedures described in Example 1, Steps A–G. $^1H$ NMR (300 MHz, $CDCl_3$): δ7.18 (m, 2 H), 7.08 (m, 6 H), 6.63 (d, J=17 Hz, 1 H), 6.23 (d, J=17 Hz, 1 H), 4.43 (d, J=5 Hz, 2 H), 3.47 (sept, J=6.6 Hz, 2 H), 2.31 (s, 3 H), 1.36 (d, J=6.6 Hz, 6 H), 1.30 (d, J=6.6 Hz, 6 H), 1.26 (m, 1 H). FAB-MS: calculated for ($C_{27}H_{30}FNO$) 403, found 404 (M+H). Anal Calcd for $C_{27}H_{30}FNO$: C, 80.36; H, 7.49; N, 3.47. Found: C, 79.93; H, 7.34; N, 3.47. mp 131–133° C. $R_f$=0.3 (20% ethyl acetate/hexane).

EXAMPLE 43

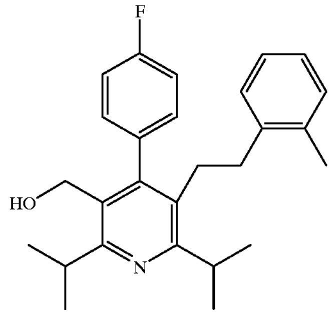

2,6-Diisopropyl-3-hydroxymethyl-4-(4-fluorophenyl)-5-[2-(2-methyl-phenyl)ethyl]pyridine The title compound was prepared from 2,6diisopropyl-3-hydroxymethyl-(4-fluorophenyl)-5-[2(E)-(2-methylphenyl) ethenyl]pyridine (Example 40) according to the procedure described in Example 1, Step H. $^1H$ NMR (300 MHz, $CDCl_3$): δ7.16 (m, 4 H), 7.06 (m, 3 H), 6.81 (m, 1 H), 4.35 (d, J=4 Hz, 2 H), 3.42 (sept, J=6.6 Hz, 2 H), 2.57 (m, 4 H), 1.97 (s, 3 H), 1.36 (d, J=6.6 Hz, 6 H), 1.35 (d, J=6.6 Hz, 6 H), 1.19 (m, 1 H). FAB-MS: calculated for ($C_{27}H_{32}FNO$) 405, found 406 (M+H). Anal. Calcd for $C_{27}H_{32}FNO$: C, 79.96; H, 7.95; N, 3.45. Found: C, 80.08; H, 8.05; N, 3.46. mp 125–126° C. $R_f$=0.3 (20% ethyl acetate/hexane).

EXAMPLE 44

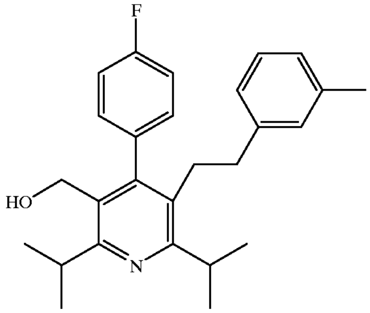

2,6-Diisopropyl-3-hydroxymethyl-4-(4-fluorophenyl)-5-[2-(3-methyl-phenyl)ethyl]pyridine The title compound was prepared 2,6-diisopropyl-3-hydroxymethyl-4-(4-fluorophenyl)-5-[2-(E)-(3-methylphenyl)ethenyl]pyridine (Example 41) according to the procedure described in Example 1, Step H. $^1$H NMR (300 MHz, $CDCl_3$): δ7.18 (d, J=7 Hz, 4 H), 7.10 (m, 1 H), 6.97 (m, 1 H), 6.65 (m, 2 H), 4.36 (s, 2 H), 3.44 (sept, J =6.6 Hz, 1 H), 3.35 (d, J=6.6 Hz, 1 H), 2.57 (m, 4 H), 2.28 (s, 3 H), 1.35 (d, J=6.6 Hz, 6 H), 1.34 (d, J=6.6 Hz, 6 H), 1.20 (m, 1 H). FAB-MS: calculated for ($C_{27}H_{32}FNO$) 405, found 406 (M+H). Anal. Calcd for $C_{27}H_{32}FNO$: C, 79.96; H, 7.95; N, 3.45. Found: C, 79.30; H, 8.10; N, 3.36. mp 148–150° C. $R_f$=0.3 (20% ethyl acetate/hexane).

EXAMPLE 45

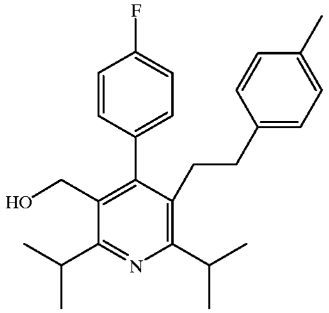

2,6-Diisopropyl-3-hydroxyl methyl-4-(4-fluorophenyl)-5-[2-(4-methyl-phenyl)ethyl]pyridine The title compound was prepared from 2,6diisopropyl-3-hydroxymethyl-4-(4-fluorophenyl)-5-[2(E)-(4-methylphenyl)ethenyl]pyridine (Example 42 ) according to the procedure described in Example 1, Step H. $^1$H NMR (300 MHz, $CDCl_3$): δ7.17 (m, 4 H), 7.02 (d, J=7.7 Hz, 2 H), 6.75 (d, J=7.7 Hz, 2 H), 4.36 (d, J=4 Hz, 2 H), 3.43 (sept, J=6.6 Hz, 1 H), 3.34 (sept, J=6.6 Hz, 1 H), 2.55 (m, 4 H), 2.29 (s, 3 H), 1.34 (d, J=6.6 Hz, 6 H), 1.33 (d, J=6.6 Hz, 6 H), 1.20 (m, 1 H). FAB-MS: calculated for ($C_{27}H_{32}FNO$) 405, found 406 (M+H). Anal. Calcd for C27H32FNO: C, 79.96; H, 7.95; N, 3.45. Found: C, 79.40; H, 7.84; N, 3.44. mp 121–123° C. $R_f$=0.3 (20% ethyl acetate/hexane). vl)propyllpyridine

EXAMPLE 46

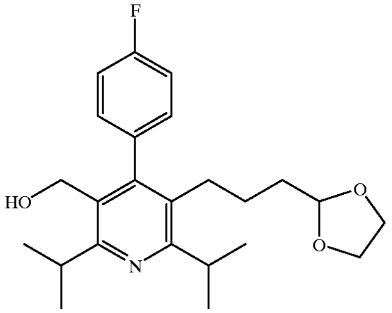

2,6-Diisopropyl-3-hydroxymethyl-4-(4-fluorophenyl)-5-[3-(1,3-dioxolan-2-yl-propyl ]pyridine The title compound was prepared from ethyl isobutyrylacetate, 4-fluorobenzaldehyde and [2-(13dioxolan-2-yl)ethyl]triphenylphosphonium bromide according to the procedures described in Example 1, Steps A–G. $^1$H NMR (300 MHz, $CDCl_3$): δ7.16 (m, 4 H), 4.63 (t, J=4 Hz, 1 H), 4.33 (d, J=5 Hz, 2 H), 3.88 (m, 2 H), 3.77 (m, 2 H), 3.41 (bm, 1 H, 3.24 (bm, 1 H), 2.34 (m, 2 H), 1.47 (m, 4 H), 1.32 (m, 12 H), 1.18 (m, 1 H). FAR-MS: calculated for ($C_{24}H_{32}FNO_3$) 401, found 402 (M+H). mp 90–91° C. $R_f$=0.2 (20% ethyl acetate/hexane).

EXAMPLE 47

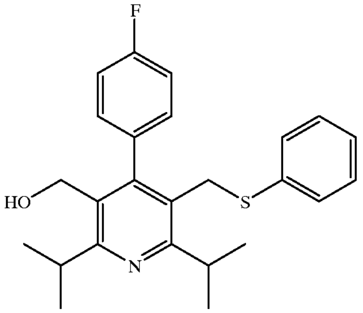

2,6Diisopropyl-3-hydroxymethyl-4-(4fluorophenyl)-5[(phenylthio)-methyl]pyridine

Step A: Methyl 2,6diisopropyl-4-(4-fluorophenyl)-5-hydroxymethyl-3-pyridinecarboxylate Prepared from methyl isobutyrylacetate, 4-fluorobenzaldehyde and ammonium acetate by the procedures described in Example 1, Steps A–D.

Step B: Methyl-2,6-diisopropyl-4-(4fluorophenyl)-5-bromomethyl-3-pyridinecarboxylate A solution of the intermediate obtained in Step A (20 g, 57.9 mmol) in acetonitrile (500 mL) was stirred at 0° C. and treated with dibromo-triphenylphosphorane (36.7 g, 86.9 mmol) in portions. The suspension was then allowed to warm to room temperature and stirred for 2 hr. The solvent was removed in vacuo and the residue partitioned between diethyl ether (400 mL) and water (350 mL). The ether layer was washed with brine (150 mL), dried ($MgSO_4$) and concentrated. Purification by chromatography through silica (5% diethyl ether/hexane) gave a white solid (20.6 g, 50.5 mmol, 87%). $^1$H NMR (300 MHz, $CDCl_3$): δ7.31 (m, 2 H), 7.12 (m, 2 H), 4.29 (s, 2 H), 3.49 (s, 3H), 3.41 (sept, J=6.6 Hz, 1 H), 3.06 (sept, J=6.6 Hz, 1 H), 1.33 (m, 12 H). mp 109–111° C. $R_f$=0.6 (50% $CH_2Cl_2$/hexane).

Step C: 2,6Diisopropyl-3hydroxymethyl-4(4-fluorophenyl)-5-[(phenylthio)methyl]pyridine A solution of the intermediate obtained in Step B (200 mg, 0.47 mmol) in anhydrous THF (5 mL), stirred under argon, was treated with benzenethiol (73 uL, 0.71 mmol) and N-methylmorpholine (0.26 mL, 2.4 mmol). The reaction mixture was stirred at reflux for 14 hr, allowed to cool to room temperature and treated with lithium aluminum hydride (1.9 mL, 1.9 mmol, 1.0.M in THF). The reaction mixture was heated at reflux for 1 hr then allowed to cool to room temperature. The mixture was quenched by the successive addition of water (80 uL), 20% NaOH (80 uL) and water (240 uL). The resulting suspension was filtered through a cake of celite and concentrated. Purification by flash silica gel chromatography (5% ethyl acetate/hexane) afforded a white solid (160 mg, 0.39 mmol, 83%). $^1$H NMR (300 MHz, $CDCl_3$): δ7.23 (m, 5 H), 7.11 (m, 4 H), 4.36 (d, J=5.5 Hz, 2 H), 3.81 (s, 2 H), 3.45 (sept, J=6.6 Hz, 1 H), 3.43 (sept, J=6.6 Hz, 1 H), 1.35 (d, J=6.6 Hz, 6 H), 1.33 (d, J=6.6 Hz, 6 H), 1.21 (t, J=5.5 Hz, 1 H). FAB-MS calcd for ($C_{25}H_{28}FNOS$) 409, found 410 (M+H). Anal. Calcd for $C_{25}H_{28}FNOS$: C, 73.32; H, 6.89; N, 3.42; S, 7.83. Found: C, 73.24; H, 6.90; N, 3.35; S, 8.01. mp 119–121° C. $R_f$=0.3 (20% ethyl acetate/hexane).

EXAMPLE 48

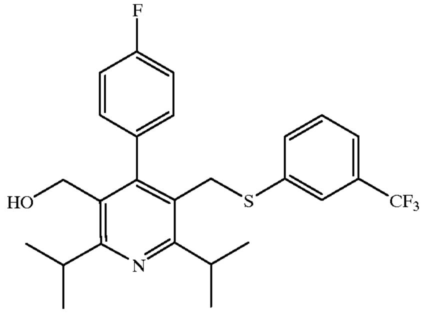

2,6-Diisopropyl-3-hydroxymethyl-4-(4-fluorophenyl)-5-[((3-trifluoro-methyl)phenyl)thio]methylpyridine The title compound was prepared from 3-trifluoromethylthiophenol according to the procedures described in Example 47. $^1$H NMR (300 MHz, $CDCl_3$): δ7.34 (m, 2 H), 7.24 (m, 4 H), 7.10 (m, 2 H), 4.36 (d, J=5.5 Hz, 2 H), 3.85 (s, 2 H), 3.45 (sept, J=6.6 Hz, 1 H), 3.38 (sept, J=6.6 Hz, 1 H), 1.35 (d, J=6.6 H, 6 H), 1.34 (d, J=6.6 Hz, 6 H), 1.23 (t, J=5.5 Hz, 1 H). FAB-MS calcd for ($C_{26}H_{27}F_4NOS$) 477, found 478 (M+H). Anal. Calcd for $C_{26}H_{27}F_4NOS$: C, 65.39; H, 5.70; N, 2.93; S, 6.71. Found: C, 65.39; H, 5.76; N, 2.88; S, 6.62. mp 110–111° C. $R_f$=0.3 (20% ethyl acetate/hexane).

EXAMPLE 49

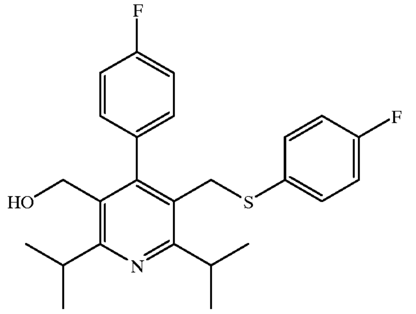

2,6-Diisopropyl-3-hydroxymethyl-4-(4-fluorophenyl)-5-[(4-fluoro-phenyl)thio]methylpyridine The title compound was prepared from 4-fluorothiophenol according to the procedures described in Example 47. $^1$H NMR (300 MHz, $CDCl_3$): δ7.24 (m, 2 H), 7.12 (m, 4 H), 6.93 (m, 2 H), 4.35 (d, J=5.5 Hz, 2 H), 3.76 (s, 2 H), 3.44 (sept, J=6.6 Hz,1H),3.40(sept, J=6.6Hz,1H), 1.34 (d, J=6.6Hz,6H),1.33(d, J=6.6Hz, 6 H), 1.22 (t, J=5.5 Hz, 1 H). FAB-MS calcd for ($C_{25}H_{27}F_2NOS$) 427, found 428 (M+H). Anal. Calcd for $C_{25}H_{27}F_2NOS$: C, 70.23; H, 6.37; N, 3.28; S, 7.50. Found: C, 70.22; H, 6.41; N, 3.22; S, 7.39. mp 119–121° C. $R_f$=0.3 (20% ethyl acetate/hexane).

EXAMPLE 50

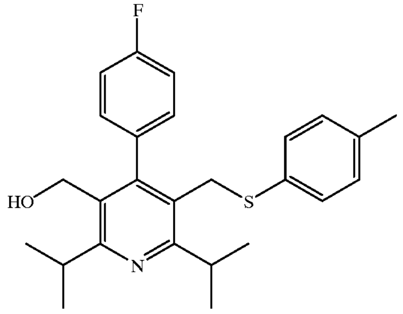

2,6-Diisopropyl-3-hydroxymethyl-4-(4-fluorophenyl)-5-[((4-methyl)-phenyl)thio]methylpyridine The title compound was prepared from ρ-thiocresol according to the procedures described in Example 47. $^1$H NMR (300 MHz, $CDCl_3$): δ7.27 (m, 2 H), 7.13 (m, 2 H), 7.03 (m, 4 H), 4.35 (d, J=5.5 Hz, 2 H), 3.77 (s, 2 H), 3.44 (m, 2 H), 2.31 (s, 3 H), 1.34 (d, J=6.6 Hz, 6 H), 1.33 (d, J=6.6 Hz, 6 H), 1.22 (t, J=5.5 FAB-MS calcd for ($C_{26}H_{30}FNOS$) 423, found 424 (M+H). Anal. Calcd for $C_{26}H_{30}FNOS$: C, 73.72; H, 7.14; N, 3.31; S, 7.57. Found: C, 74.00; H, 7.15; N, 3.36; S, 7.32. mp 90–91° C. $R_f$=0.3 (20% ethyl acetate/hexane).

EXAMPLE 51

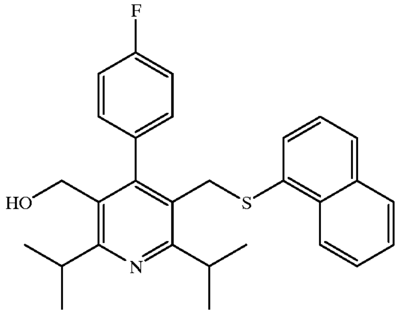

2,6-Diisopropyl-3-hydroxymethyl-4-(4-fluorophenyl)-5-(1-naphthylthio)-methylpyridine The title compound was prepared from 1-naphthalenethiol according to the procedures described in Example 47. $^1$H NMR (300 Mz, $CDCl_3$): δ8.01 (d, J=8.5 Hz, 1 H), 7.82 (d, J=8.5 Hz, 1 H), 7.74 (d, J=8 Hz, 1 H), 7.46 (m, 3 H), 7.34 (m, 1 H), 7.20 (m, 2 H), 7.06 (m, 2 H), 4.34 (d, J=5.5 Hz, 2 H), 3.82 (s, 2 H), 3.51 (sept, J=6.6 Hz, 1 H), 3.45 (sept, J=6.6 Hz, 1 H), 1.36 (d, J=6.6 Hz, 6 H), 1.35 (d, J=6.6 Hz, 6 H), 1.19 (t, J=5.5 Hz, 1 H). FAB-MS calcd for ($C_{29}H_{30}FNOS$) 459, found 460 (M+H). Anal. Calcd for $C_{29}H_{30}FNOS$: C, 75.78; H, 6.58; N, 3.05; S, 6.98. Found: C, 75.36; H, 6.52; N, 2.91; S, 6.74. mp 77–79° C. $R_f$=0.4 (20% ethyl acetate/hexane).

EXAMPLE 52

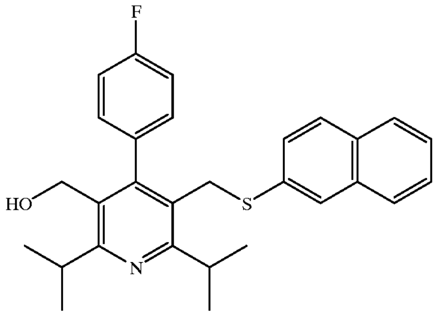

2,6Diisopropyl-3hydroxymethyl-4-(4-fluorophenyl)-5-(2-naphthyl-thio)methlpyridine The title compound was prepared from 2-naphthalenethiol according to the procedures described in Example 47. $^1$H NMR (300 MHz, $CDCl_3$): δ7.77 (d, J =9 Hz, 1 H), 7.68 (d, J=9 Hz, 2 H), 7.52 (d, J=1.5 Hz, 1 H), 7.45 (m, 2 H), 7.2 (m, 2 H), 7.17 (dd, J=1.8,8.5 Hz, 1 H), 7.07 (m, 2 H), 4.35 (d, J=5.5 Hz, 2 H), 3.91 (s, 2 H), 3.45 (sept, J=6.6 Hz, 2 H), 1.35 (d, J=6.6 Hz, 6 H), 1.34 (d, J=6.6 Hz, 6 H), 1.21 (t, J=5.5 Hz, 1 H). FAB-MS calcd for ($C_{29}H_{30}FNOS$) 459, found 460 (M+H). Anal. Calcd for $C_{29}H_{30}FNOS$: C, 75.78; H, 6.58; N, 3.05; S, 6.98. Found: C, 75.55; H, 6.60; N, 2.95; S, 6.91. mp 127–129° C. $R_f$=0.4 (20% ethyl acetate/hexane).

EXAMPLE 53

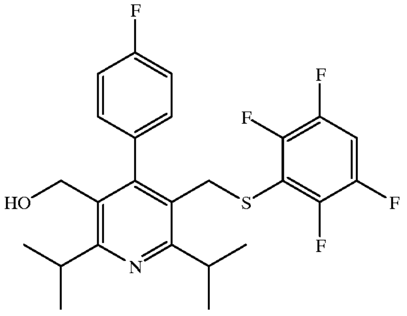

2,6-Diisopropyl-3-hydroxymethyl-4-(4-fluorophenyl)-5-[(2,3,5,6-tetra-fluorophenyl)thio]methylpyridine The title compound was prepared from pentafluorothiophenol according to the procedures described in Example 47. $^1$H NMR (300 MHz, $CDCl_3$): δ7.27 (m, 2 H), 7.11 (m, 2 H), 6.99 (m, 1 H), 4.35 (d, J=5.5 Hz, 2 H), 3.84 (s, 2 H), 3.84 (s, 2 H), 3.44 (sept, J=6.6 Hz, 1 H), 3.43 (sept, J=6.6 Hz, 1 H), 1.34 (d, J=6.6 Hz, 6 H), 1.33 (d, J=6.6 Hz, 6 H), 1.23 (t, J=5.5 Hz, 1 H). FAB-MS calcd for ($C_{25}H_{24}F_5NOS$) 481, found 482 (M+H). Anal. Calcd for $C_{25}H_{24}F_5NOS$: C, 62.36; H, 5.02; N, 2.91; S, 6.66; F, 19.73. Found: C, 62.40; H, 4.96; N, 2.82; S, 6.74; F, 19.49. mp 109–110° C. $R_f$=0.4 (20% ethyl acetate/hexane).

EXAMPLE 54

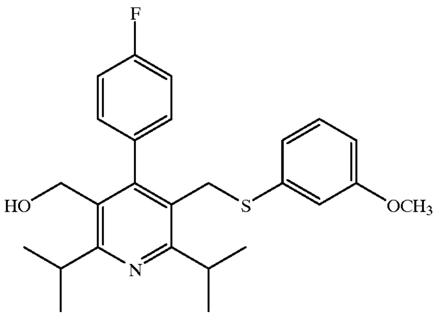

2,6-Diisopropyl-3-hydroxymethyl-4-(4-fluorophenyl)-5-[(3-methyoxy-phenyl)thio]methylpyridine The title compound was prepared from 3-methoxybenzenethiol according to the procedures described in Example 47. $^1$H NMR (300 MHz, $CDCl_3$): δ7.24 (m, 2 H), 7.13 (m, 3 H), 6.72 (m, 2 H), 6.62 (m, 1 H), 4.35 (d, J=5.5 Hz, 2 H), 3.81 (s, 2 H), 3.75 (s, 3 H), 3.44 (sept, J=6.6 Hz, 1 H), 3.42 (sept, J=6.6 Hz, 1 H), 1.34 (d, J=6.6 Hz, 6 H), 1.33 (d, J=6.6 Hz, 6 H), 1.23 (t, J=5.5 Hz, 1 H). FAB-MS calcd for ($C_{26}H_{30}FNO_2S$) 339, found 440 (M+H). Anal. Calcd for $C_{26}H_{30}FNO_2S$: C, 71.04; H, 6.88; N, 3.19; S, 7.29. Found: C, 70.94; H, 6.77; N, 2.96; S, 7.41. mp 93–94° C. $R_f$=0.4 (20% ethyl acetate/hexane).

EXAMPLE 55

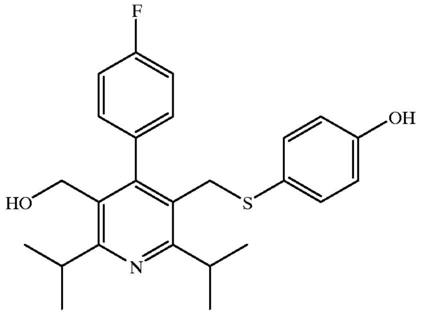

2,6-Diisopropyl-3-hydroxymethyl-4-(4-fluorophenyl)-5-[(4-hydroxy-phenyl)thio]methylpyridine The title compound was prepared from 4hydroxythlophenol according to the procedures described in Example 47. $^1$H NMR (300 MHz, 5:1 $CDCl_3/CD_3OD$): δ7.15 (m, 2 H), 7.06 (m, 2 H), 6.97 (d, J=8.5 Hz, 2 H), 6.64 (d, J=8.5 Hz, 2 H), 4.27 (s, 2 H), 3.66 (s, 2 H), 3.40 (m, 2 H), 1.29 (d, J=6.6 Hz, 6 H), 1.28 (d, J=6.6 Hz, 6 H). FAB-MS calcd for ($C_{25}H_{28}FNO_2S$) 425, found 426 (M+H). Anal. Calcd for $C_{25}H_{28}FNO_2S$: C, 70.56; H, 6.63; N, 3.29; S, 7.53. Found: C, 70.29; H, 6.34; N, 3.12; S, 7.44. mp 178–179° C. $R_f$=0.3 (30% ethyl acetate/hexane).

EXAMPLE 56

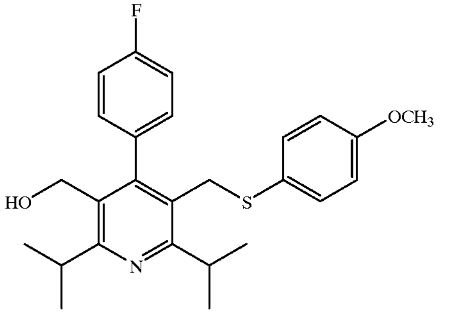

2,6-Diisopropyl-3-hydroxymethyl-4-(4-fluorophenyl)-5-[(4-methoxy-phenyl)thio]methylpyridine The title compound was prepared from 4-methoxybenzenethiol according to the procedures described in Example 47. $^1$H NMR (300 MHz, $CDCl_3$): δ7.23 (m, 2 H), 7.12 (m, 4 H), 6.77 (d, J=9 Hz, 2 H), 4.35 (d, J=5.5 Hz, 2 H), 3.79 (s, 3 H), 3.73 (s, 2 H), 3.44 (sept, J=6.6 Hz, 2 H), 1.34 (d, J=6.6 Hz, 6 H), 1.33 (d,J=6.6 Hz, 6 H), 1.33 (d, J=6.6 Hz, 6 H), 1.21 (t, J=5.5 Hz, 1 H). FAB-MS calcd for ($C_{26}H_{30}FNO_2S$) 339, found 440 (M+H). Anal. Calcd for $C_{26}H_{30}FNO_2S$: C, 71.04; H, 6.88; N, 3.19; S, 7.29. Found: C, 70.96; H, 6.90; N, 3.15; S, 7.35. mp 92–93° C. $R_f$=0.4 (20% ethyl acetate/hexane).

EXAMPLE 57

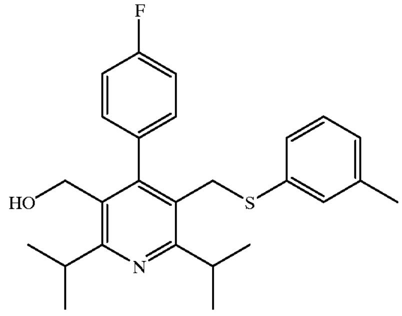

2,6-Diisopropyl-3-hydroxymethyl-4-(4-fluorophenyl)-5-[(3-methyl-phenyl)thio]methylpyridine The title compound was prepared from m-thiocresol according to the procedures described in Example 47. $^1$H NMR (300 MHz, $CDCl_3$): δ7.25 (m, 2 H), 7.11 (m, 3 H), 7.00 (m, 1 H), 6.94 (m, 2 H), 4.36 (d, J=5.5 Hz, 2 H), 3.81 (s, 2 H), 3.45 (sept, J=6.6 Hz, 1 H), 3.43 (sept, J=6.6 Hz, 1 H), 2.28 (s, 3 H), 1.35 (d, J=6.6 Hz, 6 H), 1.34 (d, J=6.6 Hz, 6 H), 1.22 (t, J=5.5 Hz, 1 H). FAB-MS calcd for ($C_{26}H_{30}FNOS$) 423, found 424 (M+H). Anal. Calcd for $C_{26}H_{30}FNOS$: C, 73.72; H, 7.14; N, 3.31; S, 7.57. Found: C, 73.76; H, 7.09; N, 3.27; S, 7.42. mp 92–93° C. $R_f$=0.4 (20% ethyl acetate/hexane).

EXAMPLE 58

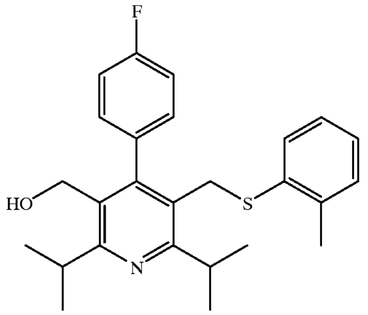

2,6Diisopropyl-3-hydroxymethyl-4-(4-fluorophenyl)-5-[(2-methyl-phenyl)thio]methylpyridine The title compound was prepared from o-thiocresol according to the procedures described in Example 47. $^1$H NMR (300 MHz, $CDCl_3$): δ7.25 (m, 2 H), 7.11 (m, 6 H), 4.36 (d, J=5.5 Hz, 2 H), 3.74 (s, 2 H), 3.45 (sept, J=6.6 Hz, 2 H); 2.26 (s, 3 H), 1.35 (d, J=6.6 Hz, 12 H), 1.21 (t, J=5.5 Hz, 1 H). FAB-MS calcd for ($C_{26}H_{30}FNOS$) 423, found 424 (M+H). Anal. Calcd for $C_{26}H_{30}FNOS$: C, 73.72; H, 7.14; N, 3.31; S, 7.57. Found: C, 73.54; H, 7.09; N, 3.06; S, 7.37. mp 140–141° C. $R_f$0.4 (20% ethyl acetate/hexane).

EXAMPLE 59

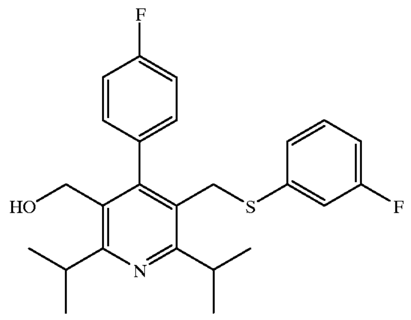

2,6-Diisopropyl-3-hydroxymethyl-4-(4-fluorophenyl)-5-[(3-fluoro-phenyl)thio]methylpyridine The title compound was prepared from 3-fluorothiophenol according to the procedures described in Example 47. $^1$H NMR (300 MHz, $CDCl_3$): δ 7.27 (m, 3 H), 7.11 (m, 2 H), 6.87 (m, 2 H), 6.78 (m, 1 H), 4.36 (d, J=5.5 Hz, 2 H), 3.82 (s, 2 H), 3.45 (sept, J=6.6 Hz, 1 H), 3.38 (sept, J=6.6 Hz, 1 H), 1.35 (d, J=6.6 Hz, 6 H), 1.33 (d, J=6.6 Hz, 6 H), 1.23 (t, J=5.5 Hz, 1 H). FAB-MS calcd for ($C_{25}H_{27}F_2NOS$) 427, found 428 (M+H). Anal. Calcd for $C_{25}H_{27}F_2NOS$: C, 70.23; H, 6.37; N, 3.28; S, 7.50. Found: C, 70.22; H, 6.31; N, 3.20; S, 7.41. mp 99–100° C. $R_f$=0.4 (20% ethyl acetate/hexane).

EXAMPLE 60

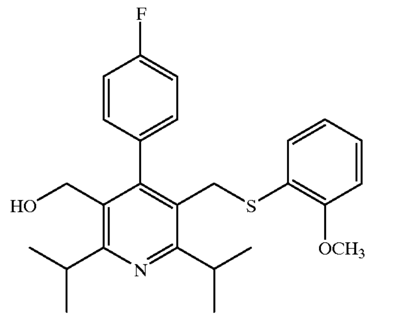

2,6-Diisopropyl-3-hydroxymethyl-4-(4-fluorophenyl)-5-[(2-methoxy-phenyl)thio]methylpyridine The title compound was prepared from 2-methoxythiophenol according to the procedures described in Example 47. $^1$H NMR (300 MHz, $CDCl_3$): δ 7.22 (m, 3 H), 7.07 (m, 3 H), 6.83 (m, 2 H), 4.34 (d, J=5.5 Hz, 2 H), 3.78 (s, 3 H), 3.75 (s, 2 H), 3.49 (sept, J=6.6 Hz, 1 H), 3.43 (sept, J=6.6 Hz, 1 H), 1.34 (d, J=6.6 Hz, 12 H), 1.19 (t, J=5.5 Hz, 1 H). FAB-MS calcd for ($C_{26}H_{30}FNO_2S$) 339, found 440 (M+H). Anal. Calcd for $C_{26}H_{30}FNO_2S$: C, 71.04; H, 6.88; N, 3.19; S, 7.29. Found: C, 70.93; H, 6.67; N, 3.12; S, 7.48. mp 129–131° C. $R_f$=0.4 (20% ethyl acetate/hexane).

EXAMPLE 61

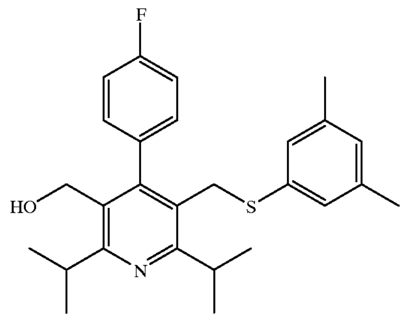

2,6-Diisopropyl-3-hydroxymethyl-4-(4-fluorophenyl)-5-[(3,5dimethylphenyl)thio]methylpyridine The title compound was prepared from 3,5-dimethylthiophenol according to the procedures described in Example 47. $^1$H NMR (300 MHz, $CDCl_3$): δ 7.24 (m, 2 H), 7.11 (m, 2 H), 6.80 (s, 1 H), 6.69 (s, 2 H), 4.35 (d, J=5.5 Hz, 2 H), 3.79 (s, 2 H), 3.44 (sept, J=6.6 Hz, 1 H), 3.42 (sept, J=6.6 Hz, 1 H), 2.23 (s, 6 H), 1.34 (d, J=6.6 Hz, 6 H), 1.33 (d, J=6.6 Hz, 6 H), 1.21 (t, J=5.5 Hz, 1 H). FAB-MS calcd for ($C_{27}H_{32}FNOS$) 437, found 438 (M+H). Anal. Calcd for $C_{27}H_{32}FNOS$: C, 74.11; H, 7.37; N, 3.20; S, 7.33. Found: C, 74.18; H, 7.22; N, 3.13; S, 6.86. mp 109–110° C. $R_f$=0.5 (20% ethyl acetate/hexane).

EXAMPLE 62

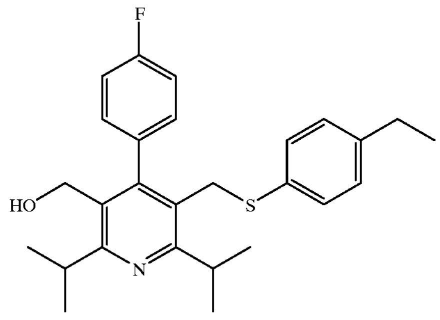

2,6-Diisopropyl-3-hydroxymethyl-4-(4-fluorophenyl)-5-[(4-ethyl-phenyl)thio]methylpyridine The title compound was prepared from 4-ethylthiophenol according to the procedures described in Example 47. $^1$H NMR (300 MHz, $CDCl_3$): δ 7.24 (m, 2 H), 7.05 (m, 6 H), 4.35 (d, J=5.5 Hz, 2 H), 3.77 (s, 2 H), 3.43 (m, 2 H), 2.60 (q, J=7.7 Hz, 2 H), 1.34 (d, J=6.6 Hz, 6 H), 1.32 (d, J=6.6 Hz, 6 H), 1.21 (m, 4 H). FAB-MS calcd for ($C_{27}H_{32}FNOS$) 437, found 438 (M+H). Anal. Calcd for $C_{27}H_{32}FNOS$: C, 74.11; H, 7.37; N, 3.20; S, 7.33. Found: C, 74.07; H, 7.23; N, 3.09; S, 7.23. mp 102–103° C. $R_f$=0.5 (20% ethyl acetate/hexane).

EXAMPLE 63

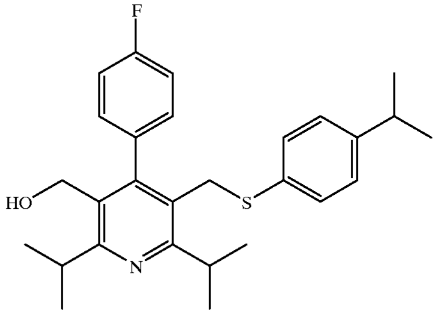

2,6-Diisopropyl-3-hydroxymethyl-4-(4-fluorophenyl)-5-[(4-isopropyl-phenyl)thio]methylpyridine The title compound was prepared from 4-isopropylthiophenol according to the procedures described in Example 47. $^1$H NMR (300 MHz, $CDCl_3$): δ 7.25 (m, 2 H), 7.06 (m, 6 H), 4.35 (d, J=5.5 Hz, 2 H), 3.79 (s, 2 H), 3.43 (m, 2 H), 2.86 (sept, J=7 Hz, 1 H), 1.34 (d, J=6.6 Hz, 6 H), 1.32 (d, J=6.6 Hz, 6 H), 1.22 (d, J=7 Hz, 6 H), 1.20 (t, J=5.5 Hz, 1 H). FAB-MS calcd for ($C_{28}H_{34}FNOS$) 451, found 452 (M+H). Anal. Calcd for $C_{28}H_{34}FNOS$: C, 74.46; H, 7.59; N, 3.10; S, 7.10. Found: C, 74.51; H, 7.48; N, 3.04; S, 6.85. mp 108–109° C. $R_f$=0.5 (20% ethyl acetate/hexane).

EXAMPLE 64

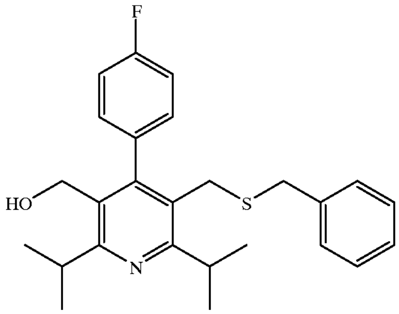

2,6-Diisopropyl-3-hydroxymethyl-4-(4-fluorophenyl5-benzylthio-methylpyridine

The title compound was prepared from benzyl mercaptan according to the procedures described in Example 47. $^1$H NMR (300 MHz, $CDCl_3$): δ 7.23 (m, 5 H), 7.08 (m, 4 H), 4.31 (d, J=5.5 Hz, 2 H), 3.55 (s, 2 H), 3.40 (sept, J=6.6 Hz, 1 H), 3.24 (s, 2 H), 3.19 (sept, J=6.6 Hz, 1 H), 1.31 (d, J=6.6 Hz, 6 H), 1.24 (d, J=6.6 Hz, 6 H), 1.17 (t, J=5.5 Hz, 1 H). FAB-MS calcd for ($C_{26}H_{30}FNOS$) 423, found 424 (M+H). Anal. Calcd for $C_{26}H_{30}FNOS$: C, 73.72; H, 7.14; N, 3.31; S, 7.57. Found: C, 73.58; H, 7.25; N, 3.05; S, 7.45. mp 150–151° C. $R_f$=0.5 (20% ethyl acetate/hexane).

EXAMPLE 65

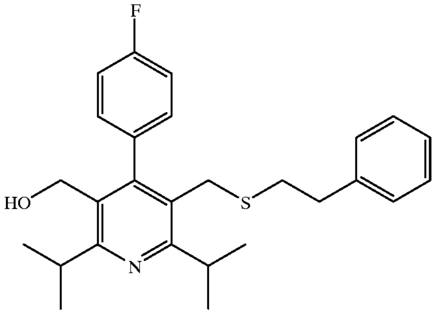

2,6-Diisopropyl-3-hydroxymethyl-4-(4-fluorophenyl)-5-[(phenethyl)-thiomethyl]pyridine The title compound was prepared from phenethyl mercaptan according to the procedures described in Example 47. $^1$H NMR (300 MHz, $CDCl_3$): δ 7.28 (m, 5 H), 7.11 (m, 4 H), 4.34 (d, J=5.5 Hz, 2 H), 3.39 (m, 4 H), 2.70 (m, 2 H), 2.61 (m, 2 H), 1.33 (d, J=6.6 Hz, 6 H), 1.32 (d, J=6.6 Hz, 6 H), 1.20 (t, J=5.5 Hz, 1 H). FAB-MS calcd for ($C_{27}H_{32}FNOS$) 437, found 438 (M+H). Anal. Calcd for $C_{27}H_{32}FNOS$: C, 74.11; H, 7.37; N, 3.20; S, 7.33. Found: C, 73.99; H, 7.46; N, 2.96; S, 7.23. Gummy oil. $R_f$=0.5 (20% ethyl acetate/hexane).

EXAMPLE 66

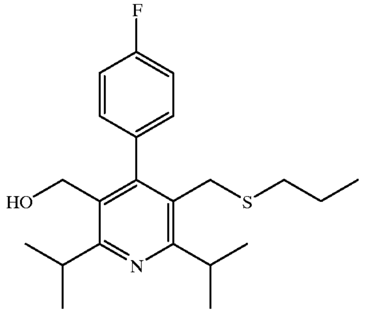

2,6-Diisopropyl-3-hydroxymethyl4-(4-fluorophenyl)-5-(propylthio)-methylpyridine

The title compound was prepared from propyl mercaptan according to the procedures described in Example 47. $^1$H NMR (300 MHz, $CDCl_3$): δ 7.30 (m, 2 H), 7.14 (m, 2 H), 4.34 (d, J=5.5 Hz, 2 H), 3.41 (m, 2 H), 3.37 (m, 2 H), 2.31 (t, J=7.0 Hz, 2 H), 1.31 (m, 15 H), 0.89 (t, J=7.4 Hz, 3 H). FAB-MS calcd for ($C_{22}H_{30}NFOS$) 375, found 376 (M+H); Anal. Calcd for $C_{22}H_{30}NOFS$: C, 70.36; H, 8.05; N, 3.73; F, 5.06; S, 8.54. Found: C, 70.32; H, 7.97; N, 3.58; F, 4.76; S, 8.49. mp 98° C. (dec.). $R_f$=0.3 (10% ethyl acetate/hexane).

EXAMPLE 67

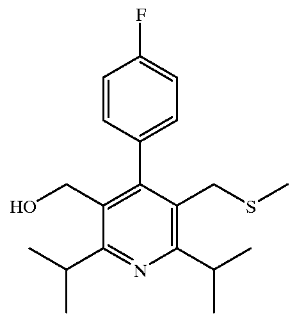

2,6-Diisopropyl-3-hydroxymethyl-4-(4-fluorophenyl)-5-(methylthio)-methylpyridine The title compound was prepared from methyl mercaptan according to the procedures described in Example 47. $^1$H NMR (300 MHz, $CDCl_3$): δ 7.30 (m, 2 H), 7.16 (m, 2 H), 4.35 (d, J=55 Hz, 2 H), 3.43 (m, 2 H), 3.38 (m, 2 H), 1.95 (s, 3 H), 1.30 (m, 12 H). FAB-MS calcd for ($C_{20}H_{26}NFOS$) 347, found 348 (M+). Anal. Calcd for $C_{20}H_{26}NOFS$: C, 69.13; H, 7.54; N, 4.03; F, 5.47. Found: C, 69.29; H, 7.54; N, 3.91; F, 5.45. mp 49° C. (dec.). $R_f$=0.2 (10% ethyl acetate/hexane).

EXAMPLE 68

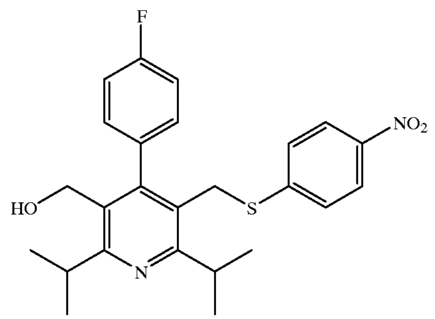

2,6-Diisopropyl-3-hydroxymethyl-4-(4-fluorophenyl)-5-[(4-nitrophenyl)-thio]methylpyridine Step A: 2,6-Diisopropyl-3-hydroxymethyl-4-(4-fluorophenyl)-5-[(t-butyldimethylsiloxy)methyl]pyridine A solution of 3 g (8.3 mmol) of methyl 2,6-diisopropyl-4-(4-fluorophenyl)-5-hydroxymethyl-3pyridinecarboxylate (Example 47, Step A) in anhydrous DMF (75 mL), was treated at room temperature with imidazole (1.3 g, 19 mmol), 4-dimethylaminopyridine (50 mg, 0.4 mmol) and t-butyldimethylsilyl chloride (1.4 g, 9.3 mmol). The reaction mixture was allowed to stir at room temperature for 48 hr. The solution was diluted with diethyl ether (200 mL) and washed with water (2×100 mL), 1N HCl (100 mL), sat. $NaHCO_3$ (50 mL) and brine (100 mL), dried ($MgSO_4$) and concentrated to 4 g as an oil: $R_f$=0.4 (10% ethyl acetate/hexane).

This intermediate (4 g) was dissolved in anhydrous THF (100 mL), stirred under argon and treated with lithium aluminum hydride (17 mL, 17 mmol, 1.0M in THF). The reaction mixture was stirred at reflux for 1 hr, then allowed to cool to room temperature. The reaction was quenched by the successive dropwise addition of water (0.6 mL), 20% NaOH (0.6 mL) and water (1.9 mL). The resulting suspension was filtered through a cake of celite and concentrated. Purification by flash silica gel chromatography (5% ethyl acetate/hexane) afforded a colorless resin (1.8 g, 4.2 mmol, 51%). $^1$H NMR (300 MHz, $CDCl_3$) δ 7.25 (m, 2 H), 7.12 (m, 2 H), 4.38 (d, J=5 Hz, 2 H), 4.28 (s, 2 H), 3.44 (sept, J=6.6 Hz, 1 H), 3.39 (sept, J=6.6 Hz, 1 H), 1.33 (t, J=6.6 Hz, 12 H), 1.24 (t, J=5.5 Hz, 1 H), 0.84 (s, 9 H), −0.08 (s, 6 H). FAB-MS calcd for ($C_{25}H_{38}FNSiO_2$) 431, found 432 (M+H). Anal. Calcd for $C_{25}H_{38}FNSiO_2$: C, 69.56; H, 8.87; N, 3.24. Found: C, 69.70; H, 8.82; N, 3.12. $R_f$=0.2 (10% ethyl acetate/hexane).

Step B: 2,6-Diisopropyl-3-bromomethyl-4-(4fluorophenyl)-5-[(t-butyldimethylsiloxy)methyl]pyridine The intermediate obtained in Step A (1.7 g, 3.9 mmol) was dissolved in acetonitrile (50 mL) at 0° C. and treated with dibromotriphenylphosphorane (2.6 g, 6.2 mmol) in portions. The suspension was then allowed to warm to room temperature and stirred for 2 hr. The solvent was removed in vacuo and the residue partitioned between diethyl ether (150 mL) and water (100 mL). The ether layer was washed with brine (50 mL), dried ($MgSO_4$) and concentrated. Purification by chromatography through silica (5% diethyl ether/hexane) afforded a viscous oil (1.4 g, 2.8 mmol, 72%) which slowly solidified on standing: $^1$H NMR (300 MHz, $CDCl_3$): δ 7.28 (m, 2 H), 7.13 (m, 2 H), 4.23 (m, 4 H), 3.37 (m, 2 H), 1.34 (d, J=6.6 Hz, 6 H), 1.30 (d, J=6.6 Hz, 6 H), 0.83 (s, 9 H), −0.09 (s, 6 H). FAB-MS calcd for ($C_{27}H_{37}BrFSiNO$) 493, found 494 (M+H). mp 72–73° C. $R_f$=0.5 (10% ethyl acetate/hexane).

Step C: 2,6-Diisopropyl-3-hydroxymethyl-4-(4-fluorophenyl)-5-[(4-nitrophenyl)thio]methylpyridine The intermediate obtained in Step B (200 mg, 0.40 mmol) was dissolved in anhydrous THF (5 mL), stirred under argon at room temperature and treated with 4-nitrothiophenol (118 mg, 0.6 mmol, 80% tech. grade) and N-methylmorpholine (0.2 mL, 1.8 mmol). The reaction mixture was allowed to stir at reflux for 18 hr, then cooled to room temperature. The mixture was treated with tetrabutylammonium fluoride (0.8 mL, 0.8 mmol, 1.0M in THF) and allowed to stir at room temperature for 24 hr. The solvent was removed in vacuo, the residue dissolved in ethyl acetate (100 mL), washed with 1N HCl (50 mL), sat. $NaHCO_3$ (50 mL) and brine (50 mL), dried ($MgSO_4$) and concentrated. Purification by chromatography through silica (step gradient 5–10% ethyl acetate/hexane) afforded the title compound as a lightly colored solid (130 mg, 0.28 mmol, 70%). $^1$H NMR (300 MHz, $CDCl_3$): δ 8.08 (d, J=8.5 Hz, 2 H), 7.27 (m, 2 H), 7.13 (m, 4 H), 4.37 (d, J=5.5 Hz, 2 H), 3.91 (s, 2 H), 3.46 (sept, J=6.6 Hz, 1 H), 3.33 (sept, J=6.6 Hz, 1 H), 1.35 (d, J=6.6 Hz, 6 H), 1.34 (d, J=6.6 Hz, 6 H), 1.27 (t, J=5 Hz, 1 H). FAB-MS calcd for ($C_{25}H_{27}FSN_2O_3$) 454, found 455 (M+H). mp 178–180° C. $R_f$=0.3 (20% ethyl acetate/hexane).

EXAMPLE 69

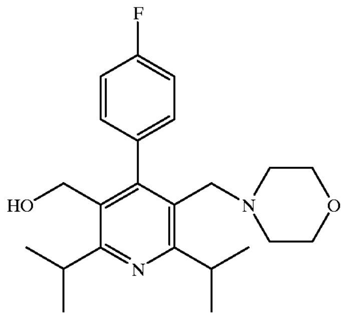

2,6-Diisopropyl-3-hydroxymethyl-4-(4-fluorophenyl)-5-(morphohino-methylpyridine

Step A: Methyl-2,6-diisopropyl-4-(4-fluorophenyl)-5-(morpholino)methyl-3-pyridinecarboxylate A solution of methyl-2,6-diisopropyl-4-(4-fluorophenyl)-5-bromomethyl-3-pyridinecarboxylate (Example 47, Step B) (500 mg, 1.22 mmol) in $CH_2Cl_2$ (20 mL) was treated with morpholine (0.14 mL, 1.61 mmol) under argon. The reaction was stirred at room temperature for 48 hours. It was then diluted with $CH_2Cl_2$ (70 mL), washed with saturated $NaHCO_3$ (2×40 mL), water (1×40 mL), and brine (1×40 mL). The organic layer was dried with $MgSO_4$, filtered, and concentrated to afford a white solid (495 mg, 1.2 mmol, 98%). $^1$H NMR (300 MHz, $CDCl_3$): δ 7.16 (m, 2 H), 7.07 (m, 2 H), 3.54 (t, J=4.4 Hz, 4 H), 3.49 (m, 4 H), 3.27 (s, 2 H), 2.98 (septet, J=6.6 Hz, 1 H), 2.19 (t, J=4.8 Hz, 4 H), 1.30 (m, 12 H). FAB-MS calcd for ($C_{24}H_{31}N_2FO_3$) 414, found 415 (M+H); Anal. Calcd for $C_{24}H_{31}N_2O_3F$: C, 69.54; H, 7.54; N, 6.76; F, 4.58. Found: C, 69.55; H, 7.43; N, 6.50; F, 4.45. mp 132–134° C. $R_f$=0.2 (20% diethyl ether/hexane).

Step B: 2,6-Diisopropyl-3-hydroxymethyl-4-(4-fluorophenyl)-5-(morpholinomethyl)pyridine The intermediate obtained in Step A (375 mg, 0.905 mmol) was dissolved in dry THF (50 mL), treated dropwise with lithium aluminum hydride (1M/THF, 1.81 mL) and the reaction stirred at reflux for 24 hours. The reaction was quenched by the successive dropwise addition of water (0.1 ml), NaOH 20% (0.1 ml), and water again (0.3 ml). Concentration in vacuo afforded a white residue which was partitioned between $CH_2Cl_2$ and water. The organic layer was dried with $MgSO_4$, filtered, and concentrated to afford an oil. The product was passed through a pad of silica (40% diethyl ether/hexanes) yielding an oil which slowly solidified to give the title compound as a white solid (295 mg, 0.76 mmol, 84%). $^1$H NMR (300 MHz, $CDCl_3$): δ 7.14 (m, 4 H), 4.35 (d, 2 H), 3.53 (t, J=4.8 Hz, 4 H), 3.45 (m, 2 H), 3.18 (s, 2 H), 2.18 (t, J=4.5 Hz, 4 H), 1.26 (m, 13 H); FAB-MS calcd for ($C_{23}H_{31}N_2FO_2$) 386, found 387 (M+H). Anal. Calcd for $C_{23}H_{31}N_2O_2F$: C, 71.47; H, 8.08; N, 7.25; F, 4.92 Found: C, 71.55; H, 8.16; N, 7.05; F, 4.70. mp 93.5–95.5° C. $R_f$=0.4 (40% diethyl ether/hexane).

EXAMPLE 70

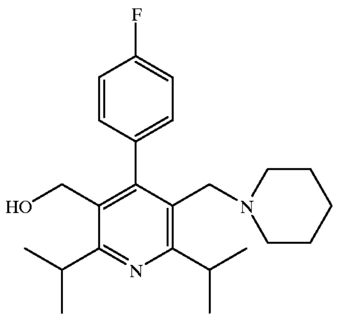

2,6-Diisopropyl-3-hydroxymethyl-4-(4-fluorophenyl)-5-(piperidinomethyl)pyridine

The title compound was prepared from piperidine according to the procedures described in Example 69. $^1$H NMR (300 MHz, $CDCl_3$): δ 7.05 (m, 4 H), 4.27 (d, J=5.5 Hz, 2 H), 3.38 (m, 2 H), 3.01 (s, 2 H), 2.02 (m, 4 H), 1.22 (m, 24 H). FAB-MS calcd for ($C_{24}H_{33}N_2FO$) 384, found 385 (M+H). Anal. Calcd for $C_{24}H_{33}N_2OF$: C, 74.96; H, 8.65; N, 7.28; F, 4.94. Found: C, 75.13; H, 8.48; N, 6.92; F, 4.77. Gummy oil. $R_f$=0.5 (40% diethyl ether/hexane).

EXAMPLE 71

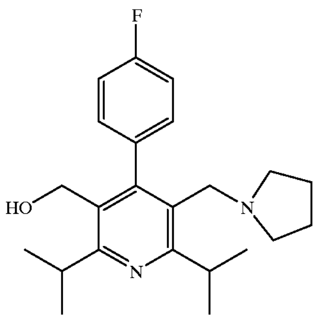

2,6-Diisopropyl-3-hydroxymethyl-4-(4-fluorophenyl)-5-(pyrrolindino-methyl)pyridine The title compound was prepared from pyrrolidine according to the procedures described in Example 69. $^1$H NMR (300 MHz, $CDCl_3$): δ 7.13 (m, 4 H), 4.34 (d, J=4.8 Hz, 2 H), 3.52 (septet, J=6.6 Hz, 1 H), 3.42 (septet, J=6.6 Hz, 1 H), 3.28 (s, 2 H), 2.22 (t, J=6.3 Hz, 4 H), 1.60 (t, J=3.3 Hz, 5 H), 1.27 (m, 12 H). FAB-MS calcd for ($C_{23}H_{31}N_2FO$) 370, found 371 (M+H). Anal. Calcd for $C_{23}H_{31}N_2OF$: C, 74.56; H, 8.43; N, 7.56; F, 5.13. Found: C, 74.67; H, 8.72; N, 7.35; F, 5.01. mp 122–124° C. $R_f$=0.3 (40% diethyl ether/hexane).

EXAMPLE 72

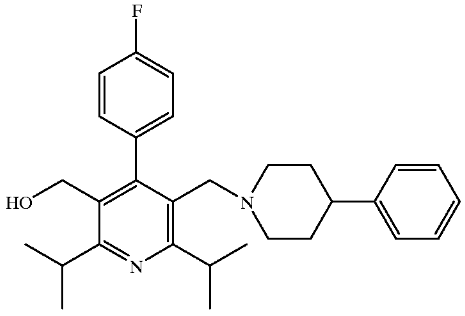

2,6-Diisopropyl-3-hydroxymethyl-4-(4-fluorophenyl)-5-[4-phenylpiperidin-1-yl)methyl] pyridine The title compound was prepared from 4-phenylpiperidine according to the procedures described in Example 69. $^1$H NMR (300 MHz, $CDCl_3$): δ 7.29 (m, 2 H), 7.15 (m, 7 H), 4.36 (d, J=5.2 Hz, 2 H), 3.48 (m, 2 H), 3.19 (s, 2 H), 2.71 (d, J=11.0 Hz, 2 H), 2.38 (m, 1 H), 1.86 (m, 2 H), 1.71 (m, 2 H), 1.58 (m, 2 H), 1.58 (m, 13 H). FAB-MS calcd for ($C_{30}H_{31}N_2FO$) 460, found 461 (M+H). Anal. Calcd for $C_{23}H_{31}N_2OF$: C, 78.22; H, 8.10; N, 6.08; F, 4.12. Found: C, 78.01; H, 8.21; N, 5.96; F, 4.41. mp 66–68° C. $R_f$=0.5 (40% diethyl ether/hexane).

EXAMPLE 73

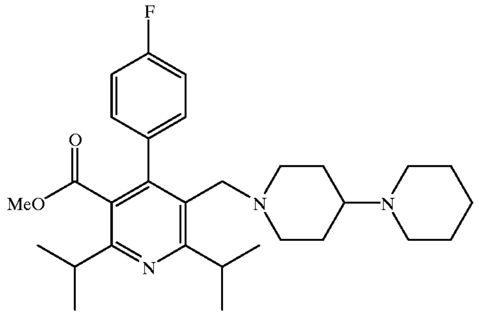

Methyl-2,6-diisopropyl-4-(4-fluorophenyl)-5-(4piperidinopiperidin-1-yl)methyl-3-pyridinecarboxylate The title compound was prepared from 4-piperdinopiperidine according to the procedure described in Example 69 (Step A). $^1$H NMR (300 MHz, $CDCl_3$): δ 7.16 (m, 2 H), 7.04 (m, 2 H), 3.51 (septet, J=5.5 Hz, 1 H), 3.47 (s, 3 H), 3.20 (s, 2 H), 2.98 (septet, J=6.6 Hz, 1 H), 2.65 (d, J=11.0 Hz, 2 H), 2.44 (m, 4 H), 2.05 (m, 1 H), 1.62 (m, 10 H), 1.31 (m, 16 H). FAB-MS calcd for ($C_{30}H_{42}N_3FO_2$) 495, found 496 (M+H). Anal. Calcd for $C_{30}H_{42}N_3O_2F$: C, 72.69; H, 8.54; N, 8.48; F, 3.83. Found: C, 72.43; H, 8.56; N, 8.37; F, 3.74. mp 59–61° C. $R_f$=0.1 (70% diethyl ether/hexane +1 drop MeOH).

EXAMPLE 74

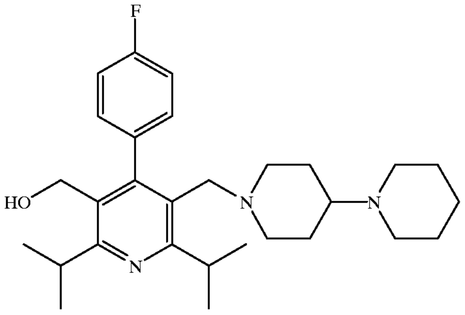

2,6-Diisopropyl-3-hydroxymethyl-4-(4-fluorophenyl)-5-[(4-piperidinopiperidin-1-yl)methyl] pyridine The title compound was prepared from 4piperidinopiperidine according to the procedures described in Example 69. $^1$H NMR (300 MHz, $CDCl_{13}$): δ 7.12 (m, 4 H), 4.34 (d, J=3.7 Hz, 2 H), 3.45 (m, 2 H), 3.10 (m, 2 H), 2.63 (d, J=11.0 Hz, 2 H), 2.44 (m, 4 H), 2.03 (m, 1 H), 1.44 (m, 29 H). FAB-MS calcd for ($C_{29}H_{42}N_3FO$) 467, found 468 (M+H). Anal. Calcd for $C_{29}H_{42}N_{30}F$: C, 74.48; H, 9.05; N, 8.98; F, 4.06. Found: C, 74.93; H, 9.35; N, 8.39; F, 3.83. mp 143–145° C. $R_f$=0.1 (50% diethyl ether/hexane +2 drops of MeOH).

EXAMPLE 75

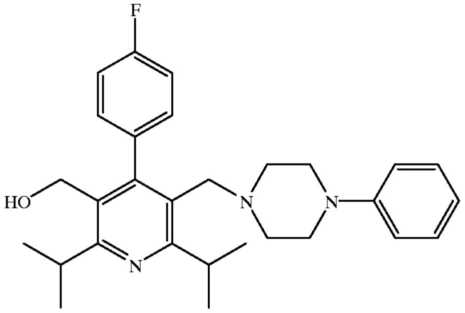

2,6-Diisopropyl-3-hydroxymethyl-4-(4-fluorophenyl)-5-[(4-phenylpiperazin-1-yl)methyl] pyridine The title compound was prepared from 4-phenylpiperazine according to the procedures described in Example 69. $^1$H NMR (300 MHz, $CDCl_3$): δ 7.16 (m, 6 H), 6.85 (m, 3 H), 4.36 (d, J=5.2 Hz, 2 H), 3.47 (m, 2 H), 3.24 (s, 2 H), 3.04 (t, J=4.8 Hz, 4 H), 2.35 (t, J=4.8 Hz, 4 H), 1.29 (m, 13 H). FAB-MS calcd for ($C_{29}H_{36}N_3FO$) 461, found 462 (M+H). Anal. Calcd for $C_{29}H_{36}N_3OF$: C, 75.46; H, 7.86; N, 9.10; F, 4.12. Found: C, 75.35; H. 7.82; N, 8.80; F. 3.99. mp 111–113° C. $R_f$=0.5 (40% diethyl ether/hexane).

EXAMPLE 76

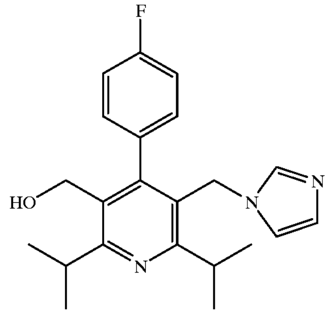

2,6-Diisopropyl-3-hydroxymethyl-4-(4-fluorophenyl)-5-(imidazol-1-yl)-methylpyridine The title compound was prepared from imidazole according to the procedures described in Example 69. $^1$H NMR (300 MHz, $CDCl_3$): δ 7.01 (m, 6 H), 6.57 (s, 1 H), 4.84 (s, 2 H), 4.39 (s, 2H), 3.49 (septet, J=6.6 Hz, 1 H), 3.23 (septet, J=6.6 Hz, 1 H), 1.70 (s, 1 H), 1.36 (d, J=6.6 Hz, 6 H), 1.27 (d, J=6.6 Hz, 6 H). FAB-MS calcd for ($C_{22}H_{26}N_3FO$) 367, found 368 (M+H). Anal. Calcd for $C_{22}H_{26}N_3OF$: C, 71.91; H, 7.13; N, 11.43; F, 5.17. Found: C, 71.26; H, 7.24; N, 11.03; F, 5.35. mp 184–186° C. $R_f$=0.1 (50% diethyl ether/hexane w/2 drops MeOH).

EXAMPLE 77

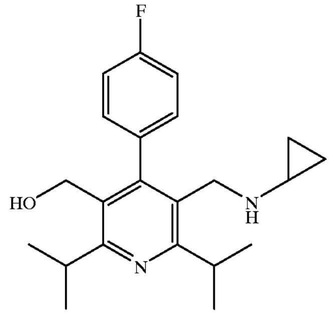

2,6-Diisopropyl-3-hydroxymethyl-4-(4-fluorophenyl)-5-(cyclopropyl-amino)methylpyridine The title compound was prepared from cyclopropylamine according to the procedures described in Example 69. $^1$H NMR (300 MHz, $CDCl_3$): δ 7.04 (m, 4 H), 4.21 (s, 2 H), 3.35 (s, 2 H), 3.26 (septet, J=6.6 Hz, 2 H), 1.78 (m, 1 H), 1.17 (m, 13 H), 0.153 (m, 2 H), -0.006 (m, 2 H). FAB-MS calcd for ($C_{22}H_{29}N_2FO$) 356, found 357 (M+H). Anal. Calcd for $C_{22}H_{29}N_2OF$: C, 74.12; H, 8.20; N, 7.86; F, 5.33. Found: C, 74.29; H, 8.62; N, 7.93; F, 4.90. mp 81–83° C. $R_f$=0.3 (40% diethyl ether/hexane).

EXAMPLE 78

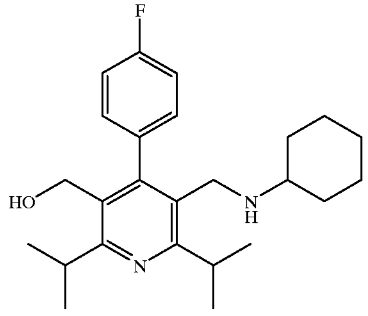

2,6-Diisopropyl-3-hydroxymethyl-4-(4-fluorophenyl)-5-(cyclohexylamino)methylpyridine The title compound was prepared from cyclohexylamine according to the procedures described in Example 69. $^1$H NMR (300 MHz, $CDCl_3$): δ 7.25 (m, 2 H), 7.13 (m, 2 H), 4.34 (s, 2 H), 3.38 (m, 4 H), 2.16 (m, 1 H), 1.58 (m, 5 H), 1.23 (m, 16 H), 0.936 (m, 2 H). FAB-MS calcd for ($C_{25}H_{35}N_2FO$) 398, found 399 (M+H). Anal. Calcd for $C_{25}H_{35}N_2OF$: C, 74.12; H, 8.20; N, 7.86; F, 5.33. Found: C, 74.29; H, 8.62; N, 7.93; F, 4.90. mp 131–133° C. $R_f$=0.1 (40% diethyl ether/hexane).

EXAMPLE 79

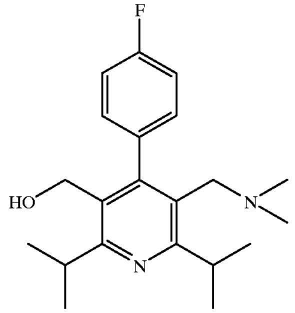

2,6-Diisopropyl-3-hydroxymethyl-4-(4-fluorophenyl)-5-(dimethylamino)-methylpyridine The title compound was prepared from dimethylamine hydrochloride according to the procedures described in Example 69. $^1$H NMR (300 MHz, $CDCl_3$): δ 7.12 (m, 4 H), 4.25 (m, 2 H), 4.09 (m, 1 H), 3.68 (septet, J=6.6 Hz, 1 H), 3.41 (septet, J=6.6 Hz, 1 H), 2.18 (m, 1 H), 1.69 (d, J=4.1 Hz, 1 H), 1.26 (m, 12 H), 0.947 (d, J=6.3 Hz, 3 H), 0.555 (d, J=7.0 Hz, 1 H). FAB-MS calcd for ($C_{22}H_{30}NFO_2$) 359, found 360 (M+H). Anal. Calcd for $C_{22}H_{30}NO_2F$: C, 73.51; H, 8.41; N, 3.90; F, 5.28. Found: C, 73.69; H, 8.40; N, 3.82; F, 5.04. mp 77–79° C. $R_f$=0.2 (40% diethyl ether/hexane).

EXAMPLE 80

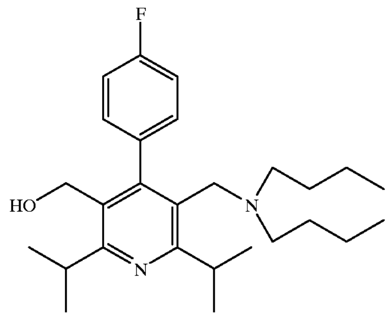

2,6-Diisopropyl-3-hydroxymethyl-4-(4fluorophenyl)-5-(dibutylamino)-methylpyridine The title compound was prepared from dibutylamine according to the procedures described in Example 69. $^1$H NMR (300 MHz, $CDCl_3$): δ 7.11 (m, 4 H), 4.33 (d, J=5.5 Hz, 2 H), 3.62 (septet, J=6.6 Hz, 1 H), 3.62 (septet, J=6.6 Hz, 1 H), 3.24 (s, 2 H), 2.12 (t, J=7.0 Hz, 4 H), 1.55 (s, 1 H), 1.33 (t, J=6.6 Hz, 6 H), 1.26 (t, J=6.6 Hz, 6 H), 1.16 (m, 8 H), 0.796 (t, J=6.6 Hz, 6 H). FAB-MS calcd for ($C_{27}H_{41}N_2FO$) 428, found 429 (M+H). Anal. Calcd for $C_{27}H_{41}N_2OF$: C, 75.66; H, 9.64; N, 6.54; F, 4.43. Found: C, 75.91; H, 9.83; N, 6.26; F, 4.33. Gummy oil. $R_f$=0.6 (40% diethyl ether/hexane).

EXAMPLE 81

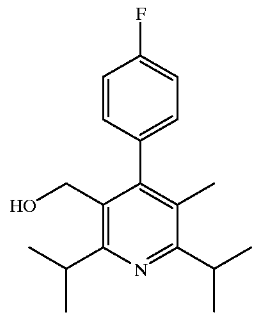

2,6-Diisopropyl-3-hydroxymethyl-4-(4-fluorophenyl-5-methylpyridine

A solution of methyl-2,6-diisopropyl-4-(4-fluorophenyl)-5-bromomethyl-3-pyridinecarboxylate (Example 47, Step B) (300 mg, 0.7 mmol), in anhydrous THF (10 mL) was stirred under argon at room temperature and treated dropwise with lithium aluminum hydride (2.1 mL, 1.0M in THF, 2.1 mmol). The reaction mixture was heated at reflux for 1 hr, then allowed to cool to room temperature. The reaction was quenched by the dropwise sequential addition at room temperature of water (80 uL), 20% NaOH (80 uL) and water (240 uL). The resulting suspension was filtered through a pad of celite and concentrated. Purification by chromatography through silica (5% ethyl acetate/hexane) afforded the title compound as a white solid (182 mg, 0.6 mmol, 85%). $^1$H NMR (300 MHz, $CDCl_3$): δ 7.15 (d, J=7 Hz, 4 H), 4.36 (d, J=5.5 Hz, 2 H), 3.42 (sept, J=6.6 Hz, 1 H), 3.26 (sept, J=6.6 Hz, 1 H), 1.94 (s, 3 H), 1.33 (d, J=6.6 Hz, 6 H), 1.29 (d, J=6.6 Hz, 6 H), 1.19 (t, J=5.5 Hz, 1 H); FAB-MS calcd for ($C_{19}H_{24}FNO$) 301, found 302 (M+H). Anal. Calcd for $C_{19}H_{24}FNO$: C, 75.72; H, 8.03; N, 4.65. Found: C, 75.62; H, 8.02; N, 4.57. mp 127–128° C. $R_f$=0.3 (20% ethyl acetate/hexane).

EXAMPLE 82

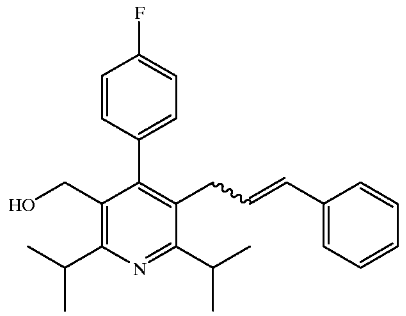

2,6-Diisopropyl-3-hydroxymethyl-4-(4-fluorophenyl)-5-(3-phenyl-2-propenyl)pyridine Step A: Methyl-2,6-diisopropyl-4-(4-fluorophenyl)-5-(2-oxoethyl)-3-pyridinecarboxylate Methoxymethyl triphenylphosphonium chloride (1.15 g, 3.35 mmol) was suspended in 25 mL of dry, distilled THF under argon and stirred at −78° C. Butyllithium (1.6M/hexane, 1.2 eq., 2.1 mL) was added dropwise and then the reaction mixture was allowed to stir at 0° C. for 1.0 hour. The solution was cooled again to −78° C., treated dropwise with a solution of 5-carboethoxy-2,6-diisopropyl-4-(4-fluorophenyl)-3-pyridinecarboxaldehyde (Example 1, Step E) (1 g, 2.8 mmol) in 20 mL of dry THF, and then warmed to room temperature and stirred overnight. The reaction was quenched 2 mL water and the THF was evaporated in vacuo. Diethyl ether was added and washed with water (2×40 mL), brine (1×40 mL), and dried with $MgSO_4$. The residue was dissolved in THF (20 ml), treated with a solution of concentrated HCl and stirred at room temperature for 1 h. The reaction mixture was diluted with diethyl ether (150 ml) washed with water (50 ml), brine (50 ml), dried with $MgSO_4$ and evaporated in vacuo. Flash chromatography (10% ethyl acetate/hexane) afforded 335 mg (0.9 mmol, 32%) of product. $^1$H NMR (300 MHz, $CDCl_3$): δ 9.62 (s, 1 H), 7.09 (m, 4 H), 3.97 (q, J=7 Hz, 2 H), 3.60 (s, 2 H), 3.06 (sept, J=6.6 Hz, 1 H), 3.00 (sept, J=6.6 Hz, 1 H), 1.32 (d, J=6.6 Hz, 6 H), 1.27 (d, J=6.6 Hz, 6 H), 0.97 (t, J=7 Hz, 3 H). FAB-MS: calcd for ($C_{22}H_{26}FNO_3$) 371, found 372 (M+H). Anal. Calcd for $C_{22}H_{26}FNO_3$: C, 71.14; H, 7.06; N, 3.77. Found: C, 70.91; H, 6.91; N, 3.63. mp 69–71° C. Rf =0.3 (10% ethyl acetate/hexane).

Step B: 2,6-Diisopropyl-3-hydroxymethyl-4-(4-fluorophenyl)-5-(3-phenyl-2-propenyl)pyridine The title compound was prepared from the intermediate obtained in Step A and benzyl triphenylphosphonium bromide/sodium amide according to the procedures described in Example 1, Steps F–G. The product was obtained as a 6:4 mixture of trans:cis isomers. $^1$H NMR (300 MHz, $CDCl_3$): δ 7.19 (m, 8 H), 6.96 (m, 1 H), 6.32 (d, J=11 Hz, 0.4 H), 6.09 (dt, J=5.5, 16 Hz, 0.6 H), 5.96 (d, J=16 Hz, 0.6 H), 5.45 (dt, J=7, 11 Hz, 0.4 H), 4.37 (d, J=5 Hz, 1.25 H), 4.33 (d, J=5.5 Hz, 0.75 H), 3.41 (m, 1.6 H), 3.25 (m, 2 H), 3.08 (m, 0.4 H), 1.35 (m, 5 H), 1.30 (d, J=6.6 Hz, 5 H), 1.21 (m, 3 H). FAB-MS: calcd for ($C_{27}H_{30}FNO$) 403, found 404 (M+H). Anal. Calcd for $C_{27}H_{30}FNO$: C, 80.36; H, 7.49; N, 3.47. Found: C, 80.15; H, 7.44; N, 3.26. mp 72–73° C. $R_f$=0.3 (20% ethyl acetate/hexane).

EXAMPLE 83

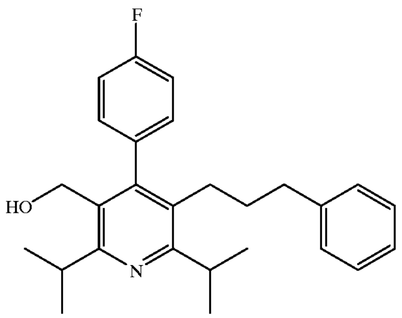

2,6-Diisopropyl-3-hydroxymethyl-4-(4-fluorophenyl-5-(3-phenyl-propyl)pyridine

The title compound was prepared from 2,6-diisopropyl-3-hydroxymethyl-4-(4fluorophenyl)-5(3-phenyl-2-propenyl)pyridine (Example 82) according to the procedure described in Example 1, Step H. $^1$H NMR (300 MHz, $CDCl_3$): δ 7.11 (m, 9 H), 4.31 (s, 2 H), 3.40 (sept, J=6.6 Hz, 1 H), 3.12 (sept, J=6.6 Hz, 1 H), 2.46 (t, J=7.35 Hz, 2 H), 2.29 (m, 2 H), 1.62 (m, 2 H), 1.32 (d, J=6.6 Hz, 6 H), 1.26 (d, J=6.6 Hz, 6 H), 1.16 (m, 1 H). FAB-MS: calcd for ($C_{27}H_{32}FNO$) 405, found 406 (M+H). mp 137–140° C. $R_f$=0.3 (20% ethyl acetate/hexane).

EXAMPLE 84

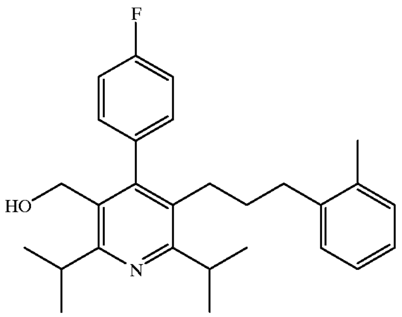

2,6-Diisopropyl-3-hydroxymethyl-4-(4-fluorophenyl)-5-[3-(2-methylphenyl)propyl]pyridine The title compound was prepared from methyl-2,6-diisopropyl-4(4-fluorophenyl)-5-(2-oxoethyl)-3-pyridinecarboxylate (Example 82, Step A) and 2-methylbenzyl triphenylphosphonium bromide according to the procedures described in Example 1, Steps F–H. $^1$H NMR (300 MHz, $CDCl_3$): δ 7.07 (m, 7 H), 6.90 (m, 1 H), 4.31 (s, 2 H), 3.39 (sept, J=6.6 Hz, 1 H), 3.15 (sept, J=6.6 Hz, 1 H), 2.43 (t, J=7.5 Hz, 2 H), 2.34 (m, 2 H), 2.17 (s, 3 H), 1.6 (m, 2 H), 1.31 (d, J=6.6 Hz, 6 H), 1.27 (d, J=6.6 Hz, 6 H), 1.15 (m, 1 H). FAB-MS: calcd for ($C_{28}H_{34}FNO$) 419, found 420 (M+H). Anal. Calcd for $C_{28}H_{34}FNO$: C, 80.15; H, 8.17; N, 3.34. Found: C, 80.12; H, 8.01; N, 3.25. mp 65–70° C. $R_f$=0.4 (20% ethyl acetate/hexane).

EXAMPLE 85

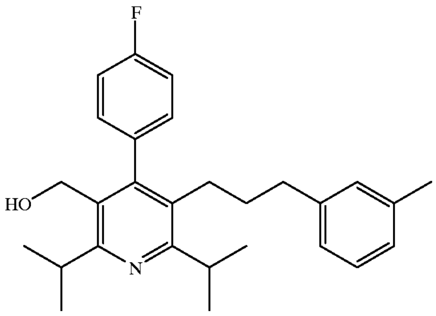

2,6-Diisopropyl-3-hydroxymethyl-4-(4-fluorophenyl)-5-[3-(3-methyl-5-phenyl)propyl]pyridine The title compound was prepared from methyl-2,6-diisopropyl-4-(4-fluorophenyl)-5-(2-oxoethyl)-3-pyridinecarboxylate (Example 82, Step A) and 3-methylbenzyl triphenylphosphonium bromide according to the procedures described in Example 1, Steps F–H. $^1$H NMR (300 MHz, $CDCl_3$): δ 7.09 (m, 5 H), 6.98 (m, 1 H), 6.78 (m, 2 H), 4.31 (s, 2 H), 3.39 (sept, J=6.6 Hz, 1 H), 3.12 (sept, J=6.6 Hz, 1 H), 2.42 (t, J=7 Hz, 2 H), 2.30 (s, 3 H), 2.28 (m, 2 H), 1.58 (m, 2 H), 1.31 (d, J=6.6 Hz, 6 H), 1.26 (d, J=6.6 Hz, 6 H), 1.15 (m, 1 H). FAB-MS: calcd for ($C_{28}H_{34}FNO$) 419, found 420 (M+H). Anal. Calcd for $C_{28}H_{34}FNO$: C, 80.15; H, 8.17; N, 3.34. Found: C, 80.23; H, 8.17; N, 3.23. mp 68–70° C. $R_f$=0.4 (20% ethyl acetate/hexane).

EXAMPLE 86

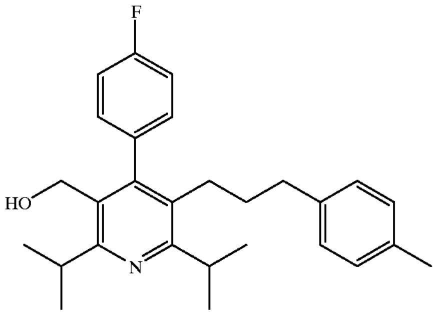

2,6-Diisopropyl-3-hydroxymethyl-4-(4-fluorophenyl)-5-[3-(4methyl-phenyl)propyl]pyridine The title compound was prepared from methyl-2,6-diisopropyl-4-(4-fluorophenyl)-5-(2-oxoethyl)-3-pyridinecarboxylate (Example 82, Step A) and 4-methylbenzyl triphenylphosphonium bromide according to the procedures described in Example 1, Steps F–H. $^1$H NMR (300 MHz, $CDCl_3$): δ 7.08 (m, 4 H), 7.01 (d, J=8 Hz, 2 H), 6.85 (d, J=8 Hz, 2 H), 4.30 (s, 2 H), 3.39 (sept, J=6.6 Hz, 1 H), 3.13 (sept, J=6.6 Hz, 1 H), 2.41 (t, J=7 Hz, 2 H), 2.31 (s, 3 H), 2.27 (m, 2 H), 1.58 (m, 2 H), 1.31 (d, J=6.6 Hz, 6 H), 1.26 (d, J=6.6 Hz, 6 H), 1.15 (m, 1 H). FAB-MS: calcd for ($C_{28}H_{34}FNO$) 419, found 420 (M+H). Anal. Calcd for $C_{28}H_{34}FNO$: C, 80.15; H, 8.17; N, 3.34. Found: C, 80.33; H, 8.28; N, 3.22. mp 79–80° C. $R_f$=0.4 (20% ethyl acetate/hexane).

EXAMPLE 87

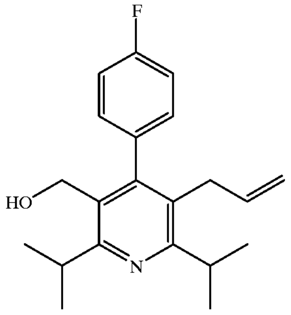

2,6-Diisopropyl-3-hydroxymethyl-4-(4fluorophenyl)-5-(2-propenyl)-pyridine

The title compound was prepared from methyl-2,6-diisopropyl-4-(4-fluorophenyl)-5-(2-oxoethyl)-3-pyridinecarboxylate (Example 82, Step A) and methyl triphenylphosphonium bromide according to the procedures described in Example 1, Steps F–H. $^1$H NMR (300 MHz, $CDCl_3$): δ 7.13 (m, 4 H), 5.73 (m, 1H) 4.81 (dd, J=4.8, 1.8 Hz, 2 H), 4.35 (s, 2 H), 3.43 (septet, J=6.6 Hz, 1 H), 3.21 (septet, J =6.6 Hz, 1 H), 3.07 (d, J=1.8 Hz, 2 H), 1.24 (m, 13 H). FAB-MS: calcd for ($C_{21}H_{26}FNO$) 327, found 328 (M+H). Anal. Calcd for $C_{21}H_{26}FNO$: C, 74.17; H, 7.71; N, 4.12; F, 5.59+0.7 $H_2O$. Found: C, 74.17; H, 7.57; N, 3.94; F, 5.26. mp 69–71° C. $R_f$=0.35 (15% ethyl acetate/hexane).

EXAMPLE 88

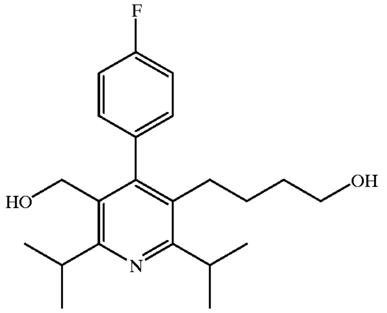

2,6-Diisopropyl-3-hydroxymethyl-4-(4-fluorophenyl)-5-(4-hydroxy-butyl)pyridine

To a solution of 2,6-diisopropyl-3-hydroxymethyl-4-(4-fluorophenyl)5-[3-(1,3-dioxolan-2-yl)propyl]pyridine (Example 46) (2 g, 5 mmol) in THF (50 mL) was added 2N aq. HCl (10 mL). The solution was allowed to stir for 17 hr at room temperature. The THF was removed in vacuo and the residual suspension carefully neutralized to pH 7 with sat. aq. $NaHCO_3$. The aqueous phase was extracted with diethyl ether (3x100 mL), the combined ether extract washed with brine (50 mL), dried ($MgSO_4$) and concentrated. Purification by chromatography through silica (step gradient, 10%–20% ethyl acetate/hexane) afforded a white solid (1.5 g, 4.2 mmol, 83%): $^1$H NMR (300 MHz, $CDCl_3$): d 9.57 (s, 1 H), 7.16 (m, 4 H), 4.33 (d, J=5 Hz, 2 H), 3.42 (m, 1 H), 3.24 (m, 1 H), 2.33 (m, 2 H), 2.27 (dt, J=1.8, 7.4 Hz, 2 H), 1.61 (m, 2 H), 1.32 (m, 12 H), 1.20 (m, 1 H). FAB-MS: calcd for ($C_{22}H_{30}FNO_2$) 359, found 340 (M+H). $R_f$=0.3 (20% ethyl acetate/hexane).

This intermediate (200 mg, 0.56 mmol) was dissolved in absolute ethanol (5 mL) and treated at room temperature, with stirring, with sodium borohydride (32 mg, 0.85 mmol). After stirring for 1 hr, the reaction was quenched by the dropwise addition of 2N HCl (3 mL). The solution was stirred 5 min, then neutralized by the careful addition of sat. $NaHCO_3$. The aqueous phase was extracted with diethyl ether (3x50 mL), the combined extracts dried ($MgSO_4$) and concentrated. Purification by chromatography through silica (20% ethyl acetate/hexane) afforded the title compound as a white solid (88 mg, 0.25 mmol, 44%): $^1$H NMR (300 MHz, $CDCl_3$): δ 7.16 (m, 4 H), 4.33 (d, J=5 Hz, 2 H), 3.46 (m, 2 H), 3.41 (m, 1 H), 2.23 (m, 1 H), 2.32 (m, 2 H), 1.40 (m, 4 H), 1.32 (m, 12 H), 1.19 (m, 1 H), 1.09 (m, 1 H). FAB-MS: calcd for ($C_{22}H_{30}FNO_2$) 359, found 360 (M+H). Anal. Calcd for $C_{22}H_{30}FNO_2$: C, 73.51; H, 8.41; N, 3.90. Found: C, 73.37; H, 8.41; N, 3.72. mp 135–137° C. $R_f$=0.4 (50% ethyl acetate/hexane);

EXAMPLE 89

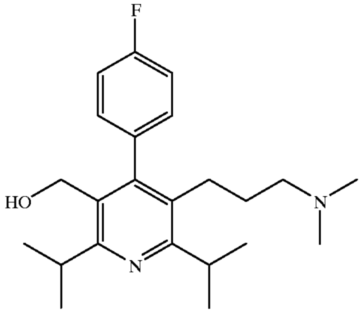

2,6-Diisopropyl-3-hydroxymethyl-4-(4fluorophenyl)-5-[(3-dimethyl-amino)propyl] pyridine The title compound was prepared from 5-carboethoxy-2,6-diisopropyl-4-(4-fluorophenyl)-3-pyridinecarboxaldehyde (Example 1, Step E) and (2-dimethylaminoethyl) triphenylphosphonium bromide according to the procedures described in Example 1, Steps F–H. $^1$H NMR (300 MHz, $CDCl_3$): δ 7.17 (m, 4 H), 4.33 (s, 2 H), 3.41 (sept, J=6.6 Hz, 1 H), 3.21 (sept, J=6.6 Hz, 1 H), 2.32 (m,2 H), 2.16 (m, 2 H), 2.14 (s, 6 H), 1.49 (m, 2 H), 1.32 (m, 13 H). FAB-MS: calcd for ($C_{23}H_{33}FN_2O$) 372, found 373 (M+H). mp 50–51° C. $R_f$=0.35 (20% ethanol/$CH_2Cl_2$).

EXAMPLE 90

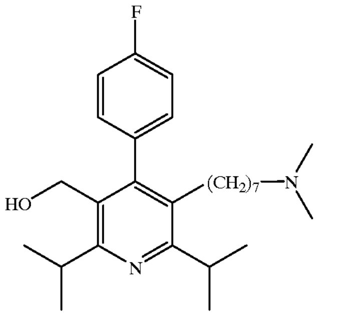

2,6-Diisopropyl-3-hydroxymethyl-4-(4-fluorophenyl)-5-[(3-dimethylamino)heptyl]pyridine Step A: 2,6-Diisopropyl-3-hydroxymethyl-4-(4-fluorophenyl)-5-(4-oxobutyl)pyridine To a solution of 2,6-diisopropyl-3-hydroxymethyl-4-(4-fluorophenyl)-5-[3-(1,3-dioxolan-2-yl)propyl]pyridine (Example 46) (2 g, 5 mmol) in THF (50 mL) was added 2N aq. HCl (10 mL). The solution was allowed to stir for 17 hr at room temperature. The THF was removed in vacuo and the residual suspension carefully neutralized to pH 7 with sat. $NaHCO_3$. The aqueous phase was extracted with diethyl ether (3×100 mL), the combined ether extract washed with brine (50 mL), dried ($MgSO_4$) and concentrated. Purification by chromatography through silica (step gradient, 10%–20% ethyl acetate/hexane) afforded a white solid (1.5 g, 4.2 mmol, 83%). $^1H$ NMR (300 MHz, $CDCl_3$): δ 9.57 (s, 1 H), 7.16 (m, 4 H), 4.33 (d, J=5 Hz, 2 H), 3.42 (m, 1 H), 3.24 (m, 1 H), 2.33 (m, 2 H, 2.27 (dt, J=1.8, 7.4 Hz, 2 H), 1.61 (m, 2 H), 1.32 (m, 12 H), 1.20 (m, 1 H). FAB-MS: calcd for ($C_{22}H_{28}FNO_2$) 357, found 358 (M+H). $R_f$=0.3 (20% ethyl acetate/hexane).

Step B: 2,6-Diisopropyl-3-hydroxymethyl-4-(4-fluorophenyl)-5[(3-dimethylamino)heptyl]pyridine The intermediate prepared in Step A was treated with (3 dimethylamino)propyl triphenylphosphonium bromide according to the procedures described in Example 1, Steps F–H, to afford the title compound as a solid. $^1H$ NMR (300 MHz, $CDCl_3$): δ 7.16 (m, 4 H), 4.32 (s, 2 H), 3.41 (sept, J=6.6 Hz, 1 H), 3.22 (sept, J=6.6 Hz, 1 H), 2.28 (s, 6 H), 2.26 (m, 4 H), 1.43 (m, 2 H), 1.33 (d, J=6.6 Hz, 6 H), 1.30 (d, J=6.6 Hz, 6 H), 1.27 (m, 3 H), 1.31 (m, 6 H). FAB-MS: calcd for ($C_{27}H_{41}FN_2O$) 428, found 429 (M+H). mp 85–87° C. $R_f$=0.1 (20% EtOH/$CH_2Cl_2$).

EXAMPLE 91

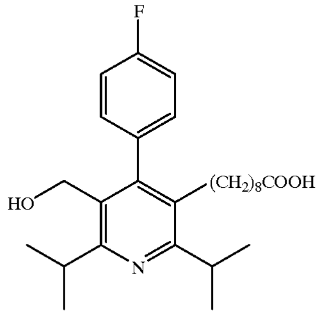

2,6-Diisopropyl-3-hydroxymethyl-4-(4-fluorophenyl)-5-(8-carboxyheptyl)pyridine

The title compound was prepared from 2,6-diisopropyl-3-hydroxymethyl-4-(4-fluorophenyl)-5-(4-oxobutyl) pyridine (Example 90, Step A) and (4-carboxybutyl) triphenylphosphonium bromide according to the procedure described in Example 90, Step B. $^1H$ NMR (300 MHz, $CD_3OD$): δ 7.17 (m, 4 H), 4.23 (s, 2 H), 3.44 (sept, J=6.6 Hz, 1 H), 3.23 (sept, J=6.6 Hz, 1 H), 2.28 (m, 2 H), 2.14 (t, J =7.5 Hz, 2 H), 1.54 (m, 2 H), 1.28 (d, J=6.6 Hz, 6 H), 1.24 (d, J=6.6 Hz, 6 H), 1.22 (m, 4 H), 1.17 (m, 2 H), 1.10 (m, 4 H). EI-MS: calcd for ($C_{27}H_{38}FNO_3$) 443, found 443 ($M^+$). mp 240° C (dec). $R_f$=0.3 (50% ethyl acetate/hexane).

EXAMPLE 92

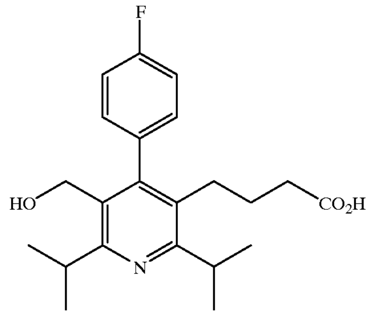

2,6-Diisopropyl-3-hydroxymethyl-4-(4-fluorophenyl)-5-(3carboxypropyl)pyridine

To a solution of 2,6-diisopropyl-3-hydroxymethyl-4-(4-fluorophenyl)-5-[3-(1,3-dioxolan-2-yl)propyl]pyridine (Example 46) (2 g, 5 mmol) in THF (50 mL) was added 2N aq. HCl (10 mL). The solution was allowed to stir for 17 hr at room temperature. The THF was removed in vacuo and the residual suspension carefully neutralized to pH 7 with sat. $NaHCO_3$. The aqueous phase was extracted with diethyl ether (3×100 mL), and the combined ether extract washed with brine (50 mL), dried ($MgSO_4$) and concentrated. Purification by chromatography through silica (step gradient, 10%–20% ethyl acetate/hexane) afforded 1.5 g of the intermediate as a white solid: $R_f$=0.3 (20% ethyl acetate/hexane).

280 mg of the intermediate was dissolved in dry pyridine (5 mL), stirred at room temperature under argon and treated with acetic anhydride (0.37 mL, 3.9 mmol). The reaction mixture was allowed to stir at room temperature for 17 hr. The pyridine was removed in vacuo, and the residue dissolved in diethyl ether (50 mL), washed with sat. $CuSO_4$ (10 mL), water (20 mL), sat. $NaHCO_3$ (20 mL) and brine (10 mL), dried ($MgSO_4$) and concentrated. Purification by chromatography through silica (20% ethyl acetate/hexane) afforded 220 mg as a viscous yellow oil: $R_f$=0.6 (50% ethyl acetate/hexane).

200 mg of the oil was dissolved in acetone (5 mL), stirred at room temperature and treated with Jones reagent (2 mL, prepared from 67 g $CrO_3$, 125 mL $H_2O$ and 58 mL con. $H_2SO_4$). The reaction mixture was stirred 0.5 hr, quenched by the addition of 2-propanol, filtered through a short pad of silica and concentrated. The residue was dissolved in MeOH (5 mL), treated with 20% NaOH (2 mL) and stirred 14 hr at room temperature. After neutralizing to pH 7 with aq. HCl, the solution was saturated with NaCl and extracted with $CHCl_3$ (3×20 mL). The combined extract was dried ($MgSO_4$) and concentrated. Purification by chromatography through silica (1:1 ethyl acetate/hexane) afforded the title compound as a white foam (22 mg). $^1H$ NMR (300 MHz, $CD_3OD$): δ 7.18 (m, 4 H), 4.24 (s, 2 H), 3.46 (sept, J=6.6 Hz, 1 H), 3.33 (sept, J=6.6 Hz, 1 H), 2.34 (m, 2 H), 1.99 (t, J=7 Hz,2 H), 1.60 (m, 2 H), 1.29 (d, J=6.6 Hz, 6 H), 1.26 (d, J=6.6 Hz, 6 H). FAB-MS: calcd for ($C_{22}H_{28}FNO_3$) 373, found 374 (M+H). mp 160° C. $R_f$=0.3 (50% ethyl acetate/hexane).

EXAMPLE 93

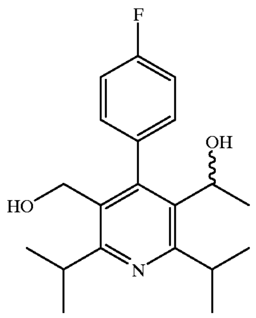

(±)-2,6-Diisopropyl-3-hydroxymethyl-4-(4-fluorophenyl-5-(1-hydroxy-ethyl)pyridine Step A: (±)-Ethyl-2,6-diisopropyl-4-(4fluorophenyl)-5-(1-hydroxy-ethyl)-3-pyridinecarboxylate To 5-carboethoxy-2,6-diisopropyl-4-(4-fluorophenyl)-3-pyridine-carboxaldehyde (Example 1, Step E) (1 g, 2.91 mmol) in THF (30 mL) was added methyllithium (1.4M, 1.0 eq., 2.08 mL) dropwise at −78° C. under argon. The reaction was stirred for 2 hours, then quenched with water and the THF evaporated to afford a white solid. The product was partitioned between diethyl ether and water. The organic layer was then dried with $MgSO_4$, filtered, and concentrated to afford a white solid. The product was passed through a plug of silica (10% ethyl acetate/hexane) to afford a white solid (857 mg, 2,4 mmol, 82%). $^1$H NMR (300 MHz, $CDCl_3$): δ 7.14 (m, 4 H), 4.86 (dq, J=3.7, J=6.6 Hz, 1 H), 3.80 (septet, J=6.6 Hz, 1 H), 3.47 (s, 3 H), 2.96 (septet, J=6.6 Hz, 1 H), 1.65 (d, J=3.7 Hz, 1 H), 1.46 (d, J=6.6 Hz, 3 H), 1.27 (m, 12 H). FAB-MS: calcd for ($C_{21}H_{26}NFO_3$) 359, found 360 (M+H). Anal. Calcd for $C_{21}H_{26}NO_3F$: C, 69.54; H, 7.54; N, 6.76; F, 4.58. Found: C, 69.55; H, 7.43; N, 6.50; F, 4.45. mp 169–171 C. $R_f$=0.2 (10% ethyl acetate/hexane).

Step B: (±)-2,6-Diisopropyl-3-(hydroxymethyl-4-(4-fluorophenyl)-1-hydroxyethyl)pyridine The intermediate obtained in Step A (300 mg, 0.835 mmol) was dissolved in 40 mL of dry THF, for a dropwise addition of a solution of LAH (1M/THF, 1.67 mL, 2 eq.). The reaction mixture was stirred at reflux for 24 hours then cooled to room temperature and quenched with water (70 μL), 20% NaOH (70 μL), and water (140 μL). After filtration, the solvent was evaporated to afford a white residue. The product was subjected to flash chromatography (20% ethyl acetate hexane) which afforded the title compound as a white solid (84 mg, 0.25 mmol, 30%). $^1$H NMR (300 MHz, $CDCl_3$): δ 7.15 (m, 4 H), 4.71 (dq, J=3.7, J=6.6 Hz, 1 H), 4.30 (m, 2 H), 3.79 (septet, J=6.6 Hz, 1 H), 3.42 (septet, J=6.6 Hz, 1 H), 1.62 (d, J=3.68 Hz, 1 H), 1.58 (s, 1H), 1.43 (d, J=6.6 Hz, 3 H), 1.28 (m, 16 H). FAB-MS: calcd for ($C_{20}H_{26}NFO_2$) 331, found 332 (M+H). Anal. Calcd for $C_{20}H_{26}NO_2F$: C, 76.84; H, 8.69; N, 3.90. Found: C, 76.67; H, 8.76; N, 3.77. mp 184–186° C. $R_f$=0.2 (20% ethyl acetate/hexane).

EXAMPLE 94

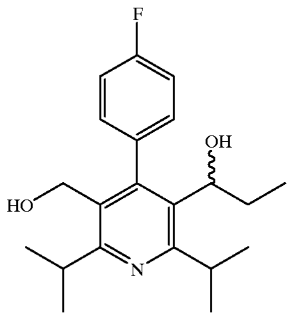

(±)-2,6-Diisopropyl-3-hydroxymethyl-4-(4-fluorophenyl)-5-(1-hydroxy-propyl)pyridine The title compound was prepared from 5-carboethoxy-2,6-diisopropyl-4-(4-fluorophenyl)-3-pyridinecarboxaldehyde (Example 1, Step E) and ethyl magnesium bromide, according to the procedures described in Example 93. $^1$H NMR (300 MHz, $CDCl_3$): δ 7.15 (m, 4 H), 4.40 (dq, J=3.7, J=5.2 Hz, 1 H), 4.30 (d, 5.5 Hz, 2 H), 3.72 (septet, J=6.6 Hz, 1 H), 3.42 (septet, 6.6 Hz, 1 H), 1.88 (m, 1 H), 1.63 (t, J=5.5 Hz, 1 H), 1.27 (m, 14 H), 0.804 (t, J=7.36 Hz, 3 H). FAB-MS: calcd for ($C_{21}H_{28}NFO_2$) 345, found 346 (M+H). Anal. Calcd for $C_{21}H_{28}NO_2F$: C, 76.84; H, 8.69; N, 3.90. Found: C, 76.67; H, 8.76; N, 3.77. mp 173–175° C. $R_f$=0.2 (20% ethyl acetate/hexane);

EXAMPLE 95

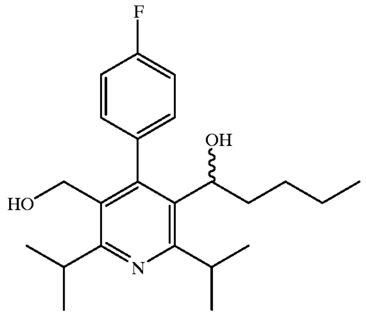

(±)-2,6-Diisopropyl-3-hydroxymethyl-4-(4-fluorophenyl)-5-(1-hydroxy-pentyl)pyridine The title compound was prepared from 5-carboethoxy-2,6-diisopropyl-4-(4-fluorophenyl)-3-pyridinecarboxaldehyde (Example 1, Step E) and n-butyllithium, according to the procedures described in Example 93. $^1$H NMR (300 MHz, $CDCl_3$): δ 7.16 (m, 4 H), 4.49 (m, 1 H), 4.31 (d, J=5.5 Hz, 2 H), 3.74 (septet, J=6.6 Hz, 1 H), 3.42 (septet, J=6.6 Hz, 1 H), 1.88 (m, 1 H), 1.58 (d, J=3.3 Hz, 1 H), 1.18 (m, 18 H), 0.821 (t, J=4.1 Hz, 3 H). FAB-MS: calcd for ($C_{23}H_{32}NFO_2$) 373, found 374 (M+H). Anal. Calcd for $C_{23}H_{32}NO_2F$: C, 73.96; H, 8.64; N, 3.75; F, 5.09. Found: C, 73.81; H, 8.60; N, 3.58; F, 5.02. mp 166–168° C. $R_f$=0.3 (20% ethyl acetate/hexane).

EXAMPLE 96

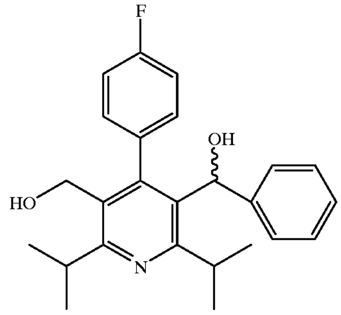

(±)-2,6-Diisopropyl-3-hydroxymethyl-4-(4-fluorophenyl)-5-(hydroxy-phenylmethyl)pyridine The title compound was prepared from 5-carboethoxy-2,6-diisopropyl-4-(4-fluorophenyl)-3-pyridinecarboxaldehyde (Example 1, Step E) and phenyllithium, according to the procedures described in Example 93. $^1$H NMR (300 MHz, $CDCl_3$): δ 7.23 (m, 7 H), 7.06 (m, 2 H), 5.71 (d, J=5.14 Hz, 1 H), 4.38 (d, J=5.5 Hz, 2 H), 3.47 (septet, J=6.6 Hz, 1 H), 3.12 (septet, J=6.6 Hz, 1 H), 2.12 (d, J=5.1 Hz, 1 H), 1.57 (s, 1H), 1.29 (m, 10 H), 0.797 (d, J=6.6 Hz, 3 H). FAB-MS: calcd for ($C_{25}H_{28}NFO_2$) 393, found 394 (M+H). Anal. Calcd for $C_{25}H_{28}NO_2F$: C, 76.84; H, 8.69; N, 3.90. Found: C, 76.67; H, 8.76; N, 3.77. mp 202–204° C. $R_f$=0.2 (20% ethyl acetate/hexane).

EXAMPLE 97

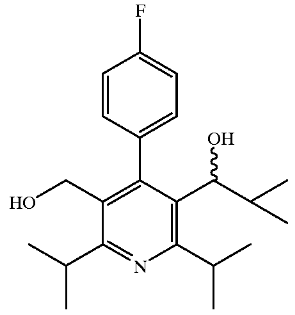

(±)-2,6-Diisopropyl-3-hydroxymethyl-4-(4-fluorophenyl)-5-[(1-hydroxy-2-methyl)propyl] pyridine The title compound was prepared from 5-carboethoxy-2,6-diisopropyl-4-(4-fluorophenyl)-3-pyridinecarboxaldehyde (Example 1, Step E) and isopropyl magnesium bromide, according to the procedures described in Example 93. $^1$H NMR (300 MHz, $CDCl_3$): δ 7.14 (m, 4 H), 4.35 (d, 2 H), 3.53 (t, J=4.8 Hz, 4 H), 3.45 (m, 2 H), 3.18 (s, 2 H), 2.18 (t, J=4.5 Hz, 4 H), 1.26 (m, 13 H). FAB-MS: calcd for ($C_{23}H_{31}N_2FO_2$) 386, found 387 (M+H). Anal. Calcd for $C_{23}H_{31}N_2O_2F$: C, 76.84; H, 8.69; N, 3.90. Found: C, 76.67; H, 8.76; N, 3.77. mp 139–140° C. $R_f$=0.3 (20% ethyl acetate/hexane).

EXAMPLE 98

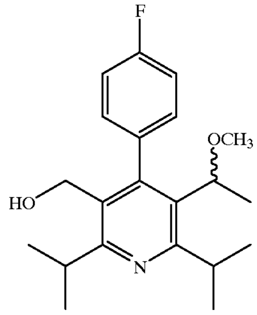

(±)-2,6-Diisopropyl-3-hydroxymethyl-4-(4-fluorophenyl)-5-(1-methoxyethyl)pyridine Step A: Methyl-2,6-diisopropyl-4-(4fluorophenyl)-5-(2-methoxyethyl)-3-pyridinecarboxylate (±)-Ethyl-2,6-diisopropyl-(4-fluorophenyl)-5-(1-hydroxyethyl)-3-pyridinecarboxylate (Example 93, Step A) ( 487 mg, 1.36 mmol) was dissolved in 50 mL of dry THF, treated with NaH (0.20 g, 8.13 mmol) under argon, stirred for 15 min. and treated with methyl iodide (0.34 mL, 5.24 mmol). The reaction mixture was stirred at reflux for 2 hours, then cooled to room temperature, quenched with water, and concentrated to afford a watery residue. The product was partitioned between diethyl ether and water, the organic layer was dried with $MgSO_4$, filtered, and concentrated to afford a white solid. The product was passed through a pad of silica (5% ethyl acetate/hexane) to yield a white solid (495 mg, 1.33 mmol, 98%). $^1$H NMR (300 MHz, $CDCl_3$): δ 7.13 (m, 4 H), 4.25 (q, J=6.6 Hz, 1 H), 3.80 (septet, J=6.6 Hz, 1 H), 3.48 (s, 3 H), 3.10 (s, 3 H), 2.97 (septet, J=6.6 Hz, 1 H), 1.41 (d, J=6.6 Hz, 3 H), 1.29 (m, 12 H). FAB-MS: calcd for ($C_{22}H_{31}FNO_3$) 373, found 374 (M+H). Anal. Calcd for $C_{24}H_{31}N_2O_3F$: C, 70.75; H, 7.56; N, 3.75; F, 5.09. Found: C, 70.70; H, 7.63; N, 3.59; F, 4.77. mp 132–134° C. $R_f$=0.5 (10% ethyl acetate/hexane).

Step B: (±)-2,6-Diisopropyl-3-hydroxymethyl-4-(4-fluorophenyl)-5-(1-methoxyethyl)pyridine The intermediate obtained in Step A (359 mg, 0.961 mmol) was dissolved in 40 mL of dry THF, for a dropwise addition of a solution of LAH (1M/THF, 1.92 mL, 2 eq.). The reaction mixture was stirred at reflux for 24 hours then cooled to room temperature and quenched with water (80 μL), 20% NaOH (80 μL), and water (160 μL). After filtration, the solvent was evaporated to afford a residue which was filtered through to a pad of silica (10% ethyl acetate/hexane) to afford the title compound as a white solid (281 mg, 0.72 mmol, 85%). $^1$H NMR (300 MHz, $CDCl_3$): δ 7.13 (m, 4 H), 4.32 (dq, J=5.2 J=11.4 Hz, 1 H), 4.11 (q, J=6.3 Hz, 1 H), 3.77 (septet, J=6.6 Hz, 1 H), 3.42 (septet, J=6.6 Hz, 1 H), 3.10 (s, 3 H), 1.29 (m, 16 H). FAB-MS: calcd for ($C_{21}H_{28}FNO_2$) 345, found 346 (M+H). Anal. Calcd for $C_{21}H_{28}NO_2F$: C, 76.84; H, 8.69; N, 3.90. Found: C, 76.67; H, 8.76; N, 3.77. mp 151–153° C. $R_f$=0.4 (20% ethyl acetate/hexane).

EXAMPLE 99

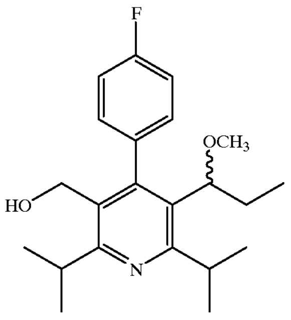

(±)-2,6-Diisopropyl-3-hydroxymethyl-4-(4-fluorophenyl)-5-(1-methoxy-5-propyl)pyridine The title compound was prepared from (±)-2,6-diisopropyl-3-hydroxymethyl-4-(4fluorophenyl)-5(1-hydroxypropyl)pyridine (Example 94) according to the procedures described in Example 98. $^1$H NMR (300 MHz, $CDCl_3$): δ 7.11 (m, 4 H), 4.32 (m, 2 H), 3.83 (m, 1 H), 3.74 (septet, J=6.6 Hz, 1 H), 3.41 (septet, J=6.6 Hz, 1 H), 3.12 (s, 2 H), 1.88 (m, 1 H), 1.56 (m, 2 H), 1.27 (m, 12 H), 0.776 (t, J=3.7 Hz, 3 H). FAB-MS: calcd for ($C_{22}H_{30}NFO_2$) 359, found 360 (M+H). Anal. Calcd for $C_{22}H_3ONO_2F$: C, 73.51; H, 8.41; N, 3.90; F, 5.28. Found: C, 73.55; H, 8.54; N, 3.75; F, 5.06. mp 147–149° C. $R_f$=0.5 (20% ethyl acetate/hexane).

EXAMPLE 100

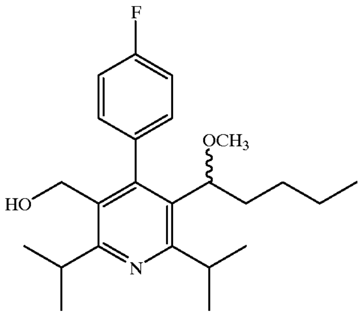

(±)-2,6-Diisopropyl-3-hydroxymethyl-4-(4-fluorophenyl)-5-(1-methoxy-pentyl)pyridine The title compound was prepared from (±)-2,6-diisopropyl-3-hydroxymethyl-4-(4-fluorophenyl)-5-(1-hydroxypentyl)pyridine (Example 95) according to the procedures described in Example 98. $^1$H NMR (300 MHz, $CDCl_3$): δ 7.10 (m, 4 H), 4.32 (m, 2 H), 3.92 (m, 1 H), 3.76 (septet, J=7.0 Hz, 1 H), 3.42 (septet, J=6.6 Hz, 1 H), 3.12 (s, 3 H), 1.87 (m, 1 H), 1.52 (m, 2 H), 1.19 (m, 16 H), 0.821 (t, J=7.4 Hz, 3 H). FAB-MS: calcd for ($C_{24}H_{34}NFO_2$) 387, found 388 (M+H). Anal. Calcd for $C_{24}H_{34}NO_2F$: C, 74.38; H, 8.84; N, 3.61; F, 4.90. Found: C, 74.38; H, 8.82; N, 3.45; F, 4.90. mp 121–123° C. $R_f$=0.5 (20% ethyl acetate/hexane).

EXAMPLE 101

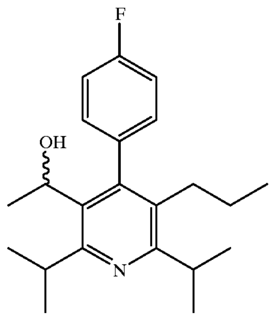

(±)-2,6-Diisopropyl-3-(1-hydroxyethyl)-4-(4-fluorophenyl)-5-propyl-pyridine

Step A: (±)-2,6-Diisopropyl-4(4-fluorophenyl-5-propyl-3pyridine-carboxaldehyde

To a solution of 2,6-diisopropyl-3-hydroxymethyl-4(4-fluorophenyl)-5-propylpyridine (Example 25) (5.7 g, 17 mmol) in dichloromethane (250 mL) was added Brockman I, neutral alumina (3.5 g, 34 mmol). The suspension was stirred at room temperature and treated with pyridinium chlorochromate (PCC) (7.5 g, 34 mmol). Stirring was continued at room temperature for 1 hr. The suspension was poured into 10% ethyl acetate/hexane (500 mL), filtered through a pad of silica and concentrated in vacuo to afford (4.2 g/12.8 mmol, 74%) as a waxy solid. $^1$H NMR ($CDCl_3$, 300 MHz): δ 9.72 (s, 1 H), 7.15 (m, 4 H), 3.83 (sept, J=6.6 Hz, 1 H), 3.28 (sept, J=6.6 Hz, 1 H), 2.31 (m, 2 H), 1.30 (m, 14 H), 0.78 (t, J=7.4 Hz, 3 H). FAB-MS: calcd for ($C_{21}H_{26}FNO$) 327, found 328 (M+H). mp 81–83° C. $R_f$=0.6 (10% ethyl acetate/hexane).

Step B: (±)-2,6-Diisopropyl-3-(1-hydroxyethyl)-4(4-fluorophenyl)-5-propylpyridine The intermediate obtained in Step A (400 mg, 1.22 mmol) in THF (10 mL) at −78° C. under argon atmosphere was added dropwise MeLi (1.4M, 1.2 eq, 1.05 mL). The reaction was stirred for 20 min, then another 0.5 eq. of MeLi was added, as starting material was still present. After 20 min., the reaction was quenched with water (2 mL) and the THF is evaporated in vacuo to afford an oil. The product was partitioned between water and $CH_2Cl_2$ (50 mL) and the organic layer was dried with $MgSO_4$, filtered, and concentrated to yield a gummy solid. Flash Chromatography using silica gel (60% $CH_2Cl_2$/hexane) to afford an oil which slowly solidified to give the title compound as a solid (0.387 g/1.13 mmol, 92%). $^1$H NMR (300 MHz, $CDCl_3$): δ 7.10 (m, 4 H), 4.66 (dq, J=3.3, 6.6 Hz, 1 H), 3.75 (septet, J =6.6 Hz, 1 H), 3.20 (septet, J=6.6 Hz, 1 H), 2.17 (t, J=1.5 Hz, 2 H), 1.58 (d, J=5.2 Hz, 1 H), 1.41 (d, J=6.6 Hz, 3 H), 1.29 (m, 14 H), 0.74 (t, J=7.4 Hz, 3 H). FAB-MS: calcd for ($C_{22}H_{30}FNO$) 343, found 344 (M+H). Anal. Calcd for $C_{22}H_{30}FNO$: C, 76.93; H, 8.80; N, 4.08; F, 5.53. Found: C, 76.98; H, 8.73; N, 3.93; F, 5.80. mp 124.5–126.5° C. $R_f$=0.2 (60% $CH_2Cl_2$/hexane).

EXAMPLE 102

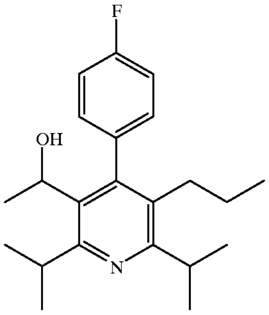

(+)-2,6-Diisopropyl-3-(1-hydroxyethyl)-4-(4-fluorophenyl)-5-propyl-pyridine

The enantiomeric mixture of (±)-2,6-diisopropyl-3-(1-hydroxyethyl)-4-(4-fluorophenyl)-5-propylpyridine (Example 101) was separated by chiral HPLC with a Chiralpak AD column, isocratic elution (99% hexane/methyl t-butyl ether). The first enantiomer to elute was obtained in 99% ee, mp 103–104° C., $[a]_D{}^{+}40.4°$.

EXAMPLE 103

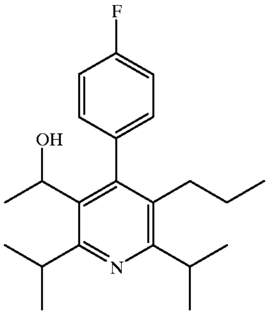

2,6-Diisopropyl-3-(1-hydroxyethyl-4-(4-propyl-pyridine

The enantiomeric mixture of (±)-2,6-diisopropyl-3-(1-hydroxyethyl)-4-(4-fluorophenyl)-5-propyl-pyridine (Example 101) was separated by chiral HPLC with a Chiralpak AD column, isocratic elution (99% hexane/methyl t-butyl ether). The second enantiomer to elute was obtained in 90% ee. mp 95–97° C.

EXAMPLE 104

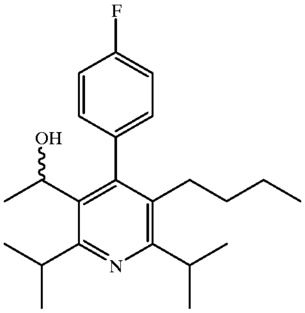

(±)-2,6-Diisopropyl-3-(1-hydroxyethyl)-4-(4-fluorophenyl)-5-butyl-pyridine

The title compound was prepared from 2,6-diisopropyl-3-hydroxymethyl-4-(4-fluorophenyl)-5butylpyridine (Example 24) according to the procedures described in Example 101. $^1$H NMR (300 MHz, $CDCl_3$): δ 7.1 (m, 4 H), 4.7 (dq, J=3 Hz, 1 H), 3.7 (septet, J=7 Hz, 1 H), 3.2 (septet, J=7 Hz, 1 H), 2.2 (t, J=1.5 Hz, 2 H), 1.6 (d, J=5 Hz, 1 H), 1.4 (d, J=7 Hz, 3 H), 1.3 (m, 16 H), 0.8 (t, J=7Hz, 3H). FAB-MS: calcd for ($C_{23}H_{32}FNO$) 357, found 358 (M+H). mp 103–104° C. $R_f$=0.2 (60% $CH_2Cl_2$/hexane).

EXAMPLE 105

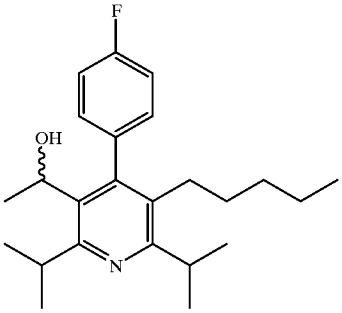

(±)-2,6-Diisopropyl-3-(1-hydroxyethyl)-4-(4-fluorophenyl)-5-pentyl-pyridine

The title compound was prepared from 2,6-diisopropyl-3-hydroxymethyl-4-(4fluorophenyl)-5-pentylpyridine (Example 1) according to the procedures described in Example 101. $^1$H NMR (300 MHz, $CDCl_3$): δ 7.10 (m, 4 H), 4.65 (dq, J=2.8, 6.6 Hz, 1 H), 3.75 (septet, J=6.6 Hz, 1 H), 3.20 (septet, J=6.6 Hz, 1 H), 2.19 (t, J =8.1 Hz, 2 H), 1.63 (d, J=2.6 Hz, 1 H), 1.40 (d, J=7.0 Hz, 3 H), 1.31 (m, 14 H), 1.11 (m, 4 H), 0.79 (t, J=6.6 Hz, 3 H). FAB-MS: calcd for ($C_{24}H_{34}FNO$) 371, found 372 (M+H). Anal. Calcd for $C_{24}H_{34}FNO$: C, 77.59; H, 9.22; N, 3.77; F, 5.11. Found: C, 77.59; H, 9.34; N, 3.75; F, 5.26. mp 99–101° C. $R_f$=0.2 (70% $CH_2Cl_2$/hexane).

EXAMPLE 106

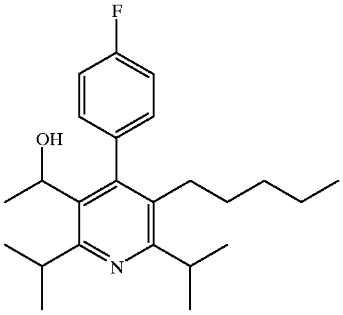

2,6-Diisopropyl-3-(1-hydroxyethyl)-4-(4-fluorophenyl)-5-pentylpyridine

The enantiomeric mixture of (±)-2,6-diisopropyl-3-(1-hydroxyethyl)-4-(4-fluorophenyl-5-pentylpyridine (Example 105) was separated by chiral HPLC with a Chiralpak AD column, isocratic elution (99% hexane/methyl t-butyl ether). The first enantiomer to elute was obtained in 99% ee. mp 83° C.

EXAMPLE 107

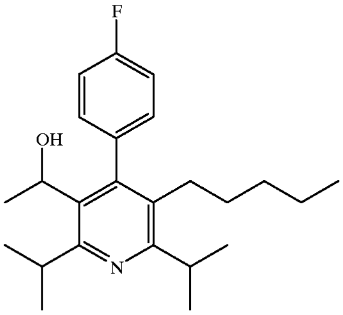

2,6-Diisopropyl-3-(1-hydroxyethyl-4-fluorophenyl)-5-pentylpyridine

The enantiomeric mixture of (±)-2,6-diisopropyl-3-(1-hydroxyethyl)-4-(4-fluorophenyl)-5-pentylpyridine (Example 105) was separated by chiral HPLC with a Chiralpak AD column, isocratic elution (99% hexanemethyl t-butyl ether). The second enantiomer to elute was obtained in 93% ee. mp 84–86° C.

EXAMPLE 108

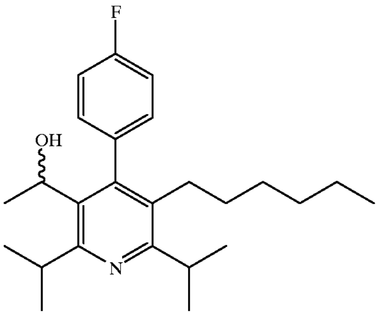

(±)-2,6-Diisopropyl-3-(1-hydroxyethyl)-4-(4-fluorophenyl)-5-hexylpyridine

The title compound was prepared from 2,6-diisopropyl-3-hydroxymethyl-4-(4-fluorophenyl)-5-hexylpyridine (Example 23) according to the procedures described in Example 101. $^{1}$H NMR (300 MHz, $CDCl_3$): δ 7.13 (m, 3 H), 7.04 (m, 1 H), 4.65 (m, 1 H), 3.73 (sept, J=6.6 Hz, 1 H), 3.19 (sept, J=6.6 Hz, 1 H), 2.18 (m, 2 H), 1.39 (d, J=6.6 Hz, 3 H), 1.30 (m, 13 H), 1.18 (m, 4 H), 1.09 (m, 4 H), 0.81 (t, J=7 Hz, 3 H). FAB-MS: calcd for ($C_{25}H_{36}FNO$) 385, found 386 (M+H). Anal. Calcd for $C_{25}H_{36}FNO$: C, 77.88; H, 9.41; N, 3.63. Found: C, 77.84; H, 9.49; N, 3.65. mp 96–99° C. $R_f$=0.3 (10% ethyl acetate/hexane).

EXAMPLE 109

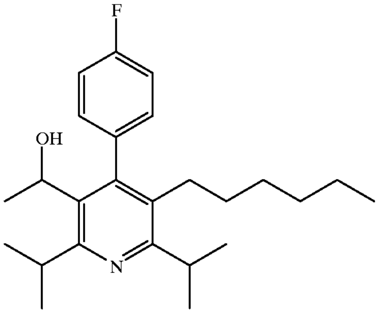

2,6-Diisopropyl-3-(1-hydroxyethyl)-4-(4-fluorophenyl)-5-hexylpyridine

The enantiomeric mixture of (±)-2,6-diisopropyl-3-(1-hydroxyethyl)-4-(4-fluorophenyl)-5-hexylpyridine (Example 108) was separated by chiral HPLC with a Chiralpak AD column, isocratic elution (99% hexane/methyl t-butyl ether). The first enantiomer to elute was obtained in 98% ee. mp 75–77° C.

EXAMPLE 110

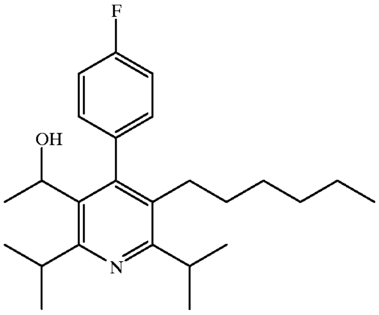

2,6-Diisopropyl-3-(1-hydroxyethyl)-4-(4-fluorophenyl)-5-hexylpyridine

The enantiomeric mixture of (±)-2,6-diisopropyl-3-(1-hydroxyethyl)-4-(4-fluorophenyl)-5-hexylpyridine (Example 108) was separated by chiral HPLC with a Chiralpak AD column, isocratic elution (99% hexane/methyl t-butyl ether). The second enantiomer to elute was obtained in 88% ee. mp 66–68° C.

EXAMPLE 111

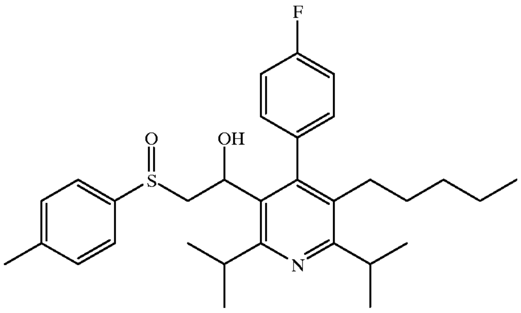

2,6-Diisopropyl-3-[1-hydroxy-2-((S)-toluylsulfoxy)ethyl]-4-(4-fluoro-phenyl)-5-pentylpyridine A solution of lithium diisopropylamide was prepared by the addition of n-butyllithium (3.5 mL, 2 eq., 1.6M/hexane) to a solution of diisopropylamine (0.73 mL, 5.57 mmol) in anhydrous tetrahydrofuran (50 mL) at 0° C. To this was added a solution of (S)-(−)-methyl p-tolylsulfoxide (0.863 g, 5.60 mmol) in anhydrous tetrahydrofuran (10 mL) dropwise, with stirring. The mixture was stirred at 0° C. for 2 hr, then treated with a solution of 2,6-diisopropyl-4-(4-fluorophenyl)-5-pentyl-3-pyridinecarboxaldehyde (Example 114, Step A) (1.0 g, 2.80 mmol) in anhydrous tetrahydrofuran (20 mL) dropwise and with stirring. After stirring 15 min at 0° C., the reaction mixture was quenched by the addition of sat. $NH_4Cl$ (1 mL). The solvent was removed in vacuo and the residue partitioned between $CHCl_3$ (150 mL) and water (50 mL). The organic phase was washed with sat. $NaHCO_3$ (100 mL), water (100 mL) and brine (50 mL), dried over $MgSO_4$ and concentrated. The crude product consisted of a 1.2:1 ratio of diastereomers. Flash chromatography (step gradient 5%–10%–20% ethyl acetate/hexane) afforded 740 mg (52%) of the first diastereomer to elute. $^1H$ NMR ($CDCl_3$, 500 MHz): δ 7.4 (m, 4 H), 7.0 (m, 2 H), 6.7 (m, 2 H), 5.1 (m, 1 H), 4.6 (s, 1 H), 3.8 (m, 2 H), 2.6 (sept, J=6.6 Hz, 1 H), 2.5 (s, 3 H), 2.3 (m, 1 H), 2.1 (m, 2 H), 1.4 (m, 18 H), 0.8 (m, 3 H). FAB-MS: calcd for ($C_{31}H_{40}FNO_2S$) 509, found 510 (M+H). Anal. calcd for $C_{31}H_{40}FNO_2S$: C, 73.05; H, 7.91; N, 2.75; S, 6.29. Found: C, 72.88; H, 7.95; N, 2.50; S, 6.38. mp 170–171° C. $R_f$=0.3 (20% ethyl acetate/hexane).

EXAMPLE 112

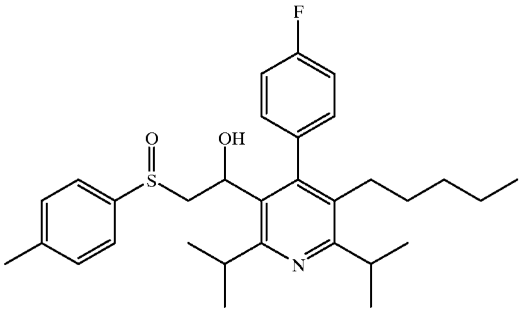

2,6-Diisopropyl-3-[1-hydroxy-2-(S)-toluylsuffoxyethyl]-4-(4-fluoro-phenyl)-5-pentylpyridine From the flash chromatography described in Example 111, the second diastereomer to elute afforded 600 mg (42%) of the title compound. $^1H$ NMR ($CDCl_3$, 500 MHz): δ 7.4 (m, 2 H), 7.2 (m, 2 H), 7.0 (m, 3 H), 6.8 (m, 1 H), 4.8 (m, 1 H), 3.8 (m, 1 H), 3.7 (m, 1 H), 3.2 (sept, J=6.6 Hz, 1 H), 3.1 (s, 1 H), 2.7 (m, 1 H), 2.4 (s, 3 H), 2.1 (m, 2 H), 1.3 (m, 18 H), 0.6 (m, 3 H). FAB-MS: calcd for ($C_{31}H_{40}FNO_2S$) 509, found 510 (M+H). Anal. calcd for $C_{31}H_{40}FNO_2S$: C, 73.05; H, 7.91; N, 2.75; S, 6.29. Found: C, 72.90; H, 7.95; N, 2.50; S, 6.54. mp 190° C. $R_f$=0.1 (20% ethyl acetate/hexane).

EXAMPLE 113

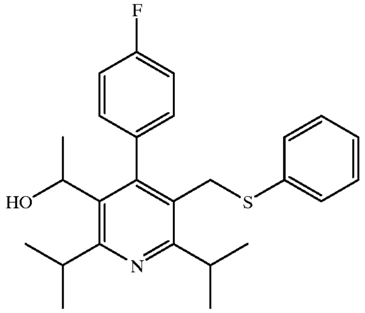

(±)-2,6-Diisopropyl-3-(1-hydroxyethyl)-4-(4-fluorophenyl)-5-phenylthio-methylpyridine The title compound was prepared from 2,6-diisopropyl-3-(1-hydroxymethyl)-4-(4-fluorophenyl)-[(phenylthio)methyl]pyridine (Example 47) according to the procedures described in Example 101. $^1H$ NMR (300 MHz, $CDCl_3$): δ 7.19 (m, 4 H), 7.09 (m, 5 H), 4.67 (m, 1 H), 3.74 (m, 3 H), 3.38 (sept, J=6.6 Hz, 1 H), 1.58 (d, J=4 Hz, 1 H), 1.41 (d, J=6.6 Hz, 3 H), 1.31 (m, 12 H). FAB-MS: calcd for ($C_{26}H_{30}FNOS$) 423, found 424 (M+H). Anal. Calcd for $C_{26}H_{30}FNOS$: C, 73.72; H, 7.14; N, 3.31; S, 7.57. Found: C, 73.52; H, 7.12; N, 3.20; S, 7.51. mp 125–128° C. $R_f$=0.5 (20% ethyl acetate/hexane).

EXAMPLE 114

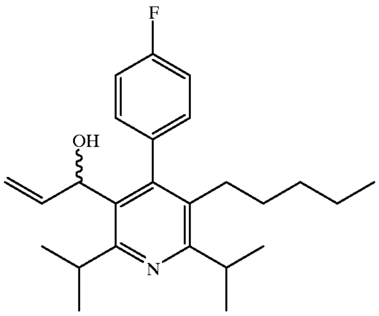

(±)-2,6-Diisopropyl-3-(1-hydroxy-2-propenyl)-4-(4-fluorophenyl)-5-pentylpyridine Step A: 2,6-Diisopropyl-4-(4-fluorophenyl)-5-pentyl-3-pyridine-carboxaldehyde 2,6-Diisopropyl-3-hydroxymethyl-4-(4-fluorophenyl)-5-pentylpyridine (Example 1) (2.30 g, 6.43 mmol) was dissolved in 175 mL of $CH_2Cl_2$ under argon atmosphere and treated with 2 eq. of alumina (neutral, 1.31 g, 12.87 mmol) followed by 2 eq of pyridinium chlorochromate (PCC) (2.77 g, 12.87 mmol). The reaction was stirred at room temperature for 1.5 h. The suspension was added to 500 mL of 1:1 hexane/diethyl ether, then filtered through a pad of silica (300 g). The pad was washed with 100 mL diethyl ether and the filtrate was combined and concentrated in vacuo to afford a solid. Flash chromatography (60:40, $CH_2Cl_2$/hexane) using silica afforded 1.84 g of an off-white solid (5.2 mmol, 80%). $^1$H NMR (300 MHz, $CDCl_3$): δ 9.74 (s, 1 H), 7.17 (m, 4 H), 3.85 (septet, J=6.6 Hz, 1 H), 3.30 (septet, J=6.6 Hz, 1 H), 2.34 (t, J=5.2 Hz, 2 H), 1.30 (m, 14 H), 1.15 (m, 4 H), 0.80 (t, J=6.6 Hz, 3 H). FAB-MS: calcd for ($C_{23}H_{30}FNO$) 355, found 356. Anal. Calcd for $C_{23}H_{30}FNO$: C, 77.71; H, 8.51; N, 3.94; F, 5.34 Found: C, 77.91; H, 8.47; N, 3.83; F, 5.42. mp 75.5–77.5° C. $R_f$=0.4 (50% $CH_2Cl_2$/hexane).

Step B: (±)-2,6-Diisopropyl-3-(1-hydroxy-2-propenyl)-4-(4-fluorophenyl)-5-pentylpyridine To a solution of the intermediate obtained in Step A (100 mg, 0.281 mmol) in THF (10 mL) at −78° C. under argon was added vinyl magnesium bromide (1M, 1.5 eq., 0.42 mL) dropwise. After 1 h., a saturated solution of $NH_4Cl$ (2 mL) was added and the aqueous phase was extracted with diethyl ether. A precipitate formed when the $NH_4Cl$ was added and was filtered off. The ether layer was dried with $MgSO_4$, filtered and concentrated to yield a gummy oil. Flash chromatography (60% $CH_2Cl_2$/hexane) afforded the title compound as a solid (38 mg, 0.1 mmol, 35%). $^1$H NMR (300 MHz, $CDCl_3$): δ 7.11 (m, 4 H), 6.06 (δ, J=17.4 Hz, J=10.3Hz, J =4.0 Hz, 1 H), 5.08 (q, J=1.5 Hz, 1 H), 5.00 (m, 2 H), 3.51 (septet, J=6.6 Hz, 1 H), 3.21 (septet, J=6.6 Hz, 1 H), 2.21 (t, J=4.4 Hz, 2 H), 1.74 (d, J=4.1 Hz, 1 H), 1.27 (m, 14 H), 1.11 (m, 4 H), 0.783 (t, J=6.6 Hz, 3 H). FAB-MS: calcd for ($C_{25}H_{34}FNO$) 383, found 384 (M+H). Anal. Calcd for $C_{25}H_{34}NOF$: C, 78.29; H, 8.93; N, 3.65; F, 4.95. Found: C, 78.28; H, 8.97; N, 3.53; F, 5.04. mp 83–85° C. $R_f$=0.2 (50% $CH_2Cl_2$/hexane).

EXAMPLE 115

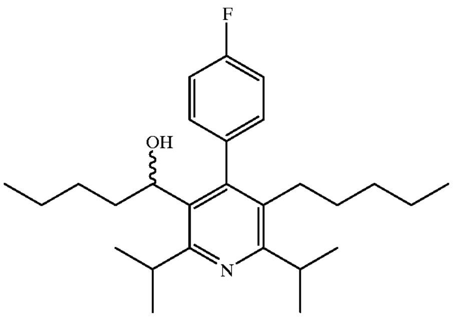

(±)-2,6-Diisopropyl-3-(1-hydroxypentyl)-4-(4-fluorophenyl)-5pentyl-pyridine

The title compound was prepared from 2,6-diisopropyl-3-hydroxymethyl-4-(4-fluorophenyl)-5-pentylpyridine (Example 1) and butyllithium according to the procedures described in Example 114. $^1$H NMR (300 MHz, $CDCl_3$): δ 6.95 (m, 4 H), 4.33 (m, 1 H), 3.59 (septet, J=6.6 Hz, 1 H), 3.09 (septet, J=6.6 Hz, 1 H), 2.08 (t, J=5.2 Hz, 2 H), 1.75 (m, 2 H), 1.47 (m, 2 H), 1.04 (m, 22 H), 0.719 (t, J=7.0 Hz, 3 H), 0.674 (t, J=7.0 Hz, 3 H). FAB-MS: calcd for ($C_{27}H_{40}FNO$) 413, found 414 (M+H). Anal. Calcd for $C_{27}H_{40}FNO$: C, 78.41; H, 9.75; N, 3.39; F, 4.59. Found: C, 77.84; H, 9.51; N, 3.27; F. 5.08. mp 66–68° C. $R_f$=0.2 (50% $CH_2Cl_2$/hexane).

EXAMPLE 116

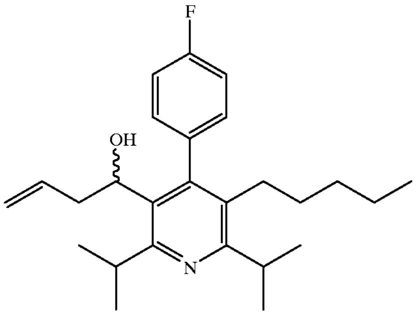

(±)-2,6-Diisopropyl-3-(1-hydroxy-2-butenyl)-4-(4-fluorophenyl)-5-pentylpyridine

The title compound was prepared from 2,6-diisopropyl-3-hydroxymethyl-4-(4-fluorophenyl)-5-pentylpyridine (Example 1) and allylmagnesium bromide according to the procedures described in Example 114. $^1$H NMR (300 MHz, $CDCl_3$): δ 7.09 (m, 4 H), 6.58 (m, 1 H), 5.06 (s, 1 H), 5.01 (m, 1 H), 4.47 (m, 1 H), 3.71 (septet, J=6.6 Hz, 1 H), 3.20 (septet, J=6.6 Hz, 1 H), 2.59 (m, 1 H), 2.35 (m, 1 H), 2.18 (t, J=4.8 Hz, 2 H), 1.72 (d, J=2.9 Hz, 1 H), 1.28 (m, 14 H), 1.11 (m, 4 H), 0.783 (t, J=6.6 Hz, 3 H). FAB-MS: calcd for ($C_{26}H_{36}FNO$) 397, found 398 (M+H). Anal. Calcd for $C_{26}H_{36}FNO$: C, 77.88; H, 9.41; N, 3.63; F, 4.93. Found: C, 78.10; H, 9.21; N, 3.43; F, 4.89. mp 70–72° C. $R_f$=0.2 (50% $CH_2Cl_2$/hexane).

EXAMPLE 117

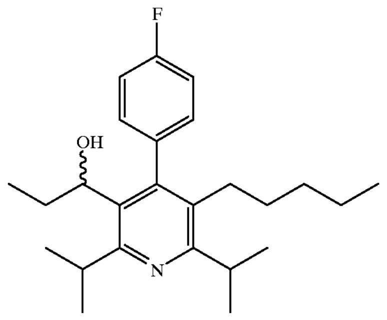

(±)-2,6-Diisopropyl-3-(1-hydroxy-2-propyl)-4-(4-fluorophenyl)-5-pentylpyridine

The title compound was prepared from 2,6-diisopropyl-3-hydroxymethyl-(4-fluorophenyl)-5-pentylpyridine (Example 1) and ethylmagnesium chloride according to the procedures described in Example 114. $^1H$ NMR (300 MHz, $CDCl_3$): δ 7.10 (m, 4 H), 4.35 (dq, J=3.7, 8.8 Hz, 1 H), 3.68 (septet, J=6.3 Hz, 1 H), 3.20 (septet, J=6.6 Hz, 1 H), 2.18 (t, J=5.2 Hz, 2 H), 1.86 (septet, J=5.5 Hz, 1 H), 1.63 (m, 2 H), 1.28 (m, 14 H), 1.09 (m, 4 H), 0.789 (m, 6 H). FAB-MS: calcd for ($C_{25}H_{36}FNO$) 385, found 386 (M+H). Anal. Calcd for $C_{25}H_{36}FNO$: C, 77.88; H, 9.41; N, 3.63; F, 4.93. Found: C, 77.44; H, 9.37; N, 3.35; F, 4.87. mp 77–79° C. $R_f$=0.2 (50% $CH_2Cl_2$/hexanes).

EXAMPLE 118

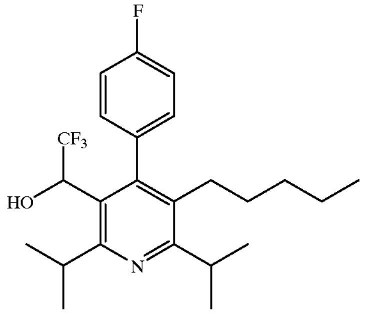

(±)-2,6-Diisopropyl-3-(2,2,2-trifluoro-1-hydroxy) ethyl-4-(4-fluoro-phenyl)-5-pentylpyridine A stirred solution of 2,6-diisopropyl-4-(4-fluorophenyl)-5-pentyl-3-pyridinecarboxaldehyde (Example 114, Step A) (190 mg, 0.53 mmol) in anhydrous THF (5 mL), under argon at 22° C., was treated with trimethyl(trifluoromethyl)silane (5.3 mL, 2.65 mmol, 0.5M in THF) followed by tetrabutylammonium fluoride (100 uL, 1.0M in THF). After stirring at 22° C. for 5 min, tetrabutylammonium fluoride (3 mL, 3 mmol, 1.0M in THF) was added and the reaction mixture stirred for 17 hr. The solvent was removed in vacuo, the residue dissolved in diethyl ether (50 mL), washed with 1N HCl (50 mL), saturated $NaHCO_3$ (50 mL), water (50 mL), brine (20 mL), dried ($MgSO_4$) and concentrated. Purification by flash silica gel chromatography (2% ethyl acetate/hexane) afforded 153 mg (68%) of the title compound as a white solid. $^1H$ NMR (300 MHz, $CDCl_3$): δ 7.11 (m, 4 H), 4.90 (bs, 1 H), 3.64 (bs, 1 H), 3.21 (sept, J=6.6 Hz, 1 H), 2.35

(m, 1 H), 2.15 (m, 2 H), 1.30 (d, J=6.6 Hz, 6 H, 1.29 (d, J=6.6 Hz, 6 H), 1.26 (m, 2 H), 1.10 (m, 4 H), 0.77 (t, J=6.6 Hz, 3 H). FAB-MS: calcd for ($C_{24}H_{31}F_4NO$) 425, found 426 (M+H). Anal. Calcd for $C_{24}H_{31}F_4NO$: C, 67.75; H, 7.34; N, 3.29; F, 17.86. Found: C, 67.82; H, 7.13; N, 3.02; F, 18.05. mp 88–89° C. $R_f$=0.35 (10% ethyl acetate/hexane).

EXAMPLE 119

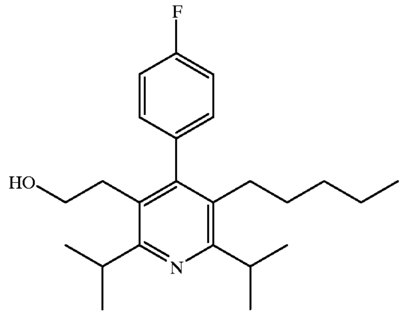

2,6-Diisopropyl-3-(2-hydroxyethyl)-4-(4fluorophenyl)-5-pentylpyridine

Step A: 2,6-Diisopropyl-3-(2-oxoethyl)-4-(4-fluorophenyl)-5-pentylpyridine

A solution of (methoxymethyl)triphenylphosphonium chloride (350 mg, 0.985 mmol) in THF (30 mL) was treated with butyllithium (1.6M, 1.2 eq., 0.74 mL) at −78° C. The reaction was stirred at 0° C. for 1 h. and then cooled to −78° C. again. 2,6-Diisopropyl-4-(4-fluorophenyl)-5-pentyl-3-pyridinecarboxaldehyde (Example 114, Step A) (350 mg, 0.985 mol) in THF (5 mL) was added dropwise and the reaction mixture allowed to come to room temperature. After 24 h., the reaction was quenched with water and the THF evaporated in vacuo. The residue was partitioned between ether and water. The organic layer was dried with $MgSO_4$, filtered, and concentrated to yield an oil. Flash chromatography (10% $CH_2Cl_2$/hexanes) afforded an oil (172 mg).

The oil (172 mg) was taken up in THF (15 mL) and treated with 4 mL conc. HCl. The solution was stirred for 1.5 hours and then diluted with ether (150 mL). The reaction was washed with $NaHCO_3$ (2×50 mL) and dried with $MgSO_4$. Filtration and concentration yielded a solid (20 mg, 0.054 mmol, 6%). The product was taken directly to the next step without further purification.

Step B: 2,6-Diisopropyl-3-(2-hydroxyethyl)-4-(4-fluorophenyl)-5-pentylpyridine

To the intermediate obtained in Step A (20 mg, 0.054 mmol) in dry THF (10 mL) was added dropwise LAH (2 eq., 1M, 0.11 mL) under argon and the mixture was stirred at reflux for 1 h. The reaction was quenched with water (3.9 μL), 20% NaOH (3.9 μL), and water (7.8 μL) again. Concentration afforded a white solid. The product was subjected to a pad of silica gel ($CH_2Cl_2$) to afford the title compound as a white solid (14 mg, 0.038mmol, 70%). $^1H$ NMR (300 MHz, $CDCl_3$): δ 7.39 (m, 2 H), 7.12 (m, 2 H), 3.52 (t, J=5.5 Hz, 2 H), 3.23 (m, 2 H), 2.60 (t, J=2.9 Hz, 2 H), 2.20 (t, J=3.7 Hz, 2 H), 1.30 (m, 14 H), 1.11 (m, 4 H), 0.771 (t, J=6.3 Hz, 3 H). FAB-MS: calcd for ($C_{24}H_{34}FNO$) 371, found 372 (M+H). Anal. Calcd for $C_{24}H_{34}FNO$: C, 77.59; H, 9.22; N, 3.77. Found: C, 77.57; H, 9.44; N, 3.05. mp 81–83° C. $R_f$=0.6 (10% ether/hexane).

EXAMPLE 120

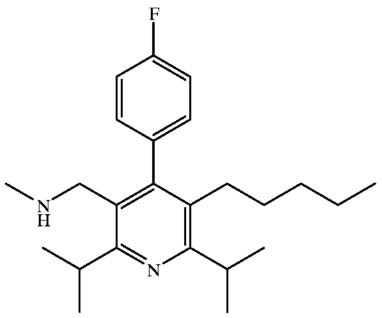

2,6-Diisopropyl-3-methylaminomethyl-4-(4-fluorophenyl)-5-pentyl-pyridine

Methylammonium chloride (37.99 mg, 0.563 mmol) was added to a stirred solution of methylamine in methanol (2M, 0.28 mL) under argon in an oven-dried round bottom flask equipped with a stir bar. Then sodium cyanoborohydride (4 eq., 10.60 mg, 0.169 mmol) was added and 2,6-diisopropyl-4-(4-fluorophenyl)-5-pentyl-3-pyridinecarboxaldehyde (Example 114, Step A) (100 mg, 0.281 mmol) was added as a solution in methanol (2 mL). The reaction was refluxed for 18 hours and then quenched with water. Concentration and addition of $CH_2Cl_2$ (25 mL) allowed washings with water (2×15 mL), brine (1×25 mL), following which the solution was dried with $MgSO_4$, filtered, and concentrated to afford a clear oil. Flash chromatography using silica gel (40% ether/$CH_2Cl_2$) yielded the title compound as a white solid (21 mg, 0.057 mmol, 20%). $^1$H NMR (300 MHz, $CDCl_3$): δ 7.13 (m, 4 H), 3.26 (m, 4 H), 2.24 (m, 5 H), 1.20 (m, 19 H), 0.783 (t, J=6.6 Hz, 3 H). FAB-MS: calcd for ($C_{24}H_{35}FN_2$) 370, found 371 (M+H). mp 77–79° C. $R_f$=0.2 (20% ether/$CH_2Cl_2$).

EXAMPLE 121

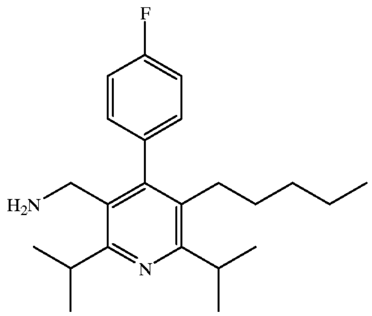

2,6-Diisopropyl-3-aminomethyl-4-(4fluorophenyl)-5-pentylpyridine

The title compound was prepared from 2,6-diisopropyl-4-(4-fluorophenyl)-5-pentyl-3-pyridinecarboxaldehyde (Example 114, Step A) and $NH_4OAc$, according to the procedures described in Example 120. $^1$H NMR (300 MHz, $CDCl_3$): δ 7.10 (m, 4 H), 2.61 (m, 4 H), 2.20 (t, J=5.5 Hz, 2 H), 1.17 (m, 20 H), 0.776 (t, J=6.6 Hz, 3 H). FAB-MS: calcd for ($C_{23}H_{33}FN_2$) 356, found 357 (M+H). Anal. Calcd for $C_{23}H_{33}N_2F$: C, 77.48; H, 9.33; N, 7.86; F, 5.33. Found: C, 77.42; H, 9.12; N, 7.64; F, 5.51. mp 47 . 49° C. $R_f$=0.6 (50% $CH_2Cl_2$/hexanes).

EXAMPLE 122

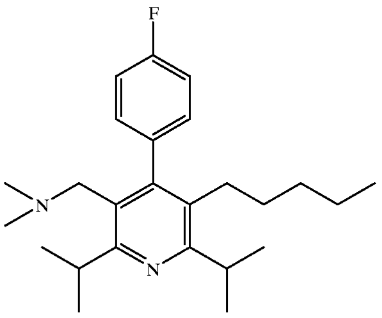

2,6-Diisopropyl-3-(dimethylamino)methyl-4-(4-fluorophenyl)-5-pentyl-pyridine

The title compound was prepared from 2,6-diisopropyl-4-(4-fluorophenyl)-5-pentyl-3-pyridinecarboxaldehyde (Example 114, Step A) and dimethylamine hydrochloride, according to the procedures described in Example 120. $^1$H NMR (300 MHz, $CDCl_3$): δ 7.09 (m, 4 H), 3.49 (septet, J=6.6 Hz, 1 H), 3.21 (septet, J=6.6 Hz, 1 H), 3.05 (s, 2 H), 2.22 (t, J=5.2 Hz, 2 H), 1.99 (s, 6 H), 1.18 (m, 18 H), 0.790 (t, J =6.3 Hz, 3 H). FAB-MS: calcd for ($C_{25}H_{37}FN_2$) 384, found 385 (M+H). Anal. Calcd for $C_{23}H_{37}FN_2$: C, 78.08; H, 9.70; N, 7.28; F, 4.94. Found: C, 77.95; H, 9.66; N, 7.12; F, 5.25. mp 69–71° C. $R_f$=0.4 (20% ether/$CH_2Cl_2$).

EXAMPLE 123

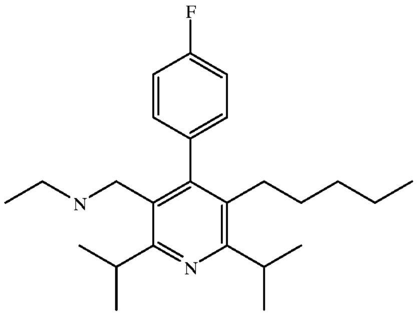

2,6-Diisopropyl-3-(ethylamino)methyl-4-(4-fluorophenyl)-5-pentylpyridine

The title compound was prepared from 2,6-diisopropyl-4-(4-fluorophenyl)-5-pentyl-3-pyridinecarboxaldehyde (Example 114, Step A) and ethylamine, according to the procedures described in Example 120. $^1$H NMR (300 MHz, $CDCl_3$): δ 7.06 (m, 4 H), 3.18 (m, 4 H), 2.32 (q, J=7.4 Hz, 2 H), 2.15 (t, J=5.2 Hz, 2 H), 1.13 (m, 18 H), 0.839 (t, J=7.4 Hz, 3 H), 0.698 (t, J=6.6 Hz, 3 H). FAB-MS: calcd for ($C_{25}H_{37}FN_2$) 384, found 385 (M+H). Anal. Calcd for $C_{23}H_{37}FN_2$: C, 78.08; H, 9.70; N, 7.28; F, 4.94. Found: C, 77.85; H, 9.50; N, 6.99; F, 4.79. mp 48–50° C. $R_f$=0.1 (20% ether/$CH_2Cl_2$).

EXAMPLE 124

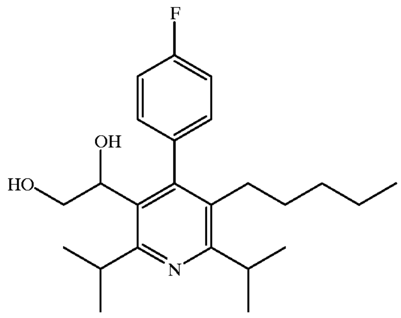

(±)-2,6-Diisopropyl-3-(1,2-dihydroxyethyl)-4-(4-fluorophenyl)-5-pentyl-pyridine

Step A: 2,6-Diisopropyl-3-ethenyl-4-(4-fluorophenyl)-5pentylpyridine

Methyl triphenylphosphonium bromide was suspended in 15 mL of dry THF under argon and stirred at −78° C. Butyllithium (1.6M, 0.42 mL) was added dropwise over 2 min. and then the reaction mixture was allowed to stir at 0° C. for 1.5 hours. The solution was cooled again to −78° C., treated dropwise with a solution of 2,6-diisopropyl-4-(4-fluorophenyl)-5-pentyl-3-pyridinecarboxaldehyde (Example 114, Step A) in 5 mL of dry THF, and then stirred at 0° C. for 2.5 hours. The reaction was quenched with water (10 mL) and the THF evaporated in vacuo. Diethyl ether was added and the mixture was washed with water (2×20 mL), brine (1×20 mL), and dried with $MgSO_4$. Filtration, concentration and flash chromatography (30% $CH_2Cl_2$/hexanes) yielded a solid (0.132 g, 0.37 mmol, 66%). $^1$H NMR (300 MHz, $CDCl_3$) δ 7.08 (m, J=1.1 Hz, 4 H), 6.34, 6.28 (d, J=11.4 Hz, J=11.4 Hz, 1 H), 5.19 (d, J=1.8 Hz, 1 H), 4.96 (d, J=1.8 Hz, 1 H), 3.39 (septet, J=6.6 Hz, 1 H), 3.24 (septet, J=6.6 Hz, 1 H), 2.30 (t, J=5.2 Hz, 2 H), 1.20 (m, J=2.2 Hz, 18 H), 0.979 (t, J=6.0 Hz, 3 H). FAB-MS: calcd for ($C_{24}H_{32}FN$) 353, found 354 (M+H). Anal. Calcd for $C_{24}H_{32}FN$: C, 81.54; H, 9.12; N, 3.96; F, 5.37. Found: C, 81.46; H, 9.06; N, 3.78; F, 5.59. mp 44–46° C. $R_f$=0.7 (30% $CH_2Cl_2$/hexanes).

Step B: (±)-2,6-Diisopropyl-3-(1,2-dihydroxyethyl)-4-(4-fluoro-phenyl)-5-pentylpyridine To an oven-dried round bottom flask equipped with a stir bar was added the intermediate obtained in Step A (150 mg, 0.424 mmol), in pyridine (10 mL) under argon. The solution was stirred and $OsO_4$ (0.129 g, 0.509 mmol) was added in one portion. The reaction turned black as stirring continued at room temperature. After 3 hours, the pyridine was evaporated in vacuo and the residue was dissolved in $CH_2Cl_2$ (10 mL) and sat. $NaHSO_3$ (10 mL). The resulting heterogenous solution was stirred very rapidly for 18 hours. The layers were separated and the aqueous layer was extracted several times with $CH_2Cl_2$. The combined organic layers were dried ($MgSO_4$), filtered, and concentrated to give a white solid. The product was subjected to a pad of silica (65/35; $CH_2Cl_2$/ether) to yield a white solid (70 mg, 0.18 mmol, 43%). $^1$H NMR (300 MHz, $CDCl_3$): δ 7.08 (m, 4 H), 4.57 (d, J=1.5 Hz, 1 H), 3.85 (m, 1H), 3.65 (septet, J=6.6 Hz, 1 H), 3.50 (m, 1 H), 3.20 (septet, J=6.6 Hz, 1 H), 2.19 (m, 2 H), 1.96 (m, 1 H), 1.24 (m, 14 H), 1.07 (m, 4 H), 0.780 (t, J=6.6 Hz, 3 H). FAB-MS: calcd for ($C_{24}H_{34}FNO$) 387, found 388 (M+H). Anal. Calcd for $C_{24}H_{34}FNO$: C, 74.38; H, 8.84; N, 3.61; F, 4.90. Found: C, 74.60; H, 9.03; N, 3.83; F, 5.04. mp 175–177° C. $R_f$=0.5 (65/35; $CH_2Cl_2$/ether).

EXAMPLE 125

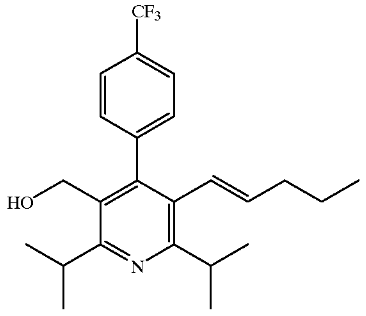

2,6-Diisopropyl-3-hydroxymethyl-4-[(4-trifluoromethyl)phenyl]-5(pent-1-enyl)pyridine Step A: Diethyl 1,4-dihydro-2,6-diisopropyl-[(4-trifluoro-methyl)phenyl]pyridine-3,5-dicarboxylate Following the procedure of Chucholowski (U.S. Pat. No. 4,950,675), to a solution of 18.0 g (0.11 mol) of ethyl isobutyrylacetate and 9.9 g (56.8 mmol) of 4-(trifluoromethyl)benzaldehyde in ethanol (25 mL) was added concentrated ammonium hydroxide (3.0 mL). This reaction mixture was heated at reflux for 12 hrs. After cooling to room temperature, the reaction mixture was concentrated under vacuum to yield a yellow oil. The crude product was taken directly to the next step without purification.

Step B: Diethyl 2,6diisopropyl-4-[(4-trifluoromethyl)phenyl]-pyridine-3,5-dicarboxylate Prepared from the intermediate obtained in Step A by the procedure described in Example 160, Step B. $^1$H NMR (300 MHz, $CDCl_3$): δ 0.92 (t, J=7.0 Hz, 6 H), 1.33 (d, J=6.6 Hz, 12 H), 3.14 (m, 4 H), 4.0 (q, J=7.0 Hz, 4 H), 7.42 (d, J=8.0 Hz, 2 H). mp 100–101° C.

Step C: Ethyl 2,6-diisopropyl-4-[(4-trifluoromethyl)phenyl]-5-hydroxymethylpyridine-3-carboxylate Prepared from the intermediate obtained in Step B by the procedure described in Example 1, Step D. $^1$H NMR (300 MHz, $CDCl_3$): δ 0.91 (t, J=7.0 Hz, 3 H), 1.32 (d, J=6.6 Hz, 6 H), 1.35 (d, J=6.6 Hz, 6 H), 3.08 (m, 1 H), 3.50 (m, 1 H), 3.96 (q, J=7.0 Hz, 2 H), 4.43 (d, J=4.0 Hz, 2 H), 7.44 (d, J=8.0 Hz, 2 H), 7.68 (d, J=8.0 Hz, 2 H). mp 102–103° C.

Step D: 5-Ethoxycarbonyl-2,6-diisopropyl-4-[(4-trifluoromethyl)-phenyl]pyridine-3-carboxaldehyde To a solution of the intermediate obtained in Step C (1.9 g, 4.6 mmol) in dichloromethane (50 mL) was added Celite (2.0 g). The suspension was stirred at room temperature and treated with pyridinium chlorochromate (PCC) (2.0 g, 9.3 mmol) in three portions. The suspension was stirred at room temperature for 1 hr, then poured into 1:1 diethyl ether/hexane (250 mL), filtered through a pad of silica, the pad washed with diethyl ether (250 mL) and the combined eluent concentrated to afford 1.7 g (93%) of the product as a viscous oil which slowly solidified. $^1$H NMR (300 MHz, $CDCl_3$): δ 0.94 (t, J=7.0 Hz, 31 ), 1.33 (d, J=6.6 Hz, 6 H), 1.34 (d, J=6.6 Hz, 6 H), 3.14 (m, 1 H), 3.88 (m, 1 H), 4.0 (q, J=7.0 Hz, 2 H), 7.42 (d, J=8.0 Hz, 2 H), 7.71 (d, J=8.0 Hz, 2 H), 9.86 (s, 1 H). mp 105–106° C.

Step E: Ethyl 2,6-diisopropyl-4-[(4-trifluoromethyl)phenyl]-5-(pent-1-enyl)pyridine-3-carboxylate Prepared from the intermediate obtained in Step D by the procedure described in Example 1, Step D. $^1$H NMR (300 MHz, $CDCl_3$): δ 0.69 (t, J=7.0 Hz, 3 H), 0.90 (t, J=7.0 Hz, 3 H), 1.09–1.34 (m, 14 H), 1.92 (δ, J=14.0, 7.0, 1.5 Hz, 2 H), 3.07 (m, 1 H), 3.38 (m, 1 H), 3.96 (q, J=7.0 Hz, 2 H), 5.29 (m, 1 H), 6.05 (m, 1 H), 7.31 (d, J=8.0 Hz, 2 H), 7.59 (d, J=8.0 Hz, 2 H). mp 70–72° C.

Step F: 2,6-Diisopropyl-3-hydroxymethyl-4[(4-trifluoromethyl)phenyl]-5-(pent-1-enyl)pyridine The intermediate obtained in Step E (0.91 g, 2.04 mmol) was dissolved in anhydrous THF (100 mL) under argon and treated dropwise at room temperature with lithium aluminum hydride (1.0M in THF, 10 mL, 10 mmol). The reaction mixture was stirred at reflux for 1 hr, cooled to room temperature and quenched by the sequential addition of $H_2O$, 20% aqueous NaOH and $H_2O$. The resulting suspension was filtered through a cake of Celite and the filtrate concentrated and purified by flash chromatography through silica (5% ethyl acetate/n-hexane) to afford 0.77 g (1.90 mmol, 93%) of the title compound as a white foam. $^1$H NMR (300 MHz, $CDCl_3$): δ 0.68 (t, J=7.0 Hz, 3 H), 1.05–1.40 (m, 14 H), 1.90 (δ, J=14. 7, 1.5 Hz, 21 H), 3.34 (m, 1 H), 3.45 (m, 1 H), 4.37 (d, J=5.5 Hz, 2 H), 5.26 (m, 1 H), 5.95 (m, 1 H), 7.30 (d, J=8.0 Hz, 2 H), 7.65 (d, J=8.0 Hz, 21 H). $R_f$=0.36 (10% ethyl acetate/n-hexane). mp 77–78° C.

EXAMPLE 126

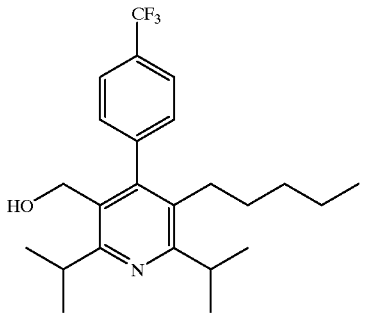

2,6-Diisopropyl-3-hydroxymethyl-4-[(4-trifluoromethyl)phenyl]-5-pentylpyridine

To 0.59 g (1.46 mmol) of the compound 2,6-diisopropyl-3-hydroxymethyl-4-[(4-trifluoromethyl)phenyl]-5-(pent-1-enyl)pyridine (Example 125) was dissolved in absolute ethanol (50 mL) and treated with 10% palladium on carbon (0.1 eq). The reaction flask was purged under aspirator vacuum and filled with hydrogen gas (3×). The reaction mixture was stirred under a hydrogen atmosphere for 6 hr. After purging the system with argon, the catalyst was removed by filtration through a pad of Celite. The solvent was removed by concentration under vacuum and the crude product was purified by flash chromatography (10% ethyl acetate/n-hexane) to yield 0.58 g (1.41 mmol, 97%) of the title compound as a white solid. $^1$H NMR (300 MHz, $CDCl_3$): δ 0.78 (t, J=7.0 Hz, 3 H), 1.12 (m, 4 H), 1.31 (m, 14 H), 2.26 (m, 2 H), 3.25 (m, 1 H), 3.42 (m, 1 H), 4.29 (s, 2 H), 7.34 (d, J=8.0 Hz, 2 H), 7.72 (d, J=8.0 Hz, 2 H). $R_f$=0.36 (10% ethyl acetate/n-hexane). mp 99–100° C.

EXAMPLE 127

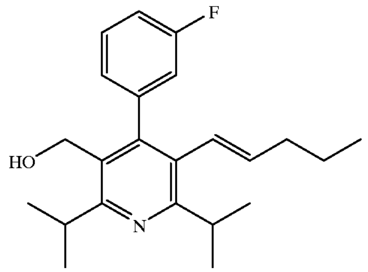

2,6-Diisopropyl-3-hydroxymethyl-4-(3-fluorophenyl)-5-(pent-1-enyl)-pyridine

Step A: Ethyl 2,6-diisopropyl-4-(3-fluorophenyl)-5-(pent-1-enyl)-pyridine3-carboxylate Prepared from 3-fluorobenzaldehyde, ethyl isobutyrylacetate and concentrated ammonium hydroxide by the procedures described in Example 125, Steps A–E. $^1$H NMR (300 MHz, $CDCl_3$): (reported as a mixture of olefin isomers): δ 0.76 (m, 3 H), 0.97 (t, J=7.0 Hz, 3 H), 1.13–1.37 (m, 14 H), 1.95 (m, 2 H), 3.07 (m, 1 H), 3.21–3.45 (m, 1 H), 4.0 (m, 2 H), 5.30–5.60 (m, 1 H), 6.06 (m, 1 H), 6.90–7.03 (m, 3 H), 7.27 (m, 1 H).

Step B: 2,6-Diisopropyl-3-hydroxymethyl-4-(3-fluorophenyl)-5-(pent-1-enyl)pyridine The title compound was prepared from the intermediate obtained in Step A by the procedure described in Example 125, Step F. $^1$H NMR (300 MHz, $CDCl_3$) (reported as a mixture of olefin isomers): δ 0.78 (m, 3 H), 1.13–1.37 (m, 14 H), 1.93 (m, 2 H), 3.41 (m, 2 H), 4.40 (s, 2 H), 5.28–5.45 (m, 1 H), 6.0 (m, 1 H), 6.87–7.07 (m, 3 H), 7.34 (m, 1 H). $R_f$=0.36 (10% ethyl acetate/n-hexane). mp 117–118° C.

EXAMPLE 128

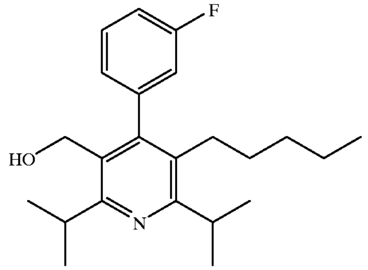

2,6-Diisopropyl-3-hydroxymethyl-4-(3-fluorophenyl)-5-pentylpyridine

The title compound was prepared from 2,6-diisopropyl-3-hydroxymethyl-4-(3-fluorophenyl)-5-(pent-1-enyl)pyridine (Example 127) by the procedure described in Example 126. $^1$H NMR (300 MHz, $CDCl_3$): δ 0.79 (t, J=7.0 Hz, 3 H), 1.10–1.35 (m, 18 H), 2.28 (m, 2 H), 3.24 (m, 1 H), 3.42 (m, 1 H), 4.33 (s, 2 H), 6.96 (m, 2 H), 7.12 (m, 1 H), 7.40 (m, 1 H). mp 117–118° C. $R_f$=0.36 (10% ethyl acetate/n-hexane).

EXAMPLE 129

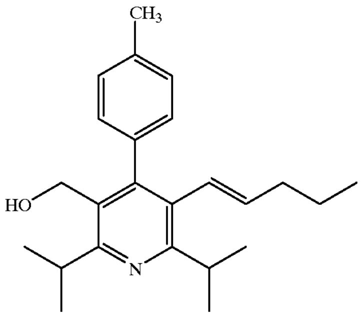

2,6-Diisopropyl-3-hydroxymethyl-4-(4-methylphenyl)-5-(Pent-1-enyl)-pyridine

Step A: Ethyl 2,6-diisopropyl-4-(4-methylphenyl)-5-(pent-1-enyl)-pyridine-3-carboxylate Prepared from 4-methylbenzaldehyde, ethyl isobutyrylacetate and concentrated ammonium hydroxide by the procedures described in Example 125, Steps A–E. $^1$H NMR (300 MHz, $CDCl_3$): δ 0.75 (t, J=7.4 Hz, 3 H), 0.95 (t, J=7.4, 3 H), 1.20–1.40 (m, 14 H), 1.95 (tdd, J=7.4, 7.4, 1.5 Hz, 2 H), 2.35 (s, 3 H), 3.10 (m, 1 H), 3.40 (m, 1 H), 3.99 (q, J=7.4, 2H), 5.30–5.40 (m, 1 H), 6.05 (dt, J=16.2, 1.5 Hz, 1 H), 7.0–7.2 (m, 4 H). mp 74–77° C.

Step B: 2,6-Diisopropyl-3-hydroxymethyl-4-(4-methylphenyl)-5-(pent-1-enyl)-pyridine The title compound was prepared from the intermediate obtained in Step A by the procedure described in Example 125, Step F. $^1$H NMR (300 MHz, $CDCl_3$) (reported as a mixture of olefin isomers): δ 0.77 (t, J=7.0 Hz, 3 H), 1.1–1.3 (m, 15 H), 2.27 (m, 2 H), 2.42 (s, 3 H), 3.4 (m, 2 H), 4.34 (d, J=6.0 Hz, 2 H), 5.30–5.40 (m, 1 H), 5.90 (d, J=16.0 Hz, 1 H), 7.0 (d, J=8.0 Hz, 2 H), 7.18 (d, J=8.0 Hz, 2 H). FAB-MS: calculated for $C_{24}H_{33}NO$ 352; found 352 (M+H, 100%). $R_f$=0.38 (10% ethyl acetate/n-hexane). mp 72–75° C.

EXAMPLE 130

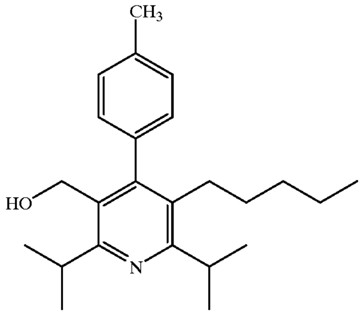

2,6-Diisopropyl-3-hydroxymethyl-4-(4-methylphenyl)-5-pentylpyridine

The title compound was prepared from 2,6-diisopropyl-3-hydroxymethyl-4-(4-methylphenyl)-5-(pent-1-enyl) pyridine (Example 129) by the procedure described in Example 126. $^1$H NMR (300 MHz, $CDCl_3$): δ 0.77 (t, J=7.0 Hz, 3 H), 1.10–1.40 (m, 19 H), 2.27 (m, 2 H), 2.42 (s, 3 H), 3.22 (m, 1 H), 3.41 (m, 1 H), 4.34 (d, J=6.0 Hz, 2 H), 7.10 (d, J=8.0 Hz, 2 H), 7.20 (d, J=8.0 Hz, 2 H). FAB-MS: calculated for $C_{24}H_{35}NO$ 354; found 354 (M+H, 100%). $R_f$=0.38 (10% ethyl acetate/n-hexane). mp 92–94° C.

EXAMPLE 131

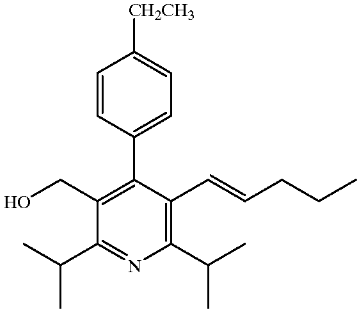

2,6-Diisopropyl-3-hydroxymethyl-4-(4-ethylphenyl)-5-(pent-1-enyl)-pyridine

Step A: Ethyl 2,6-diisopropyl-4-(4-ethylphenyl)-5-(pent-1-enyl)-pyridine-3-carboxylate Prepared from 4-ethylbenzaldehyde, ethyl isobutyrylacetate and concentrated ammonium hydroxide by the procedures described in Example 125, Steps A–E. $^1$H NMR (300 MHz, $CDCl_3$): δ 0.78 (t, J=7.4 Hz, 3 H), 0.90 (t, J=7.4 Hz, 3 H), 1.10–1.40 (m, 17 H), 1.94 (tdd, J=7.0, 7.0, 1.5 Hz, 2 H), 2.64 (q, J=7.7 Hz, 2 H), 3.0 (m, 1 H), 3.40 (m, 1 H), 3.96 (q, J=7.4 Hz, 2 H), 5.35 (m, 1 H), 6.08 (dt, J=16.2, 1.5 Hz, 1 H), 7.10 (m, 4 H). mp 67–68° C.

Step B: 2,6-Diisopropyl-3-hydroxymethyl-4-(4-ethylphenyl)-5-(pent-1-enyl)pyridine The title compound was prepared from the intermediate obtained in Step A by the procedure described in Example 125, Step F. $^1$H NMR (300 MHz, $CDCl_3$) (reported as a mixture of olefin isomers): δ 0.73 (t, J=7.0 Hz, 3 H), 1.10–1.40 (m, 18 H), 1.91 (tdd, J=7.0, 7.0, 1.0, 2 H), 2.68 (q, J=7.4 Hz, 2 H), 3.3–3.5 (m, 2 H), 4.41 (d, J=5.5 Hz, 2 H), 5.20–5.40 (m, 1 H), 6.0 (dt, J=16.0, 1.0 Hz, 1 H), 7.0 (d, J=8.5 Hz, 2 H), 7.23 (d, J=8.5 Hz, 2 H). FAB-MS: calculated for $C_{25}H_{35}NO$ 366; found 366 (M+H, 100%). $R_f$=0.31 (10% ethyl acetate/n-hexane).

EXAMPLE 132

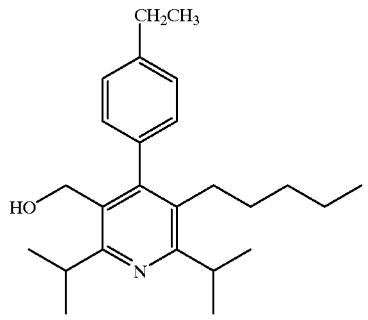

2,6-Diisopropyl-3-hydroxymethyl-4-(4-ethylphenyl)-5-pentylpyridine

The title compound was prepared from 2,6-diisopropyl-3-hydroxymethyl-4-(4ethylphenyl)5(pent-1-enyl)pyridine (Example 131) by the procedure described in Example 126. $^1H$ NMR (300 MHz, $CDCl_3$): δ 0.77 (t, J=7.0 Hz, 3 H), 1.0–1.40 (m, 22 H), 2.28 (m, 2 H), 2.73 (q, J=7.5 Hz, 2 H), 3.35 (m, 1 H), 3.45 (m, 1 H), 4.35 (s, 2 H), 7.10 (d, J=8.0 Hz, 2 H), 7.18–7.34 (d, J=8.0 Hz, 2 H). FAB-MS: calculated for $C_{25}H_{37}NO$ 368; found 368 (M+H, 100%). $R_f$=0.31 (10% ethyl acetate/n-hexane). mp 87–88° C.

EXAMPLE 133

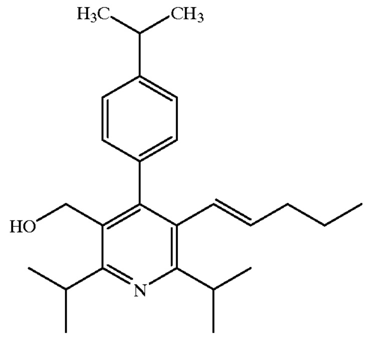

2,6-Diisopropyl-3-hydroxymethyl-4-(4-isopoplphenyl-5-(pent-1-enyl)pyridine

Step A: Ethyl 2,6-diisopropyl-4-(4-isopropylphenyl-5-(pent-1-enyl)pyridine-3-carboxylate Prepared from 4-isopropylbenzaldehyde, ethyl isobutyrylacetate and concentrated ammonium hydroxide by the procedures described in Example 125, Steps A–E. $^1H$ NMR (300 MHz, $CDCl_3$): δ 0.70 (t, J=7.7 Hz, 3 H), 0.84 (t, J=7.4, 3 H), 1.1–1.40 (m, 20 H), 1.95 (tdd, J=7.0, 7.0, 1.5 Hz, 2 H), 2.80–3.10 (m, 2 H), 3.40 (m, 1 H), 3.94 (q, J=7.4 Hz, 2 H), 5.30 (m, 1 H), 6.10 (dt, J=15.8, 1.5 Hz, 1 H), 7.0–7.20 (m, 4 H). mp 41–45° C.

Step B: 2,6-Diisopropyl-3-hydroxymethyl-4-(4-isopropylphenyl)-5-(pent-1-enyl)pyridine The title compound was prepared from the intermediate obtained in Step A by the procedure described in Example 125, Step F. $^1H$ NMR (300 MHz, $CDCl_3$) (reported as a mixture of olefins): δ 0.68 (t, J=7.4 Hz, 3 H), 1.0–1.4 (m, 21 H), 1.90 (tdd, J=7.0, 7.0, 1.5 Hz, 2 H), 2.9 (m, 1 H), 3.3–3.5 (m, 2 H), 4.43 (d, J=6.0 Hz, 2 H), 5.20–5.35 (m, 1 H), 6.0 (dt, J=16.0, 1.5 Hz, 1 H), 7.0 (d, J=8.0 Hz, 2 H), 7.25 (d, J=8.0 Hz, 2 H). FAB-MS: calculated for $C_{26}H_{37}NO$ 380; found 380 (M+H, 100%). $R_f$=0.40 (10% ethyl acetate/n-hexane).

EXAMPLE 134

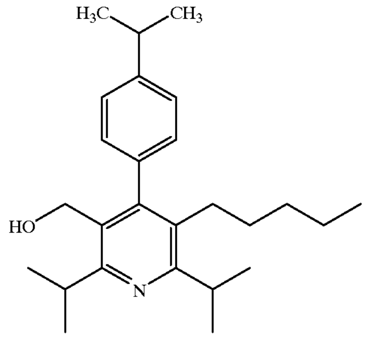

2,6-Diisopropyl-3-hydroxymethyl-4-(4-isopropylphenyl)-5-pentylpyridine

The title compound was prepared from 2,6-diisopropyl-3-hydroxymethyl-4-(4-isopropylphenyl)-5-(pent-1-enyl) pyridine (Example 133) by the procedure described in Example 126. $^1H$ NMR (300 MHz, $CDCl_3$): δ 0.74 (t, J=7.0 Hz, 3 H), 1.0–1.40 (m, 25 H), 2.25 (m, 2 H), 2.95 (m, 1 H), 3.25 (m, 1 H), 3.40 (m, 1 H), 4.35 (d, J=6.0 Hz, 2 H), 7.1, (d, J=8.5 Hz, 2 H), 7.25 (d, J=8.5 Hz, 2 H). FAB-MS: calculated for $C_{26}H_{39}NO$ 382; found 382 (M+H, 100%). $R_f$=0.40 (10% ethyl acetate/n-hexane). mp 42–44° C.

EXAMPLE 135

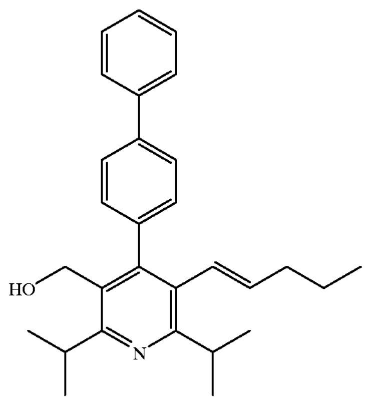

2,6-Diisopropyl-3-hydroxymethyl-4-[4-(phenyl) phenyl]-5-(pent-1-enyl)pyridine

Step A: Ethyl 2,6-diisopropyl-4-[4-(phenyl)phenyl]-5-(pent-1-enyl)pyridine-3-carboxylate Prepared from 4-phenylbenzaldehyde, ethyl isobutyrylacetate and concentrated ammonium hydroxide by the procedures described in Example 125, Steps A–E. $^1H$ NMR (300 MHz, $CDCl_3$): δ 0.73 (t, J=7.4 Hz, 3 H), 0.93 (t, J=7.0 Hz, 3 H), 1.10–1.40 (m, 14 H), 1.97 (tdd, J=7.0, 7.0, 1.1 Hz, 2 H), 3.10 (m, 1 H), 3.45 (m, 1 H), 4.0 (q, J=7.4 Hz, 2 H), 5.40

(m, 1 H), 6.10 (dt, J=16.2, 1.1 Hz, 1 H), 7.20–7.70 (m, 9 H). mp 104–106° C.

Step B: 2,6-Diisopropyl-3-hydroxymethyl-4-[4-(phenyl)phenyl]-5-(pent-1-enyl)pyridine The title compound was prepared from the intermediate obtained in Step A by the procedure described in Example 125, Step F. $^1$H NMR (300 MHz, $CDCl_3$) (reported as a mixture of olefin isomers): δ 0.70 (t, J=7.0 Hz, 3 H), 1.10–1.40 (m, 15 H), 1.90 (tdd, J=7.0, 7.0, 1.5, 2 H), 3.30–3.50 (m, 2 H), 4.40 (d, J=6.0 Hz, 2 H), 5.35 (m, 1 H), 6.05 (dt, J=16.0, 1.5 Hz, 1 H), 7.20–7.24 (m, 2 H), 7.35–7.70 (m, 7 H). FAB-MS: calculated for $C_{29}H_{35}NO$ 414; found 414 (M+H, 100 ). $R_f$=0.15 (6% ethyl acetatein-hexane). mp 50–52° C.

EXAMPLE 136

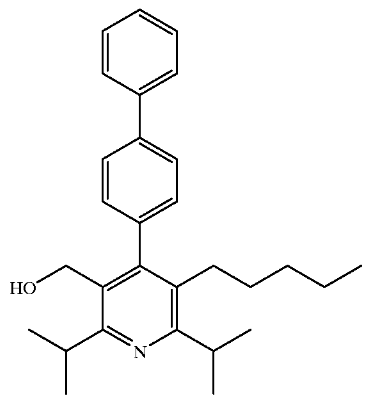

2,6-Diisopropyl-3-hydroxymethyl-4-(phenyl)phenyl-5-pentylpyridine

The title compound was prepared from 2,6-diisopropyl-3-hydroxymethyl-4-[4-(phenyl)phenyl]-5-(pent-1-enyl) pyridine (Example 135) by the procedure described in Example 126. $^1$H NMR (300 MHz, $CDCl_3$): δ 0.76 (t, J=7.0 Hz, 3 H), 1.0–1.40 (m, 19 H), 2.31 (m, 2 H), 3.25 (m, 1 H), 3.44 (m, 1 H), 4.40 (d, J=5.9 Hz, 2 H), 7.22–7.70 (m, 9 H). FAB-MS: calculated for $C_{29}H_{37}NO$ 416; found 416 (M+H, 100%). $R_f$=0.34 (10% ethyl acetate/n-hexane). mp 56–58° C.

EXAMPLE 137

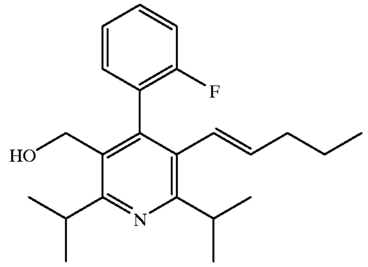

2,6-Diisopropyl-3-hydroxymethyl-4-(2-fluorophenyl)-5-(pent-1-enyl)-pyridine

Step A: Ethyl 2,6-diisopropyl-4-(2-fluorophenyl)-5 (pent-1-enyl)-pyridine-3-carboxylate Prepared from 2-fluorobenzaldehyde, ethyl isobutyrylacetate and concentrated ammonium hydroxide by the procedures described in Example 125, Steps A–E. $^1$H NMR (300 MHz, $CDCl_3$): (reported as a mixture of olefin isomers): δ 0.70 (m, 3 H), 0.92 (t, J=7.0 Hz, 3 H), 1.05–1.40 (m, 14 H), 1.90 (m, 2 H), 3.10 (m, 1 H), 3.35 (m, 1 H), 3.97 (m, 2 H), 5.29–5.50 (m, 1 H), 6.16 (m, 1 H), 7.08–7.32 (m, 4 H).

Step B: 2,6-Diisopropyl-3-hydroxymethyl-4-(2-fluorophenyl)-5-(pent-1-enyl)pyridine The title compound was prepared from the intermediate obtained in Step A by the procedure described in Example 125, Step F. $^1$H NMR (300 MHz, $CDCl_3$) (reported as a mixture of olefin isomers): δ 0.69–0.82 (m, 3 H), 1.09–1.40 (m, 14 H), 1.90 (m, 2 H), 3.20–3.45 (m, 2 H), 4.40 (m, 2 H), 5.25–5.45 (m, 1 H), 6.08 (m, 1H), 7.08–7.41 (m, 5 H). $R_f$=0.24 (10% ethyl acetate/n-hexane).

EXAMPLE 138

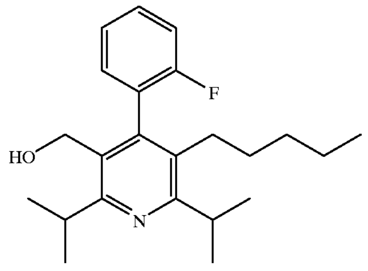

2,6-Diisopropyl-3-hydroxymethyl-4-(2-fluorophenyl)-5-pentylpyridine

The title compound was prepared from 2,6-diisopropyl-3-hydroxymethyl (2-fluorophenyl)-5-(pent-1-enyl)pyridine (Example 137) by the procedure described in Example 126. $^1$H NMR (300 MHz, $CDCl_3$): δ 0.78 (t, J=7.0 Hz, 3 H), 1.07–1.40 (m, 18 H), 2.29 (m, 2 H), 3.26 (m, 1 H), 3.46 (m, 1 H), 4.34 (m, 2 H), 7.20 (m, 3 H), 7.42 (m, 1 H). $R_f$=0.24 (10% ethyl acetate/n-hexane).

EXAMPLE 139

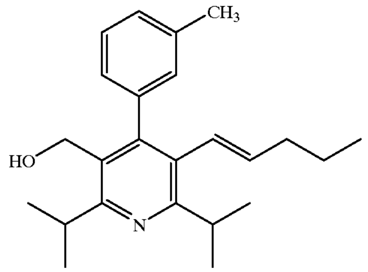

2,6-Diisopropyl-3-hydroxymethyl-4-(3-methylphenyl)-5-(pent-1-enyl)-pyridine

Step A: Ethyl 2,6-diisopropyl-4-(3-methylphenyl)-5 (Pent-1-enyl)pyridine3-carboxylate Prepared from 3-methylbenzaldehyde, ethyl isobutyrylacetate and concentrated ammonium hydroxide by the procedures described in Example 125, Steps A–E. $^1$H NMR (300 MHz, $CDCl_3$): δ 0.74 (t, J=7.4 Hz, 3 H), 0.92 (t, J=7.0 Hz, 3 H), 1.10–1.40 (m, 14 H), 1.95 (tdd, J=7.0, 7.0, 1.5 Hz, 2

H), 2.32 (s, 3 H), 3.10 (m, 1 H), 3.40 (m, 1 H), 3.96 (q, J=7.4 Hz, 2 H), 5.40 (m, 1 H), 6.05 (dt, J=16.2, 1.5 Hz, 1 H), 6.90–7.20 (m, 4 H).

Step B: 2,6-Diisopropyl-3-hydroxymethyl-4-(3methylphenyl)-5-(pent-1-enyl)pyridine The title compound was prepared from the intermediate obtained in Step A by the procedure described in Example 125, Step F. $^1$H NMR (300 MHz, $CDCl_3$) (reported as a mixture of olefins): δ 0.73 (t, J=7.0 Hz, 3 H), 1.10–1.40 (m, 15 H), 1.90 (tdd, J=7.0, 7.0, 1.0, 2 H), 2.36 (s, 3 H), 3.30–3.50 (m, 21 H), 4.40 (d, J=4.0 Hz, 2 H), 5.20–5.40 (m, 1 H), 5.95 (dt, J=16.0, 1.0 Hz, 1 H), 6.90 (m, 2 H), 7.10–7.30 (m, 2 H). FAB-MS: calculated for $C_{24}H_{33}NO$ 352; found 352 (M+H, 100%). $R_f$=0.34 (10% ethyl acetate/n-hexane). mp 94–97° C.

EXAMPLE 140

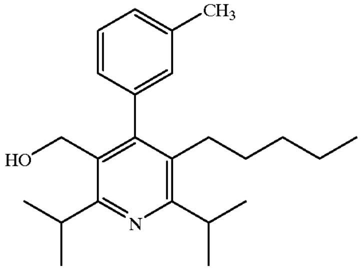

2,6-Diisopropyl-3-hydroxymethyl-4-(3-methylphenyl)-5-pentylpyridine

The title compound was prepared from 2,6-diisopropyl-3-hydroxymethyl-4-(3-methylphenyl)-5-(pent-1-enyl) pyridine (Example 139) by the procedure described in Example 126. $^1$H NMR (300 MHz, $CDCl_3$): δ 0.77 (t, J=7.0 Hz, 3 H), 1.0–1.40 (m, 19 H), 2.25 (m, 2 H), 2.39 (s, 3 H), 3.23 (m, 1 H), 3.44 (m, 1 H), 4.34 (s, 2 H), 6.97 (m, 2 H), 7.18–7.34 (m, 2 H). FAB-MS: calculated for $C_{24}H_{35}NO$ 354; found 354 (M+H, 100 %). $R_f$=0.34 (10% ethyl acetate/n-hexane). mp 88–90° C.

EXAMPLE 141

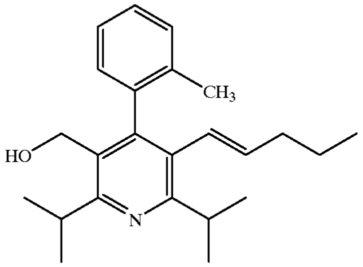

2,6-Diisopropyl-3-hydroxymethyl-4-(2-methylphenyl)-5-(pent-1-enyl)-pyridine

Step A: Ethyl 2,6-diisopropyl-4-(2-methylphenyl)-5-(pent-1-enyl)-pyridine-3-carboxylate Prepared from 2-methylbenzaldehyde, ethyl isobutyrylacetate and concentrated ammonium hydroxide by the procedures described in Example 125, Steps A–E. $^1$H NMR (300 MHz, $CDCl_3$): δ 0.70 (t, J=7.4 Hz, 3 H), 0.88 (t, J=7.0 Hz, 3 H), 1.0–1.40 (m, 14 H), 1.90 (td, J=7.0, 7.0 Hz, 2 H), 2.0 (s, 3 H), 3.10 (m, 1 H), 3.40 (m, 1 H), 3.90 (m, 2 H), 5.30–5.40 (m, 1 H), 6.0 (m, 1 H), 7.0–7.20 (m, 4 H).

Step B: 2,6-Diisopropyl-3-hydroxymethyl-4-(2-methylphenyl)-5-(pent-1-enyl)pyridine The title compound was prepared from the intermediate obtained in Step A by the procedure described in Example 125, Step F. $^1$H NMR (300 MHz, $CDCl_3$) (reported as a mixture of olefin isomers): δ 0.70 (t, J=7.5 Hz, 3 H), 1.10–1.40 (m, 15 H), 1.87 (tdd, J=7.5, 7.5, 1.5, 2 H), 1.95 (s, 3 H), 3.30–3.50 (m, 2 H), 4.20 (m, 1 H), 4.45 (m, 1 H), 5.30 (m, 1 H), 5.93 (m, 2 H), 6.90–7.30 (m, 4 H). FAB-MS: calculated for $C_{24}H_{33}NO$ 352; found 352 (M+H, 100%). $R_f$=0.32 (10% ethyl acetate/n-hexane). mp 76–79° C.

EXAMPLE 142

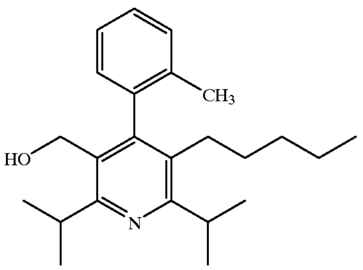

2,6-Diisopropyl-3-hydroxymethyl-4-(2-methylphenyl)-5pentylpyridine

The title compound was prepared from 2,6-diisopropyl-3-hydroxymethyl-4-(2-methylphenyl)-5-(pent-1-enyl) pyridine (Example 141) by the procedure described in Example 126. $^1$H NMR (300 MHz, $CDCl_3$): δ 0.76 (t, J=6.6 Hz, 3 H), 1.0–1.40 (m, 19 H), 1.97 (s, 3 H), 2.0 (m, 1 H), 2.35 (m, 1 H), 3.22 (m, 1 H), 3.42 (m, 1 H), 4.16 (dd, J=12.0, 5.0 Hz, 1 H), 4.40 (dd, J=12.0, 5.0 Hz, 1 H), 7.0–7.10 (m, 1 H), 7.20–7.40 (m, 3 H). FAB-MS: calculated for $C_{24}H_5NO$ 354; found 354 (M+H, 100%). $R_f$=0.32 (10% ethyl acetate/n-hexane). mp 81–83° C.

EXAMPLE 143

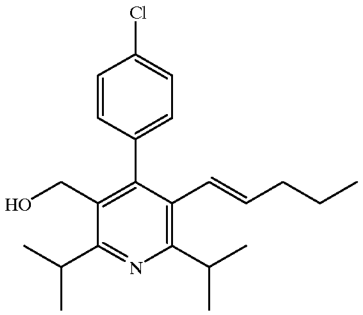

2,6-Diisopropyl-3-hydroxymethyl-4-(4-chlorophenyl-5-(pent-1-enyl)-pyridine

Step A: Ethyl 2,6-diisopropyl-4-(4-chlorophenyl)-5-(pent-1-enyl)-pyridine-3-carboxylate Prepared from 4-chlorobenzaldehyde, ethyl isobutyrylacetate and concentrated ammonium hydroxide by the procedures described in Example 125, Steps A–E. $^1$H NMR (300 MHz, $CDCl_3$) (reported as a mixture of olefin isomers): δ 0.76 (m, 3 H), 0.98 (m, 3 H), 1.15–1.35 (m, 14 H), 1.95 (m, 2 H), 3.05 (m, 1 H), 3.39 (m, 1 H), 4.0 (M, 2 H), 5.29–5.48 (m, 1 H), 6.03 (m, 1 H), 7.11 (m, 2 H), 7.30 (m, 2 H).

Step B: 2,6-Diisopropyl-3-hydroxymethyl-4-(4-chlorophenyl)-5-(pent-1-enyl)pyridine The title compound was prepared from the intermediate obtained in Step A by the procedure described in Example 125, Step F. $^1$H NMR (300 MHz, $CDCl_3$) (reported as a 6:1 mixture of olefin isomers): δ 0.73–0.83 (m, 3 H), 1.10–1.40 (14 H), 1.91 (m, 2 H), 3.93 (m, 2 H), 4.39 (d, J=5.0 Hz, 2 H), 5.25–5.45 (m, 1 H), 5.98 (m, 1 H), 7.11 (m, 2 H), 7.35 (m, 2 H). $R_f$=0.36 (10% ethyl acetate/n-hexane).

EXAMPLE 144

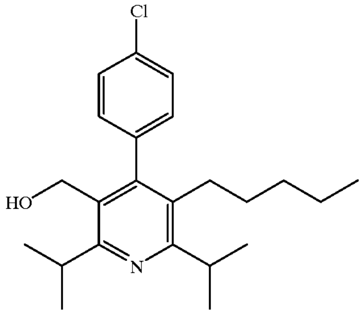

2,6-Diisopropyl-3-hydroxymethyl-4-(4-chlorophenyl)-5-pentylpyridine

The title compound was prepared from 2,6-diisopropyl-3-hydroxymethyl-4-(4-chlorophenyl)-5(pent-1-enyl) pyridine (Example 143) by the procedure described in Example 126. $^1$H NMR (300 MHz, $CDCl_3$): δ 0.79 (t, J=7.0 Hz, 3 H), 1.08–1.38 (m, 18 H), 2.26 (m, 2 H), 3.22 (m, 1 H), 3.40 (m, 1 H), 4.31 (d, J=5.0 Hz, 1 H), 7.13 (d, J=8.0 Hz, 2 H), 7.42 (d, J=8.0 Hz, 2 H). mp 83–85° C. $R_f$=0.36 (10% ethyl acetate/n-hexane).

EXAMPLE 145

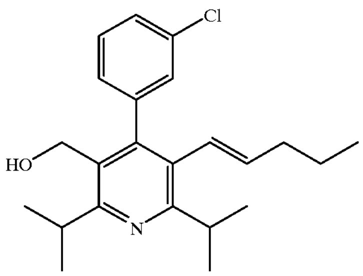

2,6-Diisopropyl-3-hydroxymethyl-4-(3-chlorophenyl)-5-(pent-1-enyl)-pyridine

Step A: Ethyl 2,6-diisopropyl-4-(3-chlorophenyl)-5-(pent-1-enyl)-pyridine-3-carboxylate Prepared from 3-chlorobenzaldehyde, ethyl isobutyrylacetate and concentrated ammonium hydroxide by the procedures described in Example 125, Steps A–E. $^1$H NMR (300 MHz, $CDCl_3$): δ 0.75 (t, J=7.4 Hz, 3 H), 0.98 (t, J=7.0 Hz, 3 H), 1.20–1.40 (m, 14 H), 1.96 (tdd, J=7.0, 7.0, 1.5 Hz, 2 H), 3.05 (m, 1 H), 3.40 (m, 1 H), 4.0 (q, J=7.0 Hz, 2 H), 5.45 (m, 1 H), 6.05 (dt, J=16.2, 1.5 Hz, 1 H), 7.0–7.30 (m, 4 H).

Step B: 2,6-Diisopropyl-3-hydroxymethyl-4-(3-chlorophenyl)-5-(pent-1-enyl)pyridine The title compound was prepared from the intermediate obtained in Step A by the procedure described in Example 125, Step F. $^1$H NMR (300 MHz, $CDCl_3$) (reported as a mixture of olefin isomers): δ 0.75 (t, J=7.5 Hz, 3 H), 1.10–1.40 (m, 15 H), 1.93 (tdd, J=7.0, 7.0, 1.0 Hz, 2 H) 3.30–3.50 (m, 2 ), 4.37 (d, J=12.0 Hz, 1 H), 4.43 (d, J=12.0 Hz, 1 H), 5.20–5.40 (m, 1 H), 5.9 (dt, J=16.0, 1.1 Hz, 1 H), 7.0–7.40 (m, 4 H). FAB-MS: calculated for $C_{23}H_{30}NOCl$ 372; found 372 (M+H, 100%). $R_f$=0.26 (10% ethyl acetate/n-hexane). mp 101–104° C.

EXAMPLE 146

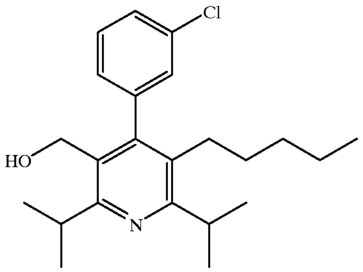

2,6-Diisopropyl-3-hydroxymethyl-4-(3-chlorophenyl)-5-pentylpyridine

The title compound was prepared from 2,6-diisopropyl-3-hydroxymethyl-4-(3-chlorophenyl)-5-(pent-1-enyl) pyridine (Example 145) by the procedure described in Example 126. $^1$H NMR (300 MHz, $CDCl_3$): δ 0.80 (t, J=7.0 Hz, 3 H), 1.0–1.40 (m, 19 H), 2.26 (m, 2 H), 3.23 (m, 1 H) 3.41 (m, 1 H), 4.34 (m, 2 H), 7.05–7.45 (m, 4 H). FAB-MS: calculated for $C_{23}H_{32}NOCl$ 374; found 374 (M+H, 100%). $R_f$0.26 (10% ethyl acetate/n-hexane). mp 94–95° C.

EXAMPLE 147

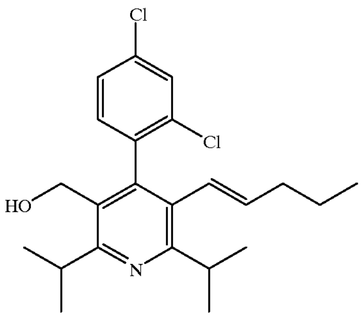

2,6-Diisopropyl-3-hydroxymethyl-4-(2,4-dichlorophenyl)-5-(pent-1-enyl)pyridine

Step A: Ethyl 2,6-diisopropyl-4-(2,4-dichlorophenyl)-5-(pent-1-enyl)pyridine-3-carboxylate Prepared from 2,4-dichlorobenzaldehyde, ethyl isobutyrylacetate and concentrated ammonium hydroxide by the procedures described in Example 125, Steps A–E. $^1$H NMR (300 MHz, $CDCl_3$) (reported as a 1:1 mixture of olefin isomers): δ 0.79 (m, 3 H), 0.99 (m, 3 H), 1.12–1.38 (m, 14 H), 1.91 (m, 2 H), 3.12 (m, 1 H), 3.32 (m, 1 H), 4.0 (m, 2H), 5.20–5.60 (m, 1 H), 6.09 (m, 1 H), 7.05–7.41 (m, 3 H).

Step B: 2,6-Diisopropyl-3-hydroxymethyl-4-(2,4-dichlorophenyl)-5-(pent-1-enyl)pyridine The title compound was prepared from the intermediate obtained in Step A by the procedure described in Example 125, Step F. $^1$H NMR (300 MHz, $CDCl_3$) (reported as a 1:1 mixture of olefins): δ 0.75–0.87 (m, 3 H), 1.13–1.37 (m, 14 H), 1.65–2.0 (m, 2 H), 3.20–3.51 (m, 2 H), 4.30 (m, 1 H), 4.42 (m, 1 H), 5.31–5.50 (m, 1 H), 6.0 (m, 1 H), 7.05 (m, 1 H), 7.28 (m, 1 H), 7.47 (m, 1 H). $R_f$0.38 (10% ethyl acetate/n-hexane).

EXAMPLE 148

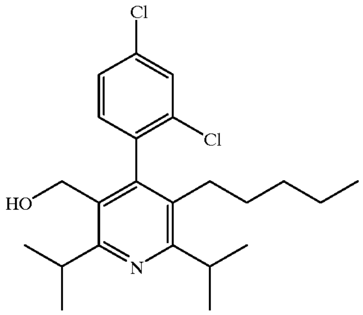

2,6-Diisopropyl-3-hydroxymethyl-4-(2,4-dichlorophenyl)-5-pentylpyridine

The title compound was prepared from 2,6-diisopropyl-3-hydroxymethyl-4-(2,4-dichlorophenyl)-5-(pent-1-enyl) pyridine (Example 147) by the procedure described in Example 126. $^1$H NMR (300 MHz, $CDCl_3$): δ 0.80 (t, J=7.0 Hz, 3 H), 1.12–1.48 (m, 18 H), 2.12 (m, 1 H), 2.35 (m, 1 H), 3.26 (m, 1 H) 3.45 (m, 1 H), 4.31 (AB, J=12.0 Hz, 2 H), 7.16 (d, J=8.0 Hz, 1 H), 7.36 (dd, J=8.0, 2.0 Hz, 1 H), 7.54 (d, J=2.0, 1 H). $R_f$0.38 (10% ethyl acetate/n-hexane).

EXAMPLE 149

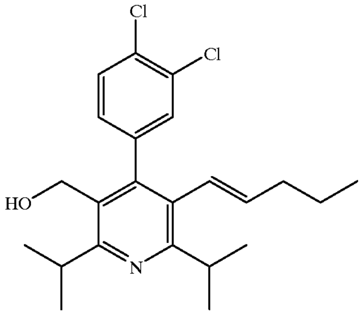

2,6-Diisopropyl-3-hydroxymethyl-4-(3,4-dichloropenyl-5-(pent-1-enyl)pyridine

Step A: Ethyl 2,6-diisopropyl-4-(3,4-chlorophenyl)-5-(pent-1-enyl)pyridine-3-carboxylate Prepared from 3,4-dichlorobenzaldehyde, ethyl isobutyrylacetate and concentrated ammonium hydroxide by the procedures described in Example 160, Steps A–E. $^1$H NMR (300 MHz, $CDCl_3$) (reported as a 6:1 mixture of olefin isomers): δ 0.78 (m, 3 H), 1.04 (m, 3 H), 1.16–1.35 (m, 14 H), 1.98 (m, 2 H), 3.04 (m, 1 H), 3.57 (m, 1 H), 5.31–5.58 (m, 1 H), 6.02 (m, 1 H), 7.04 (m, 1 H), 7.28–7.42 (m, 2 H).

Step B: 2,6-Diisopropyl3-hydroxymethyl-4-(3,4-dichlorophenyl)-5-(pent-1-enyl)pyridine The title compound was prepared from the intermediate obtained in Step A by the procedure described in Example 125, Step F. 1H NMR (300 MHz, $CDCl_3$) (reported as a 6:1 mixture of olefin isomers): δ 0.80 (m, 3 H), 1.16–1.57 (m, 14 H), 1.95 (m, 2 H), 3.40 (m, 2 H), 4.41 (m, 2 H), 5.28–5.42 (m, 1 H), 6.0 (m, 1 H), 7.05 (s, 1 H), 7.30 (s, 1 H), 7.45 (m, 1 H). mp 46–48° C. $R_f$=0.38 (10% ethyl acetate/n-hexane).

EXAMPLE 150

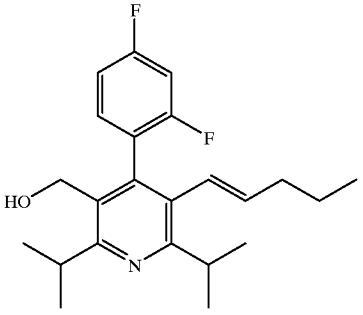

2,6-Diisopropyl-3-hydroxymethyl-4-(2,4-difluoropenyl)-5-(pent-1-enyl)pyridine

Step A: Ethyl 2,6-diisopropyl-4-(2,-difluorophenyl)-5-(pent-1-enyl)pyridine-3-carboxylate Prepared from 2,4-difluorobenzaldehyde, ethyl isobutyrylacetate and concentrated ammonium hydroxide by the procedures described in Example 125, Steps A–E. $^1$H NMR (300 MHz, $CDCl_3$): δ 0.75 (t, J=7.4 Hz, 3 H), 1.0 (t, J=7.0 Hz, 3 H), 1.10–1.40 (m, 14 H), 1.93 (tdd, J=7.4, 7.4, 1.5 Hz, 2 H), 3.10 (m, 1 H), 3.35 (m, 1 H), 4.0 (q, J=7.0 Hz, 2 H), 5.30 (dt, J=15.0, 7.0 Hz, 1 H), 6.10 (m, 1 H), 6.80–7.20 (m, 3 H).

Step B: 2,6-Diisopropyl-3-hydroxymethyl-4-(2,4-difluorophenyl)-5-(pent-1-enyl)pyridine The title compound was prepared from the intermediate obtained in Step A by the procedure described in Example 125, Step F. $^1$H NMR (300 MHz, $CDCl_3$) (reported as a mixture of olefin isomers): δ 0.75 (t, J=7.5 Hz, 3 H), 1.10–1.40 (m, 15 H), 1.92 (tdd, J=7.0, 7.0, 1.5, 2 H), 3.30–3.60 (m, 2 H), 4.34 (dd, J=12.0, 6.0 Hz, 1 H), 4.43 (dd, J=12.0, 5.0 Hz, 1 H), 5.3 (m, 1 H), 6.05 (d, J=16.0, Hz, 1 H), 6.80–7.20 (m, 3 H). FAB-MS: calculated for $C_{23}H_{29}NOF_2$ 374; found 374 (M+H, 100%). $R_f$ 0.24 (10% ethyl acetate/n-hexane). mp 59–62° C.

EXAMPLE 151

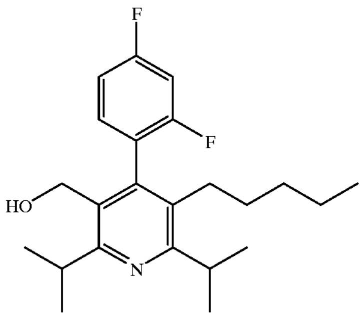

2,6-Diisopropyl-1-hydroxymethyl-4-(2,4-difluorolphenyl)-5-pentylpyridine

The title compound was prepared from 2,6-diisopropyl-3-hydroxymethyl-4-(2,4-difluorophenyl)-5-(pent-1-enyl) pyridine (Example 150) by the procedure described in Example 126. $^1$H NMR (300 MHz, $CDCl_3$): δ 0.79 (t, J=7.0 Hz, 3 H), 1.10–1.40 (m, 18 H), 2.30 (m, 2 H), 3.20 (m, 1 H), 3.40 (m, 1 H), 4.30 (d, J=12.0 Hz, 1 H),4.36 (d, J=12.0 Hz, 1 H), 6.90–7.20 (m, 3 H). FAB-MS: calculated for $C_{23}H_{31}F_2NO$ 376; found 376 (M+H, 100%). $R_f$ 0.24 (10% ethyl acetate/n-hexane). mp 93–95° C.

EXAMPLE 152

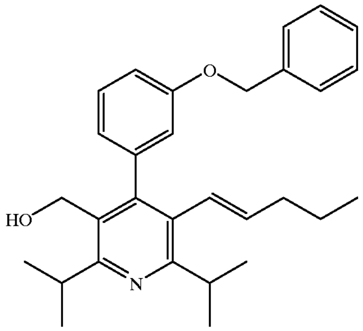

2,6-Diisopropyl-3-hydroxymethyl-4-(3-benzyloxyphenyl)-5-(pent-1-enyl)pyridine

Step A: Ethyl 2,6-diisopropyl-4-(3-benzyloxyphenyl)-5-(pent-1-enyl)pyridine-3-carboxylate Prepared from 3-benzyloxybenzaldehyde, ethyl isobutyrylacetate and concentrated ammonium hydroxide by the procedures described in Example 160, Steps A–E. $^1$H NMR (300 MHz, $CDCl_3$): δ 0.75 (t, J=7.4 Hz, 3 H), 0.93 (t, J=7.2 Hz, 3 H), 1.25 (m, 14 H), 1.93 (tdd, J=7.4, 7.4, 1.1 Hz, 2 H), 3.07 (m, 1 H), 3.40 (m, 1 H), 3.97 (m, 2 H), 5.04 (bs, 2 H), 5.35 (m, 1 H), 6.06 (dt, J=16.2, 1.5 Hz, 1 H), 6.79 (m, 2 H), 6.89 (m, 1 H), 7.31 (m, 6 H).

Step B: 2,6-Diisopropyl-3-hydroxymethyl-4-(3-benzyloxyphenyl)-5-(pent-1-enyl)pyridine The title compound was prepared from the intermediate obtained in Step A by the procedure described in Example 125, Step F. $^1$H NMR (300 MHz, $CDCl_3$) (reported as a mixture of olefin isomers): δ 0.74 (t, J=7.4 Hz, 3 H), 1.25 (m, 14 H), 1.90 (m, 2 H), 3.39 (m, 2 H), 4.39 (d, J=6.0 Hz, 2 H), 5.07 (s, 2 H), 5.32 (m, 1 H), 5.97 (m, 1 H), 6.74 (m, 2 H), 6.95 (m, 1 H), 7.35 (m, 7 H). FAB-MS: calculated for $C_{30}H_{37}NO_2$, 444; found 444 (M+H, 100%). Elemental analysis: calculated for $C_{30}H_{37}NO_2$: C 81.22; H 8.41; N 3.16, found: C 80.51; H 8.41; N 3.36. $R_f$ 0.5 (25% ethyl acetate/n-hexane).

EXAMPLE 153

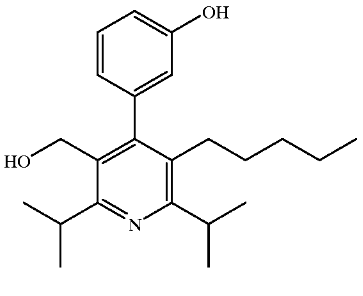

2,6-Diisopropyl-3-hydroxymethyl-4-(3-hydroxyphenyl)-5-pentylpyridine

The title compound was prepared from 2,6-diisopropyl-3-hydroxymethyl-4-(3-benzyloxyphenyl)-5-(pent-1-enyl) pyridine (Example 152) by the procedure described in Example 126. $^1$H NMR (300 MHz, $CDCl_3$): δ 0.78 (t, J=7.0 Hz, 3 H), 1.28 (m, 18 H), 2.28 (m, 2 H), 3.22 (m, 1 H), 3.39 (m, 1 H), 4.34 (m, 2 H), 5.52 (s, 1 H), 6.63 (m, 1 H), 6.71 (d, J=8.0 Hz, 1 H), 6.81 (m, 1 H), 7.26 (m, 1 H). FAB-MS: calculated for $C_{23}H_{33}NO_2$ 356; found 357 (M+H, 100%). Elemental analysis: calculated for $C_{23}H_{33}NO_2$: C 77.70; H 9.36; N 3.94, found: C 76.51; H 9.49; N 3.85. $R_f$ 0.21 (10% ethyl acetate/n-hexane). mp 121–122° C.

EXAMPLE 154

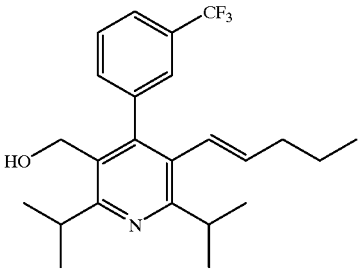

2,6-Diisopropyl-3-hydroxymethyl-4-(3-trifluoromethyl)phenyl-5-(pent-1-enyl)pyridine Step A: Ethyl 2,6-diisopropyl-4-(3-trifluoromethyl) phenyl-5-(pent-1-enyl)pyridine-3-carboxylate Prepared from 3-(trifluoromethyl)benzaldehyde, ethyl isobutyrylacetate and concentrated ammonium hydroxide by the procedures described in Example 125, Steps A–E. $^1$H NMR (300 MHz, $CDCl_3$) (reported as a 6:1 mixture of olefin isomers): δ 0.72 (m, 3 H), 0.94 (m, 3 H), 1.10–1.40 (m, 14 H), 1.94 (m, 2 H), 3.07 (m, 1 H), 3.41 (m, 1 H), 3.97 (m, 2 H), 5.33 (m, 1 H), 6.05 (m, 1 H), 7.29–7.60 (m, 4 H).

Step B: 2,6-Diisopropyl-3-hydroxymethyl-4-(3-trifluoromethyl)phenyl-5-(pent-1-enyl)pyridine The title compound was prepared from the intermediate obtained in Step A by the procedure described in Example 125, Step F. $^1$H NMR (300 MHz, $CDCl_3$) (reported as a 6:1 mixture of olefin isomers): δ 0.67–0.87 (m, 3 H), 1.08–1.38 (m, 14 H), 1.90 (m, 2 H), 3.20–3.50 (m, 2 H), 4.39 (qd, J=12.0, 5.0 Hz, 2 H), 5.24–5.50 (m, 1 H), 5.93–6.02 (m, 1 H), 7.37–7.62 (m, 3 H). mp 100–103° C. $R_f$ 0.36 (10% ethyl acetate/n-hexane).

EXAMPLE 155

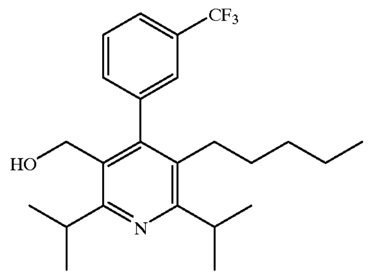

2,6-Diisopropyl-3-hydroxymethyl-4-(3-tifluoromethyl)phenyl-5-pentylpyridine

The title compound was prepared from 2,6-diisopropyl-3-hydroxymethyl-4-(3-trifluoromethyl)phenyl-5-(pent-1-enyl)pyridine (Example 154) by the procedure described in Example 126. $^1$H NMR (300 MHz, $CDCl_3$): δ 0.75 (t, J=6.5 Hz, 3 H), 1.07–1.39 (m, 18 H), 2.24 (m, 2 H), 3.24 (m, 1 H), 3.42 (m, 1 H), 4.31 (qd, J=12.0, 5.0 Hz, 2 H), 7.42 (d, J=8.0 Hz, 1 H), 7.50 (s, 1 H), 7.57 (t, J=8.0 Hz, 1 H), 7.67 (d, J=8.0 Hz, 1 H). mp 96–97° C. $R_f$ 0.36 (10% ethyl acetate/n-hexane).

EXAMPLE 156

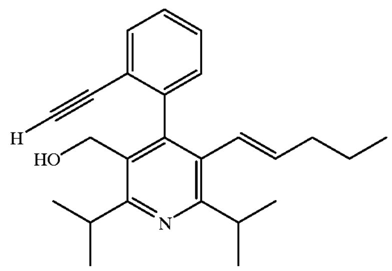

2,6-Diisopropyl-3-hydroxymethyl-4-(2-ethynylphenyl)-5-(pent-1-enyl)-pyridine

Step A: Diethyl 2,6-diisopropyl-4-(2-iodophenyl) pyridine-3,5-dicarboxylate

Prepared from 2-iodobenzaldehyde, ethyl isobutyrylacetate and concentrated ammonium hydroxide by the procedures described in Example 125, Steps A–B. $^1$H NMR (300 MHz, $CDCl_3$): δ 0.94 (t, J=7.0 Hz, 6 H), 1.30 (d, J=6.6 Hz, 6 H), 1.34 (d, J=6.6 Hz, 6 H), 3.19 (septet, J=6.6 Hz, 2 H), 4.0 (q, J=7.0 Hz, 4 H), 7.0–7.40 (m, 3 H), 7.85 (m, 1 H).

Step B: Diethyl 2,6-diisopropyl-4-[(2-trimethylsilylethynyl)phenyl]pyridine-3,5-dicarboxylate A solution of 1.50 g (3 mmole) of the intermediate obtained in Step A in toluene was treated with 1.48 g (15 mmole) of trimethylsilyl acetylene, 87.1 g (0.86 mol) of triethylamine, 0.1 g (0.15 mmol) of bis(triphenylphosphine) palladium(II) chloride, 0.2 g (0.8 mmole) of triphenyl phosphine and 0.2 g (1.17 mmole) of copper iodide. This reaction mixture was stirred at rt for 1 hr and heated at 90° C., in a sealed reaction vessel, for 16 hrs. The reaction mixture was to cooled to temperature, filtered through Celite, and stripped to give a dark oil which upon purification by flash silica gel chromatography to yield 1.22 g (2.5 mmole) of the product. $^1$H NMR (300 MHz, $CDCl_3$): δ 0.0 (s, 9 H), 0.93 (t, J=7.0, 61), 1.32 (d, J=6.6 Hz, 6 H), 1.33 (d, J=6.6 Hz, 6 H), 3.18 (septet, J=6.6, 2 H), 3.90 (q, J=7.0 Hz, 4 H), 7.20–7.50 (m, 4 H).

Step C: Diethyl 2,6-diisopropyl-4-(2-ethynylphenyl) pyridine-3,5-dicarboxylate

A solution of 5.68 g (11.9 mmole) of the intermediate obtained in Step B in 800 mL ethanol was treated with 2.8 g (20.3 mmole) of potassium carbonate and the reaction mixture was allowed to stir at room temperature for 16 hours. The mixture was diluted with ethyl acetate and washed with saturated aqueous solution of ammonium chloride, brine and separated. The organic layer was dried over magnesium sulfate, filtered and concentrated under reduced pressure. The crude material was purified by flash silica gel chromatography, eluting with 10 ethyl acetate/n-hexane, to give 3.95 g (9.6 mmole) of the product. $^1$H NMR (300 MHz, $CDCl_3$): δ 0.90 (t, J=7.0 Hz, 6 H), 1.32 (m, 12 H), 2.97 (s, 1 H), 3.21 (septet, J=6.6, 2 H), 3.90 (q, J=7.0, 4 H), 7.2–7.6 (m, 4 H).

Step D: Ethyl 2,6-diisopropyl-4-(2-ethynylphenyl)-5 (pent-1-enyl)-pyridine-3-carboxylate Prepared from the intermediate obtained in Step C by the procedures described in Example 125, Steps A–E. $^1$H NMR (300 MHz, $CDCl_3$): δ 0.68 (t, J=7.4 Hz, 3 H), 0.88 (td, J=7.0, 2.4 Hz, 3 H), 1.20–1.40 (m, 14 H), 1.88 (tdd, J=7.0, 7.0, 1.1 Hz, 2 H), 2.92 (d, J=2.4 Hz, 1 H), 3.0–3.40 (m, 2 H), 3.90 (m, 2 H), 5.28 (dt, J=16.2, 7.0 Hz, 1 H), 6.15 (dt, J=16.2, 1.5 Hz, 1 H), 7.10–7.60 (m, 4 H).

Step E: 2,6-Diisopropyl-3-hydroxymethyl-4-(2-ethynylphenyl)-5-(pent-1-enyl)pyridine The title compound was prepared from the intermediate obtained in Step D by the procedure described in Example 125, Step F. $^1$H NMR (300 MHz, $CDCl_3$) (reported as a mixture of olefin isomers): δ 0.81 (t, J=7.4 Hz, 3 H), 1.0–1.40 (m, 15 H), 1.75 (m, 2 H), 2.98 (d, J=3.3 Hz, 1 H), 3.20–3.60 (m, 2 H), 4.20–4.50 (m, 2 H), 5.40 (m, 1 H), 6.0 (m, 1 H), 7.0–7.60 (m, 4 H). $R_f$=0.23 (10% ethyl acetate/n-hexane).

EXAMPLE 157

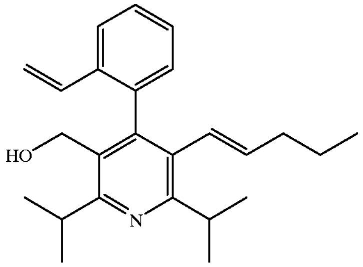

2,6-Diisopropyl-3-hydroxymethyl-4-(2-ethenylphenyl)-5-pentylpyridine

The title compound was prepared from ethyl 2,6-diisopropyl-3-hydroxymethyl-4-(2-ethynylphenyl)-5-(pent-1-enyl)pyridine-3-carboxylate by the procedure described in Example 125, Step F. $^{1}H$ NMR (300 MHz, $CDCl_3$) (reported as a mixture of olefin isomers): δ 0.60–0.90 (m, 3 H), 1.0–1.40 (m, 15 H), 1.60–1.90 (m, 2 H), 3.20–3.50 (m, 2 H), 4.20–4.40 (m, 2 H), 5.14 (dt, J=11.0, 1.0 Hz, 1 H), 5.40 (m, 1 H), 5.90 (m, 1 H), 6.30 (m, 1 H), 7.0–7.70 (m, 4 H). FAB-MS: calculated for $C_{25}H_{33}NO$ 363.5; found 364 (M+H, 100%). $R_f$ 0.28 (10% ethyl acetate/n-hexane).

EXAMPLE 158

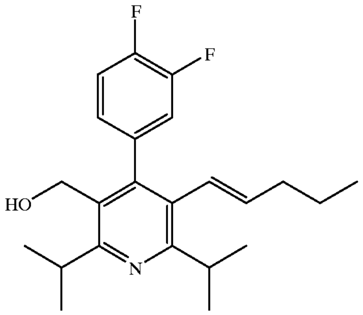

2,6-diisopropyl-3-hydroxymethyl-4-(3,4-difluorophenyl)-5-(pent-1-enyl)pyridine

Step A: Ethyl 2,6-diisopropyl-4-(3,4-difluorophenyl)-5-(pent-1-enyl)pyridine-3-carboxylate Prepared from 3,4-difluorobenzaldehyde, ethyl isobutyrylacetate and concentrated ammonium hydroxide by the procedures described in Example 1, Steps A–E. $^{1}H$ NMR (300 MHz, $CDCl_3$) (reported as a 8:1 mixture of olefin isomers): δ 0.78 (m, 3 H), 1.03 (m, 3 H), 1.18–1.33 (m, 14 H), 1.97 (m, 2 H), 3.04 (m, 1 H), 3.38 (m, 1 H), 4.04 (m, 2 H), 5.30–5.45 (m, 1 H), 6.02 (m, 1 H), 6.89–7.17 (m, 3 H).

Step B: 2,6-Diisopropyl-3-hydroxymethyl-4-(3,4-difluorophenyl)-5-(pent-1-enyl)pyridine The title compound was prepared from the intermediate obtained in Step A by the procedure described in Example 125, Step F. $^{1}H$ NMR (300 MHz, $CDCl_3$) (reported as a mixture of olefin isomers): δ 0.75 (m, 3 H), 1.05–1.38 (m; 14 H), 1.90 (m, 2 H), 3.35 (m, 2 H), 4.35 (m, 2 H), 5.25 (m, 1 H), 5.91 (m, 1 H), 6.80–7.20 (m, 41 H). mp 105–106° C. $R_f$=0.30 (10% ethyl acetatein-hexane).

EXAMPLE 159

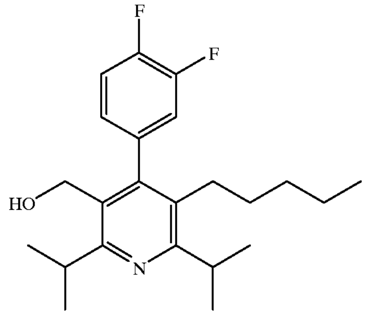

2,6-Diisopropyl-3-hydroxymethyl-4-(3,4-difluorophenyl)-5-pentyl-pyridine

The title compound was prepared from 2,6-diisopropyl-3-hydroxymethyl-4-(3,4-difluorophenyl)-5-(pent-1-enyl) pyridine (Example 158) by the procedure described in Example 126. $^{1}H$ NMR (300 MHz, $CDCl_3$): δ 0.81 (t, J=7.0 Hz, 3 H), 1.12 (m, 4 H), 1.30 (m, 14 H), 2.27 (m, 2 H), 3.24 (m, 1 H), 3.41 (m, 1 H), 4.32 (d, J=4.0 Hz, 2 H), 6.95 (m, 1 H), 7.06 (m, 1 H), 7.25 (m, 1 H). mp 106–107° C. $R_f$ 0.30 (10% ethyl acetate/n-hexane).

EXAMPLE 160

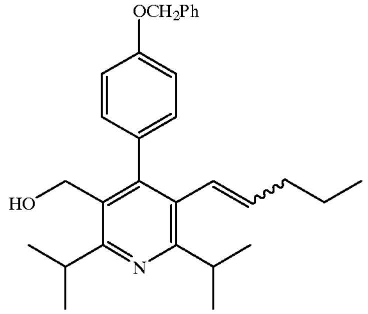

2,6-Diisopropyl-3-hydroxymethyl-4-(4-benzyloxyphenyl)-5-(pent-1-enyl)pyridine

Step A: Diethyl 1,4-dihydro-2,6-diisopropyl-4-(4-benzyloxhenyl)-3,5-pyridinedicarboxylate To 4-benzyloxybenzaldehyde (24.3 g, 114 mmol) and ethyl isobutyryl acetate (37.8 g, 239 mmol) were added ethanol (50 mL), acetic acid (1 mL), and piperidine (1.7 mL). The mixture was stirred under an argon atmosphere at 25° C. for 12 hours. Freshly prepared sodium ethoxide in ethanol (15%, 15 mL) was then added and the reaction mixture was stirred at 25° C. for 2 hours. To this mixture was added a solution of ammonium acetate (13.1 g, 171 mmol) in acetic acid (100 mL). The reaction was heated at reflux for 14 h and was then cooled to 25° C., during which time a white precipitate developed. To the mixture was added a 40% (v/v) solution of 2-propanol in water. The mixture was stirred for 0.5 hours at 25° C. and was then cooled to −20° C. for 2 hours. The white solid was collected by filtration with vacuum and washed with a 50% (v/v) solution of isopropanol in water to provide the product (41.8 g, 85 mmol, 75%) as a pure white solid (mp 140–141° C.). $^{1}H$ NMR (300 MHz, $CDCl_3$): δ 1.14–1.29 (m, 18 H), 4.10 (q, J=6.9 Hz, 4 H), 4.19 (sept, J=6.9 Hz, 2 H), 4.95 (s, 1 H), 5.01 (s, 2 H), 6.12 (s, 1 H), 6.82 (d, J=8.7 Hz, 2 H), 7.17 (d, J=8.7 Hz, 2 H), 7.27–7.45 (m, 5 H).

Step B: Diethyl 2,6-diisopropyl-4-(4-benzyloxyphenyl)-3,5-pyridine-dicarboxylate To a solution of the intermediate obtained in Step A (39.72 g, 81 mmol) in acetone (400 mL) stirred under argon at 25° C. was added an aqueous solution of ammonium cerium(IV) nitrate ("CAN") (1M, 162 mL). The mixture was stirred at 25° C. for 0.5 hours and the acetone was then removed under reduced pressure. The resultant mixture was diluted with dichloromethane (400 mL) and poured into water (100 mL). The organic layer was saved and the aqueous layer is extracted with dichloromethane (100 mL). The combined organic layer was washed with a saturated solution of sodium chloride (100 mL), dried over sodium sulfate, and concentrated under reduced pressure to afford the product as a white powder (39.51 g, 100%) (mp 87° C.). $^1$H NMR (300 MHz, $CDCl_3$): δ 0.96 (t, J=6.9 Hz, 6 H), 1.31 (d, J=6.6 Hz, 12 H), 3.10 (sept, J=6.6 Hz, 2 H), 4.01 (q, J=7.5 Hz, 4 H), 5.09 (s, 2 H), 6.95 (d, J=8.7 Hz, 2 H), 7.21 (d, J=8.7 Hz, 2 H), 7.32–7.46 (m, 5 H).

Step C: Ethyl 2,6-diisopropyl-4-(4-benzyloxyphenyl)-5-(Pent-1-enyl)-3-pyridinecarboxylate Prepared from the intermediate obtained in Step B by the procedure described in Example 1, Steps D–F. $^1$H NMR (300 MHz, $CDCl_3$): δ 0.77 (t, J=7.2 Hz, 3 H), 0.95 (t, J=7.2 Hz, 3 H), 1.21–1.34 (m, 14 H), 1.96 (q, J=7.2 Hz, 2 H), 3.05 (septet, J=6.6 Hz, 1 H), 3.42 (septet, J=6.6 Hz, 1 H), 3.94–4.03 (m, 2 H), 5.06–5.12 (m, 2 H), 5.32–5.42 (m, 1 H), 6.03–6.15 (m, 1 H), 6.94 (d, J=9.0 Hz, 2 H), 7.10 (d, J=9.0 Hz, 2 H), 7.34–7.47 (m, 5 H).

Step D: 2,6-Diisopropyl-3-hydroxymethyl-4-(4-benzyloxyphenyl)-5-(pent-1-enyl)pyridine The intermediate obtained in Step C (6 g, 12.35 mmol) was dissolved in anhydrous tetrahydrofuran ("THF") (130 mL) under argon and treated dropwise at room temperature with lithium aluminum hydride ("LAH")(1.0M in THF, 24.7 mL, 24.7 mmol). The reaction mixture was stirred at reflux for 3 hr, cooled to room temperature and quenched by the addition of 0.9 mL $H_2O$, 0.9 mL 20% aqueous NaOH, and 2.7 mL $H_2O$. The resulting suspension was filtered through a cake of Celite and the filtrate concentrated and purified by chromatography through silica (20% ethyl acetate/hexane) to afford 4.76 g of the title compound as a colorless wax. $^1$H NMR (300 MHz, $CDCl_3$): δ 0.73–0.83 (m, 3 H), 1.37–1.70 (m, 14 H), 1.56 (s, 1 H), 1.92 (dq, J=0.90, 6.90 Hz, 2 H), 3.41 (δ, J=6.60, 13.20, 24.60 Hz, 2 H), 4.43 (d, J=5.1 Hz, 2 H), 5.10 (s, 2 H), 5.27–5.37 (m, 1 H), 5.97 (d, J=15.90 Hz, 1 H), 6.97–7.09 (m, 4 H), 7.35–7.48 (m, 5 H).

EXAMPLE 161

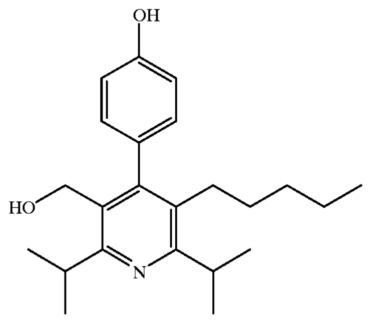

2,6-Diisopropyl-3-hydroxymethyl-4-(4-hydroxyphenyl)-5-pentylpyridine 2,6-Diisopropyl-3-hydroxymethyl-4-(4benzyloxyphenyl)-5-(pent-1-enyl)pyridine (Example 160) (500 mg, 1.13 mmol) was dissolved in absolute ethanol (10 mL) under argon, treated with 10% palladium on carbon (15 mg), then stirred under a hydrogen atmosphere for 14 h. After purging the system with argon, the catalyst was removed by filtration through a pad of Celite. The solvent was removed and the residue purified by flash chromatography (5% methanol-methylene chloride) to yield 371 mg of the title compound as a waxy solid (mp 158.5° C.). $^1$H NMR (300 MHz, $CDCl_3$): δ 0.79 (t, J=6.6 Hz, 3 H), 1.06–1.36 (m, 21 H), 2.24–2.31 (m, 2 H), 3.22 (sept, J=6.6 Hz, 1 H), 3.40 (sept, J=6.6 Hz, 1 H), 4.36 (d, J=5.4 Hz, 2 H), 4.85 (s, 1 H), 6.89 (d, J=8.4 Hz, 1 H), 7.05 (d, J=8.7 Hz, 1 H).

EXAMPLE 162

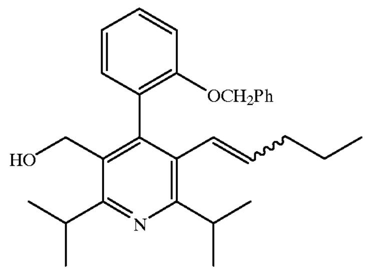

2,6-Diisopropyl-3-hydroxymethyl-4-(2-benzyloxyphenyl)-5-(pent-1-enyl)pyridine

The title compound was prepared as a waxy solid from 2-benzyl-oxybenzaldehyde by the procedures described in Example 160. $^1$H NMR (300 MHz, $CDCl_3$): δ 0.69–0.74 (m, 3 H), 1.07–1.38 (m, 14 H), 1.69–1.79 (m, 1 H) 1.84–1.99 (m, 2 H), 3.26–3.54 (m, 2 H) 4.28–4.46 (m, 2 H), 4.90–5.09 (m, 2 H), 5.26–5.47 (m, 1 H), 6.00 (dd, J=15.9, 1.2 Hz, 1 H), 7.05–7.10 (m, 5 H), 7.24–7.36 (m, 4 H).

EXAMPLE 163

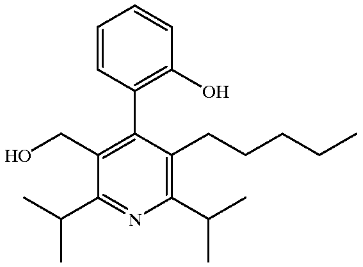

2,6-Diisopropyl-3-hydroxymethyl-4-(2-hydroxyphenyl)-5-pentylpyridine

The title compound was prepared from 2,6-diisopropyl-3-hydroxymethyl-4-(2-benzyloxyphenyl)-5(pent-1-enyl) pyridine (Example 162) by the method detailed in Example 161. $^1$H NMR (300 MHz, $CDCl_3$): δ 0.75–0.73 (m, 3 H), 1.09–1.15 (m, 41 H), 1.30–1.37 (m, 14 H), 1.70–1.73 (m, 1 H), 2.16–2.28 (m, 1 H), 2.32–2.42 (m, 1 H), 3.22–3.32 (m, 1 H), 3.39–3.51 (m, 1 H), 4.29–4.35 (m, 1 H), 4.48–4.54 (m, 1 H), 5.14 (br s, 1 H), 7.02–7.05 (m, 3 H), 7.28–7.36 (m, 1 H). FAB-MS: calcd for ($C_{23}H_{33}NO_2$) 355, found 356 (M +1). Anal. calc. for $C_{23}H_{33}NO_2$: C, 77.70; H, 9.36; N, 3.94. Found: C, 77.63; H, 9.12; N, 3.75. mp 125.5° C.

EXAMPLE 164

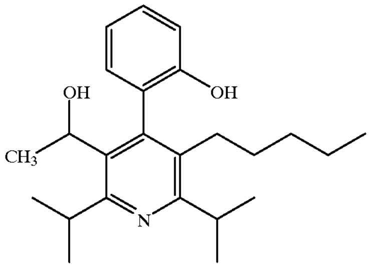

2,6-Diisopropyl-3-(1-hydroxyethyl)-4-(2-hydroxyphenyl)-5-pentyl-pyridine

Step A: 2,6-Diisopropyl-(2-benzyloxyphenyl)-5pentyl-3-pyridine-carboxaldehyde 2,6-Diisopropyl-3-hydroxymethyl-4-(2-benzyloxyphenyl)-5-(pent-1-enyl)-pyridine (Example 162) (680 mg, 1.53 mmol) was dissolved in 15 mL of methylene 25 chloride under an argon atmosphere and treated with a mixture of Celite (661 mg) and pyridinium chlorochromate ("PCC") (661 mg, 2 eq). The reaction was stirred at room temperature for 1.5 h. The suspension was filtered through a pad of silica and the pad was washed with 50 mL $CH_2Cl_2$ and the filtrate was combined and concentrated in vacuo to afford 572.4 mg of product (84%). $^1$H NMR (300 MHz, $CDCl_3$): δ 0.70 (t, J=7.2 Hz, 3 H), 1.08–1.35 (m, 61 H), 4.9–1.93 (m, 1 H), 3.26–3.45 (m, 1 H), 3.87–3.97 (m, 1 H), 4.97–5.06 (m, 2 H), 5.27–5.50 (m, 1 H), 6.01–6.10 (m, 1 H), 6.94–7.34 (m, 9 H), 9.82 (d, J=3.6 Hz, 1 H).

Step B: 2,6-Diisopropyl-3-(1-hydroxyethyl)-4-(2-benzyloxyphenyl)-5-(pent-1-enyl)pyridine Prepared as a separable mixture of two diastereomers from the intermediate from Step A by the method detailed in Ex ample 101, Step B. The two diastereomers were separated by flash chromatography on silica eluting with 10% ethyl acetate-hexane.

Diastereomer 1: colorless oil, $^1$H NMR (300 MHz, $CDCl_3$): δ 0.68–1.91 (m, 23 H), 3.19–3.40 (m, 1 H), 3.77 (sept, J=6.6 Hz, 1 H), 4.69–4.79 (m, 1 H), 4.94 (dd, J=12.3, 3.9 Hz, 1 H), 5.05 (d, J=12.3 Hz, 1 H), 5.20–5.43 (m, 1 H), 5.90–6.05 (m, 1 H), 6.94–7.38 (m, 9 H). FAB-MS: calcd for ($C_{31}H_{39}NO_2$) 457, found 458 (M+1).

Diastereomer 2: colorless oil, $^1$H NMR (300 MHz, $CDCl_3$): δ 0.69 (t, J=7.2 Hz, 3 H), 1.05–1.40 (m, 17 H), 1.67–1.73 (m, 1 H), 1.80–1.88 (m, 2 H), 3.18–3.41 (m, 1 H), 3.68–3.80 (m, 1 H), 4.84–5.08 (m, 3 H), 5.25–5.42 (m, 1 H), 5.86–6.08 (m, 1 H), 6.90–7.38 (m, 9 H). FAB-MS: calcd for ($C_{39}H_{39}N_2$) 457, found 458 (M+1).

Step C: 2,6-Diisopropyl-3-(1-hydroxyethyl)-4-(2-hydroxyphenyl)-5-pentylpyridine

The diastereomeric mixture of intermediates from Step B (39 mg) was dissolved in absolute ethanol (1.5 mL) under argon, treated with 10% palladium on carbon (4 mg), then stirred under a hydrogen atmosphere for 8 hr. After purging the system with argon, the catalyst was removed by filtration through a pad of Celite. The solvent was removed and the product dried in vacuo to afford 32 mg of the title compound as a colorless solid. Preparative thin layer chromatography ("prep TLC") using a 20% ethyl acetate-hexane mixture as the eluent provided the two diastereomers.

Diastereomer 1 (D1) (11.2 mg): $^1$H NMR (300 MHz, $CDCl_3$): δ 0.68 (t, J=7.30 Hz, 3 H), 0.99–1.03 (m, 4 H), 1.19–1.34 (m, 17 H), 1.62 (d, J=3.60 Hz, 1 H), 1.97–2.07 (m, 1 H), 2.16–2.26 (m, 1 H), 3.14 (septet, J=7.30 Hz, 1 H), 3.67 (septet, J=7.30 Hz, 1 H), 4.72 (br, s, 1 H), 4.83 (dq, J=4.20, 6.60 Hz, 1 H), 6.89–6.97 (m, 3 H), 7.19–7.25 (m, 1 H). FAB-MS: calcd for ($C_{24}H_{35}NO_2$) 369, found 370 (M+1).

Diastereomer 1 (D1) could be resolved into the constituent enantiomers as follows. A Waters Prep LC 2000 HPLC system was equipped with a chiral HPLC column (BRB-9668A; 6×50 cm ID). The system was equilibrated with a mobile phase consisting of 2% (1% acetic acid, 99% ethanol) and 98% hexane at a flow rate of 175 mL/min. The sample was dissolved in mobile phase (20 mg/mL) and 5 mL aliquots were injected at 30 minute intervals. The effluent was monitored at 280 nm and two fractions (corresponding to the enantiomers) were collected at (15–17 min, 100% ee) and (19–26 min, >99% ee), respectively.

Diastereomer 2 (D2) (11.8 mg): $^1$H NMR (300 MHz, $CDCl_3$): δ 0.68 (t, J=6.60 Hz, 3 H), 0.99–1.03 (m, 4 H), 1.16–1.32 (m, 17 H), 1.86 (br s, H, 1 H), 2.00–2.10 (m, 1 H), 2.19–2.29 (m, 1 H), 3.14 (septet, J=6.60 Hz, 1 H), 3.67 (septet, J=6.60 Hz, 1 H), 4.57 (q, J=6.60 Hz, 1 H), 4.76 (br, s, 1 H), 6.84–6.93 (m, 3 H), 7.19–7.24 (m, 1 H). FAB-MS: calcd for ($C_{24}H_{35}NO_2$) 369, found 370 (M+1).

EXAMPLE 165

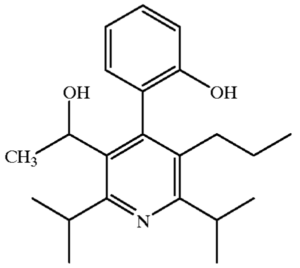

2,6-Diisopropyl-3-(1-hydroxyethyl)-4-(2-hydroxyphenyl-5-propylpyridine

Step A: Diethyl-2,6-diisopropyl-4-(2-benzyloxyphenyl)-3,5-pyridine-dicarboncroate Prepared from 2-benzyloxybenzaldehyde by the methods detailed in Example 160, Steps A–B. $^1$H NMR (300 MHz, $CDCl_3$): δ 0.87 (t, J=6.9 Hz, 6 H), 1.32 (d, J=6.6 Hz, 6 H), 1.33 (d, J=6.6 Hz, 6 H), 3.19 (sept, J=6.6 Hz, 2 H), 3.97 (q, J=7.2 Hz, 4 H), 5.01 (s, 2 H), 6.88 (d, J=8.1 Hz, 1 H), 6.94 (dt, J=7.2, 0.6 Hz, 1 H), 7.16 (dd, J=7.8, 1.8 Hz, 1 H), 7.14–7.30 (m, 6 H).

Step B: 5-Ethoxycarbonyl-2,6-diisopropyl-4-(2-benzyloxyphenyl)-3-pyridinecarboxaldehyde Prepared from the intermediate from Step A by the methods detailed in Example 1, Steps D–E. $^1$H NMR (300 MHz, $CDCl_3$): δ 0.91 (t, J=6.6 Hz, 3 H), 1.30–1.39 (m, 12 H), 3.18 (septet, J=6.0 Hz, 1 H), 3.91–4.03 (m, 3 H), 5.04 (dd, J=6.6, 12.6 Hz, 2 H), 6.96–7.05 (m, 2 H), 7.17–7.28 (m, 6 H), 7.34–7.40 (m, 1 H).

Step C: 2,6-Diisopropyl-4-(2-benzyloxyphenyl)-3-ethoxycarbonyl-5-(prop-1-enyl)pyridine Ethyltriphenylphosphonium bromide (4.01 g, 10.8 mmol) was suspended in anhydrous THF (130 mL) under argon and stirred at −78° C. A 1.6M solution of n-butyllithium in hexanes (6.75 mL, 10.8 mmol) was added dropwise. The reaction mixture was allowed to come to 0° C. and stirred at that temperature for 1 hr. The resulting brightly colored solution was cooled again to −78° C. and treated dropwise with a solution of the intermediate obtained in Step B (4.0 g, 9.0 mmol) in THF (20 mL). The reaction mixture was allowed to stir at 25° C. for 3 hrs, then quenched by the addition of water (5 mL). The THF was removed in vacuo, the residue partitioned between ethyl ether (200 mL) and water (50 mL). The organic layer was washed with brine (50 mL), dried over $MgSO_4$ and concentrated. Flash chromatography through silica (5% ethyl acetate/hex) afforded 4.1 g of the product (E, Z mixture) as a viscous oil. $^1$H NMR (300 MHz, $CDCl_3$): δ 0.86–0.92 (m, 3 H), 1.40–1.21 (m,15 H), 3.06–3.28 (m, 2 H), 3.91–4.01 (m, 2 H), 5.00 (br s, 2 H), 5.29–5.56 (m, 1 H), 6.10–6.19 (m, 1 H), 6.89–6.97 (m, 2 H), 7.08–7.12 (m, 1 H), 7.15–7.19 (m, 2 H), 7.22–7.29 (m, 4 H).

Step D: 2,6-Diisopropyl-3-hydroxyethyl-4-(2-benzyloxyphenyl)-5-(prop-1-enyl)pyridine Prepared from the intermediate from Step C by the method detailed in Example 160, Step D. $^1$H NMR (300 MHz, $CDCl_3$): δ 1.21–1.60 (m, 15 H), 1.90–1.95 (m, 1 H), 3.18–3.53 (m,2 H), 4.26–4.58 (M, 2 H), 4.87–4.94 (m, 1 H), 5.06 (d, J=12.3 Hz, 1 H), 5.27–5.57 (m, 1 H), 5.95–6.05 (m, 1 H), 7.00–7.06 (m, 5 H), 7.22–7.37 (m, 4 H).

Step E: 2,6-Diisopropyl-3-(1-hydroxyethyl)-4-(2-hydroxyphenyl)-5-propylpyridine

The intermediate from Step D was converted into the title compound by the methods detailed in Example 164, Steps A–C. The diastereomers were separated by radial band chromatography using a gradient eluent of 100% hexane to 5% ethyl acetate-hexane.

Diastereomer 1 (D1): $^1$H NMR (300 MHz, $CDCl_3$): δ 0.66 (t, J=7.50 Hz, 3 H), 1.15–1.34 (m, 15 H), 1.59 (br s, 1 H), 1.96–2.06 (m, 1 H), 2.15–2.25 (m, 1 H), 3.15 (sept, J=6.60 Hz, 1 H), 3.56 (sept, J=6.60 Hz, 1 H), 4.70 (br s, 1 H), 4.81–4.87 (m, 1 H), 6.90–6.97 (m, 3 H), 7.19–7.26 (m, 1 H). FAB-MS: calcd for ($C_{22}H_{31}NO_2$) 341, found 342 (M+1).

Diastereomer 1 (D1) was resolved into its constituent enantiomers as follows. A Waters Prep LC 2000 HPLC system was equipped with a chiral HPLC column (BRB-9466AD; 6×50 cm ID). The system was equilibrated with a mobile phase consisting of 25% hexane and 75% of a mixture of (15% THF in heptane) at 150 mL/min. The sample was dissolved in mobile phase (10 mg/mL) and 5 mL aliquots were injected at 35 min intervals. The effluent was monitored at 280 nm. Peaks overlapped and were thus shaved. Mixed fractions were then evaporated and reinjected. The collected enantiomers were assayed off line on an analytical column (BRB-9705A) at 1.5 mL/min with a mobile phase of 1% (1% acetic acid in ethanol) and 99% hexane. The low $R_t$ enantiomer from the preparative column was the high $R_t$ enantiomer on the analytical column with $R_t$=8.80 min; 98.8% ee. The high $R_t$ enantiomer from the preparative column was the low $R_t$ enantiomer on the analytical column with $R_t$=3.71 min; 81% ee.

Diastereomer 2 (D2): $^1$H NMR (300 MHz, $CDCl_3$): δ 0.72 (t, J=7.50 Hz, 3 H), 1.22–1.36 (m, 15 H), 2.03–2.15 (m, 1 H), 2.23–2.33 (m, 1 H), 2.56 (d, J=3.0 Hz, 1 H), 3.21 (septet, J=6.60 Hz, 1 H), 3.73 (septet, J=6.60 Hz, 1 H), 4.56–4.63 (dq, J=3.0, 6.0 Hz, 1 H), 5.66 (br s, 1 H), 6.88–6.99 (m, 3 H), 7.25–7.28 (m, 1 H). FAB-MS: calcd for ($C_{22}H_{31}NO_2$) 341, found 342 (M+1).

EXAMPLE 166

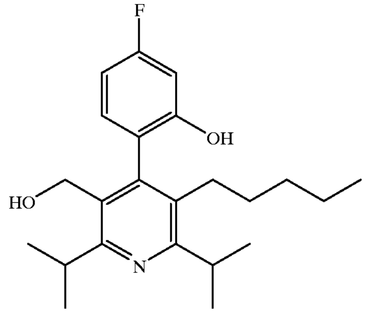

2,6-Diisopropyl-3-hydroxymethyl-4-[(4-fluoro-2-hydroxy)phenyl]-5-pentylpyridine

Step A: 2-Benzyloxy-4-fluorobromobenzene

To a solution containing 2-bromo-5-fluorophenol (50 g, 0.26 mol) in 500 mL acetone was added potassium carbonate (54.2 g, 0.39 mmol) and benzyl bromide (34.3 mL, 0.288 mol). The reaction was heated at reflux under an argon atmosphere for 2 h and then allowed to cool to 25° C. The acetone was removed under reduced pressure and the residue was taken up in ether (400 mL). The organic layer was washed with water (5×100 mL) and brine (1×100 mL) and then dried ($MgSO_4$). The solution was then concentrated under reduced pressure and subjected to flash chromatography using hexane as the eluent. In this manner, 2-benzyloxy-4-fluorobenzene was obtained as a white solid. 1H NMR (300 MHz, $CDCl_3$): δ 5.14 (s, 2 H), 6.57–6.63 (m, 1 H), 6.69 (dd, J=2.7, 10.2 Hz, 1 H), 7.32–7.52 (m, 6 H).

Step B: 2-Benzyloxy-4-fluorobenzaldehyde

To a slurry of magnesium (9.52 g, 0.39 mol) in THF (25 mL) in a 1 L round bottom flask fitted with a condenser was added the intermediate obtained in Step A (1 g). A vigorous reflux commenced at once. To this refluxing mixture was added a solution of the intermediate from Step A (109 g) at a rate which maintained reflux. After completion of addition the reaction was allowed to proceed until it cooled to 25° C. and was then heated at reflux for 1 h. The reaction was allowed to cool to 25° C. and DMF (48 mL) was then added portionwise. The reaction was allowed to cool to 25° C. and was then filtered through a plug of Celite. The THF was removed under reduced pressure and the residue was dissolved in ethyl acetate (500 mL) and washed sequentially with water (100 mL), 10% HCl (100 mL), saturated sodium bicarbonate solution (100 mL), and brine (100 mL). The organic layer was dried ($Na_2SO_4$) and concentrated under reduced pressure. The resultant residue was purified by flash chromatography (10% ethyl acetate-hexane) to provide 77.3 g of 2-benzyloxy-4-fluorobenzaldehyde. $^1$H NMR (300 MHz, $CDCl_3$): δ 5.16 (s, 2 H), 6.70–6.76 (m, 2 H), 7.34–7.44 (m, 5 H), 7.87–7.92 (m, 1 H), 10.43 (s, 1 H). FAB-MS: calcd for ($C_{14}H_{11}O_2F$) 230; found 231 (M+1).

Step C: 2,6-Diisopropyl-3-hydroxymethyl-4-[(2-benzyloxy-4-fluoro)phenyl]-5-(pent-1-enyl)pyridine Prepeared from the intermediate obtained in Step B by the methods described in Example 160, Steps A–D. $^1$H NMR (300 MHz, $CDCl_3$): δ 0.73 (t, J=7.4 Hz, 3 H), 1.09–1.36 (m, 14 H), 1.63–1.73 (m, 2 H), 1.89 (q, J=6.9 Hz, 1 H), 3.25 (septet, J =6.6 Hz, 1 H), 3.46 (d septet, J=2.7, 6.6 Hz, 1 H), 4.29–4.42 (m, 2 H), 4.89–5.06 (m, 2 H), 5.24–5.47 (m, 1 H), 5.95–6.00 (m, 1 H), 6.70–6.79 (m, 3 H), 7.00–7.07 (m, 5 H). FAB-MS: calcd for ($C_{30}H_{36}NO_2F$) 461, found 462.

Step D: 2,6-Diisopropyl-3-hydroxymethyl)-4-[(4-fluoro-2-hydroxy)phenyl]-5-pentylpyridine The title compound was prepared as a racemate from the intermediate obtained in Step C by the method detailed in Example 161. $^1$H NMR (300 MHz, $CDCl_3$): δ 0.78 (t, J=6.6 Hz, 3 H), 1.09–1.35 (m, 18 H), 1.65 (t, J=5.0 Hz, 1 H), 2.13–2.23 (m, 1 H), 2.28–2.38 (m, 1 H), 3.24 (sept, J=6.6 Hz, 1 H), 3.39 (sept, J=6.6 Hz, 1 H), 4.29 (dd, J=11.1, 5.0 Hz, 1 H), 4.52 (dd, J=11.1, 5.1 Hz, 1 H), 5.45 (bs, 1 H), 6.71–6.78 (m, 2 H), 6.95–7.00 (m, 1 H). FAB-MS: calcd for ($C_{23}H_{32}NO_2F$) 373, found 374 (M+1). $R_f$=0.15 (20% ether-hexanes). mp 152° C.

EXAMPLE 167

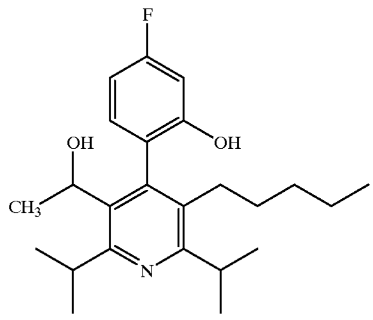

2,6-Diisopropyl-3-(1-hydroxyethyl)-4-[(4-fluoro-2-hydroxy)phenyl-pentylpyridine

The title compound was prepared as two separable diastereomers from 2,6-diisopropyl-3-hydroxymethyl-4-[(2-benzyloxy-4-fluoro)phenyl]-5-(pent-1-enyl)pyridine (Example 166, Step C) by the methods detailed in Example 164, Steps A–C. The diastereomers were separated by radial band chromatography using a gradient eluent of 100% hexane to 20% ether-hexane.

Diastereomer 1 (D1): $^1$H NMR (300 MHz, $CDCl_3$): δ 0.80 (t, J=6.6 Hz, 3 H), 1.10–1.42 (m, 21 H), 1.64 (d, J=3.6 Hz, 1 H), 2.03–2.13 (m, 1 H), 2.21–2.31 (m, 1 H), 3.15–3.26 (septet, 1 H), 3.54–3.65 (septet, 1 H), 4.89–4.98 (m, 1 H), 4.99 (br s, 1 H), 6.69–6.75 (m, 2 H), 6.94–6.99 (δ, J=2.7, 6.5, 6.5 Hz, 1 H). FAB-MS: calcd for ($C_{24}H_{34}NO_2F$) 387, found 388 (M+1). $R_f$=0.41 (40% ether-hexanes). mp 124–126 ° C.

Diastereomer 1 (D1) was resolved into its constituent enantiomers as follows. A Waters Prep LC 2000 HPLC system was equipped with a chiral HPLC column (BRB9668A; 6×50 cm ID). The system was equilibrated with a mobile phase consisting of 2% (1% acetic acid, 99% ethanol) and 98% hexane at a flow rate of 175 mL/min. The sample was dissolved in mobile phase (50 mg/mL) and 5 mL aliquots were injected at 30 min intervals. The effluent was monitored at 280 nm and two fractions (corresponding to the two enantiomers) were collected at (13–18 min,100% ee) and (18.5–27 min, >99% ee), respectively.

Diastereomer 2 (D2): $^1$H NMR (300 MHz, $CDCl_3$): δ 0.78 (t, J=6.5 Hz, 3 H), 1.06–1.40 (m, 21 H), 1.75 (d, J=3.6 Hz, 1 H), 2.06–2.16 (m, 1 H), 2.26–2.37 (m, 1 H), 3.21 (septet, J=6.6 Hz, 1 H), 3.74 (septet, J=6.6, 1 H), 4.59–4.67 m, 1 H), 4.83 (br s, 1 H), 6.68–6.75 (m, 2 H), 6.86–6.91 (δ, J=3.0, 6.6, 6.6 Hz, 1 H); FAB-MS: calcd for ($C_{24}H_{34}NO_2F$) 387, found 388 (M+1). $R_f$=0.24 (40% ether-hexanes). mp 157–159° C.

EXAMPLE 168

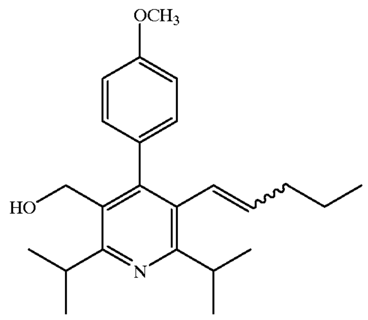

2,6-Diisopropyl-3-hydroxymethyl-4-(4-methoxyphenyl)-5-(pent-1-enyl)pyridine

The title compound was prepared from 4-methoxybenzaldehyde by the methods detailed in Example 125. $^1$H NMR (300 MHz, $CDCl_3$): δ 0.76 and 0.81 (t, J =7.2 Hz, 3 H), 1.12–1.39 (m, 14 H), 1.60–1.80 (bs, 1 H), 1.86–1.97 (m, 2 H), 3.33–3.50 (m, 2 H), 3.85 (s, 3 H), 4.43 (m, 2 H), 5.27–5.48 (m, 1 H), 5.93–6.05 (m, 1 H), 6.92 (d, J=8.4 Hz, 2 H), 7.07 (d, J=8.4 Hz, 2 H). FAB-MS: calcd for ($C_{24}H_{33}NO_2$) 367, found 368 (M+1).

EXAMPLE 169

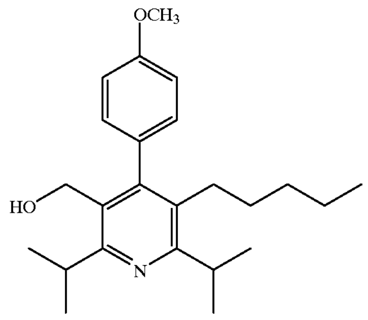

2,6-Diisopropyl-3-hydroxymethyl-4-(4-methoxyphenyl)-5-pentyl-pyridine

The title compound was prepared as a white solid from 2,6-diisopropyl-3-hydroxymethyl-4-(4-methoxyphenyl)-5 (pent-1-enyl)pyridine (Example 168) by the methods detailed in Example 126. $^1$H NMR (300 MHz, $CDCl_3$): δ 0.80 (t, J=6.6 Hz, 3 H), 1.08–1.19 (m, 4 H), 1.24–1.38 (m, 15 H), 2.27–2.33 (m, 2 H), 3.24 (sept, J=6.6 Hz, 1 H), 3.42 (sept, J=6.6 Hz, 1 H), 3.87 (s, 3 H), 4.35 (d, J=5.7 Hz, 2 H), 6.97 (d, J=8.7 Hz, 2 H), 7.11 (d, J=8.7 Hz, 2 H). FAB-MS: calcd for ($C_{24}H_{35}NO_2$) 369, found 370 (M+1). mp 47–49° C.

EXAMPLE 170

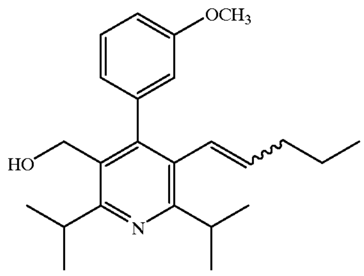

2,6-Diisopropyl-3-hydroxymethyl-4-(3-methoxyphenyl)-5-(pent-1-enyl)pyridine

The title compound was prepared from 3-methoxybenzaldehyde by the methods detailed in Example 125. $^1$H NMR (300 MHz, $CDCl_3$): δ 0.78 (t, J=7.5 Hz, 3 H), 1.17–1.41 (m, 14 H), 1.65 (s, 1 H), 1.97 (δ, J=14.0, 7.2, 1.5 Hz, 2 H), 3.39–3.55 (m, 2 H), 3.81 (s, 3 H), 4.45 (s, 2 H), 5.35–5.50 (m, 1 H), 6.01–6.09 (m, 1 H), 6.73–6.77 (m, 2 H), 6.89 (δ, J=8.1, 2.1, 0.9 Hz, 1 H), 7.30 (t, J=8.0 Hz, 1 H). FAB-MS: calcd for ($C_{24}H_{33}NO_2$) 367, found 368 (M+1). mp 71–75° C.

EXAMPLE 171

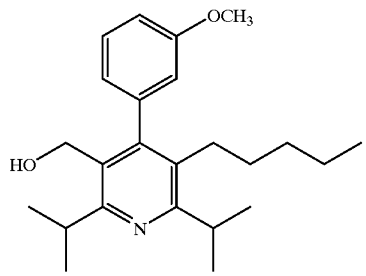

2,6-Diisopropyl-3-hydroxymethyl-4-(3-methoxyphenyl)-5-pentylpyridine

The title compound was prepared from 2,6-diisopropyl-3-hydroxymethyl-4-(3-methoxyphenyl)-5-(pent-1-enyl) pyridine (Example 170) by the methods detailed in Example 126. $^1$H NMR (300 MHz, $CDCl_3$): δ 0.79 (t, J=6.6 Hz, 3 H), 1.09–1.33 (m, 7 H), 1.30 (d, J=6.6 Hz, 6 H), 1.33 (d, J=6.6 Hz, 6 H), 2.25–2.31 (m, 2 H), 3.23 (sept, J=6.6 Hz, 1 H), 3.42 (sept, J=6.6 Hz, 1 H), 3.82 (s, 3 H), 4.35 (d, J=6.0 Hz, 2 H), 6.73 (dd, J=2.4, 1.5 Hz, 1 H), 6.76 (dt, J=7.5, 1.4 Hz), 6.93 (δ, J=8.4, 3.6, 1.2 Hz, 1 H), 7.34 (t, J =8.1 Hz, 1 H). FAB-MS: calcd for ($C_{24}H_{35}NO_2$) 369, found 370 (M+1). mp 65–66°.

EXAMPLE 172

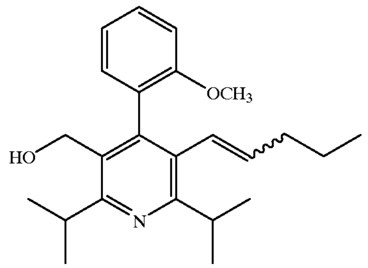

2,6-Diisopropyl-3-hydroxymethyl-4-(2-methoxyphenyl)-5-(pent-1-enyl)pyridine

The title compound was prepared from 2-methoxybenzaldehyde by the methods detailed in Example 125. $^1$H NMR (300 MHz, $CDCl_3$): δ 0.82 and 0.72 (t, J =7 Hz, 3 H), 1.05–1.47 (m, 15 H), 1.80–2.00 (m, 1 H), 2.05 (bs, 1 H), 3.21–3.60 (m, 2 H), 3.75 and 3.76 (s, 3 H), 4.27 (d, J=11.4 Hz, 1 H), 4.43 (d, J=11.4 Hz, 1 H), 5.25–5.44 (m, 1 H), 6.01–6.07 (m, 1 H), 6.93–7.03 (m, 3 H), 7.29–7.37 (m, 1 H).

EXAMPLE 173

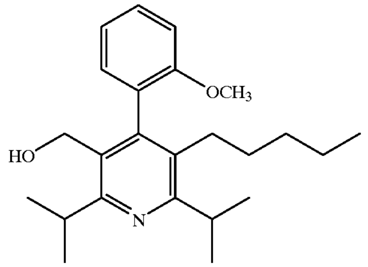

2,6-Diisopropyl-3-hydroxymethyl-4-(2-methoxyphenyl)-5-pentylpyridine

The title compound was prepared from 2,6-diisopropyl-3-hydroxymethyl-4-(2-methoxyphenyl)-5-(pent-1-enyl) pyridine (Example 172) by the methods detailed in Example 126. $^1$H NMR (300 MHz, $CDCl_3$): δ 0.77 (t, J=6.6 Hz, 3 H), 1.06–1.11 (m, 4 H), 1.22–1.38 (m, 14 H), 1.87 (dd, J=9.3, 3.3 Hz, 1 H), 2.14–2.40 (m, 2 H), 3.25 (sept, J =6.6 Hz, 1 H), 3.46 (sept, J=6.6 Hz, 1 H), 3.76 (s, 3 H), 4.19 (dd, J=11.7, 3.0 Hz, 1 H), 4.39 (dd, J=11.7, 9.0 Hz), 7.00–7.08 (m, 3 H), 7.35–7.42 (m, 1 H).

EXAMPLE 174

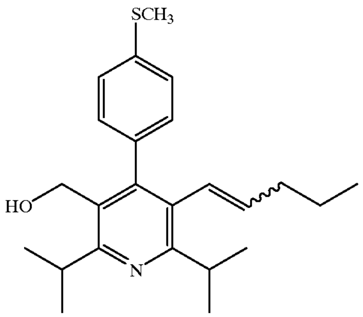

2,6-Diisopropyl-3hydroxymethyl-4-[4-(methylthio) phenyl]-5-(pent-1-enyl)pyridine The title compound was prepared as a thick colorless oil from 4-(methylthio)benzaldehyde by the methods detailed in Example 125. $^1$H NMR (300 MHz, $CDCl_3$): δ 0.66 and 0.72 (t, J=7.5 Hz, 3 H), 1.05–1.32 (m, 14 H), 1.51–1.70 (bs, 1 H), 1.80–1.89 (m, 2 H), 2.43 (s, 3 H), 3.12–3.41 (m, 2 H), 4.32 (bs, 2 H), 5.17–5.40 (m, 1 H), 5.85–5.97 (m, 1 H), 6.99 (d, J=8.1 Hz), 7.18 (d, J=8.1 Hz, 2 H).

EXAMPLE 175

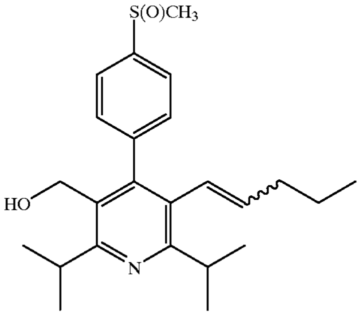

2,6-Diisopropyl-3-hydroxymethyl-4-[4-(methylsulfinyl)phenyl]-5-(pent-1-enyl)pyridine 2,6Diisopropyl-3-hydroxymethyl-4-[4-(methylthio) phenyl]-5-(pent-1-enyl)pyridine (100 mg, 0.261 mmol) (Example 174) was dissolved in methylene chloride (1.5 mL) and stirred at 0° C. under an argon atmosphere. To this mixture was added a solution containing 3-chloroperoxybenzoic add ("mCPBA") (85%, 53 mg, 0.261 mmol) in methylene chloride (1 mL). The mixture was stirred for 1.5 h at 0° C. and quenched with the addition of a saturated aqueous solution of $NaHSO_3$ (3 mL). The reaction mixture was further diluted through the addition of water (5 mL) and then extracted with methylene chloride (3×10 mL). The combined organic layer was washed sequentially with a saturated aqueous solution of sodium bicarbonate (10 mL) and brine (10 mL), dried ($Na_2SO_4$), and concentrated under reduced pressure. The resultant residue was purified by flash chromatography to yield the title compound (52 mg, 50%) as a white solid, mp 133–135° C. $^1$H NMR (300 MHz, $CDCl_3$): δ 0.77 and 0.69 (t, J=7.5 Hz, 3 H), 1.08–1.36 (m, 14 H), 1.70–1.92 (m, 3 H), 2.75 and 2.76 (s, 3 H), 3.19–3.51 (m, 2 H), 4.32–4.40 (m, 2 H), 5.20–5.45 (m, 1 H), 5.93–6.00 (m, 1 H), 7.31–7.38 (m, 2 H), 7.59–7.70

(m, 2 H). Anal. calc. for $C_{24}H_{33}NO_2S$: C, 71.86; H, 8.29; N, 3.39; S, 7.73. Found: C, 72.14; H, 8.32; N, 3.51; S, 8.02.

EXAMPLE 176

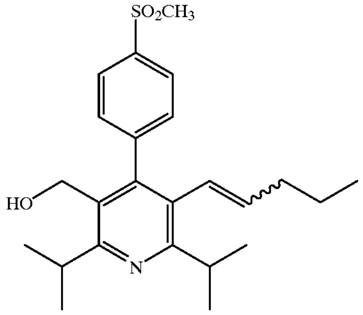

2,6-Diisopropyl-3-hydroxymethyl-4-[4-(methylsulfonyl)phenyl]-5-(pent-1-enyl)pyridine 2,6-Diisopropyl-3-hydroxymethyl-4-[4-(methysulfinyl)phenyl]-5-(pent-1-enyl)pyridine (100 mg, 0.261 mmol) (Example 174) was dissolved in methylene chloride (1.5 mL) and stirred at 0° C. under an argon atmosphere. To this mixture was added a solution containing 3-chloroperoxybenzoic acid ("mCPBA") (85%, 53 mg, 0.261 mmol) in methylene chloride (1 mL). The mixture was stirred for 1.5 h at 0° C. and quenched with the addition of a saturated aqueous solution of $NaHO_3$ (3 mL). The reaction mixture was further diluted through the addition of water (5 mL) and then extracted with methylene chloride (3×10 mL). The combined organic layer was washed sequentially with a saturated aqueous solution of sodium bicarbonate (10 mL) and brine (10 mL), dried ($Na_2SO_4$), and concentrated under reduced pressure. The resultant residue was purified by flash chromatography to yield the title compound (31.1 mg, 29%). $^1H$ NMR (300 MHz, $CDCl_3$): δ 0.69 and 0.79 (t, J=7.2 Hz, 3 H), 1.08–1.37 (m, 14 H), 1.45 (t, J=4.2 Hz, 1 H), 1.86–1.93 (m, 2 H), 3.10 and 3.11 (s, 3 H), 3.2–3.50 (m, 2 H), 4.34–4.36 (m, 2 H), 5.20–5.50 (m, 1 H), 5.93–6.00 (m, 1 H), 7.41 (d, J=8.4 Hz, 2 H), 7.96 (d, J=8.4 Hz, 2 H). Anal. calc. for $C_{24}H_{33}NO_3S$: C, 69.28; H, 7.91; N, 3.18; S, 7.50. Found: C, 69.36; H, 8.00; N, 3.37; S, 7.71.

EXAMPLE 177

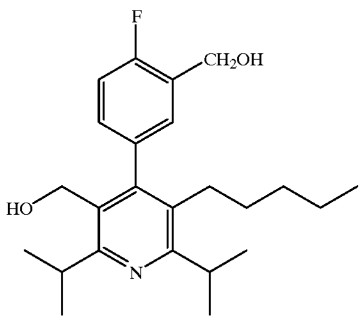

2,6-Diisopropyl-3-hydroxymethyl-4-[(4-fluoro-3-hydroxymethyl)phenyl]-5-pentylpyridine Step A: 2,6-Diisopropyl-3-[(t-butyldimethylsiloxy)methyl]-4-(4-fluorophenyl)-5-pentylpyridine To a solution of 2,6-diisopropyl-3-hydroxymethyl-4-(4-fluorophenyl)-5-pentylpyridine (3.14 g, 8.78 mmol) (Example 1, Step H) in methylene chloride (45 mL) were added imidazole (0.9 g, 13.17 mmol, 1.5 eq) and t-butyldimethylsilyl chloride (2.0 g, 13.17 mmol, 1.5 eq). A white precipitate began to form immediately. The mixture was stirred for 14 h at 25° C. and was then diluted with methylene chloride (100 mL) and washed sequentially with 10% hydrochloric add (20 mL), saturated aqueous sodium bicarbonate (20 mL), and brine (20 mL). The organic layer was concentrated under reduced pressure and the resultant residue was recrystallized from methanol to provide the product (3.27 g, 79%) as a white fluffy crystalline solid. $^1H$ NMR (300 MHz, $CDCl_3$): δ −0.10 (s, 6 H), 0.79 (t, J=6.9 Hz, 3 H), 0.83 (s, 9 H), 1.07–1.20 (m, 4 H), 1.29–1.32 (m, 14 H), 2.23–2.30 (m, 2 H), 3.21 (sept, J=6.6 Hz, 1 H), 3.35 (sept, J=6.6 Hz, 1 H), 4.24 (s, 2 H), 7.05–7.18 (m, 4 H). Anal. calc. for $C_{29}H_{46}NOFSi$: C, 73.83; H, 9.83; N, 2.97. Found: C, 73.82; H, 9.95; N, 2.86.

Step B: 2,6-Diisopropyl-3-[(t-butyldimethylsiloxy)methyl]-4-[(4-fluoro-3-hydroxymethyl)phenyl]-5-pentylpyridine To a solution of the intermediate from Step A (5.4 g, 11.4 mmol) in THF (80 mL) was added sec-butyllithium (1.3M, 26.4 mL, 3 eq) at −78° C. under an argon atmosphere. The yellow solution was stirred for 1 h at −78° C. and quenched through the addition of of water (50 mL). The mixture was allowed to warm to 25° C. and extracted with ethyl acetate (3×50 mL) and the organic layer was washed with water (50 mL) and brine (50 mL), dried ($Na_2SO_4$), and concentrated under reduced pressure to afford the crude intermediate. (6.41 g).

This intermediate (3.2 g) was dissolved in THF (50 mL) and stirred at 0° C. as lithium aluminum hydride ("LAH") (1M in THF, 25.7 mL, 25.7 mmol) was added to it. The resultant mixture was stirred at 0° C. for 1.5 h and quenched through the sequential addition of water (1 mL), 1N aqueous sodium hydroxide (1 mL), and water (3 mL). The resultant mixture was filtered and the precipitate rinsed with ether (100 mL). The combined organic layer was washed with water (25 mL) and brine (25 mL), dried ($Na_2SO_4$), and concentrated under reduced pressure. The resultant residue was subjected to flash chromatography using a 10% ether-hexane mixture as the eluent. In this manner, 1.1 g of the product was obtained. $^1H$ NMR (300 MHz, $CDCl_3$): δ −0.09 (s, 6 H), 0.83 (s, 9 H), 1.07–1.20 (m, 4 H), 1.29–1.33 (m, 17 H), 1.96–2.02 (m, 1 H), 2.22–2.31 (m, 2 H), 3.23 (sept, J=6.6 Hz, 1 H), 3.36 (sept, J=6.6 Hz, 1 H), 4.22–4.32 (m, 2 H), 4.70–4.90 (m, 2 H), 7.09–7.12 (m, 2 H), 7.23–7.28 (m, 1 H).

Step C: 2,6-Diisopropyl-3-hydroxymethyl-4-[(4-fluoro-3-hydroxymethyl)phenyl]-5-pentylpyridine To a solution of the intermediate from Step B (123 mg, 0.245 mmol) in THF (3 mL) was added tetrabutylammonim fluoride (1M in THF, 0.7 mL, 0.7 mmol) at 25° C. under an argon atmosphere. The mixture was stirred for 14 h at 25° C. and is then diluted with water (5 mL) and extracted with methylene chloride (3×5 mL). The combined organic layer was washed with brine (5 mL), dried ($Na_2SO_4$) and concentrated under reduced pressure. The resultant residue was purified by flash chromatography using a 40% ethyl acetate-hexane mixture as the eluent. In this manner, the title compound (79 mg, 83%) was produced as a colorless oil. $^1H$ NMR (300 MHz, $CDCl_3$): δ 0.78 (t, J=6.6 Hz, 3 H), 1.10–1.17 (m, 4 H), 1.24–1.35 (m, 14 H), 2.10–2.40 (m, 2 H), 2.73 (bs, 1 H), 3.22 (sept J=6.6 Hz, 1 H), 3.34 (sept, J=6.6 Hz, 1 H), 3.85 (bs, 1 H), 4.06 (d, J=11.4 Hz, 1 H), 4.35

(d, J=11.4 Hz, 1 H), 4.48 (d, J=14.1 Hz, 1 H), 4.73 (d, J=14.1 Hz, 1 H), 7.00–7.06 (m, 2 H), 7.25 (d, J=7.2 Hz, 1 H).

EXAMPLE 178

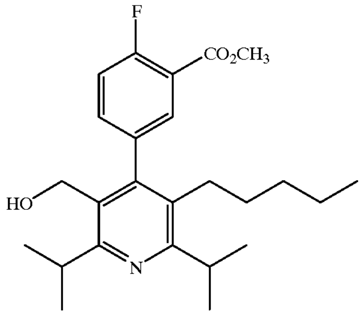

2,6-Diisopropyl-3-hydroxymethyl-4-[(4-fluoro-3-methoxycarbonyl)-phenyl]-5-pentylpyridine Step A: 2,6-Diisopropyl-3-[(t-butyldimethylsiloxy) methyl-4-[(4-fluoro-3-formyl)phenl]-5-pentylpyridine To a solution of 2,6-diisopropyl-3-[(t-butyldimethylsiloxy)methyl]-4[(4-fluoro-3-hydroxymethyl) phenyl]-5pentylpyridine (Example 177, Step B) (1.09 g, 2.18 mmol) in methylene chloride (100 mL) was added a mixture of PCC (0.94 g, 4.35 mmol, 2 eq) and Celite (0.94 g). The resultant mixture was stirred for 2 h at 25° C. and then filtered through a pad of silica gel. The silica gel pad was rinsed with a 10% ethyl acetate-hexane mixture (200 mL) and the combined organic layer was concentrated to afford the crude product (0.78 g) as a white waxy solid.

Step B: 2,6Diisopropyl-3-[(t-butyldimethylsiloxy) methyl]-4-[(4-fluoro-3-methoxycarbonyl)phenyl]-5-pentylpyridine To a solution of the intermediate from Step A (82 mg, 0.164 mmol) in methanol (3 mL) were added potassium cyanide (53 mg, 0.82 mmol) and activated manganese dioxide (71 mg, 5 eq). The mixture was stirred at 25° C. for 14 h and is then filtered through a pad of Celite. The Celite pad was rinsed with ethyl acetate (25 mL) and the combined organic layer was washed with brine (5 mL), dried ($Na_2SO_4$), and concentrated under reduced pressure. The resultant residue was purified by flash chromatography to provide the intermediate (70 mg). $^1H$ NMR (300 MHz, $CDCl_3$): δ -0.13 (s, 6 H), 0.75 (t, J=6.6 Hz, 3 H), 1.06–1.40 (m, 27 H), 2.20–2.35 (m, 2 H), 3.20 (sept, J=6.6 Hz, 1 H), 3.32 (sept, J=6.6 Hz, 1 H), 4.15 (d, J=10.8 Hz, 1 H), 4.25 (d, J=10.8 Hz, 1 H), 7.15–7.25 (m, 1 H), 7.40–7.50 (m, 1 H), 7.69 (dd, J=6.6, 2.4 Hz, 1 H), 10.41 (s, 1 H). FAB-MS: calcd for ($C_{30}H_{46}NO_2FSi$) 499, found 500 (M+1).

Step C: 2,6-Diisopropyl-3-hydroxymethyl-4-[(4-fluoro-3-methoxy-carbonyl)phenyl]-5-pentylpyridine The title compound was prepared from the intermediate obtained in Step B by the method detailed in Example 177, Step C. $^1H$ NMR (300 MHz, $CDCl_3$): δ 0.78 (t, J=6.6 Hz, 3 H), 1.08–1.16 (m, 4 H), 1.23–1.34 (m, 15 H), 2.20–2.30 (m, 2 H), 3.22 (sept, J=6.6 Hz, 1 H), 3.40 (sept, J=6.6 Hz, 1 H), 3.93 (s, 3 H), 4.25–4.39 (m, 2 H), 7.12 (dd, J=10.3, 8.5 Hz, 1 H), 7.28 (δ, J=8.5, 4.8, 2.2 Hz, 1 H), 7.69 (dd, J=6.6, 2.2 Hz, 1 H).

EXAMPLE 179

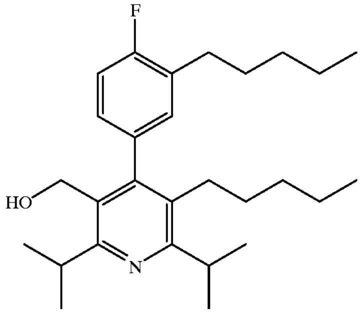

2,6-Diisopropyl-3-hydroxymethyl-4-[(4-fluoro-3-pentyl)phenyl]-5-pentylpridine

Step A: 2,6-Diisopropyl-3-[(t-butyldimethysiloxy) methyl]-4-(4-fluoro-3-(pent-1-enyl))phenyl]-5-pentylpyridine To a solution of 2,6-diisopropyl-3-[(t-butyldimethylsiloxy)methyl]-4-[(4-fluoro-3-formyl) phenyl]-5-pentylpyridine (Example 178, Step A) (200 mg, 0.40 mmol) in THF (10 mL) was added a butyltriphenylphosphonium bromide/sodium 20 amide mixture (Fluka, 0.55 g, 3 eq) under an argon atmosphere. The reaction was stirred at 25° C. for 1.5 h and is quenched by dropwise addition of water (3 mL) and further diluted with brine (5 mL). The mixture was extracted with ethyl acetate (2×20 mL) and the combined organic layer was dried ($Na_2SO_4$) and concentrated under reduced pressure. The resultant residue was subjected to flash 25 chromatography to yield the intermediate (205 mg). $^1H$ NMR (300 MHz, $CDCl_3$): δ -0.13 (s, 6 H), 0.7–1.47 (m, 35 H), 2.13–2.33 (m, 4 H), 3.21 (septet, J=6.6 Hz, 1 H), 3.34 (septet, J=6.6 Hz, 1 H), 2.7 (d, J=2.7 Hz, 2 H), 5.75–6.31 (m, 1 H), 6.41–6.59 (m, 1 H), 6.98–7.09 (m, 3 H). FAB-MS: calcd for ($C_{34}H_{54}NOFSi$) 539, found 540 (M+1).

Step B: 2,6-Diisopropyl-3-[(t-butyldimethylsiloxy) methyl]-4-[(4-fluoro-3-pentyl)phenyl]-5-pentylpyridine The intermediate from Step A (200 mg) was dissolved in ethanol (10 mL) and the mixture purged with argon. A quantity of 10% Pd-C (20 mg) was then added and the mixture was purged with hydrogen and stirred under a hydrogen atmosphere at 25° C. for 16 h. The mixture was then filtered through a pad of silica and the silica pad as rinsed with ethanol (25 mL). The organic layer was concentrated under reduced pressure and the resultant residue was subjected to flash chromatography using hexane as the eluent to afford the intermediate (150 mg, 75%). $^1H$ NMR (300 MHz, $CDCl_3$): δ -0.11 (s, 6 H), 0.76–1.65 (m, 39 H), 2.17–2.33 (m, 2 H), 2.51–2.78 (m, 2 H), 3.21 (septet, J=6.6 Hz, 1 H), 3.35 (septet, J=6.6 Hz, 1 H), 4.42 (dd, J=10.2, 16.2, 2 H), 6.92–7.05 (m, 3 H). FAB-MS: calcd for ($C_{34}H_{56}NOFSi$) 541, found 542 (M+1).

Step C: 2,6-Diisopropyl-3-hydroxymethyl-4-[(4-fluoro-3-pentyl)-phenyl]-5-pentylpyridine The title compound was prepared as a colorless oil from the intermediate from Step B by the method detailed in Example 177, Step C. $^1H$ NMR (300 MHz, $CDCl_3$): δ 0.77

(t, J=6.9 Hz, 3 H), 0.88 (t, J=6.9 Hz, 3 H), 1.08–1.34 (m, 24 H), 1.57–1.65 (m, 1 H), 2.22–2.29 (m, 2 H), 2.57–2.75 (m, 2 H), 3.21 (sept, J=6.6 Hz, 1 H), 3.40 (sept, J=6.6 Hz, 1 H), 4.33 (dd, J=5.6, 1.4 Hz, 2 H), 6.93–7.09 (m, 3 H). FAB-MS: calcd for ($C_{28}H_{42}NOF$) 427, found 428 (M+1). $R_f$=0.42 (20% ether-hexanes).

EXAMPLE 180

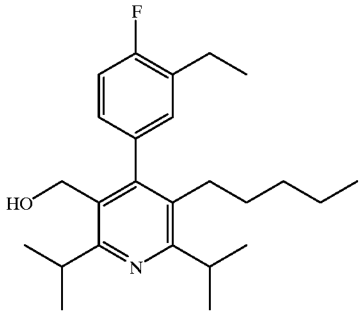

2,6-Diisopropyl-3-hydroxymethyl-4-[(4-fluoro-3-pentyl)-pentyl]-5-pentylpyridine

The title compound was prepared as a white wax from 2,6diisopropyl-3-[-(t-butyldimethylsiloxy)methyl]-4-[(4fluoro-3-formyl)phenyl]-5pentylpyridine (Example 178, Step A) (200 mg, 0.40 mmol) and an ethyltriphenylphosphonium bromide/sodium amide mixture (Fluka) by the methods detailed in Example 179, Steps A–C. $^1$H NMR (300 MHz, $CDCl_3$): δ 0.77 (t, J=6.9 Hz, 3 H), 1.10–1.33 (m, 22 H), 2.17–2.33 (m, 2 H), 2.60–2.80 (m, 2 H), 3.21 (sept, J=6.6 Hz, 1 H), 3.40 (sept, J=6.6 Hz, 1 H), 4.34 (dd, J=5.7, 1.8 Hz, 2 H), 6.94–7.09 (m, 3 H). FAB-MS: calcd for ($C_{25}H_{36}NOF$) 385, found 386 (M+1). $R_f$=0.38 (20% ether-hexanes).

EXAMPLE 181

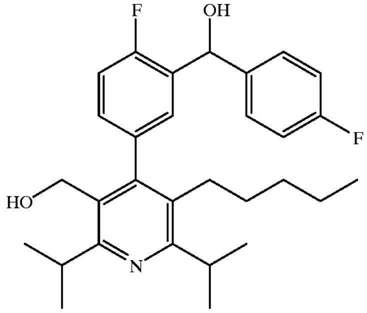

2,6-Diisopropyl-3-hydroxymethyl-4-[-fluoro-3-(α-hydroxy-4-fluoro-benzyl)]-5-pentylpyridine Step A: 2,6-Diisopropyl-3-(t-butyldimethylsilyloxymethyl)]-4-[4-fluoro-3-(α-hydroxy-4-fluorobenzyl)phenyl]-5-pentyl-pyridine To a solution of 2,6-diisopropyl-3[(t-butyldimethylsiloxy)methyl]-4-[(4-fluoro-3-formyl)phenyl]-5-pentylpyridine (160 mg, 0.321 mmol) (Example 178, Step A) in THF (10 mL) was added 4-fluorophenyl magnesium bromide (1.0M in THF, 0.4 mL, 2.5 eq) under an argon atmosphere at 25° C. The mixture was stirred for 30 min and then quenched by the dropwise addition of water (5 mL). The mixture was extracted with ether (2×10 mL) and the combined organic layer was washed with brine, dried ($Na_2SO_4$), and concentrated under reduced pressure. The resultant residue was purified by flash chromatography using a 10% ether-hexane mixture as the eluent to provide 150 mg of the intermediate. $^1$H NMR (300 MHz, $CDCl_3$): δ -0.19 (d, 6.3 Hz, 3 H), -0.10 (d, J=7.2 Hz, 3 H), 0.71–1.30 (m, 30 H), 2.17–25 2.28 (m, 3 H), 3.18 (septet, J=6.6 Hz, 1 H), 3.25–3.40 (m, 1 H), 4.04–4.38 (m, 2 H), 6.14 (dd, J=4.4, 17.9 Hz, 1 H), 6.97–7.38 (m, 7 H). FAB-MS: calcd for ($C_{36}H_{51}NOF_2Si$) 595, found 596 (M+1).

Step B: 2,6-Diisopropyl-3-hydroxymethyl-4-[4-fluoro-3-(α-hydroxy-4-fluorobenzyl)phenyl]-5-pentylpyridine The title compound was prepared from the intermediate from Step A by the method detailed in Example 177, Step C. $^1$H NMR (300 MHz, $CDCl_3$): δ 0.72–1.45 (m, 22 H), 2.13–2.36 (m, 2 H), 2.65 (d, J=4.2 Hz, 1 H), 3.21 (sept, J=6.6 Hz, 1 H), 3.39 (sept, J=6.6 Hz, 1 H), 4.21–4.39 (m, 2 H), 6.14–6.17 (m, 1 H), 6.98–7.12 (m, 4 H), 7.35–7.42 (m, 3 H). FAB-MS: calcd for ($C_{30}H_{37}NO_2F_2$) 481, found 482 (M+1). $R_f$=0.21, 0.51 (50% ether-hexanes). mp 118–120° C.

EXAMPLE 182

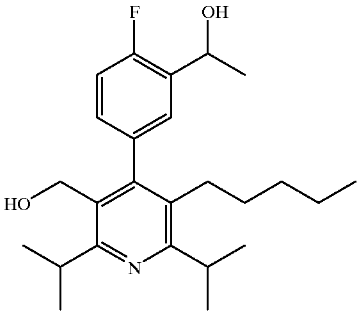

2,6-Diisopropyl-3-hydroxymethyl-4-[4-fluoro-3-(1-hydroxyethyl)phenyl]-5-pentylpyridine The title compound was prepared as an oil from 2,6-diisopropyl-3-[(t-butyldimetylsiloxy)methyl]-4-[(4-fluoro-3-formyl)phenyl]-5-pentylpyridine (Example 178, Step A) and methylmagnesium bromide by the methods detailed in Example 181, Steps A–B. $^1$H NMR (300 MHz, $CDCl_3$): δ 0.76 (t, J=6.0 Hz, 3 H), 1.09–1.53 (m, 21 H), 1.84 (br s, 1 H), 2.18–2.27 (m, 2 H), 2.87 (br s, 1 H), 3.20 (septet, J=6.6 Hz, 1 H), 3.37 (septet, J=6.6 Hz, 1 H), 4.16 (d, J=11.4 Hz, 1 H), 4.28–4.35 (m, 1 H), 5.16–5.19 (m, 1 H), 7.01–7.07 (m, 2 H), 7.25–7.34 (m, 1 H). FAB-MS: calcd for ($C_{25}H_{36}NO_2F$) 401, found 402 (M+1). $R_f$=0.32 and 0.20 (50% ether-hexanes).

EXAMPLE 183

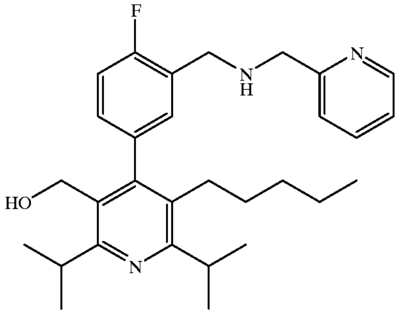

2,6-Diisopropyl-3-hydroxymethyl-4-[4-fluoro-3-((N-((pyridin-2-yl)-methyl)amino)methyl)]phenyl-5-pentylpyridine Step A: 2,6-Diisopropyl-3-[(t-butyldimethylsiloxy)methyl]-4-[4-fluoro-3-((N-((pyridin-2-yl)methyl)amino)methyl)]phenyl-5-pentylpyridine To a solution of 2,6-diisopropyl-3-[(t-butyldimethylsiloxy)methyl]-4-[(4-fluoro-3-formyl)phenyl]-5-pentylpyridine (500 mg, 1 mmol) (Example 178, Step A) in methanol (10 mL) and ether (2 mL) was added 2-methylaminopyridine (0.42 mL, 4 mmol, 4 eq) under an argon atmosphere at 25° C. To this solution were added $ZnCl_2$ (68.1 mg, 0.5 eq) and sodium cyanoborohydride (62.8 mg, 1 eq) in methanol (6 mL). The reaction was allowed to stir for 20 h and was then quenched with the addition of aqueous sodium hydroxide (0.1N, 7 mL). The methanol was removed under reduced pressure and the aqueous residue was extracted with ethyl acetate (3×30 mL). The organic layer was washed with water (10 mL) and brine (10 mL), dried ($Na_2SO_4$), and concentrated under reduced pressure. The resultant residue was subjected to flash chromatography using a 60% ether-hexane mixture as the eluent to provide the intermediate (260 mg, 44%). $^1$H NMR (300 MHz, $CDCl_3$): δ−0.12 (s, 6 H), 0.72–0.81 (m, 12 H), 1.80 (br s, 1 H), 1.07–1.15 (m, 4 H), 1.27–1.31 (m, 14 H), 2.23–2.29 (m, 2 H), 3.20 (septet, J=6.6Hz, 1 H), 3.34 (septet, J=6.6 Hz, 1 H), 3.83–4.03. (m, 4 H), 4.25 (dd, J=10.5, 27.6 Hz, 2 H), 7.06–7.33 (m, 5 H), 7.64 (δ, J=1.8, 7.5, 7.5 Hz, 1 H), 8.54–8.56 (m, 1 H). FAB-MS: calcd for ($C_{36}H_{54}NO_3FSi$) 591, found 592 (M+1).

Step B: 2,6-Diisopropyl-3-hydroxymethyl-4-[4-fluoro-3-((N-((pyridin-2-yl)methyl)amino)methyl)]phenyl-5-pentylpyridine The title compound was prepared as a colorless oil from the intermediate obtained in Step A by the method detailed in Example 177, Step C. $^1$H NMR (300 MHz, $CDCl_3$): δ 0.75 (t, J=6.9 Hz, 3H), 1.07–1.36 (m, 18 H), 1.75 (bs, 21 ), 2.19–2.36 (m, 2 H), 3.20 (sept, J=6.6 Hz, 1 H), 3.47 (sept, J=6.6 Hz, 1 H), 3.74 (d, J=14.1 Hz, 1 H), 3.79 (d, J=13.5 Hz, 1 H), 3.89 (d, J=13.5 Hz, 1 H), 4.07 (d, J=14.1 Hz, 1 H), 4.20 (d, J=11.4 Hz, 1 H), 4.41 (d, J=11.4 Hz, 1 H), 7.02–7.25 (m, 4 H), 7.38 (d, J=7.8 Hz, 1 H), 7.66 (δ, J=7.5, 7.5, 1.8 Hz, 1 H), 8.47 (m, 1 H). FAB-MS: calcd for ($C_{30}H_{40}N_{30}F$) 477, found 478 (M+1). $R_f$=0.4 (ethyl acetate).

EXAMPLE 184

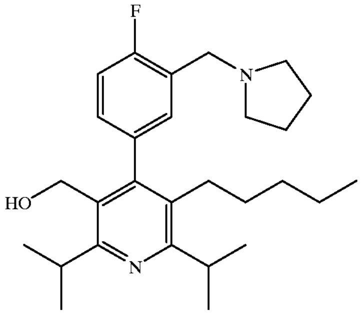

2,6-Diisopropyl-3-hydroxymethyl-4-[4-fluoro-3-(pyrrolidin-1-yl)methyl]phenyl-5-pentylpyridine The title compound was prepared from 2,6-diisopropyl-3[(t-butyldimethylsiloxy)methyl]-4-[(fluoro-3-formyl)phenyl]-5-pentylpyridine (Example 178, Step A) by the methods detailed in Example 183, Steps A–B. $^1$H NMR (300 MHz, $CDCl_3$): δ 0.77 (t, J=6.6 Hz, 3 H), 1.05–1.31 (m, 18 H), 1.75–1.85 (m, 5 H), 2.23–2.29 (m, 2 H), 2.50–3.50 (m, 4 H), 3.20 (sept, J=6.6 Hz, 1 H), 3.41 (sept, J=6.6 Hz, 1 H), 3.71 (d, J=12.9 Hz, 1 H), 3.82 (d, J=12.9 Hz, 1 H), 4.29 (dd, J=11.7, 20.4 Hz, 2 H), 7.03–7.13 (m, 2 H), 7.26–7.30 (m, 1 H). FAB-MS: calcd for ($C_{28}H_{41}NO_2F$) 440, found 441 (M+1). $R_f$=0.2 (ethyl acetate).

EXAMPLE 185

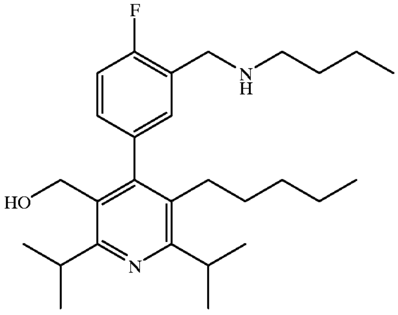

2,6-Diisopropyl-3-hydroxymethyl-4-[4-fluoro-3-(butylamino)methyl]phenyl-5-pentylpyridine The title compound was prepared from 2,6-diisopropyl-3-[(t-butyldimetylsiloxy)methyl]-4-[(4-fluoro-3-formyl)phenyl]-5-pentylpyridine (Example 178, Step A) by the methods detailed in Example 183, Steps A–B. $^1$H NMR (300 MHz, $CDCl_3$): δ 0.79 (t, J=6.8 Hz, 3 H), 0.91 (t, J=7.4 Hz, 3 H), 1.10–1.61 (m, 24 H), 2.25–2.31 (m, 2 H), 2.62 (t, J=7.2 Hz, 2 H), 3.23 (sept, J=6.6 Hz, 1 H), 3.42 (sept, J=6.6 Hz, 1 H), 3.89 (s, 2 H), 4.32 (dd, 11.7 Hz, 2 H), 7.04–7.20 (m, 3 H). FAB-MS: calcd for ($C_{28}H_{43}NO_2F$) 442, found 443 (M+1). $R_f$=0.33 (ethyl acetate).

EXAMPLE 186

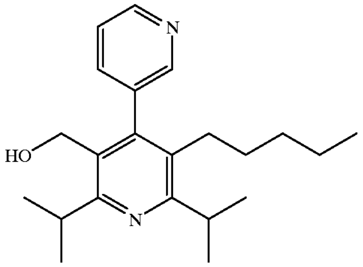

2,6-Diisopropyl-3-hydroxymethyl-4-(pyridin-3-yl)-5-pentylpyridine

The title compound was prepared as an oil from ethyl isobutyryl acetate, ammonium acetate and pyridine-3-carboxaldehyde in 0.56% yield by the methods described in Example 125. FAB-MS: calculated for $C_{22}H_{32}N_2O$ 340; found 341 (M+1). $^1H$ NMR (300 MHz, $CD_3OD$): δ 0.77 (t, J=6.5 Hz, 3 H), 1.08–1.32 (m, 18 H), 2.27–2.33 (m, 2 H), 3.28 (septet, J=6.6 Hz, 1 H), 3.48 (septet, J=6.6 Hz, 1 H), 4.25 (s, 2 H), 7.52–7.57 (m, 1 H), 7.73–7.76 (m, 1 H), 8.42–8.43 (m, 2 H), 8.59 (dd, J=5.1, 1.5 Hz, 1 H). Anal. calc for $C_{22}H_{32}N_2O$: C, 77.60; H, 9.47; N, 8.23. Found: C, 75.96; H, 9.32; N, 7.88. $R_f$=0.40 (diethyl ether).

EXAMPLE 187

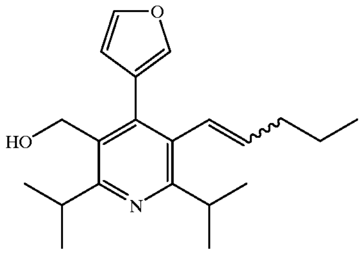

2,6-Diisopropyl-3-hydroxymethyl-4-(3-furyl)-5-(pent-1-enyl)pyridine

Substituting 2,3-dichloro-5,6-dicyano-1,4-benzoquinone (DDQ) for ceric ammonium nitrate (CAN) to oxidize the dihydropyridine intermediate to the phenyl pyridine, the title compound was prepared as a mixture of E and Z isomers (4.5:1, E:Z) from ethyl isobutyryl acetate, ammonium acetate and furan-3-carboxaldehyde in 10% yield by the methods described in Example 125. FAB-MS: calculated for $C_{21}H_{29}NO_2$ 327; found 328 (M+1). $^1H$ NMR (300 MHz, $CD_3OD$): δ 0.84 (t, J=7.4 Hz, 3 H), 1.17–1.38 (m, 14 H), 2.01–2.04 (m, 2 H), 3.39 (septet, J=6.6 Hz, 1 H), 3.47 (septet, J=6.6 Hz, 1 H), 4.44 (s, 2 H), 5.40–5.58 (m, 2 H), 6.11–6.25 (m, 1 H), 6.38–6.40 (m, 1 H), 7.41–7.54 (m, 2 H).

EXAMPLE 188

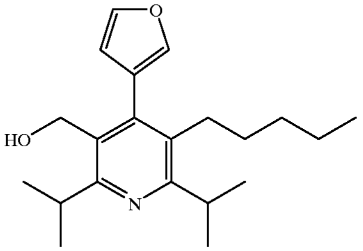

2,6-Diisopropyl-3-hydroxymethyl-4-(3-furyl)-5-pentylpyridine

The title compound was prepared from 2,6-diisopropyl-3-hydroxymethyl-4-(3-furyl)-5-(pent-1-enyl)pyridine (Example 187) in 6% yield by the methods described in Example 125. FAB-MS: calculated for $C_{21}H_{31}NO_2$ 329; found 330 (M+1). $^1H$ NMR (300 MHz, $CD_3OD$): δ 0.83 (t, J=6.8 Hz, 3 H), 1.19–1.36 (m, 19 H), 2.42–2.48 (m, 2 H), 3.25 (septet, J=6.6 Hz, 1 H, 3.45 (septet, J=6.6 Hz, 1 H), 4.38 (s, 2 H), 6.42 (m, 1 H), 7.45–7.46 (m, 1 H), 7.61–7.62 (t, J=1.7 Hz, 1 H). Anal. calc for $C_{21}H_{31}NO2$: C, 76.55; H, 9.48; N, 4.25. Found: C, 76.41; H, 9.76; N, 4.24. $R_f$=0.59 (20% EtOAc/hex). mp 98–100 ° C.

EXAMPLE 189

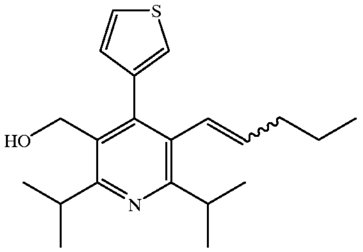

2,6-Diisopropyl-3-hydroxymethyl-4-(thiophen-3-yl)-5-(pent-1-enyl-pyridine

The title compound was prepared as a mixture of E and Z isomers (5.5:1, E:Z) from ethyl isobutyrylacetate, ammonium acetate and thiophene-3-carboxaldehyde in 7% yield by the methods described in Example 125. FAB-MS: calculated for $C_{21}H_{29}NOS$ 343; found 344 (M+1). $^1H$ NMR (300 MHz, $CDCl_3$): δ 0.78–0.84 (m, 3 H), 1.22–1.37 (m, 15 H), 1.96–2.00 (m, 2 H), 3.37–3.50 (m, 2 H), 4.47 (d, J=5.7 Hz, 2H), 5.32–5.43 (m, 1 H), 6.02–6.12 (m, 1 H), 6.95–6.97 (m, 1 H), 7.12–7.13 (m, 1 H), 7.35–7.38 (m, 1 H). Anal. calc for $C_{21}H_{29}NOS$: C, 73.43; H, 8.52; N, 4.08; S, 9.32. Found: C, 73.38; H, 8.75; N, 3.97; S, 9.03. $R_f$=0.65 (20% EtOAc/hex). mp 85–87° C.

EXAMPLE 190

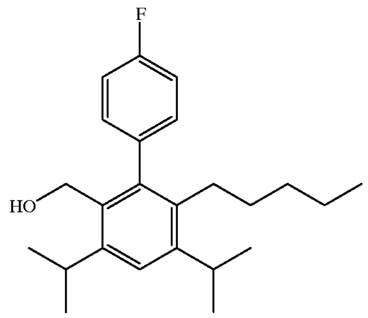

3,5-Diisopropyl-2-hydroxymethyl-6-pentyl-4'-fluoro-1,1'-biphenyl

Step A: 1-(2-Methoxyethoxy)methoxymethyl-2,4-diisopropyl-5-hydroxymethylbenzene

A mixture of 1,5-bis(hydroxymethyl)-2,4-diisopropylbenzene (0.947 g, 4.26 mmol) (prepared by the method of Fey, et al. U.S. Pat. No. 5,138,090), methoxyethoxymethyl chloride (0.49 mL, 4.29 mmol), and diisopropylethylamine (1.1 mL, 6.31 mmol) in $CH_2Cl_2$ (9.6 mL) was stirred overnight. The mixture was diluted with water (50 mL) and extracted with $CH_2Cl_2$ (3×50 mL). Silica gel chromatography (67:33 hexanes/ethyl acetate) provided a colorless oil (0.679 g, 51%). $^1$H NMR ($CDCl_3$, 300 MHz): δ 7.31 (s, 1 H), 7.29 (s, 1 H), 4.83 (s, 21 H), 4.72 (s, 2 H), 4.66 (s, 2 H), 3.76 (m, 2 H), 3.60 (m, 2 H), 3.43 (s, 3 H), 3.26 (m, 2 H), 1.27 (d, 7.0 Hz, 12 H). EI-MS: calculated for $C_{18}H_{30}O_4$ 310; found 292 (M-$H_2O$, 24%), 221 (100%).

Step B: 3-(2-Methoxyethoxy)methoxymethyl-4,6-diisopropylbenzaldehyde

Prepared from the intermediate obtained in Step A by the procedure described in Example 1, Step E. $^1$H NMR ($CDCl_3$, 300 MHz): δ 10.29 (s, 1 H), 7.80 (s, 1 H), 7.39 (s, 1 H), 4.83 (s, 2 H), 4.70 (s, 2 H), 3.98 (sept, 6.8 Hz, 1 H), 3.76 (m, 2 H), 3.59 (m, 2 H), 3.42 (s, 3 H), 3.26 (sept, 6.8 Hz, 1 H), 1.30 (d, 7.0 Hz, 6 H), 1.28 (d, 7.0 Hz, 6 H). FAB-MS: calculated for $C_{18}H_{28}O_4$ 308; found 309 (M+H).

Step C: N-Phenyl 3-(2-methoxyethoxy)methoxymethyl-4,6-diisopropylbenzimine

A mixture of the intermediate from Step B (2.35 g, 7.62 mmol), aniline (700 mL, 7.68 mmol), p-toluenesulfonic add (58.8 mg, 309 mmol), and molecular sieves (20.7 g) in toluene was refluxed overnight. The mixture was cooled to room temperature and filtered. The filtrate was diluted with ethyl acetate (65 mL) and washed with saturated aqueous $NaHCO_3$ solution (50 mL) and water (50 mL), dried ($MgSO_4$), and concentrated to give an orange oil (2.78 g, 96%). The product was used in the next step without purification. $^1$H NMR ($C_6D_6$, 300 MHz): δ 8.70 (s, 1 H), 8.48 (s, 1 H), 7.31 (s, 1 H), 7.17 (m, 4 H), 7.00 (m, 1 H), 4.61 (s, 2 H), 4.60 (s, 2 H), 3.56 (m, 2 H), 3.46 (sept, 6.8 Hz, 1 H), 3.29 (m, 2 H), 3.20 (sept, 6.8 Hz, 1 H), 3.07 (s, 3 H), 1.17 (d, 7.0 Hz, 6 H), 1.12 (d, 7.0 Hz, 6 H).

Step D: Bis[(2-N-phenylmethylimino)-3,5-diisopropyl-6-(2-methoxyethoxy)methoxymethylphenyl]dipalladium A mixture of the intermediate from Step C (2.78 g, 7.27 mmol) and $Pd(OAc)_2$ (1.63 g, 7.26 mmol) in acetic add (34 mL) was refluxed for 1 h. The mixture was cooled to rt, poured into water (135 mL), and filtered through a medium porosity fritted funnel. The filtrate was lyophilized. The residue was dissolved in ethyl acetate (100 mL) and washed with saturated aqueous $NaHCO_3$ (50 mL) and saturated aqueous NaCl (50 mL), dried ($MgSO_4$), and concentrated to give a brown solid. The solid was mixed with 50:50 petroleum ether/ethyl acetate (17 mL) and cooled in the freezer. The resulting precipitate was collected and dried to give a brown solid (0.951 g, 27%). $^1$H NMR ($C_6D_6$, 300 MHz): δ 7.70 (s, 1 H), 7.65 (s, 1 H), 7.63 (s, 1 H), 7.11 (s, 1 H), 7.08 (s, 1 H), 6.99 (m, 1 H), 6.73 (s, 1 H), 5.33 (s, 2 H), 5.08 (s, 2 H), 4.19 (m, 2 H), 3.35 (m, 2 H), 3.04 (s, 3 H), 2.68 (sept, 6.8 Hz, 1 H), 2.15 (sept, 6.8 Hz, 1 H), 1.01 (d, 7.0 Hz, 6 H), 0.96 (d, 7.0 Hz, 6 H). FAB-MS: calculated for $C_{48}H_{64}N_2O_6Pd_2$ 976; found 488 (M/2).

Step E: 3,5-Diisopropyl-2-formyl-6-(2-methoxyethoxy)methoxymethyl-4'-fluoro-1,1'-biphenyl A mixture of 1,2-dibromoethane (80 mL) and magnesium turnings (0.349 g, 14.4 mmol) in diethyl ether (1 mL) was heated to reflux for several minutes. The mixture was diluted with diethyl ether and a solution of 1-bromo-4-fluorobenzene (950 mL, 8.65 mmol) and 1,2-dibromoethane (160 mL) in diethyl ether (3 mL) was added over several minutes. The reflux was continued for 1 h then the mixture was cooled to room temperature. The supernatant liquid was added via cannula to a solution of the intermediate obtained in Step D (0.951 g, 973 mmol) and triphenylphosphine (2.02 g, 7.71 mmol) in benzene (19 mL) and the mixture stirred overnight. Aqueous 6N HCl (6 mL) was added and the mixture stirred for 2 h. The mixture was filtered and the solids washed with diethyl ether (75 mL). The combined filtrates were washed with saturated aqueous sodium chloride solution (50 mL). Silica gel chromatography provided a colorless solid (0.413 g, 53%). $^1$H NMR ($CDCl_3$, 300 MHz): δ 9.70 (s, 1 H), 7.50 (s, 1 H), 7.26 (m, 2 H), 7.11 (m, 2 H), 4.59 (s, 2 H), 4.30 (s, 2 H), 3.89 (sept, 6.8 Hz, 2 H), 3.55 (m, 2 H), 3.44 (m, 2 H), 3.37 (s, 3 H), 1.33 (d, 6.6 Hz, 6 H), 0.96 (d, 7.0 Hz, 6 H). FAB-MS: calculated for $C_{24}H_{31}FO_4$ 402; found 403 (M+H).

Step F: 3,5-Diisopropyl-2-(2-methoxyethoxy)methoxymethyl-6-(pent-1-enyl)-4'-fluoro-1,1'-biphenyl Prepared from the intermediate obtained in Step E by the procedure described in Example 1, Step F. The olefin was a mixture of cis and trans isomers in a ratio of 9:91. $^1$H NMR ($CDCl_3$, 300 MHz): δ 7.32 (s, 1 H), 7.12 (m, 2 H), 7.01 (m, 2 H), 5.95 (d, 16.2 Hz, 1 H), 5.23 (dt, 16.2 Hz, 7.0 Hz, 1 H), 4.57 (s, 2 H), 4.29 (s, 2 H), 3.53 (m, 2 H), 3.43 (m, 2 H), 3.37 (s. 3 H), 3.31 (m, 2 H), 1.89 (m, 2 H), 1.32 (d, 6.6 Hz, 6 H), 1.23 (d, 7.0 Hz, 6 H), 1.2 (m, 2 H), 0.74 (t, 7.4 Hz, 3 H). FAB-MS: calculated for $C_{28}H_{39}FO_3$ 442; found 442 ($M^+$).

Step G: 3,5-Diisopropyl-2-(2-methoxyethoxy)methoxymethyl-6-pentyl-4'-fluoro-1,1'-biphenyl Prepared from the intermediate obtained in Step F by the procedure described in Example 1, Step H. $^1$H NMR ($CDCl_3$, 300 MHz): δ 7.29 (s, 1 H), 7.19 (m, 2 H), 7.07 (m, 2 H), 4.52 (s, 2 H), 4.21 (s, 2 H), 3.51 (m, 2 H), 3.41 (m, 2 H), 3.37 (s, 3 H), 3.27 (sept, 6.8 Hz, 1 H), 3.16 (sept, 6.8 Hz, 1 H), 2.27 (m, 2 H), 1.30 (d, 7.0 Hz, 6 H), 1.27 (m, 2 H), 1.23 (d, 7.0 Hz, 6 H), 1.10 (m, 4 H), 0.77 (t, 6.8 Hz, 3 H). FAB-MS: calculated for $C_{28}H_{41}FO_3$ 444; found 445 (M+H).

Step H: 3,5Diisopropyl-2-acetoxymethyl-6-pentyl4'-fluoro-1,1'-biphenyl

Chlorotrimethylsilane (110 mL, 867 mmol) was added to a cooled (0° C.) mixture of the intermediate from Step G (62.4 mg, 140 mmol) and NaI (132 mg, 880 mmol) in $CH_3CN$ (1.4 mL). After 25 min. the mixture was filtered through silica gel (5:1 hexanes/ethyl acetate) and the filtrate concentrated. A mixture of the residue and sodium acetate (122 mg, 1.49 mmol) in dimethyl formamide (2.3 mL) was heated to 80° C. overnight. The solvent was removed and the residue dissolved in water (15 mL) and extracted with $CH_2Cl_2$ (3x15 mL). Silica gel chromatography (95:5 hexane/ethyl acetate) provided a colorless oil (38.2 mg, 69%). $^1$H NMR ($CDCl_3$, 300 MHz): δ 7.31 (s, 1 H), 7.15 (m, 2 H), 7.07 (m, 2 H), 4.76 (s, 2 H), 3.18 (sept, 6.8 Hz, 1 H), 3.12 (sept, 6.8 Hz), 2.28 (m, 2 H), 1.97 (s, 3 H), 1.29 (d, 6.6 Hz, 6 H), 1.29 (m, 2 H), 1.29 (d, 6.6 Hz, 6 H), 1.14–1.07 (m, 4 H), 0.78 (t, 6.8 Hz, 3 H). FAB-MS: calculated for $C_{26}H_{35}FO_2$ 398; found 338 (M-AcOH).

Step I: 3,5-Diisopropyl-2-hydroxymethyl-6-penty4'-fluoro-1,1'-biphenyl

A solution of the intermediate obtained in Step H (11.2 mg, 28.1 mmol) and potassium hydroxide (109 mg, 1.65 mmol) in methanol (2 mL) was heated at 50° C. for 3 h. The solvent was removed, and the residue dissolved in saturated aqueous ammonium chloride (15 mL) and extracted with diethyl ether (3x15 mL). Silica gel chromatography (5:1 hexane/ethyl acetate) provided the title compound as a colorless crystalline solid (12.0 mg, 120%). $^1$H NMR ($CDCl_3$, 300 MHz): δ 7.30 (s, 1 H), 7.19 (m, 2 H), 7.11 (m, 2 H), 4.32 (s, 2 H), 3.37 (sept, 6.9 Hz, 1 H), 3.16 (sept, 6.9 Hz, 1 H), 2.26 (m, 2 H), 1.31 (d, 6.6 Hz, 6 H), 1.29 (m, 2 H), 1.28 (d, 7.0 Hz, 6 H), 1.17–1.03 (m, 4 H), 0.77 (t, 6.8 Hz, 3 H). FAB-MS: calculated for $C_{24}H_{33}FO$ 356; found 356 ($M^+$). $R_f$=0.33 (83:17 hexanes/ethyl acetate). Anal. calculated for $C_{24}H_{33}FO$: C, 80.85; H, 9.33 Found: C, 80.63; H, 9.40. mp 98–99° C.

EXAMPLE 191

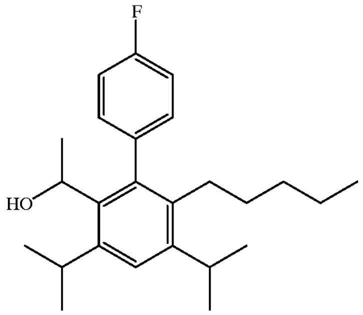

3,5-Diisopropyl-2-(1-hydroxyethyl)-6-pentyl-4'-fluoro-1,1'-biphenyl

Step A: 3,5-Diisopropyl-2-formyl-6-pentyl-4'-fluoro-1,1'-biphenyl

Prepared from 3,5-diisopropyl-2-hydroxymethyl-6-pentyl-4'-fluoro-1,1'-biphenyl (Example 190) by the procedure described in Example 1, Step E. $^1$H NMR ($CDCl_3$, 300 MHz): δ 9.70 (s, 1 H), 7.42 (s, 1 H), 7.23–7.10 (m, 4 H), 3.88 (sept, 6.8 Hz, 1 H), 3.23 (sept, 6.8 Hz, 1 H), 2.34 (m, 2 H), 1.31 (d, 6.6 Hz, 6 H), 1.29 (d, 7.0 Hz, 6 H), 1.28 (m, 2 H), 1.14 (m, 4 H), 0.79 (t, 6.6 Hz, 3 H). FAB-MS: calculated for $C_{24}H_{31}FO$ 354; found 355 (M+H).

Step B: 3,5-Diisopropyl-2-(1-hydroxyethyl)-6-pentyl-4'-fluoro-1,1'-biphenyl

The title compound was prepared from the intermediate obtained in Step A by the procedure described in Example 101, Step B. $^1$H NMR ($CDCl_3$, 300 MHz): δ 7.32 (s, 1 H), 7.19–7.06 (m, 4 H), 4.70 (dq, 7.0 Hz, 2.9 Hz, 1 H), 3.88 (sept, 6.8 Hz, 1 H), 3.13 (sept, 6.8 Hz, 1 H), 2.20 (m, 2 H), 1.63 (d, 2.9 Hz, 1 H), 1.40 (d, 6.6 Hz, 3 H), 1.30 (d, 7.0 Hz, 6 H), 1.3 (m, 2 H), 1.27 (d, 7.0 Hz, 6 H), 1.08 (m, 4 H), 0.78 (t, 6.8 Hz, 3 H). FAB-MS: calculated for $C_{25}H_{35}FO$ 370; found 370 ($M^+$). $R_f$=0.36 (83:17 hexanes/ethyl acetate). mp 126° C.

EXAMPLE 192

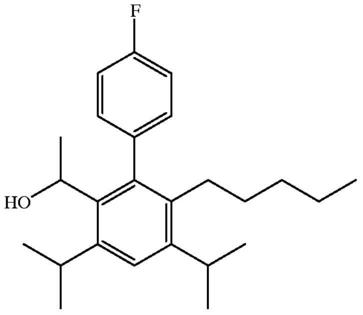

3,5-Diisopropyl-2-(1-hydroxyethyl)-6-pentyl-4'-fluoro-1,1'-biphenyl

In a separate experiment, the title compound was prepared by the methods described in Example 191. $^1$H NMR (300 MHz, $CDCl_3$): δ 0.76–0.80 (m, 3 H), 1.04–1.31 (m, 19 H), 1.40 (d, J=6.6 Hz, 3 H), 2.17–2.22 (m, 2 H), 3.11–3.16 (m, 1 H), 3.86–3.90 (m, 1 H), 4.66–4.73 (m, 1 H), 7.06–7.22 (m, 4 H), 7.32 (s, 1 H). $^{13}$C NMR (75 MHz, $CDCl_3$) d 13.87, 22.01, 23.37, 24.22, 24.55, 24.61, 25.08, 28.66, 28.94, 29.91, 31.02, 32.22, 68.89, 114.65–115.15 (2 d, 2 C), 124.25, 130.33–131.28 (2 d, 2 C), 135.51, 136.96, 137.72, 139.00, 145.80 (2 C), 161.67 (d, J=245.7 Hz, 1 C). FAB-MS: calculated for $C_{25}H_{35}OF$ 370; found 370 (M+). Anal. calc for $C_{25}H_{35}OF$: C, 81.03; H, 9.52. Found: C, 81.05; H, 9.70. $R_f$=0.37 (9:1 hexanes:ethyl acetate). HPLC: (C-18, A=0.05% aqueous trifluoroacetic acid, B=$CH_3CN$; linear gradient. 75%–100% B over 30 min; 254 nm, 1 mL/min): R.T. 20.0 min. (91.1 area %); (Daicel Chiralcel OD-H; isocratic 99:1 hexanes:methyl t-butyl ether; 254 nm, 1.5 mL/min); R.T.=5.83 min (49.0 area %), 7.67 min.(51 area %). mp 124.0–125.0° C.

EXAMPLE 193

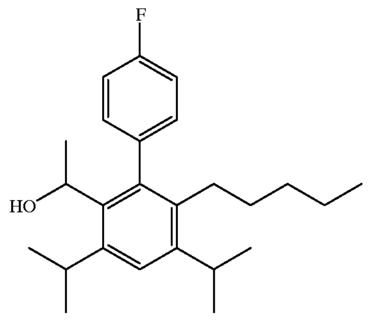

(+)-3,5-Diisopropyl-2-(1-hydroxyethyl)-6-pentyl-4'-fluoro-1,1-biphenyl

Step A: 3,5-Diisopropyl-2-(1-hydroxyethyl)-6-pentyl-4'-fluoro-1,1'-biphenyl, hemi-phthalate ester A solution of 1.90 g (5.36 mmol) of 3,5-diisopropyl-2-formyl-6-pentyl-4'-fluoro-1,1'-biphenyl (Example 191, Step A) in 36 mL of tetrahydrofuran at −78° C. under an argon atmosphere was treated with a dropwise addition of 4.6 mL (6.43 mmol) of a 1.4 M solution of methyllithium in ether. The reaction mixture was allowed to warm to room temperature over one hour. 1.03 g (6.97 mmol) of phthalic anhydride was then added as a solid and stirring was continued for another hour. The reaction was quenched with 30 mL saturated aqueous ammonium chloride and extracted with 60 mL ethyl acetate. Separated organic phase was washed again with 30 mL saturated aqueous ammonium chloride. Combined aqueous portions were extracted with several portions of 20 mL of ethyl acetate. Combined organic portions were dried ($Na_2SO_4$) and concentrated in vacuo. The crude mixture was purified by flash column chromatography on silica using hexanes:ethyl acetate:acetic acid (75:24:1) as eluent to provide 2.55 g (4.94 mmol, 97%) of the product. FAB-MS: calculated for $C_{33}H_{39}O_4F$ 518; found 519 (M+H). $^1$H NMR (300 MHz, $CDCl_3$): δ 0.77 (t, J=7.0 Hz, 3H), 1.03–1.30 (m, 18H), 1.53 (d, J=7.0 Hz, 3H), 2.16–2.22 (m, 2H), 3.05–3.20 (m, 1H), 3.53–3.65 (m, 1H), 5.87–5.93 (m, 1H), 7.05–7.37 (m, 4H), 7.54–8.06 (m, 5H). $R_f$=0.47 (75:24:1 hexanes:ethyl acetate:acetic acid).

Step B: (+)-3,5-Diisopropyl-2-(1-hydroxyethyl)-6-pentyl-4'-fluoro-1,1'-biphenyl

A solution of 2.54 g (4.90 mmol) of the hemi-phthalate ester from Step A in 50 mL of hexane and 0.5 mL of methanol at reflux was treated with 0.63 mL (4.90 mmol) of (R)-(+)-a-methylbenzylamine. Reflux was continued until solids began to precipitate. At this point, the flask was removed from the hot plate and allowed to cool. Further cooling was achieved by placing the flask in a freezer (−25° C.) overnight. Crystals were harvested via filtration and washed with hexane. The amine salt crystals were then suspended in hexane and methanol was added at reflux until the crystals dissolved. Reflux was continued until solids began to precipitate. At this point, the flask was removed from the hot plate and allowed to cool. Further cooling was not necessary and the salt crystals were harvested as above. The salts were crystallized a third time via the second method described, and the harvested crystals were placed in a vacuum oven overnight at 50° C to afford 0.57 g (0.89 mmol, 18%) of crystalline amine salt. A solution of 0.57 g (0.89 mmol) of the amine salt in 5 mL dioxane was treated with a 20% solution (w/v) of $NaOH/H_2O$ and was held at reflux for 3.5 hours. After cooling to room temperature, the reaction mixture was diluted with 20 mL of ethyl acetate. The separated aqueous phase was extracted with ethyl acetate (2×10 mL). Combined organic extracts were dried ($Na_2SO_4$) and concentrated in vacuo. The crude oil was purified by flash column chromatography on silica using hexanes:ethyl acetate (19:1) and the resulting material placed in a vacuum oven overnight (at 50° C.) to afford 0.26 g (0.70 mmol, 79%) of the title compound as a white solid. $^1$H NMR (300 MHz, $CDCl_3$): δ 0.75–0.80 (m, 3H), 1.02–1.31 (m, 19H), 1.40 (d, J=6.6 Hz, 3H), 2.17–2.22 (m, 2H), 3.08–3.18 (m, 1H), 3.83–3.92 (m, 1H), 4.66–4.73 (m, 1H), 7.05–7.23 (m, 4H), 7.32 (s, 1H). $^{13}$C NMR (75 MHz, $CDCl_3$): δ 13.88, 22.02, 23.38, 24.23, 24.56, 24.63, 25.09, 28.68, 28.96, 29.92, 31.04, 32.23, 68.91, 114.66–115.16 (2d, 2C), 124.27, 130.34–131.30 (2d, 2C), 135.53, 136.98, 137.74, 139.02, 145.82 (2C), 161.68 (d, J=245.4 Hz, 1C). FAB-MS: calculated for $C_{25}H_{35}OF$ 370; found 370 (M+). Anal. calc for $C_{25}H_{35}OF$: C, 81.03; H, 9.52. Found: C, 81.15; H, 9.68. $R_f$=0.36 (9:1 hexanes:ethyl acetate). HPLC: (C-18, A=0.05% aqueous trifluoroacetic acid, B=$CH_3CN$; linear gradient 75%–100% B over 30 min; 254 nm, 1 mL/min): R.T. 20.0 min (93.9 area %), (Daicel Chiralcel OD-H; isocratic 99:1 hexanes:methyl t-butyl ether; 254 nm, 1.5 mL/min); R.T. 5.23 min.(98.0 area %), 8.37 min. (0.89 area %); 98.2 % e.e. $[a]_D$=+26.9° (c=0.00196 g/mL, $CH_2Cl_2$).

mp 95.0–96.0° C.

EXAMPLE 194

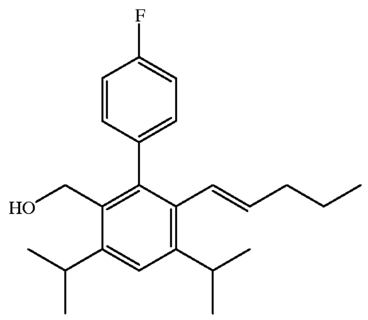

3,5-Diisopropyl-2-hydroxymethyl-6-(pent-1-enyl)-4'-fluoro-1,1'-biphenyl

The title compound was prepared from the intermediate obtained in Example 190, Step F by the procedures described in Example 190, Steps H and I. The olefin was a mixture of cis and trans isomers in a ratio of 17:83. $^1$H NMR ($CDCl_3$, 300 MHz): δ 7.33 (s, 1H), 7.15–7.02 (m, 4H), 5.95 (d, 16.2 Hz, 1H), 5.24 (dt, 16.2 Hz, 7.0 Hz, 1H), 4.40 (s, 2H), 3.41 (sept, 6.8 Hz, 1H), 3.30 (sept, 6.8 Hz, 1H), 1.89 (dt, 7.2 Hz, 7.2 Hz, 2H), 1.33 (d, 6.6 Hz, 6H), 1.24 (d, 7.0 Hz, 6H), 1.2 (m, 2H), 0.74 (t, 7.4 Hz, 3H). FAB-MS: calculated for $C_{24}H_{31}FO$ 354; found 354 ($M^+$). $R_f$=0.36 (83:17 hexanes/ethyl acetate). Anal. calculated for $C_{24}H_{31}FO$: C, 81.31; H, 8.81 Found: C, 81.04; H, 8.65. mp 85–95° C.

EXAMPLE 195

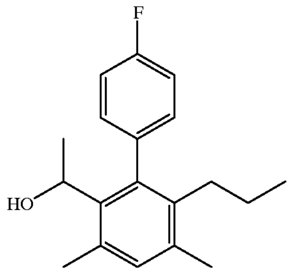

3,5-Dimethyl-2-(1-hydroxyethyl)-6-propyl-4'-fluoro-1,1'-biphenyl

Step A: 2-Allyloxy-4,6-dimethylacetophenone

A solution of 2-hydroxy-4,6-dimethylacetophenone (4.99 g, 30.4 mmol) in dimethylformamide (31 mL) was added to a cooled (0° C.) suspension of sodium hydride (0.772 g, 32.1 mmol) in dimethylformamide (8 mL). The mixture was warmed to room temperature for 2.5 h. The mixture was recooled to 0° C. and allyl bromide (5.4 mL, 62.4 mmol) added. The mixture was warmed to room temperature and stirred 25 h. The mixture was diluted with saturated aqueous sodium chloride solution (150 mL) and extracted with diethyl ether (250 mL+2×125 mL). The combined organic phase was washed with 1N KOH (2×125 mL) and saturated aqueous sodium chloride solution. Silica gel chromatography provided a colorless oil (5.74 g, 92%). $^1$H NMR ($CDCl_3$, 300 MHz): δ 6.64 (s, 1H), 6.56 (s, 1H), 6.03 (ddt, 17.3 Hz, 10.7 Hz, 5.2 Hz, 1H), 5.38 (d, 17.3 Hz, 1H), 5.27 (d, 10.7 Hz, 1H), 4.55 (d, 5.0 Hz, 2H), 2.51 (s, 3H), 2.31 (s, 3H), 2.22 (s, 3H).

Step B: 2-Hydroxy-3-(prop-2-enyl)-4,6-dimethylacetophenone

A solution of the intermediate obtained in Step A (6.30 g, 30.8 mmol) and 2,6-di-t-butyl-4-methylphenol (71.9 mg, 326 mmol) in xylenes was degassed by three freeze-pump-thaw cycles. The mixture was heated in an oil bath at 225° C. for 8 h. The mixture was cooled to room temperature and concentrated in vacuo. Silica gel chromatography provided a yellow oil (5.47 g, 87%). $^1$H NMR ($CDCl_3$, 300 MHz): δ 13.09 (s, 1H), 6.56 (s, 1H), 5.93 (m, 1H), 4.95 (m, 2H), 3.42 (d, 6.0 Hz, 2H), 2.65 (s, 3H), 2.55 (s, 3H), 2.27 (s, 3H). EI MS: 204 ($M^+$, 70), 189 (100).

Step C: 2-Acetyl-3,5-diethyl-6-(prop-2-enyl)phenyltriflate

A solution of triflic anhydride (1.10 mL, 6.54 mmol) in $CH_2Cl_2$ (3.8 mL) was added to a cooled (−10° C.) solution of pyridine (0.58 mL, 6.54 mmol) in $CH_2Cl_2$ (9.6 mL). After 35 min. a solution of the intermediate obtained in Step B (0.271 g, 1.33 mmol) in $CH_2Cl_2$ (6.4 mL) was added and the mixture allowed to warm to room temperature. After 5 h the mixture was poured into ice water and extracted with $CH_2Cl_2$ (2×15 mL). Silica gel chromatography provided a yellow oil (0.426 g, 95%). $^1$H NMR ($CDCl_3$, 300 MHz): δ 7.09 (s, 1H), 5.86 (m, 1H), 5.09 (d, 10.3 Hz, 1H), 4.93 (d, 17.1 Hz, 1H), 3.51 (d, 5.6 Hz, 2H), 2.52 (s, 3H), 2.34 (s, 3H), 2.30 (s, 3H).

Step D: 3,5-Dimethyl-2-acetyl-6-(prop-2-enyl)-4'-fluoro-1,1'-biphenyl

A mixture of the intermediate obtained in Step C (3.25 g, 9.68 mmol), 4-fluorophenylboronic acid (2.06 g, 14.7 mmol), $Pd(PPh_3)_4$ (1.13 g, 976 mmol), $K_3PO_4$ (4.10 g, 19.3 mmol), and KBr (1.97 g, 16.6 mmol) in 1,4-dioxane (50 mL) was heated at 85° C. for 16.5 h. The mixture was poured into saturated aqueous ammonium chloride (100 mL) and extracted with diethyl ether (100 mL+2×75 mL). Silica gel chromatography (95:5 hexanes/ethyl acetate) provided a yellow oil (1.03 g, 38%). $^1$H NMR ($CDCl_3$, 300 MHz): δ 7.18 (m, 2H), 7.06 (m, 3H), 5.76 (m, 1H), 4.97 (d, 10.2 Hz, 1H), 4.72 (d, 17.0 Hz, 1H), 3.15 (d, 5.5 Hz, 2H), 2.32 (s, 3H), 2.24 (s, 3H), 1.91 (s, 3H).

Step E: 3,5-Dimethyl-2-acetyl-6-propyl-4'-fluoro-1,1'-biphenyl

Prepared from the intermediate obtained in Step D by the procedure described in Example 1, Step H. $^1$H NMR ($CDCl_3$, 300 MHz): δ 7.19 (m, 2H), 7.07 (m, 3H), 2.36 (m, 5H), 2.22 (s, 3H), 1.91 (s, 3H), 1.32 (m, 2H), 0.75 (t, 7.2 Hz, 3H). FAB-MS: calculated for $C_{19}H_{21}FO$ 284; found 285 (M+H).

Step F: 3,5-Dimethyl-2-(1-hydroxyethyl)-6-propyl-4'-fluoro-1,1'-biphenyl

A mixture of the intermediate obtained in Step E (21.0 mg, 73.8 mmol) and lithium aluminum hydride (31.0 mg, 0.818 mmol) in tetrahydrofuran (2 mL) was refluxed overnight. Aqueous hydrochloric acid (5%, 1 mL) was added and the mixture stirred 1 h. The mixture was diluted with 5% aqueous hydrochloric add (25 mL) and extracted with diethyl ether (3×15 mL). Silica gel chromatography provided the title compound as a colorless crystalline solid (15.7 mg, 74%). $^1$H NMR ($CDCl_3$, 300 MHz): δ 7.19–7.01 (m, 5H), 4.71 (dq, 6.7 Hz, 3.2 Hz, 1H), 2.56 (s, 3H), 2.32 (s, 3H), 2.20 (m, 2H), 1.52 (d, 3.3 Hz, 1H), 1.38 (d, 7.0 Hz, 3H), 1.28 (m, 2H), 0.73 (t, 7.2 Hz). EI-MS: calculated for $C_{19}H_{23}FO$ 286; found 286 ($M^+$, 29), 225 (100). $R_f$=0.31 (83:17 hexanes/ethyl acetate). Anal calculated for $C_{19}H_{23}FO$: C, 79.68; H, 8.10 found: C, 79.46; H, 7.95. mp 98–99° C.

EXAMPLE 196

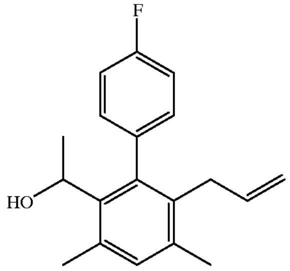

3,5-Dimethyl-2-(1-hydroxyethyl)-6-(prop-2-enyl)-4'-fluoro-1,1'-biphenyl

The title compound was prepared from the intermediate obtained in Example 195, Step D by the procedure described in Example 195, Step F. $^1$H NMR ($CDCl_3$, 300 MHz): δ 7.16–7.02 (m, 5H), 5.66 (m, 1H), 4.90 (d, 10.2 Hz, 1H), 4.75–4.62 (m, 2H), 2.99 (d, 5.5 Hz, 2H), 2.57 (s, 3H), 2.28 (s, 3H), 1.50 (d, 3.7 Hz, 1H), 1.38 (d, 7.0 Hz, 3H). $R_f$=0.27 (83:17 hexanes/ethyl acetate). Anal. calculated for $C_{19}H_{21}FO$: C, 80.25; H, 7.44 Found: C, 80.14; H, 7.36. mp 92° C.

EXAMPLE 197

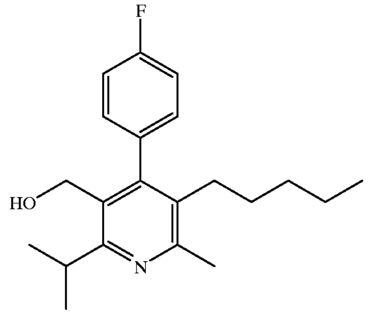

2-Isopropyl-3-hydroxymethyl-4-(4-fluorophenyl)-5-pentyl-6-methyl-pyridine

Step A: 2-Isopropyl-3-carboethoxy-4-(4-fluorophenyl)-5-carbomethoxy-6-methyl-1,4-dihydropyridine A mixture of methyl 3-aminocrotonate (13 g, 114 mmol) and 4-carboethoxy-5-(4-fluorophenyl)-2-methylpent-4-en-2-one (30 g, 114 mmol) (prepared by the method of Angerbauer, et al. U.S. Pat. No. 5,169,857) in absolute ethanol (300 mL) was refluxed overnight. The mixture was concentrated in vacuo and the crude product taken to the next step without purification.

Step B: 2-Isopropyl-3-carboethoxy-4-(4-fluorophenyl)-5-(pent-1-enyl)-6-methylpyridine Prepared from the intermediate obtained in Step A by the procedures described in Example 1, Steps C–F. The olefin was obtained as a mixture of cis and trans isomers in a ratio of 34:66. $^1$H NMR (300 MHz, $CDCl_3$): δ 7.16 (m, 2H), 7.04 (m, 2H), 6.02 (m, 1H), 5.46 (m, 1H), 4.01 (m, 2H), 3.06 (m, 1H), 2.61 (s, 3H, major isomer), 2.50 (s, 3H, minor isomer), 1.99 (m, 1H), 1.67 (m, 1H), 1.4–1.15 (m, 8H), 0.98 (m, 3H), 0.79 (m, 3H).

Step C: 2-Isopropyl-3-hydroxymethyl-4-(4-fluorophenyl)-5-(pent-1-enyl)-6-methylpyridine A mixture of 1.25 g (3.38 mmol) the intermediate obtained in Step B and lithium aluminum hydride (0.28 g, 6.8 mmol) in tetrahydrofuran (50 mL) was refluxed for 2.5 h. The mixture was quenched with water (10 mL) and extracted with ethyl acetate to provide a colorless crystalline solid (1.0 g, 90%). The olefin was obtained as a mixture of cis and trans isomers in a ratio of 19:81. $^1$H NMR (300 MHz, $CDCl_3$): δ 7.10 (m, 4H), 5.88 (d, 16.2 Hz, 1H), 5.39 (dt, 16.2 Hz, 7.0 Hz, 1H), 4.39 (d, 5.5 Hz, 2H), 3.44 (sept, 7.0 Hz, 1H), 2.57 (s, 3H, major isomer), 2.46 (s, 3H, minor isomer), 1.92 (m, 2H), 1.4–1.15 (m, 4H), 1.33 (d, 6.6 Hz, 6H), 0.75 (t, 7.4 Hz, 3H). FAB-MS: calculated for $C_{21}H_{26}FNO$ 310; found 326 ($(M-H)^+$). $R_f$=0.44 (80:20 hexanes/ethyl acetate). Anal. calculated for $C_{21}H_{26}FNO$: C, 77.03; H, 8.00; F, 5.80; N, 4.28. Found: C, 77.02; H, 8.14; F, 5.99; N, 4.22. mp 106–108° C.

Step D: 2-lsopropyl-3-hydroxymethyl-4-(4-fluorophenyl)-5-pentyl-6-methylpyridine A mixture of the intermediate obtained in Step C (1.3 g) and 10% Pd/C (0.1 g) in absolute ethanol (50 mL) was stirred under an atmosphere of hydrogen overnight. The mixture was filtered through a pad of silica gel and the pad washed with ethyl acetate. Silica gel chromatography (80:20 hexanes/ethyl acetate) followed by recrystallization from ethyl acetate afforded the title compound as colorless crystals (650 mg, 50%). $^1$H NMR (300 MHz, $CDCl_3$): δ 7.25 (s, 2H), 7.23 (s, 2H), 4.43 (d, 5.5 Hz, 2H), 3.53 (sept, 7.0 Hz, 1H), 2.69 (s, 3H), 2.35 (m, 2H), 1.44 (d, 6.6 Hz, 6H), 1.4 (m, 2H), 1.2 (m, 4H), 0.88 (t, 6.6 Hz, 3H). FAB-MS: calculated for $C_{21}H_{28}FNO$ 310; found 328 ($(M-H)^+$). $R_f$=0.43 (80:20 hexanes/ethyl acetate). Anal. calculated for $C_{21}H_{28}FNO$: C, 76.56; H, 8.57; F, 5.77; N, 4.25. Found: C, 76.71; H, 8.60; F, 6.04; N, 4.21. mp 83–85° C.

EXAMPLE 198

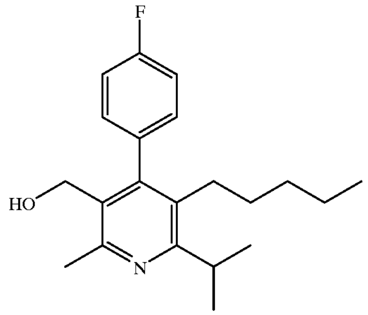

2-Isopropyl-3-pentyl-4-(4-fluorophenyl)-5-hydroxymethyl-6-methylpyridine

Step A: 2-Isopropyl-3-carboethoxy-4-(4-fluorophenyl)-5-hydroxymethyl-6-methylpyridine Prepared from the intermediate obtained in Example 197, Step A by the procedures described in Example 1, Steps C and D. $^1$H NMR (300 MHz, $CDCl_3$): δ 7.25 (m, 2H), 7.09 (m, 2H), 4.44 (d, 5.1 Hz, 2H), 3.97 (q, 7.1 Hz, 2H), 3.04 (sept, 6.8 Hz, 1H), 2.71 (s, 3H), 1.53 (t, 5.2 Hz, 1H), 1.30 (d, 6.6 Hz, 6H), 0.96 (t, 7.2 Hz, 3H). EI-MS: calculated for $C_{19}H_{22}FNO_3$ 331; found 331.

Step B: 2-Isopropyl-3-carboxyethoxy-4-(4-fluorophenyl)-5-(t-butyldimethylsiloxy)methyl-6-methylpyridine A solution of the intermediate obtained in Step A (3.41 g, 10.3 mmol) t-butyldimethylsilylchloride (1.86 g, 1.2 equiv), and imidazole (1.75 g, 2.5 equiv) in dimethylformamide (6 mL) was stirred overnight. The mixture was diluted with water and extracted with ethyl acetate. Silica gel chromatography (95:5 hexanes/ethyl acetate) provided a colorless solid (3.5 g, 76%). $^1$H NMR (300 MHz, $CD_3OD$): δ 7.30 (m, 2H), 7.20 (m, 2H), 4.49 (s, 2H), 4.03 (q, 7 Hz, 2H), 3.1 (sept, 1H), 2.72 (s, 3H), 1.34 (d, 7.0 Hz, 6H), 1.01 (t, 7.0 Hz, 3H), 0.90 (s, 9H), 0.00 (s, 6H). FAB-MS: calculated for $C_{25}H_{36}FNO_3Si$ 331; found 446 (M+H).

Step C: 2-Isopropyl-3-(pent-1-enyl)-4-(4-fluorophenyl)-5-(t-butyldimethylsiloxy)methyl-6-methylpyridine Prepared from the intermediate obtained in Step B by the procedures described in Example 1, Steps D, E, and F. $^1$H NMR (300 MHz, $CD_3OD$): δ 7.2–7.0 (m, 4H), 5.99 (d, 16.2 Hz, 1H), 5.28 (dt, 15.6 Hz, 7.2 Hz, 1H), 4.30 (s, 2H), 3.38 (m, 1H), 2.67 (m, 3H), 1.92 (m, 2H), 1.4–1.2 (m, 8H), 0.85 (s, 9H), 0.75 (t, 7.4 Hz, 3H), 0.06 (s, 6H).

Step D: 2-Isopropyl-3-(pent-1-enyl)-4-(4-fluorophenyl)-5-hydroxymethyl-6-methylpyridine Tetrabutylammonium fluoride (1 mL of 1.0 M solution in tetrahydrofuran, 2.5 equiv) was added to a solution of the intermediate obtained in Step C (200 mg, 0.45 mmol) in tetrahydrofuran (10 mL). After 2 h the mixture was concentrated in vacuo. The residue was dissolved in water and extracted with ethyl acetate. Silica gel chromatography (80:20 hexanes/ethyl acetate) provided a colorless solid (120 mg, 81%). The olefin was obtained as a mixture of cis and trans isomers in a ratio of 8:92. $^1H$ NMR (300 MHz, $CDCl_3$): δ 7.09 (m, 4H), 5.96 (d, 16.2 Hz, 1H), 5.27 (dt, 16.2 Hz, 1H), 4.38 (d, 5.5 Hz, 2H), 3.36 (sept, 1H), 2.69 (s, 3H), 1.90 (m, 2H), 1.4–1.1 (m, 4H), 1.25 (d, 6.6 Hz, 6H), 0.73 (t, 7.4 Hz, 3H). FAB-MS: calculated for $C_{21}H_{26}FNO$ 327; found 327 ($M^+$). $R_f$=0.23 (80:20 hexanes/ethyl acetate). Anal. calculated for $C_{21}H_{26}FNO$: C, 77.03; H, 8.00; F, 5.80; N, 4.28. Found: C, 76.92; H, 8.07; F, 5.92; N, 4.15. mp 119–120° C.

Step E: 2-Isopropyl-3-pentyl-4-(4-fluorophenyl)-5-hydroxymethyl-6-methylpyridine The title compound was obtained as a colorless solid in 86% yield from the intermediate obtained in Step D by the procedure described in Example 1, Step H. $^1H$ NMR (300 MHz, $CDCl_3$): δ 7.2 (m, 4H), 4.29 (d, 5.5 Hz, 2H), 3.24 (sept, 6.6 Hz, 1H), 2.65 (s, 3H), 2.26 (m, 2H), 1.29 (d, 6.6 Hz, 6H), 1.25 (m, 4H), 1.1 (m, 4H), 0.76 (t, 7.0 Hz, 3H). FAB-MS: calculated for $C_{21}H_{28}FNO$ 329; found 328 ($(M-H)^+$). $R_f$=0.20 (80:20 hexanes/ethyl acetate). Anal. calculated for $C_{21}H_{28}FNO$: C, 76.56; H, 8.57; F, 5.77; N, 4.25. Found: C, 76.49; H, 8.55; F, 5.78; N, 4.21. mp 110–112° C.

EXAMPLE 199

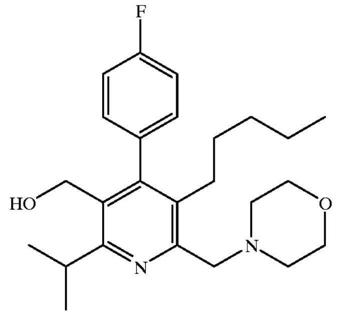

2-Morpholinomethyl-3-pentyl-4-(4-fluorophenyl)-5-hydroxymethyl-6-isopropylpyridine Step A: 2-Isopropyl-3-(t-butyldiphenylsiloxy)methyl-4-(4-fluorophenyl)-5-pentyl-6-methylpyridine A solution of the intermediate from Example 197, Step D (50 mg, 0.15 mmol), t-butyldiphenylsilylchloride (50 mg, 1.2 equiv), and imidazole (25 mg, 2.5 equiv) in dimethylformamide (0.5 mL) was stirred for 2 h. The mixture was diluted with water and extracted with ethyl acetate. Silica gel chromatography (95:5 hexanes/ethyl acetate) provided a colorless solid (64 mg, 75%). $^1H$ NMR (300 MHz, $CD_3OD$): δ 7.41 (m, 6H), 7.33 (m, 4H), 7.05 (m, 4H), 4.25 (s, 2H), 3.13 (sept, 6.8 Hz, 1H), 2.57 (s, 3H), 2.23 (m, 2H), 1.3 (m, 2H), 1.17 (d, 6.6 Hz, 6H), 1.15 (m, 4H), 0.99 (s, 9H), 0.78 (t, 6.4 Hz, 3H).

Step B: 2-Isopropyl-3-(t-butyldiphenylsiloxy)methyl-4-(4-fluorophenyl)-5-pentyl-6-methylpyridine N-oxide A mixture of the intermediate from Step A (60 mg, 0.11 mmol) and 3-chloroperoxybenzoic acid (52 mg, 1.4 equiv) in chloroform (5 mL) was refluxed for 15 min. The mixture was diluted with ethyl acetate (30 mL) and washed with saturated aqueous sodium bicarbonate solution (3×25 mL). The organic phase was filtered through a shoroom temperature pad of silica gel and concentrated to give a yellow solid (54 mg, 84%). $^1H$ NMR (300 MHz, $CDCl_3$): δ 7.31 (m, 6H), 7.24 (m, 4H), 6.96 (m, 4H), 4.13 (s, 2H), 3.16 (br s, 1H), 2.47 (s, 3H), 2.18 (m, 2H), 1.33 (d, 6.6 Hz, 6H), 1.25 (m, 2H), 1.05 (m, 4H), 0.93 (s, 9H), 0.70 (t, 6.4 Hz, 3H).

Step C: 2-Chloromethyl-3-pentyl-4-(4-fluorophenyl)-5-(t-butyldiphenylsiloxy)methyl-6-isopropylpyridine Phosphorus oxychloride (9.5 g) and triethyl amine (8.6 mL) were added simultaneously to a refluxing solution of the intermediate obtained in Step B (15 g, 25.8 mmol) in $CH_2Cl_2$ (30 mL). After 3 h , the mixture was diluted with $CH_2Cl_2$ (100 mL) and washed with saturated aqueous sodium bicarbonate solution (3×100 mL). Silica gel chromatography (90:10 hexanes/ethyl acetate) provided a solid (9.4 g, 61%). $^1H$ NMR (300 MHz, $CDCl_3$): δ 7.41 (m, 6H), 7.32 (m, 41H), 7.06 (m, 4H), 4.75 (s, 2H), 4.27 (s, 2H), 3.15 (sept, 6.8 Hz, 1H), 2.39 (m, 2H), 1.35 (m, 2H), 1.18 (d, 6.6 Hz, 6H), 1.12 (m, 4H), 1.00 (s, 9H), 0.79 (t, 6.6 Hz, 3H).

Step D: 2-Morpholinomethyl-3-pentyl-4-(4-fluorophenyl)-5-(t-butyldiphenylsiloxy)methyl-6-isopropylpyridine A mixture of the intermediate prepared in Step C (0.5 g, 0.83 mmol), morpholine (0.108 g, 1.5 equiv), and 4-dimethylaminopyridine (0.172 g, 1.7 equiv) in $CH_2Cl_2$ (15 mL) was refluxed for 2 h. The mixture was washed with saturated aqueous sodium chloride solution. Silica gel chromatography (90:10 hexanes/ethyl acetate) provided a yellow oil (170 mg, 30%). $^1H$ NMR (300 MHz, $CDCl_3$): δ 7.41 (m, 6H), 7.34 (m, 4H), 7.05 (m, 4H), 4.26 (s, 2H), 3.71 (m, 4H), 3.67 (s, 2H), 3.13 (sept, 6.8 Hz, 1H), 2.61 (m, 4H), 2.35 (m, 2H), 1.15 (d, 6.6 Hz, 6H), 1.1 (m, 4H), 0.99 (s, 9H), 0.9 (m, 2H), 0.78 (t, 7.0 Hz, 3H).

Step E: 2-Morpholinomethyl-3-pentyl-4-(4-fluorophenyl)-5-hydroxymethyl-6-isopropylpyridine The title compound was prepared from the intermediate obtained in Step D by the procedure described in Example 198, Step D. $^1H$ NMR (300 MHz, $CDCl_3$): δ 7.17 (m, 4H), 4.36 (d, 5.1 Hz, 2H), 3.68 (m, 6H), 3.42 (sept, 6.6 Hz, 1H), 2.59 (m, 4H), 2.39 (m, 2H), 1.32 (d, 6.6 Hz, 6H), 1.25 (m, 2H), 1.1 (m, 4H), 0.78 (t, 6.6 Hz, 3H). FAB-MS: calculated for $C_{25}H_{35}FN_2O_2$ 414; found 415 (M+H). Anal. calculated for $C_{25}H_{35}FN_2O_2$: C, 72.43; H, 8.51; F, 4.58; N, 6.76. Found: C, 72.49; H, 8.42; F, 4.71; N, 7.05.

EXAMPLE 200

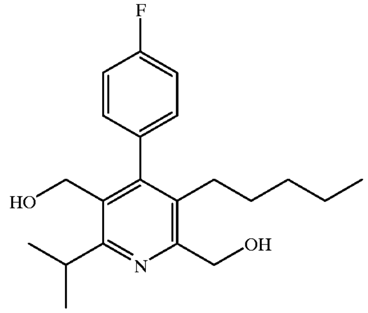

2,5-Bis(hydroxymethyl)-3-pentyl-4-(4-fluorophenyl)-6-isopropylpyridine

Step A: 2-Acetoxymethyl-3-pentyl-4-(4-fluorophenyl)-5-(t-butyldiphenylsiloxy)methyl-6-isopropylpyridine A mixture of the intermediate obtained in Example 199, Step B (4.8 g, 7.97 mmol) and acetic anhydride (20 mL) was heated to 100° C. for 20 min. The mixture was poured onto ice and the aqueous phase extracted with ethyl acetate (3x30 mL). The combined organic phase was washed with saturated aqueous sodium bicarbonate solution (3x50 mL), and saturated aqueous sodium chloride solution (3x50 mL). Silica gel chromatography provided a yellow oil (4.4 g, 90%). $^1$H NMR (300 MHz, $CDCl_3$): δ 7.40 (m, 6H), 7.31 (m, 4H), 7.06 (m, 4H), 5.29 (s, 2H), 4.26 (s, 2H), 3.14 (sept, 6.8 Hz, 1H), 2.2 (m, 2H), 2.18 (s, 3H), 1.2 (m, 2H), 1.16 (d, 6.6 Hz, 6H), 1.05 (m, 4H), 0.99 (s, 9H), 0.77 (t, 6.8 Hz, 3H).

Step B: 2-Hydroxymethyl-3-pentyl-4-(4-fluorophenyl)-5-(t-butyldiphenylsiloxy)methyl-6-isopropylpyridine A mixture of the intermediate obtained in Step A (60 mg, 0.096 mmol) and potassium carbonate (5 equiv) in methanol (8 mL) and water (2 mL) was refluxed for 1.5 h. The mixture was diluted with ethyl acetate and washed with saturated aqueous sodium chloride solution. Concentration of the organic phase provided a colorless solid (60 mg, 100%) that was used in the next step without purification. $^1$H NMR (300 MHz, $CDCl_3$): δ 7.4–7.2 (m, 10H), 7.11 (m, 4H), 4.90 (s, 2H), 4.39 (s, 2H), 3.34 (sept, 7.0 Hz, 1H), 2.34 (m, 2H), 1.25 (d, 7.0 Hz, 6H), 1.2 (m, 2H), 1.04 (m, 4H), 0.90 (s, 9H), 0.68 (t, 7.0 Hz, 3H).

Step C: 2,5-Bis(hydroxymethyl)-3-pentyl-4-(4-fluorophenyl)-6-isopropylpyridine

The title compound was prepared from the intermediate obtained in Step B by the procedure described in Example 198, Step D. $^1$H NMR (300 MHz, CD3OD): δ 7.21 (m, 4H), 4.70 (s, 2H), 4.30 (s, 2H), 3.54 (sept, 6.6 Hz, 1H), 2.28 (m, 2H), 1.32 (d, 6.6 Hz, 6H), 1.25 (m, 2H), 1.1 (m, 4H), 0.75 (t, 6.8 Hz, 3H). FAB-MS: calculated for $C_{21}H_{28}FNO_2$ 345; found 346 (M+H). Anal. calculated for $C_{21}H_{28}FNO_2$: C, 73.01; H, 8.17; F, 5.50; N, 4.05. Found: C, 72.89; H, 8.25; F, 5.21; N, 4.41. mp 135–136° C.

EXAMPLE 201

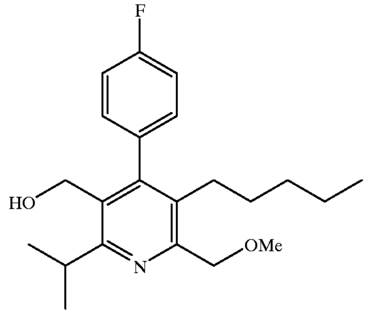

2-Methoxymethyl-3-pentyl-4-(4-fluorophenyl)-5-hydroxymethyl-6-isopropylpyridine

Step A: 2-Methoxymethyl-3-pentyl-4-(4-fluorophenyl)-5-(t-butyldiphenylsiloxy)methyl-6-isopropylpyridine A mixture of the intermediate obtained in Example 200, Step B (0.1 g, 0.17 mmol), methyl iodide (0.013 mL, 1.2 equiv), and sodium hydride (8 mg of a 60% dispersion in mineral oil, 1.2 equiv) in tetrahydrofuran (1 mL) was heated at 40° C. for 3 h. The mixture was diluted with water and extracted with ethyl acetate (3x10 mL). The combined organic phase was washed with saturated aqueous sodium chloride solution (3x10 mL). Silica gel chromatography provided a colorless solid (40 mg, 40%). $^1$H NMR (300 MHz, $CDCl_3$): δ 7.41 (m, 6H), 7.32 (m, 4H), 7.06 (m, 4H), 4.62 (s, 2H), 4.27 (s, 2H), 3.48 (s, 3H), 3.15 (sept, 6.6 Hz, 1H), 2.36 (m, 2H), 1.27 (m, 2H), 1.18 (d, 6.6 Hz, 6H), 1.12 (m, 2H), 1.00 (s, 9H), 0.87 (m, 2H), 0.78 (t, 6.6 Hz, 3H).

Step B: 2-Methoxymethyl-3-pentyl-4-(4-fluorophenyl)-5-hydroxymethyl-6-isopropylpyridine The title compound was prepared from the intermediate obtained in Step A by the procedure described in Example 198, Step D. $^1$H NMR (300 MHz, $CDCl_3$): δ 7.14 (m, 4H), 4.62 (s, 2H), 4.36 (d, 5.2 Hz, 2H), 3.46 (s, 3H), 3.44 (sept, 6.6 Hz, 1H), 2.38 (m, 2H), 1.34 (d, 7.0 Hz, 6H), 1.23 (m, 2H), 1.12 (m, 4H), 0.77 (t, 6.8 Hz, 3H). FAB-MS: calculated for $C_{22}H_{30}FNO_2$ 359; found 360 (M+H). Anal. calculated for $C_{22}H_{30}FNO_2$: C, 73.51; H, 8.41; F, 5.28; N, 3.90. Found: C, 73.40; H, 8.47; F, 5.19; N, 3.91.

EXAMPLE 202

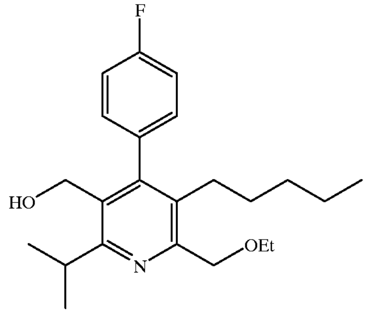

2-Ethoxymethyl-3-pentyl-4-(4-fluorophenyl)-5-hydroxymethyl-6-isopropylpyridine

The title compound was prepared from the intermediate obtained in Example 200, Step B by the procedures described in Example 201, Step A, and Example 198, Step D. $^1$H NMR (300 MHz, $CDCl_3$): δ 7.18 (m, 4H), 4.68 (s, 2H), 4.35 (d, 4.4 Hz, 2H), 3.65 (q, 7.0 Hz, 2H), 3.44 (sept, 6.6 Hz, 1H), 2.40 (m, 2H), 1.4 (m, 2H), 1.34 (d, 6.6 Hz, 6H), 1.26 (t, 7.0 Hz, 3H), 1.13 (m, 4H), 0.78 (t, 6.6 Hz, 3H). FAB-MS: calculated for $C_{23}H_{32}FNO_2$ 373; found 374 (M+H). Anal. calculated for $C_{23}H_{32}FNO_2$: C, 73.96; H, 8.64; F, 5.09; N, 3.75. Found: C, 73.97; H, 8.83; F, 5.33; N, 3.52.

EXAMPLE 203

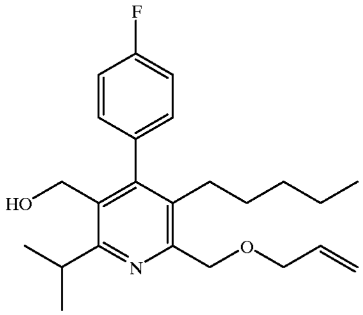

2-(Prop-2-enyloxy)methyl-3-pentyl-4-(4-fluorophenyl)-5-hydroxymethyl-6-isopropylpyridine The title compound was prepared from the intermediate obtained in Example 200, Step B by the procedures described in Example 201, Step A, and Example 198, Step D. $^1$H NMR (300 MHz, $CDCl_3$): δ 7.15 (m, 4H), 5.97 (ddt, 17.1 Hz, 10.5 Hz, 6 Hz, 2H), 5.33 (d, 17.3 Hz, 1H), 5.21 (d, 10.3 Hz, 1H), 4.68 (s, 2H), 4.34 (s, 2H), 4.12 (d, 5.5 Hz, 2H), 3.44 (sept, 6.8 Hz, 1H), 2.39 (m, 2H), 1.33 (d, 6.6 Hz, 6H), 1.29 (m, 2H), 1.10 (m, 4H), 0.77 (t, 6.8 Hz, 3H). FAB-MS: calculated for $C_{24}H_{32}FNO_2$ 385; found 386 (M+H). Anal. calculated for $C_{24}H_{32}FNO_2$: C, 74.8; H, 8.37; F, 4.93; N, 3.63. Found: C, 75.2; H, 8.54; F, 4.90; N, 3.52.

EXAMPLE 204

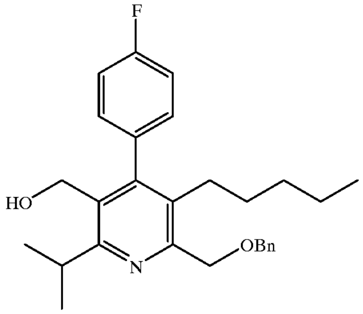

2-Benxyloxymethyl-3-pentyl-4-(4-fluorophenyl)-5-hydroxymethyl-6-isopropylpyridine The title compound was prepared from the intermediate obtained in Example 200, Step B by the procedures described in Example 201, Step A, and Example 198, Step D. $^1$H NMR (300 MHz, $CDCl_3$): δ 7.43–7.30 (m, 5H), 7.17 (m, 4H), 4.73 (s, 2H), 4.66 (s, 2H), 4.36 (s, 2H), 3.46 (sept, 6.6 Hz, 1H), 2.38 (m, 2H), 1.36 (d, 6.6 Hz, 6H), 1.25 (m, 2H), 1.05 (m, 4H), 0.75 (t, 6.6 Hz, 3H). FAB-MS: calculated for $C_{24}H_{32}FNO_2$ 435; found 436 (M+H). Anal. calculated for $C_{28}H_{34}FNO_2$: C, 77.21; H, 7.87; F, 4.36; N, 3.22. Found: C, 77.26; H, 7.84; F, 4.42; N, 3.11. mp 110–112° C.

EXAMPLE 205

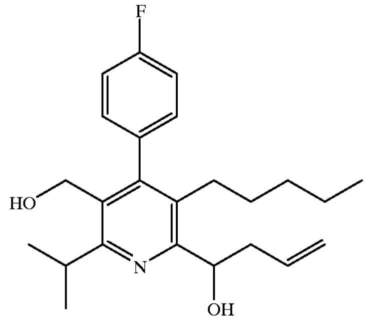

2-(1-Hydroxybut-3-enyl)-3-pentyl-4-(4-fluorophenyl)-5-hydroxymethyl-6-isopropylpyridine

Step A: 2-Formyl-3-pentyl-4-(4-fluorophenyl)-5-(t-butyldiphenylsiloxy)methyl-6-isopropylpyridine Prepared from 2-hydroxymethyl-3-pentyl-4-(4fluorophenyl)-5-[(t-butyldiphenylsiloxy)methyl]-6-isopropylpyridine (Example 200, Step B) by the procedure described in Example 1, Step E. $^1$H NMR (300 MHz, $CDCl_3$): δ 10.20 (s, 1H), 7.41 (m, 6H), 7.33 (m, 4H), 7.04 (m, 4H), 4.33 (s, 2H), 3.23 (sept, 6.6 Hz, 1H), 2.66 (m, 2H), 1.3–1.1 (m, 6H), 1.22 (d, 6.6 Hz, 6H), 1.01 (s, 9H), 0.79 (t, 7.0 Hz, 3H). FAB-MS: calculated for $C_{37}H_{44}FNO_2Si$ 581; found 582 (M+H).

Step B: 2-(1-Hydroxybut-3-enyl)-3-pentyl-4-(4-fluorophenyl)-5-(t-butyldiphenylsiloxy)methyl-6-isopropylpyridine A mixture of the intermediate obtained in Step A (0.2 g, 0.34 mmol) and allylmagnesium bromide (1 mL of 1.0 M solution in tetrahydrofuran, 3 equiv) in tetrahydrofuran (10 mL) was refluxed for 1.5 h. The mixture was concentrated in 20 vacuo. The residue was dissolved in ethyl acetate and washed with saturated aqueous sodium chloride solution. Silica gel chromatography (97:3 hexanes/ethyl acetate) provided a yellow oil (110 mg, 52%). $^1$H NMR (300 MHz, $CDCl_3$): δ 7.42 (m, 6H), 7.2 (m, 4H), 7.06 (m, 4H), 5.94 (m, 1H), 5.14–5.08 (m, 2H), 4.99–4.90 (m, 2H), 4.28 (d, 2.2 Hz, 2H), 3.16 (sept, 6.8 Hz, 1H), 2.55 (m, 1H), 2.45–2.15 (m, 3H), 1.3 (m, 2H), 1.20 (d, 6.6 Hz, 3H), 1.15 (d, 6.6 Hz, 3H), 1.1 (m, 4H), 0.76 (t, 6.6 Hz, 3H).

Step C: 2-(1-Hydroxybut-3-enyl)-3-pentyl-4-(4-fluorophenyl)-5-hydroxymethyl-6-isopropylpyridine The title compound was prepared from the intermediate obtained in Step B by the procedure described in Example 198, Step D. $^1$H NMR (300 MHz, $CDCl_3$): δ 7.16 (m, 4H), 5.94 (m, 1H), 5.13 (d, 7.7 Hz, 1H), 5.08 (s, 1H), 4.92 (s, 2H), 4.38 (m, 21H), 3.47 (sept, 6.7 Hz, 1H), 2.51 (m, 1H), 2.4–2.1 (m, 3H), 1.35 (d, 6.6 Hz, 3H), 1.34 (d, 6.6 Hz, 3H), 1.29 (m, 2H), 1.10 (m, 4H), 0.77 (t, 6.6 Hz, 3H). FAB-MS: calculated for $C_{24}H_{32}FNO_2$ 385; found 386 (M+H). $R_f$=0.15 (85:15 hexanes/ethyl acetate).

Anal. calculated for $C_{24}H_{32}FNO_2$: C, 74.77; H, 8.37; F, 4.93; N, 3.63. Found: C, 74.85; H, 8.53; F, 4.99; N, 3.50.

EXAMPLE 206

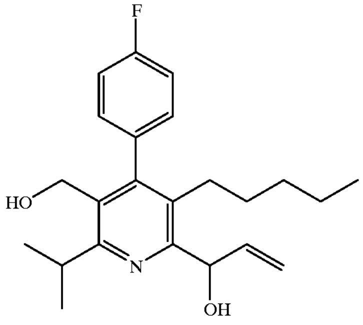

2-(1-Hydroxyprop-2-enyl)-3-pentyl-4-(4-fluorophenyl)-5-hydroxymethyl-6-isopropylpyridine Prepared from the intermediate in Example 205, Step A by the procedures described in Example 205, Step B, and Example 198, Step D. $^1$H NMR (300 MHz, $CDCl_3$): δ 7.16 (m, 4H), 5.89 (δ, 17.0 Hz, 10.0 Hz, 7.1 Hz, 1H), 5.66 (d, 5.5 Hz, 1H), 5.37 (d, 16.9 Hz, 1H), 5.26 (t, 5.7 Hz, 1H), 5.20 (d, 9.9 Hz, 1H), 4.38 (d, 4.8 Hz, 2H), 3.49 (sept, 6.7 Hz, 1H), 2.33 (m, 1H), 2.13 (m, 2H), 1.35 (d, 6.6 Hz, 3H), 1.34 (d, 6.6 Hz, 3H), 1.2 (m, 2H), 1.10 (m, 4H), 0.76 (t, 6.8 Hz, 3H). FAB-MS: calculated for $C_{23}H_{30}FNO_2$ 371; found 372 (M+H). $R_f$=0.15 (85:15 hexanes/ethyl acetate). MP=113–115° C. Anal. calculated for $C_{23}H_{30}FNO_2$: C, 74.36; H, 8.14; F, 5.11; N, 3.77. Found: C, 74.16; H, 8.28; F, 5.11; N, 3.60.

EXAMPLE 207

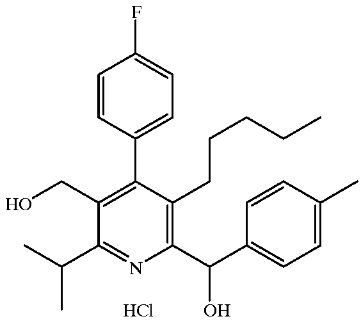

2-(Hydroxy-p-tolyl)methyl-3-pentyl-4-(4-fluorophenyl)-5-hydroxymethyl-6-isopropylpyridine, Hydrochloride Prepared from the intermediate in Example 205, Step A by the procedures described in Example 205, Step B, and Example 198, Step D. $^1$H NMR ($CD_3OD$, 300 MHz): δ 7.28 (m, 6H), 7.21 (m, 2H), 6.90 (d, 7.7 Hz, 1H), 6.43 (s, 1H), 4.48 (d, 11.8 Hz, 1H), 4.41 (d, 11.8 Hz, 1H), 3.96 (sept, 6.8 Hz, 1H), 2.46 (s, 3H), 2.19 (m, 2H), 1.61 (d, 7.0 Hz, 3H), 1.58 (d, 7.0 Hz, 3H), 1.0–0.6 (m, 5H), 0.57 (t, 7.0 Hz, 3H), 0.3 (m, 1H). FAB-MS: calculated for $C_{28}H_{34}FNO_2$ 435; found 436 (M+H). Anal. calculated for $C_{28}H_{34}FNO_2$.HCl: C, 71.25; H, 7.47; Cl, 7.51; F, 4.02; N, 2.97. Found: C, 71.43; H, 7.49; Cl, 7.48; F, 4.10; N, 2.87. mp 178–180° C.

EXAMPLE 208

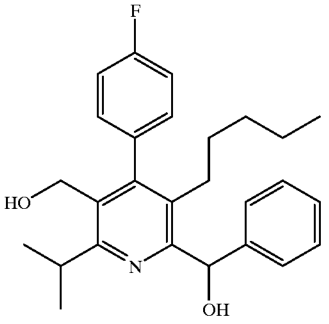

2-(a-Hydroxy)benzyl-3-pentyl-4-(4-fluorophenyl)-5-hydroxymethyl-6-isopropylpyridine Prepared from the intermediate in Example 205, Step A by the procedures described in Example 205, Step B, and Example 198, Step D. $^1$H NMR ($CDCl_3$, 300 MHz): δ 7.30 (m, 5H), 7.17 (m, 4H), 6.43 (d, 6.6 Hz, 1H), 5.79 (d, 6.6 Hz, 1H), 4.40 (m, 2H), 3.55 (sept, 6.6 Hz, 1H), 2.21–2.09 (m, 2H), 1.45 (d, 6.6 Hz, 3H), 1.43 (d, 6.6 Hz, 3H), 1.32 (m, 1H), 1.14–0.88 (m, 6H), 0.69 (t, 3H). FAB-MS: calculated for $C_{27}H_{32}FNO_2$ 421; found 422 (M+H). $R_f$=0.10 (85:15 hexanes/ethyl acetate). Anal. calculated for $C_{27}H_{32}FNO_2$: C, 76.93; H, 7.65; F, 4.51; N, 3.32. Found: C, 76.70; H, 7.86; F, 4.45; N, 3.14.

EXAMPLE 209

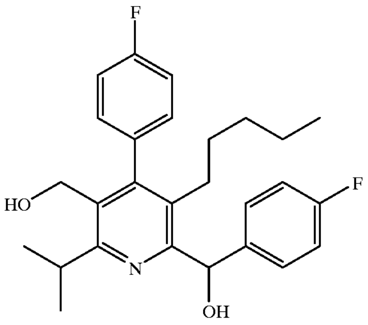

2-(4-Fluorophenyl)hydroxymethyl-3-pentyl-4-(4-fluorophenyl)-5-hydroxymethyl-6-isopropylpyridine Prepared from the intermediate in Example 205, Step A by the procedures described in Example 205, Step B, and Example 198, Step D. $^1$H NMR ($CDCl_3$, 300 MHz): δ 7.24 (m, 2H), 7.15 (m, 4H), 6.98 (m, 2H), 6.40 (d, 5.9 Hz, 1H), 5.77 (d, 5.5 Hz, 1H), 4.40 (m, 2H), 3.55 (sept, 6.6 Hz, 1H), 2.13 (m, 2H), 1.43 (d, 6.3 Hz, 3H), 1.41 (d, 6.6 Hz, 3H), 1.08 (m, 1H), 0.99 (m, 6H), 0.69 (t, 6.6 Hz, 3H). FAB-MS: calculated for $C_{27}H_{31}F_2NO_2$ 439; found 440 (M+H). $R_f$=0.15 (85:15 hexanes/ethyl acetate). Anal. calculated for $C_{27}H_{31}F_2NO_2$: C, 73.78; H, 7.11; F, 8.64; N, 3.19. Found: C, 73.49; H, 7.23; F, 8.45; N, 3.01.

EXAMPLE 210

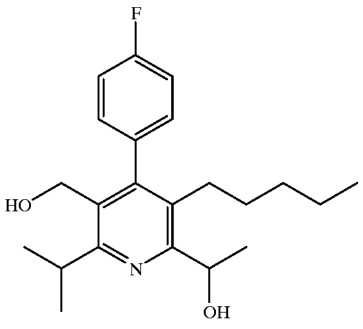

2-(1-Hydroxyethyl)-3-pentyl-4-(4-fluorophenyl)-5-hydroxymethyl-6-isopropylpyridine Step A: 2-(1-Hydroxyethyl)-3-pentyl-4-(4-fluorophenyl)-5-(t-butyldiphenysiloxy)methyl-6-isopropylpyridine Prepared from the intermediate in Example 205, Step A by the procedure described in Example 205, Step B. $^1$H NMR (300 MHz, $CDCl_3$): δ 7.42 (m, 6H), 7.32 (m, 4H), 7.05 (m, 4H), 5.16 (d, 7.7 Hz, 1H), 4.99 (m, 1H), 4.28 (s, 2H), 3.16 (sept, 6.8 Hz, 1H), 2.25 (m, 2H), 1.45 (d, 6.3 Hz, 2H), 1.19 (d, 6.6 Hz, 3H), 1.16 (d, 6.6 Hz, 3H), 1.10 (m, 6H), 0.76 (t, 6.8 Hz, 3H).

Step B: 2-(1-Hydroxyethyl)-3-pentyl-4-(4-fluorophenyl)-5-hydroxymethyl-6-isopropylpyridine The title compound was prepared from the intermediate in Step A by the procedure described in Example 198, Step D. $^1$H NMR ($CDCl_3$, 300 MHz): δ 7.19–7.15 (m, 4H), 5.12 (d, 7.0 H, 1H), 4.99 (t, 1H), 4.38 (d, 5.5 Hz, 2H), 3.48 (sept, 6.8 Hz, 1H), 2.27 (m, 2H), 1.43 (d, 6.3 Hz, 1H), 1.35 (d, 6.6 Hz, 6H), 1.30 (m 2H), 1.09 (m, 7H), 0.76 (t, 6.6 Hz, 3H). FAB-MS: calculated for $C_{22}H_{30}FNO_2$ 359; found 360 (M+H). $R_f$=0.15 (85:15 hexanes/ethyl acetate). Anal. calculated for $C_{22}H_{30}FNO_2$: C, 73.51; H, 8.41; F, 5.28; N, 3.90. Found: C, 73.24; H, 8.40; F, 5.41; N, 3.85. mp 125–127° C.

EXAMPLE 211

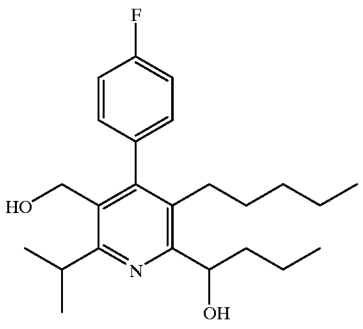

2-(1-Hydroxybutyl)-3-pentyl-4-(4-fluorophenyl)-5-hydroxymethyl-6-isopropylpyridine Prepared from the compound obtained in Example 205 by the procedure described in Example 1, Step H. $^1$H NMR (300 MHz, $CDCl_3$): δ 7.17 (m, 4H), 4.92 (br s, 2H), 4.85 (br s, 2H), 4.37 (d, 5.2 Hz, 2H), 3.47 (sept, 6.6 Hz, 1H), 2.29–2.23 (m, 2H), 1.62–1.53 (m, 5H), 1.35 (d, 6.6 Hz, 3H), 1.34 (d, 6.6 Hz, 3H), 1.3 (m, 1H), 1.11 (m, 5H), 0.94 (t, 7.0 Hz, 3H), 0.77 (t, 6.4 Hz, 3H). FAB-MS: calculated for $C_{24}H_{34}FNO_2$ 387; found 388 (M+H). Anal. calculated for $C_{24}H_{34}FNO_2$: C, 74.38; H, 8.84; F, 4.90; N, 3.61. Found: C, 74.11; H, 8.93; F, 4.96; N, 3.51.

EXAMPLE 212

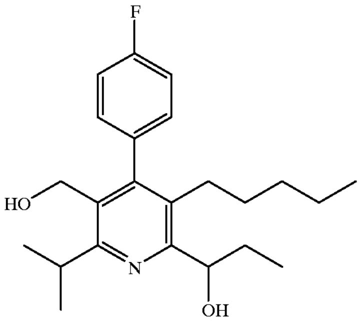

2-(1-Hydroxypropyl)-3-pentyl-4-(4-fluorophenyl)-5-hydroxymethyl-6-isopropylpyridine The title compound was prepared from the intermediate obtained in Example 206 by the procedure described in Example 1, Step H. $^1$H NMR (300 MHz, $CDCl_3$): δ 7.18 (m, 4H), 4.94 (br s, 1H), 4.82 (br s, 1H), 4.39 (d, 4.8 Hz, 2H), 3.48 (sept, 6.6 Hz, 1H), 2.3–2.1 (m, 2H), 1.82 (m, 1H), 1.36 (d, 5.5 Hz, 3H), 1.34 (d, 6.3 Hz, 3H), 1.11 (m, 8H), 1.02 (t, 7.4 Hz, 3H), 0.78 (t, 6.6 Hz, 3H). FAB-MS: calculated for $C_{23}H_{32}FNO_2$ 373; found 374 (M+H). $R_f$=0.15 (85:15 hexanes/ethyl acetate). Anal. calculated for $C_{23}H_{32}FNO_2$: C, 73.96; H, 8.64; F, 5.09; N, 3.75. Found: C, 73.88; H, 8.57; F, 5.17; N, 3.53. mp 89–90° C.

EXAMPLE 213

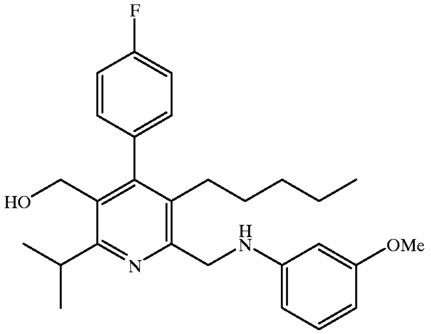

2-N-(2-Methoxyphenyl)aminomethyl-3-pentyl-4-(4-fluorophenyl)-5-hydroxymethyl-6-isopropylpyridine Step A: 2-N-(2-Methoxyphenyl)aminomethyl-3-pentyl-4-(4-fluorophenyl)-5-(t-butyldiphenylsiloxy)methyl-6-isopropylpyridine A mixture of the intermediate from Example 205, Step A (60 mg, 0.10 mmol) and m-anisidine (50 mg, 4 equiv) in methanol (10 mL) was treated with a mixture of zinc chloride (7 mg, 0.5 equiv) and sodium cyanoborohydride (6 mg, 1 equiv) in methanol (15 mL). After stirring at room temperature overnight the mixture was quenched with water and extracted with ethyl actetate (3x15 mL). The combined organic phase was washed with saturated aqueous sodium chloride solution (3x15 mL). Silica gel chromatography provided a colorless solid (70 mg, 99%). $^1$H NMR (300 MHz, $CDCl_3$): δ 7.43 (m, 6H), 7.32 (m, 4H), 7.16 (m, 1H), 7.06 (m, 4H), 6A3 (m, 1H), 6.32 (m, 2H), 5.98 (br s, 1H), 4.38 (s, 2H), 4.29 (s, 2H), 3.83 (s, 3H), 3.19 (sept, 6.6 Hz, 1H), 2.28 (m, 2H), 1.25 (m, 2H), 1.22 (d, 6.6 Hz, 6H), 1.14 (m, 2H), 0.99 (s, 9H), 0.80 (t, 6.8 Hz, 3H).

Step B: 2-N-(2-Methoxyphenyl)aminomethyl-3-pentyl-4-(4-fluorophenyl)-5-hydroxymethyl-6-isopropylpyridine The title compound was prepared from the intermediate obtained in Step A by the procedure described in Example 198, Step D. $^1$H NMR (300 MHz, $CDCl_3$): δ 7.16 (m, 5H), 6.43 (m, 1H), 6.32 (m, 2H), 4.40 (s, 2H), 4.39 (s, 2H), 3.83 (s, 3H), 3.50 (sept, 6.6 Hz, 1H), 2.32 (m, 2H), 1.39 (d, 6.6 Hz, 6H), 1.31 (m, 2H), 1.16 (m, 4H), 0.80 (t, 6.4 Hz, 3H). FAB-MS: calculated for $C_{28}H_{35}FN_2O_2$ 450; found 451 (M+H). Anal. calculated for $C_{28}H_{35}FN_2O_2$: C, 74.64; H, 7.83; N, 6.22. Found: C, 74.44; H, 7.75; N, 6.03. mp 109–110° C.

EXAMPLE 214

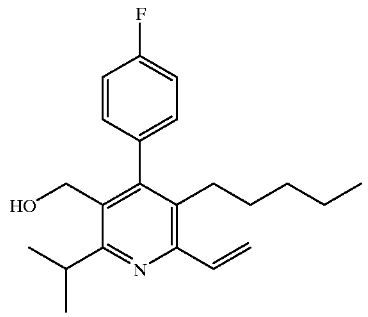

2-Ethenyl-3-pentyl-4-(4-fluorophenyl)-5-hydroxymethyl-6-isopropylpyridine

Step A: 2-Ethenyl-3-pentyl-4-(4-fluorophenyl)-5-(t-butyldiphenylsiloxy)methyl-6-isopropylpyridine n-Butyl lithium (0.03 mL of 1.6 M solution in hexanes) was added to a cooled (0° C.) solution of methyltriphenylphosphonium bromide (18 mg) in tetrahydrofuran (3 mL). After 2 h, a solution of 2-formyl-3-pentyl-4-(4-fluorophenyl)-5-(t-butyldiphenylsiloxy)methyl-6-isopropylpyridine (Example 205, Step A) in tetrahydrofuran (1 mL) was added and the mixture warmed to room temperature. After 30 min. the mixture was quenched with water and extracted with ethyl acetate. Silica gel chromatography (95:5 hexanes/ethyl acetate) afforded a colorless solid (20 mg). $^1$H NMR ($CDCl_3$, 300 MHz): δ 7.44–7.36 (m, 6H), 7.34–7.27 (m, 4H), 7.08–6.98 (m, 5H), 6.59 (dd, 16.7 Hz, 2.7 Hz, 1H), 5.48 (dd, 10.5 Hz, 2.8 Hz, 1H), 4.26 (s, 2H), 3.16 (sept, 6.6 Hz, 1H), 2.29 (m, 2H), 1.4–1.2 (m, 2H), 1.19 (d, 6.6 Hz, 6H), 1.15 (m, 4H), 0.98 (s, 9H), 0.78 (t, 6.8 Hz, 3H).

Step B: 2-Ethenyl-3-pentyl-4-(4-fluorophenyl)-5-hydroxymethyl-6-isopropylpyridine The title compound was prepared from the intermediate obtained in Step A by the procedure described in Example 198, Step D. $^1$H NMR ($CDCl_3$, 300 MHz): δ 7.17 (s, 2H), 7.14 (s, 2H), 7.04 (dd, 16.7 Hz, 10.5 Hz, 1H), 6.61 (dd, 16.7 Hz, 2.8 Hz, 1H), 5.51 (dd, 10.5 Hz, 2.8 Hz, 1H), 4.36 (s, 2H), 3.45 (sept, 6.7 Hz, 1H), 2.32 (m, 2H), 1.37 (d, 6.6 Hz, 6H), 1.34 (m 2H), 1.15 (m, 4H), 0.80 (t, 6.6 Hz, 3H). FAB-MS: calculated for $C_{22}H_{28}FNO$ 341; found 342 (M+H). Anal. calculated for $C_{22}H_{28}FNO$: C, 77.38; H, 8.27; N, 4.10. Found: C, 77.15; H, 7.98; N, 4.06.

EXAMPLE 215

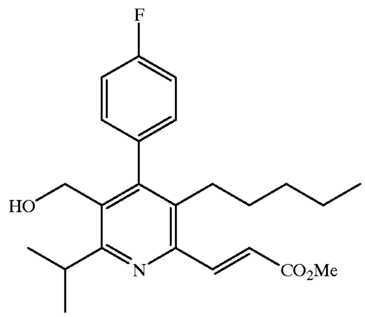

2-(2-Carbomethoxyethenyl)-3-pentyl-4-(4-fluorophenyl)-5-hydroxymethyl-6-isopropylpyridine Step A: 2-(2-Carbomethoxyethenyl)-3-pentyl-4-(4-fluorophenyl)-5-(t-butyldiphenylsiloxy)methyl-6-isopropylpyridine A mixture of the intermediate obtained in Example 205, Step A (50 mg, 85 mmol) and methyl (triphenylphosphoranylidene)acetate (31 mg, 1.1 equiv) in toluene (5 mL) was heated to reflux for 5 h. The mixture was cooled to rt and concentrated in vacuo. Silica gel chromatography provided a yellow oil (60 mg). $^1$H NMR ($CDCl_3$, 300 MHz): δ 7.96 (d, 15.1 Hz, 1H), 7.42 (m, 6H), 7.34–7.21 (m, 5H), 7.05 (s, 2H), 7.03 (s, 2H), 4.28 (s, 2H), 3.84 (s, 3H), 3.17 (sept, 6.8 Hz, 1H), 2.38 (m, 2H), 1.31 (m, 2H), 1.19 (d, 6.6 Hz, 6H), 1.14 (m, 4H), 1.00 (s, 9H), 0.79 (t, 6.6 Hz, 3H).

Step B: 2-(2-Carbomethoxyethenyl)-3-pentyl-4-(4-fluorophenyl)-5-hydroxymethyl-6-isopropylpyridine The title compound was prepared from the intermediate obtained in Step A by the procedure described in Example 198, Step D. $^1$H NMR ($CDCl_3$, 300 MHz): d 7.95 (d, 15.1 Hz, 1H), 7.25 (d, 15.1 Hz, 1H), 7.17 (s, 2H), 7.15 (s, 2H), 4.37 (d, 3.7 Hz, 2H), 3.84 (s, 3H), 3.45 (sept, 6.6 Hz, 1H), 2.40 (m, 2H), 1.35 (d, 6.6 Hz, 6H), 1.3 (m, 4H), 1.14 (m, 4H), 1.00 (s, 9H), 0.79 (t, 6.6 Hz, 3H). EI-MS: calculated for $C_{24}H_{30}FNO_3$ 399; found 399 ($M^+$). Anal. calculated for $C_{24}H_{30}FNO_3$: C, 72.16; H, 7.57; N, 3.51. Found: C, 71.79; H, 7.50; N, 3.32. mp 82–83° C.

EXAMPLE 216

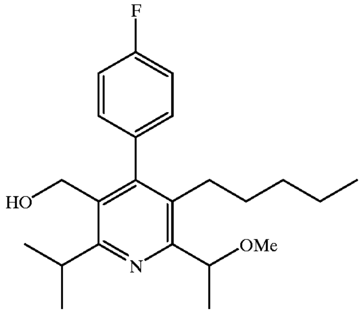

2-(1-Methoxyethyl)-3-pentyl-4-(4-fluorophenyl)-5-hydroxymethyl-6-isopropylpyridine The title compound was prepared from the intermediate obtained in Example 210, Step A by the procedures described in Example 201, Step A, and Example 198, Step D. $^1$H NMR ($CDCl_3$, 300 MHz): δ 7.15 (m, 4H), 4.75 (q, 6.3 Hz, 1H), 4.35 (d, 3.7 Hz, 2H), 3.44 (sept, 6.4 Hz, 1H), 3.31 (s, 3H), 2.4–2.2 (m, 2H), 1.58 (d, 6.3 Hz, 3H), 1.35 (d, 6.3 Hz, 3H), 1.34 (d, 6.6 Hz, 3H), 1.27 (m, 2H), 1.11 (m, 4H), 0.78 (t, 6.6 Hz, 3H). FAB-MS: calculated for $C_{23}H_{32}FNO_2$ 373; found 374 (M+H). Anal. calculated for $C_{23}H_{32}FNO_2$: C, 73.96; H, 8.64; F, 5.09; N, 3.75. Found: C, 73.92; H, 8.75; F, 4.93; N, 3.60.

EXAMPLE 217

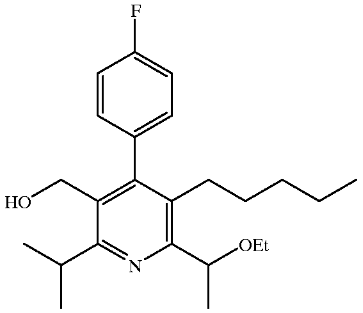

2-(1-Ethoxyethyl)-3-pentyl-4-(4-fluorophenyl)-5-hydroxymethyl-6-isopropylpyridine The title compound was prepared from the intermediate obtained in Example 210, Step A by the procedures described in Example 201, Step A, and Example 198, Step D. $^1$H NMR ($CDCl_3$, 300 MHz): δ 7.16 (m, 4H), 4.83 (q, 6.5 Hz, 1H), 4.34 (d, 4.4 Hz, 2H), 3.5–3.2 (m, 3H), 2.4–2.2 (m, 2H), 1.57 (d, 6.6 Hz, 3H), 1.34 (d, 6.6 Hz, 3H), 1.33 (d, 6.6 Hz, 3H), 1.27 (m 2H), 1.10 (m, 4H), 1.20 (t, 7.2 Hz, 3H), 0.77 (t, 6.8 Hz, 3H). FAB-MS: calculated for $C_{24}H_{34}FNO_2$ 387; found 388 (M+H). Anal. calculated for $C_{24}H_{34}FNO_2$: C, 74.38; H, 8.84; F, 4.90; N, 3.61. Found: C, 74.67; H, 9.00; F, 5.14; N, 3.27.

EXAMPLE 218

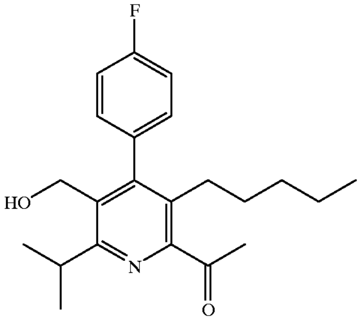

2-Acetyl-3-pentyl-4-(4-fluorophenyl)-5-hydroxymethyl-6-isopropylpyridine

Step A: 2-Acetyl-3-pentyl-4-(4-fluorophenyl)-5-(t-butyldiphenylsiloxy)methyl-6-isopropylpyridine A mixture of the intermediate obtained in Example 210, Step A (210 mg, 0.35 mmol), pyridinium chlorochromate (113 mg, 1.5 equiv), and Celite (110 mg) in $CH_2Cl_2$ (13 mL) was stirred overnight. The mixture was filtered through a short pad of silica gel. Silica gel chromatography (95:5 hexanes/ethyl acetate) afforded a colorless solid (120 mg, 57%). $^1$H NMR ($CDCl_3$, 300 MHz): δ 7.41 (m, 6H), 7.34 (m, 4H), 7.06 (s, 2H), 7.03 (s, 2H), 4.29 (s, 2H), 3.18 (sept, 6.6 Hz, 1H), 2.75 (s, 3H), 2.54 (m, 2H), 1.3 (m, 2H), 1.19 (d, 6.6 Hz, 6H), 1.15 (m, 4H), 1.00 (s, 9H), 0.77 (m, 3H).

Step B: 2-Acetyl-3-pentyl-4-(4-fluorophenyl)-5-hydroxymethyl-6-isopropylpyridine The title compound was prepared from the intermediate obtained in Step A by the procedure described in Example 198, Step D. $^1$H NMR ($CDCl_3$, 300 MHz): δ 7.17 (s, 2H), 7.15 (s, 2H), 4.39 (d, 5.2 Hz, 2H), 3.48 (sept, 6.8 Hz, 3H), 2.74 (s, 3H), 2.55 (m, 2H), 1.35 (d, 6.6 Hz, 6H), 1.3 (m, 2H), 1.1 (m, 4H), 0.77 (t, 6.6 Hz, 3H). FAB-MS: calculated for $C_{22}H_{28}FNO_2$ 357; found 358 (M+H). Anal. calculated for $C_{22}H_{28}FNO_2$: C, 73.92; H, 7.90; N, 3.92. Found: C, 73.89; H. 8.14; N, 3.88. mp 69–70° C.

EXAMPLE 219

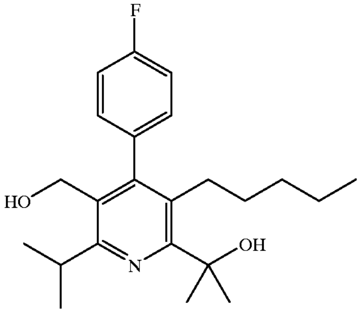

2-(1-Hydroxy-1-methylethyl)-3-pentyl-4-(4-fluorophenyl)-5-hydroxymethyl-6-isopropylpyridine Step A: 2-(1-Hydroxy-1-methylethyl)-3-pentyl-4-(4-fluorophenyl)-5-(t-butyldiphenylsiloxy)methyl-6-isopropylpyridine Prepared from the intermediate obtained in Example 218, Step A by the procedure described in Example 205, Step B.

$^1H$ NMR ($CDCl_3$, 300 MHz): δ 7.41 (m, 6H), 7.32 (m, 4H), 7.08 (m, 4H), 4.25 (s, 2H), 3.13 (sept, 6.8 Hz, 1H), 2.44 (m, 2H), 1.62 (s, 6H), 1.2 (m, 2H), 1.17 (d, 6.6 Hz, 6H), 1.03 (m, 4H), 1.01 (s, 9H), 0.72 (t, 6.8 Hz, 3H).

Step B: 2-(1-Hydroxy-1-methylethyl)-3-pentyl-4-(4-fluorophenyl)-5-hydroxymethyl-6-isopropylpyridine The title compound was prepared from the intermediate obtained in Step A by the procedure described in Example 198, Step D. $^1H$ NMR ($CDCl_3$, 300 MHz): δ 7.19 (m, 4H), 4.36 (d, 5.5 Hz, 2H), 3.48 6 (sept, 6.6 Hz, 1H), 2.47 (m, 2H), 1.60 (s, 6H), 1.35 (d, 6.6 Hz, 6H), 1.25 (m, 2H), 1.05 (m, 4H), 0.72 (t, 6.6 Hz, 3H). FAB-MS: calculated for $C_{23}H_{32}FNO_2$ 373; found 374 (M+H). Anal. calculated for $C_{23}H_{32}FNO_2$: C, 73.96; H, 8.63; F, 5.09; N, 3.75. Found: C, 73.88; H, 8.64; F, 4.81; N, 3.59. mp 180–182° C.

EXAMPLE 220

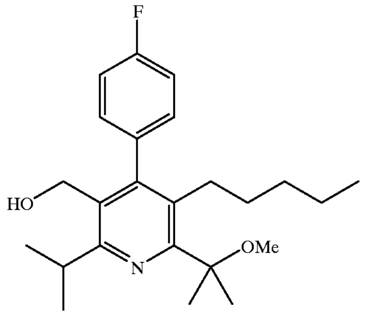

2-(1-Methoxy-1-methyl)ethyl-3-pentyl-4-(4-fluorophenyl)-5-hydroxymethyl-6-isopropylpyridine The title compound was prepared from the intermediate obtained in Example 219, Step A by the procedures described in Example 201, Step A, and Example 198, Step D. $^1H$ NMR ($CDCl_3$, 300 MHz): δ 7.26–7.12 (m, 4H), 4.34 (d, 5.5 Hz, 2H), 3.40 (sept, 6.5 Hz, 1H), 3.12 (s, 3H), 2.76 (m, 2H), 1.67 (s, 6H), 1.31 (d, 6.6 Hz, 6H), 1.3–0.9 (m, 6H), 0.72 (t, 6.8 Hz, 3H). FAB-MS: calculated for $C_{24}H_{34}FNO_2$ 387; found 388 (M+H). Anal. calculated for $C_{24}H_{34}FNO_2$: C, 74.38; H, 8.84; N, 3.61. Found: C, 74.64; H, 8.97; N, 3.61. mp 57–59° C.

EXAMPLE 221

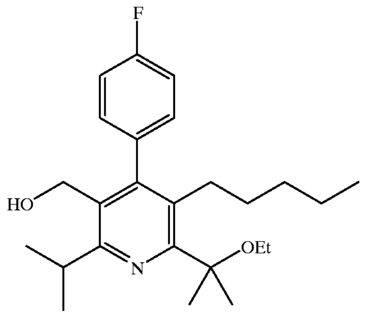

2-(1-Ethoxy-1-methyl)ethyl-3-pentyl-4-(4-fluorophenyl)-5-hydroxymethyl-6-isopropylpyridine The title compound was prepared from the intermediate obtained in Example 219, Step A by the procedures described in Example 201, Step A, and Example 198, Step D. $^1H$ NMR ($CDCl_3$, 300 MHz): δ 7.23–7.11 (m, 4H), 4.33 (d, 5.1 Hz, 2H), 3.39 (sept, 6.6 Hz, 1H), 3.28 (q, 7.0 Hz, 2H), 2.80 (m, 2H), 1.67 (s, 6H), 1.30 (d, 6.6 Hz, 6H), 1.15 (t, 7.0 Hz, 3H), 1.15–0.9 (m, 6H), 0.71 (t, 6.6 Hz, 3H). FAB-MS: calculated for $C_{25}H_{36}FNO_2$ 401; found 402 (M+H). Anal. calculated for $C_{25}H_{36}FNO_2$: C, 74.78; H, 9.04; N, 3.49. Found: C, 74.89; H, 9.22; N, 3.24.

EXAMPLE 222

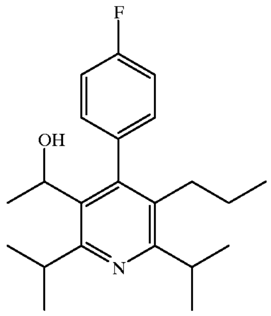

(+)-2,6-Diisopropyl-3-(1-hydroxyethyl)-4-(4-fluorophenyl)-5-propyl-pyridine

Step A: (±)-2,6-Diisopropyl-3-[1-hydroxy-2-(S)-toluylsulfoxyethyl]-4-(4-fluorophenyl)-5-propylpyridine A solution of lithium diisopropylamide was prepared by the addition of n-butyllithium (15 mL, 23 mmol, 1.6 M/hexane) to a solution of diisopropylamine (3 mL, 23 mmol) in anhydrous tetrahydrofuran (100 mL) at 0° C. To this was added a solution of (S)-(−)-methyl p-tolylsulfoxide (3.6 g, 23 mmol) in anhydrous tetrahydrofuran (20 mL) dropwise, with stirring. The mixture was stirred at 0° C. for 2 hr, then treated with a solution of 2,6-diisopropyl-4-(4-fluorophenyl)-5-propyl-3-pyridinecarboxaldehyde (Example 101, Step A) (3.8 g, 11 mmol) in anhydrous tetrahydrofuran (50 mL) dropwise and with stirring. After stirring 15 min at 0° C., the reaction mixture was quenched by the addition of saturated $NH_4Cl$ (5 mL). The solvent was removed in vacuo and the residue partitioned between $CHCl_3$ (300 mL) and water (100 mL). The organic phase was washed with saturated $NaHCO_3$ (100 mL), water (100 mL) and brine (50 mL), dried over $MgSO_4$ and concentrated. The crude product consisted of a 1.3:1 ratio of diastereomers which were separated by flash chromatography (step gradient 5%-15%-20% ethyl acetate/hexane), which afforded 1.5 g of the faster diastereomer (I), followed by 2.7 g of the slower diastereomer (II) and 0.83 g of a mixed fraction. Diastereomer II is recrystallized once from ethanol/hexane to afford fine white needles (1.7 g, 3.5 mmol, 30% yield). I: mp 225–227° C.; $R_f$=0.4 (30% ethyl acetate/hexane); $^1H$ NMR ($CDCl_3$, 500 MHz): δ 7.23 (m, 4H), 6.95 (m, 2H), 6.63 (m, 1H), 6.55 (m, 1H), 5.03 (d, J=11.0 Hz, 1H), 4.53 (s, 1H), 3.79 (m, 2H), 3.11 (sept, J=6.6 Hz, 1H), 2.46 (s, 3 H), 2.30 (dd, J=1.9, 14.1 Hz, 1H), 2.01 (m, 2H), 1.25 (m, 12H), 1.16 (m, 2H), 0.64 (t, J=7.3 Hz, 3H). FAB-MS: calcd for $C_{29}H_{36}FNO_2S$, 481, found 482 (M+H). II: mp 205–206° C.; $R_f$=0.2 (30% ethyl acetate/hexane); $^1H$ NMR ($CDCl_3$, 500 MHz): δ 7.38 (d, J=8.2 Hz, 2H), 7.24 (m, 2H), 7.05 (m, 1H), 7.03 (m, 1H), 6.97 (m, 1H), 6.87 (m, 1H), 4.84 (dt, J=2.7, 10.8 Hz, 1H), 3.69 (sept, J=6.6 Hz, 1H), 3.49 (dd, J=10.8, 13.1 Hz, 1H), 3.14 (sept, J=6.6 Hz, 1H), 3.00 (d, J=2.5 Hz, 1H), 2.68 (dd, J=2.5, 13.1 Hz, 1H), 2.41 (s, 3H), 2.10 (m, 2H), 1.23 (m, 14H), 0.69 (t, J=7.3 Hz, 3H). FAB-MS calcd for $C_{29}H_{36}FNO_2S$, 481, found 482 (M+H).

Step B: (+)-2,6-Diisopropyl-3-(1-hydroxyethyl)-4-(4-fluorophenyl)-5-propylpyridine A suspension of Raney nickel (20 g) in methanol (50 mL) was stirred under a hydrogen atmosphere for 1 hr. The suspension was cooled to 0° C. and treated with a solution of the intermediate II obtained in Step A (1.6 g, 3.3 mmol) in methanol (50 mL). The suspension was stirred vigorously under hydrogen at 0° C. for 16 hr. After purging with argon, the methanolic solution was decanted from the catalyst, the catalyst washed and decanted 3 more times with methanol. The combined decanted solution was filtered through celite and concentrated. Flash chromatography through a plug of silica (10% ethyl acetatehexane) afforded the title compound (99% e.e.) as a white solid (1.1 g, 3.2 mmol, 96%). $^1$H NMR ($CDCl_3$, 300 MHz): δ 7.11 (m, 3H), 7.04 (m, 1H), 4.64 (dq, J=3.7, 6.6 Hz, 1H), 3.73 (sept, J=6.6 Hz, 1H), 3.18 (sept, J=6.6 Hz, 1H), 2.15 (m, 2H), 1.56 (d, J=3.7 Hz, 1H), 1.39 (d, J=6.6 Hz, 3H), 1.28 (m, 14H), 0.73 (t, J=7.35 Hz, 3H). FAB-MS calcd for $C_{22}H_{30}FNO$, 343, found 344 (M+H). Anal. Calcd for $C_{22}H_{30}FNO$: C, 76.93; H, 8.80; N, 4.08; F, 5.53. Found: C, 76.98; H, 8.71; N, 3.76; F, 5.73. $[a]_D$=+41.5° ($CHCl_3$). mp 101–103° C. $R_f$=0.3 (10% ethyl acetate/hexane).

EXAMPLE 223

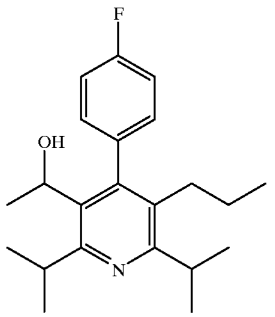

(+)-2,6-Diisopropyl-3-(1-hydroxyethyl)-4-(4-fluorophenyl)-5-propyl-pyridine

Step A: 2,6-Diisopropyl-4-(4-fluorophenyl)-5-propyl-3-[(1-oxo-2-toluylsulfoxy)ethyl)]pyridine To a solution of diisopropylamine (4.8 mL, 36.7 mmol) in anhydrous tetrahydrofuran (160 mL) was added n-butyllithium (23 mL, 33.4 mmol, 1.45 M/THF) at 0° C. To the reaction mixture was added a solution of (S)-(−)-methyl p-tolylsulfoxide (5.65 g, 36.7 mmol) in anhydrous tetrahydrofuran (30 mL). The mixture was stirred for 1.5 hours, then treated with a solution of 2,6-diisopropyl-4-(4-fluorophenyl)-5-propyl-3-pyridinecarboxaldehyde (Example 101, Step A) (8.0 g, 24.4 mmol) in anhydrous tetrahydrofuran (100 mL) at 0° C. After stirring 15 minutes at 0° C., the reaction was quenched by addition of saturated ammonium chloride solution (8 mL). The solvent was removed in vacuo and the residue dissolved in choroform (480 mL). The organic phase was washed with water (2×160 mL) and brine (160 mL), dried over magnesium sulfate and concentrated. The residue was dissolved in dichloromethane (800 mL) and manganese (IV) dioxide (40 g, 464 mmol) is added. The suspension was stirred vigorously with a mechanical stirrer and refluxed for 16 hours. The manganese (IV) dioxide was removed by filtration through celite, washed with dichloromethane (100 mL) and the solvent removed in vacuo. Filtration through a pad of silica gel (7.5% diethyl ether-dichloromethane) afforded a white solid (10.2 g, 21.3 mmol, 87%). $^1$H NMR (300 MHz, $CDCl_3$): δ 7.39 (m, 2H), 7.26 (m, 2H), 7.05 (m, 4H), 3.72 (d, J=16 Hz, 1H), 3.38 (d, J=16 Hz, 1H), 3.24 (sept, J=6.6 Hz, 1H), 2.59 (sept, J=6.6 Hz, 1H), 2.42 (s, 3H), 2.32 (m, 2H), 1.27 (m, 8H), 1.20 (m, 8H), 0.75 (t, J=7.35 Hz, 3H). FAB-MS: calculated for $C_{29}H_{34}FNO_2S$, 479, found 480 (M+H). mp 140–142° C. $R_f$=0.2 (20% ethyl acetate/hexane).

Step B: 2,6-Diisopropyl-3-(1-hydroxy-2-(S)-toluylsulfoxyethyl)-4-(4-fluorophenyl)-5-propylpyridine To a solution of the intermediate obtained in Step A (5.8 g, 12.1 mmol) in anhydrous tetrahydrofuran (145 mL) at −78° C. was added rapidly a solution of lithium aluminum hydride (169 mL, 169 mmol, 1.0 M/THF). After 15 minutes the reaction mixture became turbid and was slowly quenched at −78° C. with water (6 mL), 20% aqueous sodium hydroxide solution (6 mL) and water (18 mL). The reaction mixture was allowed to warm to room temperature and the resulting suspension was filtered through a pad of celite. The solvent was evaporated and the residue purified by silica gel chromatography (10% diethyl ether/dichloromethane) to afford a white solid (4.8 g, 10 mmol, 83%). $^1$H NMR (300 MHz, $CDCl_3$): δ 7.41 (d, J=8.5 Hz, 2H), 7.27 (m, 2H), 7.06 (d, J=7 Hz, 2H), 7.00 (m, 1H), 6.89 (m, 1H), 4.85 (dt, J=2.2, 11 Hz, 1H), 3.71 (sept, J=6.6 Hz, 1H), 3.51 (dd, J=11, 13 Hz, 1H), 3.16 (sept, J=6.6 Hz, 1H), 3.02 (d, J=2.2 Hz, 1H), 2.70 (dd,=2.2, 13 Hz, 1H), 2.43 (s, 3H), 2.12 (m, 2H), 1.25 (m, 14H), 0.71 (t, J=7.35 Hz, 3H). FAB-MS calculated for $C_{29}H_{36}FNO_2S$, 481, found 482 (M+H). mp 204–206° C. $R_f$=0.2 (30% ethyl acetate/hexane).

Step C: (+)-2,6-Diisopropyl-3-(1-hydroxyethyl)-4-(4-fluorophenyl)-5-propylpyridine A suspension of Raney nickel (40 g, washed with 3×100 mL ethanol) in ethanol (80 mL) was stirred under hydrogen atmosphere for 1.5 hours. The suspension was treated with a solution of the intermediate obtained in Step B (4.1 g, 8.5 mmol) in ethanol (180 mL) at room temperature and stirred vigorously for 5 hours. The suspension was carefully filtered through celite and concentrated. Filtration through silica gel ($CH_2Cl_2$) afforded the title compound (99% e.e.) as a white solid (2.74 g, 8 mmol, 94%). $^1$H NMR (300 MHz, $CDCl_3$): δ 7.11 (m, 3H), 7.04 (m, 1H), 4.64 (dq, J=3.7, 6.6 Hz, 1H), 3.73 (sept, J=6.6 Hz, 1H), 3.18 (sept,. J=6.6 Hz, 1H), 2.15 (m, 2H), 1.56 (d, J=3.7 Hz, 1H), 1.39 (d, J=6.6 Hz, 3H), 1.28 (m, 14H), 0.73.(t, J=7.35 Hz, 3H). FAB-MS calculated for ($C_{22}H_{31}FNO$, M+H) 344, found 344. Anal. Calcd for $C_{22}H_{30}FNO$: C, 76.93; H, 8.80; N, 4.08; F, 5.53; Found: C, 77.20; H, 8.97; N, 4.01; F, 5.60. $[a]_D$=+39.4° ($CH_2Cl_2$). mp 104–106° C. $R_f$=0.4 ($CH_2Cl_2$).

EXAMPLE 224

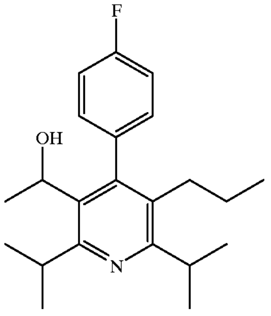

(+)-2,6-Diisopropyl-3-(1-hydroxyethyl)-4-(4-fluorophenyl)-5-propyl-pyridine

Step A: 2,6-Diisopropyl-3-(1-oxoethyl)-4-(4-fluorophenyl)-5-propylpyridine (±)-2,6-diisopropyl-3-(1-hydroxyethyl)-4-(4-fluorophenyl)-5-propylpyridine (Example 101) (8.03 g, 23.4 mmol) in $CH_2Cl_2$ (600 mL) was added pyridinium chlorochromate (10.08 g, 46.76 mmol) and celite (10.1 g) under argon. The reaction was stirred at room temperature for 16 hours. The reaction was added to a 1:1 mixture of diethyl ether/hexane (1 L), then filtered through a plug of silica. The pad was washed with 150 mL of diethyl ether and the combined filtrates were concentrated in vacuo to afford a white solid (7.95 g, 23.3 mmol, 98%). $^1$H NMR (300 MHz, $CDCl_3$): δ 7.12 (m, 4H), 3.26 (septet, J=6.6 Hz, 1H), 2.85 (septet, J=6.6 Hz, 1H), 2.36 (m, 2H), 1.97 (s, 3H), 1.33 (m, 14H), 0.774 (t, J=7.4 Hz, 3H). FAB-MS calcd for ($C_{22}H_{28}NOF$) 341, found 342 (M+H). mp 131–133° C. $R_f$=0.5 (50% $CH_2Cl_2$/hexane).

Step B: (+)-2,6-Diisopropyl-3-(1-hydroxyethyl)-4-(4-fluorophenyl)-5-propylpyridine To a solution of (1S,2R)-(+)-N-methylephedrine (31.1 g, 0.174 mol) in ether (208 mL) was added lithium aluminum hydride (1M/diethylether, 1.5 eq., 174 mL) dropwise at 0° C. under argon. The reaction was refluxed for 1.5 h. turning from a clear solution to a white milky solution. The reaction was cooled to room temperature and then −78° C. The intermediate obtained in Step A (39.53g, 0.116 mmol) was dissolved in 400 mL of dry diethyl ether and cooled to 0° C. for a dropwise addition to the reaction mixture (~2 mL/min., the temperature should not rise above −60° C.). The reaction was kept at −78° C. for 4.0 hours and then allowed to warm overnight. The reaction was quenched at 0° C. with isopropanol (70 mL) and diluted with ether (700 mL), washed with water (4×500 mL), 10% HCl (2×500 mL), brine (2×500 mL) and dried with $MgSO_4$. Filtration and concentration afforded a residue which was filtered through a pad of silica (600 g, 10% diethyl ether/hexane) to give the title compound (97% e.e.) as a white solid (36.67 g, 107 mmol, 92%). $^1$H NMR (300 MHz, $CDCl_3$): δ 7.11 (m, 4H), 4.67 (dq, J=3.3, 6.6 Hz, 1H), 3.74 (septet, J=6.6 Hz, 1H), 3.20 (septet, J=6.6 Hz, 1H), 2.17 (m, 2 H), 1.61 (d, J=2.9 Hz, 1H), 1.40 (d, J=7.0 Hz, 3H), 1.30 (m, 14H), 0.741 (t, J=7.4 Hz, 3H). FAB-MS: calcd for ($C_{22}H_{30}NOF$) 343, found 344 (M+H). mp 102–104° C. $R_f$=0.2 (60% $CH_2Cl_2$/hexane).

EXAMPLE 225

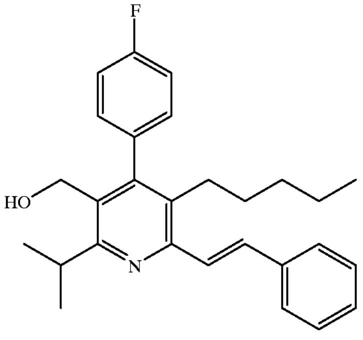

2-Isopropyl-3-hydroxymethyl-4-(4-fluorophenyl)-5-pentyl-6-(2-trans-phenylethyl)pyridine Step A: 2-Bromomethyl-3-pentyl-4-(4-fluorophenyl)-5-(t-butyldiphenylsiloxy)methyl-6-isopropylpyridine Prepared from the intermediate obtained in Example 200, Step B by the procedure described in Example 47, Step B. $^1$H NMR (300 MHz, $CDCl_3$): δ 7.40 (m, 6H), 7.32 (m, 4H), 7.04 (m, 4H), 4.64 (s, 2H), 4.26 (s, 2H), 3.14 (sept, 6.8 Hz, 1H), 2.38 (m, 2H), 1.34 (m, 2H), 1.17 (d, 7.0 Hz, 6H), 1.12 (m, 4H), 1.00 (s, 9H), 0.78 (t, 6.6 Hz, 3H).

Step B: 2-(Diethylphosphono)methyl-3-pentyl-4-(4-fluorophenyl)-5-(t-butyldiphenylsiloxy)methyl-6-isopropylpyridine A mixture of diethylphosphite (280 mg) and sodium metal (50 mg) in benzene (5 mL) was stirred overnight. A mixture of the sodium diethylphosphite solution (1 mL) and the intermediate obtained in Step A (110 mg, 0.17 mmol) in benzene (5 mL) was refluxed for 2 h. The mixture was concentrated in vacuo. The residue was dissolved in ethyl acetate (30 mL) and washed with saturated aqueous sodium chloride solution (3×10 mL). Silica gel chromatography (70:30 hexanes/ethyl acetate) provided a yellow oil (80 mg, 67%). $^1$H NMR (300 MHz, $CDCl_3$): δ 7.41 (m, 6H), 7.32 (m, 4H), 7.04 (m, 4H), 4.25 (s, 2H), 4.15 (dq, 7.2 Hz, 4H), 3.49 (d, 22.4 Hz, 2H), 3.14 (sept, 6.8 Hz, 1H), 2.38 (m, 2H), 1.30 (t, 7.2 Hz, 6H), 1.25 (m, 2H), 1.16 (d, 6.6 Hz, 6H), 1.10 (m, 4.), 0.99 (s, 9H), 0.77 (t, 6.8 Hz, 3H).

Step C: 2-(trans-2-Phenylethenyl)-3-pentyl-4-(4-fluorophenyl)-5-(t-butyldiphenylsiloxy)methyl-6-isopropylpyridine Sodium hydride (8 mg) was added to a mixture of the intermediate obtained in Step B (90 mg, 128 μmol) and benzaldehyde (20 mg) in THF (2.7 mL). After 15 min. the mixture was diluted with ethyl acetate and washed with saturated aqueous sodium chloride solution. Silica gel chromatography (97:3 hexanes/ethyl acetate) provided a yellow oil (100 mg). $^1$H NMR (300 MHz, $CDCl_3$): δ 8.00 (d, 15.4 Hz, 1H), 7.61 (m, 2H), 7.45–7.27 (m, 14H), 7.04 (m, 4H), 4.29 (s, 2H), 3.20 (sept, 6.4 Hz, 1H), 2.38 (m, 2H), 1.40 (m, 2H), 1.25 (d, 6.6 Hz, 6H), 1.18 (m, 4H), 1.00 (s, 9H), 0.81 (m, 3H).

Step D: 2-(trans-2-Phenylethenyl)-3-pentyl-4-(4-fluorophenyl)-5-hydroxymethyl-6-isopropylpyridine The title compound was prepared from the intermediate obtained in Step C by the procedure described in Example 198, Step D. Silica gel chromatography (94:6 hexanes/ethyl acetate) provided a yellow oil (24 mg, 38%). $^1$H NMR (300 MHz, $CDCl_3$): δ 8.02 (d, 15.5 Hz, 1H), 7.63 (m, 2H), 7.43–7.31 (m, 4H), 7.16 (m, 4H), 4.38 (s, 2H), 3.48 (sept, 6.6 Hz, 1H), 2.41 (m, 2H), 1.42 (d, 6.6 Hz, 6H), 1.4 (m, 2H), 1.19 (m, 4H), 0.82 (t, 6.8 Hz, 3H). FAB-MS: calculated for $C_{28}H_{32}FNO$ 417; found 418 (M+H). $R_f$=0.13 (90:10 hexanes/ethyl acetate). Anal. calculated for $C_{28}H_{32}FNO$: C, 80.54; H, 7.72; N, 3.35. Found: C, 80.34; H, 7.79; N, 3.10. mp 98–100° C.

EXAMPLE 226

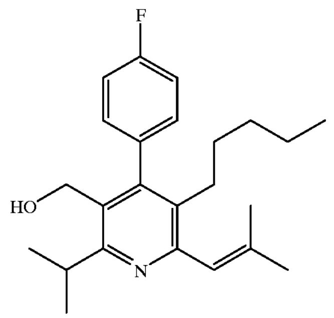

2-Isopropyl-3-hydroxymethyl-4-(4-fluorophenyl)-5-pentyl-6-(2-methylpropenyl)pyridine The title compound was prepared as a yellow oil from the intermediate obtained in Example 225, Step B by the procedure described in Example 225, Step C and Example 198, Step D. The product was obtained as an inseparable mixture of the title compound and the corresponding deconjugated olefin in a ratio of 84:16. $^1$H NMR (300 MHz, $CDCl_3$): δ 7.16 (m, 4H), 6.43 (s, 1H), 4.82 (s, 1H, minor isomer), 4.60 (s, 1H, minor isomer), 4.36 (s, 2H), 3.58 (s, 2H, minor isomer), 3.46 (sept, 6.6 Hz, 1H), 2.26 (m, 2H), 2.07 (s, 3H), 1.99 (s, 3H), 1.82 (s, 3H, minor isomer), 1.35 (d, 7.0 Hz, 6H), 1.28 (m, 2H), 1.13 (m, 4H), 0.79 (t, 6.8 Hz, 3H). FAB-MS: calculated for $C_{24}H_{32}FNO$ 369; found 370 (M+H). $R_f$=0.16 (90:10 hexanes/ethyl acetate). Anal. calculated for $C_{24}H_{32}FNO$: C, 78.01; H, 8.73; N, 3.79. Found: C, 77.73; H, 8.86; N, 3.97.

EXAMPLE 227

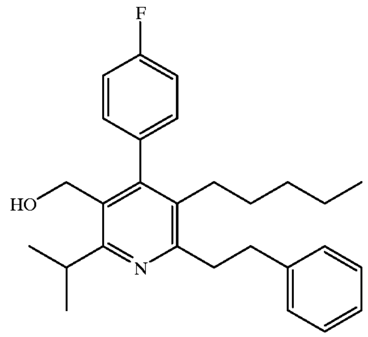

2-Isopropyl-3-hydroxymethyl-4-(4-fluorophenyl)-5-pentyl-6-(2-phenylethyl)pyridine The title compound was prepared as a yellow oil from the intermediate obtained in Example 225, Step D by the procedure described in Example 1, Step H. $^1$H NMR (300 MHz, $CDCl_3$): δ 7.29–7.19 (m, 5H), 7.14 (s, 2H), 7.12 (s, 2H), 4.34 (s, 2H), 3.44 (sept, 6.6 Hz, 1H), 3.18–3.10 (m, 4H), 2.20 (m, 2H), 1.35 (d, 6.6 Hz, 6H), 1.22 (m, 2H), 1.08 (m, 4H), 0.76 (t, 6.8 Hz, 3H). FAB-MS: calculated for $C_{28}H_{34}FNO$ 419; found 420 (M+H). $R_f$=0.21 (90:10 hexanes/ethyl acetate). Anal. calculated for $C_{28}H_{34}FNO$: C, 80.18; H, 8.17; N, 3.34. Found: C, 80.12; H, 8.15; N, 3.24.

EXAMPLE 228

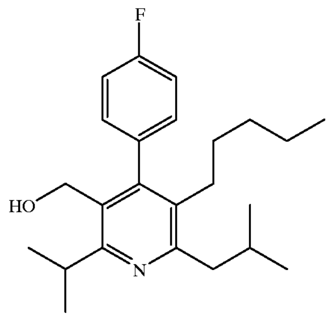

2-Isopropyl-3-hydroxymethyl-4-(4-fluorophenyl)-5-pentyl-6-(2-methylpropyl)pyridine The title compound was prepared as a colorless crystalline solid from the intermediate obtained in Example 226 by the procedure described in Example 1, Step H. $^1$H NMR (300 MHz, $CDCl_3$): δ 7.15 (m, 4H), 4.33 (d, 5.2 Hz, 2H), 3.41 (sept, 6.6 Hz, 1H), 2.67 (d, 7.0 Hz, 2H), 2.34 (m, 2H), 2.25 (m, 2H), 1.32 (d, 6.6 Hz, 6H), 1.20 (m, 2H), 1.12 (m, 4H), 0.99 (d, 6.6 Hz, 6H), 0.78 (t, 6.6 Hz, 3H). FAB-MS: calculated for $C_{24}H_{34}FNO$ 371; found 372 (M+H). $R_f$=0.77 (90:10 hexanes/ethyl acetate). Anal. calculated for $C_{24}H_{34}FNO$: C, 77.59; H, 9.22; N, 3.77. Found: C, 77.49; H, 9.20; N. 3.73.

EXAMPLE 229

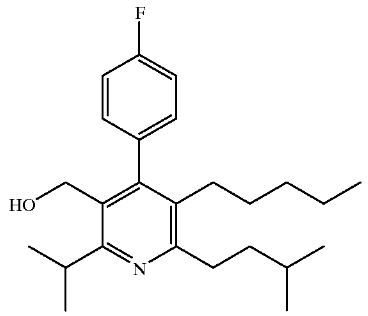

2-Isopropyl-3-hydroxymethyl-4-(4-fluorophenyl)-5-pentyl-6-(3-methylbutyl)pyridine The title compound was prepared as a yellow oil from the intermediate obtained in Example 225, Step B by the procedures described in Example 225, Steps C and D, and Example 1, Step H. $^1$H NMR (300 MHz, $CDCl_3$): δ 7.14 (m, 4H), 4.34 (d, 3.7 Hz, 2H), 3.41 (sept, 6.8 Hz, 1H), 2.80 (m, 2H), 2.26 (m, 2H), 1.68 (m, 3H), 1.33 (d, 6.6 Hz, 6H), 1.29 (m, 2H), 1.12 (m, 4H), 0.98 (d, 6.3 Hz, 6H), 0.79 (t, 6.6 Hz, 3H). FAB-MS: calculated for $C_{25}H_{36}FNO$ 385; found 386

(M+H). $R_f$=0.15 (90:10 hexanes/ethyl acetate). Anal. calculated for $C_{25}H_{36}FNO$: C, 77.88; H, 9.41; N, 3.63. Found: C, 77.62; H, 9.13; N, 3.42.

EXAMPLE 230

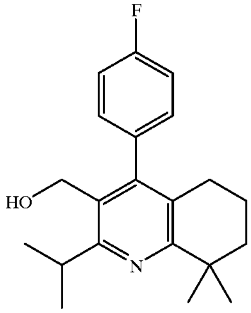

2-Isopropyl-3-hydroxymethyl-4-(4-fluorophenyl)-5,6,7,8-tetrahydro-8,8-dimethylquinoline Step A: 2-[(4-Fluorophenyl)methylene]-4-methyl-3-oxopentanoic Acid To a solution of ethyl isobutyryl acetate (30 g, 0.190 mol) in ethanol (75 mL) was added cyclohexane (120 mL), acetic add (0.6 mL), piperidine (0.6 mL), and 4-fluorobenzaldehyde (20.35 mL, 0.190 mol). The reaction was heated at reflux with a Dean-Starck trap for 5 hours. The mixture was poured into 200 mL of diethyl ether and washed with brine (1×75 mL). The organic layer was dried with $MgSO_4$, filtered, and concentrated to afford an orange oil. The product was taken directly to the next step without any further purification. $R_f$=0.1 (50% $CH_2Cl_2$/hexane).

Step B: 2-Isopropyl-3-carboethoxy-4-(4-fluorophenyl)-5,6,7,8-tetrahydro-8,8-dimethylquinoline To a solution of lithium bis(trimethylsilyl)amide (1.0 M/THF, 2 eq. 13.6 mL) in THF (15 mL) was added 2,2-dimethylcyclohexanone (1.88 mL, 13.6 mmol) at −78° C. The reaction was stirred for 15 minutes, and then the intermediate obtained in Step A (3 g, 11.4 mmol) was added dropwise. The reaction was stirred overnight and allowed to warm to room temperature. To the crude product was added acetic add (19.4 mL), ammonium acetate (2.62 g, 34.0 mmol) and copper acetate (5.14 g, 28.3 mmol). The reaction mixture was heated at 100° C. and the THF was removed by distillation. The reaction was heated to 130° C. and allowed to reflux for 24 hours. Ethyl acetate (100 mL) was added and washed with sodium bicarbonate (2×30 mL), water (2×20 mL), brine (2×20 mL), dried with $MgSO_4$, filtered, and concentrated to afford an oil. Flash chromatography (5% ethyl acetate/hexane) afforded a white solid (1.36, 3.7 mmol, 32%). $^1$H NMR (300 MHz, $CDCl_3$): δ 7.17 (m, 2H), 7.08 (m, 2H), 3.98 (q, J=7.4 Hz, 2H), 3.03 (septet, J=7.0 Hz, 1H), 2.35 (t, J=5.9 Hz, 2H), 1.70 (m, 4H), 1.36 (s, 6H), 1.31 (d, J=4.1 Hz, 6H), 0.965 (t, J=7.4 Hz, 3H). FAB-MS: calculated for ($C_{23}H_{28}FNO$) 369, found 370 (M+H. mp 124–126° C. $R_f$=0.6 (50% $CH_2Cl_2$/hexane).

Step C: 2-Isopropyl-3-hydroxymethyl-4-(4-fluorophenyl)-5,6,7,8-tetrahydro-8,8-dimethylquinoline To the intermediate obtained in Step B (1.32 g, 3.6 mmol) in THF (35 mL) was added lithium aluminum hydride (1 M/THF, 2 eq., 7.2 mL) dropwise. The reaction was refluxed for 1.5 hours and cooled to room temperature. Then the reaction was quenched with water and the THF was evaporated. The residue was partitioned between diethyl ether (150 mL) and water (100 mL). The organic layer was washed with brine (1×100 mL), dried with $MgSO_4$, filtered, and concentrated to afford a solid. Flash chromatography (40% $CH_2Cl_2$/hexane) afforded the title compound as a white solid (808 mg, 2.5 mmol, 70%). $^1$H NMR (300 MHz, $CDCl_3$): δ 7.13 (d, J=7.0 Hz, 4H), 4.36 (d, J=5.5 Hz, 2H), 3.42 (septet, J=6.6 Hz, 1H), 2.24 (t, J=5.5 Hz, 2H), 1.67 (m, 4H), 1.32 (m, 13H). FAB-MS: calculated for ($C_{21}H_{26}FNO$) 327, found 328 (M+H). mp 146–149° C. $R_f$=0.2 (50% $CH_2Cl_2$/hexane).

EXAMPLE 231

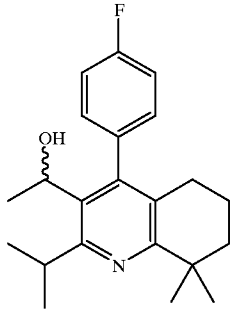

2-Isopropyl-3-(1-hydroxyethyl)-4-(4-fluorophenyl)-5,6,7,8-tetrahydro-8,8-dimethylquinoline Step A: 2-Isopropyl-3-carboxaldehyde-4-(4-fluorophenyl)-5,6,7,8-tetrahydro-8,8-dimethylquinoline To a solution of 2-isopropyl-3-hydroxymethyl-4-(4-fluorophenyl)-5,6,7,8-tetrahydro-8,8-dimethylquinoline (Example 230) (765 mg, 2.34 mmol) in dichloromethane (30 mL) was added Celite (1.01 g) and pyridinium chlorochromate (1.01 g, 4.69 mmol). The reaction was stirred at room temperature for 2 hours and then added to a 1:1 diethyl ether/hexane solution (500 mL). The solution was passed through a pad of silica and washed several times with diethyl ether. Concentration yielded a white solid (568 mg, 1.75 mmol, 75%). $^1$H NMR (300 MHz, $CDCl_3$): δ 9.78 (s, 1H), 7.15 (m, 4H), 3.86 (septet, J=6.6 Hz, 1H), 2.31 (t, J=5.9 Hz, 2H), 1.70 (m, 4H), 1.37 (s, 6H), 1.30 (m, 6H). FAB-MS: calculated for ($C_{21}H_{24}FNO$) 325, found 326 (M+H). mp 94–96° C. $R_f$=0.7 (50% $CH_2Cl_2$/hexane).

Step B: 2-Isopropyl-3-(1-hydroxyethyl)-4-(4-fluorophenyl)-5,6,7,8-tetrahydro-8,8-dimethylquinoline To the intermediate obtained in Step A (508 mg, 1.56 mmol) in THF (20 mL) was added methylmagnesium bromide (0.57 mL, 3.0 M/ether, 1.1 eq.) dropwise at −78° C. After 2 hours, the reaction was quenched with saturated ammonium chloride (30 mL) and diluted with dichloromethane (100 mL). The solid was filtered and the mother liquor was washed with water (1×50 mL), brine (1×50 mL), dried with $MgSO_4$, filtered, and concentrated to afford a white solid. Flash chromatography (50% dichloromethane/hexane) gave a white solid (205 mg, 0.6 mmol, 39%). $^1$H NMR (300 MHz, $CDCl_3$): δ 7.13 (m, 3H), 7.01 (m, 1H), 4.73, 4.71 (dq, J=3.7, 6.6 Hz, 1H), 3.74 (septet, J=6.6 Hz, 1H), 2.13 (q, J=4.4 Hz, 2H), 1.64 (m, 3H), 1.31 (m, 17H). FAB-MS: calculated for ($C_{22}H_{27}FNO$) 341, found 342 (M+H). mp 56.5–58.5° C. $R_f$=0.2 (50% $CH_2Cl_2$/hexane).

EXAMPLE 232

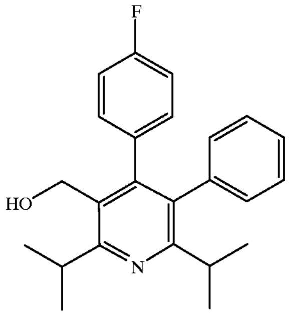

2,6-Diisopropyl-3-hydroxymethyl-4-(4-fluorophenyl)-5-(1-butenyl)pyridine

The title compound was prepared from ethyl isobutyrylacetate, 4-fluorobenzaldehyde and 3-methyl-1-phenyl-2-butanone according to the procedures described in Example 230. $^1$H NMR (300 MHz, $CDCl_3$): δ 7.16 (m, 3H), 6.91 (m, 6H), 4.45 (d, J=5.1 Hz, 2H), 3.52 (sept., J=6.6 Hz, 1H), 2.86 (sept., J=6.6 Hz, 1H), 1.55 (s, 1H), 1.36 (m, 6H), 1.17 (d, J=6.6 Hz, 6H). FAB-MS: calculated for ($C_{24}H_{26}FNO$) 363, found 364 (M+H). mp 115–117° C. $R_f$=0.3 (60% $CH_2Cl_2$/hexane).

EXAMPLE 233

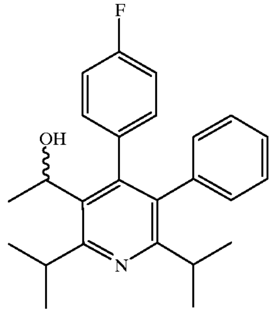

2,6-Diisopropyl-3-(1-hydroxyethyl)-4-(4-fluorophenyl)-5-phenylpyridine

The title compound was prepared according to the procedures described in Example 231. $^1$H NMR (300 MHz, $CDCl_3$): δ 7.14 (m, 3H), 6.88 (m, 6 H), 4.80 (dq, J=7.0, 3.7 Hz, 1H), 3.84 (sept., J=6.6 Hz, 1H), 2.79 (sept., J=6.6 Hz, 1 H), 1.66 (d, J=3.7 Hz, 1H), 1.48 (d, J=7.0 Hz, 3H), 1.39 (m, 6H). FAB-MS: calculated for ($C_{25}H_{28}FNO$) 377, found 378 (M+H). mp 155–157° C. $R_f$=0.4 (60% $CH_2Cl_2$/hexane).

EXAMPLE 234

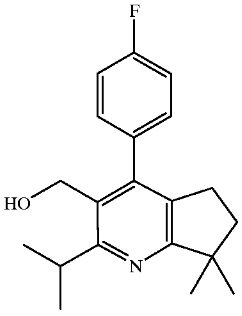

2-Isopropyl-3-hydroxymethyl-4-(4-fluorophenyl)-7,7-dimethyl-5H-cyclopenta[b]pyridine The title compound was prepared from ethyl isobutyrylacetate, 4-fluorobenzaldehyde and 2,2-dimethylcyclopentanone according to the procedures described in Example 230. $^1$H NMR (300 MHz, $CDCl_3$): δ 7.29 (m, 2H), 7.14 (m, 2H), 4.49 (d, J=5.2 Hz, 2H), 3.46 (sept., J=6.6 Hz, 1H), 2.56 (t, J=7.0 Hz, 2H), 1.90 (t, J=7.0 Hz, 2H), 1.34 (m, 13H). FAB-MS: calculated for ($C_{20}H_{24}FNO$) 313, found 314 (M+H). mp 141–143° C. $R_f$=0.1 (60% $CH_2Cl_2$/hexane).

EXAMPLE 235

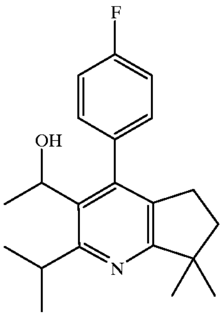

2-Isopropyl-3-(1-hydroxyethyl)-4-(4-fluorophenyl)-7,7-dimethyl-5H-cyclopenta[b]pyridine The title compound was prepared according to the procedures described in Example 231. $^1$H NMR (300 MHz, $CDCl_3$): δ 7.15 (m, 4H), 4.95 (dq, J=6.6, 3.7 Hz, 1H), 3.77 (sept., J=6.6 Hz, 1H), 2.44 (m, 2H), 1.88 (t, J=7.4 Hz, 2H), 1.62 (d, J=3.7 Hz, 1H), 1.48 (d,=7.0 Hz, 3H), 1.32 (m, 12H). FAB-MS: calculated for ($C_{21}H_{26}FNO$) 327, found 328 (M+H). mp 90–92° C. $R_f$=0.1 (60% $CH_2Cl_2$/hexane).

EXAMPLE 236

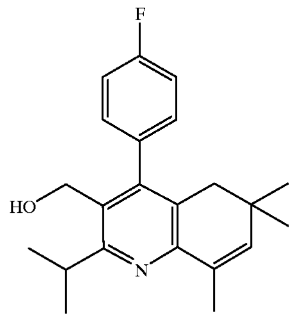

2-Isopropyl-3-hydroxymethyl-4-(4-fluorophenyl)-5,6-dihydro-6,6,8-trimethylquinoline The title compound was prepared from ethyl isobutyrylacetate, 4-fluorobenzaldehyde and 2,4,4-trimethyl-2-cyclohexen-1-one according to the procedures described in Example 230. $^1$H NMR (300 MHz, $CDCl_3$): δ 7.16 (m, 4H), 5.81 (s, 1H), 4.41 (d, J=5.2 Hz, 2H), 3.45 (sept., J=6.6 Hz, 1H), 2.29 (s, 2H), 2.16 (s, 3H), 1.58 (s, 1H), 1.35 (d, J=6.6 Hz, 6H), 0.95 (s, 6H). FAB-MS: calculated for ($C_{22}H_{26}FNO$) 339, found 340 (M+H). mp 112–114° C. $R_f$=0.2 (60% $CH_2Cl_2$/hexane).

EXAMPLE 237

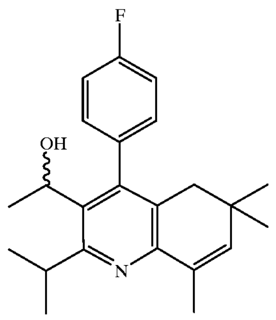

2-Isopropyl-3-(1-hydroxyethyl)-4-(4-fluorophenyl)-5,6-dihydro-6,6,8-trimethylquinoline The title compound was prepared according to the procedures described in Example 231. $^1$H NMR (300 MHz, $CDCl_3$): δ 7.14 (m, 3H), 7.00 (m, 1H), 5.78 (s, 1 H), 4.77 (dq, J=6.6, 3.7 Hz, 1H), 3.76 (sept., J=6.6 Hz, 1H), 2.18 (s, 2H), 2.14 (s, 3 H), 1.61 (d, J=3.7 Hz, 1H), 1.43 (d, J=6.6 Hz, 3H), 1.33 (m, 6H), 0.91 (s, 6H). FAB-MS: calculated for ($C_{23}H_{28}FNO$) 353, found 354 (M+H). mp 117–119° C. $R_f$=0.3 (60% $CH_2Cl_2$/hexane).

EXAMPLE 238

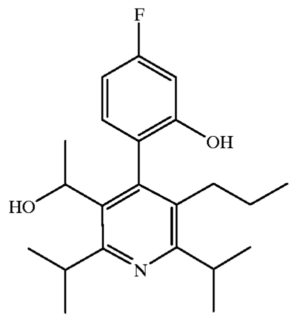

2,6-Diisopropyl-3-(1-hydroxyethyl)-4-(4-fluoro-2-hydroxyphenyl)-5-propylpyridine Step A: 2,6-Diisopropyl-3-hydroxymethyl-4-[(2-benzyloxy-4-fluoro)phenyl]-5-prop-1-enyl)pyridine Prepared from the intermediate obtained in Example 166, Step B by the methods described in Example 160, Steps A–D. $^1$H NMR (300 MHz, $CDCl_3$): δ 1.20–1.34 (m, 12H), 1.56–1.59 (m, 3H), 1.68–1.74 (m, 1H), 3.13–3.50 (m, 2H), 4.23–4.42 (m, 2H), 4.87–5.05 (m, 2H), 5.25–5.56 (m, 1H), 5.23–6.03 (m, 1H), 6.69–6.77 (m, 2H), 6.95–7.08 (m, 3H), 7.22–7.27 (m, 3H). FAB-MS: calcd for ($C_{28}H_{32}NO_2F$) 433; found 434 (M+1). $R_f$=0.30 (10% ethyl acetate-hexane).

Step B: 2,6-Diisopropyl-3-(1-hydroxyethyl)-4-(4-fluoro-2-hydroxyphenyl)-5-propylpyridine The title compound was prepared as two separable diastereomers from the intermediate obtained in Step A by the methods described in Example 164, Steps A–C. The diastereomers were separated by radial band chromatography using a gradient eluent of 100% hexane to 20% ether-hexane.

Diastereomer 1: $^1$H NMR (300 MHz, $CDCl_3$): δ 0.75 (t, J=7.2 Hz, 3H), 1.27–1.40 (m, 17H), 1.66 (br s, 1H), 2.02–2.12 (m, 1H), 2.20–2.31 (m, 1H), 3.21 (sept, J=6.6 Hz, 1H), 3.60 (sept, J=6.6 Hz, 1H), 4.94 (m, 1H), 5.03 (br s, 1H), 6.70–6.76 (m, 2H), 6.94–7.00 (m, 1H); FAB-MS: calcd for ($C_{22}H_{30}NO_2F$) 359, found 360 (M+1). $R_f$=0.29 (20% ethyl acetate-hexane). mp 152–153° C.

Diastereomer 1 was resolved into its constituent enantiomers as follows. A Waters Prep LC 2000 HPLC system was equipped with a chiral HPLC column (BRB-9668A; 6×50 cm ID). The system was equilibrated with a mobile phase consisting of 1% (1% acetic acid, 99% ethanol) and 99% hexane at a flow rate of 150 mL/min. The sample was dissolved in chloroform (50 mg/mL) and 5 mL aliquots were injected at 40 min intervals. The effluent was monitored at 280 nm and two fractions (corresponding to the two enantiomers) were collected at (17–23 min,100% ee) and (23–32 min, 98% ee), respectively.

Diastereomer 2: $^1$H NMR (300 MHz, $CDCl_3$): δ 0.75 (t, J=7.2 Hz, 3H), 1.26–1.31 (m, 14H), 1.38 (d, J=6.9 Hz, 3H), 1.84–1.87 (m, 1H), 2.05–2.14 (m, 1H), 2.24–2.34 (m, 1H), 3.20 (septet, J=6.6 Hz, 1H), 3.72 (septet, J=6.6, 1H), 4.58–4.65 (m, 1H), 5.06 (br s, 1H), 6.67–6.74 (m, 2H), 6.85–6.90 (m, 1H); FAB-MS: calcd for ($C_{22}H_{30}NO_2F$) 359, found 360 (M+1). $R_f$=0.19 (20% ether-hexanes). mp 157–159° C.

EXAMPLE 239

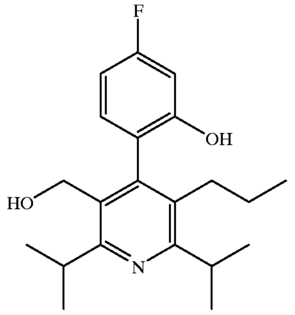

2,6-Diisopropyl-3-(1-hydroxymethyl)-4-(4-fluoro-2-hydroxyphenyl)-5-propylpyridine The title compound was prepared from 2,6-diisopropyl-3-hydroxymethyl-4-[(2-benzyloxy-4-fluoro)phenyl]-5-(prop-1-enyl)pyridine (Example 238, Step A) by the method described in Example 161, Step A (mp 138–141° C.). $^1$H NMR (300 MHz, $CDCl_3$): δ 0.76 (t, J=7.2 Hz, 3H), 1.24–1.35 (m, 14H), 1.82 (br s, 1H), 2.12–2.22 (m, 1H), 2.27–2.37 (m, 1H), 3.24 (sept, J=6.6 Hz, 1H), 3.39 (sept, J=6.6 Hz, 1H), 4.29 (d, J=11.4 Hz, 1H), 4.52 (d, J=10.8 Hz, 1H), 5.72 (br s, 1H), 7.70–6.77 (m, 2H), 6.94–7.00 (m, 1H). FAB-MS: calcd for ($C_{21}H_{28}NO_2F$) 345; found 346 (M+1). $R_f$=0.30 (10% ethyl acetate-hexane).

The racemate was resolved into its constituent enantiomers as follows. A Waters Prep LC 2000 HPLC system was equipped with a chiral HPLC column (BRB-9668A; 6×50 cm ID). The system was equilibrated with a mobile phase consisting of 1% (1% acetic acid, 95% ethanol) and 99% hexane at a flow rate of 100 mL/min. The sample was dissolved in mobile phase (5 mg/mL) and 3 mL aliquots were injected at 30 min intervals. The effluent was monitored at 280 nm and two fractions (corresponding to the two enantiomers) were collected at (24–36 min, 100% ee) and (26–30 min, 95.5% ee), respectively.

EXAMPLE 240

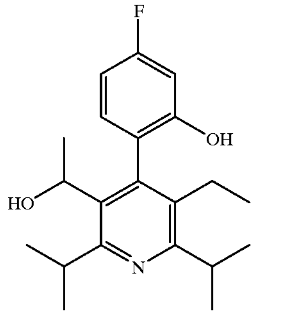

2,6-Diisopropyl-3-(1-hydroxyethyl)-4-(4-fluoro-2-hydroxyphenyl)-5-ethylpyridine

Step A: 2,6-Diisopropyl-3-hydroxymethyl-4-[(2-benzyloxy-4-fluoro)phenyl]-5-ethenyl)pyridine Prepared from the intermediate obtained in Example 166, Step B by the methods described in Example 160, Steps A–D. $^1$H NMR (300 MHz, $CDCl_3$): δ 1.25–1.33 (m, 12H), 1.66–1.70 (m, 1H), 3.34–3.50 (m, 2H), 4.28–4.41 (m, 2H), 4.89–5.18 (m, 4H), 6.29–6.39 (m, 1H), 6.67–6.78 (m, 2H), 7.23–7.25 (m, 3H). FAB-MS: calcd for ($C_{27}H_{30}NO_2F$) 419; found 420 (M+1). $R_f$=0.29 (10% ethyl acetate-hexane).

Step B: 2,6Diisopropyl-3-carboxyaldehyde-4-[(2-benzyloxy-4-fluoro)phenyl]-5-ethenyl)pyridine Prepared from the intermediate obtained in Step A by the method described in Example 164, Step A. $^1$H NMR (300 MHz, $CDCl_3$): δ 1.25–1.33 (m, 12H), 3.24 (sept, 1H, J=6.6 Hz), 3.89 (sept, 1H, J=6.6 Hz), 4.93–5.04 (m, 3H), 5.23 (dd, 1H, J=1.5, 11.4 Hz), 6.40 (dd, 1H, J=11.4, 17.7 Hz), 6.70–7.04 (m, 2H), 6.99–7.04 (m, 1H), 7.10–7.14 (m, 2H), 7.24–7.29 (m, 3H), 9.82 (s, 1H). FAB-MS: calcd for ($C_{27}H_{28}NO_2F$) 417; found 418 (M+1). $R_f$=0.68 (10% ethyl acetate-hexane).

Step C: 2,6-Diisopropyl-3-(2-hydroxyethyl)-4-[(2-hydroxy-4-fluoro)phenyl]-5-ethyl)pyridine To an oven-dried 250 mL three-neck round bottom flask equipped with a thermometer were added copper(I) iodide (3.21 g, 16.9 mmol) and toluene (40 mL) under an argon atmosphere. The slurry was cooled to an internal temperature of 0° C . Methyllithium (1.4M in ether, 25 mL, 0.03314 mol) was added at a rate to maintain reaction temperature <5° C. The reaction was then allowed to stir at 0° C. for 50 min. At the end of this time the intermediate from Step B (1.33 g, 3.19 mmol) in 10 mL toluene was added via syringe at a rate to maintain reaction temperature <5° C. The syringe was rinsed with an additional 4 mL toluene and this rinse was added to the reaction mixture at a rate to maintain reaction temperature <5° C. The reaction was stirred at 0° C. for 35 min. The reaction was then quenched by the addition of a saturated solution of ammonium chloride (20 mL) and was allowed to stir for 36 h at 25° C. The reaction mixture was poured into a separtory funnel and was extracted with ethyl acetate (3×50 mL). The combined organic layer was then concentrated to yield the crude intermediate (1.4 g, yellow oil, 9:1 ratio of diastereomers). The crude intermediate was dissolved in a mixture of ethanol (30 mL) and tetrahydrofuran (10 mL) under argon, treated with 10% palladium on carbon (140 mg), and was then stirred under a hydrogen atmosphere for 14 h. After purging the system with argon, the catalyst was removed by filtration through a pad of Celite. The solvent was removed and the residue was purified by flash chromatography (12–15% ethyl acetate-hexane) to yield 1.0 g of the title compound as two separate diastereomers.

Diastereomer 1: $^1$H NMR (300 MHz, $CDCl_3$): δ 0.91 (t, J=7.4 Hz, 3H), 1.28–1.40 (m, 15H), 1.70 (d, J=3.9 Hz, 1H), 2.12–2.24 (m, 1H), 2.29–2.41 (m, 1H), 3.24 (sept, J=6.6 Hz, 1H), 3.61 (sept, J=6.6 Hz, 1H), 4.89–5.00 (m, 1H), 5.10 (br s, 1H), 6.70–6.76 (m, 2H), 6.96–7.01 (m, 1H); FAB-MS: calcd for ($C_{21}H_{28}NO_2F$) 345, found 346 (M+1). $R_f$=0.43 (30% ether-hexane). mp 190–191° C.

Diastereomer 1 was resolved into its constituent enantiomers as follows. A Waters Prep LC 2000 HPLC system was equipped with a chiral HPLC column (BRB-9668A; 6×50 cm ID). The system was equilibrated with a mobile phase consisting of 1% (1% acetic acid, 99% ethanol) and 99% hexane at a flow rate of 100 mL/min. The sample (1 g) was dissolved in a mixture of $CH_2CL_2$ (40 mL), ethanol (1 mL), and 10 mL of the mobile phase. The mixture was injected and the effluent was monitored at 280 nm and two fractions (corresponding to the two enantiomers) were collected at (27–29 min, 99.8% ee) and (37–57 min, 99.4% ee), respectively. Fraction 1 (27–29 min): $[\alpha]^{25}_D$+4.7° (c=0.54, $CH_2Cl_2$).

Diastereomer 2: 1H NMR (300 MHz, $CDCl_3$): δ 0.89 (t, J=7.5 Hz, 3H), 1.26–1.38 (m, 15H), 1.92 (d, J=3Hz, 1H), 2.12–2.25 (m, 1H), 2.31–2.43 (m, 1H), 3.23 (septet, J=6.6 Hz, 1H), 3.72 (septet, J=6.6, 1H), 4.56–4.63 (m, 1H), 5.14 (br s, 1H), 6.68–6.74 (m, 2H), 6.85–6.91 (m, 1H); FAB-MS: calcd for ($C_{21}H_{28}NO_2F$) 345, found 346 (M+1). $R_f$=0.27 (30% ether-hexane). mp 201–202° C.

EXAMPLE 241

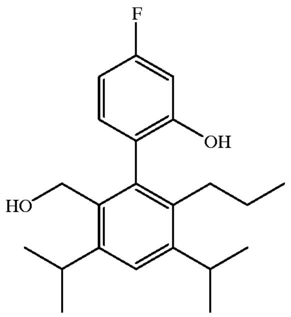

3,5-Diisopropyl-2-hydroxymethyl-6-propyl-4'-fluoro-2'-hydroxy-1,1'-biphenyl

Step A: Dimethyl-4,6-diethyl-2-hydroxy-1,3-benzenedicarboxylate

A mixture of dimethyl 1,3-acetonedicarboxylate (200 g, 1.15 mol), 3,5-heptanedione (140 g, 1.09 mol) and sodium methoxide (70 g, 1.25 mol) in methanol (1.5 L) was held at reflux overnight. Methanol was removed via rotary evaporation and the resulting orange sludge was partitioned between diethyl ether (1 L) and 10% aqueous hydrochloric acid (1 L). The separated aqueous layer was extracted with diethyl ether (0.5 L×2). The combined organic portions were washed with saturated aqueous sodium chloride (0.1 L), dried over sodium sulfate, filtered through a pad of silica (40 mm×100 mm) and concentrated in vacuo. The crude oil was purified via vacuum distillation at 0.25 Torr to afford the clean product as translucent yellow oil (bp: 125–145° C., 202 g, 70%): $^1$H NMR (300 MHz, $CDCl_3$): δ 1.20 (t, J=7.4 Hz, 6H), 2.71–2.80 (m, 4H), 3.95 (s, 6H), 6.64 (s, 1H), 11.67 (s, 1H). $^{13}$C NMR (75 MHz, $CDCl_3$): δ 15.42, 28.31, 52.27, 115.22, 121.91, 148.63, 159.71, 169.86. EI-MS: calculated for $C_{14}H_{18}O_5$ 266; found 266 (M+). Anal. calc for $C_{14}H_{18}O_5$: C, 63.15; H, 6.81. Found: C, 63.23; H, 6.92. $R_f$=0.38 (9:1 hexanes:ethyl acetate). HPLC: (C-18, A=0.05% aqueous trifluoroacetic acid, B=$CH_3CN$; linear gradient: 50%–100% B over 30 min; 254 nm, 1 mL/min): R.T. 14.4 min (100.0 area %).

Step B: Dimethyl 4,6-diethyl-2-methoxy-1,3-benzenedicarboxylate

A mixture of the crude intermediate obtained in Step A (241.6 g, 0.91 mol), potassium carbonate (204 g, 1.48 mol) and dimethyl sulfate (129 mL, 1.37 mol) in acetone (1 L) was stirred vigorously overnight. After six hours at reflux, the reaction was cooled to room temperature, additional dimethyl sulfate (43 mL, 0.46 mol) was added, and reflux was continued overnight. The mixture was filtered through a pad of Celite, diethyl ether (1 L) was used to wash the Celite pad, and the combined filtrates were concentrated in vacuo. The resulting crude oil was purified via vacuum distillation to afford the pure product as a translucent yellow oil (bp: 180–190° C., 178.1 g, 58% (2 steps)): $^1$H NMR (300 MHz, $CDCl_3$): δ 1.16–1.25 (m, 6H), 2.55–2.66 (m, 4H), 3.81 (s, 3H), 3.91 (s, 6H), 6.89 (s, 1H). $R_f$=0.34 (9:1 hexanes:ethyl acetate).

Step C: Dimethyl 4,6-diisopropyl-2-methoxy-1,3-benzenedicarboxylate

A solution of diisopropylamine (26.7 mL, 0.20 mol) in dry tetrahydrofuran (0.2 L) at −78° C. under an argon atmosphere was treated with slow addition of n-butyllthium (2.47M in hexanes, 85.0 mL, 0.20 mol). After the reaction stirred for fifteen minutes, a solution of the intermediate from Step B (58.0 g, 0.16 mol) in dry tetrahydrofuran (0.2 L) was added to the solution of LDA over 45 minutes. Stirring was continued for 80 minutes while the internal temperature was held at −76° C. Neat iodomethane (13.2 mL, 0.21 mol) was added to the reaction mixture via syringe; two-thirds of the charge was transferred at the outset, the reaction was allowed to stir for 30 minutes, then the final third of the charge was added, followed by another 30 minutes of stirring. A second pot of LDA (0.2 mol) in dry tetrahydrofuran (0.2 L) was produced by the above procedure and was transferred to the reaction mixture via cannula over 45 minutes. Stirring was continued for 80 minutes at −76 ° C. then a second portion of neat iodomethane (13.2 mL, 0.21 mol) was added to the reaction mixture using the addition sequence described above. The cooling bath was removed and the reaction mixture was quenched with saturated aqueous ammonium chloride solution (0.4 L). The mixture was extracted with diethyl ether (3×0.4 L) and the combined organic portions were dried over magnesium sulfate, filtered through a plug of silica gel and concentrated in vacuo to afford the clean product as an off-white solid (60.2 g, 98%). $^1$H NMR (300 MHz, $CDCl_3$): δ 1.24 (d, J=6.6 Hz, 12H), 2.84–2.96 (m, 2H), 3.82 (s, 3H), 3.92 (s, 6H), 7.04 (s, 1H). $^{13}$C NMR (75 MHz, $CDCl_3$): δ 23.72, 31.36, 52.30, 63.56, 117.95, 125.66, 148.68, 153.76, 168.36. FAB-MS: calculated for $C_{17}H_{24}O_5$ 308; found 309 ((M+H)+). Anal. calc for $C_{17}H_{24}O_5$: C, 66.21; H, 7.84. Found: C, 66.22; H, 7.94. $R_f$=0.3 (9:1 hexanes:ethyl acetate). HPLC: (C-18, A=0.05% aqueous trifluoroacetic acid, B=$CH_3CN$; linear gradient: 50%–100% B over 30 min; 254 nm, 1 mL/min): R.T. 16.2 min (97.6 area %). mp 70.5–71.5° C.

Step D: Diisopropyl 4,6-diisopropyl-2-methoxy-1,3-benzenedicarboxylate

Isopropanol (50 mL) was cautiously added to a flask charged with sodium hydride (95%, 0.33 g, 13.8 mmol). A solution of the intermediate obtained in Step C (8.5 g, 27.6 mmol) in isopropanol (100 mL) was added and the resulting mixture was held at reflux overnight. Additional sodium hydride (95%, 0.33 g, 13.8 mmol) and isopropanol (50 mL) were added to push the reaction to completion. Reflux was continued for five hours then the reaction mixture was cooled to ambient temperature and quenched with 10% aqueous hydrochloric acid (60 mL). Isopropanol was removed in vacuo and the residual aqueous layer was extracted with diethyl ether (2×150 mL). The combined ethereal extracts were dried over magnesium sulfate, concentrated in vacuo, and chromatographed on silica (300 g) using dichloromethane:hexanes (1:1) as eluent to provide the clean product as a colorless crystalline solid (8.5 g, 85%). $^1$H NMR (300 MHz, $CDCl_3$): δ 1.25 (d, J=7.0 Hz, 12H), 1.37 (d, J=6.3 Hz, 12H), 2.90–2.98 (m, 2H), 3.85 (s, 3H), 5.30 (septet, J=6.3 Hz, 2H), 7.02 (s, 1H). $^{13}$C NMR (75 MHz, $CDCl_3$): δ 21.77, 23.74, 31.12, 63.59, 68.92, 117.78, 126.44, 148.08, 153.20, 167.40. FAB-MS: calculated for C21H32O$_5$ 364; found 365 ((M+H)+). Anal. calc for $C_{21}H_{32}O_5$: C, 69.20; H, 8.85. Found: C, 69.23; H, 8.86. $R_f$=0.42 (9:1 hexanes:ethyl acetate). HPLC: (C-18, A=0.05% aqueous trifluoroacetic acid, B=$CH_3CN$; linear gradient: 50%–100% B over 30 min; 254 nm, 1 mL/min): R.T. 24.4 min (96.6 area %). mp 68.0–69.0° C.

Step E: Diisopropyl 3,5-diisopropyl-2'-benzyloxy-4'-fluoro-1,1-biphenyl-2,6-dicarboxylate A dry flask containing freshly ground magnesium turnings (2.88 g, 120 mmol) and a crystal of iodine was heated until a dark purple iodine atmosphere had formed. The flask was cooled to ambient temperature and a solution of 2-bromo-5-fluorophenyl benzyl ether (33.8 g, 120 mmol, Example 166, Step A) in dry tetrahydrofuran (60 mL) was added in several portions over 40 minutes at a rate sufficient to maintain reflux. Reflux was continued for 45 minutes, then the reaction was cooled to room temperature. This solution of Grignard reagent was transferred via syringe to a second flask containing a solution of the intermediate from Step D (11.0 g, 30.2 mmol) in dry benzene (66 mL). The reaction mixture was held at reflux for one hour, quenched with 10% aqueous hydrochloric acid (300 mL) and extracted with diethyl ether (3×300 mL). The combined extracts were dried over magnesium sulfate and concentrated in vacuo to give a brown oil which was subjected to flash column chromatography on silica (80 mm×19.5") using a stepwise gradient elution of dichloromethane:hexanes (1:3, 1:2, 1:1, 4L each). The fractions containing the product were combined and concentrated to afford an inseparable mixture of the product and an unidentified side product in about a 1:1 ratio as a pale yellow gum (5.3 g, 33% mass balance). This material was not fully characterized and was used without further purification.

Step F: Isopropyl 3,5-diisopropyl-6-hydroxymethyl-2'-benzyloxy-4'-fluoro-1,1'-biphenyl-2-carboxylate A mixture of the intermediate from Step E (5.83 g, 10.9 mmol) and Red-Al (3.3 mL, 10.9 mmol) in dry tetrahydrofuran (100 mL) was held at reflux for 2.5 hours. Additional Red-Al was added (in 3.3 mL aliquots) and reflux maintained until the lower Rf spot disappeared (21 hours, total 8 eq. Red-Al; i.e. the by-product from the previous step reacted faster than the desired diester). The reaction mixture was cooled to 0° C., carefully quenched with water (14 mL), and vigorously stirred for 2 hours. The precipitated solids were removed via vacuum filtration through paper and the collected solids were washed with ethyl acetate (3×100 mL) and refiltered. The combined filtrates were washed with a 1:1 mixture of water and saturated aqueous sodium chloride (100 mL), followed by water (75 mL) and saturated aqueous sodium chloride (50 mL). The organic portion was separated, dried over sodium sulfate and concentrated in vacuo. Purification by flash column chromatography on silica (80 mm×6") using hexanes:ethyl acetate (19:1) as eluent gave pure diisopropyl 3,diisopropyl-2'-benzyloxy-4'-fluoro-1,1'-biphenyl-2,6-dicarboxylate (2.63 g, 4.92 mmol). This was resubjected to the reaction conditions with Red-Al (2.95 mL, 9.84 mmol) in dry tetrahydrofuran (45 mL). Additional Red-Al was added (in 2.95 mL aliquots) and reflux maintained until the reaction was complete (30 hours, total 12 eq. Red-Al). Worked up as above and subjected crude product to flash column chromatography on silica (40 mm×7") using hexanes:ethyl acetate (19:1) as eluent to provide the desired product as a translucent colorless oil (1.25 g, 55%). $^1$H NMR (300 MHz, $CDCl_3$): δ 0.91 (d, J=6.6 Hz, 3H), 1.09 (d, J=6.3 Hz, 3H), 1.20–1.33 (m, 9H), 1.35 (d, J=7.0 Hz, 3H), 1.91–2.00 (br s, 1H), 2.94–3.07 (m, 1H), 3.37–3.50 (m, 1H), 4.24–4.46 (m, 2H), 4.84–5.06 (m, 3H), 6.73–6.87 (m, 2H), 7.01–7.08 (m, 2H), 7.14–7.29 (m, 4H), 7.39 (s, 1H). FAB-MS: calculated for $C_{30}H_{35}O_4F$ 478; found 479 ((M+H)+). $R_f$=0.23 (9:1 hexanes:ethyl acetate).

Step G: Isopropyl 3,5-diisopropyl-6-formyl-2'-benzyloxy-4'-fluoro-1,1'-biphenyl-2-carboxylate A chilled (0° C.) mixture of the intermediate from Step F (0.73 g, 1.52 mmol), Celite (1.46 g), and pyridinium chlorochromate (0.61 g, 2.84 mmol) in dry dichloromethane (30 mL) was stirred for 5 hours, while warming to room temperature. The mixture was diluted with ethyl acetate (30 mL) and hexane (60 mL) and filtered through a plug of silica (30 mm×3"). Elution was continued with ethyl acetate:hexanes (1:1 mixture, 2×120 mL). The combined filtrates were concentrated in vacuo to afford the desired product as a clear colorless oil (0.72 g, 99%). $^1$H NMR (300 MHz, $CDCl_3$): δ 0.90 (d, J=6.3 Hz, 3H), 1.07 (d, J=6.3 Hz, 3H), 1.23–1.36 (m, 12H), 2.99–3.10 (m, 1H), 3.92–4.02 (m, 1H), 4.85–5.06 (m, 3H), 6.65–6.76 (m, 2H), 7.15–7.30 (m, 6H), 7.46 (s, 1H), 9.84 (s, 1H). FAB-MS: calculated for $C_{30}H_{33}O_4F$ 476; found 477 ((M+H)+). $R_f$=0.47 (9:1 hexanes:ethyl acetate).

Step H: Isopropyl 3,5-diisopropyl-6-(prop-1-enyl)-2'-benzyloxy-4'-fluoro-1,1'-biphenyl-2-carboxylate A chilled (−70° C.) suspension of (ethyl) triphenylphosphonium bromide (0.88 g, 2.37 mmol) in dry tetrahydrofuran (6 mL) was treated with dropwise addition of n-butyllithium (2.47M in hexanes, 1.04 mL, 2.56 mmol). The mixture was immediately warmed to 0° C., stirred for 90 minutes at 0° C., and recooled to −70 ° C. A solution of the intermediate from Step G (0.94 g, 1.97 mmol) in dry tetrahydrofuran (6 mL) was added to the solution of ylide over several minutes and the reaction mixture was warmed again to 0° C. and stirred for one hour. The reaction was quenched with water (3 mL) and diluted with ethyl acetate (25 mL). The organic portion was washed with saturated aqueous sodium chloride solution (2×15 mL). The combined aqueous portions were back-extracted with ethyl acetate (10 mL). The combined organic portions were dried over sodium sulfate and concentrated in vacuo to provide the crude solid which was subjected to flash column chromatography on silica (30 mm×6") using hexanes:ethyl acetate (19:1) as eluent. The clean fractions were combined and concentrated in vacuo to afford the desired product as a pale yellow oil (0.81 g, 84%). $^1$H NMR (300 MHz, $CDCl_3$): δ 0.84–0.92 (m, 3H), 1.02–1.59 (m, 18H), 2.96–3.31 (m, 2H), 4.82–4.97 (m, 1H), 4.98 (s, 2H), 5.19–5.52 (m, 1H), 6.07–6.19 (m, 1H), 6.57–6.69 (m, 2H), 7.05–7.31 (m, 7H). FAB-MS: calculated for $C_{32}H_{37}O_3F$ 488; found 489 (M+H)+. $R_f$=0.58 (9:1 hexanes:ethyl acetate).

Step I: 3,5-Diisopropyl-2-hydroxymethyl-(prop-1-enyl)-2'-benzyloxy-4'-fluoro-1,1'-biphenyl A reaction flask was charged with a suspension of lithium aluminum hydride (95%, 0.14 g, 3.3 mmol) in dry tetrahydrofuran (5 mL) and heated to reflux. A solution of the intermediate from Step H (0.80 g, 1.64 mmol) in dry tetrahydrofuran (10 mL) was added to the refluxing suspension dropwise from a syringe. The reaction mixture was held at reflux for 23 hours, cooled to ambient temperature and quenched using saturated aqueous sodium sulfate solution which was added dropwise until gas evolution stopped. The mixture was then diluted with ethyl acetate (15 mL), stirred for several minutes and filtered through a pad of Celite. The pad was washed copiously with additional ethyl acetate. The combined filtrates were concentrated in vacuo and subjected to flash column chromatography on silica (30 mmx3") to afford the clean product as a clear oil (0.53 g, 75%). $^1$H NMR (300 MHz, $CDCl_3$): δ 1.05–1.46 (m, 15H), 1.68–1.78 (br s, 1H), 3.07–3.49 (m, 2H), 4.27–4.47 (m, 2H), 4.85–5.05 (m, 2H), 5.25–5.52 (m, 1H), 5.92–6.08 (m, 1H), 6.68–6.76 (m, 2H), 6.98–7.13 (m, 3H), 7.18–7.29 (m, 3H), 7.35 (s, 1H). FAB-MS: calculated for $C_{29}H_{33}O_2F$ 432; found 432 (M)+. $R_f$=0.29 (9:1 hexanes:ethyl acetate).

Step J: 3,5-Diisopropyl-2-hydroxymethyl-6-propyl-4'-fluoro-2'-hydroxy-1,1'-biphenyl A mixture of the intermediate from Step I (0.53 g, 1.23 mmol), and 10% Pd/C (53 mg) in methanol (12 mL) was stirred under one atmosphere of hydrogen gas for 18 hours. The reaction mixture was then filtered through a pad of Celite and the pad was rinsed thoroughly with methanol (100 mL). The combined filtrates were concentrated in vacuo and subjected to flash column chromatography on silica (20 mmx4") using hexanes:ethyl acetate (9:1) as eluent. In this manner, the pure product was obtained as a dear oil which slowly solidified to provide the title compounds as a white solid (0.37 g, 87%). $^1$H NMR (300 MHz, $CDCl_3$): δ 0.76 (t, J=7.4 Hz, 3H), 1.16–1.36 (m, 15H), 2.11–2.42 (m, 2H), 3.12–3.25 (m, 1H), 3.30–3.43 (m, 1H), 4.29–4.47 (m, 2H), 6.69–6.80 (m, 2H), 7.00–7.07 (m, 1H), 7.36 (s, 1H). $^{13}$C NMR (75 MHz, $CDCl_3$): δ 14.65, 24.29, 24.34, 24.50, 24.58, 29.21, 32.18, 59.61, 103.6 (d, J=24.4 Hz), 107.6 (d, J=22.0 Hz), 123.50, 123.67 (d, J=2.4 Hz), 131.21 (d, J=9.8 Hz), 134.07, 134.66, 137.42, 146.30, 148.12, 154.26 (d, J=12.2 Hz), 163.01 (d, J=244.2 Hz). FAB-MS: calculated for $C_{22}H_{29}O_2F$ 344; found 344 (M)+. Anal. calc for $C_{22}H_{29}O_2F$: C, 76.71; H, 8.49. Found: C, 76.66; H, 8.34. $R_f$=0.41 (4:1 hexanes:ethyl acetate). HPLC: (C-18, A=0.05% aqueous trifluoroacetic acid, B=$CH_3CN$; linear gradient: 50%–100% B over 30 min; 254 nm, 1 mL/min): R.T. 17.1 min (97.5 area %). mp 127.5–129.0° C.

EXAMPLE 242

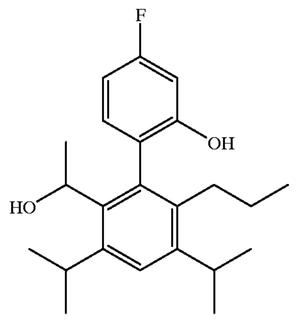

3,5-Diisopropyl-2-(1-hydroxyethyl)-6-propyl-4'-fluoro-2'-hydroxy-1,1'-biphenyl

Step A: 3,5-Diisopropyl-2-hydroxymethyl-6-propyl-4'-fluoro-2'-benzyloxy-1,1'-biphenyl A mixture of the racemic compound prepared in Example 241 (293 mg, 851 μmol), benzyl bromide (110 μL, 925 μmol), and potassium carbonate (303 mg, 2.19 mmol) in acetone (29 mL) was heated to reflux for 3 h. The mixture was diluted with saturated aqueous ammonium chloride solution (50 mL) and extracted with $Et_2O$ (3x50 mL). Silica gel chromatography (90:10 hexane/ethyl acetate) provided a colorless oil (0.369 g, 100%). $^1$H NMR ($CDCl_3$, 300 MHz): δ 7.34 (s, 1H), 7.23 (m, 3H), 7.12 (m, 1H), 7.03 (m, 2H), 6.84–6.75 (m, 2H), 5.04 (d, 12.1 Hz, 1H), 4.94 (d, 12.1 Hz, 1H), 4.38 (dd, 11.4 Hz, 8.5 Hz, 1H), 4.25 (dd, 11.4 Hz, 3.3 Hz, 1H), 3.39 (sept, 6.9 Hz, 1H), 3.18 (sept, 6.9 Hz, 1H), 2.30–2.40 (m, 1H), 2.09–2.20 (m, 1H), 1.65 (dd, 8.5 Hz, 3.3 Hz, 1H), 1.26–1.34 (m, 14H), 0.72 (t, 7.4 Hz, 3H).

Step B: 3,5-Diisopropyl-2-formyl-6-propyl-4'-fluoro-2'-benzyloxy-1,1'-biphenyl

Prepared from the intermediate obtained in Step A by the procedure described in Example 218, Step A. Silica gel chromatography (95:5 hexane/EtOAc) provided a colorless crystalline solid (0.323 g, 88%). $^1$H NMR ($CDCl_3$, 300 MHz): δ 9.74 (s, 1H), 7.41 (s, 1H), 7.22–7.28 (m, 3H), 7.06–7.13 (m, 3H), 6.72–6.80 (m, 2H), 5.00 (s, 2H), 3.91 (sept, 6.8 Hz, 1H), 3.23 (sept, 6.7 Hz, 1H), 2.37–2.46 (m, 1H), 2.17–2.27 (m, 1H), 1.20–1.36 (m, 14H), 0.73 (t, 7.4 Hz, 3H). FAB-MS: calculated for $C_{29}H_{33}FO_2$ 432; found 433 (M+H).

Step C: 3,5-Diisopropyl-2-(1-hydroxyethyl)-6-propyl-4'-fluoro-2'-benzyloxy-1,1'-biphenyl Methyl lithium (2.7 mL of 1.4 M solution in $Et_2O$, 3.78 mmol) was added dropwise over five minutes to a cooled (ice-water bath) suspension of CuI (715 mg, 3.75 mmol, purified by extraction with THF) in toluene (10.8 mL) such that the internal temperature of the mixture was ≦3° C. The addition produced first a yellow-orange suspension and then a colorless solution. After 25 minutes the mixture was again a yellow-orange suspension. A solution of the intermediate obtained in Step B (306 mg, 707 μmol) in toluene (1 mL) was added dropwise over four minutes such that the internal temperature of the mixture was ≦2° C. After 30 minutes ⅓ saturated aqueous $NH_4OH$ solution (40 mL) was added. After an additional 60 minutes the mixture was diluted with saturated aqueous $NH_4Cl$ solution (40 mL) and extracted with $Et_2O$ (3x40 mL). Silica gel chromatography (83:17 hexane/EtOAc) provided a colorless solid (0.290 g, 91%). The product was a mixture of diastereomers in a ratio of 93:7 as judged by HPLC. $^1$H NMR ($CDCl_3$, 300 MHz, only peaks corresponding to the major diastereomer were visible): δ 7.35 (s, 1H), 7.22–7.24 (m, 3H), 7.11 (dd, 8.1 Hz, 7.0 Hz, 1H), 7.04 (m, 2H), 6.70–6.78 (m, 2H), 4.99 (d, 2.6 Hz, 2H), 4.83 (qd, $J_q$=6.8 Hz, $J_d$=2.8 Hz, 1H), 3.84 (sept, 6.8 Hz, 1H), 3.14 (sept, 6.9 Hz, 1H), 2.29 (m, 1H), 2.07 (m, 1H), 1.74 (d, 2.9 Hz, 1H), 1.25–1.35 (m, 17H), 0.70 (t, 7.4 Hz, 3H). EI-MS: calculated for $C_{30}H_{37}FO_2$ 448; found 448 ($M^+$).

Step D: 3,5-Diisopropyl-2-(1-hydroxyethyl)-6-propyl-4'-fluoro-2'-hydroxy-1,1'-biphenyl The title compound was prepared from the intermediate obtained in Step C by the procedure described in Example 1, Step H. Silica gel chromatography (83:17 hexane/EtOAc) provided two colorless solids (0.229 g, 99%).

Diastereomer 1 was obtained as a colorless crystalline solid (0.214 g, 92%). $^1$H NMR ($CDCl_3$, 300 MHz): δ 7.37 (s, 1H), 7.03 (m, 1H), 6.72 (m, 2H), 4.80–4.89 (m, 2H), 3.79 (sept, 6.8 Hz, 1H), 3.14 (sept, 6.8 Hz, 1H), 2.31 (m, 1H), 2.08 (m, 1H), 1.64 (d, 3.3 Hz, 1H), 1.41 (d, 7.0 Hz, 3H), 1.26–1.31 (m, 14H), 0.74 (t, 7.4 Hz, 3H). FAB-MS: calculated for $C_{23}H_{31}FO_2$ 358; found 341 (M—OH). mp 149–150° C. $R_f$=0.25 (83:17 hexane/ethyl acetate).

Diastereomer 1 (212 mg) was resolved into its constituent enantiomers as follows: a Waters Prep LC 4000 HPLC system was equipped with a chiral HPLC column (BRB-9668A; 6×50 cm ID). The system was equilibrated with a mobile phase consisting of 1% butanol and 99% heptane at a flow rate of 100 mL/min. The sample was dissolved in dichloromethane (70 mg/mL) and 1 mL aliquots were injected at 40 min intervals. The effluent was monitored at 285 nm and two fractions (corresponding to the two enantiomers) were collected at (19–23 min,100% ee) and (30–37 min, ≧98% ee), respectively.

Enantiomer 1 was obtained as a colorless solid (78 mg). $^1H$ NMR ($CDCl_3$, 300 MHz): δ 7.37 (s, 1H), 7.02 (m, 1H), 6.71 (m, 2H), 4.77–4.89 (m, 2H), 3.77 (m, 1H), 3.14 (sept, 6.8 Hz, 1H), 2.31 (m, 1H), 2.08 (m, 1H), 1.63 (d, 2.9 Hz, 1H), 1.41 (d, 6.6 Hz, 3H), 1.26–1.31 (m, 14H), 0.74 (t, 7.2 Hz, 3H). FAB-MS: calculated for $C_{23}H_{31}FO_2$ 358; found 341 (M—OH).

Enantiomer 2 was obtained as a colorless solid (74 mg). $^1H$ NMR ($CDCl_3$, 300 MHz): δ 7.38 (s, 1H), 7.03 (m, 1H), 6.72 (m, 2H), 4.80–4.90 (m, 2H), 3.79 (sept, 6.6 Hz, 1H), 3.14 (sept, 6.7 Hz, 1H), 2.30 (m, 1H), 2.07 (m, 1H), 1.63 (d, 3.3 Hz, 1H), 1.41 (d, 6.6 Hz, 3H), 1.26–1.31 (m, 14H), 0.74 (t, 7.2 Hz, 3H). FAB-MS: calculated for $C_{23}H_{31}FO_2$ 358; found 341 (M—OH).

Diastereomer 2 was obtained as a colorless crystalline solid (15.3 mg, 7%). $^1H$ NMR ($CDCl_3$, 300 MHz): δ 7.37 (s, 1H), 6.92 (m, 1H), 6.70 (m, 2H), 5.1 (br s, 1H), 4.64 (q, 6.7 Hz, 1H), 3.85 (sept, 6.7 Hz, 1H), 3.14 (sept, 6.8 Hz, 1H), 2.32 (m, 1H), 2.09 (m, 1H), 1.8 (br s, 1H), 1.37 (d, 6.6 Hz, 3H), 1.24–1.30 (m, 14H), 0.74 (t, 7.2 Hz, 3H). FAB-MS: calculated for $C_{23}H_{31}FO_2$ 358; found 341 (M—OH). mp 179–180° C.

EXAMPLE 243

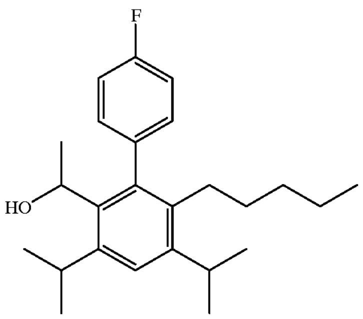

(+)-3,5-Diisopropyl-2-(1-hydroxyethyl)-6-pentyl-4'-fluoro-1,1'-biphenyl

Step A: 3,5-Diisopropyl-2-(1-oxoethyl)-6-pentyl-4'-fluoro-1,1'-biphenyl

A mixture of 3,5-diisopropyl-2-(1-hydroxyethyl)-6-pentyl-4'-fluoro-1,1'-biphenyl (Example 192, 13.7 g, 37.1 mmol), Celite (26 g), and pyridinium chlorochromate (14.9 g, 69.3 mmol) in dichloromethane (750 mL) was stirred for 45 minutes. The mixture was diluted with ethyl acetate (750 mL) and hexane (1.5 L) and filtered through a plug of silica (100 mm×2") topped with Celite (100 mm×0.5"). Elution was continued with ethyl acetate:hexanes (1:1 mixture, 3L×2). The combined filtrates were concentrated in vacuo to afford the desired product as a white solid (13.5 g, 99%). $^1H$ NMR (300 MHz, $CDCl_3$): δ 0.75–0.80 (m, 3H), 1.06–1.31 (m, 18H), 1.95 (s, 3H), 2.33–2.39 (m, 2H), 2.78 (septet, J=7.0 Hz, 1H), 3.18 (septet, J=7.0 Hz, 1H), 7.03–7.09 (m, 2H), 7.17–7.22 (m, 2H) 7.26 (s, 1H). $^{13}C$ NMR (75 MHz, CDCl3): δ 13.75, 22.02, 24.32, 24.37, 28.99, 29.10, 29.28, 30.60, 31.04, 32.06, 33.03, 114.85 (d, J=20.8 Hz, 2C), 122.06, 132.03 (d, J=7.3 Hz, 2C), 135.52 (d, J=2.4 Hz, 1C) 135.58, 135.76, 140.13, 140.85, 147.66 161.99 (d, J=246.6 Hz, 1C), 208.23. EI-MS: calculated for $C_{25}H_{33}OF$ 368; found 368 (M+). Anal. calc for $C_{25}H_{33}OF$: C, 80.86; H, 8.96. Found: C, 81.04; H, 9.06. $R_f$=0.65 (9:1 hexanes:ethyl acetate). HPLC: (C-18, A=0.05% aqueous trifluoroacetic add, B=$CH_3CN$; linear gradient: 75%–100% B over 30 min; 254 nm, 1 mL/min): R.T. 22.7 min (94.0 area %). mp 123.0–124.5° C.

Step B: (+)-3,5-Diisopropyl-2-(1-hydroxyethyl)-6-pentyl-4'-fluoro-1,1'-biphenyl

A mixture of (1S,2R)-(+)-N-methylephedrine (13.9 g, 77.3 mmol) in diethyl ether (225 mL) at 0 ° C. under an argon atmosphere was treated with slow addition of lithium aluminum hydride (1M in diethyl ether, 77.3 mL, 77.3 mmol). The mixture was held at reflux for one hour and then cooled to −75° C. A solution of the intermediate from Step A (13.5 g, 36.7 mmol) in diethyl ether (500 mL, 50 mL rinse) was then added to the reaction mixture in such a manner that the internal temperature did not rise above −68 ° C. The reaction stirred for 3 hours at −75° C. and was warmed to ambient temperature overnight. The reaction was cooled to 0° C., quenched by adding water (500 mL), and diluted with diethyl ether (750 mL).

The aqueous portion was separated and back-extracted with diethyl ether (200 mL).

The combined organic portions were washed with water (2×500 mL), 10% aqueous hydrochloric add (500 mL), and saturated aqueous sodium chloride (2×500 mL), dried over sodium sulfate, filtered through a pad of silica (80 mm×1.25") and concentrated in vacuo. The resulting solid was recrystallized from ethanol:water (2:1) and dried in vacuo with several minutes of heating to provide the title compound as a fine white powder (11.08 g, 82%). $^1H$ NMR (300 MHz, $CDCl_3$): δ 0.75–0.80 (m, 3H), 1.02–1.31 (m, 19H), 1.40 (d, J=6.6 Hz, 3H), 2.17–2.22 (m, 2H), 3.08–3.18 (m, 1H), 3.83–3.92 (m, 1H), 4.66–4.73 (m, 1H), 7.05–7.23 (m, 4H), 7.32 (s, 1H). $^{13}C$ NMR (75 MHz, $CDCl_3$): δ 13.88, 22.02, 23.38, 24.23, 24.56, 24.63, 25.09, 28.68, 28.96, 29.92, 31.04, 32.23, 68.91, 114.80 (d, J=20.8 Hz, 1C), 115.02 (d, J=20.8 Hz, 1C), 124.27, 130.40 (d, J=8.5 Hz, 1C), 131.25 (d, J=7.3 Hz, 1C), 135.53, 136.98, 137.73 (d, J=2.4 Hz, 1C), 139.02, 145.82 (2C), 161.68 (d, J=245.4 Hz, 1C). FAB-MS: calculated for $C_{25}H_{35}OF$ 370; found 370 (M+). Anal. calc for $C_{25}H_{35}OF$: C, 81.03; H, 9.52. Found: C, 81.15; H, 9.68. $R_f$=0.36 (9:1 hexanes:ethyl acetate). HPLC: (C-18, A=0.05% aqueous trifluoroacetic acid, B=$CH_3CN$; linear gradient: 75%–100% B over 30 min; 254 nm, 1 mL/min): R.T. 22.6 min (98.3 area %), (Daicel Chiralcel OD-H; isocratic 99:1 hexanes:methyl t-butyl ether; 254 nm, 1.5 mL/min); R.T. 6.20 min.(97.2 area %), 8.37 min. (0.36 area %); 99.5% e.e. $[a]_D$=+26.9° (c=0.00196 g/mL, $CH_2Cl_2$). mp 108.5–109.5° C.

EXAMPLE 244

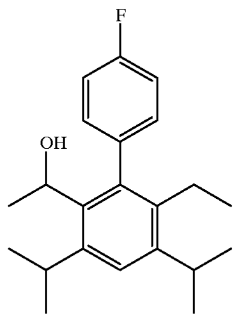

(+)-3,5-Diisopropyl-2-(1-hydroxyethyl)-6-ethyl-4'-fluoro-1,1'-biphenyl

Step A: Dimethyl 4,6-diethyl-2-trifluoromethanesulfonyloxy-1,3-benzenedicarboxylate A solution of 90 g (338 mmol) of dimethyl 4,6-diethyl-2-hydroxy-1,3-benzenedicarboxylate (Example 241, Step A) in dichloromethane (1 L) was treated with pyridine (109 mL, 1.35 mol). The mixture was stirred under argon at 0° C. and treated dropwise with triflic anhydride (83 mL, 507 mmol). The reaction mixture was warmed to room temperature and stirred for 3 hours. Then was washed with 5% HCl (1.5 L), water (1 L), saturated sodium bicarbonate (2×500 mL), and dried with $MgSO_4$. Filtration and concentration afforded a dark oil (129.7 g, 326 mmol, 96%). $R_f$=0.4 (10% ethyl acetate/hexane). $^1H$ NMR (300 MHz, $CDCl_3$): δ 7.20 (s, 1H), 3.93 (s, 6H), 2.74 (q,=7.4 Hz, 4H), 1.22 (t, J=4.8 Hz, 6H). FAB-MS: calculated for ($C_{15}H_{27}F_3O_7$) 398, found 399 (M+H).

Step B: 3,5-Diethyl-2,6-dicarboxymethyl-4'-fluoro-1,1'-biphenyl

To a solution of the intermediate obtained in Step A (129.7 g, 326 mmol) in dioxane (2.5 L) was added 4-fluorobenzene boronic acid (68.4 g, 492 mmol), potassium phosphate (145 g, 683 mmol), potassium bromide (58.1 g, 488 mmol), tetrakis(triphenylphosphine)palladium (18.8 g, 16.3 mmol), and water (20 mL). The reaction mixture was stirred under argon at reflux for 24 hrs. The reaction mixture was filtered through a pad of celite and concentrated in vacuo. The oily residue was filtered twice through a pad of silica (700 g, 40% dichloromethane/hexane) to afford a yellow solid. Recrystallization from hexane afforded a white solid (52.6 g, 153 mmol, 47%). mp=98–99° C. $R_f$=0.4 (10% ethyl acetate/hexane). $^1H$ NMR (300 MHz, $CDCl_3$): δ 7.26 (m, 2H), 7.17 (s, 1H), 7.04 (m, 2H), 3.49 (s, 6H), 2.67 (q, J=7.7 Hz, 4H), 1.25 (t, J=7.7 Hz, 6H). FAB-MS: calculated for ($C_{20}H_{21}FO_4$) 344, found 345 (M+H).

Step C: 3,5-Diisopropyl-2,6-dicarboxymethyl-4'-fluoro-1,1'-biphenyl

A solution of diisopropylamine (22.7 mL, 0.174 mol) in dry tetrahydrofuran (0.2 L) at −78° C. under an argon atmosphere was treated with slow addition of n-butyllithium (2.5M in hexanes, 70 mL, 0.174 mol). After the reaction stirred for fifteen minutes, a solution of the intermediate from Step B (46.0 g, 0.133 mol) in dry tetrahydrofuran (0.2 L) was added to the solution of LDA over 15 minutes.

Stirring was continued for 30 minutes while the temperature was held at −78° C. Neat iodomethane (11.2 mL, 0.180 mol) was added to the reaction mixture via syringe; two-thirds of the charge was transferred at the outset, the reaction was allowed to stir for 20 minutes, then the final third of the charge was added, followed by another 10 minutes of stirring. A second pot of LDA (0.174 mol) in dry tetrahydrofuran (0.2 L) was produced by the above procedure and was transferred to the reaction mixture via cannula over 15 minutes. Stirring was continued for 30 minutes at −78 ° C. then a second portion of neat iodomethane (11.2 mL, 0.180 mol) was added to the reaction mixture using the addition sequence described above. The cooling bath was removed and the reaction mixture was quenched with saturated aqueous ammonium chloride solution (0.4 L). The mixture was extracted with diethyl ether (3×0.4 L) and the combined organic portions were dried over magnesium sulfate and concentrated in vacuo to afford an oil, which crystallized upon standing. The white solid was washed with a small portion of hexane (41.7 g, 84%). mp 128–130° C. $R_f$=0.5 (10% ethyl acetate/hexane). $^1H$ NMR (300 MHz, $CDCl_3$): δ 7.33 (s, 1H), 7.26 (m, 2H), 7.03 (m, 2H), 3.49 (s, 6H), 2.97 (sept, J=6.6 Hz, 2H), 1.29 (d, J=7.0 Hz, 6H). FAB-MS: calculated for ($C_{22}H_{25}FO_4$) 372, found 373 (M+H).

Step D: 3,5-Diisopropyl-2-hydroxymethyl-6-carboxymethyl-4'-fluoro-1,1'-biphenyl

To a solution of the intermediate obtained in Step C (37.3 g, 100 mmol) in anhydrous tetrahydrofuran (350 mL) stirred under argon at 0° C. was added a solution of 3.4M of sodium bis(2-methoxyethoxy)aluminum hydride in toluene (Red-Al) (105 mL, 204 mmol, 65 wt % in toluene) via syringe over 20 min. The reaction mixture was allowed to stir at room temperature for 24 hr, then cooled again to 0° C. and carefully quenched by the dropwise addition of water. The solution was decanted from the solid which forms and the solvent removed in vacuo. The residue was purified by flash chromatography (500 g silica) via step gradient. Elution with 5% diethyl ether/hexane affords 9.8 g (26.3 mmol, 28%) of recovered starting material and elution with 40% diethyl ether ($Et_2O$)/hexane affords the desired product as a white solid (26.8 g, 77.8 mmol, 78%). mp 124–126° C. $R_f$=0.2 (10% ethyl acetate/hexane). $^1H$ NMR (300 MHz, $CDCl_3$): δ 7.35 (s, 1H), 7.27 (m, 2H), 7.08 (m, 2H), 4.44 (d, J=5.5 Hz, 2H), 3.43 (m, 4H), 2.92 (sept, J=6.6 Hz, 1H), 1.59 (s, 1H), 1.28 (m, 12H). FAB-MS: calculated for ($C_{21}H_{25}FO_3$) 344, found 345 (M+H).

Step E: 3,5-Diisopropyl-2-carboxaldehyde-6-carboxymethyl-4'-fluoro-1,1'-biphenyl To a solution of the intermediate obtained in Step D (26.8 g, 77.8 mmol) in dichloromethane (400 mL) was added celite (33.6 g). The suspension was stirred at room temperature and treated with pyridinium chlorochromate (PCC) (33.6 g, 15.6 mmol) in three portions. The suspension was stirred at room temperature for 2 hr, then poured into 1:1 diethyl ether/hexane (1 L), filtered through a pad of silica, the pad was washed with diethyl ether (600 mL) and the combined eluent concentrated to afford an gummy oil (23.3 g, 68.1 mmol, 87%): $R_f$=0.4 (10% ethyl acetate/hexane). $^1H$ NMR (300 MHz, $CDCl_3$): δ 9.87 (s, 1H), 7.36 (s, 1H), 7.28 (m, 2H), 7.15 (m, 2H), 3.48 (s, 3H), 3.89 (sept, J=6.6 Hz, 1H), 3.10 (sept, J=6.6 Hz, 1 H), 1.35 (m, 12H); FAB-MS calcd for ($C_{21}H_{23}FO_3$) 342, found 343 (M+H).

Step F: 3,5-Diisopropyl-2-carboxymethyl-6-ethenyl-4'-fluoro-1,1'-biphenyl

Methyltriphenylphosphonium bromide (15.5 g, 43.4 mmol) was suspended in anhydrous THF (250 mL) under argon and stirred at −78° C. A 1.6 M solution of n-butyllithium in hexanes (25 mL, 40.2 mmol) was added dropwise. The reaction mixture was allowed to come to 0° C. and was stirred at that temperature for 1.5 hr. The resulting brightly colored solution was cooled again to −78° C. and treated dropwise with a solution of the intermediate obtained in Step E (11.4 g, 33.3 mmol) in THF (100 mL). The reaction mixture was allowed to stir at 0° C. for 1 hr, then quenched by the addition of water (30 mL). The THF was removed in vacuo, the residue partitioned between diethyl ether (400 mL) and water (400 mL). The organic layer was washed with brine (100 mL), dried over $MgSO_4$ and concentrated. Flash chromatography through silica (5% diethyl ether/hexane) affords a solid (10.3 g, 30.3 mmol, 91%) (E, Z mixture). $^1$H NMR (300 MHz, $CDCl_3$): δ 7.31 (s, 1H), 7.16 (m, 2H), 7.02 (m, 2H), 6.10 (dd, J=6.3, 11.4 Hz, 1H), 6.04 (dd, J=1.8, 13.6 Hz, 1H), 5.48 (dd, J=1.8, 19.9 Hz, 1H), 3.46 (s, 3H), 3.35 (sept, J=6.6 Hz, 1H), 2.93 (sept, J=6.6 Hz, 1H), 1.29 (m, 12H). EI-MS calculated for ($C_{22}H_{25}FO_2$) 340, found 340 (M+). mp 58–61° C. $R_f$=0.6 (10% ethyl acetate/hexane).

Step G: 3,5-Diisopropyl-2-hydroxymethyl-6-ethenyl-4'-fluoro-1,1'-biphenyl

The intermediate obtained in Step F (10.0 g, 29.4 mmol) was dissolved in anhydrous THF (150 mL) under argon and treated dropwise at room temperature with lithium aluminum hydride (1.0 M in THF, 41 mL, 41 mmol). The reaction mixture was stirred at reflux for 2 hours, cooled to room temperature and quenched by the addition of 30 mL $H_2O$. The THF was removed in vacuo, the residue partitioned between diethyl ether (400 mL) and water (3×400 mL). The organic layer was washed with brine (300 mL), dried over $MgSO_4$ and concentrated. Flash chromatography through silica (5% diethyl ether/hexane) affords a solid (7.7 g, 24.7 mmol, 84%). $^1$H NMR (300 MHz, $CDCl_3$): δ 7.38 (s, 1H), 7.14 (m, 4H), 6.35 (dd, J=6.3, 11.4 Hz, 1H), 5.20 (dd, J=1.8, 13.6 Hz, 1H), 4.98 (dd, J=1.8, 19.9 Hz, 1H), 4.40 (d, J=5.5 Hz, 2H), 3.39 (m, 2H), 1.29 (m, 12H). FAB-MS calculated for ($C_{21}H_{25}FO$) 312, found 312 (M+). mp 97–99° C. $R_f$=0.1 (50% dichloromethane/hexane).

Step H: 3,5-Diisopropyl-2-hydroxymethyl-6-ethyl-4'-fluoro-1,1'-biphenyl

The intermediate obtained in Step G (7.7 g, 24.7 mmol) was dissolved in absolute ethanol (200 mL) under argon, treated with 10% palladium on carbon (610 mg, 0.1 eq), then stirred under a hydrogen atmosphere for 2 hr. After purging the system with argon, the catalyst was removed by filtration through a pad of Celite. The solvent was removed and the product dried in vacuo to afford the title compound as a white solid (7.7 g, 25 mmol, 99%). $^1$H NMR (300 MHz, $CDCl_3$): δ 7.32 (s, 1H), 7.15 (m, 4H), 4.33 (m, 2H), 3.39 (septet, J=7 Hz, 1H), 3.32 (septet, J=7 Hz, 1H), 2.37 (q, J=7.7 Hz, 2H), 1.29 (m, 13H), 0.92 (t, J=7.7 Hz, 3H). FAB-MS calculated for ($C_{21}H_{27}FO$) 314, found 314 (M+). mp 106–108° C. $R_f$=0.1 (50% dichloromethane/hexane).

Step I: 3,5-Diisopropyl-2-(1-hydroxyethyl)-6-ethyl-4'-fluoro-1,1'-biphenyl

The intermediate obtained in Step H (7.65 g, 24.3 mmol) was dissolved in dichloromethane (250 mL), treated with celite (10.5 g). The suspension was stirred at room temperature and treated with pyridinium chlorochromate (PCC) (10.5 g, 48.7 mmol). Stirring was continued at room temperature for 2 hrs. The suspension was poured into 1:1 diethyl ether/hex (1 L), filtered through a pad of silica, the pad washed with diethyl ether (600 mL) and the combined eluent concentrated to afford a solid (7.25 g, 23.2 mmol, 95%).

The intermediate (7.25 g, 23.2 mmol) was dissolved in THF (75 mL) at 0° C. under argon atmosphere and treated dropwise with Methyl magnesium bromide (3 M, 1.3 eq, 10.1 mL). The reaction was stirred for 1 hr. The reaction was quenched with saturated ammonium chloride (7 mL) and the THF was evaporated in vacuo to afford an oil. The product was partitioned between water (100 mL) and diethyl ether (250 mL) and the organic layer was dried with $MgSO_4$, filtered, and concentrated to yield a white solid. Flash chromatography using silica gel (60% $CH_2Cl_2$/hexane) afforded a white solid (7.2 g, 22 mmol, 99%). mp 138–140° C.; $R_f$=0.1 (50% $CH_2Cl_2$/hexane); $^1$H NMR (300 MHz, $CDCl_3$): δ 7.34 (s, 1H), 7.15 (m, 4H), 4.69 (dq, J=2.9, 7 Hz, 1H), 3.88 (septet, J=7 Hz, 1H), 3.17 (septet, J=6.6 Hz, 1H), 2.28 (q, J=7.4 Hz, 2H), 1.64 (d, J=2.9 Hz, 1H), 1.39 (d, J=6.6 Hz, 3H), 1.27 (m, 12H), 0.89 (t, J=7.4 Hz, 3H); FAB-MS calcd for ($C_{22}H_{29}FO$) 328, found 328 (M+).

Step J: 3,5Diisopropyl-2-(1-oxoethyl)-6-ethyl-4'-fluoro-1,1'-biphenyl

The intermediate obtained in Step I (7.23 g, 22 mmol) in dichloromethane (100 mL) was added pyridinium chlorochromate (9.49 g, 44 mmol) and celite (9.49 g) under argon. The reaction was stirred at room temperature for 24 hours. The reaction was added to a 1:1 mixture of diethyl ether/hexane (1 L), then filtered through a plug of silica. The pad was washed with 650 mL of diethyl ether and the combined filtrates were concentrated in vacuo to afford a white solid (7.18 g, 22 mmol, 99%). mp 121–23° C.; $R_f$=0.3 (50% $CH_2Cl_2$/hexane); $^1$H NMR (300 MHz, $CDCl_3$): δ 7.27 (s, 1H), 7.21 (m, 2H), 7.07 (m, 2 ), 3.22 (septet, J=7 Hz, 1H), 2.78 (septet, J=7 Hz, 1H), 2.43 (q, J=7.4 Hz, 2H), 1.96 (s, 3H), 1.28 (m, 12H), 0.930 (t, J=7.7 Hz, 3H); FAB-MS calcd for ($C_{22}H_{27}FO$) 326, found 327 (M+H).

Step K: (+)-3,5-Diisopropyl-2-(1-hydroxyethyl)-6-ethyl-4'-fluoro-1,1'-biphenyl

To a solution of (1S,2R)-(+)-N-methylephedrine (6.29 g, 35.1 mol) in diethyl ether (45 mL) was added lithium aluminum hydride (1M/diethyl ether, 1.5 eq., 35 mL) dropwise at 0° C. under argon. The reaction was refluxed for 1.5 h. turning from a clear solution to a white milky solution. The reaction was cooled to room temperature and then −78° C. The intermediate obtained in Step J (6.64 g, 20.3 mmol) was dissolved in 60 mL of dry diethyl ether for a dropwise addition to the reaction mixture (~2 mL/min., the temperature should not rise above −60° C.). The reaction was kept at −78° C. for 2.0 hours and then allowed to warm overnight. The reaction was quenched at 0° C. with water (30 mL) and diluted with diethyl ether (250 mL), washed with water (3×200 mL), brine (100 mL) and dried with $MgSO_4$ Filtration and concentration afford a residue which was filtered through a pad of silica (400 g, 80% dichloromethane/hexane) to give the titled compound (99% e.e.) as a white solid (5.85 g, 17.8 mmol, 88%). mp 143–145° C.; $R_f$=0.1 (50% $CH_2Cl_2$/hexane); $^1$H NMR (300 MHz, $CDCl_3$): δ 7.34 (s, 1H), 7.15 (m, 4H), 4.68 (dq, J=3.3, 7 Hz, 1H), 3.88 (septet, J=7 Hz, 1H), 3.18 (septet, J=7 Hz, 1H), 2.29 (q, J=7.7 Hz, 2H), 1.68 (s, 1H), 1.37 (d, J=4.8 Hz, 3H), 1.26 (m, 12H), 0.890 (t, J=7.4 Hz, 3H); FAB-MS calcd for ($C_{22}H_{29}FO$) 328, found 328 (M+); Anal. Calcd for $C_{22}H_{29}FO$: C, 80.45; H, 8.90; F, 5.78. Found: C, 80.19; H, 8.77; F, 5.84; $[\alpha]^{22}$=+26.6.

EXAMPLE 245

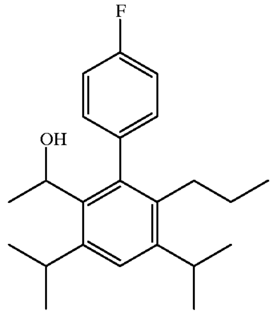

(+)-3,5-Diisopropyl-2-(1-hydroxyethyl)-6-propyl-4'-fluoro-1,1'-biphenyl

The title compound (99% ee) was prepared from the intermediate obtained in Step E, Example 244 and ethyl triphenylphosphonium bromide according to the procedures described in Example 244, Steps F–K. $^1$H NMR (300 MHz, $CDCl_3$): δ 7.33 (s, 1H), 7.14 (m, 4H), 4.70 (dq, J=2.9, 7 Hz, 1H), 3.88 (septet, J=6.62 Hz, 1H), 3.14 (septet, J=6.62 Hz, 1H), 2.18 (m, 2H), 1.67 (d, J=2.9 Hz, 1H), 1.37 (d, J=7 Hz, 3H), 1.29 (m, 14H), 0.719 (t, J=7 Hz, 3H); FAB-MS calcd for ($C_{23}H_{31}FO$) 342, found 342 (M+); Anal. Calcd for $C_{23}H_{31}FO$: C, 80.66; H, 9.12; F, 5.55. Found: C, 80.71; H, 8.99; F, 5.34; $[\alpha]^{22}$ =+23.8. mp 114–116° C.; $R_f$=0.1 (50% $CH_2Cl_2$/hexane).

EXAMPLE 246

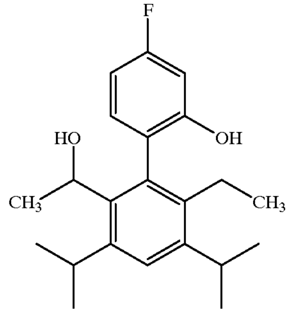

3,5-Diisopropyl-2-(1-hydroxyethyl)-6-ethyl-4'-fluoro-2'-hydroxy-1,1'-biphenyl

Step A: Di-tert-butyl 4,6-diethyl-2-hydroxy-1,3-benzenedicarboxylate

A mixture of di-tert-butyl 1,3-acetonedicarboxylate (10 g, 38.7 mmol), 3,5-heptanedione (6.5 g, 50.3 mmol) and sodium methoxide (2.7 g, 50.3 mmol) in methanol (100 mL) was stirred at room temperature overnight. Methanol was removed via rotary evaporation and the resulting orange sludge was partitioned between diethyl ether (100 mL) and 10% aqueous hydrochloric acid (100 mL). The separated aqueous layer was extracted with diethyl ether (50 mL×2). The combined organic portions were washed with saturated aqueous sodium chloride (20 mL), dried over sodium sulfate, filtered through a pad of silica (20 mm×40 mm) and concentrated in vacuo to yield a yellow oil (13.23 g, 97%): $^1$H NMR (300 MHz, $CDCl_3$): δ 1.20 (t, 6H), 1.60 (s, 18H) 2.74 (q, 4H), 6.55 (s, 1H), 11.73 (s, 1H).

Step B: Di-tert-butyl 3,5-diisopropyl-2'-benzyloxy-4'-fluoro-1,1'-biphenyl-2,6-dicarboxylate The title compound was prepared from the intermediate obtained in Step A by the methods described in Example 241, Steps B, C, and E. $^1$H NMR (300 MHz, $CDCl_3$): δ 1.15 (s, 18H), 1.27 (dd, J=5.15, 1.65 Hz, 12H), 3.06 (m, 2H), 4.95 (s, 2H), 6.65 (m, 2H), 7.27 (m, 7H).

Step C: 3,5-Diisopropyl-2'-benzyloxy-4'-fluoro-1,1'-biphenyl-2,6-dicarboxylate

To a solution of 14.37 g (25.53 mmol) of the intermediate obtained in Step B in dichloromethane (150 mL) at 0° C. was added trifluoroacetic acid (20 mL, 259.60 mmol). This reaction mixture was allowed to warm to room temperature overnight. The reaction mixture was concentrated to dryness and the residue was partioned between diethyl ether and aqueous sodium hydroxide. The organic layer was removed, washed with aqueous sodium hydroxide and the two aqueous layers were combined. The combined aqueous layers were washed with diethyl ether (1×) then made acidic by addition of HCl (10%) and extracted with diethyl ether (3×). The combined organic layers were dried over magnesium sulfate, filtered and concentrated to yield an off-white solid. The crude product was taken directly to the next step without any further purification.

Step D: Dimethyl 3,5-diisopropyl-2'-benzyloxy-4'-fluoro-1,1'-biphenyl-2,6-dicarboxylate To a suspension of 7.17 g (15.93 mmol) of the intermediate obtained in Step C in dichloromethane (200 mL) at 0° C. was added solid potassium carbonate (10.05 g, 72.71 mmol) followed by iodomethane (5.0 mL, 80.31 mmol). The mixture was allowed to warm to room temperature. After stirring for 1 day the mixture was diluted with water and extracted with diethyl ether (3×). The combined extracts were washed with brine (1×), dried over magnesium sulfate, filtered and concentrated to yield an off-white solid. $^1$H NMR (300 MHz, $CDCl_3$): δ 1.22 (dd, J=4.41, 2.4 Hz, 121H), 2.94 (m, 2H), 3.39 (s, 6H), 4.93 (s, 2H), 6.55 (m, 2H), 7.05 (m, 1H), 7.18 (m, 6H).

Step E: 3,5-Diisopropyl-2-(1-hydroxyethyl-6-ethyl-4'-fluoro-2'-hydroxy-1,1'-biphenyl The title compound was prepared from the intermediate obtained in Step D by the methods described in Example 241 steps F–I (using ethyl triphenylphosphonium bromide in Step H) followed by Example 242 steps B–D. Silica gel chromatography (90% hexane/10% EtOAc) provided two colorless solids (1.129g, 84%).

Diastereomer 1 was obtained as a colorless crystalline solid (1.029 g, 77%). $^1$H NMR (300 MHz, $CDCl_3$): δ 0.89 (t, J=7.36 Hz, 3H), 1.28 (m, 12H), 1.40 (d, J=6.62 Hz, 3H) 1.63 (bs, 1H), 2.29 (m, 2H), 3.17 (m, 1H), 3.78 (m, 1H), 4.84 (m, 1H), 6.70 (m, 2H), 7.03 (m, 1H), 7.38 (s, 1H). FAB-MS: calculated for $C_{22}H_{29}O_2F$, 344; found 367 [M+Na]. mp 174–175° C.

Diastereomer 1 (1.029 g) was resolved into its constituent enantiomers as follows: a Waters Prep LC 4000 HPLC system was equipped with a chiral HPLC column (BRB9668A; 6×50 cm ID). The system was equilibrated with a mobile phase consisting of 0.75% butanol and 99.25% hexane at a flow rate of 100 mL/min. The sample was dissolved in dichloromethane (20 mg/mL) and the sample was injected in one injection. The effluent was monitored at 285 nm and two fractions (corresponding to the two enantiomers) were collected at (26–32 min, ≧98% ee) and (34–48 min, ≧99% ee), respectively.

Enantiomer 1 was obtained as a colorless solid (480 mg). $^1$H NMR (300 MHz, $CDCl_3$): δ 0.89 (t, J=7.54 Hz, 3H), 1.28 (m, 12H), 1.40 (d, J=5.14 Hz, 3H), 1.65 (bs, 1H), 2.19 (m, 1H), 2.35 (m, 1H), 3.17 (m, 1H), 3.78 (m, 1H), 4.85 (m, 1H), 6.71 (m, 2H), 7.03 (m, 1H), 7.38 (s, 1H). mp condenses at 57–59° C.

Enantiomer 2 was obtained as a colorless solid (483 mg). $^1$H NMR (300 MHz, $CDCl_3$): δ 0.89 (t, J=7.36 Hz, 3H), 1.28 (m, 12H), 1.39 (d, J=6.99 Hz, 3H), 1.63 (bs, 1H), 2.29 (m, 2H), 3.17 (m, 1H), 3.78 (m, 1H3, 4.84 (m, 1H), 6.70 (m, 2H), 7.03 (m, 1H), 7.38 (s, 1H). FAB-MS: calculated for $C_{22}H_{29}O_2F$, 344; found 367 [M+Na]. mp condenses at 57–59° C.

Diastereomer 2 was obtained as a colorless crystalline solid (100 mg, 7%). $^1$H NMR ($CDCl_3$, 300 MHz): δ 0.88 (t, J=7.54 Hz, 3H), 1.27 (m, 12H), 1.36 (d, J=6.62 Hz, 3H), 1.8 (bs, 1H), 2.19 (m, 1H), 2.39 (m, 1H), 3.16 (m, 1H), 3.84 (m. 1H), 4.63 (q, J=6.62 Hz, 1H), 5.09 (bs, 1H), 6.69 (m, 2H), 6.92 (t, J=7.35 Hz, 1H), 7.37 (s, 1H). mp 183–184° C.

EXAMPLE 247

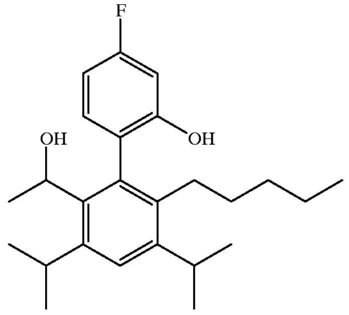

3,5-Diisopropyl-2-(1-hydroxyethyl)-6-pentyl-4'-fluoro-2'-hydroxy-1,1'-biphenyl

Step A: 3,5-Diisopropyl-2-hydroxymethyl-6-(pent-1-enyl)-2'-benzyloxy-4'-fluoro-1,1'-biphenyl The desired compound was prepared from dimethyl 3,5-diisopropyl-2'-benzyloxy-4'-fluoro-1,1'-biphenyl-2,6-dicarboxylate (Example 246, Step D) by the procedure described in Example 241, Steps F–I (using pentyl triphenylphosphonium bromide in Step H). The pure product obtained was a clear oil (4.73 g, 52% over 4 steps). $^1$H NMR (300 MHz, $CDCl_3$): δ 0.67–0.78 (m, 3H), 1.09–1.34 (m, 14H), 1.66–1.88 (m, 3H), 3.16–3.46 (m, 2H), 4.29–4.44 (m, 2H), 4.88–5.04 (m, 2H), 5.27–5.41 (m, 1H), 5.94–6.01 (m, 1H), 6.69–6.78 (m, 2H), 7.00–7.06 (m, 3H), 7.22–7.26 (m, 3H), 7.35 (s, 1H). $^{13}$C NMR (75 MHz, $CDCl_3$): δ 14.18, 14.52, 22.89, 23.05, 24.39, 24.64, 24.94, 25.11, 25.38, 29.73, 30.50, 30.66, 31.68, 35.85, 60.78, 71.07, 71.45, 102.25, 102.59, 108.08, 108.37, 122.33, 122.54, 127.11, 127.22, 127.92, 128.11, 128.51, 129.16, 132.70, 132.83, 133.39, 134.06, 135.96, 136.96, 137.29, 137.35, 147.48, 147.63, 147.79, 156.90, 156.93, 163.26 (d, J=246.6 Hz, 1C). FAB-MS: calculated for $C_{31}H_{37}O_2F$ 460; found 460 (M+). Anal. calc for $C_{31}H_{37}O_2F$: C, 80.83; H, 8.10. Found: C, 80.91; H, 8.01. $R_f$=0.34 (9:1 hexanes:ethyl acetate). HPLC: (C-18, A=0.05% aqueous trifluoroacetic acid, B=$CH_3CN$; linear gradient: 80%–100% B over 20 min; 254 nm, 1 mL/min): R.T. 14.8 min (37.7 area %), 15.2 min (56.0 area %); 93.7% purity (cis- and trans-).

Step B: 3,5-Diisopropyl-2-(1-hydroxyethyl)-6-pentyl-4'-fluoro-2'-hydroxy-1,1'-biphenyl The title compound was prepared from the intermediate obtained in Step A utilizing the procedures outlined in Example 242, Steps B–D. The crude product was subjected to flash column chromatography on silica (50 mm×6") using hexanes:ethyl acetate (19:1 and 9:1) as eluent to separate the diastereomers (2.19 g, 90%, 75% over 3 steps).

Diastereomer 1 was obtained as a white solid (2.03 g, 83%). $^1$H NMR (300 MHz, $CDCl_3$): δ 0.78 (t, J=6.6 Hz, 3H), 0.96–1.23 (m, 19H), 1.41 (d, J=7.0 Hz, 3H), 2.04–2.37 (m, 2H), 3.09–3.19 (m, 1H), 3.74–3.84 (m, 1H), 4.81–4.90 (m, 2H), 6.68–6.75 (m, 2H), 6.99–7.06 (m, 1H), 7.37 (s, 1H). $^{13}$C NMR (75 MHz, $CDCl_3$): δ 13.83, 21.94, 23.83, 24.27, 24.38, 24.50, 24.88, 28.70, 29.05, 29.80, 30.76, 32.20, 68.21, 102.98 (d, J=24.4 Hz, 1C), 107.33 (d, J=20.8 Hz, 1C), 123.58 (d, J=2.4 Hz, 1C), 125.45, 130.70 (d, J=9.8 Hz, 1C), 131.78, 137.45, 138.55, 146.48, 146.94, 154.29 (d, J=6.1 Hz, 1C), 163.04 (d, J=244.2 Hz, 1C). FAB-MS: calculated for $C_{25}H_{35}O_2F$ 386; found 409 (M+Na)+. Anal. calc for $C_{25}H_{35}O_2F$: C, 77.68; H, 9.13. Found: C, 77.38; H, 9.20. $R_f$=0.30 (9:1 hexanes:ethyl acetate). HPLC: (C-18, A=0.05% aqueous trifluoroacetic add, B=$CH_3CN$; linear gradient: 70%–100% B over 30 min; 254 nm, 1 mL/min): R.T. 12.9 min (91.3 area %); (silica, A=hexanes, B=isopropanol, isocratic run: 3% B over 15 min; 254 nm, 1 mL/min): R.T. 5.1 min (100 area %). mp 122.5–124.0° C.

Diastereomer 1 (1.92 g) was resolved into its constituent enantiomers as follows: a Waters Prep LC 4000 HPLC system was equipped with a chiral HPLC column (BRB-9668A; 6×50 cm ID). The system was equilibrated with a mobile phase consisting of 0.75% butanol and 99.25% hexane at a flow rate of 100 mL/min. The sample was dissolved in dichloromethane (40 mg/mL) and the sample was loaded in two injections. The effluent was monitored at 285 nm and two fractions (corresponding to the two enantiomers) were collected.

Enantiomer 1 was obtained as a white crystalline solid (0.78 g). $^1$H NMR (300 MHz, $CDCl_3$): δ 0.78 (t, J=6.6 Hz, 3H), 0.96–1.23 (m, 19H), 1.41 (d, J=7.0 Hz, 3H), 2.04–2.37 (m, 2H), 3.09–3.19 (m, 1H), 3.74–3.84 (m, 1H), 4.81–4.90 (m, 2H), 6.68–6.75 (m, 2H), 6.99–7.06 (m, 1H), 7.37 (s, 1H). $^{13}$C NMR (75 MHz, $CDCl_3$): δ 13.83, 21.94, 23.83, 24.27, 24.38, 24.50, 24.88, 28.70, 29.05, 29.80, 30.76, 32.20, 68.21, 102.98 (d, J=24.4 Hz, 1C), 107.33 (d, J=20.8 Hz, 1C), 123.58 (d, J=2.4 Hz, 1C), 125.45, 130.70 (d, J=9.8 Hz, 1C), 131.78, 137.45, 138.55, 146.48, 146.94, 154.29 (d, J=6.1 Hz, 1C), 163.04 (d, J=244.2 Hz, 1C). FAB-MS: calculated for $C_{25}H_{35}O_2F$ 386; found 409 (M+Na)+. Anal. calc for $C_{25}H_{35}O_2F$: C, 77.68; H, 9.13. Found: C, 77.74; H, 9.00. $R_f$=0.30 (9:1 hexanes:ethyl acetate). HPLC: (C-18, A=0.05% aqueous trifluoroacetic add, B=$CH_3CN$; linear gradient: 70%–100% B over 30 min; 254 nm, 1 mL/min): R.T. 12.8 min (94.9 area %); (BRB-9668, 99% (1% butanol in hexanes), 5 min, 285 nm, 2 mL/min): R.T. 2.6 min (100 area %, 100% e.e.). $[a]_D$=−14.3° (c=0.00200 g/mL, $CH_2Cl_2$). mp 105.0–106.5° C.

Enantiomer 2 was obtained as a white flaky solid (0.73 g). $^1$H NMR (300 MHz, $CDCl_3$): δ 0.78 (t, J=6.6 Hz, 3H), 0.96–1.23 (m, 19H), 1.41 (d, J=7.0 Hz,3H), 2.04–2.37 (m, 2H), 3.09–3.19 (m, 1H), 3.74–3.84 (m, 1H), 4.81–4.90 (m, 2H), 6.68–6.75 (m, 2H), 6.99–7.06 (m, 1H), 7.37 (s, 1H). $^{13}$C NMR (75 MHz, $CDCl_3$): δ 13.83, 21.94, 23.83, 24.27, 24.38, 24.50, 24.88, 28.70, 29.05, 29.80, 30.76, 32.20, 68.21, 102.98 (d, J=24.4 Hz, 1C), 107.33 (d, J=20.8 Hz, 1C), 123.58 (d, J=2.4 Hz, 1C), 125.45, 130.70 (d, J=9.8 Hz, 1C), 131.78, 137.45, 138.55, 146.48, 146.94, 154.29 (d, J=6.1 Hz, 1C), 163.04 (d, J=244.2 Hz, 1C). FAB-MS: calculated for $C_{25}H_{35}O_2F$ 386; found 409 (M+Na)+. Anal. calc for $C_{25}H_{35}O_2F$: C, 77.68; H, 9.13. Found: C, 77.64; H, 9.06. $R_f$=0.30 (9:1 hexanes:ethyl acetate). HPLC: (C-18, A=0.05% aqueous trifluoroacetic acid, B=$CH_3CN$; linear gradient: 70%–100% B over 30 min; 254 nm, 1 mL/min): R.T. 12.8 min (94.7 area %); (BRB-9668, 99% (1% butanol in hexanes), 5 min, 285 nm, 2 mL/min): R.T. 1.7 min (0.51 area %), 2.9 min (0.97 area %), 4.0 min (98.5 area %, 98% e.e.). $[a]_D$=+16.0° (c=0.00200 g/mL, $CH_2Cl_2$). mp 103.5–105.5° C.

Diastereomer 2 was obtained as a white solid (0.16 g, 7%). $^1$H NMR ($CDCl_3$, 300 MHz): δ 0.78 (t, J=6.6 Hz, 3H), 0.96–1.33 (m, 19H), 1.37 (d, J=6.6 Hz, 3H), 2.05–2.38 (m, 2H), 3.09–3.19 (m, 1H), 3.80–3.89 (m, 1H), 4.61–4.68 (m, 1H), 4.75–5.25 (br s, 1H), 6.66–6.74 (m, 2H), 6.90–6.96 (m, 1H), 7.37 (s, 1H). $^{13}$C NMR (75 MHz, $CDCl_3$): δ 13.83, 21.94, 23.43, 24.08, 24.48, 24.56, 24.98, 28.70, 29.04, 29.80, 30.76, 32.19, 68.89, 102.80 (d, J=24.4 Hz, 1C), 107.36 (d, J=22.0 Hz, 1C), 123.24 (d, J=2.4 Hz, 1C), 125.64, 131.25 (d, J=9.8 Hz, 1C), 131.56, 137.08, 138.44, 146.81, 146.84, 154.37 (d, J=12.2 Hz, 1C), 163.03 (d, J=244.2 Hz, 1C). FAB-MS: calculated for $C_{25}H_{35}O_2F$ 386; found 409 (M+Na)+. Anal. calc for $C_{25}H_{35}O_2F$: C, 77.68; H, 9.13. Found: C, 77.70; H, 9.12. $R_f$=0.17 (9:1 hexanes:ethyl acetate). HPLC: (C-18, A=0.05% aqueous trifluoroacetic acid, B=$CH_3CN$; linear gradient: 70%–100% B over 30 min; 254 nm, 1 mL/min): R.T. 17.6 min (86.9 area %); (silica, A=hexanes, B=isopropanol, isocratic run: 3% B over 15 min; 254 nm, 1 mL/min): R.T. 4.9 min (100 area %). mp 148.0–150.0° C.

EXAMPLE 248

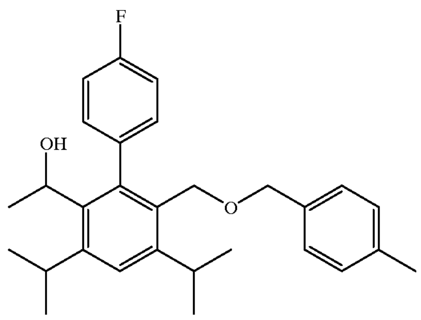

(+)-3,5-Diisopropyl-2-[(p-methylbenzyloxy)methyl]-6-(1-hydroxyethyl)-4'-fluoro-1,1'-biphenyl Step A: 3,5-Diisopropyl-2-[(p-methylbenzyloxy) methyl]-6-hydroxymethyl-4'-fluoro-1,1'-biphenyl To a solution of 3,5-diisopropyl-2-hydroxymethyl-6-carboxymethyl-4'-fluoro-1,1'-biphenyl (Example 244, Step D) (4.09 g, 11.9 mmol) in THF (70 mL) was added at room temperature sodium hydride (0.85 g, 35.4 mmol) in portions. The reaction mixture was stirred for 10 min. and then treated with α-bromo-p-xylene (2.64 g, 14.3 mmol). The reaction mixture was heated at reflux for 24 hrs then cooled to room temperature and quenched with water (30 mL). The solvent was removed in vacuo and the residue partitioned between diethyl ether (300 mL) and water (200 mL). The ether layer was dried ($MgSO_4$) and concentrated, the residue was purified through silica (70% $CH_2C_2$/hexane) which afforded a white solid (4.5 g, 10.3 mmol, 84%). The product was dissolved in THF (40 mL) was treated with lithium aluminum hydride (19.8 mL, 19.8 mmol, 1.0M in THF). The reaction mixture was heated at reflux for 2 hrs then allowed to cool to room temperature. The mixture was quenched with water (6 mL), and the solvent was removed in vacuo. The residue was partitioned between diethyl ether (200 mL) and water (300 mL). The organic layer was washed with water (3×300 mL), brine (100 mL), dried ($MgSO_4$), filtered and concentrated. The residue was filtered through a cake of silica ($CH_2Cl_2$, 1L) and evaporated to afford a white solid (3.26 g, 7.7 mmol, 78%). mp 99–101° C.; $R_f$=0.07 (80% $CH_2Cl_2$/hexane); $^1$H NMR (300 MHz, $CDCl_3$): δ 7.38 (s, 1 H), 7.24 (m, 2H), 7.09 (m, 6H), 4.36 (d, J=5.5 Hz, 2H), 4.27 (s, 2H), 4.11 (s, 2H), 3.42 (septet, J=6.6 Hz, 1H), 3.32 (septet, J=6.6 Hz, 1H), 2.35 (s, 3H), 1.60 (s, 1H), 1.22 (m, 12H); FAB-MS calcd for ($C_{28}H_{33}FO_2$) 420, found 403 (M—OH).

Step B: (+)-3,5-Diisopropyl-2-[(p-methylbenzyloxy) methyl]-6-(1-hydroxyethyl)-4'-fluoro-1,1'-biphenyl The title compound was prepared by subjecting the intermediate obtained in Step A to the procedures described in Example 244, Steps I–K. mp 84–86° C.; $R_f$=0.1 (80% $CH_2Cl_2$/hexane); $^1$H NMR (300 MHz, $CDCl_3$): δ 7.39 (s, 1H), 7.27 (m, 2H), 7.09 (m, 6H), 4.76 (dq, J=1.5, 7 Hz, 1H), 4.22 (s, 2H), 4.03 (s, 2H), 3.89 (septet, J=6.6 Hz, 1H), 3.26 (septet, J=6.6 Hz, 1H), 2.35 (s, 3H), 1.66 (s, 1H), 1.40 (d, J=6.6 Hz, 3H), 1.26 (m, 12H); FAB-MS calcd for ($C_{29}H_{35}FO_2$) 434, found 417 (M—OH); Anal. Calcd for $C_{29}H_{35}FO_2$: C, 80.15; H, 8.12; F, 4.37. Found: C, 80.10; H, 8.30; F, 4.24; $[\alpha]^{22}$=+30.7.

EXAMPLE 249

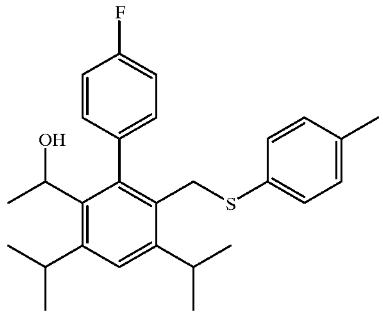

(+)-3,5-Diisopropyl-2-[(p-tolylthio)methyl]-6-(1-hydroxyethyl)-4'-fluoro-1,1'-biphenyl The title compound was prepared from p-thiocresol and 3,5-diisopropyl-2-hydroxymethyl-6-carboxymethyl-4'-fluoro-1,1'-biphenyl (Example 244, Step D), according to the procedures described in Example 47, Steps B and C, followed by the procedures described in Example 244, Steps I–K. $R_f$=0.36 (70% $CH_2Cl_2$/hexane); $^1$H NMR (300 MHz, $CDCl_3$): δ 7.40 (s, 1H), 7.28 (m, 2H), 7.11 (m, 6H), 4.76 (dq, J=1.8, 7 Hz, 1H), 3.92 (septet, J=6.6 Hz, 1H), 3.78 (s, 2H), 3.26 (septet, J=6.6 Hz, 1H), 2.36 (s, 3H), 1.66 (s, 1H), 1.40 (d, J=6.6 Hz, 3H), 1.28 (m, 12H); FAB-MS calcd for ($C_{28}H_{33}FOS$) 436, found 436 (M+); Anal. Calcd for $C_{29}H_{35}FOS$: C, 77.02; H, 7.62; S, 7.34; F, 4.35. Found: C, 76.90; H, 7.77; S, 7.30; F, 4.37; $[\alpha]^{22}$=+32.2.

EXAMPLE 250

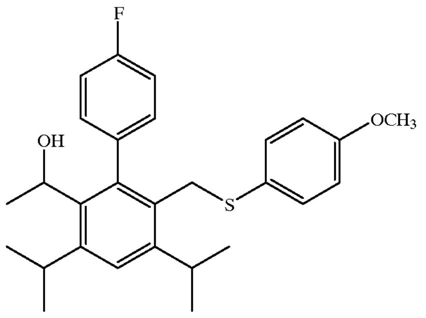

(+)-3,5-Diisopropyl-2-[(4-methoxythiophenyl) methyl]-6-(1-hydroxyethyl)-4'-fluoro-1,1'-biphenyl The title compound was prepared from 4-methoxy thiophenol and 3,5-diisopropyl-2-hydroxymethyl-carboxymethyl-4'-fluoro-1,1'-biphenyl (Example 244, Step D), according to the procedures described in Example 47, Steps B and C, followed by the procedures described in Example 244, Steps I–K. $R_f$=0.23 (70% $CH_2Cl_2$/hexane); mp 140–2° C.; $^1$H NMR (300 MHz, $CDCl_3$): δ 7.36 (s, 1H), 7.30 (m, 2H), 7.08 (m, 4H), 6.75 (m, 2H), 4.72 (q, J=7 Hz, 1H), 3.89 (septet, J=7 Hz, 1H), 3.78 (s, 3H), 3.68 (m, 2H), 3.38 (septet, J=7 Hz, 1H), 1.57 (m, 1H), 1.40 (d, J=6.6 Hz, 3H), 1.31 (m, 12H); FAB-MS calcd for ($C_{28}H_{33}FO_2S$) 452, found 452 (M+); Anal. Calcd for $C_{28}H_{33}FO_2S$: C, 74.30; H, 7.35; S, 7.08; F, 4.20. Found: C, 74.06; H, 7.46; S, 6.87; F, 4.09; $[\alpha]^{22}$ =+24.5.

EXAMPLE 251

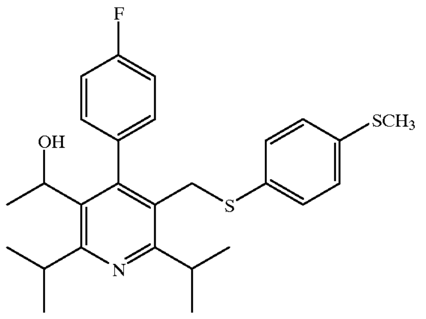

(+)-3,5-Diisopropyl-2-[(4-thiomethylthiophenyl)-methyl]-6-(1-hydroxyethyl)-4'-fluoro-1,1'-biphenyl The title compound was prepared from 4-(methylthio) phenol and 3,5-diisopropyl-2-hydroxymethyl-6-carboxymethyl-4'-fluoro-1,1'-biphenyl. (Example 244, Step D), according to the procedures described in Example 47, Steps B and C, followed by the procedures described in Example 244, Steps I–K. $R_f$=0.52 (90% $CH_2Cl_2$/hexane); mp 157–9° C.; $^1$H NMR (300 MHz, $CDCl_3$): δ 7.37 (s, 1H), 7.30 (m, 2H), 7.12 (m, 6H), 4.71 (q, J=7 Hz, 1H), 3.90 (septet, J=7 Hz, 1H), 3.75 (d, J=11 Hz, 1H), 3.70 (d, J=11 Hz, 1H), 3.33 (septet, J=7 Hz, 1H), 2.46 (s, 3H), 1.58 (s, 1 H), 1.40 (d, J=6.6 Hz, 3H), 1.29 (m, 12H); EI-MS calcd for ($C_{28}H_{33}FOS_2$) 468, found 468 (M+); Anal. Calcd for $C_{28}H_{33}FOS_2$: C, 71.76; H, 7.10; 5, 13.68; F, 4.05. Found: C, 71.54; H, 7.22; S, 13.26; F, 4.17; $[\alpha]^{22}$ =+40.6.

EXAMPLE 252

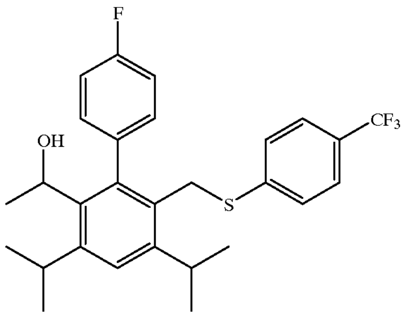

(+)-3,5-Diisopropyl-2-[(4-trifluoromethylthiophenyl)-methyl]-6-(1-hydroxyethyl)-4'-fluoro-1,1'-biphenyl The title compound was prepared from 4-(trifluoromethyl)benzene thiol and 3,5-diisopropyl-2-hydroxymethyl-6-carboxymethyl-4'-fluoro-1,1'-biphenyl (Example 244, Step D), according to the procedures described in Example 47, Steps B and C, followed by the procedures described in Example 244, Steps I–K. $R_f$=0.39 (80% $CH_2Cl_2$/hexane); mp 171–3° C.; $^1$H NMR (300 MHz, $CDCl_3$): δ 7.45 (s, 1H), 7.42 (s, 1H), 7.39 (s, 1H), 7.30 (m, 1H), 7.09 (m, 5H), 4.72 (q, J=7 Hz, 1H), 3.91 (septet, J=7 Hz, 1H), 3.83 (d, J=11 Hz, 1H), 3.78 (d, J=11 Hz, 1H), 3.28 (septet, J=7 Hz, 1H), 1.60 (s, 1H), 1.41 (d, J=6.6 Hz, 3H), 1.29 (m, 12H) FAB-MS calcd for ($C_{28}H_{30}F_4OS$) 490, found 490 (M+); Anal. Calcd for $C_{28}H_{30}F_4OS$: C, 68.55; H, 6.16; S, 6.53; F, 15.49. Found: C, 68.67; H, 6.15; S, 6.56; F, 15.33; $[\alpha]^{22}$ =+25.6.

EXAMPLE 253

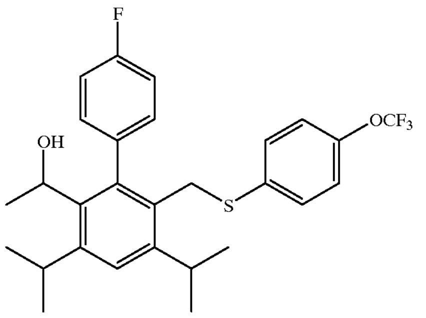

(+)-3,5-Diisopropyl-2-[(4-trifluoromethoxythiophenyl)-methyl]-6-(1-hydroxyethyl)-4'-fluoro-1,1'-biphenyl The title compound was prepared from 4-(trifluoromethoxy)benzene thiol and 3,5-diisopropyl-2-hydroxymethyl-6-carboxymethyl-4'-fluoro-1,1'-biphenyl (Example 244, Step D), according to the procedures described in Example 47, Steps B and C, followed by the procedures described in Example 244, Steps I–K. $R_f$=0.39 (80% $CH_2Cl_2$/hexane); mp 124–6° C.; $^1$H NMR (300 MHz, $CDCl_3$): δ 7.38 (s, 1H), 5 7.30 (m, 2H), 7.09 (m, 6H), 4.73 (q, J=7 Hz, 1H), 3.91 (septet, J=7 Hz, 1H), 3.78 (d, J=11 Hz, 1H), 3.73 (d, J=11 Hz, 1H), 3.31 (septet, J=7 Hz, 1H), 1.60 (s, 1H), 1.41 (d, J=7 Hz, 3H), 1.28 (m, 12H); FAB-MS calcd for ($C_{28}H_{30}F_4O_2S$) 506, found 506 (M+); Anal. Calcd for $C_{28}H_{30}F_4O_2S$: C, 66.39; H, 5.97; S, 6.33; F, 15.00. Found: C, 66.71; H, 6.06; S, 6.22; F, 15.24; $[\alpha]^{22}$ =+25.8.

EXAMPLE 254

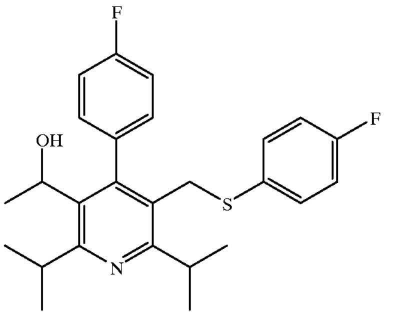

(+)-3,5-Diisopropyl-2-[(4-fluorothiophenyl)-methyl]-6-(1-hydroxyethyl)-4'-fluoro-1,1'-biphenyl The title compound was prepared from 4-fluorothiolphenol and 3,5-diisopropyl-2-hydroxymethyl-6-carboxymethyl-4'-fluoro-1,1'-biphenyl (Example 244, Step D), according to the procedures described in Example 47, Steps B and C, followed by the procedures described in Example 244, Steps I–K. $R_f$=0.35 (70% $CH_2Cl_2$/hexane); mp 138–140° C.; $^1H$ NMR (300 MHz, $CDCl_3$): δ 7.37 (s, 1H), 7.30 (m, 2H), 7.05 (m, 4H), 6.90 (m, 2H), 4.71 (q, J=7 Hz, 1H), 3.90 (septet, J=6.6 Hz, 1 H), 3.72 (m, 2H), 3.33 (septet, J=6.6 Hz, 1H), 1.52 (s, 1H), 1.39 (d, J=6.6 Hz, 3H), 1.27 (m, 12H); FAB-MS calcd for ($C_{28}H_{30}FO_2S$) 506, found 506 (M+); Anal. Calcd for $C_{28}H_{33}FO_2S$: C, 74.30; H, 7.35; S, 7.08; F, 4.20. Found: C, 74.06; H, 7.46; S, 6.87; F, 4.09; $[\alpha]^{22}$ =+17.6.

EXAMPLE 255

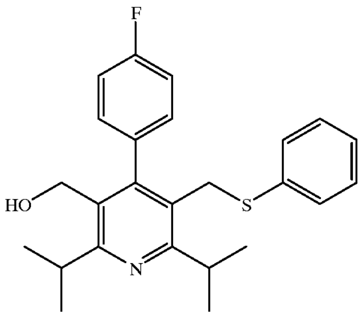

3,5-Diisopropyl-2-(thiophenylmethyl)-6-(hydroxymethyl)-4'-fluoro-1,1'-biphenyl

A suspension of Wang-resin (100 g, 1.09 mmol/g hydroxylated) was suspended in 1 L of a solution of 4N HCl in dioxane and gently stirred at room temperature for two days. After filtration, the chlorinated resin was washed 6 times with each of the following solvents; dioxane, isopropanol and finally THF. The resin was then dried at 60° C overnight. From this resin, 2.5 g (2.2 mmol based on the chlorine content detected by elemental analysis) was suspended in DMF (25 mL) and stirred at room temperature for 5 minutes, then the DMF was decanted off for the addition of a solution of 3,5-diisopropyl-2-hydroxymethyl-6carboxymethyl-4'-fluoro-1,1'-biphenyl (Example 244, Step D) (1.13 g, 3.3 mmol) in DMF (25 mL), followed by a solution of sodium hydride (60% in mineral oil, 170 mg, 3.3 mmol) in DMF (12.5 mL). The suspension was stirred at room temperature for two days under an argon atmosphere. The suspension was then filtered and the resulting resin was successively washed 10 times with each of the following solvents; DMF, a mixture THF/water (1:1), THF and finally with $CH_2Cl_2$. The resin residue was then treated with a solution of lithium aluminum hydride (1 M in THF, 15 mL, 15 mmol) and heated at reflux for 2 days. The suspension was filtered and the resulting residue was washed successively 10 times with each of the following solvents; THF, a mixture of THF/water (1:1), a mixture of THF/water (2:1), THF and finally with $CH_2Cl_2$.

The residue was suspended in THF (25 mL) and slowly treated with $PBr_3$ (835 μL, 8.7 mmol) at room temperature. The resin was filtered out and washed 10 times with each of the following solvents; THF, mixture of THF/1N sodium bicarbonate (1:1), THF/water (1:1), THF and finally $CH_2Cl_2$, then dried at 60° C. overnight which afforded 2.25 g of resin (0.62 mmol/g based on the bromine content detected by elemental analysis).

To 25 mg of this intermediate coupled with a resin was added thiophenol (26.4 mg, 0.24 mmol) in dry THF (500 μL) and N-methylmorpholine (26 μL, 0.24 mmol), then the suspension was refluxed for 8 hours. After filtration, the resin was washed successively 10 times with each of the following solvents; THF, a mixture of THF/water (1:1) and THF. The resin was then suspended in a mixture of TFA and $CH_2Cl_2$ (1:1) and stirred at room temperature for one hour. The resin was filtered off and the solvent recovered then evaporated. The residue was dissolved in a mixture of methanol and acetonitrile (1:1) and one drop of diisopropylethylamine, then stirred for one hour; HPLC: 12.5 min (Hypersil BDS-C18, 5 μm, 125×2 mm/Hewlett Packard, Flow 0.5 mL, 0–13 min 30–90% C, 13–15 min 90% C, Solvent A: Water/0.1% TFA; Solvent B: Acetonitrile). After evaporation of the solvent, the remaining residue was transferred in a microtiterplate for testing.

The compounds identified in the following Table as Examples 256–288 were prepared analogously to the compound of Example 255.

Table of Exemplary Compounds 255–288

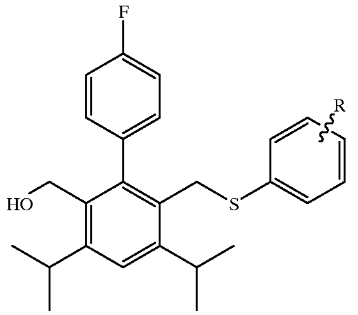

| Example | R | HPLC R.T. (method) | Est.'d Purity (%) |
|---|---|---|---|
| 255 | H | 12.5 (I) | 60–70 |
| 256 | 4-tBu | 14.9 (I) | 90 |

-continued

Table of Exemplary Compounds 255–288

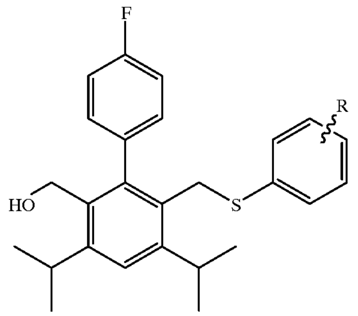

| Example | R | HPLC R.T. (method) | Est.'d Purity (%) |
|---|---|---|---|
| 257 | 4-OMe | 12.2 (I) | 60–70 |
| 258 | 4-Me | 13.2 (I) | 50–60 |
| 259 | 4-ipr | 14.4 (I) | 50–60 |
| 260 | 4-F | 12.5 (I) | 90 |
| 261 | 4-Et | 15.1 (I) | 90 |
| 262 | 4-$CF_3$ | 13.4 (I) | 70–80 |
| 263 | 4-Br | 13.9 (I) | 90 |
| 264 | 3-Me | 13.2 (I) | 90 |
| 265 | 3-F | 13.0 (I) | 70–80 |
| 266 | 3-Cl | 13.5 (I) | 90 |
| 267 | 3-$CF_3$ | 13.4 (I) | 90 |
| 268 | 2-Me | 13.2 (I) | 90 |
| 269 | 2-F | 12.4 (I) | 60–70 |
| 270 | 2-Cl | 12.9 (I) | 50–60 |
| 271 | 2,3-Me | ND | ND |
| 272 | 2,3-Cl | 6.8 (III) | 50–60 |
| 273 | 2,4-Me | 13.9 (I) | 50–60 |
| 274 | 2,4-Cl | 14.2 (I) | 60–70 |
| 275 | 2,4-F | 12.6 (I) | 60–70 |
| 276 | 2-Me-4-Cl | 14.2 (I) | 90 |
| 277 | 2-Cl-4-F | 13.3 (I) | 80–90 |
| 278 | 2,5-Cl | 14.0 (I) | 60–70 |
| 279 | 2,6-Cl | 13.7 (II) | 50 |
| 280 | 3,4-Me | 15.0 (I) | 90 |
| 281 | 3,4-Cl | 14.3 (I) | 90 |
| 282 | 3-Cl-4-F | 13.5 (I) | 90 |
| 283 | 3,5-Me | 13.9 (I) | 90 |
| 284 | 3,5-$CF_3$ | 14.4 (I) | 90 |
| 285 | 3,5-Cl | 14.8 (I) | 90 |
| 286 | 2,3,5,6-F-4-Me | 14.0 (I) | 80–90 |
| 287 | 2,3,5,6-F-4-Cl | 14.0 (I) | 60–70 |
| 288 | 2,3,5,6-F | 12.9 (I) | 60–70 |

HPLC: The Retention times (R.T.) for the compounds shown in the above table of exemplary compounds 255–290 were measured in minutes according to one of the three methods described below:

(I) Hypersil BDS-C18, 5 μm, 125x2 mm/Hewlett Packard, Flow 0.5 mL, 0–13 min 30–90% C, 13–15 min 90% C, Solvent A: Water/0.1% TFA; Solvent B: Acetonitrile..

(II) Hypersil BDS-C18, 5 μm, 125x2 mm/Hewlett Packard, Flow 0.5 mL, 0–13 min 30–90% C, 13–25 min 90% C, Solvent A: Water/0.1% TFA; Solvent B: Acetonitrile.

(III) NPS ODS-1, 1.5 mm, 33x4.6 mm/Micra, Flow 1.0 mL, 0–8 min 15–70% C, Solvent A: Water/0.1% TFA; Solvent B: Acetonitrile.

The estimated purity numbers were determined by comparison of peak areas, not by reference to standards.

The pharmaceutical utility of compounds of this invention is indicated by the following assay for glucagon receptor activity.

The affinity for the glucagon receptor of compounds of the present invention is determined by the glucagon receptor binding assay. Membranes were prepared from Chinese Hamster Ovary cells expressing the glucagon receptor (CHO-HGR) by scraping the cells into hypotonic lysis buffer (10 mM Tris, pH 7.4, 2 mM EDTA, 5 mM $MgCl_2$ and 1 mM PMSF) and subjecting the material to Polytron homogenization. Nuclei were removed by a 15-min 800×g centrifugation step conducted at 4° C. Membranes containing the receptor were collected by centrifugation at 15,000×g for 15 min at 4° C. The membranes were washed once in lysis buffer and suspended in 0.25 M sucrose, 10 mM Tris, 5 mM EDTA, pH 7.4. The membranes were used in ligand binding studies as reported (Yoo-Warren, H., Willse, A. G., Hancock, N., Hull, J., McCaleb, M., and Livingston, J. Regulation of Rat Glucagon Receptor Expression. *Biochem. Biophysical Res. Commun.* 1994, 205, 347–353). In brief, 10 ug of membrane protein was incubated in 130 μl of binding buffer that consisted of 20 mM Tris, pH 7A, 1 mM EDTA, 1 mg/ml BSA, and 1 mg/ml bacitracin. The membrane suspension was placed in each well of a 96-well filtration plate (glass fiber type C, Millipore). Twenty μl of test compound was added to each well to give final concentrations ranging from 2 nM to 20 μM. Following the addition of test compound, 50 μl of $^{125}$I-glucagon (9 fmol) (NEN) was added to each well. Control wells contained membranes, 0.5% DMSO (solvent for test compounds), radiolabeled glucagon without and with excess native glucagon (1 μM) to establish nonspecific binding. The plates were incubated for 60 min at room temperature, and then filtered on a Mllipore vacuum apparatus. Following a wash step with ice-cold PBS/0.1% BSA, the filters were punched into test tubes, and the membrane bound radioactivity was determined. An $IC_{50}$ value (the concentration of test compound needed to reduce membrane binding of radiolabelled glucagon by 50%) was calculated for each compound. If 20 μM compound did not reduce glucagon binding by 50%, the % reduction at 20 μM was reported in place of an $IC_{50}$ value. The binding characteristics for compounds of this invention are shown in Table I(C).

TABLE I(C)

| Example | $IC_{50}$ (μM) | % Inhibition (20 μM) |
|---|---|---|
| 1 | 0.6 | |
| 2 | | 2.73 |
| 3 | | 1.52 |
| 4 | | 1.98 |
| 5 | | 12.42 |
| 6 | | 34.23 |
| 7 | | 42.14 |
| 8 | | 17.02 |
| 9 | | 16.56 |
| 11 | 8 | |
| 12 | 1.7 | |
| 13 | 3 | |
| 14 | 1.4 | |
| 15 | 1.7 | |
| 16 | 0.85 | |
| 17 | 0.6 | |
| 18 | 0.75 | |
| 19 | 0.7 | |
| 20 | 1.3 | |
| 21 | 0.8 | |
| 22 | 1.1 | |
| 23 | 0.39 | |
| 24 | 0.75 | |
| 25 | 0.4 | |

TABLE I(C)-continued

| Example | $IC_{50}$ ($\mu$M) | % Inhibition (20 $\mu$M) |
|---|---|---|
| 26 | 1 | |
| 27 | 20 | |
| 28 | 1 | |
| 29 | 1 | |
| 30 | 0.9 | |
| 31 | 2.6 | |
| 32 | 1.1 | |
| 33 | 1.8 | |
| 34 | 0.6 | |
| 35 | 0.7 | |
| 36 | 1.8 | |
| 37 | 0.75 | |
| 38 | 0.6 | |
| 39 | 1.3 | |
| 40 | 0.75 | |
| 41 | 0.6 | |
| 42 | 0.7 | |
| 43 | 1.8 | |
| 44 | 1.0 | |
| 45 | 1.1 | |
| 46 | 9 | |
| 47 | 1.5 | |
| 48 | 1.8 | |
| 49 | 1.1 | |
| 50 | 0.9 | |
| 51 | 16 | |
| 52 | 20 | |
| 53 | 4.9 | |
| 54 | 1.8 | |
| 55 | | 15.66 |
| 56 | 1.9 | |
| 57 | 1.1 | |
| 58 | 1.5 | |
| 59 | 1 | |
| 60 | 1.6 | |
| 61 | 3.4 | |
| 62 | 1.1 | |
| 63 | 1.7 | |
| 64 | 1.1 | |
| 65 | 0.75 | |
| 66 | 1 | |
| 67 | 1.1 | |
| 68 | 13 | |
| 69 | | 40.21 |
| 70 | 12 | |
| 71 | | 46.33 |
| 72 | | 42.15 |
| 73 | | 17.46 |
| 74 | | 27.08 |
| 75 | | 34.16 |
| 76 | | 5.18 |
| 77 | 6 | |
| 78 | 7.5 | |
| 79 | 10 | |
| 80 | | 38.76 |
| 81 | 7.5 | |
| 82 | 1.9 | |
| 83 | 0.65 | |
| 84 | 1.9 | |
| 85 | 1.5 | |
| 86 | 1.1 | |
| 87 | 1.9 | |
| 88 | | 24.75 |
| 89 | | 36.03 |
| 90 | | 29.14 |
| 91 | | 14.15 |
| 92 | | 11.59 |
| 93 | | 28.33 |
| 94 | | 38.54 |
| 95 | | 26.53 |
| 96 | | 27.84 |
| 97 | | 29.25 |
| 98 | 14 | |
| 99 | | 43.18 |
| 100 | | 39.61 |
| 101 | 0.22 | |
| 102 | 0.11 | |
| 103 | 1.9 | |
| 104 | 0.25 | |
| 105 | 0.3 | |
| 106 | 0.15 | |
| 107 | 3 | |
| 108 | 0.24 | |
| 109 | 0.12 | |
| 110 | 2 | |
| 112 | | 4.17 |
| 113 | 0.6 | |
| 114 | | 38.49 |
| 115 | | 21.12 |
| 116 | | 17.03 |
| 117 | | 45.14 |
| 118 | 13 | |
| 119 | | 30.2 |
| 120 | | 37.01 |
| 121 | | 26.19 |
| 122 | | 7.54 |
| 123 | | 49.22 |
| 124 | 12 | |
| 125 | | 31.62 |
| 126 | | 35.29 |
| 127 | | 45.53 |
| 128 | 3 | |
| 129 | 1.5 | |
| 130 | 1 | |
| 131 | | 37.27 |
| 132 | | 42.48 |
| 133 | | 35.46 |
| 134 | | 34.41 |
| 135 | | 4.64 |
| 136 | | 2.37 |
| 137 | 11 | |
| 138 | 9 | |
| 139 | 17 | |
| 140 | | 46.28 |
| 141 | | 34.05 |
| 142 | | 33.11 |
| 143 | 0.9 | |
| 144 | 0.8 | |
| 145 | | 41.44 |
| 146 | | 48.78 |
| 148 | | 7.78 |
| 149 | | 39.03 |
| 150 | 4.5 | |
| 151 | 10.5 | |
| 152 | | 25.35 |
| 153 | 6 | |
| 154 | | 20.71 |
| 155 | | 25.25 |
| 156 | | 26.05 |
| 157 | | 32.6 |
| 158 | 1.8 | |
| 159 | 1.1 | |
| 160 | | 21.03 |
| 161 | | 23.99 |
| 162 | | 13.88 |
| 163 | 0.5 | |
| 164-D1 | 0.045 | |
| 164-D2 | 0.1 | |
| 165-D1 | 0.04 | |
| 165-D2 | 1.1 | |
| 166 | 0.19 | |
| 167-D1 | 0.03 | |
| 167-D2 | 2.2 | |
| 169 | | 37.06 |
| 170 | | 45.45 |
| 171 | | 48.37 |
| 173 | | 27.4 |
| 174 | | 33.38 |
| 175 | | 40.88 |
| 176 | | 13.83 |
| 177 | 19 | |
| 178 | | 25.98 |

TABLE I(C)-continued

| Example | $IC_{50}$ (μM) | % Inhibition (20 μM) |
|---|---|---|
| 179 | | 26.79 |
| 180 | | 38.21 |
| 181 | | 45.96 |
| 182 | | 49.07 |
| 183 | | 13.23 |
| 184 | | 28.93 |
| 185 | | 41.22 |
| 186 | 20 | |
| 187 | 12 | |
| 188 | 10.5 | |
| 189 | 12 | |
| 190 | 0.3 | |
| 191 | 0.13 | |
| 192 | 0.13 | |
| 193 | 0.086 | |
| 194 | 1 | |
| 195 | 12 | |
| 196 | | 40.32 |
| 197 | 7 | |
| 198 | 17 | |
| 199 | | 8.67 |
| 200 | | 32.77 |
| 201 | | 46.67. |
| 202 | 9 | |
| 203 | 6.3 | |
| 204 | 1.8 | |
| 205 | 18 | |
| 206 | | 44.57 |
| 207 | | 43.97 |
| 208 | 19 | |
| 210 | 18 | |
| 211 | 19 | |
| 212 | 14 | |
| 213 | 7 | |
| 214 | 5 | |
| 215 | 19 | |
| 217 | 8 | |
| 218 | 6.5 | |
| 219 | | 5.11 |
| 220 | 1.3 | |
| 221 | 1.3 | |
| 222 | 0.11 | |
| 223 | 0.11 | |
| 224 | 0.11 | |
| 225 | 7 | |
| 226 | 3 | |
| 227 | 1.3 | |
| 228 | 2 | |
| 229 | 0.8 | |
| 230 | 0.9 | |
| 231 | 0.5 | |
| 232 | 1.2 | |
| 233 | 0.6 | |
| 234 | 8 | |
| 235 | 3.1 | |
| 236 | 4 | |
| 237 | 1.2 | |
| 238 | 0.01 | |
| 239-rac | 0.08 | |
| 239-E1 | 2.5 | |
| 239-E2 | 0.05 | |
| 240 | 0.016 | |
| 241 | 0.11 | |
| 242 | 0.005 | |
| 243 | 0.086 | |
| 244 | 0.18 | |
| 245 | 0.3 | |
| 246 | 0.011 | |
| 247 | 0.006 | |
| 248 | 0.31 | |
| 249 | 0.13 | |
| 250 | 0.2 | |
| 251 | 0.4 | |
| 252 | 0.18 | |
| 253 | 0.18 | |
| 254 | 0.11 | |

TABLE I(C)-continued

| Example | $IC_{50}$ (μM) | % Inhibition (20 μM) |
|---|---|---|
| 255 | 3 | |
| 256 | 7 | |
| 257 | 7.3 | |
| 258 | 7 | |
| 259 | 6 | |
| 260 | 2.5 | |
| 261 | 5.4 | |
| 262 | 1.7 | |
| 263 | 4.4 | |
| 264 | 3.4 | |
| 265 | 3 | |
| 266 | 2 | |
| 267 | 1.7 | |
| 268 | 4.1 | |
| 269 | 3.4 | |
| 270 | 5 | |
| 271 | 12 | |
| 272 | 2.6 | |
| 273 | 5 | |
| 274 | 12 | |
| 275 | 3 | |
| 276 | 20 | |
| 277 | 2 | |
| 278 | 10 | |
| 279 | 20 | |
| 280 | 10 | |
| 281 | 5.4 | |
| 282 | 1.7 | |
| 283 | 12 | |
| 284 | 7 | |
| 285 | 9 | |
| 286 | 18 | |
| 287 | 20 | |
| 288 | 2 | |

Preferred phenyl pyridine compounds of general formula (IC) and more particularly of general formula 1B are shown in the following list:

2,6-Diisopropyl-3-hydroxymethyl-4-phenyl-5-ethylpyridine;

2,6-Diisopropyl-3-hydroxymethyl-4-(4fluorophenyl)-5-ethylpyridine;

2,6-Diisopropyl-3-hydroxymethyl-4-(4-chlorophenyl)-5-ethylpyridine;

2,6-Diisopropyl-3-hydroxymethyl-4-(4-methylphenyl)-5-ethylpyridine;

2,6-Diisopropyl-3-hydroxymethyl-(2-hydroxyphenyl)-5-ethylpyridine;

2,6-Diisopropyl-3-hydroxymethyl-4-(2-hydroxy-4-fluorophenyl)-5-ethylpyridine;

2,6-Diisopropyl-3-hydroxymethyl-4phenyl-5-propylpyridine;

2,6-Diisopropyl-3-hydroxymethyl-4-(4-fluorophenyl)-5-propylpyridine;

2,6-Diisopropyl-3-hydroxymethyl-4-(4chlorophenyl)-5-propylpyridine;

2,6-Diisopropyl-3-hydroxymethyl-4-(4methylphenyl)-5-propylpyridine;

2,6-Diisopropyl-3-hydroxymethyl-4-(2-hydroxyphenyl)-5-propylpyridine;

2,6-Diisopropyl-3-hydroxymethyl-4-(2-hydroxy-4-fluorophenyl)-5-propylpyridine;

2,6-Diisopropyl-3-hydroxymethyl-4-phenyl-5-butylpyridine;

2,6-Diisopropyl-3-hydroxymethyl-4-(4-fluorophenyl)-5-butylpyridine;

2,6-Diisopropyl-3-hydroxymethyl-4-(4-chlorophenyl)-5-butylpyridine;

2,6-Diisopropyl-3-hydroxymethyl-4-(4-methylphenyl)-5-butylpyridine;

2,6-Diisopropyl-3-hydroxymethyl-4-(2-hydroxyphenyl)-5-butyl-pyridine;
2,6-Diisopropyl-3-hydroxymethyl-4-(2-hydroxy-4-fluorophenyl)-5-butylpyridine;
2,6-Diisopropyl-3-hydroxymethyl-4-phenyl-5-pentylpyridine;
2,6-Diisopropyl-3-hydroxymethyl-4-(4-fluorophenyl)-5-pentylpyridine;
2,6-Diisopropyl-3-hydroxymethyl-4-(4-chlorophenyl)-5-pentylpyridine;
2,6-Diisopropyl-3-hydroxymethyl-4-(4-methylphenyl)-5-pentyl-pyridine;
2,6-Diisopropyl-3-hydroxymethyl-4-(2-hydroxyphenyl)-5-pentyl-pyridine;
2,6-Diisopropyl-3-hydroxymethyl-4-(2-hydroxy-4-fluorophenyl)-5-pentylpyridine;
2,6-Diisopropyl-3-hydroxymethyl-4-phenyl-5-hexylpyridine;
2,6-Diisopropyl-3-hydroxymethyl-4-(4-fluorophenyl)-5-hexylpyridine;
2,6-Diisopropyl-3-hydroxymethyl-4-(4-chlorophenyl)-5-hexylpyridine;
2,6-Diisopropyl-3-hydroxymethyl-4-(4-methylphenyl)-5-hexylpyridine;
2,6-Diisopropyl-3-hydroxymethyl-4-(2-hydroxyphenyl)-5-hexylpyridine;
2,6-Diisopropyl-3-hydroxymethyl-4-(2-hydroxy-4-fluorophenyl)-5-hexylpyridine;
2,6-Diisopropyl-3-[(p-tolylthio)methyl]-4-phenyl-5-hydroxymethyl-pyridine;
2,6-Diisopropyl-3-[(p-tolylthio)methyl]-4-(4-fluorophenyl)-5-hydroxymethyl-pyridine; pyridine;
2,6-Diisopropyl-3-[(p-tolylthio)methyl]-4-(4-chlorophenyl)-5-hydroxymethyl-pyridine;
2,6-Diisopropyl-3-[(p-tolylthio)methyl]-4-(4-methylphenyl)-5-hydroxymethyl-pyridine;
2,6-Diisopropyl-3-[(p-tolylthio)methyl]-4-(2-hydroxyphenyl)-5-hydroxymethyl-pyridine;
2,6-Diisopropyl-3-[(p-tolylthio)methyl]-4-(2-hydroxy-4-fluorophenyl)-5-hydroxymethyl-pyridine;
2,6-Diisopropyl-3-[((4-fluorophenyl)thio)methyl]-4-phenyl-5-hydroxymethyl-pyridine;
2,6-Diisopropyl-3-[((4-fluorophenyl)thio)methyl]-4-(4-fluorophenyl)-5-hydroxymethyl-pyridine;
2,6-Diisopropyl-3-[((4-fluorophenyl)thio)methyl]-4-(4-chlorophenyl)-5-hydroxymethyl-pyridine;
2,6-Diisopropyl-3-[((4-fluorophenyl)thio)methyl]-4-(4-methylphenyl)-5-hydroxymethyl-pyridine;
2,6-Diisopropyl-3-[((4-fluorophenyl)thio)methyl]-4-(2-hydroxyphenyl)-5-hydroxymethyl-pyridine;
2,6-Diisopropyl-3-[((4-fluorophenyl)thio)methyl]-4-(2-hydroxy-4-fluorophenyl)-5-hydroxymethyl-pyridine;
2,6-Diisopropyl-3-(1-hydroxyethyl)-4-phenyl-5-ethylpyridine;
2,6-Diisopropyl-3-(1-hydroxyethyl)-4-(4-fluorophenyl)-5-ethylpyridine;
2,6-Diisopropyl-3-(1-hydroxyethyl)-4-(4-chlorophenyl)-5-ethylpyridine;
2,6-Diisopropyl-3-(1-hydroxyethyl)-4-(4-methylphenyl)-5-ethylpyridine;
2,6-Diisopropyl-3-(1-hydroxyethyl)-4-(2-hydroxyphenyl)-5-ethylpyridine;
2,6-Diisopropyl-3-(1-hydroxyethyl)-4-(2-hydroxy-4-fluorophenyl)-5-ethylpyridine;
2,6-Diisopropyl-3-(1-hydroxyethyl)-4-phenyl-5-propylpyridine;
2,6-Diisopropyl-3-(1-hydroxyethyl)-4-(4-fluorophenyl)-5-propylpyridine;
2,6-Diisopropyl-3-(1-hydroxyethyl)-4-(4-chlorophenyl)-5-propylpyridine;
2,6-Diisopropyl-3-(1-hydroxyethyl)-4-(4-methylphenyl)-5-propylpyridine;
2,6-Diisopropyl-3-(1-hydroxyethyl)-4-(2-hydroxyphenyl)-5-propylpyridine;
2,6-Diisopropyl-3-(1-hydroxyethyl)-4-(2-hydroxy-4-fluorophenyl)-5-propylpyridine;
2,6-Diisopropyl-3-(1-hydroxyethyl)-4-phenyl-5-butylpyridine;
2,6-Diisopropyl-3-(1-hydroxyethyl)-4-(4-fluorophenyl)-5-butylpyridine;
2,6-Diisopropyl-3-(1-hydroxyethyl)-4-(4-chlorophenyl)-5-butylpyridine;
2,6-Diisopropyl-3-(1-hydroxyethyl)-4-(4-methylphenyl)-5-butylpyridine;
2,6-Diisopropyl-3-(1-hydroxyethyl)-4-(2-hydroxyphenyl)-5-butylpyridine;
2,6-Diisopropyl-3-(1-hydroxyethyl)-4-(2-hydroxy-4-fluorophenyl)-5-butylpyridine;
2,6-Diisopropyl-3-(1-hydroxyethyl)-4-phenyl-5-pentylpyridine;
2,6-Diisopropyl-3-(1-hydroxyethyl)-4-(4-fluorophenyl)-5-pentylpyridine;
2,6-Diisopropyl-3-(1-hydroxyethyl)-4-(4-chlorophenyl)-5-pentylpyridine;
2,6-Diisopropyl-3-(1-hydroxyethyl)-4-(4-methylphenyl)-5-pentylpyridine;
2,6-Diisopropyl-3-(1-hydroxyethyl)-4-(2-hydroxyphenyl)-5-pentylpyridine;
2,6-Diisopropyl-3-(1-hydroxyethyl)-4-(2-hydroxy-4-fluorophenyl)-5-pentylpyridine;
2,6-Diisopropyl-3-(1-hydroxyethyl)-4-phenyl-5-hexylpyridine;
2,6-Diisopropyl-3-(1-hydroxyethyl)-4-(4-fluorophenyl)-5-hexyl-pyridine;
2,6-Diisopropyl-3-(1-hydroxyethyl)-4-(4-chlorophenyl)-5-hexylpyridine;
2,6-Diisopropyl-3-(1-hydroxyethyl)-4-(4-methylphenyl)-5-hexylpyridine;
2,6-Diisopropyl-3-(1-hydroxyethyl)-4-(2-hydroxyphenyl)-5-hexylpyridine;
2,6-Diisopropyl-3-(1-hydroxyethyl)-4-(2-hydroxy-4-fluorophenyl)-5-hexylpyridine;
2,6-Diisopropyl-3-[(p-tolylthio)methyl]-4-phenyl-5-(1-hydroxyethyl)-pyridine;
2,6-Diisopropyl-3-[(p-tolylthio)methyl]-4-(4-fluorophenyl)-5-(1-hydroxyethyl)-pyridine;
2,6-Diisopropyl-3-[(p-tolylthio)methyl]-4-(4-chlorophenyl)-5-(1-hydroxyethyl)-pyridine;
2,6-Diisopropyl-3-[(p-tolylthio)methyl]-4-(4-methylphenyl)-5-(1-hydroxyethyl)-pyridine;
2,6-Diisopropyl-3-[(p-tolylthio)methyl]-4-(2-hydroxyphenyl)-5-(1-hydroxyethyl)-pyridine;
2,6-Diisopropyl-3-[(p-tolylthio)methyl]-4-(2-hydroxy-4-fluorophenyl)-5-(1-hydroxyethyl)-pyridine;
2,6-Diisopropyl-3-[((4-fluorophenyl)thio)methyl]-4-phenyl-5-(1-hydroxyethyl)-pyridine;
2,6-Diisopropyl-3-[((4-fluorophenyl)thio)methyl]-4-(4-fluorophenyl)-5-(1-hydroxyethyl)-pyridine;
2,6-Diisopropyl-3-[((4-fluorophenyl)thio)methyl]-4-(4-chlorophenyl)-5-(1-hydroxyethyl)pyridine;
2,6-Diisopropyl-3-[((4-fluorophenyl)thio)methyl]-4-(4-methylphenyl)-5-(1-hydroxyethyl)pyridine;
2,6-Diisopropyl-3-[((4-fluorophenyl)thio)methyl]-4-(2-hydroxyphenyl)-5-(1-hydroxyethyl)pyridine;
2,6-Diisopropyl-3-[((4-fluorophenyl)thio)methyl]-4-(2-hydroxy-4-fluorophenyl)-5-(1-hydroxyethyl)-pyridine.

Preferred biphenyl compounds of general formula (IC) and more particularly of general formula 1D are shown in the following list:

3,5-Diisopropyl-2-hydroxymethyl-6-ethyl-1,1'-biphenyl;
3,5-Diisopropyl-2-hydroxymethyl-6-ethyl-4'-fluoro-1,1'-biphenyl;
3,5-Diisopropyl-2-hydroxymethyl-6-ethyl-4'-chloro-1,1'-biphenyl;
3,5-Diisopropyl-2-hydroxymethyl-6-ethyl-4'-methyl-1,1'-biphenyl;
3,5-Diisopropyl-2-hydroxymethyl-6-ethyl-2'-hydroxy-1,1'-biphenyl;
3,5-Diisopropyl-2-hydroxymethyl-6-ethyl-2'-hydroxy-4'-fluoro-1,1'-biphenyl;
3,5-Diisopropyl-2-hydroxymethyl-6-propyl-1,1'-biphenyl;
3,5-Diisopropyl-2-hydroxymethyl-6-propyl-4'-fluoro-1,1'-biphenyl;
3,5-Diisopropyl-2-hydroxymethyl-6-propyl-4'-chloro-1,1'-biphenyl;
3,5-Diisopropyl-2-hydroxymethyl-6-propyl-4'-methyl-1,1'-biphenyl;
3,5-Diisopropyl-2-hydroxymethyl-6-propyl-2'-hydroxyl-1,1'-biphenyl;
3,5-Diisopropyl-2-hydroxymethyl-6-propyl-2'-hydroxy-4'-fluoro-1,1'-biphenyl;
3,5-Diisopropyl-2-hydroxymethyl-6-butyl-1,1'-biphenyl;
3,5-Diisopropyl-2-hydroxymethyl-6-butyl-4'-fluoro-1,1'-biphenyl;
3,5-Diisopropyl-2-hydroxymethyl-6-butyl-4'-chloro-1,1'-biphenyl;
3,5-Diisopropyl-2-hydroxymethyl-6-butyl-4'-methyl-1,1'-biphenyl;
3,5-Diisopropyl-2-hydroxymethyl-6-butyl-2'-hydroxy-1,1'-biphenyl;
3,5-Diisopropyl-2-hydroxymethyl-6-butyl-2'-hydroxy-4'-fluoro-1,1'-biphenyl;
3,5-Diisopropyl-2-hydroxymethyl-6-pentyl-1,1'-biphenyl;
3,5-Diisopropyl-2-hydroxymethyl-6-pentyl-4'-fluoro-1,1'-biphenyl;
3,5-Diisopropyl-2-hydroxymethyl-6-pentyl-4'-chloro-1,1'-biphenyl;
3,5-Diisopropyl-2-hydroxymethyl-6-pentyl-4'-methyl-1,1'-biphenyl;
3,5-Diisopropyl-2-hydroxymethyl-6-pentyl-2'-hydroxy-1,1'-biphenyl;
3,5-Diisopropyl-2-hydroxymethyl-6-pentyl-2'-hydroxy-4'-fluoro-1,1'-biphenyl;
3,5-Diisopropyl-2-hydroxymethyl-6-hexyl-1,1'-biphenyl;
3,5-Diisopropyl-2-hydroxymethyl-6-hexyl-4'-fluoro-1,1'-biphenyl;
3,5-Diisopropyl-2-hydroxymethyl-6-hexyl-4'-chloro-1,1'-biphenyl;
3,5-Diisopropyl-2-hydroxymethyl-6-hexyl-4'-methyl-1,1'-biphenyl;
3,5-Diisopropyl-2-hydroxymethyl-6-hexyl-2'-hydroxy-1,1'-biphenyl;
3,5-Diisopropyl-2-hydroxymethyl-6-hexyl-2'-hydroxy-4'-fluoro-1,1'-biphenyl;
3,5-Diisopropyl-2-[(p-tolylthio)methyl]-6-hydroxymethyl-1,1'-biphenyl;
3,5-Diisopropyl-2-[(p-tolylthio)methyl]-6-hydroxymethyl-4'-fluoro-1,1'-biphenyl;
3,5-Diisopropyl-2-[(p-tolylthio)methyl]-6-hydroxymethyl-4'-chloro-1,1'-biphenyl;
3,5-Diisopropyl-2-[(p-tolylthio)methyl]-6-hydroxymethyl-4'-methyl-1,1'-biphenyl;
3,5-Diisopropyl-2-[(p-tolylthio)methyl]-6-hydroxymethyl-2'-hydroxy-1,1'-biphenyl;
3,5-Diisopropyl-2-[(p-tolylthio)methyl]-6-hydroxymethyl-2'-hydroxy4'-fluoro-1,1'-biphenyl;
3,5-Diisopropyl-2-[((4-fluorophenyl)thio)methyl]-6-hydroxymethyl-1,1'-biphenyl;
3,5-Diisopropyl-2-[((4-fluorophenyl)thio)methyl]-6-hydroxymethyl-4'-fluoro-1,1'-biphenyl;
3,5-Diisopropyl-2-[((4-fluorophenyl)thio)methyl]-6-hydroxymethyl-4'-chloro-1,1'-biphenyl;
3,5-Diisopropyl-2-[((4-fluorophenyl)thio)methyl]-6-hydroxymethyl-4'-methyl-1,1'-biphenyl;
3,5-Diisopropyl-2-[((4-fluorophenyl)thio)methyl]-6-hydroxymethyl-2'-hydroxy-1,1'-biphenyl;
3,5-Diisopropyl-2-[((4-fluorophenyl)thio)methyl]-6-hydroxymethyl-2'-hydroxy-4'-fluoro-1,1'-biphenyl;
3,5-Diisopropyl-2-(1-hydroxyethyl)-6-ethyl-1,1'-biphenyl;
3,5-Diisopropyl-2-(1-hydroxyethyl)-6-ethyl-4'-fluoro-1,1'-biphenyl;
3,5-Diisopropyl-2-(1-hydroxyethyl)-6-ethyl-4'-chloro-1,1'-biphenyl;
3,5-Diisopropyl-2-(1-hydroxyethyl)-6-ethyl-4'-methyl-1,1'-biphenyl;
3,5-Diisopropyl-2-(1-hydroxyethyl)-6-ethyl-2'-hydroxy-1,1'-biphenyl;
3,5-Diisopropyl-2-(1-hydroxyethyl)-6-ethyl-2'-hydroxy4'-fluoro-1,1'-biphenyl;
3,5-Diisopropyl-2-(1-hydroxyethyl)-6-propyl-1,1'-biphenyl;
3,5-Diisopropyl-2-(1-hydroxyethyl)-6-propyl-4'-fluoro-1,1'-biphenyl;
3,5-Diisopropyl-2-(1-hydroxyethyl)-6-propyl-4'-chloro-1,1'-biphenyl;
3,5-Diisopropyl-2-(1-hydroxyethyl)-6-propyl-4'-methyl-1,1'-biphenyl;
3,5-Diisopropyl-2-(1-hydroxyethyl)-6-propyl-2'-hydroxy-1,1'-biphenyl;
3,5-Diisopropyl-2-(1-hydroxyethyl)-6-propyl-2'-hydroxy-4'-fluoro-1,1'-biphenyl;
3,5-Diisopropyl-2-(1-hydroxyethyl)-6-butyl-1,1'-biphenyl;
3,5-Diisopropyl-2-(1-hydroxyethyl)-6-butyl-4'-fluoro-1,1'-biphenyl;
3,5-Diisopropyl-2-(1-hydroxyethyl)-6-butyl-4'-chloro-1,1'-biphenyl;
3,5-Diisopropyl-2-(1-hydroxyethyl)-6-butyl-4'-methyl-1,1'-biphenyl;
3,5-Diisopropyl-2-(1-hydroxyethyl)-6-butyl-2'-hydroxy-1,1'-biphenyl;
3,5-Diisopropyl-2-(1-hydroxyethyl)-6-butyl-2'-hydroxy-4'-fluoro-1,1'-biphenyl;
3,5-Diisopropyl-2-(1-hydroxyethyl)-6-pentyl-1,1'-biphenyl;
3,5-Diisopropyl-2-(1-hydroxyethyl)-6-pentyl-4'-fluoro-1,1'-biphenyl;
3,5-Diisopropyl-2-(1-hydroxyethyl)-6-pentyl-4'-chloro-1,1'-biphenyl;
3,5-Diisopropyl-2-(1-hydroxyethyl)-6-pentyl-4'-methyl-1,1'-biphenyl;
3,5-Diisopropyl-2-(1-hydroxyethyl)-6-pentyl-2'-hydroxy-1,1'-biphenyl;
3,5-Diisopropyl-2-(1-hydroxyethyl)-6-pentyl-2'-hydroxy-4'-fluoro-1,1'-biphenyl;
3,5-Diisopropyl-2-(1-hydroxyethyl)-6-hexyl-1,1'-biphenyl;
3,5-Diisopropyl-2-(1-hydroxyethyl)-6-hexyl-4'-fluoro-1,1'-biphenyl;
3,5-Diisopropyl-2-(1-hydroxyethyl)-6-hexyl-4'-chloro-1,1'-biphenyl
3,5-Diisopropyl-2-(1-hydroxyethyl)-6-hexyl-4'-methyl-1,1'-biphenyl;
3,5-Diisopropyl-2-(1-hydroxyethyl)-6-hexyl-2'-hydroxy-1,1'-biphenyl;

3,5-Diisopropyl-2-(1-hydroxyethyl)-6-hexyl-2'-hydroxy-4'-fluoro-1,1'-biphenyl;
3,5-Diisopropyl-2-[(p-tolylthio)methyl]-6-(1-hydroxyethyl)-1,1'-biphenyl;
3,5-Diisopropyl-2-[(p-tolylthio)methyl]-6-(1-hydroxyethyl)-4'-fluoro-1,1'-biphenyl;
3,5-Diisopropyl-2-[(p-tolylthio)methyl]-6-(1-hydroxyethyl)-4'-chloro-1,1'-biphenyl;
3,5-Diisopropyl-2-[(p-tolylthio)methyl]-6-(1-hydroxyethyl)-4'-methyl-1,1'-biphenyl;
3,5-Diisopropyl-2-[(p-tolylthio)methyl]-6-(1-hydroxyethyl)-2'-hydroxy-1,1'-biphenyl;
3,5-Diisopropyl-2-[(p-tolylthio)methyl]-6-(1-hydroxyethyl)-2'-hydroxy-4'-fluoro-1,1'-biphenyl;
3,5-Diisopropyl-2-[((4-fluorophenyl)thio)methyl]-6-(1-hydroxyethyl)-1,1'-biphenyl;
3,5-Diisopropyl-2-[((4-fluorophenyl)thio)methyl]-6-(1-hydroxyethyl)-4'-fluoro-1,1'-biphenyl;
3,5-Diisopropyl-2-[((4-fluorophenyl)thio)methyl]-6-(1-hydroxyethyl)-4'-chloro-1,1'-biphenyl;
3,5-Diisopropyl-2-[((4-fluorophenyl)thio)methyl]-6-(1-hydroxyethyl)-4'-methyl-1,1'-biphenyl;
3,5-Diisopropyl-2-[((4-fluorophenyl)thio)methyl]-6-(1-hydroxyethyl)-2'-hydroxy-1,1'-biphenyl;
3,5-Diisopropyl-2-[((4-fluorophenyl)thio)methyl]-6-(1-hydroxyethyl)-2'-hydroxy-4'-fluoro-1,1'-biphenyl.

Other embodiments of the invention will be apparent to the skilled in the art from a consideration of this specification or practice of the invention disclosed herein. It is intended that the specification and examples be considered as exemplary only, with the true scope and spirit of the invention being indicated by the following claims.

We claim:

1. A compound having glucagon receptor antagonistic activity and the structural formula

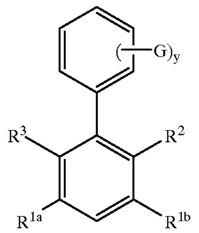

wherein:

$R^{1a}$ and $R^{1b}$ independently represent $(C_1–C_6)$ alkyl;

$R^2$ represents $(C_1–C_{10})$ alkyl, or substituted $(C_1–C_{10})$ alkyl wherein the substituents are independently from 1 to 3 of —$SR^7$;

R7 represents phenyl, or substituted phenyl wherein the substituents are independently 1–5 of halogen, trifluoromethyl, $(C_1–C_6)$ alkyl, $(C_1–C_6)$ alkoxy, nitro, cyano, or hydroxyl;

$R^3$ represents substituted $(C_1–C_6)$ alkyl wherein the substituents are 1–2 hydroxyl groups;

G represents a substituent selected from the group consisting of halogen, $(C_1–C_6)$ alkyl, and $OR^4$, wherein $R^4$ is H or $(C_1–C_6)$ alkyl; and y is 0 or an integer of 1–3.

2. The compound of claim 1 wherein the substituent shown as $R^3$ is a hydroxyethyl group having the following stereochemistry:

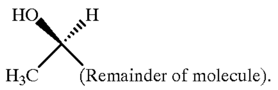

3. A pharmaceutical composition for use in treating a glucagon-mediated condition, which comprises: an effective amount of a compound of claim 1, in admixture with a pharmaceutically acceptable carrier.

4. A method for treating a glucagon-mediated condition which comprises:

administering to a subject in need of such treatment an effective amount of a compound of claim 1.

5. The method of claim 4, wherein the subject is human, the glucagon-mediated condition is diabetes, and the treatment results in lowering of blood glucose.

6. A compound of claim 1, selected from the following group of compounds:

3,5-Diisopropyl-2-hydroxymethyl-6-ethyl-1,1'-biphenyl;
3,5-Diisopropyl-2-hydroxymethyl-6-ethyl-4'-fluoro-1,1'-biphenyl;
3,5-Diisopropyl-2-hydroxymethyl-6-ethyl-4'-chloro-1,1'-biphenyl;
3,5-Diisopropyl-2-hydroxymethyl-6-ethyl-4'-methyl-1,1'-biphenyl;
3,5-Diisopropyl-2-hydroxymethyl-6-ethyl-2'-hydroxy-1,1'-biphenyl;
3,5-Diisopropyl-2-hydroxymethyl-6-ethyl-2'-hydroxy-4'-fluoro-1,1'-biphenyl;
3,5-Diisopropyl-2-hydroxymethyl-6-propyl-1,1'-biphenyl;
3,5-Diisopropyl-2-hydroxymethyl-6-propyl-4'-fluoro-1,1'-biphenyl;
3,5-Diisopropyl-2-hydroxymethyl-6-propyl-4'-chloro-1,1'-biphenyl;
3,5-Diisopropyl-2-hydroxymethyl-6-propyl-4'-methyl-1,1'-biphenyl;
3,5-Diisopropyl-2-hydroxymethyl-6-propyl-2'-hydroxy-1,1'-biphenyl;
3,5-Diisopropyl-2-hydroxymethyl-6-propyl-2'-hydroxy-4'-fluoro-1,1'-biphenyl;
3,5-Diisopropyl-2-hydroxymethyl-6-butyl-1,1'-biphenyl;
3,5-Diisopropyl-2-hydroxymethyl-6-butyl-4'-fluoro-1,1'-biphenyl;
3,5-Diisopropyl-2-hydroxymethyl-6-butyl-4'-chloro-1,1'-biphenyl;
3,5-Diisopropyl-2-hydroxymethyl-6-butyl-4'-methyl-1,1'-biphenyl;
3,5-Diisopropyl-2-hydroxymethyl-6-butyl-2'-hydroxy-1,1'-biphenyl;
3,5-Diisopropyl-2-hydroxymethyl-6-butyl-2'-hydroxy-4'-fluoro-1,1'-biphenyl;
3,5-Diisopropyl-2-hydroxymethyl-6-pentyl-1,1'-biphenyl;
3,5-Diisopropyl-2-hydroxymethyl-6-pentyl-4'-fluoro-1,1'-biphenyl;
3,5-Diisopropyl-2-hydroxymethyl-6-pentyl-4'-chloro-1,1'-biphenyl;
3,5-Diisopropyl-2-hydroxymethyl-6-pentyl-4'-methyl-1,1'-biphenyl;
3,5-Diisopropyl-2-hydroxymethyl-6-pentyl-2'-hydroxy-1,1'-biphenyl;
3,5-Diisopropyl-2-hydroxymethyl-6-pentyl-2'-hydroxy-4'-fluoro-1,1'-biphenyl;
3,5-Diisopropyl-2-hydroxymethyl-6-hexyl-1,1'-biphenyl;
3,5-Diisopropyl-2-hydroxymethyl-6-hexyl-4'-fluoro-1,1'-biphenyl;
3,5-Diisopropyl-2-hydroxymethyl-6-hexyl-4'-chloro-1,1'-biphenyl;

3,5-Diisopropyl-2-hydroxymethyl-6-hexyl-4'-methyl-1,1'-biphenyl;

3,5-Diisopropyl-2-hydroxymethyl-6-hexyl-2'-hydroxy-1,1'-biphenyl;

3,5-Diisopropyl-2-hydroxymethyl-6-hexyl-2'-hydroxy-4'-fluoro-1,1'-biphenyl;

3,5-Diisopropyl-2-[(p-tolylthio)methyl]-6-hydroxymethyl-1,1'-biphenyl;

3,5-Diisopropyl-2-[(p-tolylthio)methyl]-6-hydroxymethyl-4'-fluoro-1,1'-biphenyl;

3,5-Diisopropyl-2-[(p-tolylthio)methyl]-6-hydroxymethyl-4'-chloro-1,1'-biphenyl;

3,5-Diisopropyl-2-[(p-tolylthio)methyl]-6-hydroxymethyl-4'-methyl-1,1'-biphenyl;

3,5-Diisopropyl-2-[(p-tolylthio)methyl]-6-hydroxymethyl-2'-hydroxy-1,1'-biphenyl;

3,5-Diisopropyl-2-[(p-tolylthio)methyl]-6-hydroxymethyl-2'-hydroxy4'-fluoro-1,1'-biphenyl;

3,5-Diisopropyl-2-[((4-fluorophenyl)thio)methyl]-6-hydroxymethyl-1,1'-biphenyl;

3,5-Diisopropyl-2-[((4-fluorophenyl)thio)methyl]-6-hydroxymethyl-4'-fluoro-1,1'-biphenyl;

3,5-Diisopropyl-2-[((4-fluorophenyl)thio)methyl]-6-hydroxymethyl-4'-chloro-1,1'-biphenyl;

3,5-Diisopropyl-2-[((4-fluorophenyl)thio)methyl]-6-hydroxymethyl-4'-methyl-1,1'-biphenyl;

3,5-Diisopropyl-2-[((4-fluorophenyl)thio)methyl]-6-hydroxymethyl-2'-hydroxy-1,1'-biphenyl;

3,5-Diisopropyl-2-[((4-fluorophenyl)thio)methyl]-6-hydroxymethyl-2'-hydroxy-4'-fluoro-1,1'-biphenyl;

3,5-Diisopropyl-2-(1-hydroxyethyl)-6-ethyl-1,1'-biphenyl;

3,5-Diisopropyl-2-(1-hydroxyethyl)-6-ethyl-4'-fluoro-1,1'-biphenyl;

3,5-Diisopropyl-2-(1-hydroxyethyl)-6-ethyl-4'-chloro-1,1'-biphenyl;

3,5-Diisopropyl-2-(1-hydroxyethyl)-6-ethyl-4'-methyl-1,1'-biphenyl;

3,5-Diisopropyl-2-(1-hydroxyethyl)-6-ethyl-2'-hydroxy-1,1'-biphenyl;

3,5-Diisopropyl-2-(1-hydroxyethyl)-6-ethyl-2'-hydroxy-4'-fluoro-1,1'-biphenyl;

3,5-Diisopropyl-2-(1-hydroxyethyl)-6-propyl-1,1'-biphenyl;

3,5-Diisopropyl-2-(1-hydroxyethyl)-6-propyl-4'-fluoro-1,1'-biphenyl;

3,5-Diisopropyl-2-(1-hydroxyethyl)-6-propyl-4'-chloro-1,1'-biphenyl;

3,5-Diisopropyl-2-(1-hydroxyethyl)-6-propyl-4'-methyl-1,1'-biphenyl;

3,5-Diisopropyl-2-(1-hydroxyethyl)-6propyl-2'-hydroxy-1,1'-biphenyl;

3,5-Diisopropyl-2-(1-hydroxyethyl)-6propyl-2'-hydroxy-4'-fluoro-1,1'-biphenyl;

3,5-Diisopropyl-2-(1-hydroxyethyl)-6-butyl-1,1'-biphenyl;

3,5-Diisopropyl-2-(1-hydroxyethyl)-6-butyl-4'-fluoro-1,1'-biphenyl;

3,5-Diisopropyl-2-(1-hydroxyethyl)-6-butyl-4'-chloro-1,1'-biphenyl;

3,5-Diisopropyl-2-(1-hydroxyethyl)-6-butyl-4'-methyl-1,1'-biphenyl;

3,5-Diisopropyl-2-(1-hydroxyethyl)-6-butyl-2'-hydroxy-1,1'-biphenyl;

3,5-Diisopropyl-2-(1-hydroxyethyl)-6-butyl-2'-hydroxy-4'-fluoro-1,1'-biphenyl;

3,5-Diisopropyl-2-(1-hydroxyethyl)-6-pentyl-1,1'-biphenyl;

3,5-Diisopropyl-2-(1-hydroxyethyl)-6-pentyl-4'-fluoro-1,1'-biphenyl;

3,5-Diisopropyl-2-(1-hydroxyethyl)-6-pentyl-4'-chloro-1,1'-biphenyl;

3,5-Diisopropyl-2-(1-hydroxyethyl)-6-pentyl-4'-methyl-1,1'-biphenyl;

3,5-Diisopropyl-2-(1-hydroxyethyl)-6-pentyl-2'-hydroxy-1,1'-biphenyl;

3,5-Diisopropyl-2-(1-hydroxyethyl)-6-pentyl-2'-hydroxy-4'-fluoro-1,1'-biphenyl;

3,5-Diisopropyl-2-(1-hydroxyethyl)-6-hexyl-1,1'-biphenyl;

3,5-Diisopropyl-2-(1-hydroxyethyl)-6-hexyl-4'-fluoro-1,1'-biphenyl;

3,5-Diisopropyl-2-(1-hydroxyethyl)-6-hexyl-4'-chloro-1,1'-biphenyl;

3,5-Diisopropyl-2-(1-hydroxyethyl)-6-hexyl-4'-methyl-1,1'-biphenyl;

3,5-Diisopropyl-2-(1-hydroxyethyl)-6-hexyl-2'-hydroxy-1,1'-biphenyl;

3,5-Diisopropyl-2-(1-hydroxyethyl)-6-hexyl-2'-hydroxy-4'-fluoro-1,1'-biphenyl;

3,5-Diisopropyl-2-[(p-tolylthio)methyl]-6-(1-hydroxyethyl)-1,1'-biphenyl;

3,5-Diisopropyl-2-[(p-tolylthio)methyl]-6-(1-hydroxyethyl)-4'-fluoro-1,1'-biphenyl;

3,5-Diisopropyl-2-[(p-tolylthio)methyl]-6-(1-hydroxyethyl)-4'-chloro-1,1'-biphenyl;

3,5-Diisopropyl-2-[(p-tolylthio)methyl]-6-(1-hydroxyethyl)-4'-methyl-1,1'-biphenyl;

3,5-Diisopropyl-2-[(p-tolylthio)methyl]-6-(1-hydroxyethyl)-2'-hydroxy-1,1'-biphenyl;

3,5-Diisopropyl-2-[(p-tolylthio)methyl]-6-(1-hydroxyethyl)-2'-hydroxy-4'-fluoro-1,1'-biphenyl;

3,5-Diisopropyl-2-[((4-fluorophenyl)thio)methyl]-6-(1-hydroxyethyl)-1,1'-biphenyl;

3,5-Diisopropyl-2-[((4-fluorophenyl)thio)methyl]-6-(1-hydroxyethyl)-4'-fluoro-1,1'-biphenyl;

3,5-Diisopropyl-2-[((4-fluorophenyl)thio)methyl]-6(1-hydroxyethyl)-4'-chloro-1,1'-biphenyl;

3,5-Diisopropyl-2-[((4-fluorophenyl)thio)methyl]-6(1-hydroxyethyl)-4'-methyl-1,1'-biphenyl;

3,5-Diisopropyl-2-[((4-fluorophenyl)thio)methyl]-6(1-hydroxyethyl)-2'-hydroxy-1,1'-biphenyl.

* * * * *